(12) United States Patent
Loo et al.

(10) Patent No.: US 11,673,879 B2
(45) Date of Patent: Jun. 13, 2023

(54) SUBSTITUTED PYRIMIDINES AND METHODS OF USE

(71) Applicant: THERAVANCE BIOPHARMA R&D IP, LLC, South San Francisco, CA (US)

(72) Inventors: Mandy Loo, San Jose, CA (US); Svitlana Kulyk, Redwood City, CA (US); Christopher Bailey, Mountain View, CA (US); Jennifer Kozak, Pacifica, CA (US); Matthew B. Soellner, Ann Arbor, MI (US); Adam D. Hughes, Half Moon Bay, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 112 days.

(21) Appl. No.: 17/301,242

(22) Filed: Mar. 30, 2021

(65) Prior Publication Data

US 2022/0372015 A1 Nov. 24, 2022

Related U.S. Application Data

(60) Provisional application No. 63/200,310, filed on Mar. 1, 2021, provisional application No. 63/002,658, filed on Mar. 31, 2020.

(51) Int. Cl.

| | | |
|---|---|---|
| *C07D 401/14* | (2006.01) |
| *A61K 31/506* | (2006.01) |
| *A61K 9/12* | (2006.01) |
| *A61P 1/16* | (2006.01) |
| *A61P 9/00* | (2006.01) |
| *A61P 11/00* | (2006.01) |
| *A61P 35/00* | (2006.01) |
| *A61K 9/00* | (2006.01) |
| *A61K 45/06* | (2006.01) |

(52) U.S. Cl.
CPC .......... *C07D 401/14* (2013.01); *A61K 9/008* (2013.01); *A61K 9/0075* (2013.01); *A61K 9/0078* (2013.01); *A61K 45/06* (2013.01); *A61P 1/16* (2018.01); *A61P 9/00* (2018.01); *A61P 11/00* (2018.01); *A61P 35/00* (2018.01); *A61K 31/506* (2013.01)

(58) Field of Classification Search
CPC ........ C07D 401/14; A61K 9/0075; A61P 1/16
See application file for complete search history.

(56) References Cited

U.S. PATENT DOCUMENTS 6,838,464 B2   1/2005   Pease et al.

FOREIGN PATENT DOCUMENTS

| EP | 1794135 A1 | 6/2007 |
| EP | 3539951 B1 | 10/2020 |
| WO | 2006069258 A1 | 6/2006 |
| WO | 2008005538 A2 | 1/2008 |
| WO | 2008006583 A1 | 1/2008 |
| WO | 2009143389 A1 | 11/2009 |
| WO | 2011153553 A2 | 12/2011 |
| WO | 2016033100 A1 | 3/2016 |

OTHER PUBLICATIONS

International Search Report for PCT/US2021/070337, dated May 28, 2021.
Written Opinion of the International Searching Authority for PCT/US2021/070337, dated May 28, 2021.

*Primary Examiner* — Shengjun Wang
(74) *Attorney, Agent, or Firm* — Sheppard Mullin Richter & Hampton LLP

(57) ABSTRACT

The present disclosure provides inhibitors of activin receptor-like kinase 5 (ALK5). Also disclosed are methods to modulate the activity of ALK5 and methods of treatment of disorders mediated by ALK5.

23 Claims, No Drawings

SUBSTITUTED PYRIMIDINES AND METHODS OF USE

CROSS-REFERENCE

This application claims the benefit of U.S. Provisional Application No. 63/002,658, filed Mar. 31, 2020; and U.S. Provisional Application No. 63/200,310, filed Mar. 1, 2021, each of which is incorporated herein by reference in its entirety.

BACKGROUND

Human fibrotic diseases such as systemic sclerosis (SSc), sclerodermatous graft vs. host disease, nephrogenic system fibrosis, and radiation-induced fibrosis, as well as cardiac, pulmonary, skin, liver, bladder and kidney fibrosis, constitute a major health problem. These diseases often progress to organ dysfunction with eventual organ failure and death due to lack of treatment available, mainly because the etiologic mechanisms of runaway fibrosis are complex, heterogeneous, and difficult to decipher. Activated myofibroblasts may be responsible for replacing normal tissues with nonfunctional fibrotic tissue. Therefore, signaling pathways responsible for stimulating profibrotic reactions in myofibroblasts have potential as targets for development of therapies to treat fibrotic diseases.

Normal tissue repair involves fibrotic reactions through homeostatic regulatory mechanisms. Uncontrolled fibrosis, however, may result in excess deposition of the extracellular matrix (ECM) macromolecules in interstitial space that stiffens over time. There are many sites along the molecular pathway leading up to myofibroblast activation, including, but not limited to, transforming growth factor-β (TGF-β) and bone morphogenic protein (BMP) signaling pathways. Of importance in this disclosure is the pathway involving transforming growth factor-β (TGF-β), TGF-β receptor I (TGF-βRI), and TGF-β receptor II (TGF-βRII).

TGF-β signaling is typically initiated by binding of a TGF-β ligand to a TGF-βRII. This in turn may recruit and phosphorylate TGF-βRI, also known as the activin receptor-like kinase 5 (ALK5). Once phosphorylated, ALK5 typically adopts an active conformation and is free to associate with and phosphorylate Smad2 or Smad3. Once phosphorylated, Smad 2 and 3 proteins then may form heterodimeric complexes with Smad4 which can translocate across the nuclear membrane and modulate Smad-mediated gene expression, including, for example, the production of collagen. Smad proteins are intracellular regulators of transcription and therefore may serve as modulators of TGF-β-regulated genes involving, inter alia, cell cycle arrest in epithelial and hematopoietic cells, control of mesenchymal cell proliferation and differentiation, wound healing, extracellular matrix production, immunosuppression and carcinogenesis.

ALK5 is believed to be the most relevant of the activin-like kinases (ALKs) in the fibrotic process (Rosenbloom, et al., *Fibrosis: Methods and Protocols, Methods in Molecular Biology*, 2017, Vol. 1627, Chapter 1, pp. 1-21). Several small molecules have been developed to inhibit the activity of ALK5 for various therapeutic indications, related mostly to oncology (see Yingling, et al., *Nature Reviews: Drug Discovery*, December 2004, Vol. 3, pp. 1011-1022).

SUMMARY OF THE INVENTION

One of the main problems with ALK5 inhibitors developed to date is that these molecules have been associated with ventricular or cardiac remodeling in preclinical safety studies resulting from significant systemic exposure from oral administration. In view of the foregoing, a need exists for small molecules that target ALK5 and for use of such compounds in the treatment of various diseases, such as cancer and fibrosis, while limiting adverse side effects. The present disclosure provides these and other related advantages. One objective of the present disclosure is to deliver a potent ALK5 inhibitor locally with minimal systemic exposure in order to address any unintended and unwanted systemic side effects of ALK5 inhibition during treatment. Therefore, in some aspects, the present disclosure provides inhaled, long-acting and lung-selective ALK5 inhibitors for the treatment of idiopathic pulmonary fibrosis. Compounds of the present disclosure may be used to treat other diseases, including, but not limited to, pulmonary fibrosis, liver fibrosis, renal glomerulosclerosis, and cancer. Compounds of the present disclosure may be used as a monotherapy or co-dosed with other therapies, whether delivered by inhalation, orally, intravenously, subcutaneously, or topically.

In certain aspects, the present disclosure provides a compound of Formula (I):

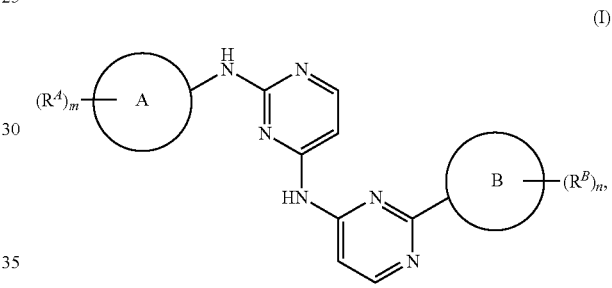

(I)

or a pharmaceutically acceptable salt thereof, wherein:

A and B are each independently selected from $C_{3-12}$ carbocycle and 3- to 12-membered heterocycle;

$R^A$ is independently selected at each occurrence from:
halogen, $-NO_2$, $-CN$, $-OR^1$, $-SR^1$, $-N(R^1)_2$, $-NR^2R^3$, $-S(=O)R^1$, $-S(=O)_2R^1$, $-S(=O)_2N(R^1)_2$, $-S(=O)_2NR^2R^3$, $-NR^1S(=O)_2R^1$, $-NR^1S(=O)_2N(R^1)_2$, $-NR^1S(=O)_2NR^2R^3$, $-C(O)R^1$, $-C(O)OR^1$, $-OC(O)R^1$, $-OC(O)OR^1$, $-OC(O)N(R^1)_2$, $-OC(O)NR^2R^3$, $-NR^1C(O)R^1$, $-NR^1C(O)OR^1$, $-NR^1C(O)N(R^1)_2$, $-NR^1C(O)NR^2R^3$, $-C(O)N(R^1)_2$, $-C(O)NR^2R^3$, $-P(O)(OR^1)_2$, $-P(O)(R^1)_2$, $=O$, $=S$, $=N(R^1)$;

$C_{1-10}$ alkyl, $C_{2-10}$ alkenyl, $C_{2-10}$ alkynyl, and $-N(R^1)-C_{1-10}$ alkyl, each of which is independently optionally substituted at each occurrence with one or more substituents selected from halogen, $-NO_2$, $-CN$, $-OR^1$, $-SR^1$, $-N(R^1)_2$, $-NR^2R^3$, $-S(=O)R^1$, $-S(=O)_2R^1$, $-S(=O)_2N(R^1)_2$, $-S(=O)_2NR^2R^3$, $-NR^1S(=O)_2R^1$, $-NR^1S(=O)_2N(R^1)_2$, $-NR^1S(=O)_2NR^2R^3$, $-C(O)R^1$, $-C(O)OR^1$, $-OC(O)R^1$, $-OC(O)OR^1$, $-OC(O)N(R^1)_2$, $-OC(O)NR^2R^3$, $-NR^1C(O)R^1$, $-NR^1C(O)OR^1$, $-NR^1C(O)N(R^1)_2$, $-NR^1C(O)NR^2R^3$, $-C(O)N(R^1)_2$, $-C(O)NR^2R^3$, $-P(O)(OR^1)_2$, $-P(O)(R^1)_2$, $=O$, $=S$, $=N(R^1)$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^A$ is independently optionally substituted with one or more substituents selected from halogen, —NO$_2$, —CN, —OR$^1$, —SR$^1$, —CH$_2$N(R$^1$)$_2$, —N(R$^1$)$_2$, —NR$^2$R$^3$, —S(=O)R$^1$, —S(=O)$_2$R$^1$, —S(=O)$_2$N(R$^1$)$_2$, —S(=O)$_2$NR$^2$R$^3$, —NR$^1$S(=O)$_2$R$^1$, —NR$^1$S(=O)$_2$N(R$^1$)$_2$, —NR$^1$S(=O)$_2$NR$^2$R$^3$, —C(O)R$^1$, —CH$_2$C(O)OR$^1$, —C(O)OR$^1$, —OC(O)R$^1$, —OC(O)OR$^1$, —OC(O)N(R$^1$)$_2$, —OC(O)NR$^2$R$^3$, —NR$^1$C(O)R$^1$, —NR$^1$C(O)OR$^1$, —NR$^1$C(O)N(R$^1$)$_2$, —NR$^1$C(O)NR$^2$R$^3$, —C(O)N(R$^1$)$_2$, —C(O)NR$^2$R$^3$, —P(O)(OR$^1$)$_2$, —P(O)(R$^1$)$_2$, =O, =S, =N(R$^1$), R$^1$, C$_{1-6}$ alkyl, C$_{1-6}$ haloalkyl, C$_{2-6}$ alkenyl, and C$_{2-6}$ alkynyl;

R$^B$ is independently selected at each occurrence from halogen, —CN, —NH$_2$, —NHCH$_3$, —NHCH$_2$CH$_3$, —C(O)CH$_3$, —OH, —OCH$_3$, —OCH$_2$CH$_3$, —CH$_3$, —CH$_2$CH$_3$, —CH(CH$_3$)$_2$, —C(CH$_3$)$_3$, —CH$_2$F, —CHF$_2$, —CF$_3$, C$_{3-4}$ carbocycle, and 3- to 4-membered heterocycle;

m and n are each independently an integer from 0 to 3;

R$^1$ is independently selected at each occurrence from hydrogen; and C$_{1-6}$ alkyl, C$_{2-6}$ alkenyl, C$_{2-6}$ alkynyl, 1- to 6-membered heteroalkyl, C$_{0-3}$ alkyl-(C$_{3-12}$ carbocycle), and C$_{0-3}$ alkyl-(3- to 12-membered heterocycle), each of which is optionally substituted by one or more substituents selected from halogen, —CN, —NO$_2$, —NH$_2$, —NHCH$_3$, —N(CH$_3$)$_2$, —NHCH$_2$CH$_3$, —CH$_2$CH$_2$N(CH$_3$)$_2$, —C(O)CH$_3$, —C(O)OH, —C(O)NH$_2$, =O, —OH, —CH$_2$OH, —CH$_2$CH$_2$OH, —OCH$_3$, —OCH$_2$CH$_3$, —CH$_3$, —CH$_2$CH$_3$, —CH(CH$_3$)$_2$, —C(CH$_3$)$_3$, C$_{3-12}$ carbocycle, and 3- to 6-membered heterocycle; and R$^2$ and R$^3$ are taken together with the nitrogen atom to which they are attached to form a heterocycle, optionally substituted with one or more R$^1$.

The compound of Formula (I) may be a compound of Formula (I-A):

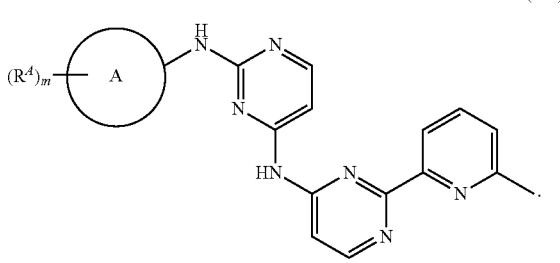

(I-A)

For a compound of Formula (I) or (I-A), A may be selected from C$_{6-10}$ aryl and 5- to 10-membered heteroaryl. In some embodiments, A is selected from phenyl and 5- to 6-membered heteroaryl. In some embodiments, A is selected from phenyl, indanyl, thiazolyl, thiophenyl, pyrazolyl, pyridyl, pyrimidinyl, indazolyl, benzotriazolyl, tetrahydroquinolinyl, tetrahydroisoquinolinyl, benzodioxanyl, and tetrahydrobenzazepinyl, such as A is phenyl. In some embodiments, A is thiazolyl. In some embodiments, A is thiophenyl. In some embodiments, A is pyridyl.

The compound of Formula (I) may be a compound of Formula (I-B):

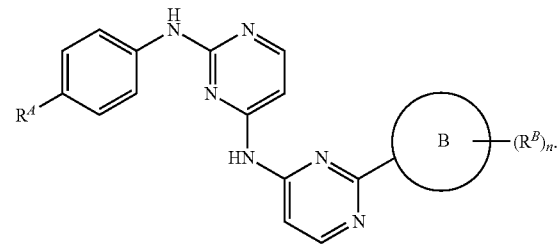

(I-B)

The compound of Formula (I) may be a compound of Formula (I-C):

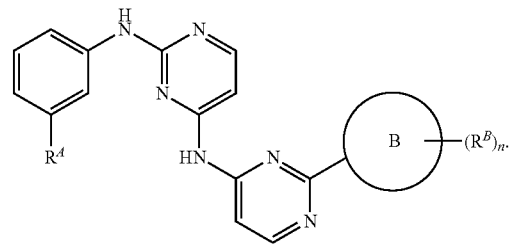

(I-C)

For a compound of Formula (I), (I-A), (I-B) or (I-C), R$^A$ may independently be selected at each occurrence from:
halogen, —OR$^1$, —N(R$^1$)$_2$, —S(=O)$_2$R$^1$, —S(=O)$_2$N(R$^1$)$_2$, —S(=O)$_2$NR$^2$R$^3$, —NR$^1$S(=O)$_2$R$^1$, —NR$^1$S(=O)$_2$N(R$^1$)$_2$, —C(O)R$^1$, —C(O)OR$^1$, —NR$^1$C(O)R$^1$, —NR$^1$C(O)N(R$^1$)$_2$, —C(O)N(R$^1$)$_2$, —C(O)NR$^2$R$^3$;

C$_{1-6}$ alkyl and —N(R$^1$)—C$_{1-10}$ alkyl, each of which is independently optionally substituted at each occurrence with one or more substituents selected from halogen, —OR$^1$, —N(R$^1$)$_2$, —S(=O)$_2$R$^1$, —S(=O)$_2$N(R$^1$)$_2$, —S(=O)$_2$NR$^2$R$^3$, —NR$^1$S(=O)$_2$R$^1$, —NR$^1$S(=O)$_2$N(R$^1$)$_2$, —C(O)R$^1$, —C(O)OR$^1$, —NR$^1$C(O)R$^1$, —NR$^1$C(O)N(R$^1$)$_2$, —C(O)N(R$^1$)$_2$, —C(O)NR$^2$R$^3$, C$_{3-8}$ carbocycle, and 3- to 10-membered heterocycle; and C$_{3-8}$ carbocycle and 3- to 10-membered heterocycle, wherein each C$_{3-8}$ carbocycle and 3- to 10-membered heterocycle in R$^A$ is independently optionally substituted with one or more substituents selected from halogen, —OR$^1$, —CH$_2$N(R$^1$)$_2$, —N(R$^1$)$_2$, —S(=O)$_2$R$^1$, —S(=O)$_2$N(R$^1$)$_2$, —S(=O)$_2$NR$^2$R$^3$, —NR$^1$S(=O)$_2$R$^1$, —NR$^1$S(=O)$_2$N(R$^1$)$_2$, —C(O)R$^1$, —CH$_2$C(O)OR$^1$, —C(O)OR$^1$, —NR$^1$C(O)R$^1$, —NR$^1$C(O)N(R$^1$)$_2$, —C(O)N(R$^1$)$_2$, —C(O)NR$^2$R$^3$, R$^1$, and C$_{1-6}$ alkyl.

In some embodiments, for a compound of Formula (I), (I-A), (I-B) or (I-C), R$^A$ is independently selected at each occurrence from:
halogen, —OR$^1$, —N(R$^1$)$_2$, —S(=O)$_2$R$^1$, —S(=O)$_2$N(R)$_2$, —S(=O)$_2$NR$^2$R$^3$, —NR$^1$S(=O)$_2$R$^1$, —NR$^1$S(=O)$_2$N(R$^1$)$_2$, —C(O)R$^1$, —C(O)OR$^1$, —NR$^1$C(O)R$^1$, —NR$^1$C(O)N(R$^1$)$_2$, —C(O)N(R$^1$)$_2$, —C(O)NR$^2$R$^3$;

C$_{1-6}$ alkyl and —N(R$^1$)—C$_{1-10}$ alkyl, each of which is independently optionally substituted at each occurrence with one or more substituents selected from —OR$^1$, —N(R$^1$)$_2$, —C(O)OR$^1$, C$_{3-8}$ carbocycle, and 3- to 10-membered heterocycle; and C$_{3-8}$ carbocycle and 3- to 10-membered heterocycle, wherein each $C_{3-8}$ carbocycle and 3- to 10-membered heterocycle in $R^A$ is independently optionally substituted with one or more substituents selected from —$OR^1$, —$CH_2N(R^1)_2$, —$N(R^1)_2$, —$C(O)R^1$, —$CH_2C(O)OR^1$, —$C(O)OR^1$, —$C(O)N(R^1)_2$, $R^1$, and $C_{1-6}$ alkyl.

For a compound of Formula (I), (I-A), (I-B) or (I-C), $R^A$ may independently be selected at each occurrence from:

halogen, —$OR^1$, —$N(R^1)_2$, —$S(=O)_2R^1$, —$S(=O)_2N(R^1)_2$, —$NR^1S(=O)_2R^1$, —$NR^1S(=O)_2N(R^1)_2$, —$C(O)R^1$, —$C(O)OR^1$, —$NR^1C(O)R^1$, —$NR^1C(O)N(R^1)_2$, —$C(O)N(R^1)_2$;

$C_{1-6}$ alkyl and —$N(R^1)$—$C_{1-10}$ alkyl, each of which is independently optionally substituted at each occurrence with one or more substituents selected from —$OR^1$, —$N(R^1)_2$, and 3- to 10-membered heterocycle; and 3- to 10-membered heterocycle, wherein each 3- to 10-membered heterocycle in $R^A$ is independently optionally substituted with one or more substituents selected from —$OR^1$, —$N(R^1)_2$, —$C(O)R^1$, —$CH_2C(O)OR^1$, —$C(O)OR^1$, —$C(O)N(R^1)_2$, and $R^1$.

For a compound of Formula (I), (I-A), (I-B) or (I-C), $R^A$ may independently be selected at each occurrence from:

—$N(R^1)_2$ and —$NR^1C(O)R^1$;

$C_{1-6}$ alkyl and —$N(R^1)$—$C_{1-6}$ alkyl, each of which is substituted with 4- to 8-membered heterocycle; and 4- to 8-membered heterocycle, wherein each 4- to 8-membered heterocycle in $R^A$ is independently optionally substituted with one or more substituents selected from —$C(O)OR^1$ and $R^1$.

For a compound of Formula (I), (I-A), (I-B) or (I-C), $R^A$ may be —$N(R^1)_2$. In some embodiments, $R^A$ is —$NR^1C(O)R^1$. In some embodiments, $R^A$ is $C_{1-6}$ alkyl substituted with 4- to 8-membered heterocycle, wherein the 4- to 8-membered heterocycle is substituted with —$C(O)OR^1$. In some embodiments, $R^A$ is —$N(R^1)$—$C_{1-6}$ alkyl substituted with 4- to 8-membered heterocycle. In some embodiments, $R^A$ is 4- to 8-membered heterocycle, wherein the 4- to 8-membered heterocycle is optionally substituted with one or more substituents selected from —$C(O)OR^1$ and $R^1$.

For a compound of Formula (I), (I-A), (I-B) or (I-C), $R^1$ may independently be selected at each occurrence from hydrogen; and $C_{1-6}$ alkyl, 1- to 6-membered heteroalkyl, $C_{0-3}$ alkyl-($C_{3-8}$ carbocycle), and $C_{0-3}$ alkyl-(3- to 10-membered heterocycle), each of which is optionally substituted by one or more substituents selected from —$NH_2$, —$NHCH_3$, —$N(CH_3)_2$, —$CH_2CH_2N(CH_3)_2$, —$C(O)CH_3$, —$C(O)OH$, —$C(O)NH_2$, =O, —OH, —$CH_2OH$, —$CH_2CH_2OH$, —$OCH_3$, —$OCH_2CH_3$, —$CH_3$, —$CH_2CH_3$, —$CH(CH_3)_2$, —$C(CH_3)_3$, $C_{3-8}$ carbocycle, and 3- to 6-membered heterocycle. In some embodiments, $R^1$ is independently selected at each occurrence from hydrogen; and $C_{1-6}$ alkyl and $C_{0-3}$ alkyl-(3- to 10-membered heterocycle), each of which is optionally substituted by one or more substituents selected from —OH, —$CH_2OH$, —$CH_3$, —$CH_2CH_3$, —$CH(CH_3)_2$, —$C(CH_3)_3$, and 3- to 6-membered heterocycle.

For a compound of Formula (I), (I-A), (I-B) or (I-C), m may be 1 or 2, such as m is 1.

For a compound of Formula (I), (I-A), (I-B) or (I-C), B may be selected from $C_{6-10}$ aryl and 5- to 10-membered heteroaryl. In some embodiments, B is selected from phenyl and pyridyl. In some embodiments, B is pyridyl, such as 2-pyridyl.

For a compound of Formula (I), (I-A), (I-B) or (I-C), $R^B$ may independently be selected at each occurrence from halogen, —$NH_2$, —$NHCH_3$, —$NHCH_2CH_3$, —$C(O)CH_3$, —OH, —$OCH_3$, —$OCH_2CH_3$, —$CH_3$, —$CH_2CH_3$, —$CH(CH_3)_2$, —$C(CH_3)_3$, —$CH_2F$, —$CHF_2$, and —$CF_3$. In some embodiments, $R^B$ is independently selected at each occurrence from halogen, —OH, —$CH_3$, and —$CHF_2$, such as —$CH_3$.

For a compound of Formula (I), (I-A), (I-B) or (I-C), n may be 1 or 2, such as n is 1.

The compound of Formula (I) may be a compound of Formula (I-D):

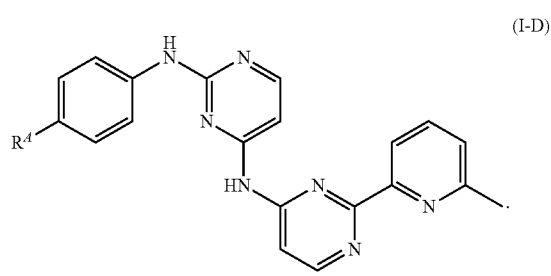

(I-D)

The compound of Formula (I) may be a compound of Formula (I-E):

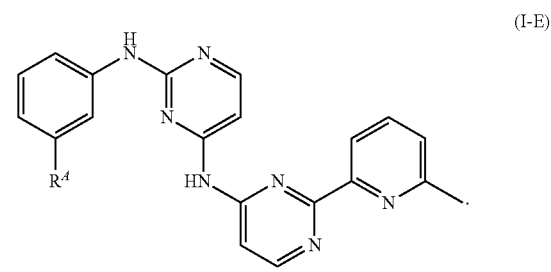

(I-E)

In some embodiments, for a compound of Formula (I):

A is selected from phenyl and 5- to 6-membered heteroaryl;

B is pyridyl;

$R^A$ is independently selected at each occurrence from:

halogen, —$OR^1$, —$N(R^1)_2$, —$S(=O)_2R^1$, —$S(=O)_2N(R^1)_2$, —$S(=O)_2NR^2R^3$, —$NR^1S(=O)_2R^1$, —$NR^1S(=O)_2N(R^1)_2$, —$C(O)R^1$, —$C(O)OR^1$, —$NR^1C(O)R^1$, —$NR^1C(O)N(R^1)_2$, —$C(O)N(R^1)_2$, —$C(O)NR^2R^3$;

$C_{1-6}$ alkyl and —$N(R^1)$—$C_{1-10}$ alkyl, each of which is independently optionally substituted at each occurrence with one or more substituents selected from —$OR^1$, —$N(R^1)_2$, —$C(O)OR^1$, $C_{3-8}$ carbocycle, and 3- to 10-membered heterocycle; and $C_{3-8}$ carbocycle and 3- to 10-membered heterocycle, wherein each $C_{3-8}$ carbocycle and 3- to 10-membered heterocycle in $R^A$ is independently optionally substituted with one or more substituents selected from —$OR^1$, —$CH_2N(R^1)_2$, —$N(R^1)_2$, —$C(O)R^1$, —$CH_2C(O)OR^1$, —$C(O)OR^1$, —$C(O)N(R^1)_2$, $R^1$, and $C_{1-6}$ alkyl;

$R^1$ is independently selected at each occurrence from hydrogen; and $C_{1-6}$ alkyl, 1- to 6-membered heteroalkyl, $C_{0-3}$ alkyl-($C_{3-8}$ carbocycle), and $C_{0-3}$ alkyl-(3- to 10-membered heterocycle), each of which is optionally substituted by one or more substituents selected from —$NH_2$, —$NHCH_3$, —$N(CH_3)_2$, —$CH_2CH_2N(CH_3)_2$, —$C(O)CH_3$, —$C(O)OH$, —$C(O)NH_2$, =O, —OH, —$CH_2OH$, —$CH_2CH_2OH$, —$OCH_3$, —$OCH_2CH_3$, —$CH_3$, —$CH_2CH_3$, —$CH(CH_3)_2$, —$C(CH_3)_3$, $C_{3-8}$ carbocycle, and 3- to 6-membered heterocycle;

m is 1 or 2;

$R^B$ is selected from halogen, —OH, —$CH_3$, and —$CHF_2$; and n is 1.

In some embodiments, for a compound of Formula (I):

A is phenyl;

B is pyridyl;

$R^A$ is independently selected at each occurrence from:
—$N(R^1)_2$ and —$NR^1C(O)R^1$;
$C_{1-6}$ alkyl and —$N(R^1)$—$C_{1-6}$ alkyl, each of which is substituted with 4- to 8-membered heterocycle; and
4- to 8-membered heterocycle,
wherein each 4- to 8-membered heterocycle in $R^A$ is independently optionally substituted with one or more substituents selected from —$C(O)OR^1$ and $R^1$;

$R^1$ is independently selected at each occurrence from hydrogen; and $C_{1-6}$ alkyl and $C_{0-3}$ alkyl-(3- to 10-membered heterocycle), each of which is optionally substituted by one or more substituents selected from —OH, —$CH_2OH$, —$CH_3$, —$CH_2CH_3$, —$CH(CH_3)_2$, —$C(CH_3)_3$, and 3- to 6-membered heterocycle;

m is 1;

$R^B$ is —$CH_3$; and n is 1.

In some embodiments, for a compound of Formula (I):

A is phenyl;

B is pyridyl;

$R^A$ is $C_{1-6}$ alkyl substituted with 4- to 8-membered heterocycle, wherein the 4- to 8-membered heterocycle is substituted with —$C(O)OR^1$;

$R^1$ is independently selected at each occurrence from hydrogen; and $C_{1-6}$ alkyl and $C_{0-3}$ alkyl-(3- to 10-membered heterocycle), each of which is optionally substituted by one or more substituents selected from —OH, —$CH_2OH$, —$CH_3$, —$CH_2CH_3$, —$CH(CH_3)_2$, —$C(CH_3)_3$, and 3- to 6-membered heterocycle;

m is 1;

$R^B$ is —$CH_3$; and n is 1.

In certain aspects, the present disclosure provides a substantially pure stereoisomer of a compound disclosed herein. The stereoisomer may be provided in at least 90% enantiomeric excess.

In certain aspects, the present disclosure provides a compound selected from Table 1. In some embodiments, the present disclosure provides a compound selected from Table 2.

In certain aspects, the present disclosure provides a conjugate of the formula:

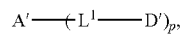

wherein:

A' is an antibody construct or targeting moiety;

$L^1$ is a linker;

D' is a compound or salt disclosed herein; and p is an integer from 1 to 20

In certain aspects, the present disclosure provides a pharmaceutical composition comprising a compound disclosed herein and a pharmaceutically acceptable carrier. The pharmaceutical composition may be formulated for inhalation.

In certain aspects, the present disclosure provides a method of inhibiting ALK5, comprising contacting ALK5 with an effective amount of a compound disclosed herein. In certain aspects, the present disclosure provides a method of treating an ALK5-mediated disease or condition in a subject, comprising administering to the subject a therapeutically effective amount of a compound disclosed herein. In practicing any of the subject methods, the disease or condition may be selected from fibrosis, alopecia and cancer. In some embodiments, the disease or condition is fibrosis. In some embodiments, the present disclosure provides a method of treating fibrosis, comprising administering to a patient a therapeutically effective amount of a compound disclosed herein. The fibrosis may be selected from systemic sclerosis, nephrogenic systemic fibrosis, organ-specific fibrosis, fibrosis associated with cancer, cystic fibrosis, and fibrosis associated with an autoimmune disease. Optionally, the organ-specific fibrosis is selected from cardiac fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis. In some embodiments, the organ-specific fibrosis is intestinal fibrosis. Optionally, the pulmonary fibrosis is selected from idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis and chemotherapy-induced lung fibrosis. Optionally, the pulmonary fibrosis is idiopathic pulmonary fibrosis (IPF). In some embodiments, the pulmonary fibrosis was induced by a viral infection.

In practicing any of the subject methods, the disease or condition may be cancer, optionally wherein the cancer is selected from breast cancer, colon cancer, prostate cancer, lung cancer, hepatocellular carcinoma, glioblastoma, melanoma, and pancreatic cancer. In some embodiments, the cancer is lung cancer, optionally non-small cell lung cancer. A method of the subject disclosure may further comprise administering a second therapeutic agent. Optionally, the second therapeutic agent is an immunotherapeutic agent, such as a PD-1 inhibitor or a CTLA-4 inhibitor. In some embodiments, the immunotherapeutic agent is selected from pembrolizumab and durvalumab. A method of the present disclosure may further comprise administering an effective amount of radiation. In practicing any of the subject methods, the compound or salt disclosed herein may be administered by inhalation.

In certain aspects, the present disclosure provides a compound disclosed herein for use in treating fibrosis. In certain aspects, the present disclosure provides the use of a compound disclosed herein for the manufacture of a medicament for treating fibrosis.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

Unless defined otherwise, all technical and scientific terms used herein have the same meaning as is commonly understood by one of skill in the art to which this disclosure belongs.

Chemical structures are named herein according to IUPAC conventions as implemented in ChemDraw® software (Perkin Elmer, Inc., Cambridge, Mass.).

As used in the specification and claims, the singular forms "a", "an" and "the" include plural references unless the context clearly dictates otherwise.

The term "$C_{x-y}$" or "$C_x$-$C_y$" when used in conjunction with a chemical moiety, such as alkyl, alkenyl, or alkynyl, is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups, that contain from x to y carbons in the chain.

"Alkyl" refers to substituted or unsubstituted saturated hydrocarbon groups, including linear and branched alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloro methyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including linear and branched alkenyl groups, containing at least one double bond. An alkenyl group may contain from two to twelve carbon atoms (e.g., $C_{2-12}$ alkenyl), such as two to eight carbon atoms ($C_{2-8}$ alkenyl) or two to six carbon atoms ($C_{2-6}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including linear and branched alkynyl groups, containing at least one triple bond. An alkynyl group may contain from two to twelve carbon atoms (e.g., $C_{2-12}$ alkynyl), such as two to eight carbon atoms ($C_{2-8}$ alkynyl) or two to six carbon atoms ($C_{2-6}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including linear alkylene and branched alkylene groups, that contain from one to twelve carbon atoms (e.g., $C_{1-12}$ alkylene), such as one to eight carbon atoms ($C_{1-8}$ alkylene) or one to six carbon atoms ($C_{1-6}$ alkylene). Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons of the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkyl group has a chain length of 3 to 8 atoms. Connection to the rest of the molecule may be through either a heteroatom or a carbon in the heteroalkyl, heteroalkenyl or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkylene group has a chain length of 3 to 8 atoms. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkylene, heteroalkenylene or heteroalkynylene chain. Unless stated otherwise specifically in the specification, a heteroalkylene, heteroalkenylene, or heteroalkynylene group is optionally substituted by one or more substituents such as those substituents described herein.

"Carbocycle" refers to a saturated, unsaturated or aromatic ring in which each atom of the ring is a carbon atom. Carbocycle may include $C_{3-10}$ monocyclic rings, $C_{6-12}$ bicyclic rings, $C_{6-12}$ spirocyclic rings, and $C_{6-12}$ bridged rings. Each ring of a bicyclic carbocycle may be selected from saturated, unsaturated, and aromatic rings. In some embodiments, the carbocycle is a $C_{6-12}$ aryl group, such as $C_{6-10}$ aryl. In some embodiments, the carbocycle is a $C_{6-12}$ cycloalkyl group. In some embodiments, the carbocycle is a $C_{6-12}$ cycloalkenyl group. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocycle. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Heterocycle" refers to a saturated, unsaturated or aromatic ring comprising one or more heteroatoms, for example 1, 2 or 3 heteroatoms selected from O, S and N. Heterocycles include 3- to 10-membered monocyclic rings, 6- to 12-membered bicyclic rings, 6- to 12-membered spirocyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a 5- to 10-membered heteroaryl group, such as 5- or 6-membered heteroaryl. In some embodiments, the heterocycle is a 3- to 12-membered heterocycloalkyl group. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Unless stated otherwise specifically in the specification, a heterocycle is optionally substituted by one or more substituents such as those substituents described herein.

"Heteroaryl" refers to a 5- to 12-membered aromatic ring that comprises at least one heteroatom, such as 1, 2 or 3 heteroatoms, selected from O, S and N. As used herein, the heteroaryl ring may be selected from monocyclic or bicyclic—including fused, spirocyclic and bridged ring systems—wherein at least one of the rings in the ring system is aromatic. The heteroatom(s) in the heteroaryl may optionally be oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryl groups include, but are not limited to, azepinyl, benzimidazolyl, benzisothiazolyl, benzisoxazolyl, benzofuranyl, benzothiazolyl, benzothiophenyl, benzoxazolyl, furanyl, imidazolyl, indazolyl, indolyl, isoquinolinyl, isothiazolyl, isoxazolyl, oxadiazolyl, oxazolyl, purinyl, pyrazinyl, pyrazolidinyl, pyrazolyl, pyridazinyl, pyridazolyl, pyridyl, pyrimidinyl, pyrrolyl, quinazolinyl, quinolinyl, quinoxalinyl, tetrahydroquinolinyl, thiadiazolyl, thiazolyl, and thienyl groups. Unless stated otherwise specifically in the specification, a heteroaryl is optionally substituted by one or more substituents such as those substituents described herein.

Unless stated otherwise, hydrogen atoms are implied in structures depicted herein as necessary to satisfy the valence requirement.

A waved line " 〜 " drawn across a bond or a dashed bond " --- " are used interchangeably herein to denote where a bond disconnection or attachment occurs. For example, in the structure

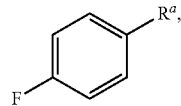

$R^a$ is attached to the para position of a fluorophenyl ring through a single bond. If $R^a$ is 2-pyridine as in

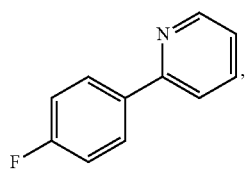 [SMILES: Fc1ccc(-c2ccccn2)cc1]

then $R^a$ may be depicted as

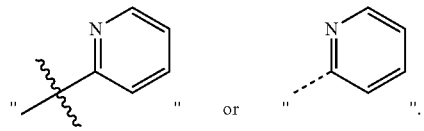

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, heteroatoms such as nitrogen may have any permissible substituents of organic compounds described herein which satisfy the valences of the heteroatoms.

A compound disclosed herein, such as a compound of Formula (I), is optionally substituted by one or more, such as 1, 2 or 3 substituents selected from:

halogen, —NO$_2$, —CN, —OR$^1$, —SR$^1$, —N(R$^1$)$_2$, —NR$^2$R$^3$, —S(═O)R$^1$, —S(═O)$_2$R$^1$, —S(═O)$_2$N(R$^1$)$_2$, —S(═O)$_2$NR$^2$R$^3$, —NR$^1$S(═O)$_2$R$^1$, —NR$^1$S(═O)$_2$N(R$^1$)$_2$, —NR$^1$S(═O)$_2$NR$^2$R$^3$, —C(O)R$^1$, —C(O)OR$^1$, —OC(O)R$^1$, —OC(O)OR$^1$, —OC(O)N(R$^1$)$_2$, —OC(O)NR$^2$R$^3$, —NR$^1$C(O)R$^1$, —NR$^1$C(O)OR$^1$, —NR$^1$C(O)N(R$^1$)$_2$, —NR$^1$C(O)NR$^2$R$^3$, —C(O)N(R$^1$)$_2$, —C(O)NR$^2$R$^3$, —P(O)(OR$^1$)$_2$, —P(O)(R$^1$)$_2$, ═O, ═S, ═N(R$^1$);

C$_{1-10}$ alkyl, C$_{2-10}$ alkenyl, C$_{2-10}$ alkynyl, and —N(R$^1$)—C$_{1-10}$ alkyl, each of which is independently optionally substituted at each occurrence with one or more substituents selected from halogen, —NO$_2$, —CN, —OR$^1$, —SR$^1$, —N(R$^1$)$_2$, —NR$^2$R$^3$, —S(═O)R$^1$, —S(═O)$_2$R$^1$, —S(═O)$_2$N(R$^1$)$_2$, —S(═O)$_2$NR$^2$R$^3$, —NR$^1$S(═O)$_2$R$^1$, —NR$^1$S(═O)$_2$N(R$^1$)$_2$, —NR$^1$S(═O)$_2$NR$^2$R$^3$, —C(O)R$^1$, —C(O)OR$^1$, —OC(O)R$^1$, —OC(O)OR$^1$, —OC(O)N(R$^1$)$_2$, —OC(O)NR$^2$R$^3$, —NR$^1$C(O)R$^1$, —NR$^1$C(O)OR$^1$, —NR$^1$C(O)N(R$^1$)$_2$, —NR$^1$C(O)NR$^2$R$^3$, —C(O)N(R$^1$)$_2$, —C(O)NR$^2$R$^3$, —P(O)(OR$^1$)$_2$, —P(O)(R$^1$)$_2$, ═O, ═S, ═N(R$^1$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle is independently optionally substituted with one or more substituents selected from halogen, —NO$_2$, —CN, —OR$^1$, —SR$^1$, —CH$_2$N(R$^1$)$_2$, —N(R$^1$)$_2$, —NR$^2$R$^3$, —S(═O)R$^1$, —S(═O)$_2$R$^1$, —S(═O)$_2$N(R$^1$)$_2$, —S(═O)$_2$NR$^2$R$^3$, —NR$^1$S(═O)$_2$R$^1$, —NR$^1$S(═O)$_2$N(R$^1$)$_2$, —NR$^1$S(═O)$_2$NR$^2$R$^3$, —C(O)R$^1$, —CH$_2$C(O)OR$^1$, —C(O)OR$^1$, —OC(O)R$^1$, —OC(O)OR$^1$, —OC(O)N(R$^1$)$_2$, —OC(O)NR$^2$R$^3$, —NR$^1$C(O)R$^1$, —NR$^1$C(O)OR$^1$, —NR$^1$C(O)N(R$^1$)$_2$, —NR$^1$C(O)NR$^2$R$^3$, —C(O)N(R$^1$)$_2$, —C(O)NR$^2$R$^3$, —P(O)(OR$^1$)$_2$, —P(O)(R$^1$)$_2$, ═O, ═S, ═N(R$^1$), R$^1$, C$_{1-6}$ alkyl, C$_{1-6}$ haloalkyl, C$_{2-6}$ alkenyl, and C$_{2-6}$ alkynyl;

$R^1$ is independently selected at each occurrence from hydrogen; and $C_{1-6}$ alkyl, $C_{2-6}$ alkenyl, $C_{2-6}$ alkynyl, 1- to 6-membered heteroalkyl, $C_{0-3}$ alkyl-($C_{3-12}$ carbocycle), and $C_{0-3}$ alkyl-(3- to 12-membered heterocycle), each of which is optionally substituted by one or more substituents selected from halogen, —CN, —NO$_2$, —NH$_2$, —NHCH$_3$, —N(CH$_3$)$_2$, —NHCH$_2$CH$_3$, —CH$_2$CH$_2$N(CH$_3$)$_2$, —C(O)CH$_3$, —C(O)OH, —C(O)NH$_2$, =O, —OH, —CH$_2$OH, —CH$_2$CH$_2$OH, —OCH$_3$, —OCH$_2$CH$_3$, —CH$_3$, —CH$_2$CH$_3$, —CH(CH$_3$)$_2$, —C(CH$_3$)$_3$, $C_{3-12}$ carbocycle, and 3- to 6-membered heterocycle; and $R^2$ and $R^3$ are taken together with the nitrogen atom to which they are attached to form a heterocycle, optionally substituted with one or more $R^1$.

In some embodiments, a compound disclosed herein, such as a compound of Formula (I), is optionally substituted by one or more, such as 1, 2 or 3 substituents selected from:

halogen, —NO$_2$, —CN, —OR$^1$, —SR$^1$, —N(R$^1$)$_2$, —NR$^2$R$^3$, —S(=O)R$^1$, —S(=O)$_2$R$^1$, —S(=O)$_2$N(R)$_2$, —S(=O)$_2$NR$^2$R$^3$, —NR$^1$S(=O)$_2$R$^1$, —NR$^1$S(=O)$_2$N(R$^1$)$_2$, —NR$^1$S(=O)$_2$NR$^2$R$^3$, —C(O)R$^1$, —C(O)OR$^1$, —OC(O)R$^1$, —OC(O)OR$^1$, —OC(O)N(R$^1$)$_2$, —OC(O)NR$^2$R$^3$, —NR$^1$C(O)R$^1$, —NR$^1$C(O)OR$^1$, —NR$^1$C(O)N(R)$_2$, —NR$^1$C(O)NR$^2$R$^3$, —C(O)N(R$^1$)$_2$, —C(O)NR$^2$R$^3$, —P(O)(OR$^1$)$_2$, —P(O)(R$^1$)$_2$, =O, =S, =N(R$^1$);

$C_{1-10}$ alkyl, $C_{2-10}$ alkenyl, $C_{2-10}$ alkynyl, and —N(R$^1$)—$C_{1-10}$ alkyl, each of which is independently optionally substituted at each occurrence with one or more substituents selected from halogen, =O, =S, =N(R$^1$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle is independently optionally substituted with one or more substituents selected from halogen, =O, =S, =N(R$^1$), $C_{1-6}$ alkyl, $C_{1-6}$ haloalkyl, $C_{2-6}$ alkenyl, and $C_{2-6}$ alkynyl;

$R^1$ is independently selected at each occurrence from hydrogen; and $C_{1-6}$ alkyl, $C_{2-6}$ alkenyl, $C_{2-6}$ alkynyl, 1- to 6-membered heteroalkyl, $C_{0-3}$ alkyl-($C_{3-12}$ carbocycle), and $C_{0-3}$ alkyl-(3- to 12-membered heterocycle), each of which is optionally substituted by one or more substituents selected from halogen, —CN, —NO$_2$, —NH$_2$, —NHCH$_3$, —N(CH$_3$)$_2$, —NHCH$_2$CH$_3$, —CH$_2$CH$_2$N(CH$_3$)$_2$, —C(O)CH$_3$, —C(O)OH, —C(O)NH$_2$, =O, —OH, —CH$_2$OH, —CH$_2$CH$_2$OH, —OCH$_3$, —OCH$_2$CH$_3$, —CH$_3$, —CH$_2$CH$_3$, —CH(CH$_3$)$_2$, —C(CH$_3$)$_3$, $C_{3-12}$ carbocycle, and 3- to 6-membered heterocycle; and $R^2$ and $R^3$ are taken together with the nitrogen atom to which they are attached to form a heterocycle, optionally substituted with one or more $R^1$.

In some embodiments, a compound disclosed herein, such as a compound of Formula (I), is optionally substituted by one or more, such as 1, 2 or 3 substituents selected from halogen, —CN, —NO$_2$, —NH$_2$, —NHCH$_3$, —NHCH$_2$CH$_3$, =O, —OH, —OCH$_3$, and —OCH$_2$CH$_3$; and $C_{1-10}$ alkyl, $C_{2-10}$ alkenyl, $C_{2-10}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, —CH$_3$, —CH$_2$CH$_3$, —CH(CH$_3$)$_2$, —C(CH$_3$)$_3$, $C_{3-12}$ carbocycle, or 3- to 6-membered heterocycle.

It will be understood by those skilled in the art that substituents can themselves be substituted, if appropriate. Unless specifically stated as "unsubstituted", references to chemical moieties herein are understood to include substituted variants. For example, reference to a "heteroaryl" group or moiety implicitly includes both substituted and unsubstituted variants.

Where bivalent substituent groups are specified herein by their conventional chemical formulae, written from left to right, they are intended to encompass the isomer that would result from writing the structure from right to left, e.g., —CH$_2$O— is also intended to encompass to —OCH$_2$—.

"Optional" or "optionally" means that the subsequently described event of circumstances may or may not occur, and that the description includes instances where the event or circumstance occurs and instances in which it does not. For example, an "optionally substituted" group may be either unsubstituted or substituted.

Compounds of the present disclosure also include crystalline and amorphous forms of those compounds, pharmaceutically acceptable salts, and active metabolites having the same type of activity, including, for example, polymorphs, pseudopolymorphs, solvates, hydrates, unsolvated polymorphs (including anhydrates), conformational polymorphs, amorphous forms of the compounds, and mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Examples of isotopes that may be incorporated into compounds of the present disclosure include, but are not limited to, $^2$H, $^3$H, $^{13}$C, $^{14}$C, $^{15}$N, $^{18}$O, $^{17}$O, $^{35}$S, $^{36}$Cl, and $^{18}$F. Of particular interest are compounds of Formula (I) enriched in tritium or carbon-14, which can be used, for example, in tissue distribution studies; compounds of the disclosure enriched in deuterium especially at a site of metabolism, resulting, for example, in compounds having greater metabolic stability; and compounds of Formula (I) enriched in a positron emitting isotope, such as $^{11}$C, $^{18}$F, $^{15}$O and $^{13}$N, which can be used, for example, in Positron Emission Topography (PET) studies. Isotopically-enriched compounds may be prepared by conventional techniques well known to those skilled in the art.

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. In some embodiments, in order to optimize the therapeutic activity of the compounds of the disclosure, e.g., to treat fibrosis, it may be desirable that the carbon atoms have a particular configuration (e.g., (R,R), (S,S), (S,R), or (R,S)) or are enriched in a stereoisomeric form having such configuration. The compounds of the disclosure may be provided as racemic mixtures.

Accordingly, the disclosure relates to racemic mixtures, pure stereoisomers (e.g., enantiomers and diastereoisomers), stereoisomer-enriched mixtures, and the like, unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the disclosure unless otherwise indicated, provided that the utility of the composition as a whole is not eliminated by the presence of such other isomers. Individual stereoisomers may be obtained by numerous methods that are known in the art, including preparation using chiral synthons or chiral reagents, resolution using chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified.

The term "tautomer", as used herein, refers to each of two or more isomers of a compound that exist in equilibrium and which ready interconvert. For example, one skilled in the art would readily understand that 1,2,3-triazole exists in two tautomeric forms:

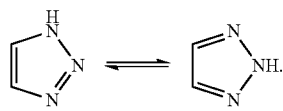 [SMILES: c1c[nH]nn1 ; c1cn[nH]n1]

Unless otherwise specified, chemical entities described herein are intended to include all possible tautomers, even when a structure depicts only one of them.

The term "pharmaceutically acceptable" refers to a material that is not biologically or otherwise unacceptable when used in the subject compositions and methods. For example, the term "pharmaceutically acceptable carrier" refers to a material—such as an adjuvant, excipient, glidant, sweetening agent, diluent, preservative, dye, colorant, flavor enhancer, surfactant, wetting agent, dispersing agent, suspending agent, stabilizer, isotonic agent, solvent or emulsifier—that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The terms "salt" and "pharmaceutically acceptable salt" refer to a salt prepared from a base or an acid. Pharmaceutically acceptable salts are suitable for administration to a patient, such as a mammal (for example, salts having acceptable mammalian safety for a given dosage regime). Salts can be formed from inorganic bases, organic bases, inorganic acids and organic acids. In addition, when a compound contains both a basic moiety, such as an amine, pyridine or imidazole, and an acidic moiety, such as a carboxylic acid or tetrazole, zwitterions may be formed and are included within the term "salt" as used herein. Salts derived from inorganic bases include ammonium, calcium, copper, ferric, ferrous, lithium, magnesium, manganic, manganous, potassium, sodium, and zinc salts, and the like. Salts derived from organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Salts derived from inorganic acids include salts of boric, carbonic, hydrohalic (hydrobromic, hydrochloric, hydrofluoric or hydroiodic), nitric, phosphoric, sulfamic and sulfuric acids. Salts derived from organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" refers to that amount of a compound described herein that is sufficient to affect treatment when administered to a subject in need thereof. For example, a therapeutically effective amount for treating pulmonary fibrosis is an amount of compound needed to, for example, reduce, suppress, eliminate, or prevent the formation of fibrosis in a subject, or to treat the underlying cause of pulmonary fibrosis. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The specific dose will vary depending on the particular compound chosen, the dosing regimen to be followed, whether it is administered in combination with other compounds, timing of administration, the tissue to which it is administered, and the physical delivery system in which it is carried. The term "effective amount" refers to an amount sufficient to obtain a desired result, which may not necessarily be a therapeutic result. For example, an "effective amount" may be the amount needed to inhibit an enzyme.

As used herein, "treating" or "treatment" refers to an approach for obtaining beneficial or desired results with respect to a disease, disorder, or medical condition (such as pulmonary fibrosis) in a subject, including but not limited to the following: (a) preventing the disease or medical condition from occurring, e.g., preventing the reoccurrence of the disease or medical condition or prophylactic treatment of a subject that is pre-disposed to the disease or medical condition; (b) ameliorating the disease or medical condition, e.g., eliminating or causing regression of the disease or medical condition in a subject; (c) suppressing the disease or medical condition, e.g., slowing or arresting the development of the disease or medical condition in a subject; or (d) alleviating symptoms of the disease or medical condition in a subject. For example, "treating pulmonary fibrosis" would include preventing fibrosis from occurring, ameliorating fibrosis, suppressing fibrosis, and alleviating the symptoms of fibrosis (for example, increasing oxygen levels in blood or improved lung function tests). Also, a therapeutic benefit is achieved with the eradication or amelioration of one or more of the physiological symptoms associated with the underlying disorder such that an improvement is observed in the subject, notwithstanding that the subject may still be afflicted with the underlying disorder A "therapeutic effect", as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "antagonist" and "inhibitor" are used interchangeably, and they refer to a compound having the ability to inhibit a biological function (e.g., activity, expression, binding, protein-protein interaction) of a target protein (e.g., ALK5). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition.

The term "selective inhibition" or "selectively inhibit" refers to the ability of a biologically active agent to preferentially reduce the target signaling activity as compared to off-target signaling activity, via direct or indirect interaction with the target.

As used herein, the term "antibody" refers to an immunoglobulin molecule that specifically binds to, or is immunologically reactive toward, a specific antigen. An antibody may be, for example, polyclonal, monoclonal, genetically engineered, or an antigen binding fragment thereof, and further may be, for example, murine, chimeric, humanized, heteroconjugate, bispecific, a diabody, a triabody, or a tetrabody. An antigen binding fragment includes an antigen binding domain and may be in the form of, for example, a Fab', F(ab')$_2$, Fab, Fv, rIgG, scFv, hcAbs (heavy chain antibodies), a single domain antibody, VHH, VNAR, sdAb, or nanobody.

The term "antigen binding domain" as used herein refers to a region of a molecule that binds to an antigen. An antigen binding domain may be an antigen-binding portion of an antibody or an antibody fragment. An antigen binding domain may be one or more fragments of an antibody that retain the ability to specifically bind to an antigen. An antigen binding domain can be an antigen binding fragment and may recognize a single antigen, two antigens, three antigens or more. As used herein, "recognize" with regard to antibody interactions refers to the association or binding between an antigen binding domain of an antibody or portion thereof and an antigen.

An "antibody construct" refers to a molecule, e.g., a protein, peptide, antibody or portion thereof, that contains an antigen binding domain and an Fc domain (e.g., an Fc domain from within the Fc region). An antibody construct may recognize, for example, one antigen or multiple antigens.

A "targeting moiety" refers to a structure that has a selective affinity for a target molecule relative to other non-target molecules. The targeting moiety binds to a target molecule. A targeting moiety may include an antibody, a peptide, a ligand, a receptor, or a binding portion thereof. The target biological molecule may be a biological receptor or other structure of a cell, such as a tumor antigen.

The terms "subject" and "patient" refer to an animal, such as a mammal, for example a human. The methods described herein can be useful in both human therapeutics and veterinary applications. In some embodiments, the subject is a mammal, and in some embodiments, the subject is human. "Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compound of Formula (I), (I'), (I-A), (I'-A), (I-B), (I'-B), (I-C), (I'-C), (I-D), (I'-D), (I-E) or (I'-E)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound, and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to a human, allowing sufficient time for metabolism to occur, and isolating its conversion products from the urine, blood or other biological samples.

Lung function tests include tests to check how well the lungs work. Spirometry, for example, measures the amount of air the lungs can hold as well as how forcefully one can empty air from the lungs. Forced expiratory volume (FEV) is a measure of the amount of air a person can exhale during a forced breath. FEV1, for example, is the amount of air a person can force from their lungs in one second. Forced vital capacity (FVC) is the total amount of air exhaled during an FEV test. The ratio of FEV1/FVC, also known as Index of Air Flow or Tiffeneau-Pinelli Index, is a measurement used to assess the health of a patient's lung function. A ratio of <80% indicates an obstructive defect is present in the lungs, such as chronic obstructive pulmonary disease (COPD). A ratio of >80% indicates a restrictive defect is present in the lungs, such as pulmonary fibrosis. The ratio of >80% in restrictive lung disease results from both FEV1 and FVC being reduced but that the decline in FVC is more than that of FEV1, resulting in a higher than 80% value.

The term "transforming growth factor-β" may also be referred to as TGF-β, transforming growth factor beta-1, or TGF-beta-1. It is also cleaved into latency-associated peptide (LAP).

The term "TGF-β receptor II" may also be referred to as TβRII, type II TGF-β receptor, TGF-βRII, TGF-beta receptor type-2, TGFR-2, TGF-beta type II receptor, transforming growth factor-beta receptor type II, TGF-beta receptor type II or TbetaR-II.

The term "TGF-β receptor I" may also be referred to as TβRI, type I TGF-β receptor, TGF-βRI, TGF-beta receptor type-1, TGFR-1, activin A receptor type II-like protein kinase of 53 kD, activin receptor-like kinase 5, ALK-5, ALK5, serine/threonine-protein kinase receptor $R^4$, SKR4, TGF-beta type I receptor, transforming growth factor-beta receptor type I, TGF-beta receptor type I, transforming growth factor beta receptor I, TGF-beta receptor 1, or TbetaR-I.

The present disclosure provides compounds that are capable of selectively binding to and/or modulating ALK5. In some embodiments, the compounds modulate ALK5 by binding to or interacting with one or more amino acids and/or one or more metal ions. The binding of these compounds may disrupt ALK5 downstream signaling.

In certain aspects, the present disclosure provides a compound of Formula (I'):

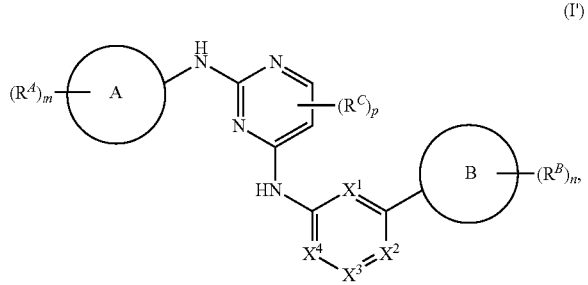

(I')

or a pharmaceutically acceptable salt thereof, wherein:

A and B are each independently selected from $C_{3-12}$ carbocycle and 3- to 12-membered heterocycle;

$X^1$ is selected from CH, $CR^D$, N and S;

$X^2$ and $X^3$ are each independently selected from CH, $CR^E$, N and S;

$X^4$ is selected from bond, CH, $CR^E$, N and S, provided that no more than one of $X^2$, $X^3$ and $X^4$ is S;

$R^A$, $R^B$, $R^C$, $R^D$ and $R^E$ are each independently selected at each occurrence from:

halogen, $-NO_2$, $-CN$, $-OR^1$, $-SR^1$, $-N(R^1)_2$, $-NR^2R^3$, $-S(=O)R^1$, $-S(=O)_2R^1$, $-S(=O)_2N(R^1)_2$, $-S(=O)_2NR^2R^3$, $-NR^1S(=O)_2R^1$, $-NR^1S(=O)_2N(R^1)_2$, $-NR^1S(=O)_2NR^2R^3$, $-C(O)R^1$, $-C(O)OR^1$, $-OC(O)R^1$, $-OC(O)OR^1$, $-OC(O)N(R^1)_2$, $-OC(O)NR^2R^3$, $-NR^1C(O)R^1$, $-NR^1C(O)OR^1$, $-NR^1C(O)N(R^1)_2$, $-NR^1C(O)NR^2R^3$, $-C(O)N(R^1)_2$, $-C(O)NR^2R^3$, $-P(O)(OR^1)_2$, $-P(O)(R^1)_2$, $=O$, $=S$, $=N(R^1)$;

$C_{1-10}$ alkyl, $C_{2-10}$ alkenyl, $C_{2-10}$ alkynyl, and $-N(R^1)-C_{1-10}$ alkyl, each of which is independently optionally substituted at each occurrence with one or more substituents selected from halogen, $-NO_2$, $-CN$, $-OR^1$, $-SR^1$, $-N(R^1)_2$, $-NR^2R^3$, $-S(=O)R^1$, $-S(=O)_2R^1$, $-S(=O)_2N(R^1)_2$, $-S(=O)_2NR^2R^3$, $-NR^1S(=O)_2R^1$, $-NR^1S(=O)_2N(R^1)_2$, $-NR^1S(=O)_2NR^2R^3$, $-C(O)R^1$, $-C(O)OR^1$, $-OC(O)R^1$, $-OC(O)OR^1$, $-OC(O)N(R^1)_2$, $-OC(O)NR^2R^3$, $-NR^1C(O)R^1$, $-NR^1C(O)OR^1$, $-NR^1C(O)N(R^1)_2$, $-NR^1C(O)NR^2R^3$, $-C(O)N(R^1)_2$, $-C(O)NR^2R^3$, $-P(O)(OR^1)_2$, $-P(O)(R^1)_2$, $=O$, $=S$, $=N(R^1)$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^A$, $R^B$, $R^C$, $R^D$ and $R^E$ is independently optionally substituted with one or more substituents selected from halogen, $-NO_2$, $-CN$, $-OR^1$, $-SR^1$, $-CH_2N(R^1)_2$, $-N(R^1)_2$, $-NR^2R^3$, $-S(=O)R^1$, $-S(=O)_2R^1$, $-S(=O)_2N(R^1)_2$, $-S(=O)_2NR^2R^3$, $-NR^1S(=O)_2R^1$, $-NR^1S(=O)_2N(R^1)_2$, $-NR^1S(=O)_2NR^2R^3$, $-C(O)R^1$, $-CH_2C(O)R^1$, $-C(O)OR^1$, $-OC(O)R^1$, $-OC(O)OR^1$, $-OC(O)N(R^1)_2$, $-OC(O)NR^2R^3$, $-NR^1C(O)R^1$, $-NR^1C(O)OR^1$, $-NR^1C(O)N(R^1)_2$, $-NR^1C(O)NR^2R^3$, $-C(O)N(R^1)_2$, $-C(O)NR^2R^3$, $-P(O)(OR^1)_2$, $-P(O)(R^1)_2$, $=O$, $=S$, $=N(R^1)$, $R^1$, $C_{1-6}$ alkyl, $C_{1-6}$ haloalkyl, $C_{2-6}$ alkenyl, and $C_{2-6}$ alkynyl;

or two $R^B$ groups, two $R^C$ groups or two $R^E$ groups can together optionally form a bridge or ring;

m and n are each independently an integer from 0 to 3;

p is an integer from 0 to 2;

$R^1$ is independently selected at each occurrence from hydrogen; and $C_{1-6}$ alkyl, $C_{2-6}$ alkenyl, $C_{2-6}$ alkynyl, 1- to 6-membered heteroalkyl, $C_{0-3}$ alkyl-($C_{3-12}$ carbocycle), and $C_{0-3}$ alkyl-(3- to 12-membered heterocycle), each of which is optionally substituted by one or more substituents selected from halogen, $-CN$, $-NO_2$, $-NH_2$, $-NHCH_3$, $-N(CH_3)_2$, $-NHCH_2CH_3$, $-CH_2CH_2N(CH_3)_2$, $-C(O)CH_3$, $-C(O)OH$, $-C(O)NH_2$, $=O$, $-OH$, $-CH_2OH$, $-CH_2CH_2OH$, $-OCH_3$, $-OCH_2CH_3$, $-CH_3$, $-CH_2CH_3$, $-CH(CH_3)_2$, $-C(CH_3)_3$, $C_{3-12}$ carbocycle, and 3- to 6-membered heterocycle; and $R^2$ and $R^3$ are taken together with the nitrogen atom to which they are attached to form a heterocycle, optionally substituted with one or more $R^1$.

In some embodiments, for a compound of Formula (I'), $R^B$, $R^C$, $R^D$ and $R^E$ are each independently selected at each occurrence from halogen, $-CN$, $-NH_2$, $-NHCH_3$, $-NHCH_2CH_3$, $-C(O)CH_3$, $-OH$, $-OCH_3$, $-OCH_2CH_3$, $-CH_3$, $-CH_2CH_3$, $-CH(CH_3)_2$, $-C(CH_3)_3$, $-CH_2F$, $-CHF_2$, $-CF_3$, $C_{3-4}$ carbocycle, and 3- to 4-membered heterocycle; or two $R^C$ groups or two $R^E$ groups can together optionally form a bridge or ring;

In some embodiments, for a compound of Formula (I'), p is 0 or 1, such as p is 0. In some embodiments, $R^C$ is selected from halogen, $-NH_2$ and $-CH_3$. In some embodiments, $X^1$ is selected from CH and N, such as $X^1$ is N. In some embodiments, $X^2$ is selected from CH, $CR^E$, N and S, such as $X^2$ is N. In some embodiments, $X^2$ is selected from CH and $CR^E$, wherein $R^E$ is selected from $-CN$, $-OCH_3$ and —CH₃. In some embodiments, X³ is selected from CH and CR^E, such as X³ is CH. In some embodiments, X³ is CR^E, wherein R^E is —OCH₃.

In some embodiments, X⁴ is selected from bond, CH, CR^E and N, such as X⁴ is CH. In some embodiments, X⁴ is N. In some embodiments, X³ and X⁴ are each independently CR^E, wherein the two R^E groups form a ring, such as a 5- or 6-membered aryl or heteroaryl ring. Non-limiting examples wherein X³ and X⁴ are each independently CR^E, wherein the two R^E groups form a ring include

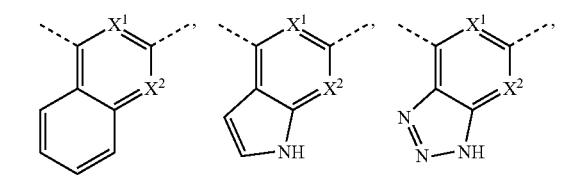

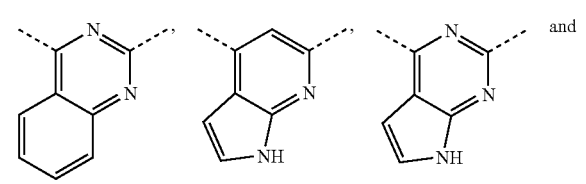

and

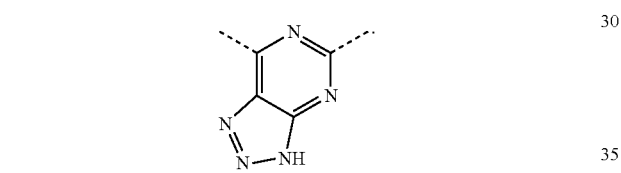

In some embodiments, X⁴ is a bond (i.e.,

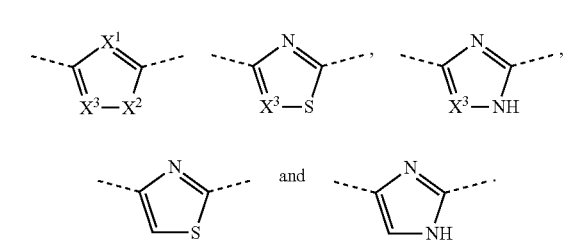

Non-limiting examples wherein X⁴ is a bond include:

In some embodiments, the compound of Formula (I') is a compound of Formula (I'-A), (I'-B), (I'-C), (I'-D) or (I'-E):

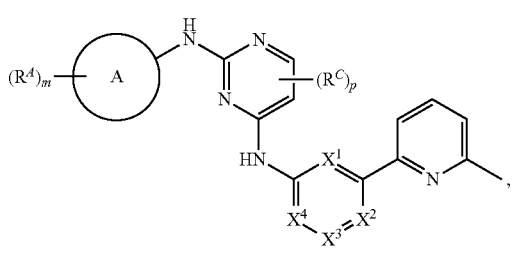
(I'-A)

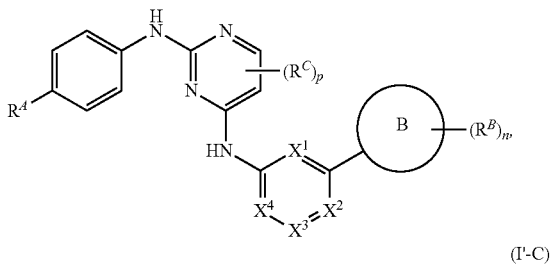
(I'-B)

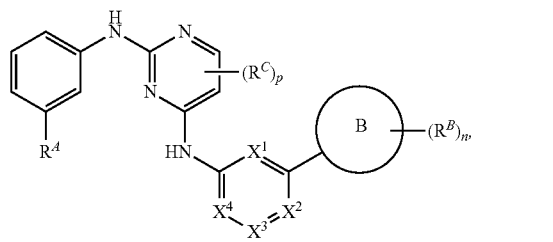
(I'-C)

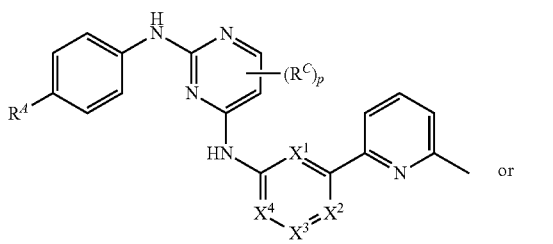
(I'-D)

or

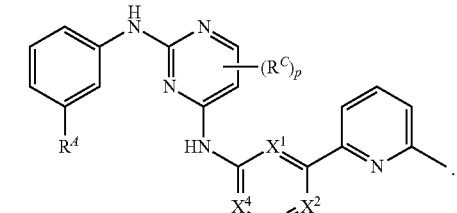
(I'-E)

In certain aspects, the present disclosure provides a compound of Formula (I):

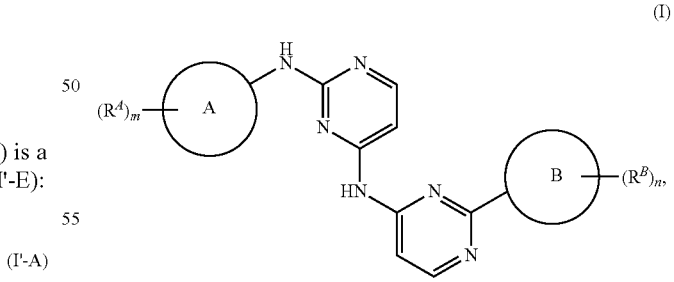
(I)

or a pharmaceutically acceptable salt thereof, wherein:
A and B are each independently selected from $C_{3-12}$ carbocycle and 3- to 12-membered heterocycle;
R^A is independently selected at each occurrence from:
halogen, —NO₂, —CN, —OR¹, —SR¹, —N(R¹)₂, —NR²R³, —S(=O)R¹, —S(=O)₂R¹, —S(=O)₂N(R¹)₂, —S(=O)₂NR²R³, —NR¹S(=O)₂R¹, —NR¹S(=O)₂N(R¹)₂, —NR¹S(=O)₂NR²R³, —C(O)R¹, —C(O)OR¹, —OC(O)R¹, —OC(O)OR¹, —OC(O)N(R¹)₂, —OC(O)NR²R³, —NR¹C(O)R¹, —NR¹C(O)

OR¹, —NR¹C(O)N(R¹)₂, —NR¹C(O)NR²R³, —C(O)
N(R¹)₂, —C(O)NR²R³, —P(O)(OR¹)₂, —P(O)(R¹)₂,
=O, =S, =N(R¹);

C₁₋₁₀ alkyl, C₂₋₁₀ alkenyl, C₂₋₁₀ alkynyl, and —N(R¹)—
C₁₋₁₀ alkyl, each of which is independently optionally substituted at each occurrence with one or more substituents selected from halogen, —NO₂, —CN, —OR¹, —SR¹, —N(R¹)₂, —NR²R³, —S(=O)R¹, —S(=O)₂R¹, —S(=O)₂N(R¹)₂, —S(=O)₂NR²R³, —NR¹S(=O)₂R¹, —NR¹S(=O)₂N(R¹)₂, —NR¹S(=O)₂NR²R³, —C(O)R¹, —C(O)OR¹, —OC(O)R¹, —OC(O)OR¹, —OC(O)N(R¹)₂, —OC(O)NR²R³, —NR¹C(O)R¹, —NR¹C(O)OR¹, —NR¹C(O)N(R¹)₂, —NR¹C(O)NR²R³, —C(O)N(R¹)₂, —C(O)NR²R³, —P(O)(OR¹)₂, —P(O)(R¹)₂, =O, =S, =N(R¹), C₃₋₁₂ carbocycle, and 3- to 12-membered heterocycle; and C₃₋₁₂ carbocycle and 3- to 12-membered heterocycle, wherein each C₃₋₁₂ carbocycle and 3- to 12-membered heterocycle in R^A is independently optionally substituted with one or more substituents selected from halogen, —NO₂, —CN, —OR¹, —SR¹, —CH₂N(R¹)₂, —N(R¹)₂, —NR²R³, —S(=O)R¹, —S(=O)₂R¹, —S(=O)₂N(R¹)₂, —S(=O)₂NR²R³, —NR¹S(=O)₂R¹, —NR¹S(=O)₂N(R¹)₂, —NR¹S(=O)₂NR²R³, —C(O)R¹, —CH₂C(O)OR¹, —C(O)OR¹, —OC(O)R¹, —OC(O)OR¹, —OC(O)N(R¹)₂, —OC(O)NR²R³, —NR¹C(O)R¹, —NR¹C(O)OR¹, —NR¹C(O)N(R¹)₂, —NR¹C(O)NR²R³, —C(O)N(R¹)₂, —C(O)NR²R³, —P(O)(OR¹)₂, —P(O)(R¹)₂, =O, =S, =N(R¹), R¹, C₁₋₆ alkyl, C₁₋₆ haloalkyl, C₂₋₆ alkenyl, and C₂₋₆ alkynyl;

R^B is independently selected at each occurrence from halogen, —CN, —NH₂, —NHCH₃, —NHCH₂CH₃, —C(O)CH₃, —OH, —OCH₃, —OCH₂CH₃, —CH₃, —CH₂CH₃, —CH(CH₃)₂, —C(CH₃)₃, —CH₂F, —CHF₂, —CF₃, C₃₋₄ carbocycle, and 3- to 4-membered heterocycle;

m and n are each independently an integer from 0 to 3;

R¹ is independently selected at each occurrence from hydrogen; and C₁₋₆ alkyl, C₂₋₆ alkenyl, C₂₋₆ alkynyl, 1- to 6-membered heteroalkyl, C₀₋₃ alkyl-(C₃₋₁₂ carbocycle), and C₀₋₃ alkyl-(3- to 12-membered heterocycle), each of which is optionally substituted by one or more substituents selected from halogen, —CN, —NO₂, —NH₂, —NHCH₃, —N(CH₃)₂, —NHCH₂CH₃, —CH₂CH₂N(CH₃)₂, —C(O)CH₃, —C(O)OH, —C(O)NH₂, =O, —OH, —CH₂OH, —CH₂CH₂OH, —OCH₃, —OCH₂CH₃, —CH₃, —CH₂CH₃, —CH(CH₃)₂, —C(CH₃)₃, C₃₋₁₂ carbocycle, and 3- to 6-membered heterocycle; and R² and R³ are taken together with the nitrogen atom to which they are attached to form a heterocycle, optionally substituted with one or more R¹.

In some embodiments, the compound of Formula (I) is a compound of Formula (I-A), (I-B), (I-C), (I-D) or (I-E):

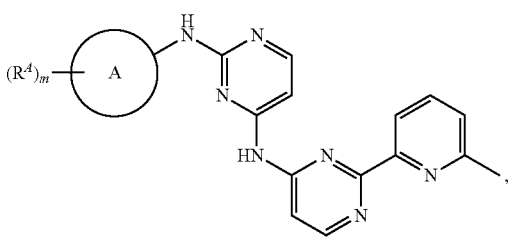

(I-A)

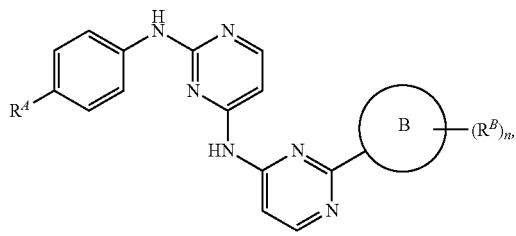

(I-B)

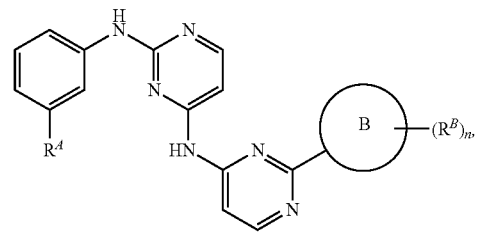

(I-C)

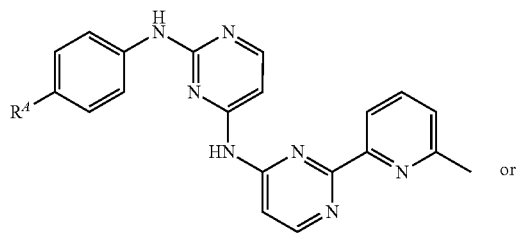

(I-D)

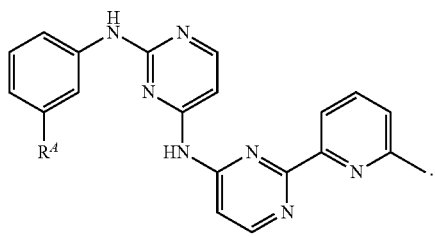

(I-E)

In some embodiments, for a compound of Formula (I), (I'), (I-A) or (I'-A), A is selected from C₆₋₁₀ aryl and 5- to 10-membered heteroaryl. In some embodiments, A is selected from phenyl and 5- to 6-membered heteroaryl, such as A is phenyl. In some embodiments, A is selected from phenyl, indanyl, thiazolyl, thiophenyl, pyrazolyl, pyridyl, pyrimidinyl, indazolyl, benzotriazolyl, tetrahydroquinolinyl, tetrahydroisoquinolinyl, benzodioxanyl, and tetrahydrobenzazepinyl. In some embodiments, A is selected from phenyl, pyridinyl, thiazolyl and thiophenyl. In some embodiments, A is phenyl. In some embodiments, A is pyridinyl. In some embodiments, A is thiazolyl. In some embodiments, A is thiophenyl.

In some embodiments, the compound of Formula (I) is a compound of the formula:

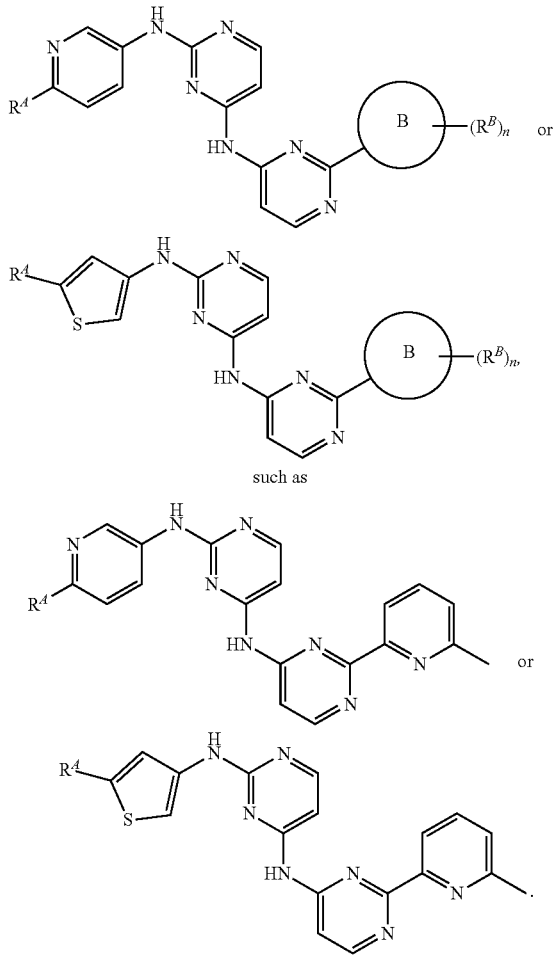

such as

In some embodiments, for a compound of Formula (I), (I'), (I-A) or (I'-A), m is 1 or 2. In some embodiments, m is 1. In some embodiments, A is $C_6$ aryl or 6-membered heteroaryl, m is 1 and $R^A$ is in the meta- or para-position.

In some embodiments, for a compound of Formula (I), (I'), (I-A), (I'-A), (I-B), (I'-B), (I-C), (I'-C), (I-D), (I'-D), (I-E) or (I'-E), $R^A$ is independently selected at each occurrence from:
halogen, —$OR^1$, —$N(R^1)_2$, —$S(=O)_2R^1$, —$S(=O)_2N(R^1)_2$, —$S(=O)_2NR^2R^3$, —$NR^1S(=O)_2R^1$, —$NR^1S(=O)_2N(R^1)_2$, —$C(O)R^1$, —$C(O)OR^1$, —$NR^1C(O)R^1$, —$NR^1C(O)N(R^1)_2$, —$C(O)N(R^1)_2$, —$C(O)NR^2R^3$, $C_{3-8}$ carbocycle, and 3- to 10-membered heterocycle; and
$C_{1-6}$ alkyl and —$N(R^1)$—$C_{1-10}$ alkyl, each of which is independently optionally substituted at each occurrence with one or more substituents selected from halogen, —$OR^1$, —$N(R^1)_2$, —$S(=O)_2R^1$, —$S(=O)_2N(R^1)_2$, —$S(=O)_2NR^2R^3$, —$NR^1S(=O)_2R^1$, —$NR^1S(=O)_2N(R^1)_2$, —$C(O)R^1$, —$C(O)OR^1$, —$NR^1C(O)R^1$, —$NR^1C(O)N(R^1)_2$, —$C(O)N(R^1)_2$, —$C(O)NR^2R^3$, $C_{3-8}$ carbocycle, and 3- to 10-membered heterocycle; and
$C_{3-8}$ carbocycle and 3- to 10-membered heterocycle,
wherein each $C_{3-8}$ carbocycle and 3- to 10-membered heterocycle in $R^A$ is independently optionally substituted with one or more substituents selected from halogen, —$OR^1$, —$CH_2N(R^1)_2$, —$N(R^1)_2$, —$S(=O)_2R^1$, —$S(=O)_2N(R^1)_2$, —$S(=O)_2NR^2R^3$, —$NR^1S(=O)_2R^1$, —$NR^1S(=O)_2N(R^1)_2$, —$C(O)R^1$, —$CH_2C(O)OR^1$, —$C(O)OR^1$, —$NR^1C(O)R^1$, —$NR^1C(O)N(R^1)_2$, —$C(O)N(R^1)_2$, —$C(O)NR^2R^3$, $R^1$, and $C_{1-6}$ alkyl.

In some embodiments, for a compound of Formula (I), (I'), (I-A), (I'-A), (I-B), (I'-B), (I-C), (I'-C), (I-D), (I'-D), (I-E) or (I'-E), $R^A$ is independently selected at each occurrence from:
halogen, —$OR^1$, —$N(R^1)_2$, —$S(=O)_2R^1$, —$S(=O)_2N(R)_2$, —$S(=O)_2NR^2R^3$, —$NR^1S(=O)_2R^1$, —$NR^1S(=O)_2N(R^1)_2$, —$C(O)R^1$, —$C(O)OR^1$, —$NR^1C(O)R^1$, —$NR^1C(O)N(R^1)_2$, —$C(O)N(R^1)_2$, —$C(O)NR^2R^3$;
$C_{1-6}$ alkyl and —$N(R^1)$—$C_{1-10}$ alkyl, each of which is independently optionally substituted at each occurrence with one or more substituents selected from —$OR^1$, —$N(R^1)_2$, —$C(O)OR^1$, $C_{3-8}$ carbocycle, and 3- to 10-membered heterocycle; and
$C_{3-8}$ carbocycle and 3- to 10-membered heterocycle,
wherein each $C_{3-8}$ carbocycle and 3- to 10-membered heterocycle in $R^A$ is independently optionally substituted with one or more substituents selected from —$OR^1$, —$CH_2N(R^1)_2$, —$N(R^1)_2$, —$C(O)R^1$, —$CH_2C(O)OR^1$, —$C(O)OR^1$, —$C(O)N(R^1)_2$, $R^1$, and $C_{1-6}$ alkyl.

In some embodiments, for a compound of Formula (I), (I'), (I-A), (I'-A), (I-B), (I'-B), (I-C), (I'-C), (I-D), (I'-D), (I-E) or (I'-E), $R^A$ is independently selected at each occurrence from:
halogen, —$OR^1$, —$N(R^1)_2$, —$S(=O)_2R^1$, —$S(=O)_2N(R)_2$, —$NR^1S(=O)_2R^1$, —$NR^1S(=O)_2N(R)_2$, —$C(O)R^1$, —$C(O)OR^1$, —$NR^1C(O)R^1$, —$NR^1C(O)N(R^1)_2$, —$C(O)N(R^1)_2$;
$C_{1-6}$ alkyl and —$N(R^1)$—$C_{1-10}$ alkyl, each of which is independently optionally substituted at each occurrence with one or more substituents selected from —$OR^1$, —$N(R^1)_2$, and 3- to 10-membered heterocycle; and
3- to 10-membered heterocycle,
wherein each 3- to 10-membered heterocycle in $R^A$ is independently optionally substituted with one or more substituents selected from —$OR^1$, —$N(R^1)_2$, —$C(O)R^1$, —$CH_2C(O)OR^1$, —$C(O)OR^1$, —$C(O)N(R^1)_2$, and $R^1$.

In some embodiments, for a compound of Formula (I), (I'), (I-A), (I'-A), (I-B), (I'-B), (I-C), (I'-C), (I-D), (I'-D), (I-E) or (I'-E), $R^A$ is independently selected at each occurrence from:
—$N(R^1)_2$ and —$NR^1C(O)R^1$;
$C_{1-6}$ alkyl and —$N(R^1)$—$C_{1-6}$ alkyl, each of which is substituted with 4- to 8-membered heterocycle; and
4- to 8-membered heterocycle,
wherein each 4- to 8-membered heterocycle in $R^A$ is independently optionally substituted with one or more substituents selected from —$C(O)OR^1$ and $R^1$.

In some embodiments, a compound of Formula (I), (I'), (I-A), (I'-A), (I-B), (I'-B), (I-C), (I'-C), (I-D), (I'-D), (I-E) or (I'-E) comprises a terminal ester of the formula —$C(O)OR^{15}$ or —$OC(O)R^{15}$, wherein $R^{15}$ comprises 1 to 12 carbon atoms and at least one basic amine. In some embodiments, the molecular weight of $R^{15}$ is between 30 and 200 g/mol. The terminal ester may be metabolizable by one or more hydrolase (e.g., an esterase) present in human plasma and/or the human liver into a carboxylic acid and an alcohol. The biological activity of the compound may be greater than that of the carboxylic acid and the alcohol. For example, the compound may exhibit a BEAS2B $pIC_{50}$ of at least 1 unit or greater than the carboxylic acid and the alcohol (assessed according to the assay provided in Example 46). In some embodiments, $R^{15}$ is —($C_{0-4}$ alkyl)(4- to 10-membered heterocycloalkyl), wherein the heterocycloalkyl comprises 1, 2 or 3 nitrogen atoms, and wherein the heterocycloalkyl is optionally substituted with one or more substituents selected from $C_{1-4}$ alkyl.

In some embodiments, for a compound of Formula (I), (I'), (I-A), (I'-A), (I-B), (I'-B), (I-C), (I'-C), (I-D), (I'-D), (I-E) or (I'-E):

$R^A$ is selected from

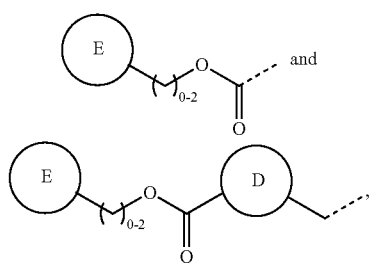

and wherein

D and E are each independently selected from 3- to 8-membered heterocycle, each of which is independently optionally substituted with one or more substituents selected from —NH$_2$, —NHCH$_3$, —N(CH$_3$)$_2$, —CH$_2$CH$_2$N(CH$_3$)$_2$, —C(O)CH$_3$, —C(O)OH, —C(O)NH$_2$, =O, —OH, —CH$_2$OH, —CH$_2$CH$_2$OH, —OCH$_3$, —OCH$_2$CH$_3$, —CH$_3$, —CH$_2$CH$_3$, —CH(CH$_3$)$_2$, —C(CH$_3$)$_3$, $C_{3-8}$ carbocycle, and 3- to 6-membered heterocycle. In some embodiments, D and E are each independently selected from 4- to 6-membered heterocycle, each of which is independently optionally substituted with one or more —CH$_3$. In some embodiments, D and E are each unsubstituted.

In some embodiments, for a compound of Formula (I), (I'), (I-A), (I'-A), (I-B), (I'-B), (I-C), (I'-C), (I-D), (I'-D), (I-E) or (I'-E), $R^A$ is —N(R$^1$)$_2$, such as

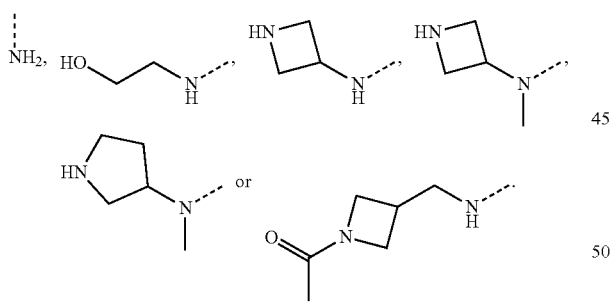

In some embodiments, $R^A$ is —NR$^1$C(O)R$^1$, such as

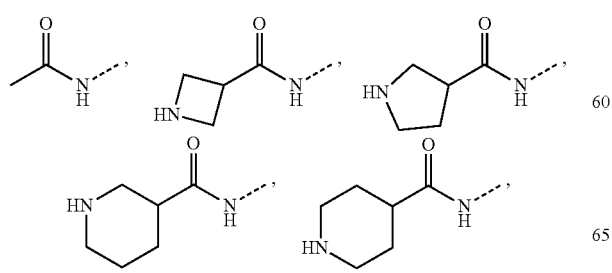

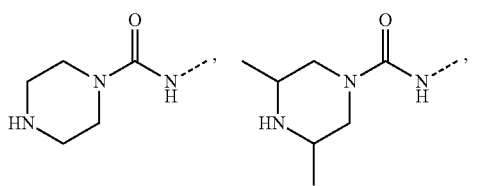

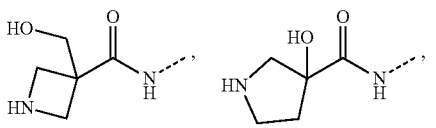

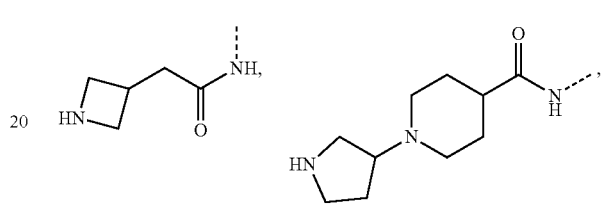

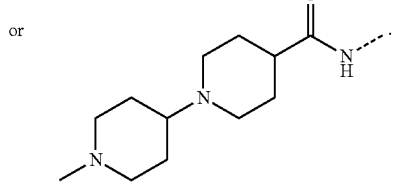

or

In some embodiments, $R^A$ is $C_{1-6}$ alkyl substituted with 4- to 8-membered heterocycle, wherein the 4- to 8-membered heterocycle is substituted with —C(O)OR$^1$, such as

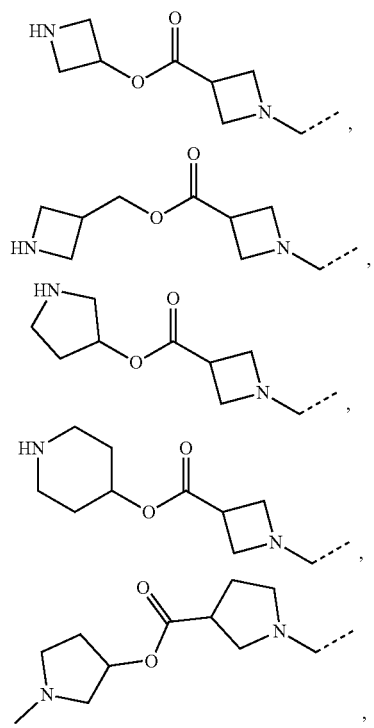

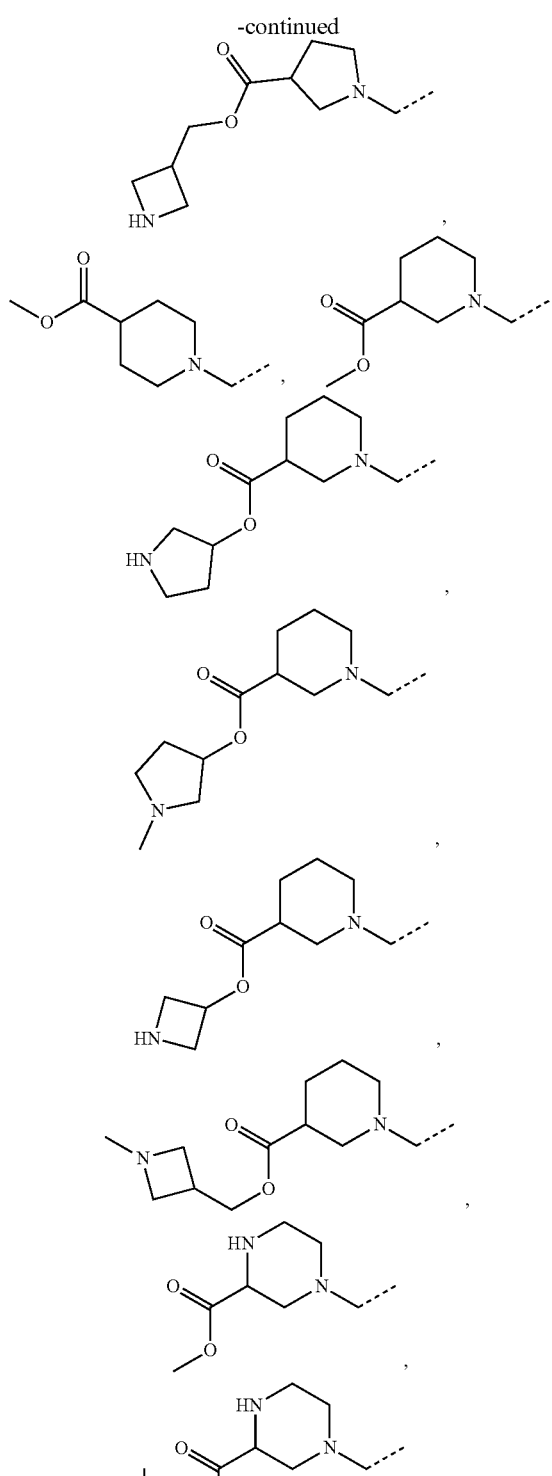
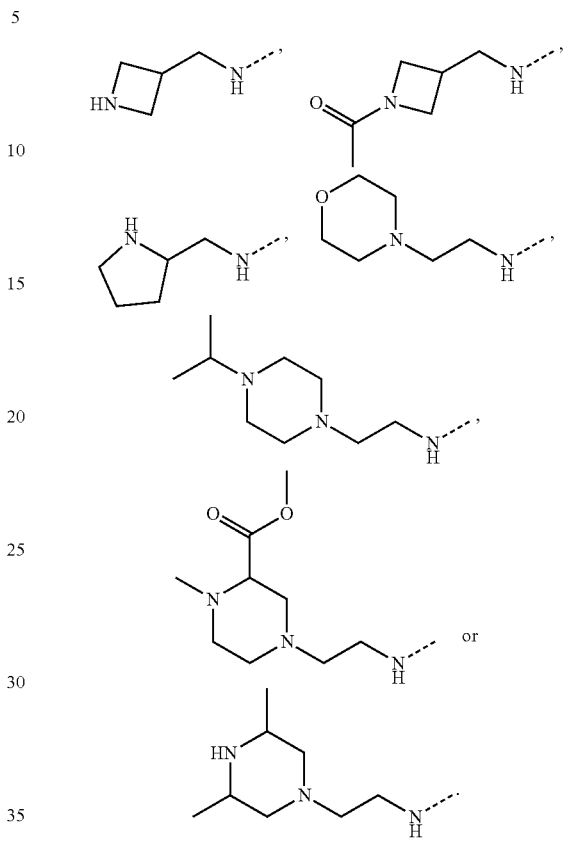
In some embodiments, $R^A$ is $-N(R^1)-C_{1-6}$ alkyl substituted with 4- to 8-membered heterocycle, wherein the 4- to 8-membered heterocycle is optionally substituted, such as
In some embodiments, $R^A$ is 4- to 8-membered heterocycle, wherein the 4- to 8-membered heterocycle is optionally substituted with one or more substituents selected from $-C(O)OR^1$ and $R^1$, such as
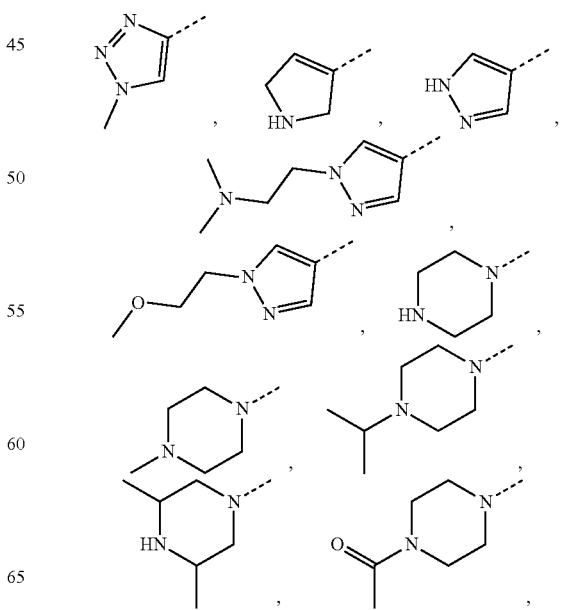

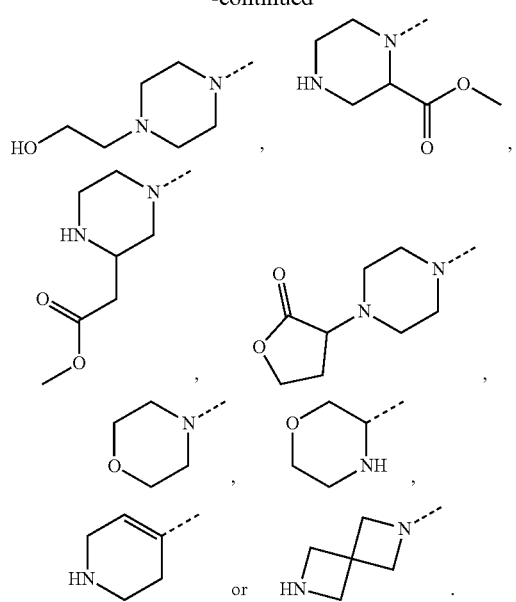
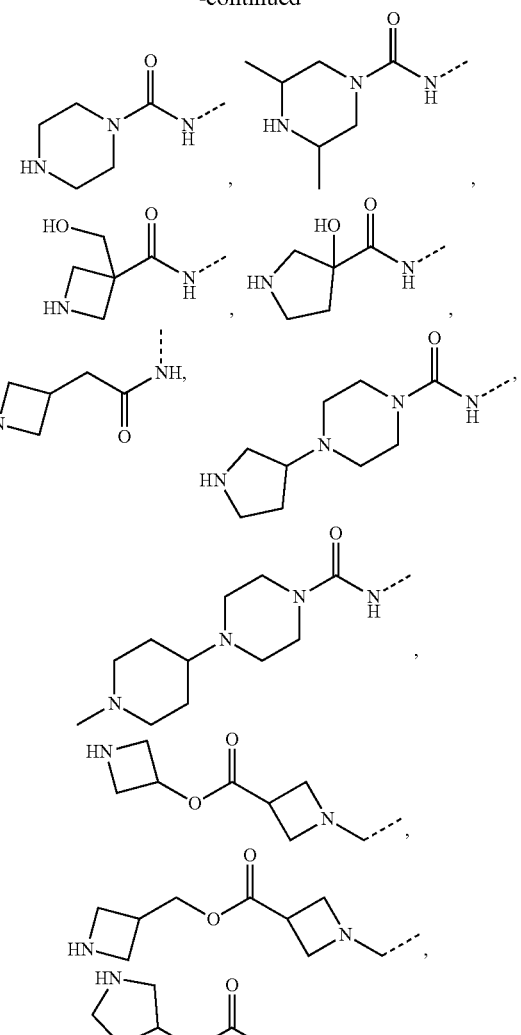
In some embodiments, $R^A$ is —C(O)OR$^1$, such as
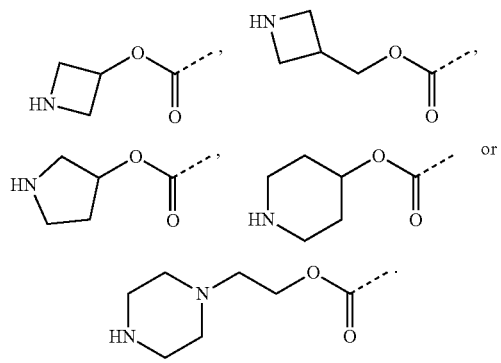
In some embodiments, $R^A$ is selected from
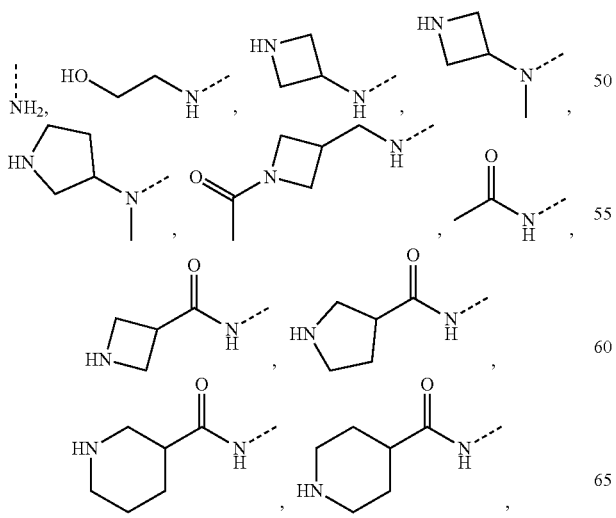
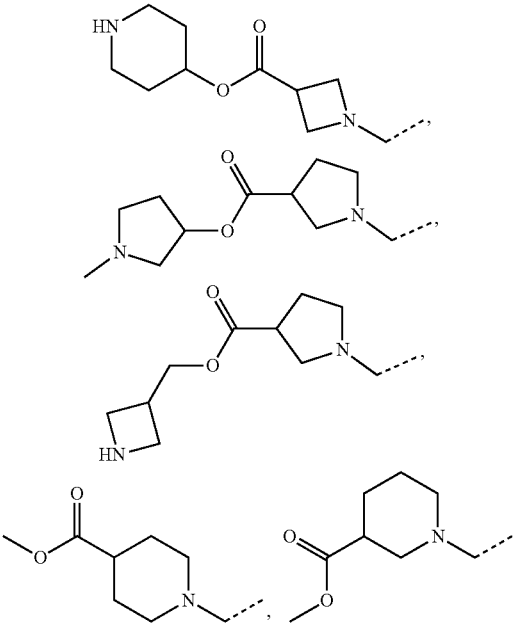

-continued
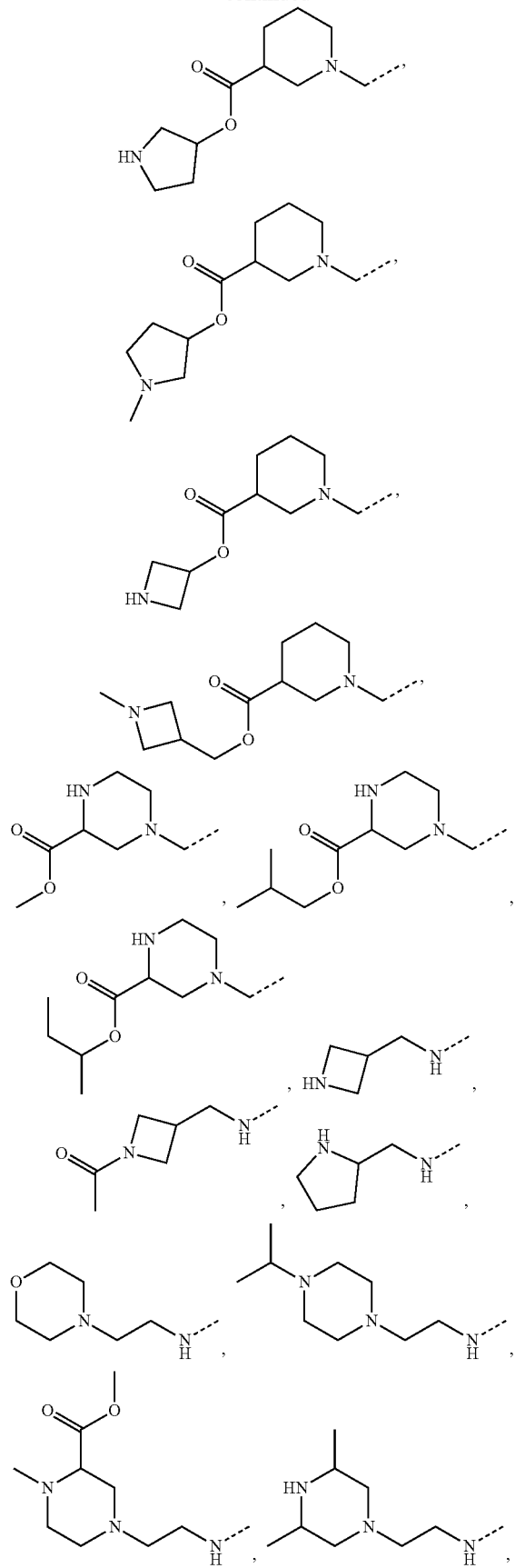
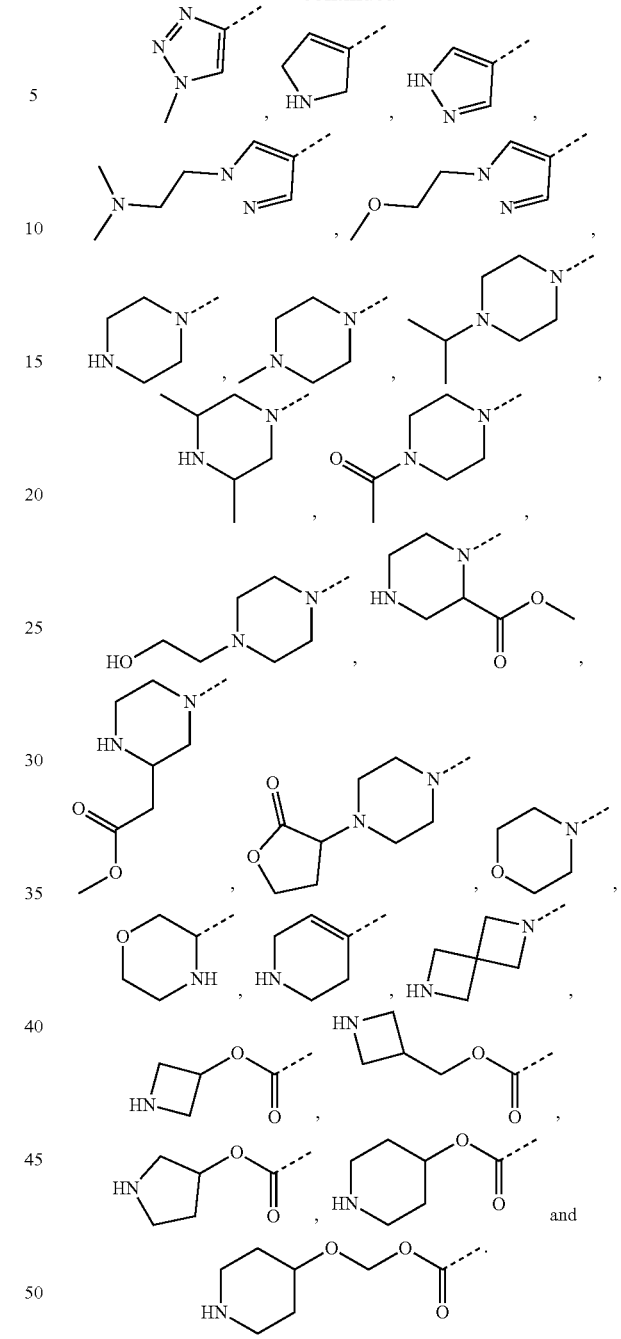
In some embodiments $R^A$ is selected from
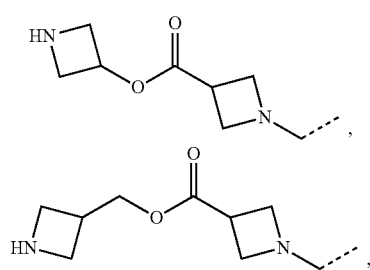

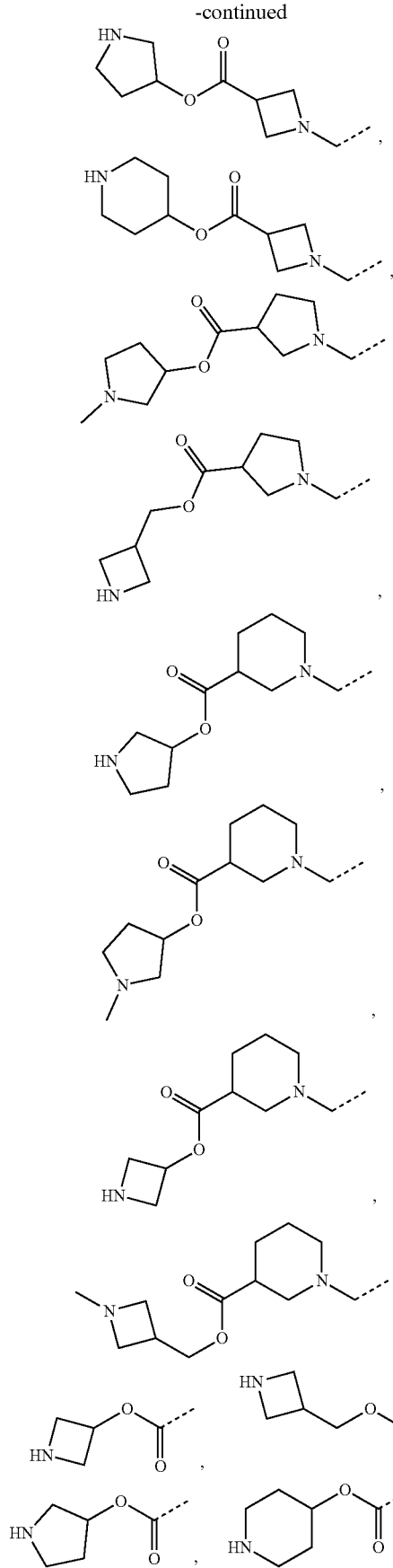
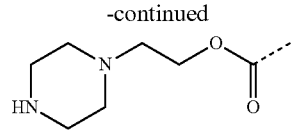
In some embodiments, $R^4$ is selected from
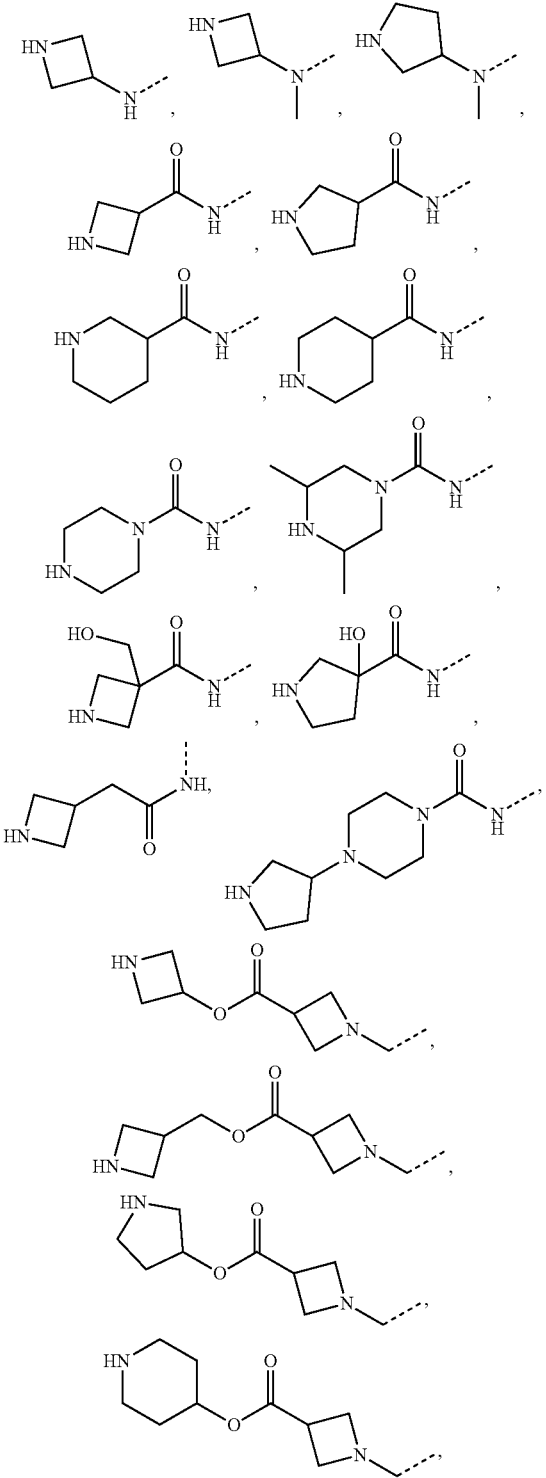

-continued

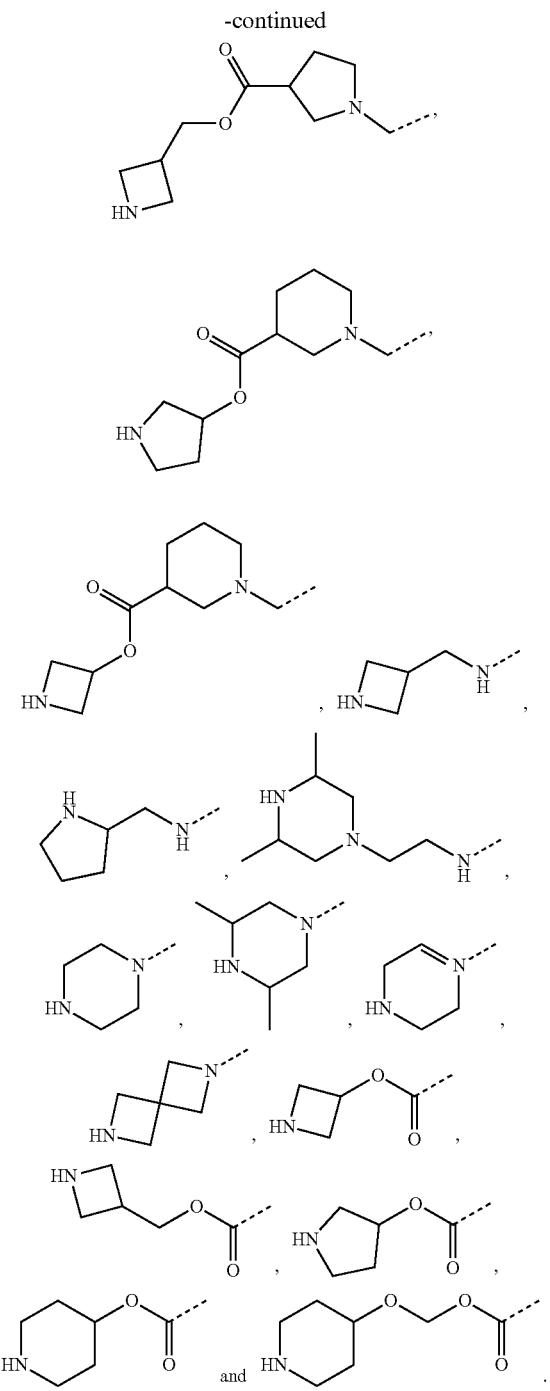

In some embodiments, $R^A$ is selected from

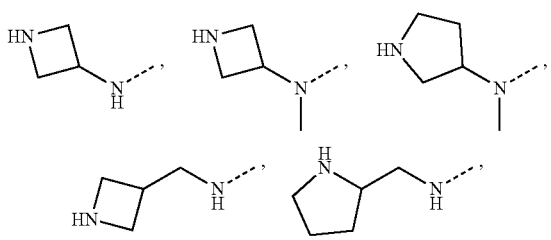

-continued

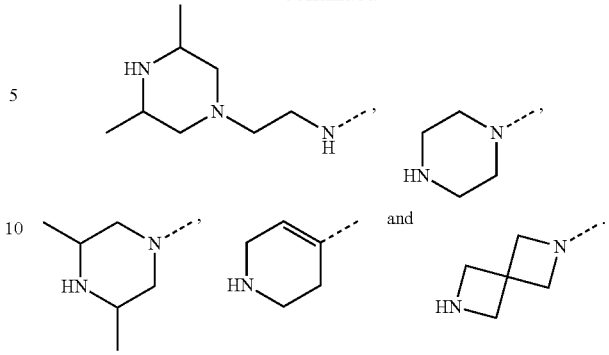

In some embodiments, for a compound of Formula (I), (I'), (I-A), (I'-A), (I-B), (I'-B), (I-C), (I'-C), (I-D), (I'-D), (I-E) or (I'-E), $R^1$ is independently selected at each occurrence from hydrogen; and $C_{1-6}$ alkyl, 1- to 6-membered heteroalkyl, $C_{0-3}$ alkyl-($C_{3-8}$ carbocycle), and $C_{0-3}$ alkyl-(3- to 10-membered heterocycle), each of which is optionally substituted by one or more substituents selected from —$NH_2$, —$NHCH_3$, —$N(CH_3)_2$, —$CH_2CH_2N(CH_3)_2$, —$C(O)CH_3$, —$C(O)OH$, —$C(O)NH_2$, =O, —OH, —$CH_2OH$, —$CH_2CH_2OH$, —$OCH_3$, —$OCH_2CH_3$, —$CH_3$, —$CH_2CH_3$, —$CH(CH_3)_2$, —$C(CH_3)_3$, $C_{3-8}$ carbocycle, and 3- to 6-membered heterocycle. In some embodiments, $R^1$ is independently selected at each occurrence from hydrogen; and $C_{1-6}$ alkyl and $C_{0-3}$ alkyl-(3- to 10-membered heterocycle), each of which is optionally substituted by one or more substituents selected from —OH, —$CH_2OH$, —$CH_3$, —$CH_2CH_3$, —$CH(CH_3)_2$, —$C(CH_3)_3$, and 3- to 6-membered heterocycle.

In some embodiments, for a compound of Formula (I), (I'), (I-B), (I'-B), (I-C) or (I'-C), B is selected from $C_{6-10}$ aryl and 5- to 10-membered heteroaryl, such as B is selected from phenyl and pyridyl. In some embodiments, B is pyridyl. In some embodiments, B is 2-pyridyl. In some embodiments, B—$(R^B)_n$ is 2-methylpyridyl.

In some embodiments, for a compound of Formula (I), (I'), (I-B), (I'-B), (I-C) or (I'-C), n is 1 or 2, such as n is 1. In some embodiments, B is pyridyl, n is 1 and $R^B$ is in the 2-position.

In some embodiments, for a compound of Formula (I), (I'), (I-B), (I'-B), (I-C) or (I'-C), $R^B$ is independently selected at each occurrence from halogen, —$NH_2$, —$NHCH_3$, —$NHCH_2CH_3$, —$C(O)CH_3$, —OH, —$OCH_3$, —$OCH_2CH_3$, —$CH_3$, —$CH_2CH_3$, —$CH(CH_3)_2$, —$C(CH_3)_3$, —$CH_2F$, —$CHF_2$, and —$CF_3$. In some embodiments, $R^B$ is independently selected at each occurrence from halogen, —OH, —$CH_3$, and —$CHF_2$. In some embodiments, $R^B$ is —$CH_3$.

In some embodiments, for a compound of Formula (I), (I'), (I-A), (I'-A), (I-B), (I'-B), (I-C), (I'-C), (I-D), (I'-D), (I-E) or (I'-E):
A is selected from phenyl and 5- to 6-membered heteroaryl;
B is pyridyl;
$R^A$ is independently selected at each occurrence from:
  halogen, —$OR^1$, —$N(R^1)_2$, —$S(=O)_2R^1$, —$S(=O)_2N(R^1)_2$, —$S(=O)_2NR^2R^3$, —$NR^1S(=O)_2R^1$, —$NR^1S(=O)_2N(R^1)_2$, —$C(O)R^1$, —$C(O)OR^1$, —$NR^1C(O)R^1$, —$NR^1C(O)N(R^1)_2$, —$C(O)N(R^1)_2$, —$C(O)NR^2R^3$;
  $C_{1-6}$ alkyl and —$N(R^1)$—$C_{1-10}$ alkyl, each of which is independently optionally substituted at each occurrence with one or more substituents selected from —OR$^1$, —N(R$^1$)$_2$, —C(O)OR$^1$, C$_{3-8}$ carbocycle, and 3- to 10-membered heterocycle; and C$_{3-8}$ carbocycle and 3- to 10-membered heterocycle,
wherein each C$_{3-8}$ carbocycle and 3- to 10-membered heterocycle in R$^A$ is independently optionally substituted with one or more substituents selected from —OR$^1$, —CH$_2$N(R$^1$)$_2$, —N(R$^1$)$_2$, —C(O)R$^1$, —CH$_2$C(O)OR$^1$, —C(O)OR$^1$, —C(O)N(R$^1$)$_2$, R$^1$, and C$_{1-6}$ alkyl;

R$^1$ is independently selected at each occurrence from hydrogen; and C$_{1-6}$ alkyl, 1- to 6-membered heteroalkyl, C$_{0-3}$ alkyl-(C$_{3-8}$ carbocycle), and C$_{0-3}$ alkyl-(3- to 10-membered heterocycle), each of which is optionally substituted by one or more substituents selected from —NH$_2$, —NHCH$_3$, —N(CH$_3$)$_2$, —CH$_2$CH$_2$N(CH$_3$)$_2$, —C(O)CH$_3$, —C(O)OH, —C(O)NH$_2$, =O, —OH, —CH$_2$OH, —CH$_2$CH$_2$OH, —OCH$_3$, —OCH$_2$CH$_3$, —CH$_3$, —CH$_2$CH$_3$, —CH(CH$_3$)$_2$, —C(CH$_3$)$_3$, C$_{3-8}$ carbocycle, and 3- to 6-membered heterocycle;

m is 1 or 2;
R$^B$ is selected from halogen, —OH, —CH$_3$, and —CHF$_2$; and
n is 1.

In some embodiments, for a compound of Formula (I), (I'), (I-A), (I'-A), (I-B), (I'-B), (I-C), (I'-C), (I-D), (I'-D), (I-E) or (I'-E):
A is phenyl;
B is pyridyl;
R$^A$ is independently selected at each occurrence from:
—N(R$^1$)$_2$ and —NR$^1$C(O)R$^1$;
C$_{1-6}$ alkyl and —N(R$^1$)—C$_{1-6}$ alkyl, each of which is substituted with 4- to 8-membered heterocycle; and
4- to 8-membered heterocycle,
wherein each 4- to 8-membered heterocycle in R$^A$ is independently optionally substituted with one or more substituents selected from —C(O)OR$^1$ and R$^1$;

R$^1$ is independently selected at each occurrence from hydrogen; and C$_{1-6}$ alkyl and C$_{0-3}$ alkyl-(3- to 10-membered heterocycle), each of which is optionally substituted by one or more substituents selected from —OH, —CH$_2$OH, —CH$_3$, —CH$_2$CH$_3$, —CH(CH$_3$)$_2$, —C(CH$_3$)$_3$, and 3- to 6-membered heterocycle;

m is 1;
R$^B$ is —CH$_3$; and
n is 1.

In some embodiments, for a compound of Formula (I), (I'), (I-A), (I'-A), (I-B), (I'-B), (I-C), (I'-C), (I-D), (I'-D), (I-E) or (I'-E):
A is phenyl;
B is pyridyl;
R$^A$ is C$_{1-6}$ alkyl substituted with 4- to 8-membered heterocycle, wherein the 4- to 8-membered heterocycle is substituted with —C(O)OR$^1$;

R$^1$ is independently selected at each occurrence from hydrogen; and C$_{1-6}$ alkyl and C$_{0-3}$ alkyl-(3- to 10-membered heterocycle), each of which is optionally substituted by one or more substituents selected from —OH, —CH$_2$OH, —CH$_3$, —CH$_2$CH$_3$, —CH(CH$_3$)$_2$, —C(CH$_3$)$_3$, and 3- to 6-membered heterocycle;

m is 1;
R$^B$ is —CH$_3$; and
n is 1.

In some embodiments, for a compound of Formula (I), (I'), (I-A), (I'-A), (I-B), (I'-B), (I-C), (I'-C), (I-D), (I'-D), (I-E) or (I'-E):

A is selected from phenyl and 5- to 6-membered heteroaryl;
B is pyridyl;
R$^A$ is selected from:
—C(O)OR$^1$; and
C$_{0-6}$ alkyl-(3- to 8-membered heterocycle), wherein the 3- to 8-membered heterocycle is substituted with —C(O)OR$^1$;

R$^1$ is C$_{0-3}$ alkyl-(3- to 8-membered heterocycle), optionally substituted by one or more substituents selected from —CH$_3$, —CH$_2$CH$_3$, —CH(CH$_3$)$_2$, and —C(CH$_3$)$_3$;

m is 1;
R$^B$ is —CH$_3$; and
n is 1.

In some embodiments, for a compound of Formula (I):
A is pyridyl;
B is pyridyl;
R$^A$ is —C(O)OR$^1$;
R$^1$ is independently selected at each occurrence from hydrogen; and C$_{1-6}$ alkyl and C$_{0-3}$ alkyl-(3- to 10-membered heterocycle), each of which is optionally substituted by one or more substituents selected from —OH, —CH$_2$OH, —CH$_3$, —CH$_2$CH$_3$, —CH(CH$_3$)$_2$, —C(CH$_3$)$_3$, and 3- to 6-membered heterocycle;

m is 1;
R$^B$ is —CH$_3$; and
n is 1.

In some embodiments, for a compound of Formula (I):
A is thiophenyl;
B is pyridyl;
R$^A$ is —C(O)OR$^1$;
R$^1$ is independently selected at each occurrence from hydrogen; and C$_{1-6}$ alkyl and C$_{0-3}$ alkyl-(3- to 10-membered heterocycle), each of which is optionally substituted by one or more substituents selected from —OH, —CH$_2$OH, —CH$_3$, —CH$_2$CH$_3$, —CH(CH$_3$)$_2$, —C(CH$_3$)$_3$, and 3- to 6-membered heterocycle;

m is 1;
R$^B$ is —CH$_3$; and
n is 1.

In some embodiments, for a compound of Formula (I):
A is selected from phenyl and thiophenyl;
B is pyridyl;
R$^A$ is —NR$^1$C(O)R$^1$;
R$^1$ is independently selected at each occurrence from hydrogen; and C$_{0-3}$ alkyl-(3- to 8-membered heterocycle), each of which is optionally substituted by one or more substituents selected from —OH, —CH$_2$OH, —CH$_3$, —CH$_2$CH$_3$, —CH(CH$_3$)$_2$, and —C(CH$_3$)$_3$;

m is 1;
R$^B$ is —CH$_3$; and
n is 1.

In some embodiments, for a compound of Formula (I), (I'), (I-A), (I'-A), (I-B), (I'-B), (I-C), (I'-C), (I-D), (I'-D), (I-E) or (I'-E):
A is selected from phenyl and 5- to 6-membered heteroaryl;
B is selected from phenyl and pyridyl;
R$^A$ is selected from

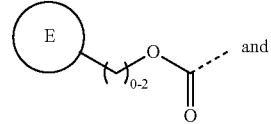

-continued

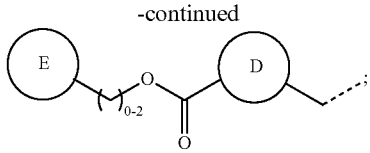

D and E are each independently selected from 3- to 8-membered heterocycle, each of which is independently optionally substituted with one or more substituents selected from —NH$_2$, —NHCH$_3$, —N(CH$_3$)$_2$, —CH$_2$CH$_2$N(CH$_3$)$_2$, —C(O)CH$_3$, —C(O)OH, —C(O)NH$_2$, =O, —OH, —CH$_2$OH, —CH$_2$CH$_2$OH, —OCH$_3$, —OCH$_2$CH$_3$, —CH$_3$, —CH$_2$CH$_3$, —CH(CH$_3$)$_2$, —C(CH$_3$)$_3$, C$_{3-8}$ carbocycle, and 3- to 6-membered heterocycle;

m is 1;

R$^B$ is selected from halogen, —OH, —CH$_3$, and —CHF$_2$; and n is 1.

In some embodiments, R$^A$ is selected from

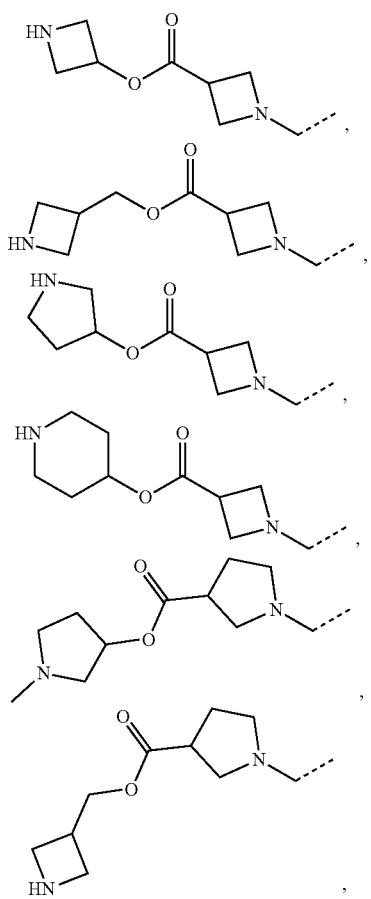

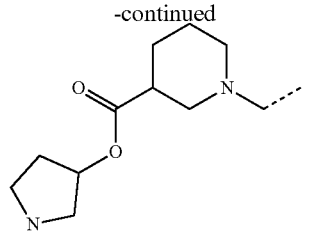

,

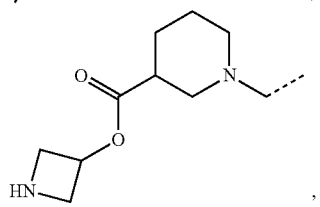

,

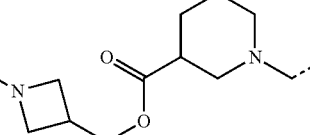

,

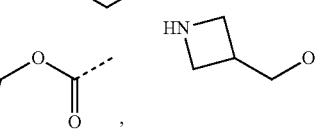

,

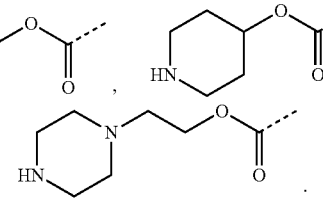 and

.

In some embodiments, D and E are each independently selected from 4- to 6-membered heterocycle, each of which is independently optionally substituted with one or more —CH$_3$. In some embodiments, D and E are each unsubstituted. In some embodiments, A is selected from phenyl, pyridinyl, thiazolyl and thiophenyl. In some embodiments, A is phenyl. In some embodiments, A is pyridinyl. In some embodiments, A is thiazolyl. In some embodiments, A is thiophenyl.

In some embodiments, a compound of Formula (I), (I'), (I-A), (I'-A), (I-B), (I'-B), (I-C), (I'-C), (I-D), (I'-D), (I-E) or (I'-E) is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99% or at least 99.9% enantiomeric excess.

In some embodiments, the present disclosure provides a soft ALK5 inhibitor. As used herein, the term "soft drug" or "soft ALK5 inhibitor" refers to a biologically active compound that is converted upon entering the systemic circulation into a predictable metabolite that exhibits reduced biological activity relative to the parent compound. A soft drug preferably exerts its desired therapeutic effect locally at the target organ or tissue, then is rapidly converted to a predictable metabolite designed to be less active than the parent soft drug upon entering the systemic circulation, thus reducing systemic exposure to the biologically active compound. Accordingly, soft drugs have a lower potential for undesired side effects relative to non-soft drug compounds having comparable biological activity. Preferably, a soft drug of the present disclosure exhibits good stability at the intended site of action (e.g., the lung), is rapidly metabolized upon entering systemic circulation, and displays more functional activity than the corresponding metabolite.

In some embodiments, a soft drug provided herein exhibits an ALK5 $pK_i$ of greater than or equal to 9, while the corresponding soft drug metabolite exhibits an ALK5 $pK_i$ of 9 or less, such as 8 or less (assessed according to the assay provided in Example 45). In some embodiments, the difference in $pK_i$ of the soft drug and the corresponding soft drug metabolite is at least 0.5, such as at least 0.6, 0.7, 0.8, 0.9, 1.0, 1.1, 1.2, 1.3, 1.4, 1.5, 1.6, 1.7, 1.8, 1.9, or at least 2.0. In some embodiments, a soft drug provided herein exhibits a BEAS2B $pIC_{50}$ of greater than or equal to 7, while the corresponding soft drug metabolite exhibits a BEAS2B $pIC_{50}$ of 6 or less (assessed according to the assay provided in Example 46). In some embodiments, the difference in $pIC_{50}$ of the soft drug and the corresponding soft drug metabolite is at least 1.0, such as at least 1.1, 1.2, 1.3, 1.4, 1.5, 1.6, 1.7, 1.8, 1.9, or at least 2.0. In some embodiments, the soft drug and corresponding soft drug metabolite exhibit similar ALK5 $pK_i$ values, but the soft drug is more active in cells (e.g., the soft drug exhibits a BEAS2B $pIC_{50}$ of at least 1.0 greater than the soft drug metabolite).

In some embodiments, the present disclosure provides a soft ALK5 inhibitor comprising an ester. Preferably, the ester inhibits ALK5 activity, while the corresponding carboxylic acid of the ester exhibits reduced ALK5 inhibitory activity. For example, the difference in ALK5 $pK_i$ of the ester and corresponding acid may be at least 1.0. In some embodiments, a soft drug ester of the present disclosure is administered to the lung, for example, by inhalation, and inhibits the activity of ALK5 in the lung. However, upon exiting the lung, the ester may be readily hydrolyzed to the corresponding carboxylic acid, thus reducing systemic exposure to the ester.

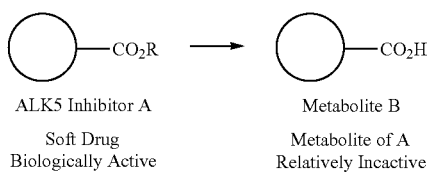

ALK5 Inhibitor A
Soft Drug
Biologically Active

Metabolite B
Metabolite of A
Relatively Inactive

In some embodiments, the present disclosure provides a conjugate comprising a compound disclosed herein linked, e.g., covalently linked, either directly or through a linker to an antibody construct or targeting moiety, thereby forming a conjugate. The linker may be a non-cleavable linker or a cleavable linker. A conjugate may be represented by the formula:

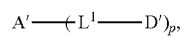

wherein A' is an antibody construct or targeting moiety; L' is a linker; D' is a compound or salt disclosed herein, such as a compound of Formula (I), (I'), (I-A), (I'-A), (I-B), (I'-B), (I-C), (I'-C), (I-D), (I'-D), (I-E) or (I'-E); and p is an integer from 1 to 20. In some embodiments, p is an integer from 1 to 10, such as from 1 to 8, 2 to 8, 1 to 6, 3 to 5, or from 1 to 3.

In some embodiments, a conjugate is represented by the formula:

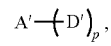

wherein A' is an antibody construct or targeting moiety; D' is a compound or salt disclosed herein, such as a compound of Formula (I), (I'), (I-A), (I'-A), (I-B), (I'-B), (I-C), (I'-C), (I-D), (I'-D), (I-E) or (I'-E); and p is an integer from 1 to 20. In some embodiments, p is an integer from 1 to 10, such as from 1 to 8, 2 to 8, 1 to 6, 3 to 5, or from 1 to 3.

Accordingly, a compound or salt of the present disclosure, such as a compound of Formula (I), (I'), (I-A), (I'-A), (I-B), (I'-B), (I-C), (I'-C), (I-D), (I'-D), (I-E) or (I'-E), may be attached to A' via a linker, $L^1$, or directly attached to A' without an intermediate linker. In some embodiments, the compound or salt is covalently attached to an A' or $L^1$. It will be understood by the skilled person that not all compounds of the present disclosure are meant to be attached to $L^1$ or A', only those that have suitable attachment sites. A compound or salt disclosed herein that does not have a suitable attachment site may be modified to introduce an attachment site.

In some embodiments, $L^1$ or D' is bound to A' via a terminus of an amino acid sequence or via a side chain of an amino acid, such as the side chain of lysine, serine, threonine, cysteine, tyrosine, aspartic acid, glutamine, a non-natural amino acid residue, or glutamic acid residue. In some embodiments, $L^1$ or D' is bound to A' via one or more glycans or short peptide tags of four to six amino acids. $L^1$ or D' may be conjugated to A' via any suitable functional group, such as a thiol, an amine, an amide, an alcohol, a ketone, a carboxylic acid, or an ester.

A linker may be attached to a compound or salt of the present disclosure at any available position. For example, a compound of Formula (I) may comprise a linker $L^1$ to A' in place of $R^4$ or through substituent $R^4$:

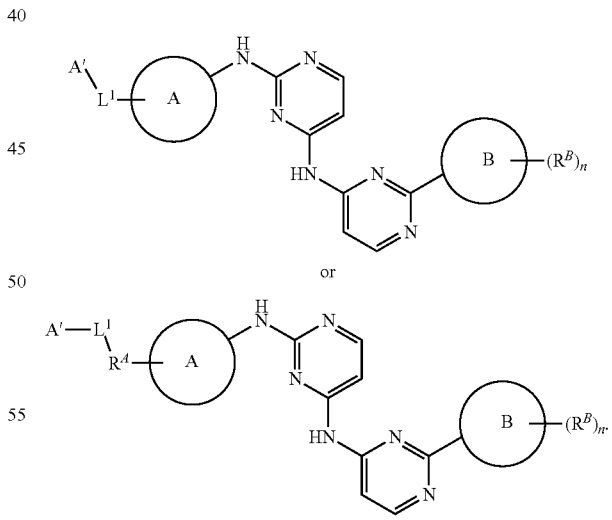

Compounds are typically depicted herein in their unconjugated form, though it will be understood by the skilled person that linker $L^1$ may be covalently bound to any suitably atom for attachment, such as a substitutable nitrogen, carbon, sulfur, phosphorous or oxygen of a compound. $L^1$ may be a cleavable or non-cleavable linker. The linker may further be bound to A'. Preferably, $L^1$ does not affect the binding of the active portions of the conjugate to the binding target(s). Covalent linkages may be formed by reaction between a functional group on the linker with a functional group on the compound, and by reaction between a functional group on the linker with a functional group on A'. As used herein in the context of conjugates, the term "linker" includes (i) unattached forms of the linker comprising a functional group capable of covalently attaching the linker to a compound disclosed herein and a functional group capable of covalently attaching the linker to an antibody construct or targeting moiety; (ii) partially attached forms of the linker bound to a compound disclosed herein, wherein the linker comprises a functional group capable of covalently attaching the linker to an antibody construct or targeting moiety; (iii) partially attached forms of the linker bound to an antibody construct or targeting moiety, wherein the linker comprises a functional group capable of covalently attaching the linker to a compound disclosed herein; and (iv) fully attached forms of the linker bound to both an antibody construct or targeting moiety and a compound disclosed herein.

Linker $L^1$ may be short, flexible, rigid, cleavable (e.g., by a lysosomal enzyme), non-cleavable, hydrophilic, or hydrophobic. A linker may contain segments having different characteristics, such as flexible segments and rigid segments. A linker may be chemically stable to extracellular environments, for example, in the bloodstream, or may include moieties that are not stable or are selectively stable. In some embodiments, a linker comprises a moiety that is selectively cleaved, for example, selectively cleaved in cells, a particular organ, or in plasma. A linker may be sensitive to enzymes, such as proteases. A linker may be insensitive to intracellular processes or proteases. A linker may be acid-labile, protease-sensitive or photolabile. In some embodiments, a linker comprises a peptide, succinimide, maleimide, polyethylene glycol, alkylene, alkenylene, alkynylene, disulfide, hydrazone, polyether, polyester, polyamide, aminobenzyl-carbamate, or a combination thereof.

In some aspects, the present disclosure provides a compound of Formula (I), (I'), (I-A), (I'-A), (I-B), (I'-B), (I-C), (I'-C), (I-D), (I'-D), (I-E) or (I'-E), or a compound disclosed in Table 1 or Table 2, wherein the compound is covalently bound to A', optionally via linker $L^1$. In some embodiments, the antibody construct is an antibody. In some embodiments, the present disclosure provides a compound of Formula (I), (I'), (I-A), (I'-A), (I-B), (I'-B), (I-C), (I'-C), (I-D), (I'-D), (I-E) or (I'-E), or a compound disclosed in Table 1 or Table 2, wherein the compound is covalently bound to a linker, $L^1$, to form a compound-linker. A' or $L^1$ may be covalently attached to any position of the compound, valence permitting. A linker $L^1$ disclosed herein may comprise from about 10 to about 500 atoms, such as 10 to 400 atoms, 10 to 300 atoms, 30 to 400 atoms, or 30 to 300 atoms.

The targets of the antibody, antibody construct, or targeting moiety may depend on the desired therapeutic applications of the conjugate. Typically, the targets are molecules present on the surfaces of cells into which it is desirable to deliver an ALK5 inhibitor, such as T cells, and the antibodies preferably internalize upon binding to the target. For applications in which the conjugates are intended to stimulate the immune system by reducing TGF-β activity, it may be desirable to generate antibodies, antibody constructs, or targeting moieties that bind to T cell surface molecules. Not wishing to be bound by any particular theory, it is believed that the delivery of ALK5 inhibitors to T cells can activate $CD4^+$ and/or $CD8^+$ T cell activity and inhibit regulatory T cell activity, both of which contribute to immune tolerance of tumors. Accordingly, antibodies, antibody constructs, or targeting moieties (A') that bind to T cell surface molecules in the conjugates of the present disclosure are useful for the treatment of various cancers, such as those described herein below. In some embodiments, A' binds to $CD4^+$ T cells, $CD8^+$ T cells, $T_{REG}$ cells, or any combination thereof. In some embodiments, A' binds to a pan T cell surface molecule, such as CD1, CD2, CD3, CD4, CD5, CD6, CD7, CD8, CD25, CD28, CD70, CD71, CD103, CD184, Tim3, LAG3, CTLA4, or PD1. Examples of antibodies that bind to T cell surface molecules and are believed to be internalizing include OKT6, OKT11, OKT3, OKT4, OKT8, 7D4, OKT9, CD28.2, UCHT1, M290, FR70, pembrolizumab, nivolumab, cemiplimab, and dostarlimab.

An antibody, antibody construct, or targeting moiety disclosed herein may comprise an antigen binding domain that specifically binds to a tumor antigen or antigen associated with the pathogenesis of fibrosis. In some embodiments, the antigen binding domain specifically binds to an antigen on a T cell, a B cell, a stellate cell, an endothelial cell, a tumor cell, an APC, a fibroblast cell, a fibrocyte cell, or a cell associated with the pathogenesis of fibrosis. In some embodiments, the antigen binding domain targets CTLA4, PD-1, OX40, LAG-3, GITR, GARP, CD25, CD27, PD-L1, TNFR2, ICOS, 41BB, CD70, CD73, CD38 or VTCN1. In some embodiments, the antigen binding domain targets PDGFRβ, integrin αvβ1, integrin αvβ3, integrin αvβ6, αvβ8, endosialin, FAP, ADAM12, LRRC15, MMP14, PDPN, CDH11, F2RL2, ASGR1, or ASGR2.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1 and 2 and Examples 1-44, the steps in some cases may be performed in a different order than the order shown in Schemes 1 and 2 and Examples 1-44. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g. taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

Scheme 1

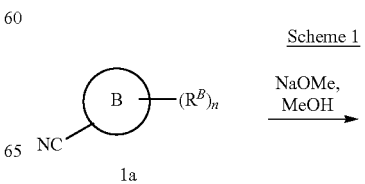

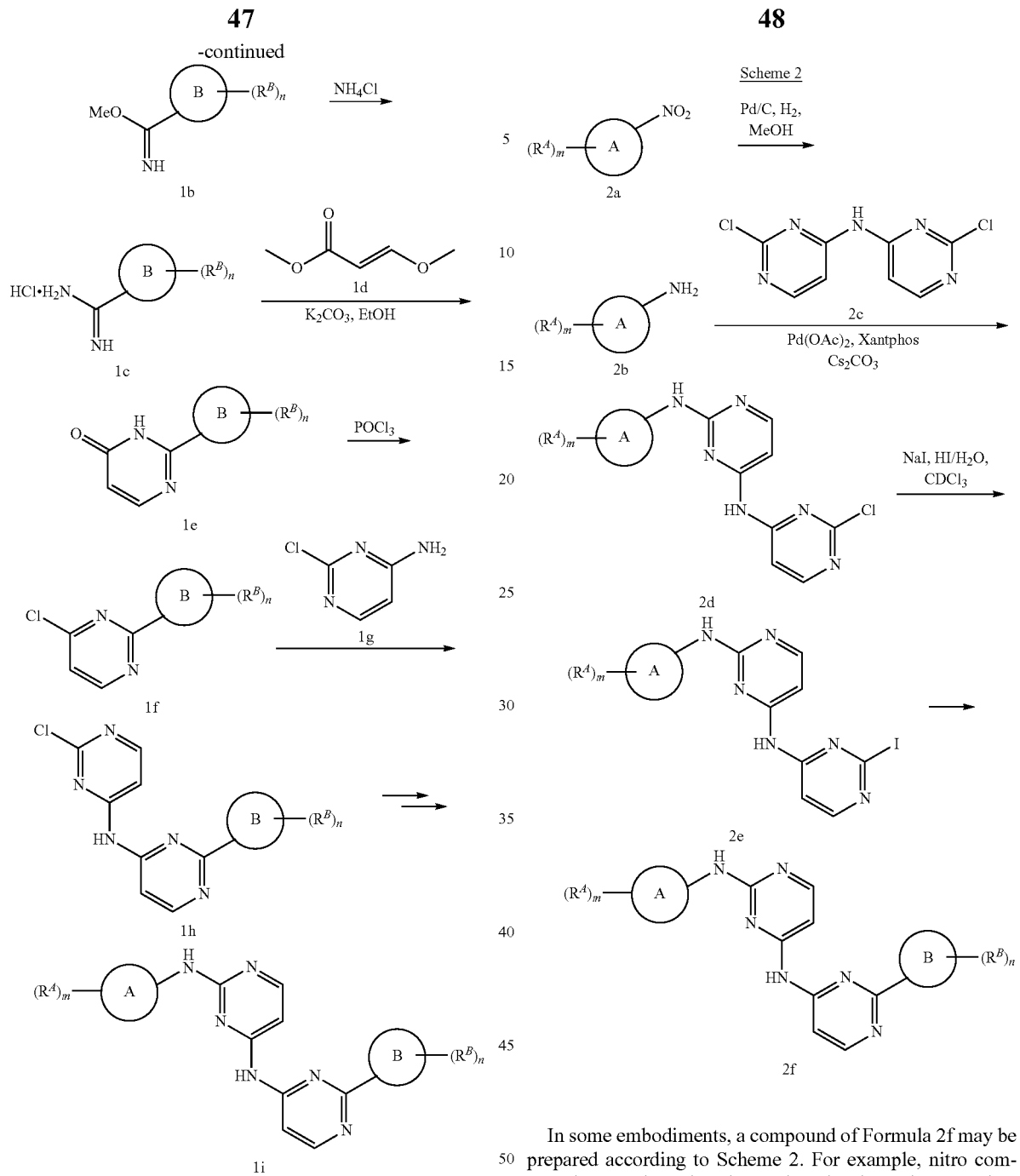

In some embodiments, a compound of Formula 1i may be prepared according to Scheme 1. For example, imidate 1b can be formed from nitrile 1a via a Pinner Reaction, then converted to amidine 1c in the presence of ammonium chloride. Cyclization with methyl 3-methoxyacrylate (1d) may proceed to give pyrimidinone 1e, which may be treated with phosphorus oxychloride to give chloropyrimidine 1f. Chloropyrimidine if can be subjected to a C—N coupling reaction—optionally a Pd-catalyzed coupling reaction such as a Buchwald-Hartwig amination—with 2-chloropyrimidin-4-amine (1g) to provide heteroaryl amine 1h. Optionally, 1h may be subjected to one or more coupling reactions, and optionally one or more protecting group manipulations, to provide a compound of Formula 1i.

In some embodiments, a compound of Formula 2f may be prepared according to Scheme 2. For example, nitro compound 2a can be reduced to amine 2b. The amine may then be subjected to a C—N coupling reaction—optionally a Pd-catalyzed coupling reaction such as a Buchwald-Hartwig amination—with bis(2-chloropyrimidin-4-yl)amine (2c) to provide heteroaryl amine 2d. A substitution reaction can provide heteroaryl iodide 2e, which may undergo a nucleophilic aromatic substitution reaction, and optionally one or more protecting group manipulations, to provide a compound of Formula 2f.

In some embodiments, a compound of the present disclosure, for example, a compound of a formula given in Table 1 or 2, is synthesized according to one of the general routes outlined in Schemes 1 and 2, Examples 1-44, or by methods generally known in the art. In some embodiments, exemplary compounds may include, but are not limited to, a compound or salt thereof selected from Table 1.

TABLE 1

| No. | Structure | Chemical Name | [M + H]+ |
|---|---|---|---|
| 1 | 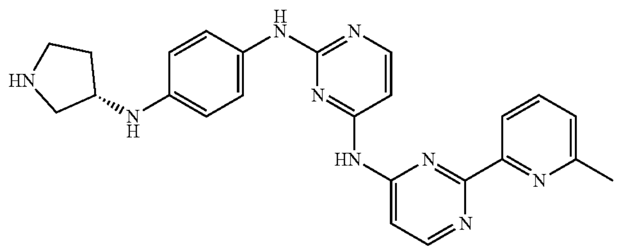 [SMILES: Cc1cccc(-c2nccc(Nc3ccnc(Nc4ccc(N[C@H]5CCNC5)cc4)n3)n2)n1] | N4-[2-(6-methyl-2-pyridyl)pyrimidin-4-yl]-N2-[4-[[(3S)-pyrrolidin-3-yl]amino]phenyl]pyrimidine-2,4-diamine | 440.2 |
| 2 | 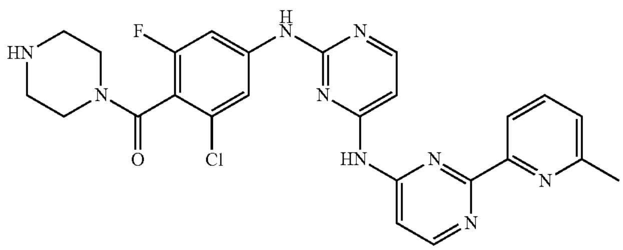 [SMILES: Cc1cccc(-c2nccc(Nc3ccnc(Nc4cc(F)c(C(=O)N5CCNCC5)c(Cl)c4)n3)n2)n1] | [2-chloro-6-fluoro-4-[[4-[[2-(6-methyl-2-pyridyl)pyrimidin-4-yl]amino]pyrimidin-2-yl]amino]phenyl]-piperazin-1-yl-methanone | 520.1 |
| 3 | 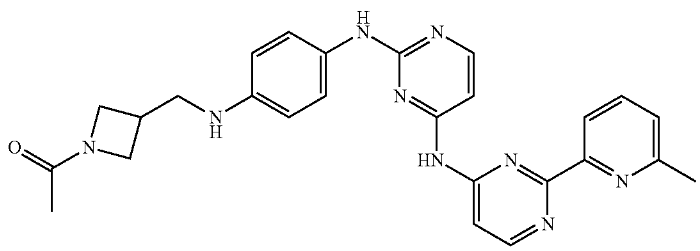 [SMILES: CC(=O)N1CC(CNc2ccc(Nc3nccc(Nc4ccnc(-c5cccc(C)n5)n4)n3)cc2)C1] | 1-[3-[[4-[[4-[[2-(6-methyl-2-pyridyl)pyrimidin-4-yl]amino]pyrimidin-2-yl]amino]anilino]methyl]azetidin-1-yl]ethanone | 482.3 |
| 4 | 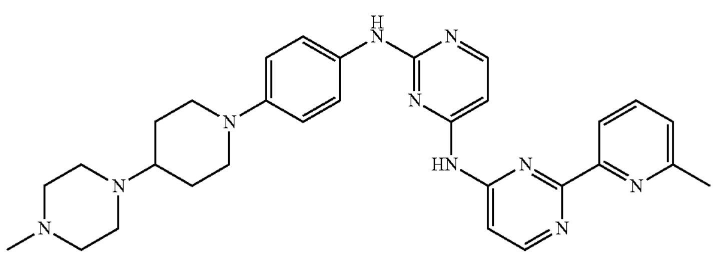 | N2-[4-[4-(4-methylpiperazin-1-yl)-1-piperidyl]phenyl]-N4-[2-(6-methyl-2-pyridyl)pyrimidin-4-yl]pyrimidine-2,4-diamine | 537.2 |
| 5 | 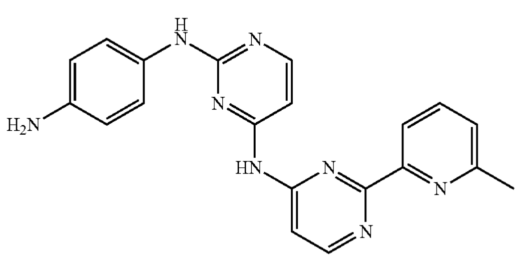 [SMILES: Cc1cccc(-c2nccc(Nc3ccnc(Nc4ccc(N)cc4)n3)n2)n1] | N2-(4-aminophenyl)-N4-[2-(6-methyl-2-pyridyl)pyrimidin-4-yl]pyrimidine-2,4-diamine | 371.1 |

TABLE 1-continued

| No. | Structure | Chemical Name | [M + H]+ |
|---|---|---|---|
| 6 | 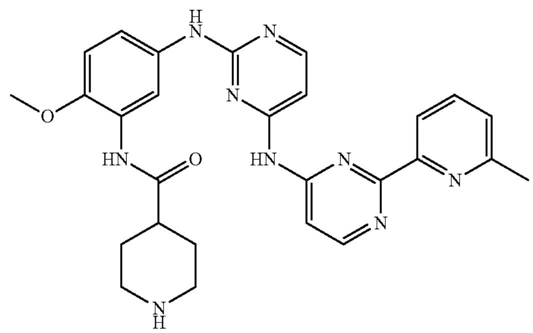 | N-[2-methoxy-5-[[4-[[2-(6-methyl-2-pyridyl)pyrimidin-4-yl]amino]pyrimidin-2-yl]amino]phenyl]piperidine-4-carboxamide | 512.2 |
| 7 | AND Enantiomer | N4-[2-(6-methyl-2-pyridyl)pyrimidin-4-yl]-N2-[4-[rac-(3R)-3-methylpiperazin-1-yl]phenyl]pyrimidine-2,4-diamine | 454.1 |
| 8 | 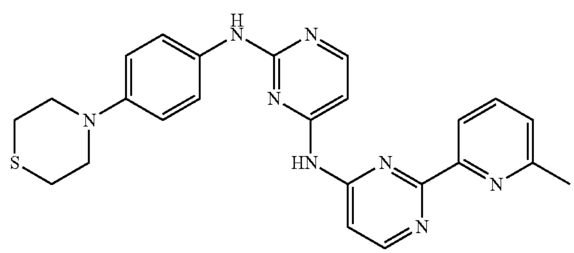 [SMILES: Cc1cccc(-c2nccc(Nc3ccnc(Nc4ccc(N5CCSCC5)cc4)n3)n2)n1] | N4-[2-(6-methyl-2-pyridyl)pyrimidin-4-yl]-N2-(4-thiomorpholinophenyl)pyrimidine-2,4-diamine | 457.2 |
| 9 | 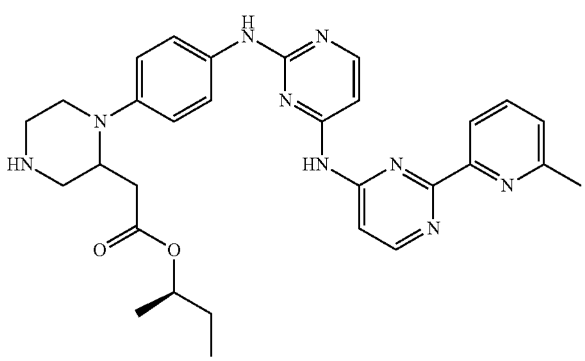 [SMILES: CC[C@@H](C)OC(=O)CC1CNCCN1c1ccc(Nc2nccc(Nc3ccnc(-c4cccc(C)n4)n3)n2)cc1] | [(1R)-1-methylpropyl] 2-[1-[4-[[4-[[2-(6-methyl-2-pyridyl)pyrimidin-4-yl]amino]pyrimidin-2-yl]amino]phenyl]piperazin-2-yl]acetate | 554.5 |
| 10 | 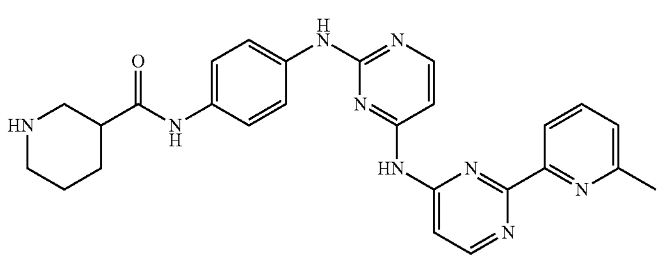 [SMILES: Cc1cccc(-c2nccc(Nc3ccnc(Nc4ccc(NC(=O)C5CCCNC5)cc4)n3)n2)n1] | N-[4-[[4-[[2-(6-methyl-2-pyridyl)pyrimidin-4-yl]amino]pyrimidin-2-yl]amino]phenyl]piperidine-3-carboxamide | 482.1 |

TABLE 1-continued

| No. | Structure | Chemical Name | [M + H]+ |
|---|---|---|---|
| 11 | 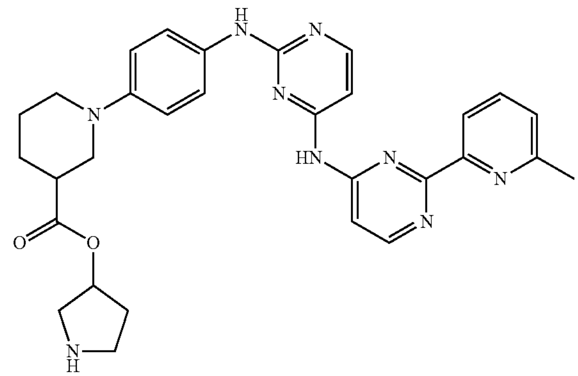 [SMILES: Cc1cccc(-c2nccc(Nc3ccnc(Nc4ccc(N5CCCC(C(=O)OC6CCNC6)C5)cc4)n3)n2)n1] | pyrrolidin-3-yl 1-[4-[[4-[[2-(6-methyl-2-pyridyl)pyrimidin-4-yl]amino]pyrimidin-2-yl]amino]phenyl]piperidine-3-carboxylate | 552.3 |
| 12 | 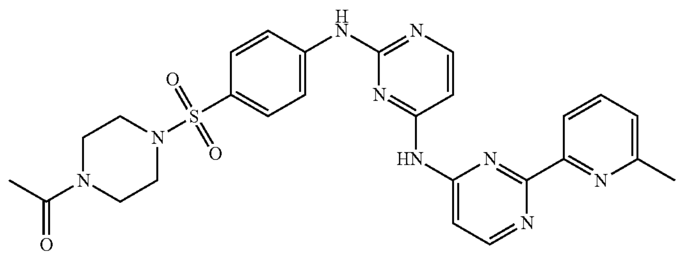 [SMILES: CC(=O)N1CCN(S(=O)(=O)c2ccc(Nc3nccc(Nc4ccnc(-c5cccc(C)n5)n4)n3)cc2)CC1] | 1-[4-[4-[[4-[[2-(6-methyl-2-pyridyl)pyrimidin-4-yl]amino]pyrimidin-2-yl]amino]phenyl]sulfonylpiperazin-1-yl]ethanone | 546.0 |
| 13 | 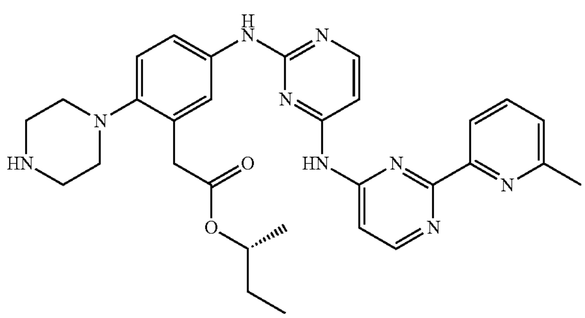 [SMILES: CC[C@@H](C)OC(=O)Cc1cc(Nc2nccc(Nc3ccnc(-c4cccc(C)n4)n3)n2)ccc1N1CCNCC1] | [(1R)-1-methylpropyl] 2-[5-[[4-[[2-(6-methyl-2-pyridyl)pyrimidin-4-yl]amino]pyrimidin-2-yl]amino]-2-piperazin-1-yl-phenyl]acetate | 554.3 |
| 14 | 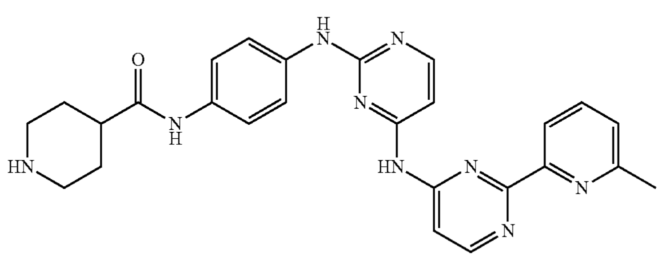 | N-[4-[[4-[[2-(6-methyl-2-pyridyl)pyrimidin-4-yl]amino]pyrimidin-2-yl]amino]phenyl]piperidine-4-carboxamide | 482.1 |
| 15 | 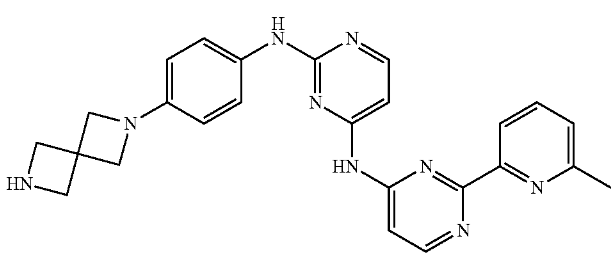 [SMILES: Cc1cccc(-c2nccc(Nc3ccnc(Nc4ccc(N5CC6(CNC6)C5)cc4)n3)n2)n1] | N2-[4-(2,6-diazaspiro[3.3]heptan-2-yl)phenyl]-N4-[2-(6-methyl-2-pyridyl)pyrimidin-4-yl]pyrimidine-2,4-diamine | 452.2 |

TABLE 1-continued

| No. | Structure | Chemical Name | [M + H]⁺ |
|---|---|---|---|
| 16 | 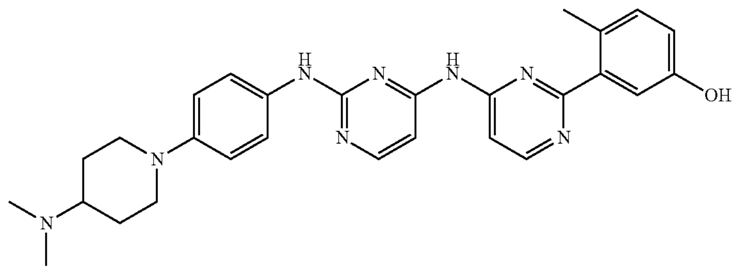 [SMILES: Cc1ccc(O)cc1-c1nccc(Nc2ccnc(Nc3ccc(N4CCC(N(C)C)CC4)cc3)n2)n1] | 3-[4-[[2-[4-[4-(dimethylamino)-1-piperidyl]anilino]pyrimidin-4-yl]amino]pyrimidin-2-yl]-4-methyl-phenol | 497.2 |
| 17 | 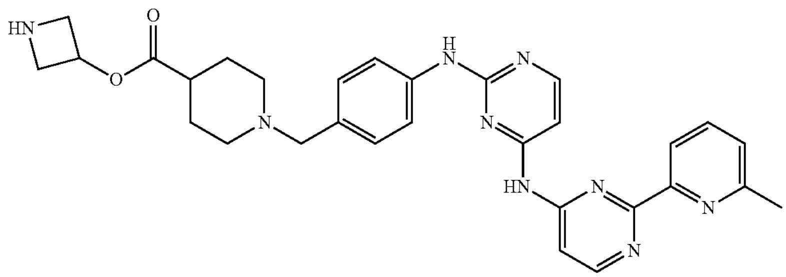 [SMILES: Cc1cccc(-c2nccc(Nc3ccnc(Nc4ccc(CN5CCC(C(=O)OC6CNC6)CC5)cc4)n3)n2)n1] | azetidin-3-yl 1-[[4-[[4-[[2-(6-methyl-2-pyridyl)pyrimidin-4-yl]amino]pyrimidin-2-yl]amino]phenyl]methyl]piperidine-4-carboxylate | 552.1 |
| 18 | 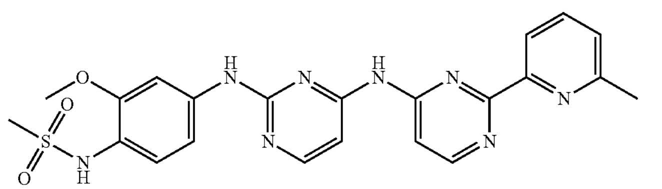 | N-[2-methoxy-4-[[4-[[2-(6-methyl-2-pyridyl)pyrimidin-4-yl]amino]pyrimidin-2-yl]amino]phenyl]methanesulfonamide | 479.0 |
| 19 | 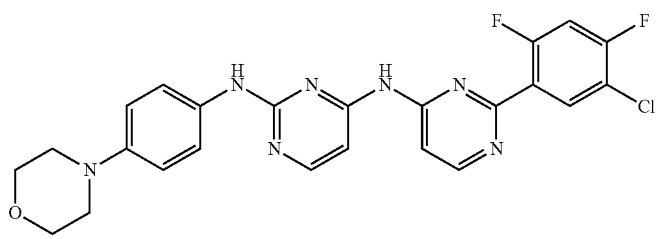 [SMILES: Fc1cc(F)c(-c2nccc(Nc3ccnc(Nc4ccc(N5CCOCC5)cc4)n3)n2)cc1Cl] | N4-[2-(5-chloro-2,4-difluoro-phenyl)pyrimidin-4-yl]-N2-(4-morpholinophenyl)pyrimidine-2,4-diamine | 496.1 |
| 20 | 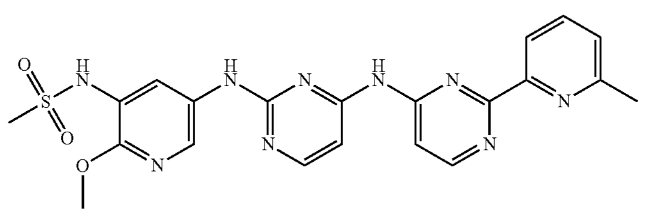 | N-[2-methoxy-5-[[4-[[2-(6-methyl-2-pyridyl)pyrimidin-4-yl]amino]pyrimidin-2-yl]amino]-3-pyridyl]methanesulfonamide | 480.0 |
| 21 | 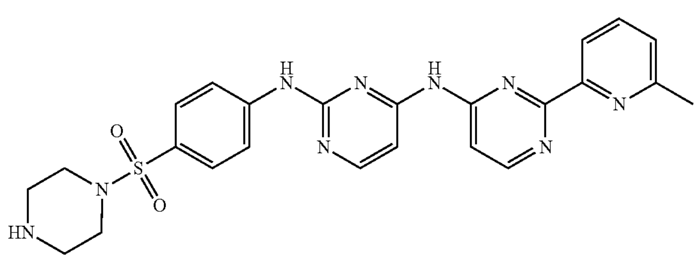 [SMILES: Cc1cccc(-c2nccc(Nc3ccnc(Nc4ccc(S(=O)(=O)N5CCNCC5)cc4)n3)n2)n1] | N4-[2-(6-methyl-2-pyridyl)pyrimidin-4-yl]-N2-(4-piperazin-1-ylsulfonylphenyl)pyrimidine-2,4-diamine | 504.2 |

TABLE 1-continued

| No. | Structure | Chemical Name | [M + H]+ |
|---|---|---|---|
| 22 | 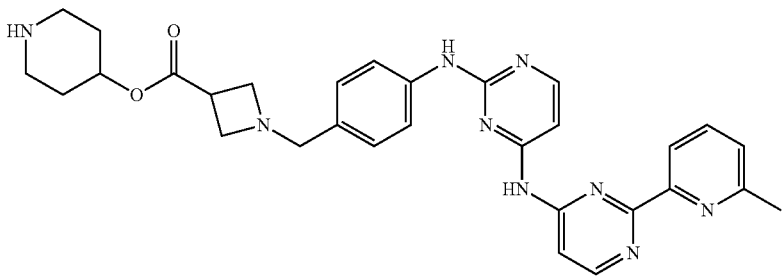 [SMILES: Cc1cccc(-c2nccc(Nc3ccnc(Nc4ccc(CN5CC(C(=O)OC6CCNCC6)C5)cc4)n3)n2)n1] | 4-piperidyl 1-[[4-[[4-[[2-(6-methyl-2-pyridyl)pyrimidin-4-yl]amino]pyrimidin-2-yl]amino]phenyl]methyl]azetidine-3-carboxylate | 552.3 |
| 23 | 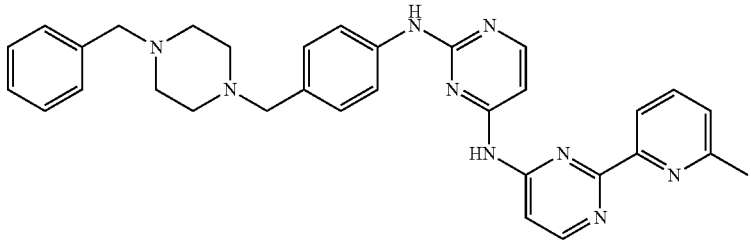 [SMILES: Cc1cccc(-c2nccc(Nc3ccnc(Nc4ccc(CN5CCN(Cc6ccccc6)CC5)cc4)n3)n2)n1] | N2-[4-[(4-benzylpiperazin-1-yl)methyl]phenyl]-N4-[2-(6-methyl-2-pyridyl)pyrimidin-4-yl]pyrimidine-2,4-diamine | 544.2 |
| 24 | 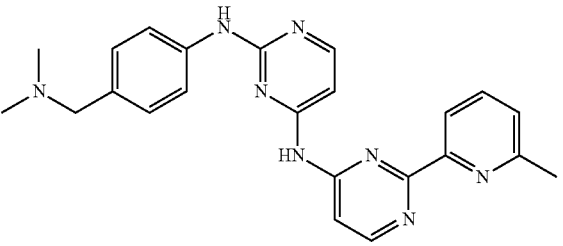 | N2-[4-[(dimethylamino)methyl]phenyl]-N4-[2-(6-methyl-2-pyridyl)pyrimidin-4-yl]pyrimidine-2,4-diamine | 413.2 |
| 25 | 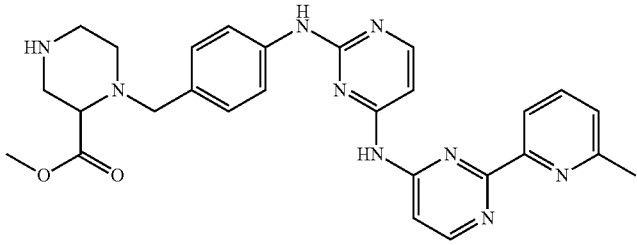 | methyl 1-[[4-[[4-[[2-(6-methyl-2-pyridyl)pyrimidin-4-yl]amino]pyrimidin-2-yl]amino]phenyl]methyl]piperazine-2-carboxylate | 512.2 |
| 26 | 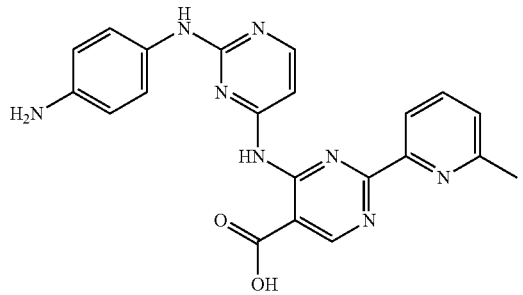 | 4-[[2-(4-aminoanilino)pyrimidin-4-yl]amino]-2-(6-methyl-2-pyridyl)pyrimidine-5-carboxylic acid | 415.0 |
| 27 | 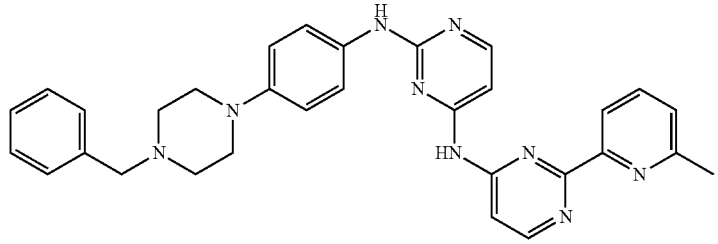 | N2-[4-(4-benzylpiperazin-1-yl)phenyl]-N4-[2-(6-methyl-2-pyridyl)pyrimidin-4-yl]pyrimidine-2,4-diamine | 530.1 |

TABLE 1-continued

| No. | Structure | Chemical Name | [M + H]+ |
|---|---|---|---|
| 28 | 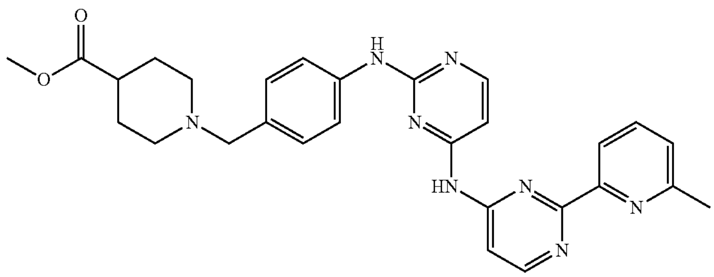 | methyl 1-[[4-[[4-[[2-(6-methyl-2-pyridyl)pyrimidin-4-yl]amino]pyrimidin-2-yl]amino]phenyl]methyl]piperidine-4-carboxylate | 511.1 |
| 29 | 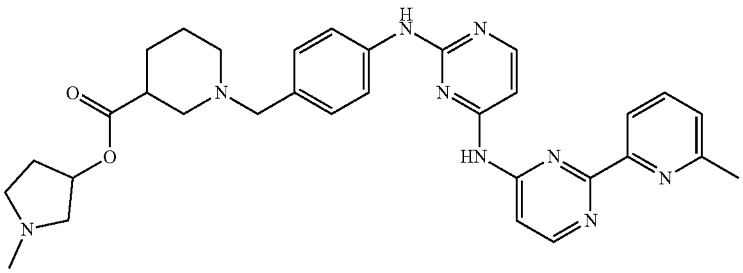 [SMILES: Cc1cccc(-c2nccc(Nc3ccnc(Nc4ccc(CN5CCCC(C(=O)OC6CCN(C)C6)C5)cc4)n3)n2)n1] | (1-methylpyrrolidin-3-yl) 1-[[4-[[4-[[2-(6-methyl-2-pyridyl)pyrimidin-4-yl]amino]pyrimidin-2-yl]amino]phenyl]methyl]piperidine-3-carboxylate | 580.2 |
| 30 | 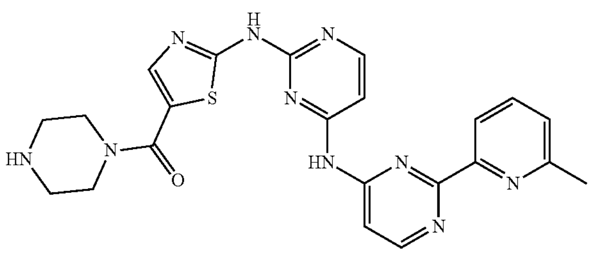 [SMILES: Cc1cccc(-c2nccc(Nc3ccnc(Nc4ncc(C(=O)N5CCNCC5)s4)n3)n2)n1] | [2-[[4-[[2-(6-methyl-2-pyridyl)pyrimidin-4-yl]amino]pyrimidin-2-yl]amino]thiazol-5-yl]-piperazin-1-yl-methanone | 475.1 |
| 31 | 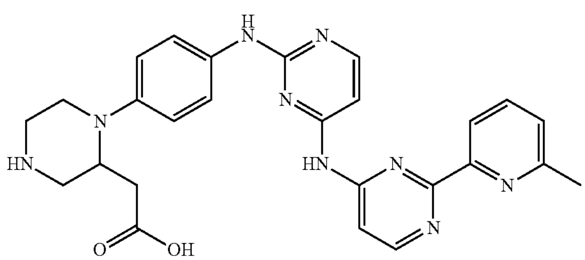 [SMILES: Cc1cccc(-c2nccc(Nc3ccnc(Nc4ccc(N5CCNCC5CC(=O)O)cc4)n3)n2)n1] | 2-[1-[4-[[4-[[2-(6-methyl-2-pyridyl)pyrimidin-4-yl]amino]pyrimidin-2-yl]amino]phenyl]piperazin-2-yl]acetic acid | 498.4 |
| 32 | 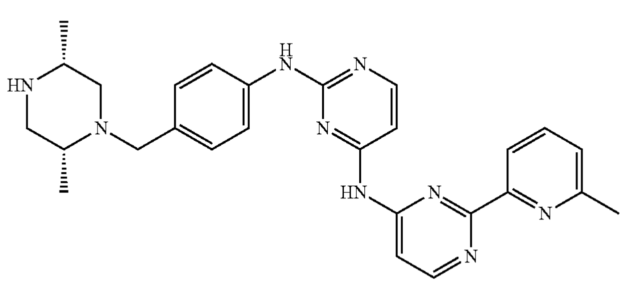 [SMILES: Cc1cccc(-c2nccc(Nc3ccnc(Nc4ccc(CN5C[C@@H](C)NC[C@H]5C)cc4)n3)n2)n1] | N2-[4-[[(2R,5R)-2,5-dimethylpiperazin-1-yl]methyl]phenyl]-N4-[2-(6-methyl-2-pyridyl)pyrimidin-4-yl]pyrimidine-2,4-diamine | 482.2 |

TABLE 1-continued

| No. | Structure | Chemical Name | [M + H]+ |
|---|---|---|---|
| 33 | 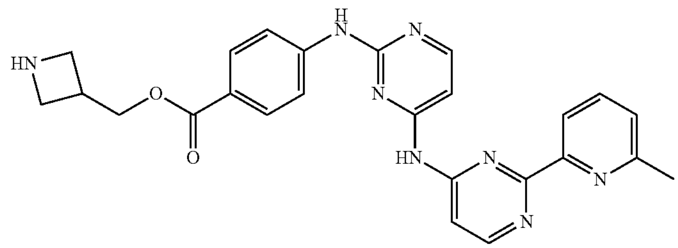 [SMILES: Cc1cccc(-c2nccc(Nc3ccnc(Nc4ccc(C(=O)OCC5CNC5)cc4)n3)n2)n1] | azetidin-3-ylmethyl 4-[[4-[[2-(6-methyl-2-pyridyl)pyrimidin-4-yl]amino]pyrimidin-2-yl]amino]benzoate | 469.1 |
| 34 | 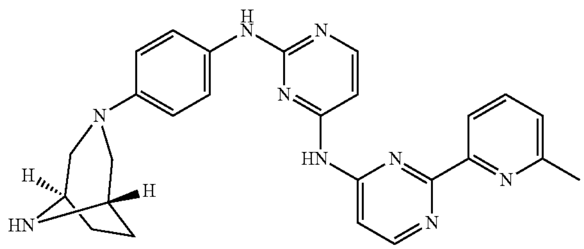 [SMILES: Cc1cccc(-c2nccc(Nc3ccnc(Nc4ccc(N5C[C@H]6CC[C@@H](C5)N6)cc4)n3)n2)n1] | N4-[2-(6-methyl-2-pyridyl)pyrimidin-4-yl]-N2-[4-[rac-(1S,5R)-3,8-diazabicyclo[3.2.1]octan-3-yl]phenyl]pyrimidine-2,4-diamine | 466.2 |
| 35 | 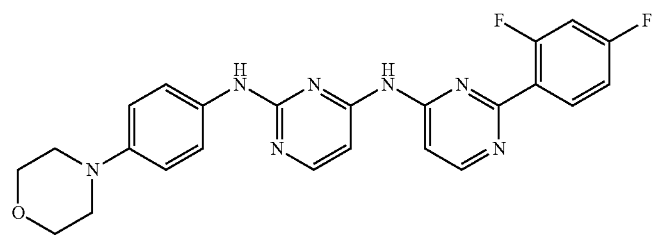 [SMILES: Fc1ccc(-c2nccc(Nc3ccnc(Nc4ccc(N5CCOCC5)cc4)n3)n2)c(F)c1] | N4-[2-(2,4-difluorophenyl)pyrimidin-4-yl]-N2-(4-morpholinophenyl)pyrimidine-2,4-diamine | 462.1 |
| 36 | 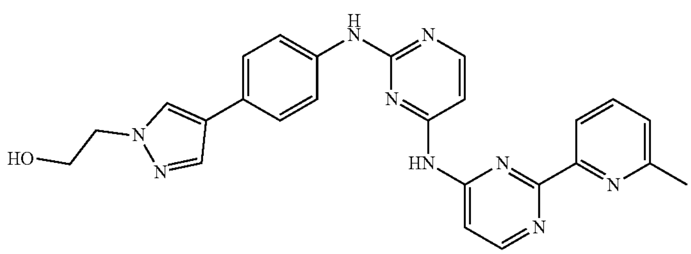 [SMILES: Cc1cccc(-c2nccc(Nc3ccnc(Nc4ccc(-c5cnn(CCO)c5)cc4)n3)n2)n1] | 2-[4-[4-[[4-[[2-(6-methyl-2-pyridyl)pyrimidin-4-yl]amino]pyrimidin-2-yl]amino]phenyl]pyrazol-1-yl]ethanol | 466.1 |
| 37 | 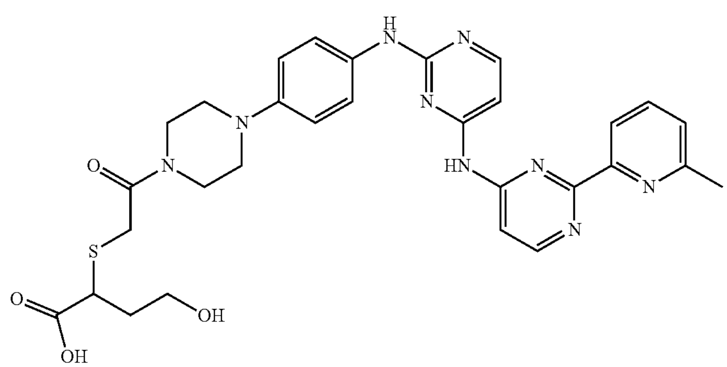 [SMILES: Cc1cccc(-c2nccc(Nc3ccnc(Nc4ccc(N5CCN(C(=O)CSC(CCO)C(=O)O)CC5)cc4)n3)n2)n1] | 4-hydroxy-2-[2-[4-[4-[[4-[[2-(6-methyl-2-pyridyl)pyrimidin-4-yl]amino]pyrimidin-2-yl]amino]phenyl]piperazin-1-yl]-2-oxo-ethyl]sulfanyl-butanoic acid | 616.3 |

TABLE 1-continued

| No. | Structure | Chemical Name | [M + H]+ |
|---|---|---|---|
| 38 | 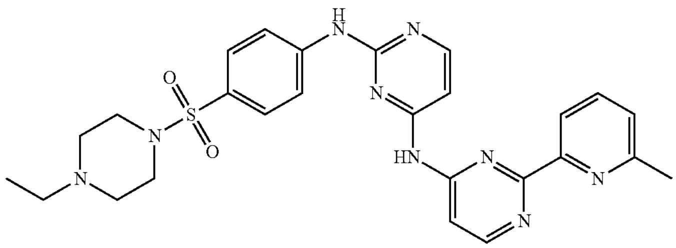 [SMILES: CCN1CCN(S(=O)(=O)c2ccc(Nc3nccc(Nc4ccnc(-c5cccc(C)n5)n4)n3)cc2)CC1] | N2-[4-(4-ethylpiperazin-1-yl)sulfonylphenyl]-N4-[2-(6-methyl-2-pyridyl)pyrimidin-4-yl]pyrimidine-2,4-diamine | 532.1 |
| 39 | 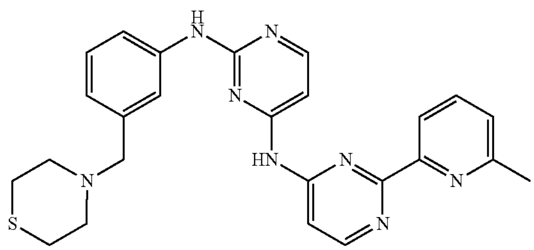 [SMILES: Cc1cccc(-c2nccc(Nc3ccnc(Nc4cccc(CN5CCSCC5)c4)n3)n2)n1] | N4-[2-(6-methyl-2-pyridyl)pyrimidin-4-yl]-N2-[3-(thiomorpholinomethyl)phenyl]pyrimidine-2,4-diamine | 471.1 |
| 40 | 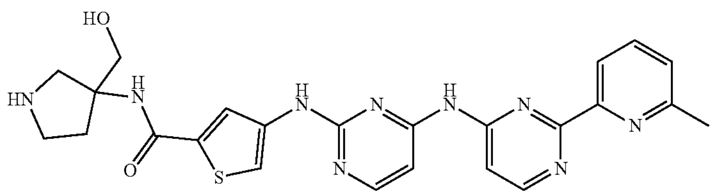 [SMILES: Cc1cccc(-c2nccc(Nc3ccnc(Nc4csc(C(=O)NC5(CO)CCNC5)c4)n3)n2)n1] | N-[3-(hydroxymethyl)pyrrolidin-3-yl]-4-[[4-[[2-(6-methyl-2-pyridyl)pyrimidin-4-yl]amino]pyrimidin-2-yl]amino]thiophene-2-carboxamide | 504.2 |
| 41 | 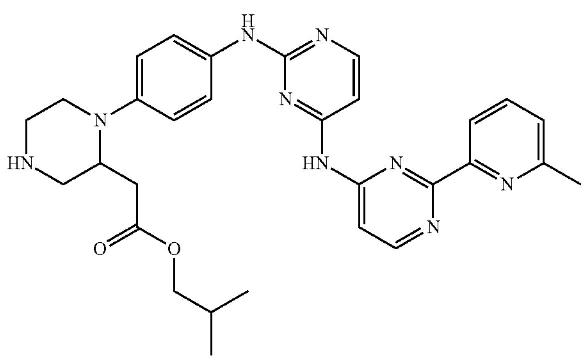 [SMILES: Cc1cccc(-c2nccc(Nc3ccnc(Nc4ccc(N5CCNCC5CC(=O)OCC(C)C)cc4)n3)n2)n1] | isobutyl 2-[1-[4-[[4-[[2-(6-methyl-2-pyridyl)pyrimidin-4-yl]amino]pyrimidin-2-yl]amino]phenyl]piperazin-2-yl]acetate | 554.5 |
| 42 | 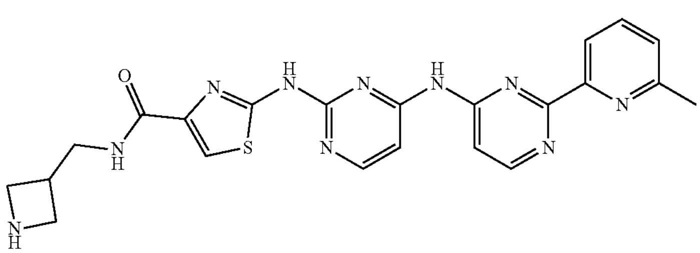 [SMILES: Cc1cccc(-c2nccc(Nc3ccnc(Nc4nc(C(=O)NCC5CNC5)cs4)n3)n2)n1] | N-(azetidin-3-ylmethyl)-2-[[4-[[2-(6-methyl-2-pyridyl)pyrimidin-4-yl]amino]pyrimidin-2-yl]amino]thiazole-4-carboxamide | 474.9 |
| 43 | 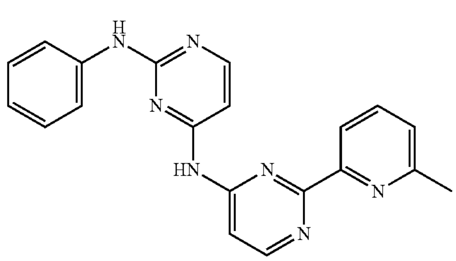 [SMILES: Cc1cccc(-c2nccc(Nc3ccnc(Nc4ccccc4)n3)n2)n1] | N4-[2-(6-methyl-2-pyridyl)pyrimidin-4-yl]-N2-phenyl-pyrimidine-2,4-diamine | 356.2 |

TABLE 1-continued

| No. | Structure | Chemical Name | [M + H]⁺ |
|---|---|---|---|
| 44 | 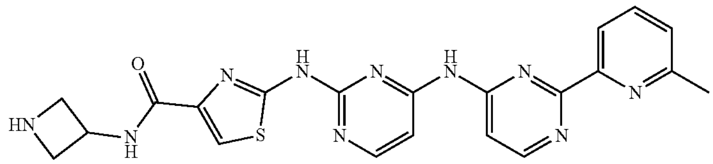 [SMILES: Cc1cccc(-c2nccc(Nc3ccnc(Nc4nc(C(=O)NC5CNC5)cs4)n3)n2)n1] | N-(azetidin-3-yl)-2-[[4-[[2-(6-methyl-2-pyridyl)pyrimidin-4-yl]amino]pyrimidin-2-yl]amino]thiazole-4-carboxamide | 461.1 |
| 45 | 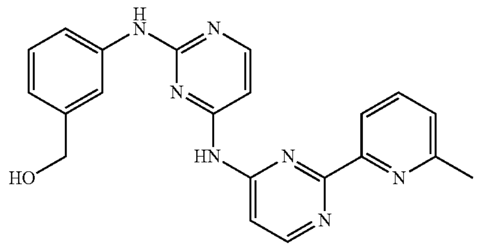 [SMILES: Cc1cccc(-c2nccc(Nc3ccnc(Nc4cccc(CO)c4)n3)n2)n1] | [3-[[4-[[2-(6-methyl-2-pyridyl)pyrimidin-4-yl]amino]pyrimidin-2-yl]amino]phenyl]methanol | 386.2 |
| 46 | 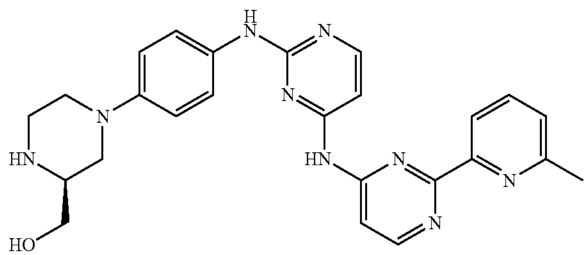 [SMILES: Cc1cccc(-c2nccc(Nc3ccnc(Nc4ccc(N5CCN[C@H](CO)C5)cc4)n3)n2)n1] | [(2S)-4-[4-[[4-[[2-(6-methyl-2-pyridyl)pyrimidin-4-yl]amino]pyrimidin-2-yl]amino]phenyl]piperazin-2-yl]methanol | 470.1 |
| 47 | 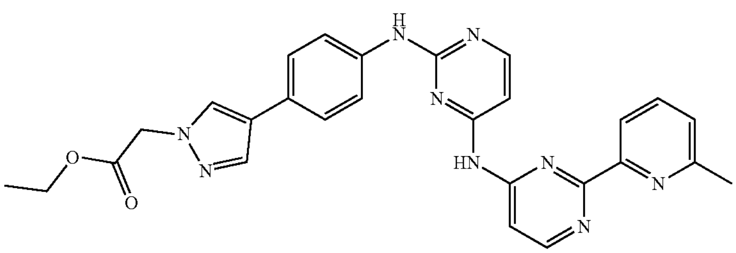 [SMILES: CCOC(=O)Cn1cc(-c2ccc(Nc3nccc(Nc4ccnc(-c5cccc(C)n5)n4)n3)cc2)cn1] | ethyl 2-[4-[4-[[4-[[2-(6-methyl-2-pyridyl)pyrimidin-4-yl]amino]pyrimidin-2-yl]amino]phenyl]pyrazol-1-yl]acetate | 508.1 |
| 48 | 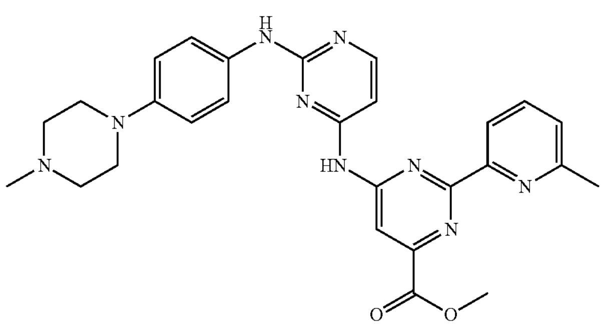 | methyl 6-[[2-[4-(4-methylpiperazin-1-yl)anilino]pyrimidin-4-yl]amino]-2-(6-methyl-2-pyridyl)pyrimidine-4-carboxylate | 512.2 |
| 49 | 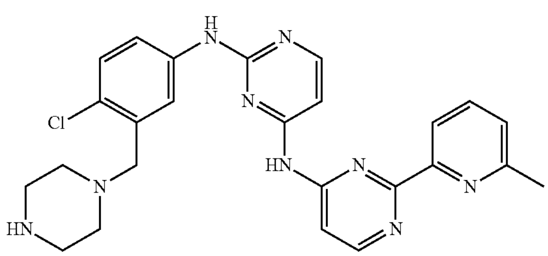 | N2-[4-chloro-3-(piperazin-1-ylmethyl)phenyl]-N4-[2-(6-methyl-2-pyridyl)pyrimidin-4-yl]pyrimidine-2,4-diamine | 488.2 |

TABLE 1-continued

| No. | Structure | Chemical Name | [M + H]+ |
|---|---|---|---|
| 50 | 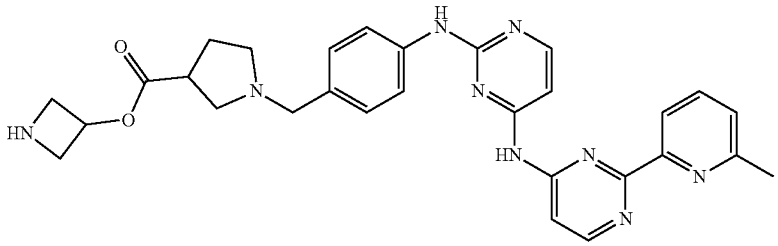 [SMILES: Cc1cccc(-c2nccc(Nc3ccnc(Nc4ccc(CN5CCC(C(=O)OC6CNC6)C5)cc4)n3)n2)n1] | azetidin-3-yl 1-[[4-[[4-[[2-(6-methyl-2-pyridyl)pyrimidin-4-yl]amino]pyrimidin-2-yl]amino]phenyl]methyl]pyrrolidine-3-carboxylate | 538.1 |
| 51 | 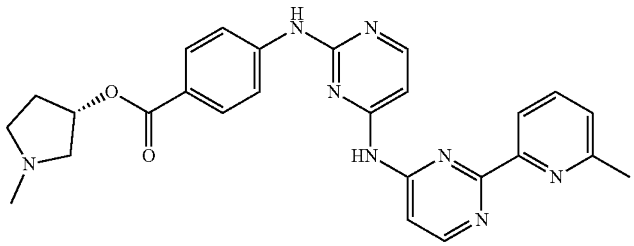 [SMILES: Cc1cccc(-c2nccc(Nc3ccnc(Nc4ccc(C(=O)O[C@H]5CCN(C)C5)cc4)n3)n2)n1] | [(3S)-1-methylpyrrolidin-3-yl] 4-[[4-[[2-(6-methyl-2-pyridyl)pyrimidin-4-yl]amino]pyrimidin-2-yl]amino]benzoate | 483.0 |
| 52 | 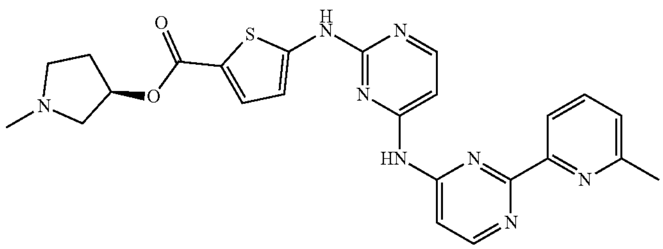 | [(3R)-1-methylpyrrolidin-3-yl] 5-[[4-[[2-(6-methyl-2-pyridyl)pyrimidin-4-yl]amino]pyrimidin-2-yl]amino]thiophene-2-carboxylate | 489.1 |
| 53 | 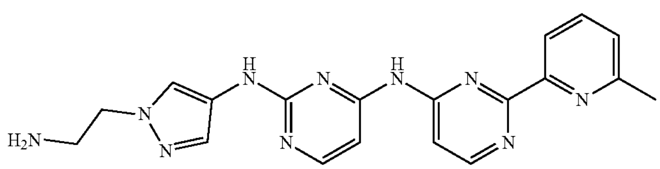 [SMILES: Cc1cccc(-c2nccc(Nc3ccnc(Nc4cnn(CCN)c4)n3)n2)n1] | N2-[1-(2-aminoethyl)pyrazol-4-yl]-N4-[2-(6-methyl-2-pyridyl)pyrimidin-4-yl]pyrimidine-2,4-diamine | 389.2 |
| 54 | 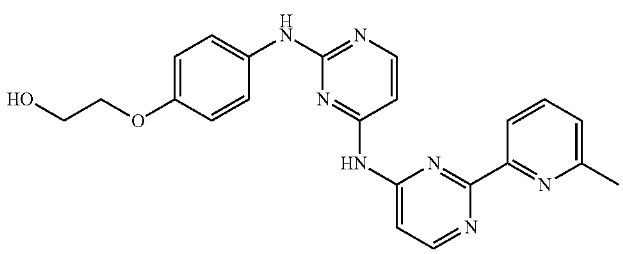 [SMILES: Cc1cccc(-c2nccc(Nc3ccnc(Nc4ccc(OCCO)cc4)n3)n2)n1] | 2-[4-[[4-[[2-(6-methyl-2-pyridyl)pyrimidin-4-yl]amino]pyrimidin-2-yl]amino]phenoxy]ethanol | 416.1 |
| 55 | 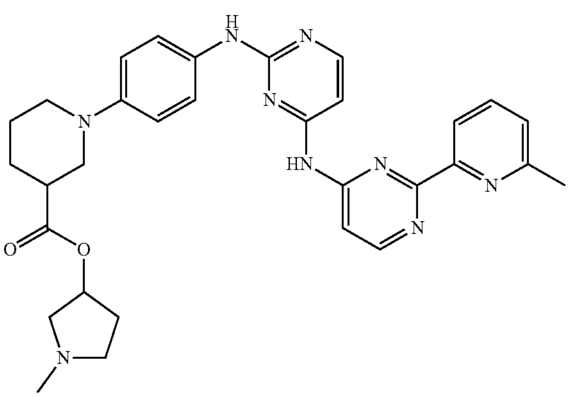 [SMILES: Cc1cccc(-c2nccc(Nc3ccnc(Nc4ccc(N5CCCC(C(=O)OC6CCN(C)C6)C5)cc4)n3)n2)n1] | (1-methylpyrrolidin-3-yl) 1-[4-[[4-[[2-(6-methyl-2-pyridyl)pyrimidin-4-yl]amino]pyrimidin-2-yl]amino]phenyl]piperidine-3-carboxylate | 566.3 |

TABLE 1-continued

| No. | Structure | Chemical Name | [M + H]+ |
|---|---|---|---|
| 56 | 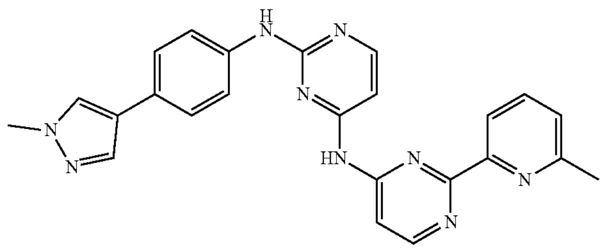 | N2-[4-(1-methylpyrazol-4-yl)phenyl]-N4-[2-(6-methyl-2-pyridyl)pyrimidin-4-yl]pyrimidine-2,4-diamine | 436.1 |
| 57 | 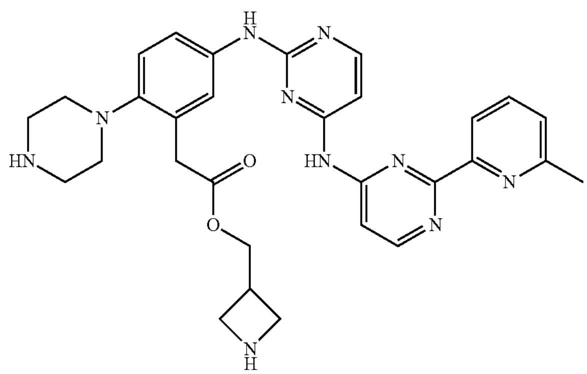 [SMILES: Cc1cccc(-c2nccc(Nc3ccnc(Nc4ccc(N5CCNCC5)c(CC(=O)OCC5CNC5)c4)n3)n2)n1] | azetidin-3-ylmethyl 2-[5-[[4-[[2-(6-methyl-2-pyridyl)pyrimidin-4-yl]amino]pyrimidin-2-yl]amino]-2-piperazin-1-yl-phenyl]acetate | 567.1 |
| 58 | 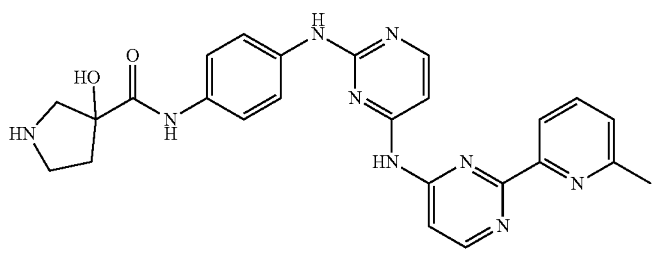 [SMILES: Cc1cccc(-c2nccc(Nc3ccnc(Nc4ccc(NC(=O)C5(O)CCNC5)cc4)n3)n2)n1] | 3-hydroxy-N-[4-[[4-[[2-(6-methyl-2-pyridyl)pyrimidin-4-yl]amino]pyrimidin-2-yl]amino]phenyl]pyrrolidine-3-carboxamide | 484.1 |
| 59 | AND Enantiomer | 1-[[4-[[4-[[2-(6-methyl-2-pyridyl)pyrimidin-4-yl]amino]pyrimidin-2-yl]amino]phenyl]methyl]-N-[rac-(3S)-pyrrolidin-3-yl]piperidine-3-carboxamide | 565.2 |
| 60 | 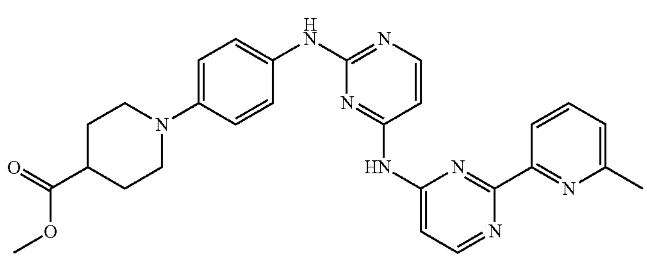 [SMILES: COC(=O)C1CCN(c2ccc(Nc3nccc(Nc4ccnc(-c5cccc(C)n5)n4)n3)cc2)CC1] | methyl 1-[4-[[4-[[2-(6-methyl-2-pyridyl)pyrimidin-4-yl]amino]pyrimidin-2-yl]amino]phenyl]piperidine-4-carboxylate | 497.1 |

TABLE 1-continued

| No. | Structure | Chemical Name | [M + H]+ |
|---|---|---|---|
| 61 | 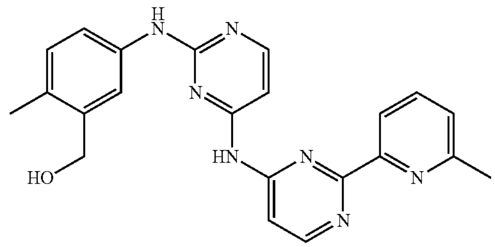 | [2-methyl-5-[[4-[[2-(6-methyl-2-pyridyl)pyrimidin-4-yl]amino]pyrimidin-2-yl]amino]phenyl]methanol | 400.3 |
| 62 | 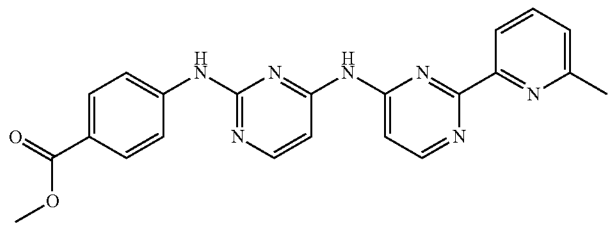 [SMILES: COC(=O)c1ccc(Nc2nccc(Nc3ccnc(-c4cccc(C)n4)n3)n2)cc1] | methyl 4-[[4-[[2-(6-methyl-2-pyridyl)pyrimidin-4-yl]amino]pyrimidin-2-yl]amino]benzoate | 414.0 |
| 63 | 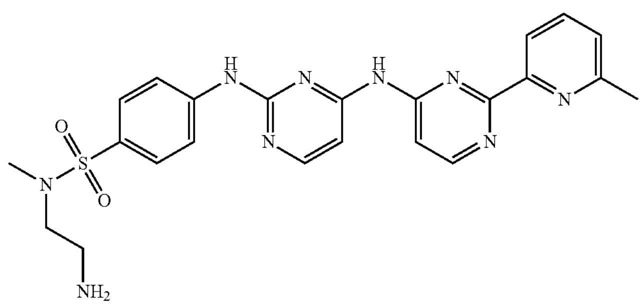 | N-(2-aminoethyl)-N-methyl-4-[[4-[[2-(6-methyl-2-pyridyl)pyrimidin-4-yl]amino]pyrimidin-2-yl]amino]benzenesulfonamide | 492.2 |
| 64 | 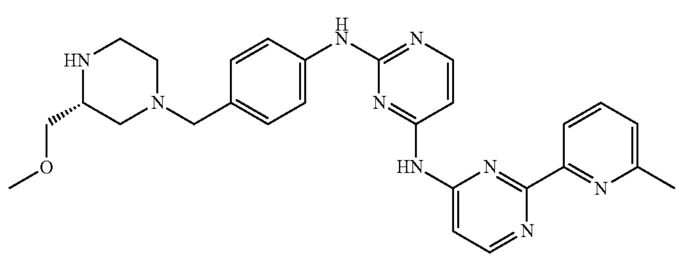 | N2-[4-[[(3R)-3-(methoxymethyl)piperazin-1-yl]methyl]phenyl]-N4-[2-(6-methyl-2-pyridyl)pyrimidin-4-yl]pyrimidine-2,4-diamine | 498.1 |
| 65 | 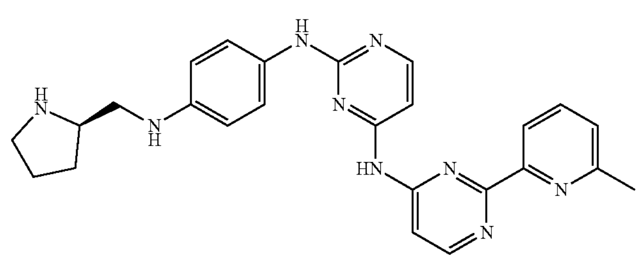 [SMILES: Cc1cccc(-c2nccc(Nc3ccnc(Nc4ccc(NC[C@H]5CCCN5)cc4)n3)n2)n1] | N4-[2-(6-methyl-2-pyridyl)pyrimidin-4-yl]-N2-[4-[[(2R)-pyrrolidin-2-yl]methylamino]phenyl]pyrimidine-2,4-diamine | 454.2 |

TABLE 1-continued

| No. | Structure | Chemical Name | [M + H]+ |
|---|---|---|---|
| 66 | 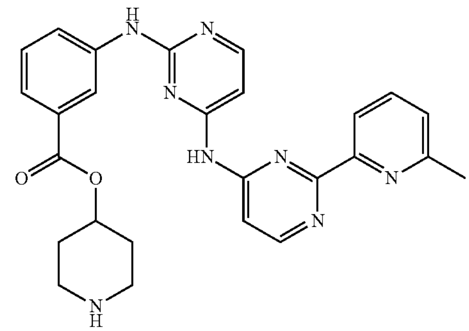 [SMILES: Cc1cccc(-c2nccc(Nc3ccnc(Nc4cccc(C(=O)OC5CCNCC5)c4)n3)n2)n1] | 4-piperidyl 3-[[4-[[2-(6-methyl-2-pyridyl)pyrimidin-4-yl]amino]pyrimidin-2-yl]amino]benzoate | 483.2 |
| 67 | 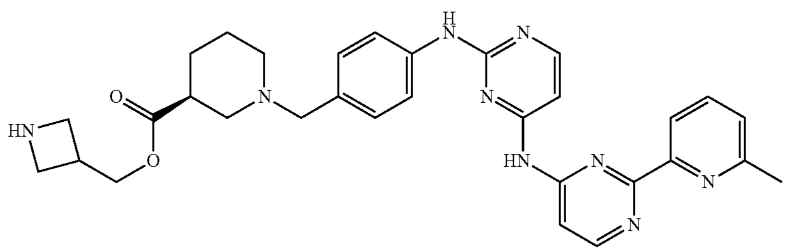 [SMILES: Cc1cccc(-c2nccc(Nc3ccnc(Nc4ccc(CN5CCC[C@H](C(=O)OCC6CNC6)C5)cc4)n3)n2)n1] | azetidin-3-ylmethyl (3S)-1-[[4-[[4-[[2-(6-methyl-2-pyridyl)pyrimidin-4-yl]amino]pyrimidin-2-yl]amino]phenyl]methyl]piperidine-3-carboxylate | 566.1 |
| 68 | 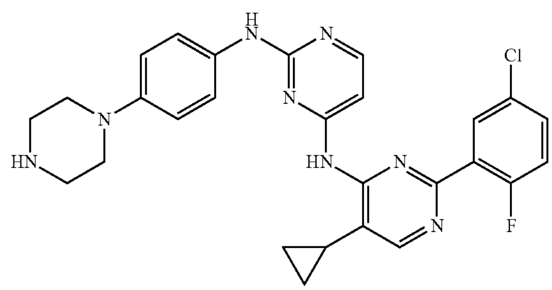 [SMILES: Fc1ccc(Cl)cc1-c1ncc(C2CC2)c(Nc2ccnc(Nc3ccc(N4CCNCC4)cc3)n2)n1] | N4-[2-(5-chloro-2-fluoro-phenyl)-5-cyclopropyl-pyrimidin-4-yl]-N2-(4-piperazin-1-ylphenyl)pyrimidine-2,4-diamine | 517.1 |
| 69 | 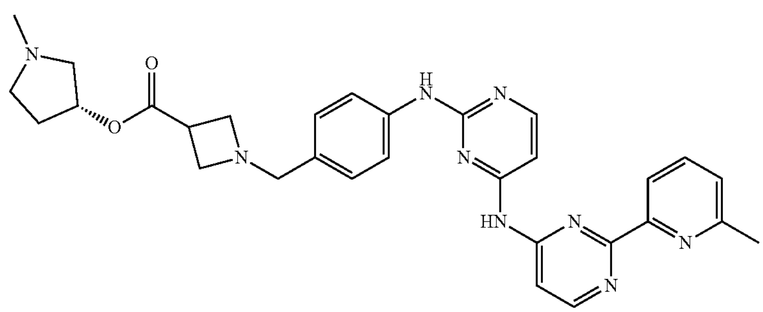 [SMILES: Cc1cccc(-c2nccc(Nc3ccnc(Nc4ccc(CN5CC(C(=O)O[C@@H]6CCN(C)C6)C5)cc4)n3)n2)n1] | [(3R)-1-methylpyrrolidin-3-yl] 1-[[4-[[4-[[2-(6-methyl-2-pyridyl)pyrimidin-4-yl]amino]pyrimidin-2-yl]amino]phenyl]methyl]azetidine-3-carboxylate | 552.1 |
| 70 | 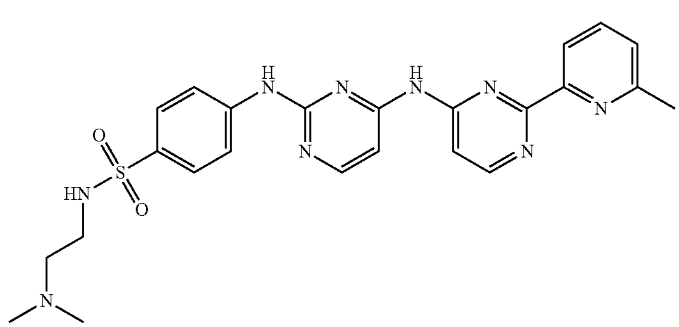 | N-[2-(dimethylamino)ethyl]-4-[[4-[[2-(6-methyl-2-pyridyl)pyrimidin-4-yl]amino]pyrimidin-2-yl]amino]benzenesulfonamide | 506.1 |

TABLE 1-continued

| No. | Structure | Chemical Name | [M + H]+ |
|---|---|---|---|
| 71 | 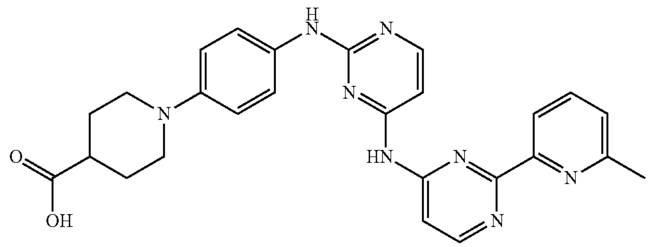 [SMILES: Cc1cccc(-c2nccc(Nc3ccnc(Nc4ccc(N5CCC(C(=O)O)CC5)cc4)n3)n2)n1] | 1-[4-[[4-[[2-(6-methyl-2-pyridyl)pyrimidin-4-yl]amino]pyrimidin-2-yl]amino]phenyl]piperidine-4-carboxylic acid | 482.2 |
| 72 | 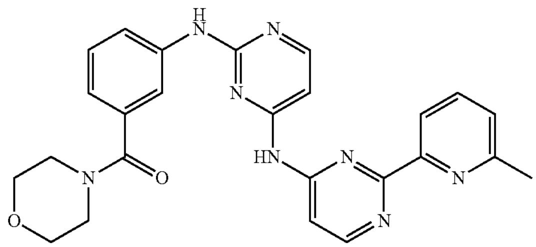 [SMILES: Cc1cccc(-c2nccc(Nc3ccnc(Nc4cccc(C(=O)N5CCOCC5)c4)n3)n2)n1] | [3-[[4-[[2-(6-methyl-2-pyridyl)pyrimidin-4-yl]amino]pyrimidin-2-yl]amino]phenyl]-morpholino-methanone | 469.2 |
| 73 | 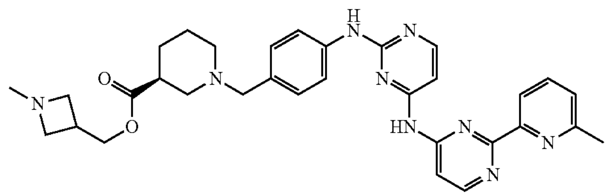 | (1-methylazetidin-3-yl)methyl (3S)-1-[[4-[[4-[[2-(6-methyl-2-pyridyl)pyrimidin-4-yl]amino]pyrimidin-2-yl]amino]phenyl]methyl]piperidine-3-carboxylate | 580.2 |
| 74 | 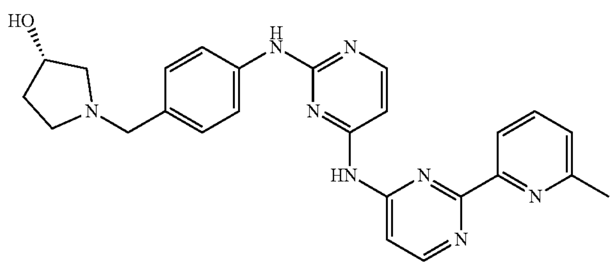 [SMILES: Cc1cccc(-c2nccc(Nc3ccnc(Nc4ccc(CN5CC[C@H](O)C5)cc4)n3)n2)n1] | (3S)-1-[[4-[[4-[[2-(6-methyl-2-pyridyl)pyrimidin-4-yl]amino]pyrimidin-2-yl]amino]phenyl]methyl]pyrrolidin-3-ol | 455.1 |
| 75 | 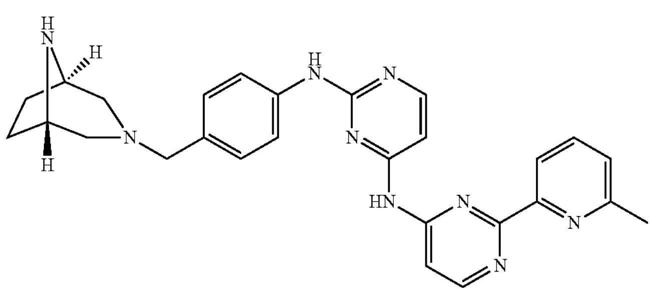 [SMILES: Cc1cccc(-c2nccc(Nc3ccnc(Nc4ccc(CN5C[C@H]6CC[C@@H](C5)N6)cc4)n3)n2)n1] | N4-[2-(6-methyl-2-pyridyl)pyrimidin-4-yl]-N2-[4-[[rac-(1S,5R)-3,8-diazabicyclo[3.2.1]octan-3-yl]methyl]phenyl]pyrimidine-2,4-diamine | 480.2 |
| 76 | 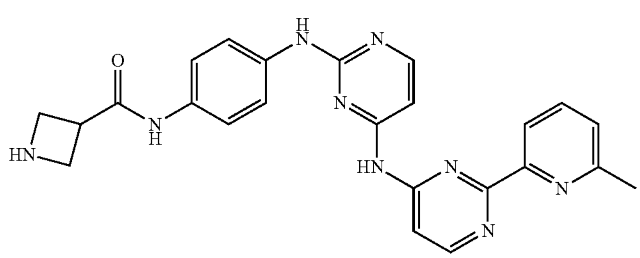 [SMILES: Cc1cccc(-c2nccc(Nc3ccnc(Nc4ccc(NC(=O)C5CNC5)cc4)n3)n2)n1] | N-[4-[[4-[[2-(6-methyl-2-pyridyl)pyrimidin-4-yl]amino]pyrimidin-2-yl]amino]phenyl]azetidine-3-carboxamide | 454.1 |

TABLE 1-continued

| No. | Structure | Chemical Name | [M + H]+ |
|---|---|---|---|
| 77 | 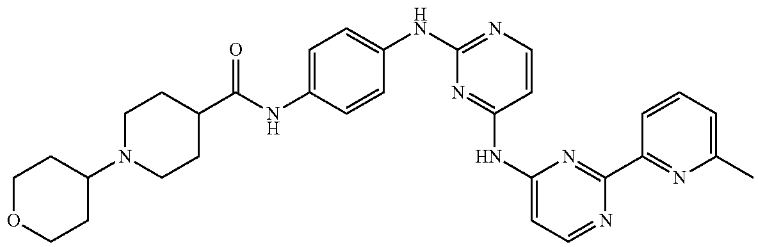 [SMILES: Cc1cccc(-c2nccc(Nc3ccnc(Nc4ccc(NC(=O)C5CCN(C6CCOCC6)CC5)cc4)n3)n2)n1] | N-[4-[[4-[[2-(6-methyl-2-pyridyl)pyrimidin-4-yl]amino]pyrimidin-2-yl]amino]phenyl]-1-tetrahydropyran-4-yl-piperidine-4-carboxamide | 566.2 |
| 78 | 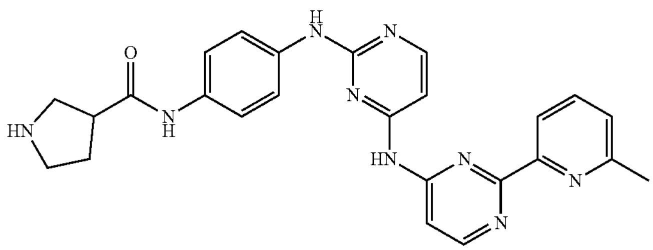 [SMILES: Cc1cccc(-c2nccc(Nc3ccnc(Nc4ccc(NC(=O)C5CCNC5)cc4)n3)n2)n1] | N-[4-[[4-[[2-(6-methyl-2-pyridyl)pyrimidin-4-yl]amino]pyrimidin-2-yl]amino]phenyl]pyrrolidine-3-carboxamide | 468.0 |
| 79 | 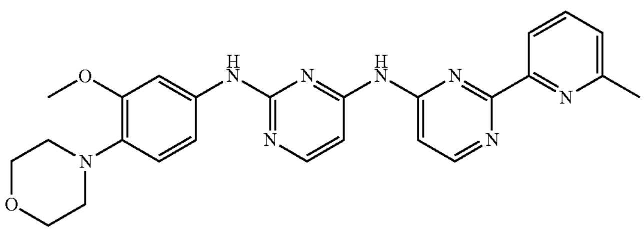 [SMILES: COc1cc(Nc2nccc(Nc3ccnc(-c4cccc(C)n4)n3)n2)ccc1N1CCOCC1] | N2-(3-methoxy-4-morpholino-phenyl)-N4-[2-(6-methyl-2-pyridyl)pyrimidin-4-yl]pyrimidine-2,4-diamine | 471.2 |
| 80 | 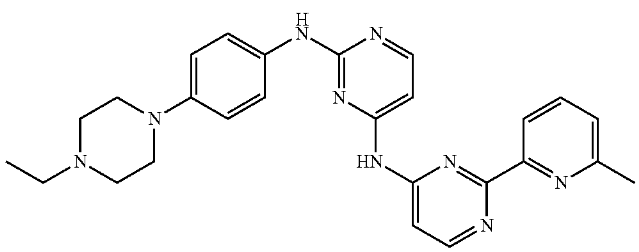 [SMILES: CCN1CCN(c2ccc(Nc3nccc(Nc4ccnc(-c5cccc(C)n5)n4)n3)cc2)CC1] | N2-[4-(4-ethylpiperazin-1-yl)phenyl]-N4-[2-(6-methyl-2-pyridyl)pyrimidin-4-yl]pyrimidine-2,4-diamine | 468.2 |
| 81 | 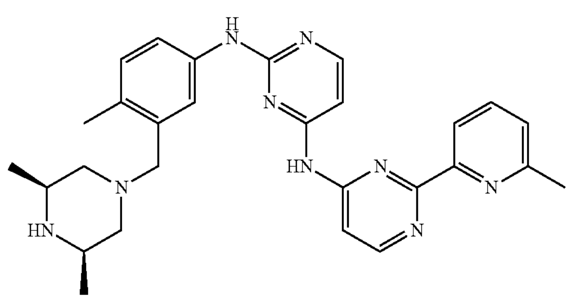 | N4-[2-(6-methyl-2-pyridyl)pyrimidin-4-yl]-N2-[4-methyl-3-[[rac-(3R,5S)-3,5-dimethylpiperazin-1-yl]methyl]phenyl]pyrimidine-2,4-diamine | 496.1 |
| 82 | 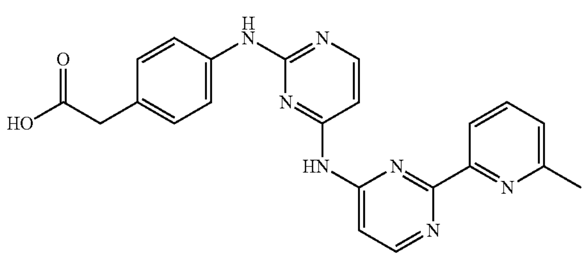 [SMILES: Cc1cccc(-c2nccc(Nc3ccnc(Nc4ccc(CC(=O)O)cc4)n3)n2)n1] | 2-[4-[[4-[[2-(6-methyl-2-pyridyl)pyrimidin-4-yl]amino]pyrimidin-2-yl]amino]phenyl]acetic acid | 414.1 |

TABLE 1-continued

| No. | Structure | Chemical Name | [M + H]+ |
|---|---|---|---|
| 83 | 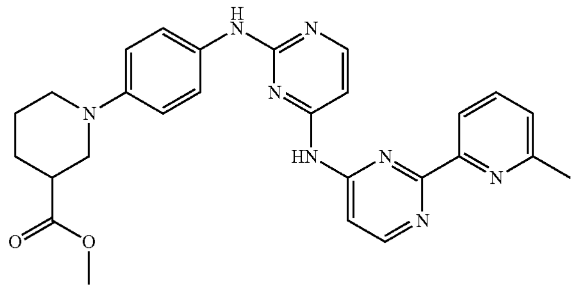 [SMILES: COC(=O)C1CCCN(c2ccc(Nc3nccc(Nc4ccnc(-c5cccc(C)n5)n4)n3)cc2)C1] | methyl 1-[4-[[4-[[2-(6-methyl-2-pyridyl)pyrimidin-4-yl]amino]pyrimidin-2-yl]amino]phenyl]piperidine-3-carboxylate | 497.1 |
| 84 | 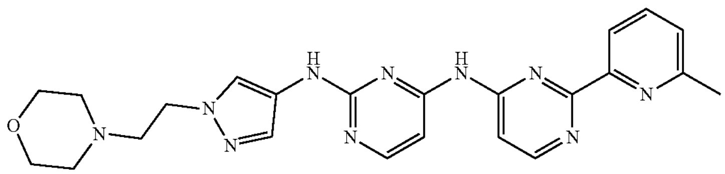 [SMILES: Cc1cccc(-c2nccc(Nc3ccnc(Nc4cnn(CCN5CCOCC5)c4)n3)n2)n1] | N4-[2-(6-methyl-2-pyridyl)pyrimidin-4-yl]-N2-[1-(2-morpholinoethyl)pyrazol-4-yl]pyrimidine-2,4-diamine | 459.2 |
| 85 | 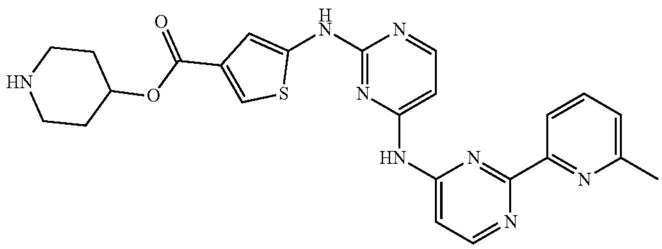 [SMILES: Cc1cccc(-c2nccc(Nc3ccnc(Nc4cc(C(=O)OC5CCNCC5)cs4)n3)n2)n1] | 4-piperidyl 5-[[4-[[2-(6-methyl-2-pyridyl)pyrimidin-4-yl]amino]pyrimidin-2-yl]amino]thiophene-3-carboxylate | 489.1 |
| 86 | 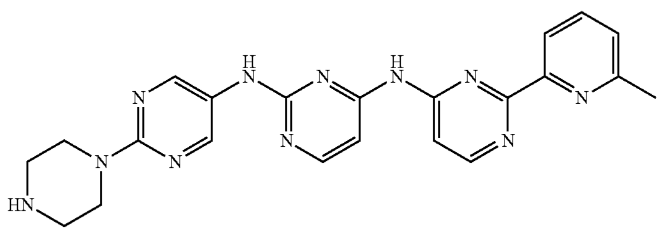 [SMILES: Cc1cccc(-c2nccc(Nc3ccnc(Nc4cnc(N5CCNCC5)nc4)n3)n2)n1] | N4-[2-(6-methyl-2-pyridyl)pyrimidin-4-yl]-N2-(2-piperazin-1-ylpyrimidin-5-yl)pyrimidine-2,4-diamine | 442.2 |
| 87 | 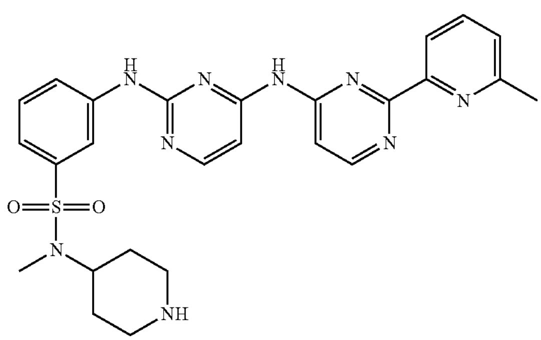 [SMILES: Cc1cccc(-c2nccc(Nc3ccnc(Nc4cccc(S(=O)(=O)N(C)C5CCNCC5)c4)n3)n2)n1] | N-methyl-3-[[4-[[2-(6-methyl-2-pyridyl)pyrimidin-4-yl]amino]pyrimidin-2-yl]amino]-N-(4-piperidyl)benzenesulfonamide | 532.2 |
| 88 | 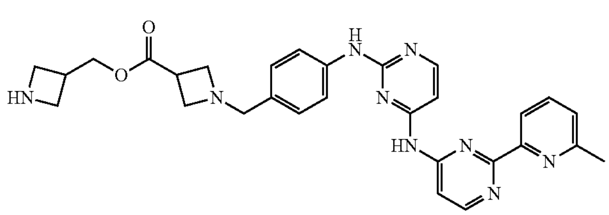 [SMILES: Cc1cccc(-c2nccc(Nc3ccnc(Nc4ccc(CN5CC(C(=O)OCC6CNC6)C5)cc4)n3)n2)n1] | azetidin-3-ylmethyl 1-[[4-[[4-[[2-(6-methyl-2-pyridyl)pyrimidin-4-yl]amino]pyrimidin-2-yl]amino]phenyl]methyl]azetidine-3-carboxylate | 538.2 |

TABLE 1-continued

| No. | Structure | Chemical Name | [M + H]+ |
|---|---|---|---|
| 89 | 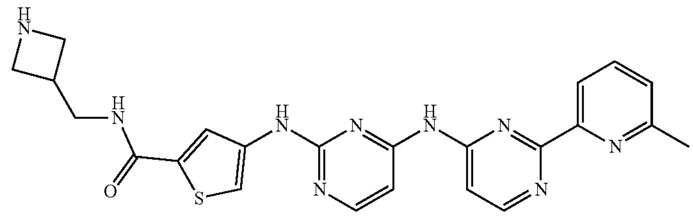 [SMILES: Cc1cccc(-c2nccc(Nc3ccnc(Nc4csc(C(=O)NCC5CNC5)c4)n3)n2)n1] | N-(azetidin-3-ylmethyl)-4-[[4-[[2-(6-methyl-2-pyridyl)pyrimidin-4-yl]amino]pyrimidin-2-yl]amino]thiophene-2-carboxamide | 474.0 |
| 90 | 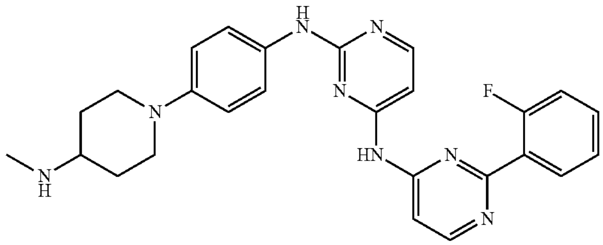 [SMILES: CNC1CCN(c2ccc(Nc3nccc(Nc4ccnc(-c5ccccc5F)n4)n3)cc2)CC1] | N4-[2-(2-fluorophenyl)pyrimidin-4-yl]-N2-[4-[4-(methylamino)-1-piperidyl]phenyl]pyrimidine-2,4-diamine | 471.1 |
| 91 | 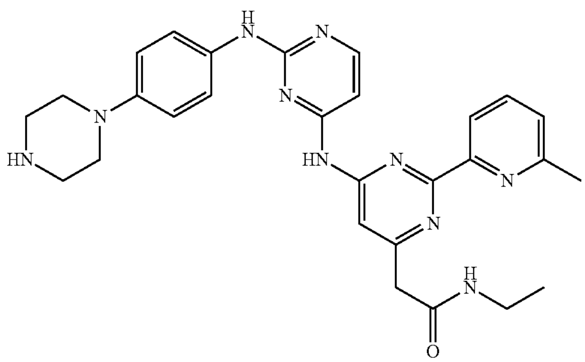 [SMILES: CCNC(=O)Cc1cc(Nc2ccnc(Nc3ccc(N4CCNCC4)cc3)n2)nc(-c2cccc(C)n2)n1] | N-ethyl-2-[2-(6-methyl-2-pyridyl)-6-[[2-(4-piperazin-1-ylanilino)pyrimidin-4-yl]amino]pyrimidin-4-yl]acetamide | 525.1 |
| 92 | 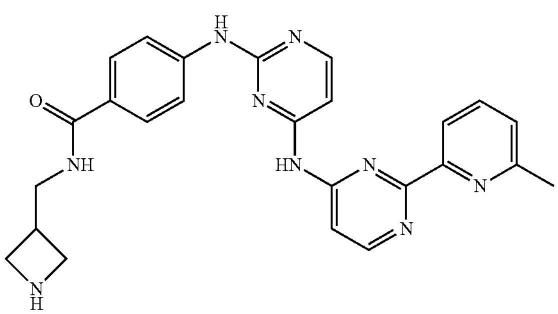 [SMILES: Cc1cccc(-c2nccc(Nc3ccnc(Nc4ccc(C(=O)NCC5CNC5)cc4)n3)n2)n1] | N-(azetidin-3-ylmethyl)-4-[[4-[[2-(6-methyl-2-pyridyl)pyrimidin-4-yl]amino]pyrimidin-2-yl]amino]benzamide | 468.1 |
| 93 | 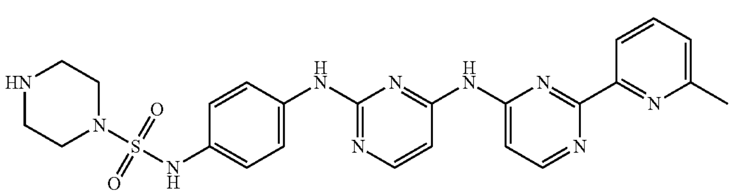 [SMILES: Cc1cccc(-c2nccc(Nc3ccnc(Nc4ccc(NS(=O)(=O)N5CCNCC5)cc4)n3)n2)n1] | N-[4-[[4-[[2-(6-methyl-2-pyridyl)pyrimidin-4-yl]amino]pyrimidin-2-yl]amino]phenyl]piperazine-1-sulfonamide | 519.1 |
| 94 | 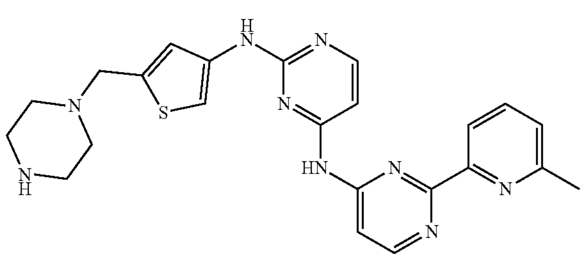 [SMILES: Cc1cccc(-c2nccc(Nc3ccnc(Nc4csc(CN5CCNCC5)c4)n3)n2)n1] | N4-[2-(6-methyl-2-pyridyl)pyrimidin-4-yl]-N2-[5-(piperazin-1-ylmethyl)-3-thienyl]pyrimidine-2,4-diamine | 460.2 |

TABLE 1-continued

| No. | Structure | Chemical Name | [M + H]+ |
|---|---|---|---|
| 95 | 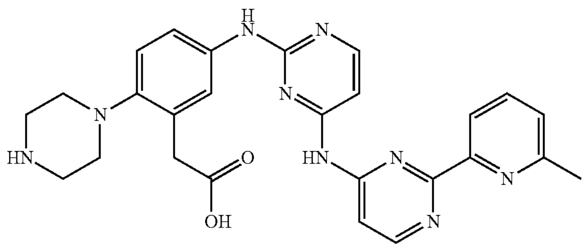 [SMILES: Cc1cccc(-c2nccc(Nc3ccnc(Nc4ccc(N5CCNCC5)c(CC(=O)O)c4)n3)n2)n1] | 2-[5-[[4-[[2-(6-methyl-2-pyridyl)pyrimidin-4-yl]amino]pyrimidin-2-yl]amino]-2-piperazin-1-yl-phenyl]acetic acid | 498.4 |
| 96 | 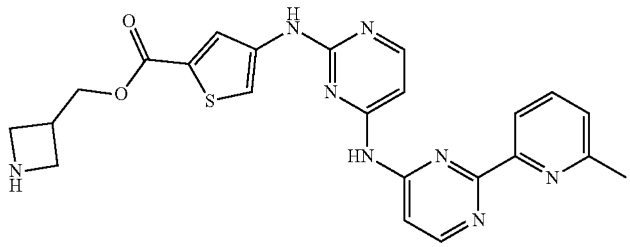 [SMILES: Cc1cccc(-c2nccc(Nc3ccnc(Nc4csc(C(=O)OCC5CNC5)c4)n3)n2)n1] | azetidin-3-ylmethyl 4-[[4-[[2-(6-methyl-2-pyridyl)pyrimidin-4-yl]amino]pyrimidin-2-yl]amino]thiophene-2-carboxylate | 475.1 |
| 97 | 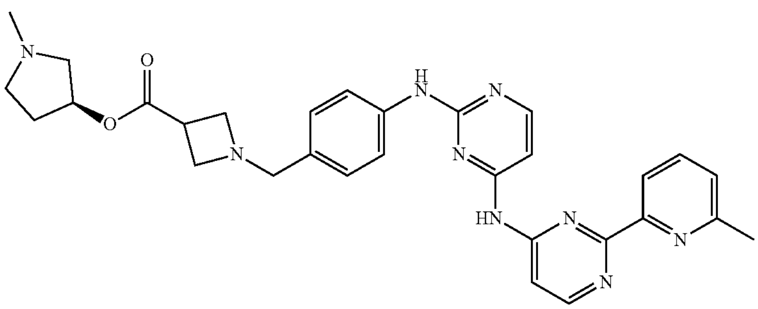 [SMILES: Cc1cccc(-c2nccc(Nc3ccnc(Nc4ccc(CN5CC(C(=O)O[C@H]6CCN(C)C6)C5)cc4)n3)n2)n1] | [(3S)-1-methylpyrrolidin-3-yl] 1-[[4-[[4-[[2-(6-methyl-2-pyridyl)pyrimidin-4-yl]amino]pyrimidin-2-yl]amino]phenyl]methyl]azetidine-3-carboxylate | 552.1 |
| 98 | 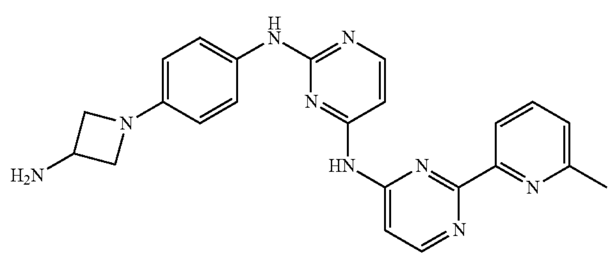 [SMILES: Cc1cccc(-c2nccc(Nc3ccnc(Nc4ccc(N5CC(N)C5)cc4)n3)n2)n1] | N2-[4-(3-aminoazetidin-1-yl)phenyl]-N4-[2-(6-methyl-2-pyridyl)pyrimidin-4-yl]pyrimidine-2,4-diamine | 426.1 |
| 99 | 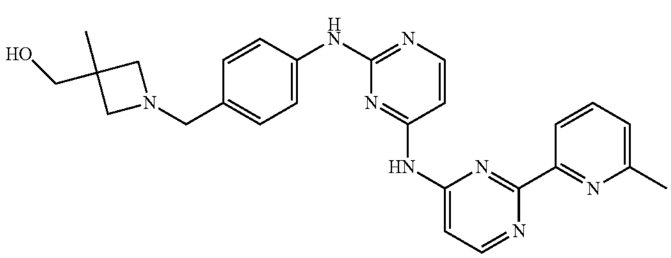 [SMILES: Cc1cccc(-c2nccc(Nc3ccnc(Nc4ccc(CN5CC(C)(CO)C5)cc4)n3)n2)n1] | [3-methyl-1-[[4-[[4-[[2-(6-methyl-2-pyridyl)pyrimidin-4-yl]amino]pyrimidin-2-yl]amino]phenyl]methyl]azetidin-3-yl]methanol | 469.2 |
| 100 | 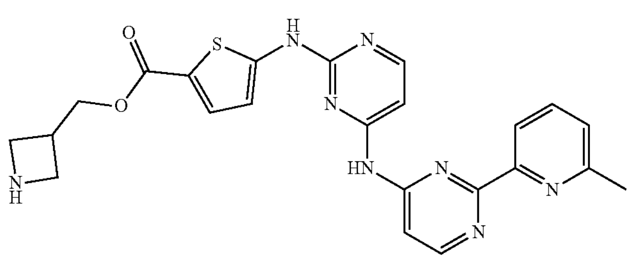 [SMILES: Cc1cccc(-c2nccc(Nc3ccnc(Nc4ccc(C(=O)OCC5CNC5)s4)n3)n2)n1] | azetidin-3-ylmethyl 5-[[4-[[2-(6-methyl-2-pyridyl)pyrimidin-4-yl]amino]pyrimidin-2-yl]amino]thiophene-2-carboxylate | 475.0 |

TABLE 1-continued

| No. | Structure | Chemical Name | [M + H]+ |
|---|---|---|---|
| 101 | 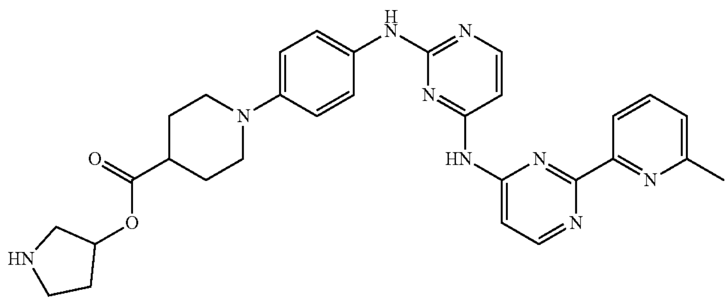 [SMILES: Cc1cccc(-c2nccc(Nc3ccnc(Nc4ccc(N5CCC(C(=O)OC6CCNC6)CC5)cc4)n3)n2)n1] | pyrrolidin-3-yl 1-[4-[[4-[[2-(6-methyl-2-pyridyl)pyrimidin-4-yl]amino]pyrimidin-2-yl]amino]phenyl]piperidine-4-carboxylate | 552.2 |
| 102 | 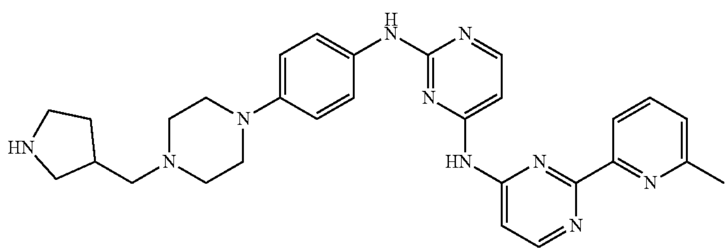 [SMILES: Cc1cccc(-c2nccc(Nc3ccnc(Nc4ccc(N5CCN(CC6CCNC6)CC5)cc4)n3)n2)n1] | N4-[2-(6-methyl-2-pyridyl)pyrimidin-4-yl]-N2-[4-[4-(pyrrolidin-3-ylmethyl)piperazin-1-yl]phenyl]pyrimidine-2,4-diamine | 523.1 |
| 103 | AND Enantiomer | [rac-(3R)-1-methylpyrrolidin-3-yl] 2-[1-[4-[[4-[[2-(6-methyl-2-pyridyl)pyrimidin-4-yl]amino]pyrimidin-2-yl]amino]phenyl]piperazin-2-yl]acetate | 581.1 |
| 104 | 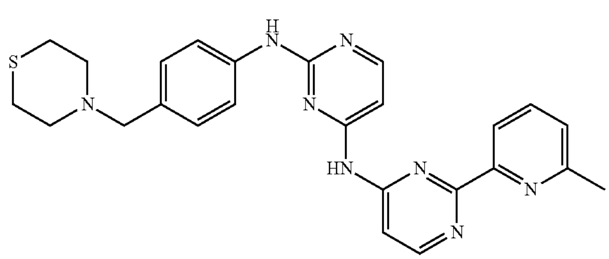 [SMILES: Cc1cccc(-c2nccc(Nc3ccnc(Nc4ccc(CN5CCSCC5)cc4)n3)n2)n1] | N4-[2-(6-methyl-2-pyridyl)pyrimidin-4-yl]-N2-[4-(thiomorpholinomethyl)phenyl]pyrimidine-2,4-diamine | 471.1 |
| 105 | AND Enantiomer | [rac-(3R)-pyrrolidin-3-yl] 1-[[4-[[4-[[2-(6-methyl-2-pyridyl)pyrimidin-4-yl]amino]pyrimidin-2-yl]amino]phenyl]methyl]piperidine-3-carboxylate | 566.2 |

TABLE 1-continued

| No. | Structure | Chemical Name | [M + H]+ |
|---|---|---|---|
| 106 | 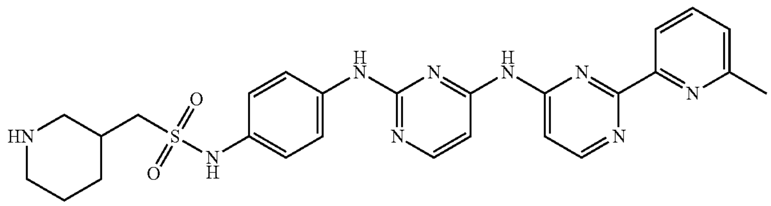 [SMILES: Cc1cccc(-c2nccc(Nc3ccnc(Nc4ccc(NS(=O)(=O)CC5CCCNC5)cc4)n3)n2)n1] | N-[4-[[4-[[2-(6-methyl-2-pyridyl)pyrimidin-4-yl]amino]pyrimidin-2-yl]amino]phenyl]-1-(3-piperidyl)methanesulfonamide | 532.1 |
| 107 | 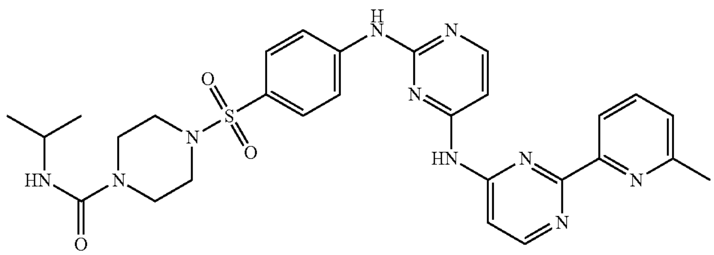 [SMILES: Cc1cccc(-c2nccc(Nc3ccnc(Nc4ccc(S(=O)(=O)N5CCN(C(=O)NC(C)C)CC5)cc4)n3)n2)n1] | N-isopropyl-4-[4-[[4-[[2-(6-methyl-2-pyridyl)pyrimidin-4-yl]amino]pyrimidin-2-yl]amino]phenyl]sulfonyl-piperazine-1-carboxamide | 589.1 |
| 108 | 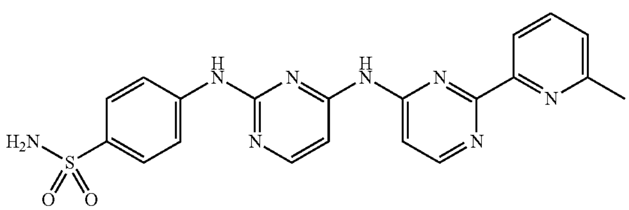 [SMILES: Cc1cccc(-c2nccc(Nc3ccnc(Nc4ccc(S(N)(=O)=O)cc4)n3)n2)n1] | 4-[[4-[[2-(6-methyl-2-pyridyl)pyrimidin-4-yl]amino]pyrimidin-2-yl]amino]benzenesulfonamide | 435.0 |
| 109 | 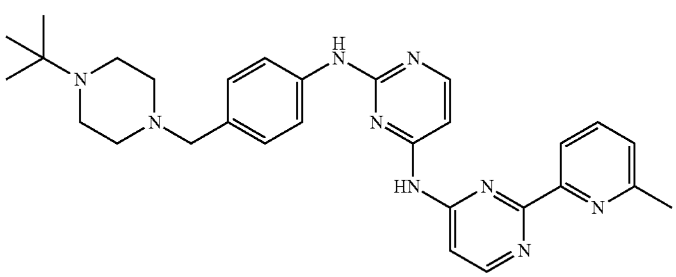 [SMILES: Cc1cccc(-c2nccc(Nc3ccnc(Nc4ccc(CN5CCN(C(C)(C)C)CC5)cc4)n3)n2)n1] | N2-[4-[(4-tert-butylpiperazin-1-yl)methyl]phenyl]-N4-[2-(6-methyl-2-pyridyl)pyrimidin-4-yl]pyrimidine-2,4-diamine | 510.3 |
| 110 | 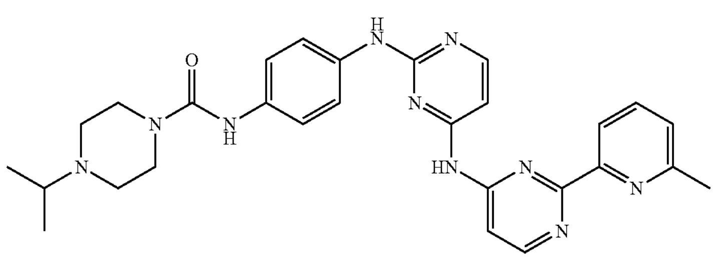 [SMILES: Cc1cccc(-c2nccc(Nc3ccnc(Nc4ccc(NC(=O)N5CCN(C(C)C)CC5)cc4)n3)n2)n1] | 4-isopropyl-N-[4-[[4-[[2-(6-methyl-2-pyridyl)pyrimidin-4-yl]amino]pyrimidin-2-yl]amino]phenyl]piperazine-1-carboxamide | 525.2 |
| 111 | 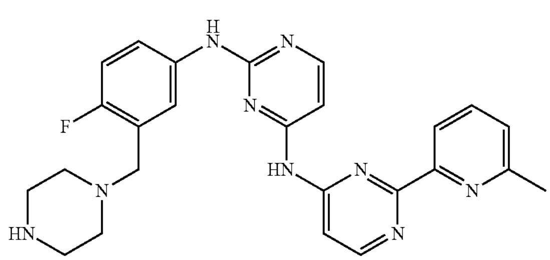 [SMILES: Cc1cccc(-c2nccc(Nc3ccnc(Nc4ccc(F)c(CN5CCNCC5)c4)n3)n2)n1] | N2-[4-fluoro-3-(piperazin-1-ylmethyl)phenyl]-N4-[2-(6-methyl-2-pyridyl)pyrimidin-4-yl]pyrimidine-2,4-diamine | 472.2 |

TABLE 1-continued

| No. | Structure | Chemical Name | [M + H]+ |
|---|---|---|---|
| 112 | 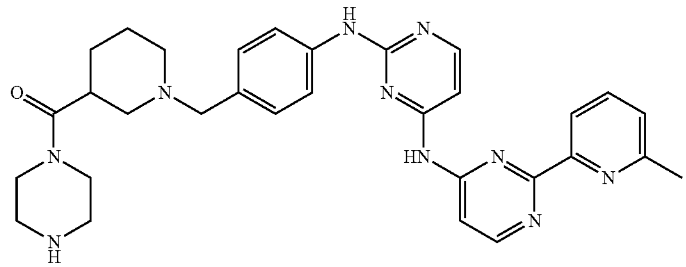 [SMILES: Cc1cccc(-c2nccc(Nc3ccnc(Nc4ccc(CN5CCCC(C(=O)N6CCNCC6)C5)cc4)n3)n2)n1] | [1-[[4-[[4-[[2-(6-methyl-2-pyridyl)pyrimidin-4-yl]amino]pyrimidin-2-yl]amino]phenyl]methyl]-3-piperidyl]-piperazin-1-yl-methanone | 565.1 |
| 113 | 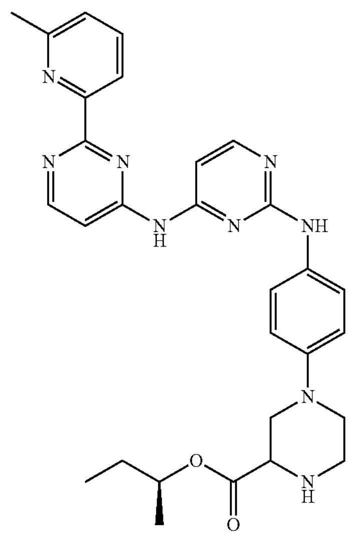 [SMILES: CC[C@H](C)OC(=O)C1CN(c2ccc(Nc3nccc(Nc4ccnc(-c5cccc(C)n5)n4)n3)cc2)CCN1] | [(1S)-1-methylpropyl] 4-[4-[[4-[[2-(6-methyl-2-pyridyl)pyrimidin-4-yl]amino]pyrimidin-2-yl]amino]phenyl]piperazine-2-carboxylate | 540.2 |
| 114 | 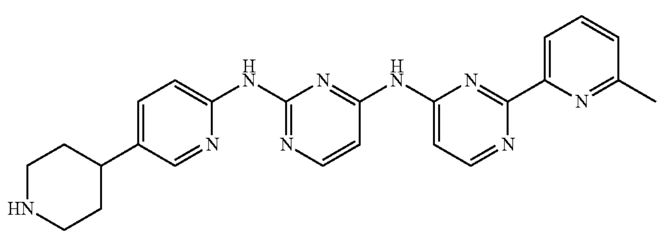 [SMILES: Cc1cccc(-c2nccc(Nc3ccnc(Nc4ccc(C5CCNCC5)cn4)n3)n2)n1] | N4-[2-(6-methyl-2-pyridyl)pyrimidin-4-yl]-N2-[5-(4-piperidyl)-2-pyridyl]pyrimidine-2,4-diamine | 440.3 |
| 115 | 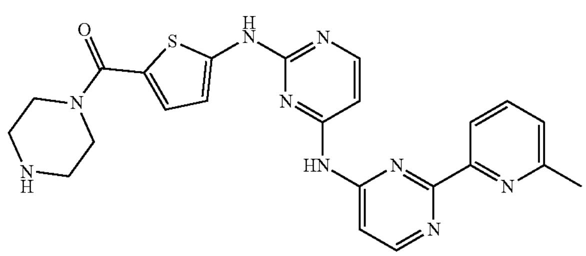 [SMILES: Cc1cccc(-c2nccc(Nc3ccnc(Nc4ccc(C(=O)N5CCNCC5)s4)n3)n2)n1] | [5-[[4-[[2-(6-methyl-2-pyridyl)pyrimidin-4-yl]amino]pyrimidin-2-yl]amino]-2-thienyl]-piperazin-1-yl-methanone | 474.1 |
| 116 | 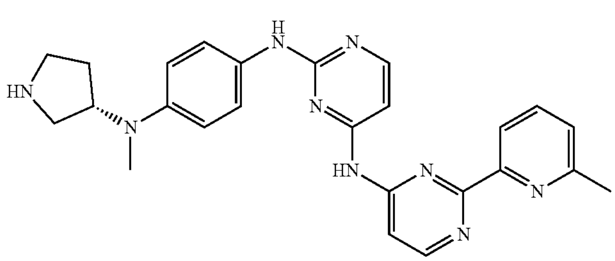 | N4-[2-(6-methyl-2-pyridyl)pyrimidin-4-yl]-N2-[4-[methyl-[(3S)-pyrrolidin-3-yl]amino]phenyl]pyrimidine-2,4-diamine | 454.3 |

TABLE 1-continued

| No. | Structure | Chemical Name | [M + H]+ |
|---|---|---|---|
| 117 | 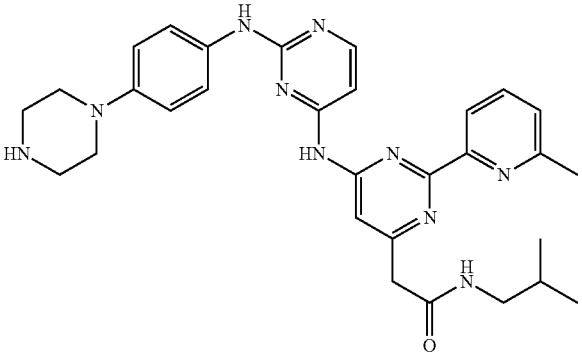 [SMILES: Cc1cccc(-c2nc(CC(=O)NCC(C)C)cc(Nc3ccnc(Nc4ccc(N5CCNCC5)cc4)n3)n2)n1] | N-isobutyl-2-[2-[(6-methyl-2-pyridyl)-6-[[2-(4-piperazin-1-ylanilino)pyrimidin-4-yl]amino]pyrimidin-4-yl]acetamide | 553.2 |
| 118 | 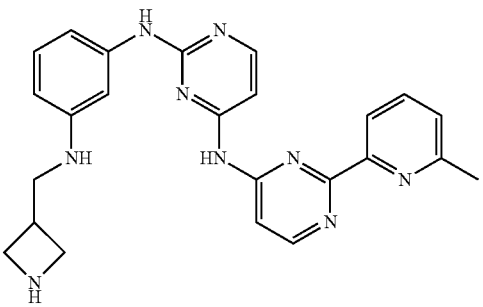 [SMILES: Cc1cccc(-c2nccc(Nc3ccnc(Nc4cccc(NCC5CNC5)c4)n3)n2)n1] | N2-[3-(azetidin-3-ylmethylamino)phenyl]-N4-[2-(6-methyl-2-pyridyl)pyrimidin-4-yl]pyrimidine-2,4-diamine | 440.4 |
| 119 | 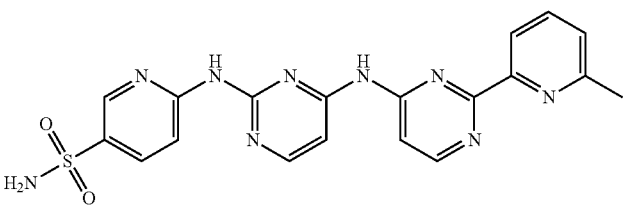 [SMILES: Cc1cccc(-c2nccc(Nc3ccnc(Nc4ccc(S(N)(=O)=O)cn4)n3)n2)n1] | 6-[[4-[[2-(6-methyl-2-pyridyl)pyrimidin-4-yl]amino]pyrimidin-2-yl]amino]pyridine-3-sulfonamide | 436.0 |
| 120 | 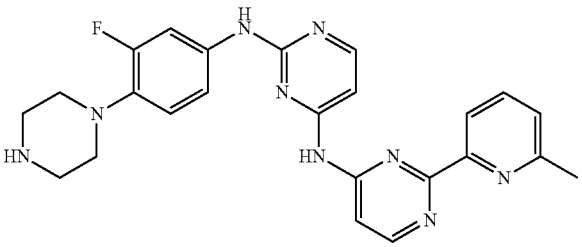 | N2-(3-fluoro-4-piperazin-1-yl-phenyl)-N4-[2-(6-methyl-2-pyridyl)pyrimidin-4-yl]pyrimidine-2,4-diamine | 458.1 |
| 121 | 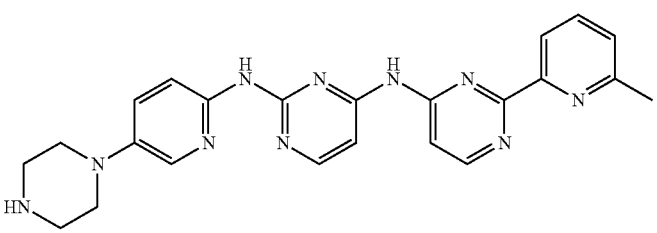 [SMILES: Cc1cccc(-c2nccc(Nc3ccnc(Nc4ccc(N5CCNCC5)cn4)n3)n2)n1] | N4-[2-(6-methyl-2-pyridyl)pyrimidin-4-yl]-N2-(5-piperazin-1-yl-2-pyridyl)pyrimidine-2,4-diamine | 441.3 |

TABLE 1-continued

| No. | Structure | Chemical Name | [M + H]+ |
|---|---|---|---|
| 122 | 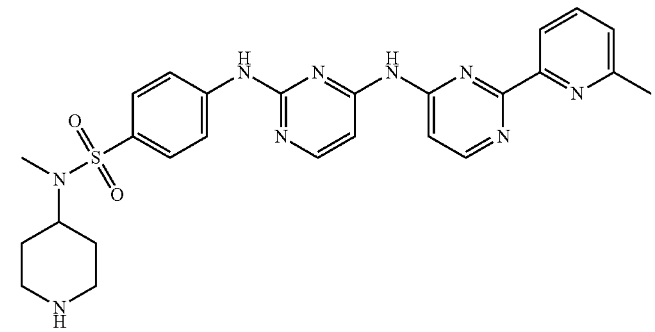 | N-methyl-4-[[4-[[2-(6-methyl-2-pyridyl)pyrimidin-4-yl]amino]pyrimidin-2-yl]amino]-N-(4-piperidyl)benzenesulfonamide | 532.2 |
| 123 | 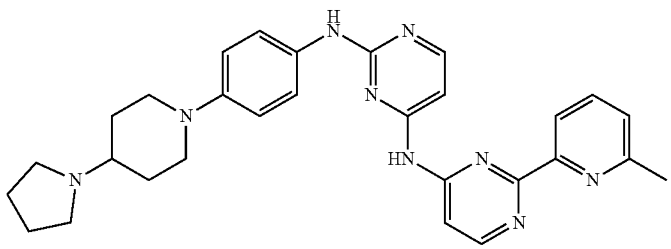 [SMILES: Cc1cccc(-c2nccc(Nc3ccnc(Nc4ccc(N5CCC(N6CCCC6)CC5)cc4)n3)n2)n1] | N4-[2-(6-methyl-2-pyridyl)pyrimidin-4-yl]-N2-[4-(4-pyrrolidin-1-yl-1-piperidyl)phenyl]pyrimidine-2,4-diamine | 508.2 |
| 124 | 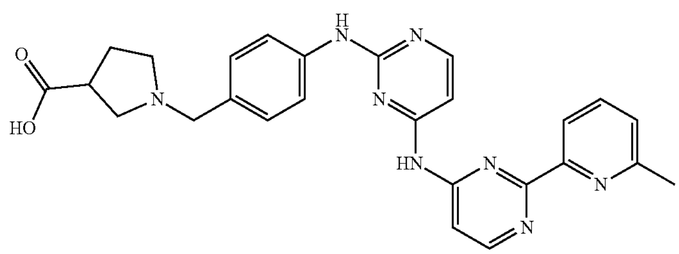 [SMILES: Cc1cccc(-c2nccc(Nc3ccnc(Nc4ccc(CN5CCC(C(=O)O)C5)cc4)n3)n2)n1] | 1-[[4-[[4-[[2-(6-methyl-2-pyridyl)pyrimidin-4-yl]amino]pyrimidin-2-yl]amino]phenyl]methyl]pyrrolidine-3-carboxylic acid | 483.0 |
| 125 | 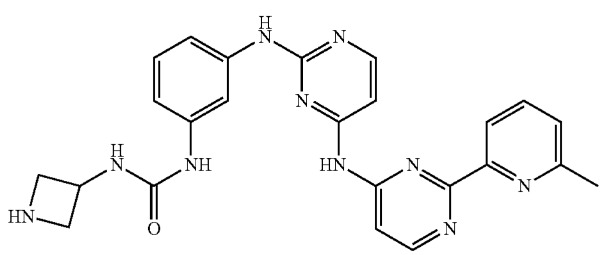 [SMILES: Cc1cccc(-c2nccc(Nc3ccnc(Nc4cccc(NC(=O)NC5CNC5)c4)n3)n2)n1] | 1-(azetidin-3-yl)-3-[3-[[4-[[2-(6-methyl-2-pyridyl)pyrimidin-4-yl]amino]pyrimidin-2-yl]amino]phenyl]urea | 469.1 |
| 126 | 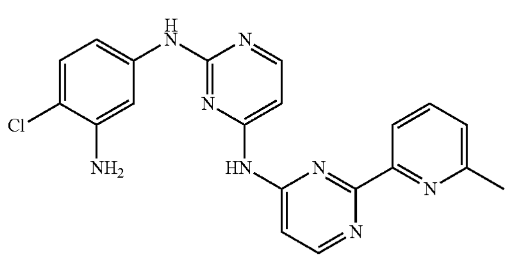 [SMILES: Cc1cccc(-c2nccc(Nc3ccnc(Nc4ccc(Cl)c(N)c4)n3)n2)n1] | N2-(3-amino-4-chloro-phenyl)-N4-[2-(6-methyl-2-pyridyl)pyrimidin-4-yl]pyrimidine-2,4-diamine | 405.0 |

TABLE 1-continued

| No. | Structure | Chemical Name | [M + H]+ |
|---|---|---|---|
| 127 | 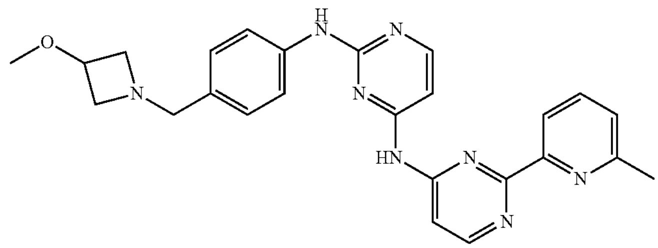 | N2-[4-[(3-methoxyazetidin-1-yl)methyl]phenyl]-N4-[2-(6-methyl-2-pyridyl)pyrimidin-4-yl]pyrimidine-2,4-diamine | 455.2 |
| 128 | 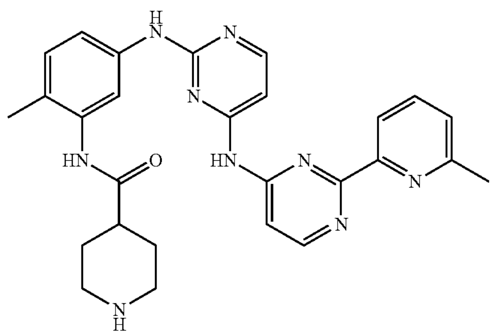 | N-[2-methyl-5-[[4-[[2-(6-methyl-2-pyridyl)pyrimidin-4-yl]amino]pyrimidin-2-yl]amino]phenyl]piperidine-4-carboxamide | 496.2 |
| 129 | 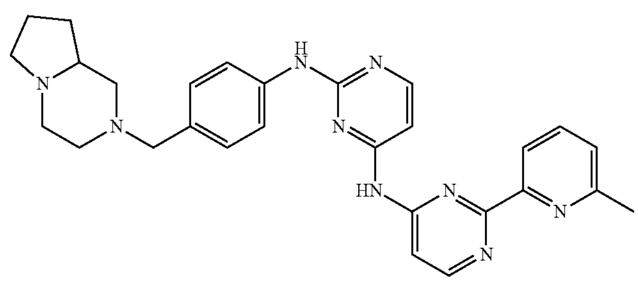 [SMILES: Cc1cccc(-c2nccc(Nc3ccnc(Nc4ccc(CN5CCN6CCCC6C5)cc4)n3)n2)n1] | N2-[4-(3,4,6,7,8,8a-hexahydro-1H-pyrrolo[1,2-a]pyrazin-2-ylmethyl]phenyl]-N4-[2-(6-methyl-2-pyridyl)pyrimidin-4-yl]pyrimidine-2,4-diamine | 494.2 |
| 130 | 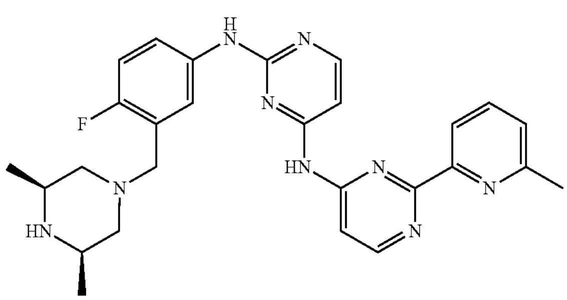 | N2-[4-fluoro-3-[[rac-(3R,5S)-3,5-dimethylpiperazin-1-yl]methyl]phenyl]-N4-[2-(6-methyl-2-pyridyl)pyrimidin-4-yl]pyrimidine-2,4-diamine | 500.1 |
| 131 | 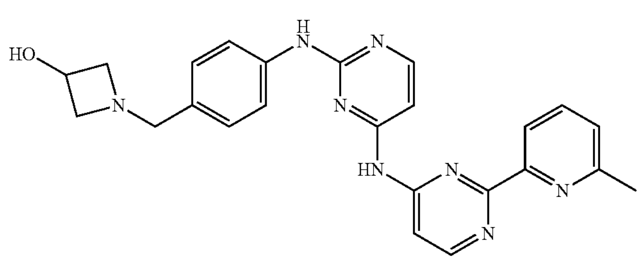 [SMILES: Cc1cccc(-c2nccc(Nc3ccnc(Nc4ccc(CN5CC(O)C5)cc4)n3)n2)n1] | 1-[[4-[[4-[[2-(6-methyl-2-pyridyl)pyrimidin-4-yl]amino]pyrimidin-2-yl]amino]phenyl]methyl]azetidin-3-ol | 441.1 |

TABLE 1-continued

| No. | Structure | Chemical Name | [M + H]+ |
|---|---|---|---|
| 132 | 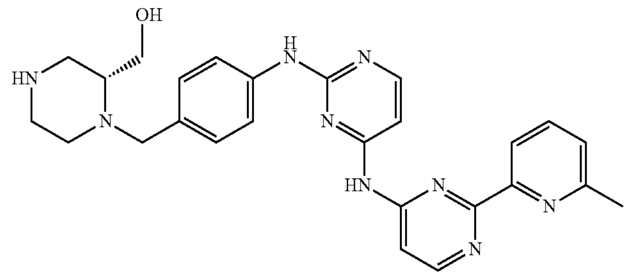 [SMILES: Cc1cccc(-c2nccc(Nc3ccnc(Nc4ccc(CN5CCNC[C@@H]5CO)cc4)n3)n2)n1] | [(2R)-1-[[4-[[4-[[2-(6-methyl-2-pyridyl)pyrimidin-4-yl]amino]pyrimidin-2-yl]amino]phenyl]methyl]piperazin-2-yl]methanol | 484.1 |
| 133 | 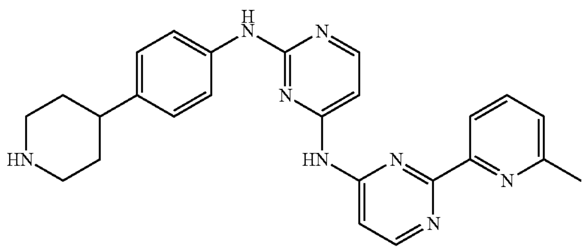 [SMILES: Cc1cccc(-c2nccc(Nc3ccnc(Nc4ccc(C5CCNCC5)cc4)n3)n2)n1] | N4-[2-(6-methyl-2-pyridyl)pyrimidin-4-yl]-N2-[4-(4-piperidyl)phenyl]pyrimidine-2,4-diamine | 439.2 |
| 134 | 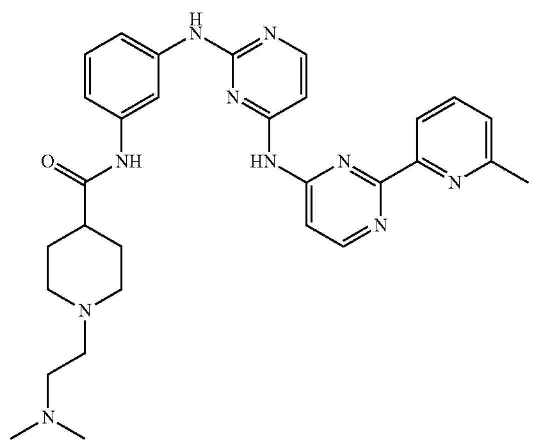 | 1-[2-(dimethylamino)ethyl]-N-[3-[[4-[[2-(6-methyl-2-pyridyl)pyrimidin-4-yl]amino]pyrimidin-2-yl]amino]phenyl]piperidine-4-carboxamide | 553.3 |
| 135 | 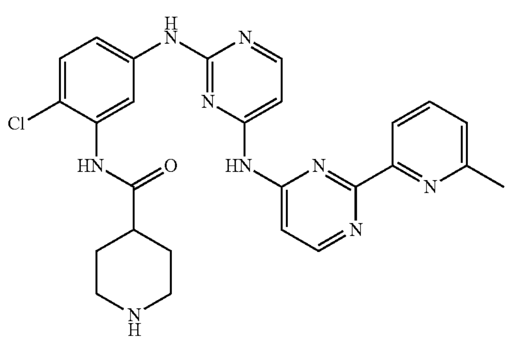 [SMILES: Cc1cccc(-c2nccc(Nc3ccnc(Nc4ccc(Cl)c(NC(=O)C5CCNCC5)c4)n3)n2)n1] | N-[2-chloro-5-[[4-[[2-(6-methyl-2-pyridyl)pyrimidin-4-yl]amino]pyrimidin-2-yl]amino]phenyl]piperidine-4-carboxamide | 516.2 |
| 136 | 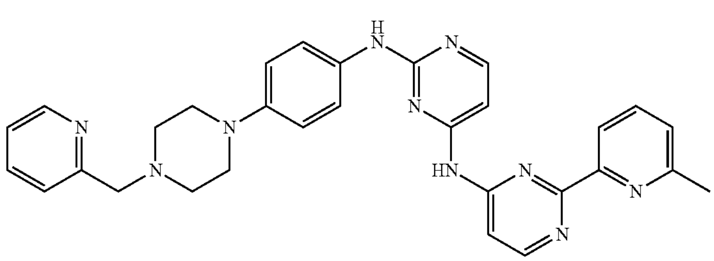 | N4-[2-(6-methyl-2-pyridyl)pyrimidin-4-yl]-N2-[4-[4-(2-pyridylmethyl)piperazin-1-yl]phenyl]pyrimidine-2,4-diamine | 531.1 |

TABLE 1-continued

| No. | Structure | Chemical Name | [M + H]+ |
|---|---|---|---|
| 137 | 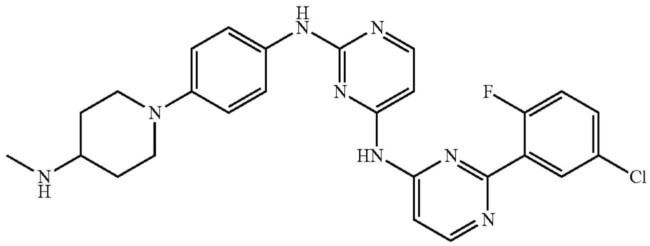 [SMILES: CNC1CCN(c2ccc(Nc3nccc(Nc4ccnc(-c5cc(Cl)ccc5F)n4)n3)cc2)CC1] | N4-[2-(5-chloro-2-fluoro-phenyl)pyrimidin-4-yl]-N2-[4-[4-(methylamino)-1-piperidyl]phenyl]pyrimidine-2,4-diamine | 505.1 |
| 138 | 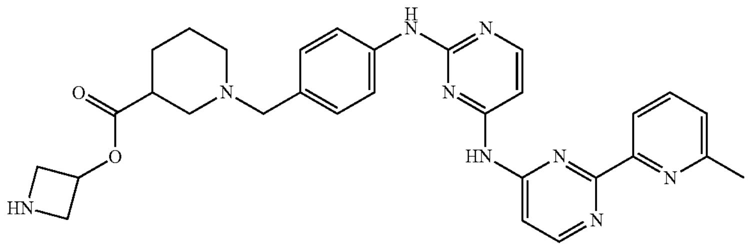 [SMILES: Cc1cccc(-c2nccc(Nc3ccnc(Nc4ccc(CN5CCCC(C(=O)OC6CNC6)C5)cc4)n3)n2)n1] | azetidin-3-yl 1-[[4-[[4-[[2-(6-methyl-2-pyridyl)pyrimidin-4-yl]amino]pyrimidin-2-yl]amino]phenyl]methyl]piperidine-3-carboxylate | 552.2 |
| 139 | 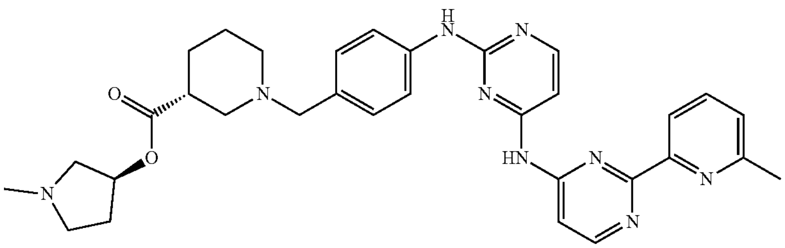 | [(3S)-1-methylpyrrolidin-3-yl] (3R)-1-[[4-[[4-[[2-(6-methyl-2-pyridyl)pyrimidin-4-yl]amino]pyrimidin-2-yl]amino]phenyl]methyl]piperidine-3-carboxylate | 580.2 |
| 140 | 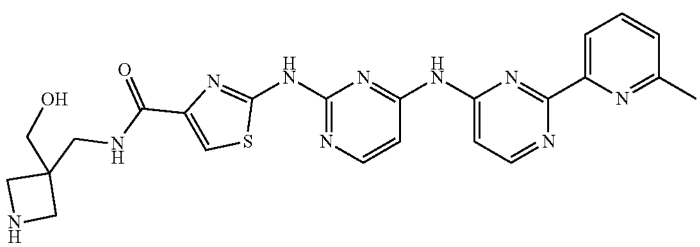 [SMILES: Cc1cccc(-c2nccc(Nc3ccnc(Nc4nc(C(=O)NCC5(CO)CNC5)cs4)n3)n2)n1] | N-[[3-(hydroxymethyl)azetidin-3-yl]methyl]-2-[[4-[[2-(6-methyl-2-pyridyl)pyrimidin-4-yl]amino]pyrimidin-2-yl]amino]thiazole-4-carboxamide | 505.1 |
| 141 | 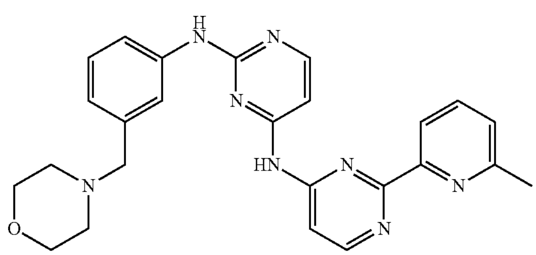 [SMILES: Cc1cccc(-c2nccc(Nc3ccnc(Nc4cccc(CN5CCOCC5)c4)n3)n2)n1] | N4-[2-(6-methyl-2-pyridyl)pyrimidin-4-yl]-N2-[3-(morpholinomethyl)phenyl]pyrimidine-2,4-diamine | 455.1 |
| 142 | 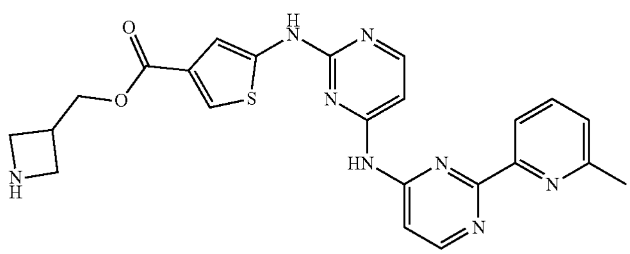 [SMILES: Cc1cccc(-c2nccc(Nc3ccnc(Nc4cc(C(=O)OCC5CNC5)cs4)n3)n2)n1] | azetidin-3-ylmethyl 5-[[4-[[2-(6-methyl-2-pyridyl)pyrimidin-4-yl]amino]pyrimidin-2-yl]amino]thiophene-3-carboxylate | 475.1 |

TABLE 1-continued

| No. | Structure | Chemical Name | [M + H]+ |
|---|---|---|---|
| 143 | 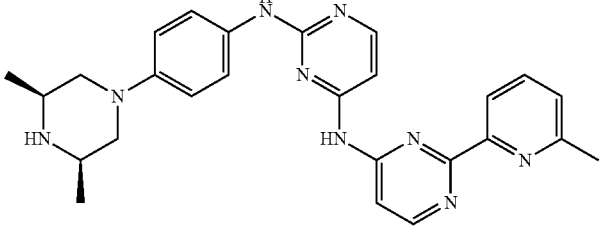 | N4-[2-(6-methyl-2-pyridyl)pyrimidin-4-yl]-N2-[4-[rac-(3S,5R)-3,5-dimethylpiperazin-1-yl]phenyl]pyrimidine-2,4-diamine | 468.2 |
| 144 | 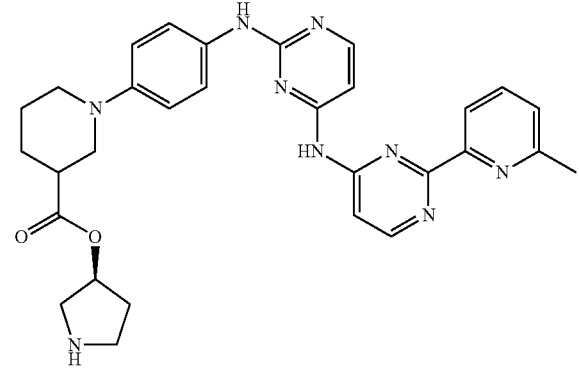 [SMILES: Cc1cccc(-c2nccc(Nc3ccnc(Nc4ccc(N5CCCC(C(=O)O[C@H]6CCNC6)C5)cc4)n3)n2)n1] | [(3S)-pyrrolidin-3-yl] 1-[4-[[4-[[2-(6-methyl-2-pyridyl)pyrimidin-4-yl]amino]pyrimidin-2-yl]amino]phenyl]piperidine-3-carboxylate | 552.3 |
| 145 | 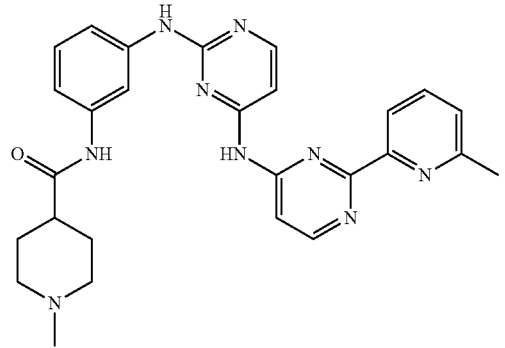 [SMILES: Cc1cccc(-c2nccc(Nc3ccnc(Nc4cccc(NC(=O)C5CCN(C)CC5)c4)n3)n2)n1] | 1-methyl-N-[3-[[4-[[2-(6-methyl-2-pyridyl)pyrimidin-4-yl]amino]pyrimidin-2-yl]amino]phenyl]piperidine-4-carboxamide | 496.2 |
| 146 | 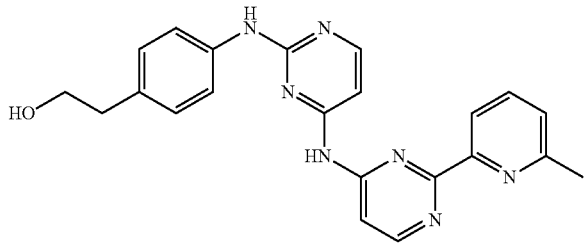 [SMILES: Cc1cccc(-c2nccc(Nc3ccnc(Nc4ccc(CCO)cc4)n3)n2)n1] | 2-[4-[[4-[[2-(6-methyl-2-pyridyl)pyrimidin-4-yl]amino]pyrimidin-2-yl]amino]phenyl]ethanol | 400.2 |
| 147 | 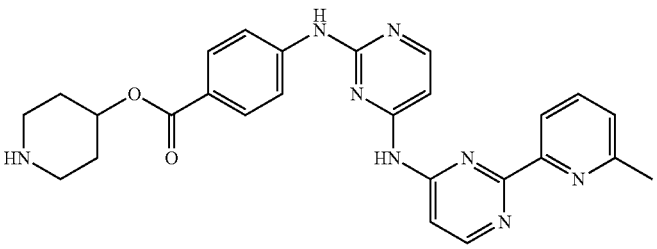 [SMILES: Cc1cccc(-c2nccc(Nc3ccnc(Nc4ccc(C(=O)OC5CCNCC5)cc4)n3)n2)n1] | 4-piperidyl 4-[[4-[[2-(6-methyl-2-pyridyl)pyrimidin-4-yl]amino]pyrimidin-2-yl]amino]benzoate | 483.1 |

TABLE 1-continued

| No. | Structure | Chemical Name | [M + H]+ |
|---|---|---|---|
| 148 | 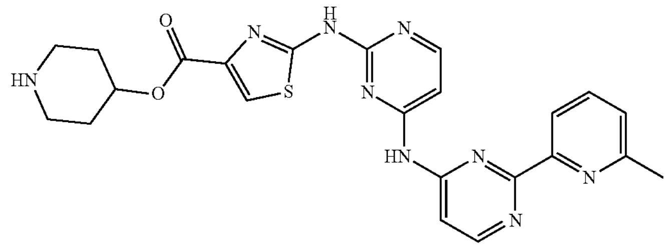 [SMILES: Cc1cccc(-c2nccc(Nc3ccnc(Nc4nc(C(=O)OC5CCNCC5)cs4)n3)n2)n1] | 4-piperidyl 2-[[4-[[2-(6-methyl-2-pyridyl)pyrimidin-4-yl]amino]pyrimidin-2-yl]amino]thiazole-4-carboxylate | 490.0 |
| 149 | 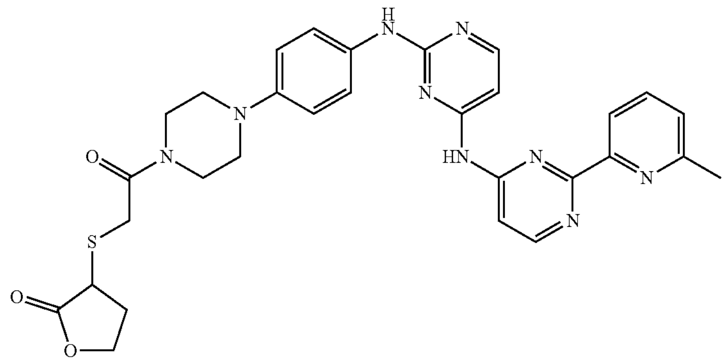 [SMILES: Cc1cccc(-c2nccc(Nc3ccnc(Nc4ccc(N5CCN(C(=O)CSC6CCOC6=O)CC5)cc4)n3)n2)n1] | 3-[2-[4-[4-[[4-[[2-(6-methyl-2-pyridyl)pyrimidin-4-yl]amino]pyrimidin-2-yl]amino]phenyl]piperazin-1-yl]-2-oxo-ethyl]sulfanyltetrahydrofuran-2-one | 598.3 |
| 150 | 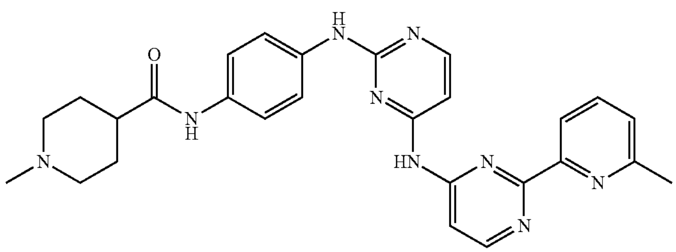 | 1-methyl-N-[4-[[4-[[2-(6-methyl-2-pyridyl)pyrimidin-4-yl]amino]pyrimidin-2-yl]amino]phenyl]piperidine-4-carboxamide | 496.2 |
| 151 | 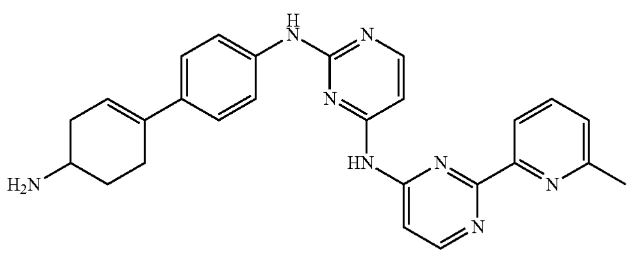 [SMILES: Cc1cccc(-c2nccc(Nc3ccnc(Nc4ccc(C5=CCC(N)CC5)cc4)n3)n2)n1] | N2-[4-(4-aminocyclohexen-1-yl)phenyl]-N4-[2-(6-methyl-2-pyridyl)pyrimidin-4-yl]pyrimidine-2,4-diamine | 451.2 |
| 152 | 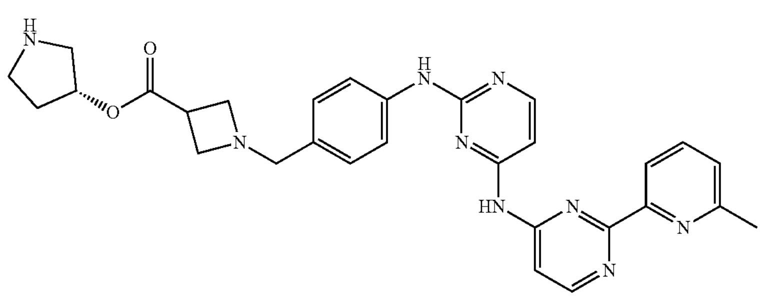 [SMILES: Cc1cccc(-c2nccc(Nc3ccnc(Nc4ccc(CN5CC(C(=O)O[C@@H]6CCNC6)C5)cc4)n3)n2)n1] | [(3R)-pyrrolidin-3-yl] 1-[[4-[[4-[[2-(6-methyl-2-pyridyl)pyrimidin-4-yl]amino]pyrimidin-2-yl]amino]phenyl]methyl]azetidine-3-carboxylate | 538.1 |

TABLE 1-continued

| No. | Structure | Chemical Name | [M + H]+ |
|---|---|---|---|
| 153 | 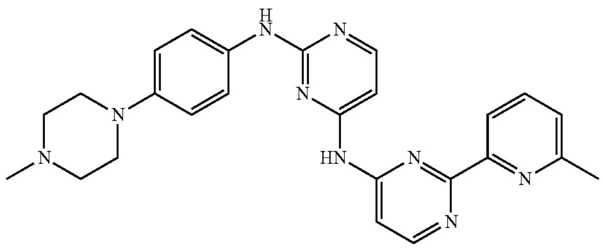 | N2-[4-(4-methylpiperazin-1-yl)phenyl]-N4-[2-(6-methyl-2-pyridyl)pyrimidin-4-yl]pyrimidine-2,4-diamine | 454.2 |
| 154 | 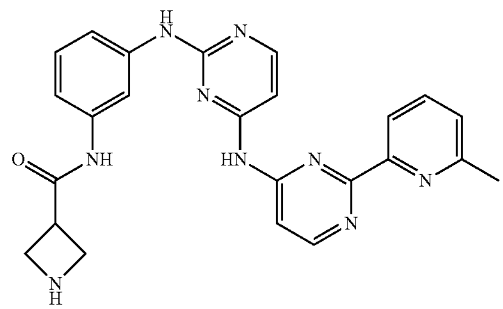 [SMILES: Cc1cccc(-c2nccc(Nc3ccnc(Nc4cccc(NC(=O)C5CNC5)c4)n3)n2)n1] | N-[3-[[4-[[2-(6-methyl-2-pyridyl)pyrimidin-4-yl]amino]pyrimidin-2-yl]amino]phenyl]azetidine-3-carboxamide | 454.1 |
| 155 | 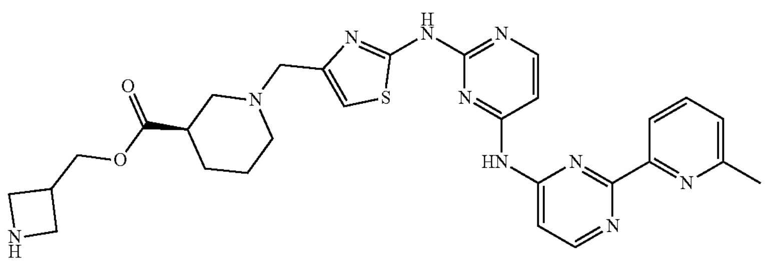 [SMILES: Cc1cccc(-c2nccc(Nc3ccnc(Nc4nc(CN5CCC[C@@H](C(=O)OCC6CNC6)C5)cs4)n3)n2)n1] | azetidin-3-ylmethyl (3R)-1-[[2-[[4-[[2-(6-methyl-2-pyridyl)pyrimidin-4-yl]amino]pyrimidin-2-yl]amino]thiazol-4-yl]methyl]piperidine-3-carboxylate | 573.1 |
| 156 | 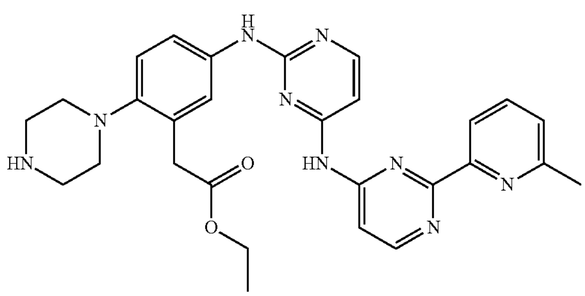 [SMILES: CCOC(=O)Cc1cc(Nc2nccc(Nc3ccnc(-c4cccc(C)n4)n3)n2)ccc1N1CCNCC1] | ethyl 2-[5-[[4-[[2-(6-methyl-2-pyridyl)pyrimidin-4-yl]amino]pyrimidin-2-yl]amino]-2-piperazin-1-yl-phenyl]acetate | 526.3 |
| 157 | 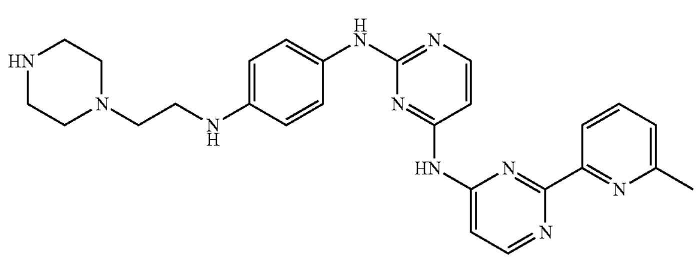 [SMILES: Cc1cccc(-c2nccc(Nc3ccnc(Nc4ccc(NCCN5CCNCC5)cc4)n3)n2)n1] | N4-[2-(6-methyl-2-pyridyl)pyrimidin-4-yl]-N2-[4-(2-piperazin-1-ylethylamino)phenyl]pyrimidine-2,4-diamine | 483.2 |

TABLE 1-continued

| No. | Structure | Chemical Name | [M + H]+ |
|---|---|---|---|
| 158 | 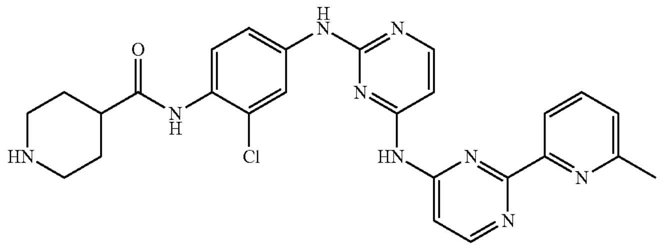 [SMILES: Cc1cccc(-c2nccc(Nc3ccnc(Nc4ccc(NC(=O)C5CCNCC5)c(Cl)c4)n3)n2)n1] | N-[2-chloro-4-[[4-[[2-(6-methyl-2-pyridyl)pyrimidin-4-yl]amino]pyrimidin-2-yl]amino]phenyl]piperidine-4-carboxamide | 516.0 |
| 159 | 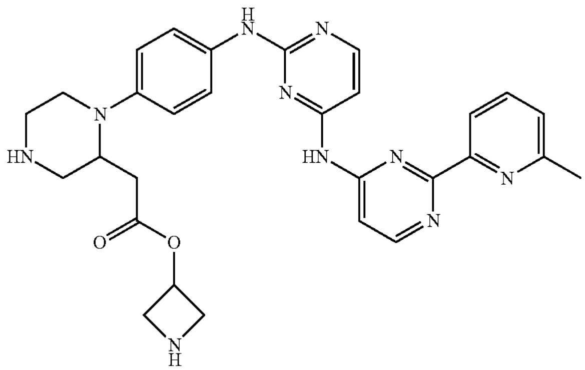 [SMILES: Cc1cccc(-c2nccc(Nc3ccnc(Nc4ccc(N5CCNCC5CC(=O)OC5CNC5)cc4)n3)n2)n1] | azetidin-3-yl 2-[1-[4-[[4-[[2-(6-methyl-2-pyridyl)pyrimidin-4-yl]amino]pyrimidin-2-yl]amino]phenyl]piperazin-2-yl]acetate | 553.1 |
| 160 | 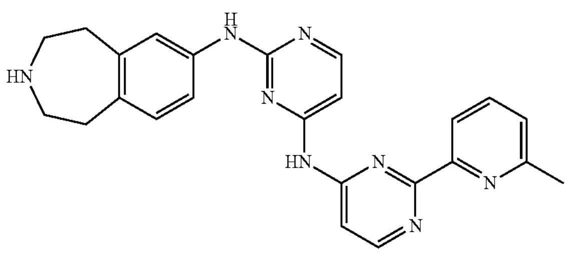 [SMILES: Cc1cccc(-c2nccc(Nc3ccnc(Nc4ccc5c(c4)CCNCC5)n3)n2)n1] | N4-[2-(6-methyl-2-pyridyl)pyrimidin-4-yl]-N2-(2,3,4,5-tetrahydro-1H-3-benzazepin-7-yl)pyrimidine-2,4-diamine | 425.1 |
| 161 | 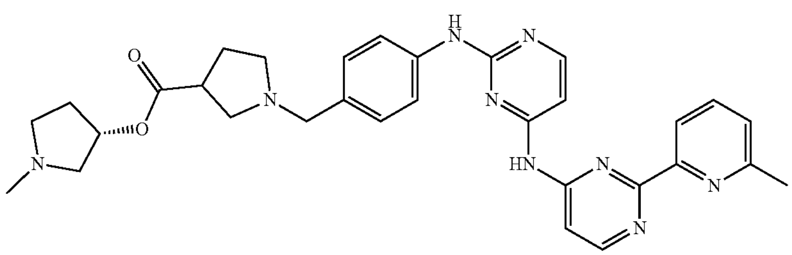 | [(3S)-1-methylpyrrolidin-3-yl] 1-[[4-[[4-[[2-(6-methyl-2-pyridyl)pyrimidin-4-yl]amino]pyrimidin-2-yl]amino]phenyl]methyl]pyrrolidine-3-carboxylate | 566.1 |
| 162 | 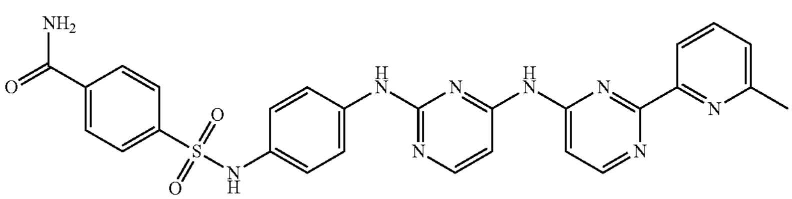 [SMILES: Cc1cccc(-c2nccc(Nc3ccnc(Nc4ccc(NS(=O)(=O)c5ccc(C(N)=O)cc5)cc4)n3)n2)n1] | 4-[[4-[[4-[[2-(6-methyl-2-pyridyl)pyrimidin-4-yl]amino]pyrimidin-2-yl]amino]phenyl]sulfamoyl]benzamide | 554.2 |
| 163 | 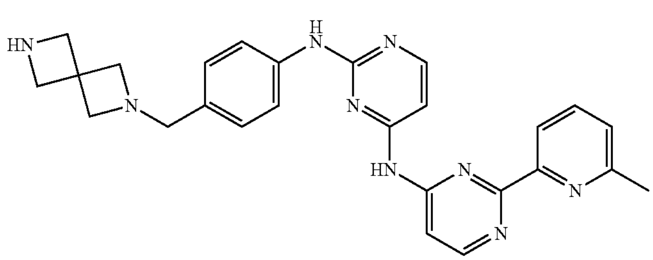 [SMILES: Cc1cccc(-c2nccc(Nc3ccnc(Nc4ccc(CN5CC6(CNC6)C5)cc4)n3)n2)n1] | N2-[4-(2,6-diazaspiro[3.3]heptan-2-ylmethyl)phenyl]-N4-[2-(6-methyl-2-pyridyl)pyrimidin-4-yl]pyrimidine-2,4-diamine | 466.2 |

TABLE 1-continued

| No. | Structure | Chemical Name | [M + H]+ |
|---|---|---|---|
| 164 | 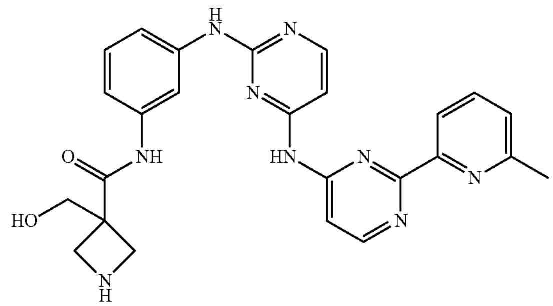 [SMILES: Cc1cccc(-c2nccc(Nc3ccnc(Nc4cccc(NC(=O)C5(CO)CNC5)c4)n3)n2)n1] | 3-(hydroxymethyl)-N-[3-[[4-[[2-(6-methyl-2-pyridyl)pyrimidin-4-yl]amino]pyrimidin-2-yl]amino]phenyl]azetidine-3-carboxamide | 484.0 |
| 165 | 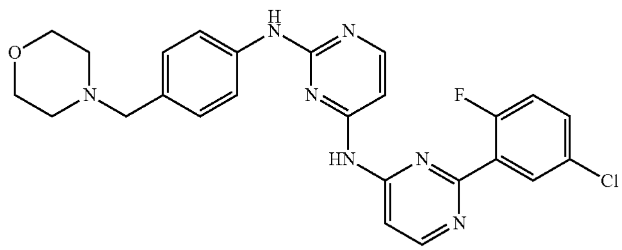 [SMILES: Fc1ccc(Cl)cc1-c1nccc(Nc2ccnc(Nc3ccc(CN4CCOCC4)cc3)n2)n1] | N4-[2-(5-chloro-2-fluoro-phenyl)pyrimidin-4-yl]-N2-[4-(morpholinomethyl)phenyl]pyrimidine-2,4-diamine | 492.1 |
| 166 | 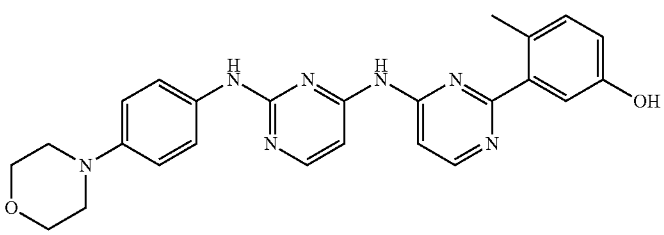 [SMILES: Cc1ccc(O)cc1-c1nccc(Nc2ccnc(Nc3ccc(N4CCOCC4)cc3)n2)n1] | 4-methyl-3-[4-[[2-(4-morpholinoanilino)pyrimidin-4-yl]amino]pyrimidin-2-yl]phenol | 456.1 |
| 167 | 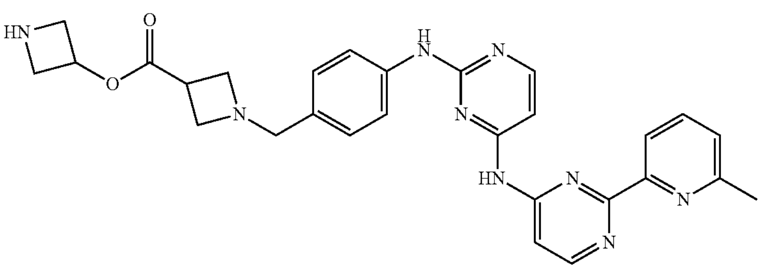 [SMILES: Cc1cccc(-c2nccc(Nc3ccnc(Nc4ccc(CN5CC(C(=O)OC6CNC6)C5)cc4)n3)n2)n1] | azetidin-3-yl 1-[[4-[[4-[[2-(6-methyl-2-pyridyl)pyrimidin-4-yl]amino]pyrimidin-2-yl]amino]phenyl]methyl]azetidine-3-carboxylate | 524.2 |
| 168 | 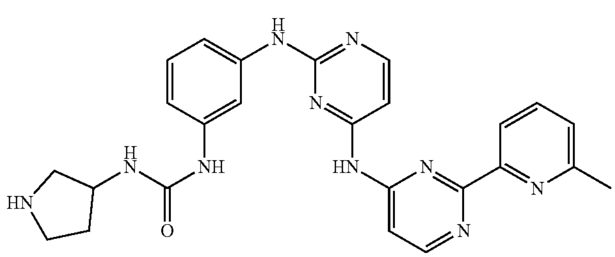 [SMILES: Cc1cccc(-c2nccc(Nc3ccnc(Nc4cccc(NC(=O)NC5CCNC5)c4)n3)n2)n1] | 1-[3-[[4-[[2-(6-methyl-2-pyridyl)pyrimidin-4-yl]amino]pyrimidin-2-yl]amino]phenyl]-3-pyrrolidin-3-yl-urea | 483.1 |
| 169 | 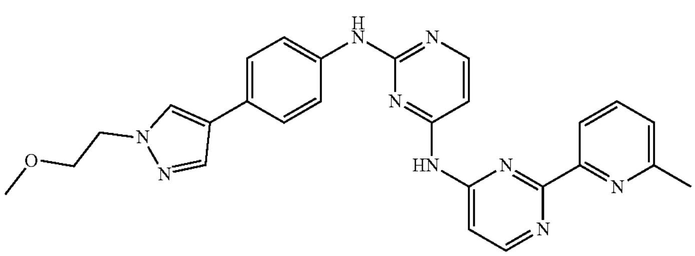 | N2-[4-[1-(2-methoxyethyl)pyrazol-4-yl]phenyl]-N4-[2-(6-methyl-2-pyridyl)pyrimidin-4-yl]pyrimidine-2,4-diamine | 480.0 |

TABLE 1-continued

| No. | Structure | Chemical Name | [M + H]+ |
|---|---|---|---|
| 170 | 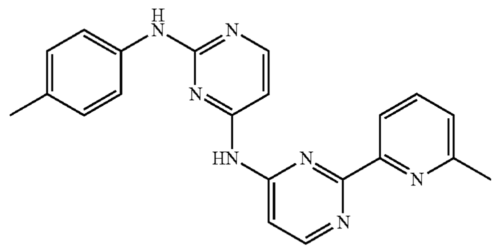 | N4-[2-(6-methyl-2-pyridyl)pyrimidin-4-yl]-N2-(p-tolyl)pyrimidine-2,4-diamine | 370.1 |
| 171 | 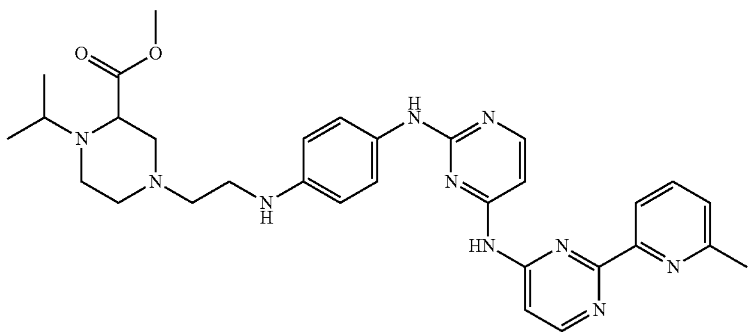 [SMILES: COC(=O)C1CN(CCNc2ccc(Nc3nccc(Nc4ccnc(-c5cccc(C)n5)n4)n3)cc2)CCN1C(C)C] | methyl 1-isopropyl-4-[2-[4-[[4-[[2-(6-methyl-2-pyridyl)pyrimidin-4-yl]amino]pyrimidin-2-yl]amino]anilino]ethyl]piperazine-2-carboxylate | 583.1 |
| 172 | 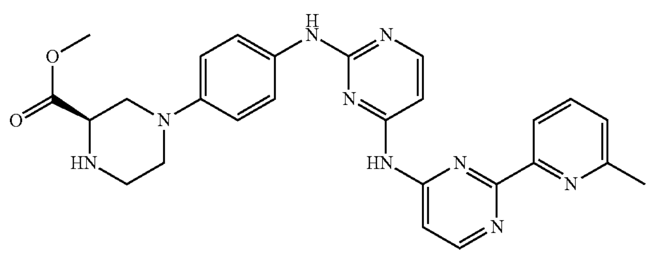 [SMILES: COC(=O)[C@H]1CN(c2ccc(Nc3nccc(Nc4ccnc(-c5cccc(C)n5)n4)n3)cc2)CCN1] | methyl (2R)-4-[4-[[4-[[2-(6-methyl-2-pyridyl)pyrimidin-4-yl]amino]pyrimidin-2-yl]amino]phenyl]piperazine-2-carboxylate | 498.0 |
| 173 | 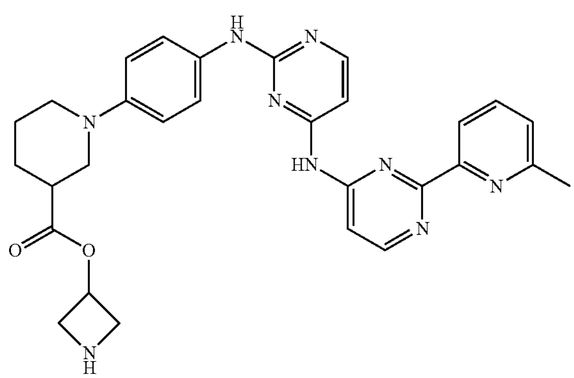 [SMILES: Cc1cccc(-c2nccc(Nc3ccnc(Nc4ccc(N5CCCC(C(=O)OC6CNC6)C5)cc4)n3)n2)n1] | azetidin-3-yl 1-[4-[[4-[[2-(6-methyl-2-pyridyl)pyrimidin-4-yl]amino]pyrimidin-2-yl]amino]phenyl]piperidine-3-carboxylate | 538.3 |
| 174 | 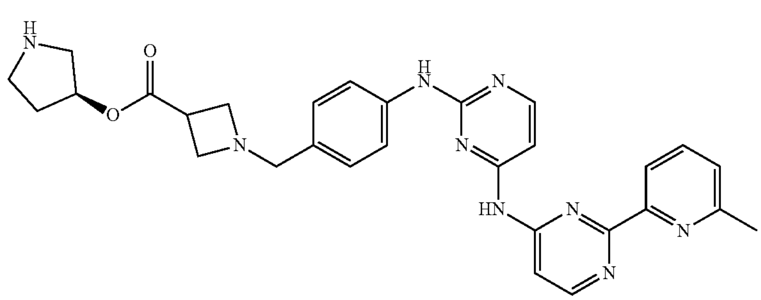 [SMILES: Cc1cccc(-c2nccc(Nc3ccnc(Nc4ccc(CN5CC(C(=O)O[C@H]6CCNC6)C5)cc4)n3)n2)n1] | [(3S)-pyrrolidin-3-yl] 1-[[4-[[4-[[2-(6-methyl-2-pyridyl)pyrimidin-4-yl]amino]pyrimidin-2-yl]amino]phenyl]methyl]azetidine-3-carboxylate | 538.2 |

TABLE 1-continued

| No. | Structure | Chemical Name | [M + H]+ |
|---|---|---|---|
| 175 | 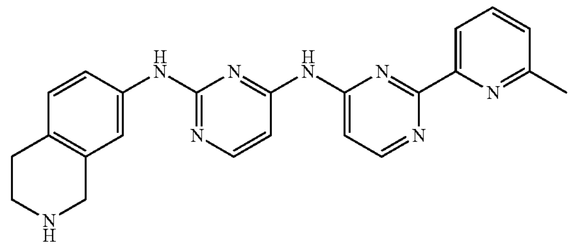 [SMILES: Cc1cccc(-c2nccc(Nc3ccnc(Nc4ccc5c(c4)CNCC5)n3)n2)n1] | N4-[2-(6-methyl-2-pyridyl)pyrimidin-4-yl]-N2-(1,2,3,4-tetrahydroisoquinolin-7-yl)pyrimidine-2,4-diamine | 411.1 |
| 176 | 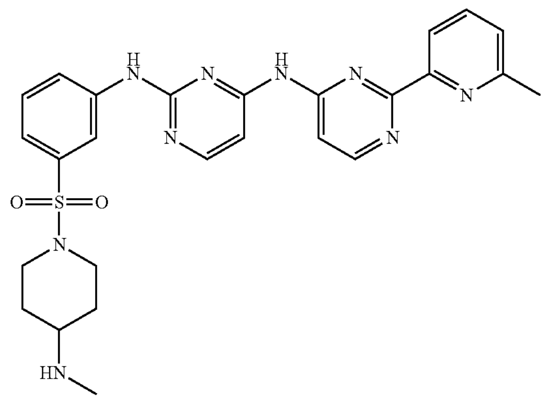 [SMILES: CNC1CCN(S(=O)(=O)c2cccc(Nc3nccc(Nc4ccnc(-c5cccc(C)n5)n4)n3)c2)CC1] | N2-[3-[[4-(methylamino)-1-piperidyl]sulfonyl]phenyl]-N4-[2-(6-methyl-2-pyridyl)pyrimidin-4-yl]pyrimidine-2,4-diamine | 532.2 |
| 177 | 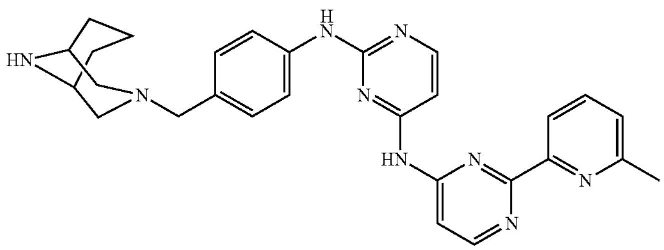 [SMILES: Cc1cccc(-c2nccc(Nc3ccnc(Nc4ccc(CN5CC6CCCC(C5)N6)cc4)n3)n2)n1] | N2-[4-(3,9-diazabicyclo[3.3.1]nonan-3-ylmethyl)phenyl]-N4-[2-(6-methyl-2-pyridyl)pyrimidin-4-yl]pyrimidine-2,4-diamine | 494.3 |
| 178 | 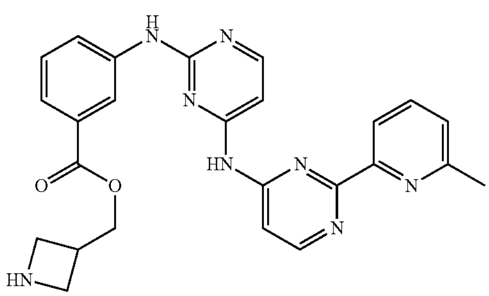 | azetidin-3-ylmethyl 3-[[4-[[2-(6-methyl-2-pyridyl)pyrimidin-4-yl]amino]pyrimidin-2-yl]amino]benzoate | 469.1 |
| 179 | 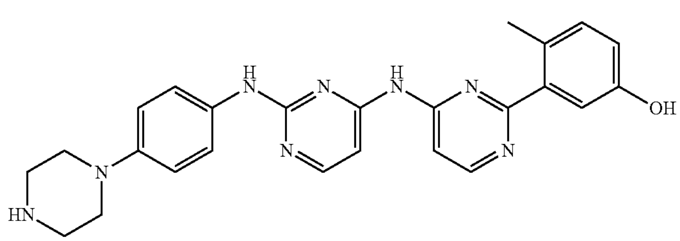 [SMILES: Cc1ccc(O)cc1-c1nccc(Nc2ccnc(Nc3ccc(N4CCNCC4)cc3)n2)n1] | 4-methyl-3-[4-[[2-(4-piperazin-1-ylanilino)pyrimidin-4-yl]amino]pyrimidin-2-yl]phenol | 455.1 |

TABLE 1-continued

| No. | Structure | Chemical Name | [M + H]+ |
|---|---|---|---|
| 180 | 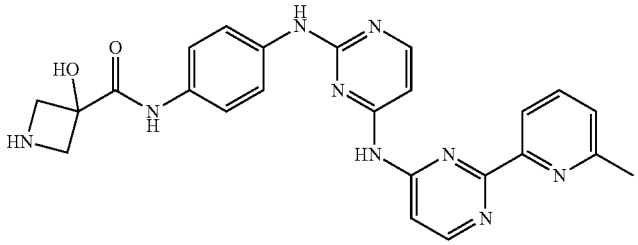 [SMILES: Cc1cccc(-c2nccc(Nc3ccnc(Nc4ccc(NC(=O)C5(O)CNC5)cc4)n3)n2)n1] | 3-hydroxy-N-[4-[[4-[[2-(6-methyl-2-pyridyl)pyrimidin-4-yl]amino]pyrimidin-2-yl]amino]phenyl]azetidine-3-carboxamide | 470.0 |
| 181 | 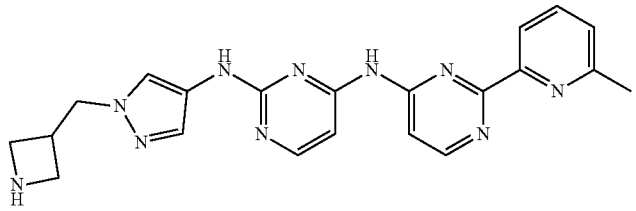 [SMILES: Cc1cccc(-c2nccc(Nc3ccnc(Nc4cnn(CC5CNC5)c4)n3)n2)n1] | N2-[1-(azetidin-3-ylmethyl)pyrazol-4-yl]-N4-[2-(6-methyl-2-pyridyl)pyrimidin-4-yl]pyrimidine-2,4-diamine | 415.1 |
| 182 | 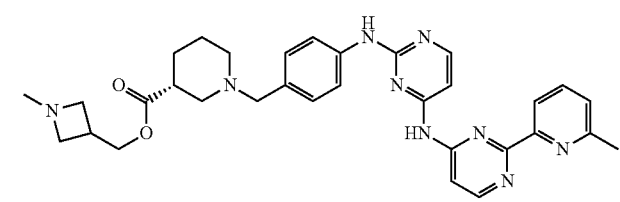 | (1-methylazetidin-3-yl)methyl (3R)-1-[[4-[[4-[[2-(6-methyl-2-pyridyl)pyrimidin-4-yl]amino]pyrimidin-2-yl]amino]phenyl]methyl]piperidine-3-carboxylate | 580.1 |
| 183 | 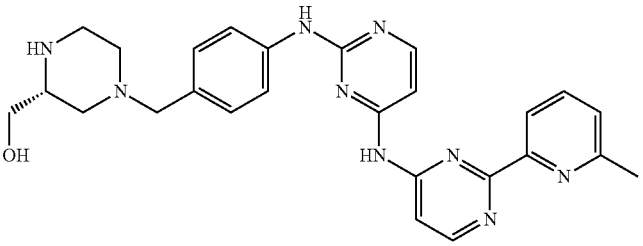 [SMILES: Cc1cccc(-c2nccc(Nc3ccnc(Nc4ccc(CN5CCN[C@@H](CO)C5)cc4)n3)n2)n1] | [(2R)-4-[[4-[[4-[[2-(6-methyl-2-pyridyl)pyrimidin-4-yl]amino]pyrimidin-2-yl]amino]phenyl]methyl]piperazin-2-yl]methanol | 484.1 |
| 184 | 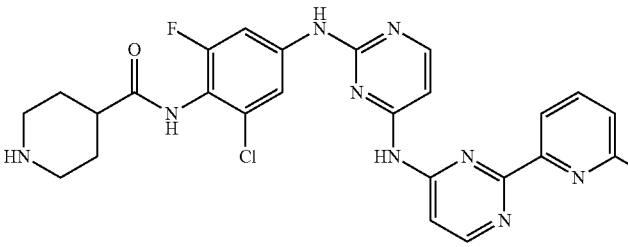 | N-[2-chloro-6-fluoro-4-[[4-[[2-(6-methyl-2-pyridyl)pyrimidin-4-yl]amino]pyrimidin-2-yl]amino]phenyl]piperidine-4-carboxamide | 534.1 |
| 185 | 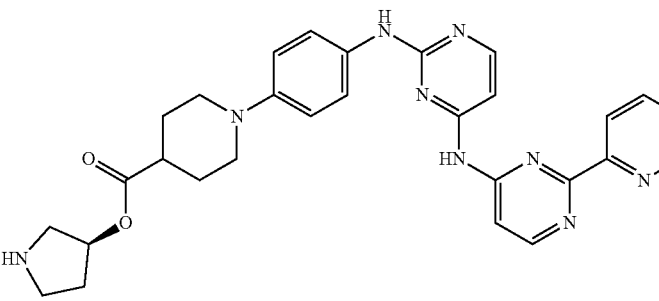 | [(3S)-pyrrolidin-3-yl] 1-[4-[[4-[[2-(6-methyl-2-pyridyl)pyrimidin-4-yl]amino]pyrimidin-2-yl]amino]phenyl]piperidine-4-carboxylate | 552.1 |

TABLE 1-continued

| No. | Structure | Chemical Name | [M + H]+ |
|---|---|---|---|
| 186 | 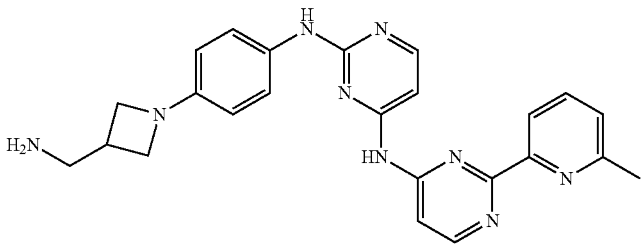 [SMILES: Cc1cccc(-c2nccc(Nc3ccnc(Nc4ccc(N5CC(CN)C5)cc4)n3)n2)n1] | N2-[4-[3-(aminomethyl)azetidin-1-yl]phenyl]-N4-[2-(6-methyl-2-pyridyl)pyrimidin-4-yl]pyrimidine-2,4-diamine | 440.2 |
| 187 | 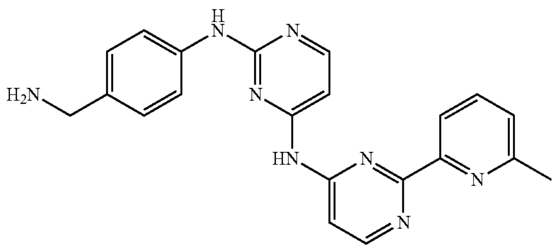 [SMILES: Cc1cccc(-c2nccc(Nc3ccnc(Nc4ccc(CN)cc4)n3)n2)n1] | N2-[4-(aminomethyl)phenyl]-N4-[2-(6-methyl-2-pyridyl)pyrimidin-4-yl]pyrimidine-2,4-diamine | 385.2 |
| 188 | 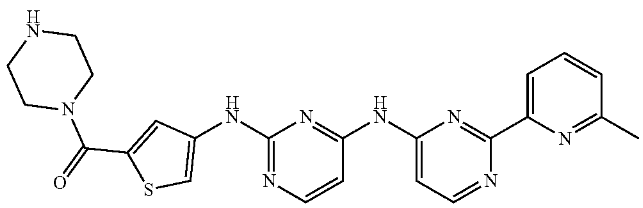 [SMILES: Cc1cccc(-c2nccc(Nc3ccnc(Nc4csc(C(=O)N5CCNCC5)c4)n3)n2)n1] | [4-[[4-[[2-(6-methyl-2-pyridyl)pyrimidin-4-yl]amino]pyrimidin-2-yl]amino]-2-thienyl]-piperazin-1-yl-methanone | 474.1 |
| 189 | 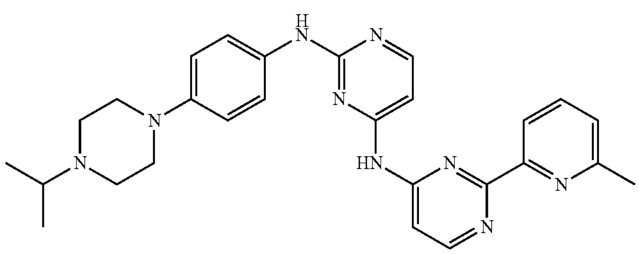 [SMILES: Cc1cccc(-c2nccc(Nc3ccnc(Nc4ccc(N5CCN(C(C)C)CC5)cc4)n3)n2)n1] | N2-[4-(4-isopropylpiperazin-1-yl)phenyl]-N4-[2-(6-methyl-2-pyridyl)pyrimidin-4-yl]pyrimidine-2,4-diamine | 482.1 |
| 190 | 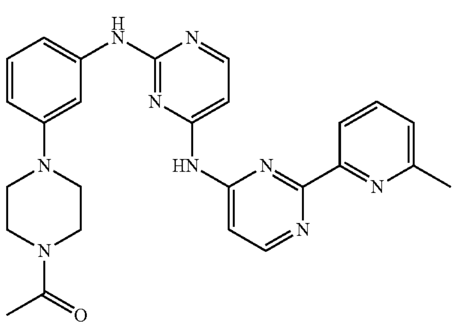 [SMILES: CC(=O)N1CCN(c2cccc(Nc3nccc(Nc4ccnc(-c5cccc(C)n5)n4)n3)c2)CC1] | 1-[4-[3-[[4-[[2-(6-methyl-2-pyridyl)pyrimidin-4-yl]amino]pyrimidin-2-yl]amino]phenyl]piperazin-1-yl]ethanone | 482.2 |
| 191 | 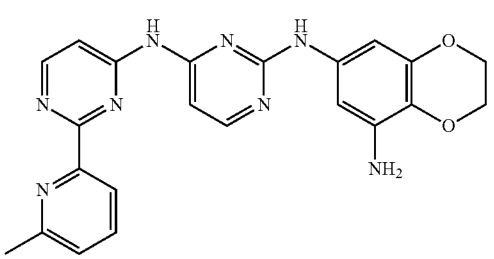 [SMILES: Cc1cccc(-c2nccc(Nc3ccnc(Nc4cc(N)c5c(c4)OCCO5)n3)n2)n1] | N2-(5-amino-2,3-dihydro-1,4-benzodioxin-7-yl)-N4-[2-(6-methyl-2-pyridyl)pyrimidin-4-yl]pyrimidine-2,4-diamine | 429.2 |

TABLE 1-continued

| No. | Structure | Chemical Name | [M + H]+ |
|---|---|---|---|
| 192 | 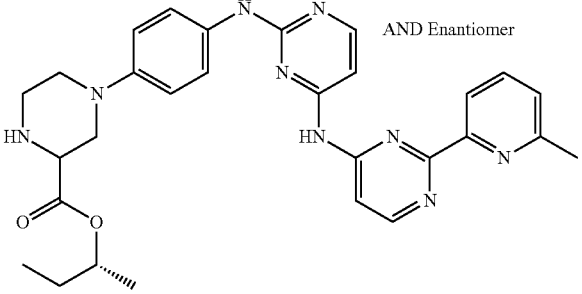 AND Enantiomer | [rac-(1R)-1-methylpropyl] 4-[4-[[4-[[2-(6-methyl-2-pyridyl)pyrimidin-4-yl]amino]pyrimidin-2-yl]amino]phenyl]piperazine-2-carboxylate | 540.2 |
| 193 | 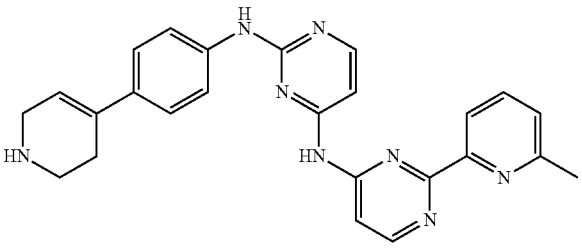 [SMILES: Cc1cccc(-c2nccc(Nc3ccnc(Nc4ccc(C5=CCNCC5)cc4)n3)n2)n1] | N4-[2-(6-methyl-2-pyridyl)pyrimidin-4-yl]-N2-[4-(1,2,3,6-tetrahydropyridin-4-yl)phenyl]pyrimidine-2,4-diamine | 437.1 |
| 194 | 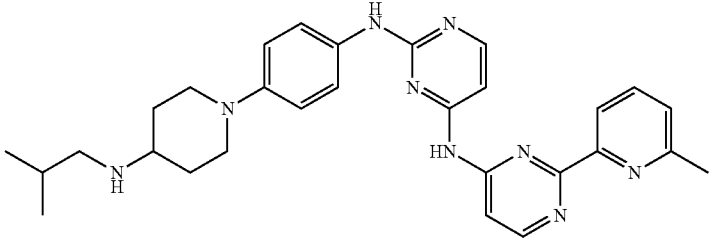 [SMILES: Cc1cccc(-c2nccc(Nc3ccnc(Nc4ccc(N5CCC(NCC(C)C)CC5)cc4)n3)n2)n1] | N2-[4-[4-(isobutylamino)-1-piperidyl]phenyl]-N4-[2-(6-methyl-2-pyridyl)pyrimidin-4-yl]pyrimidine-2,4-diamine | 510.3 |
| 195 | 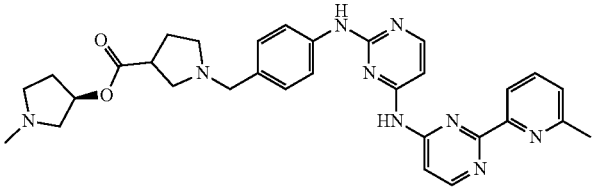 | [(3R)-1-methylpyrrolidin-3-yl] 1-[[4-[[4-[[2-(6-methyl-2-pyridyl)pyrimidin-4-yl]amino]pyrimidin-2-yl]amino]phenyl]methyl]pyrrolidine-3-carboxylate | 566.1 |
| 196 | 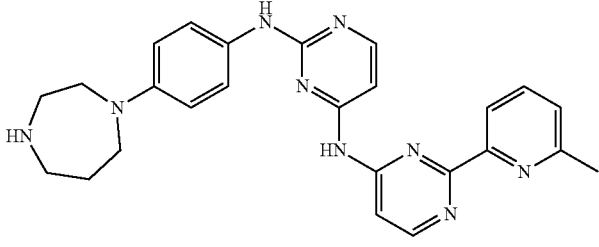 [SMILES: Cc1cccc(-c2nccc(Nc3ccnc(Nc4ccc(N5CCCNCC5)cc4)n3)n2)n1] | N2-[4-(1,4-diazepan-1-yl)phenyl]-N4-[2-(6-methyl-2-pyridyl)pyrimidin-4-yl]pyrimidine-2,4-diamine | 454.1 |
| 197 | 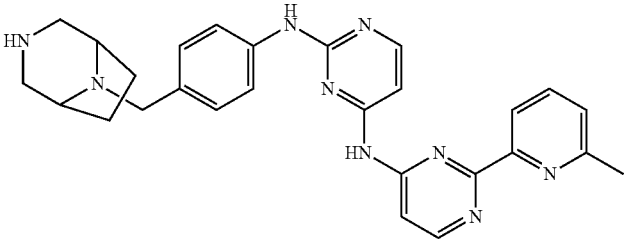 [SMILES: Cc1cccc(-c2nccc(Nc3ccnc(Nc4ccc(CN5C6CCC5CNC6)cc4)n3)n2)n1] | N2-[4-(3,8-diazabicyclo[3.2.1]octan-8-ylmethyl)phenyl]-N4-[2-(6-methyl-2-pyridyl)pyrimidin-4-yl]pyrimidine-2,4-diamine | 480.2 |

TABLE 1-continued

| No. | Structure | Chemical Name | [M + H]+ |
|---|---|---|---|
| 198 | 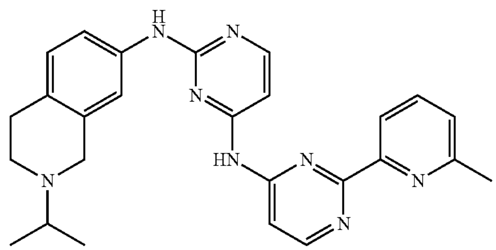 [SMILES: Cc1cccc(-c2nccc(Nc3ccnc(Nc4ccc5c(c4)CN(C(C)C)CC5)n3)n2)n1] | N2-(2-isopropyl-3,4-dihydro-1H-isoquinolin-7-yl)-N4-[2-(6-methyl-2-pyridyl)pyrimidin-4-yl]pyrimidine-2,4-diamine | 453.2 |
| 199 | 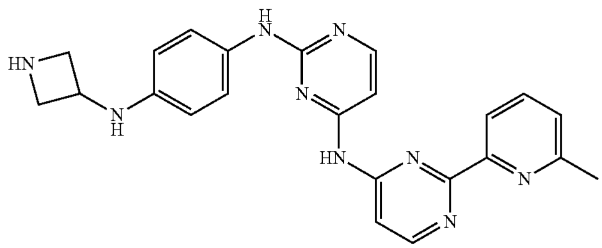 [SMILES: Cc1cccc(-c2nccc(Nc3ccnc(Nc4ccc(NC5CNC5)cc4)n3)n2)n1] | N2-[4-(azetidin-3-ylamino)phenyl]-N4-[2-(6-methyl-2-pyridyl)pyrimidin-4-yl]pyrimidine-2,4-diamine | 426.1 |
| 200 | 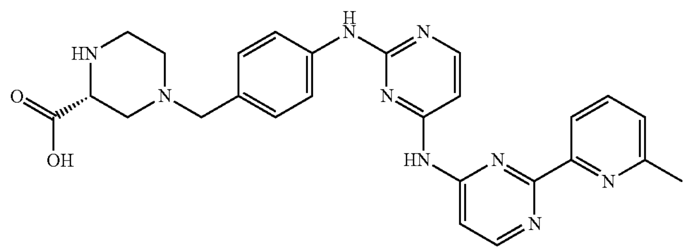 [SMILES: Cc1cccc(-c2nccc(Nc3ccnc(Nc4ccc(CN5CCN[C@@H](C(=O)O)C5)cc4)n3)n2)n1] | (2R)-4-[[4-[[4-[[2-(6-methyl-2-pyridyl)pyrimidin-4-yl]amino]pyrimidin-2-yl]amino]phenyl]methyl]piperazine-2-carboxylic acid | 498.2 |
| 201 | 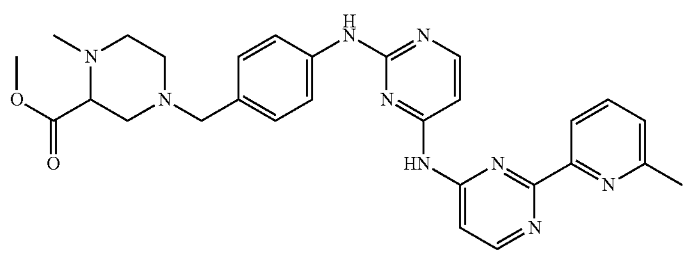 [SMILES: COC(=O)C1CN(Cc2ccc(Nc3nccc(Nc4ccnc(-c5cccc(C)n5)n4)n3)cc2)CCN1C] | methyl 1-methyl-4-[[4-[[4-[[2-(6-methyl-2-pyridyl)pyrimidin-4-yl]amino]pyrimidin-2-yl]amino]phenyl]methyl]piperazine-2-carboxylate | 526.1 |
| 202 | 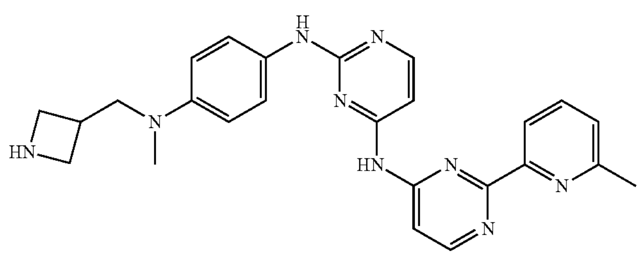 [SMILES: Cc1cccc(-c2nccc(Nc3ccnc(Nc4ccc(N(C)CC5CNC5)cc4)n3)n2)n1] | N2-[4-[azetidin-3-ylmethyl(methyl)amino]phenyl]-N4-[2-(6-methyl-2-pyridyl)pyrimidin-4-yl]pyrimidine-2,4-diamine | 454.2 |
| 203 | 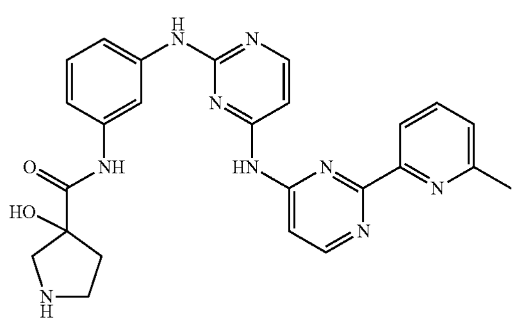 [SMILES: Cc1cccc(-c2nccc(Nc3ccnc(Nc4cccc(NC(=O)C5(O)CCNC5)c4)n3)n2)n1] | 3-hydroxy-N-[3-[[4-[[2-(6-methyl-2-pyridyl)pyrimidin-4-yl]amino]pyrimidin-2-yl]amino]phenyl]pyrrolidine-3-carboxamide | 484.1 |

TABLE 1-continued

| No. | Structure | Chemical Name | [M + H]+ |
|---|---|---|---|
| 204 | 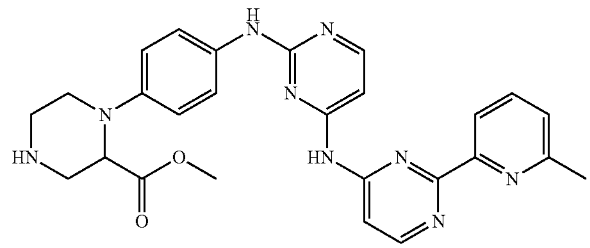 [SMILES: COC(=O)C1CNCCN1c1ccc(Nc2nccc(Nc3ccnc(-c4cccc(C)n4)n3)n2)cc1] | methyl 1-[4-[[4-[[2-(6-methyl-2-pyridyl)pyrimidin-4-yl]amino]pyrimidin-2-yl]amino]phenyl]piperazine-2-carboxylate | 498.3 |
| 205 | 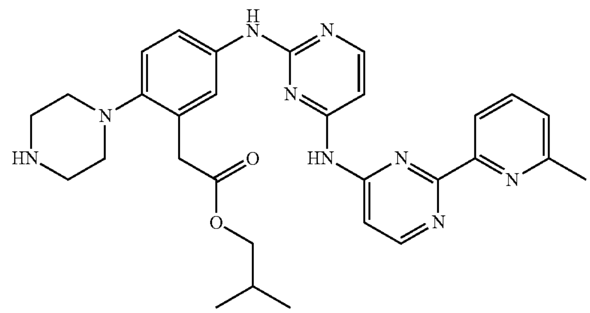 [SMILES: Cc1cccc(-c2nccc(Nc3ccnc(Nc4ccc(N5CCNCC5)c(CC(=O)OCC(C)C)c4)n3)n2)n1] | isobutyl 2-[5-[[4-[[2-(6-methyl-2-pyridyl)pyrimidin-4-yl]amino]pyrimidin-2-yl]amino]-2-piperazin-1-yl-phenyl]acetate | 554.4 |
| 206 | 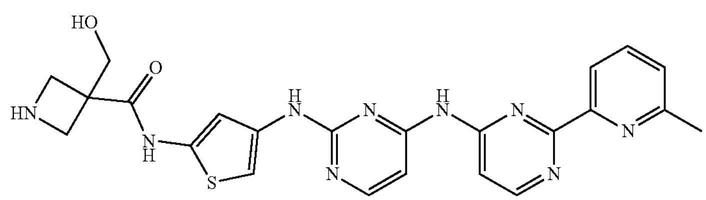 [SMILES: Cc1cccc(-c2nccc(Nc3ccnc(Nc4csc(NC(=O)C5(CO)CNC5)c4)n3)n2)n1] | 3-(hydroxymethyl)-N-[4-[[4-[[2-(6-methyl-2-pyridyl)pyrimidin-4-yl]amino]pyrimidin-2-yl]amino]-2-thienyl]azetidine-3-carboxamide | 490.2 |
| 207 | 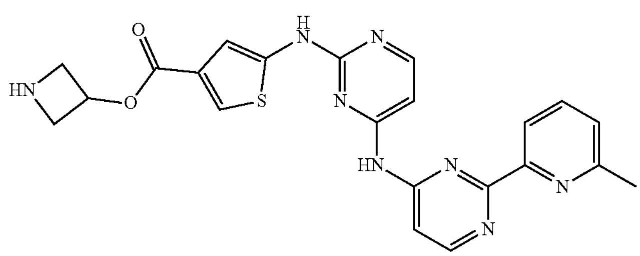 [SMILES: Cc1cccc(-c2nccc(Nc3ccnc(Nc4cc(C(=O)OC5CNC5)cs4)n3)n2)n1] | azetidin-3-yl 5-[[4-[[2-(6-methyl-2-pyridyl)pyrimidin-4-yl]amino]pyrimidin-2-yl]amino]thiophene-3-carboxylate | 461.1 |
| 208 | 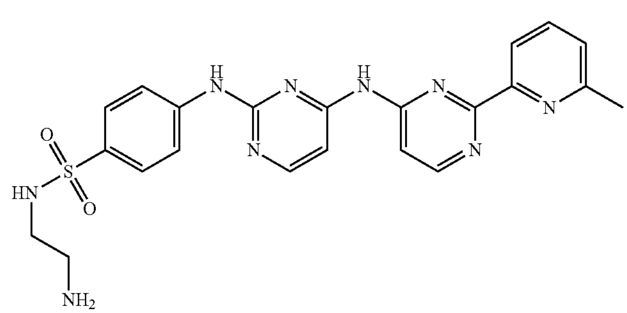 [SMILES: Cc1cccc(-c2nccc(Nc3ccnc(Nc4ccc(S(=O)(=O)NCCN)cc4)n3)n2)n1] | N-(2-aminoethyl)-4-[[4-[[2-(6-methyl-2-pyridyl)pyrimidin-4-yl]amino]pyrimidin-2-yl]amino]benzenesulfonamide | 478.2 |

TABLE 1-continued

| No. | Structure | Chemical Name | [M + H]⁺ |
|---|---|---|---|
| 209 | 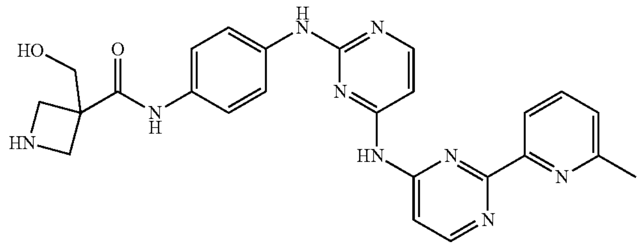 [SMILES: Cc1cccc(-c2nccc(Nc3ccnc(Nc4ccc(NC(=O)C5(CO)CNC5)cc4)n3)n2)n1] | 3-(hydroxymethyl)-N-[4-[[4-[[2-(6-methyl-2-pyridyl)pyrimidin-4-yl]amino]pyrimidin-2-yl]amino]phenyl]azetidine-3-carboxamide | 484.0 |
| 210 | 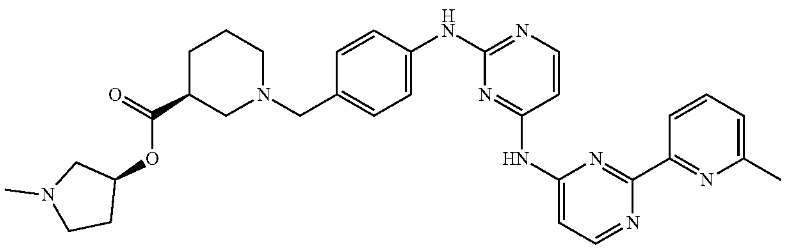 | [(3S)-1-methylpyrrolidin-3-yl] (3S)-1-[[4-[[4-[[2-(6-methyl-2-pyridyl)pyrimidin-4-yl]amino]pyrimidin-2-yl]amino]phenyl]methyl]piperidine-3-carboxylate | 580.2 |
| 211 | 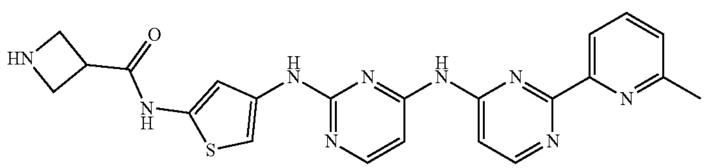 [SMILES: Cc1cccc(-c2nccc(Nc3ccnc(Nc4csc(NC(=O)C5CNC5)c4)n3)n2)n1] | N-[4-[[4-[[2-(6-methyl-2-pyridyl)pyrimidin-4-yl]amino]pyrimidin-2-yl]amino]-2-thienyl]azetidine-3-carboxamide | 460.0 |
| 212 | AND Enantiomer | [rac-(3S)-pyrrolidin-3-yl] 1-[[4-[[4-[[2-(6-methyl-2-pyridyl)pyrimidin-4-yl]amino]pyrimidin-2-yl]amino]phenyl]methyl]piperidine-3-carboxylate | 566.2 |
| 213 | 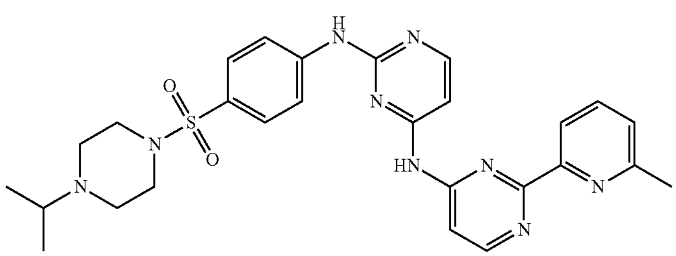 [SMILES: Cc1cccc(-c2nccc(Nc3ccnc(Nc4ccc(S(=O)(=O)N5CCN(C(C)C)CC5)cc4)n3)n2)n1] | N2-[4-(4-isopropylpiperazin-1-yl)sulfonylphenyl]-N4-[2-(6-methyl-2-pyridyl)pyrimidin-4-yl]pyrimidine-2,4-diamine | 546.1 |
| 214 | 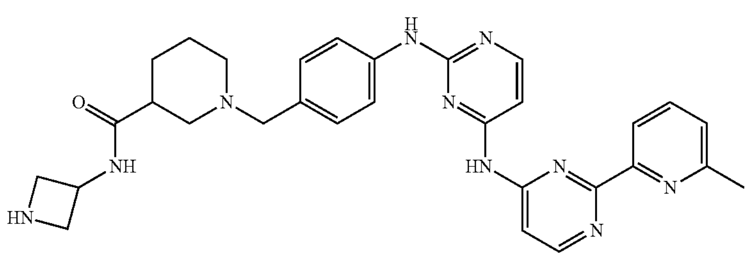 [SMILES: Cc1cccc(-c2nccc(Nc3ccnc(Nc4ccc(CN5CCCC(C(=O)NC6CNC6)C5)cc4)n3)n2)n1] | N-(azetidin-3-yl)-1-[[4-[[4-[[2-(6-methyl-2-pyridyl)pyrimidin-4-yl]amino]pyrimidin-2-yl]amino]phenyl]methyl]piperidine-3-carboxamide | 551.2 |

TABLE 1-continued

| No. | Structure | Chemical Name | [M + H]+ |
|---|---|---|---|
| 215 | 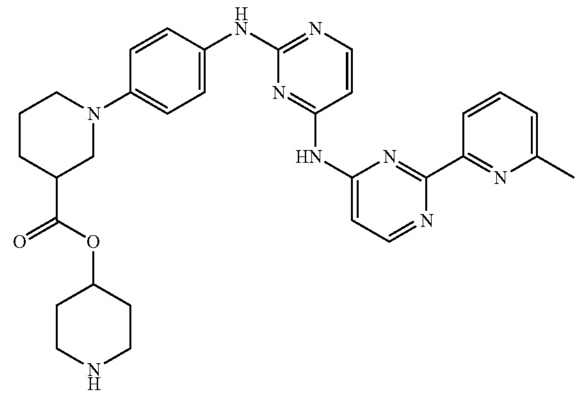 [SMILES: Cc1cccc(-c2nccc(Nc3ccnc(Nc4ccc(N5CCCC(C(=O)OC6CCNCC6)C5)cc4)n3)n2)n1] | 4-piperidyl 1-[4-[[4-[[2-(6-methyl-2-pyridyl)pyrimidin-4-yl]amino]pyrimidin-2-yl]amino]phenyl]piperidine-3-carboxylate | 566.2 |
| 216 | AND Enantiomer | N4-[2-(6-methyl-2-pyridyl)pyrimidin-4-yl]-N2-[4-[rac-(2S)-2-methylpiperazin-1-yl]phenyl]pyrimidine-2,4-diamine | 454.1 |
| 217 | 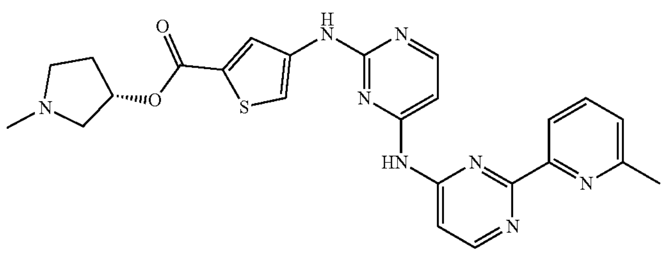 | [(3S)-1-methylpyrrolidin-3-yl] 4-[[4-[[2-(6-methyl-2-pyridyl)pyrimidin-4-yl]amino]pyrimidin-2-yl]amino]thiophene-2-carboxylate | 489.1 |
| 218 | 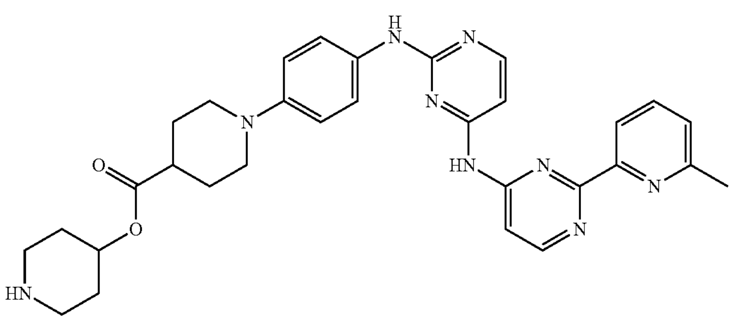 [SMILES: Cc1cccc(-c2nccc(Nc3ccnc(Nc4ccc(N5CCC(C(=O)OC6CCNCC6)CC5)cc4)n3)n2)n1] | 4-piperidyl 1-[4-[[4-[[2-(6-methyl-2-pyridyl)pyrimidin-4-yl]amino]pyrimidin-2-yl]amino]phenyl]piperidine-4-carboxylate | 566.1 |
| 219 | 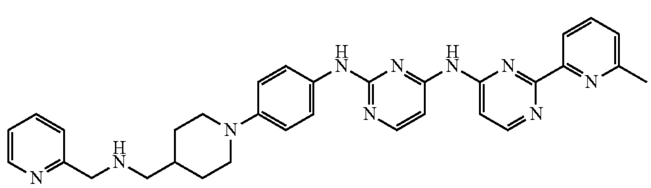 [SMILES: Cc1cccc(-c2nccc(Nc3ccnc(Nc4ccc(N5CCC(CNCc6ccccn6)CC5)cc4)n3)n2)n1] | N4-[2-(6-methyl-2-pyridyl)pyrimidin-4-yl]-N2-[4-[4-[(2-pyridylmethylamino)methyl]-1-piperidyl]phenyl]pyrimidine-2,4-diamine | 559.2 |

TABLE 1-continued

| No. | Structure | Chemical Name | [M + H]+ |
|---|---|---|---|
| 220 | 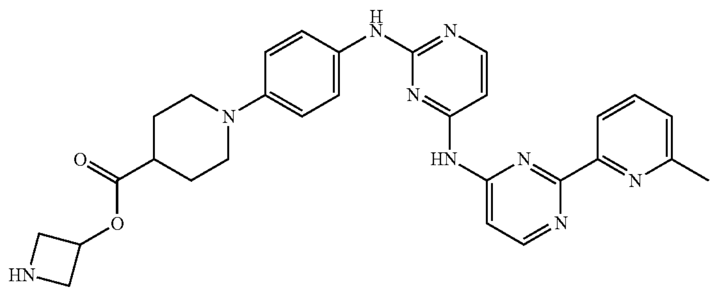 [SMILES: Cc1cccc(-c2nccc(Nc3ccnc(Nc4ccc(N5CCC(C(=O)OC6CNC6)CC5)cc4)n3)n2)n1] | azetidin-3-yl 1-[4-[[4-[[2-(6-methyl-2-pyridyl)pyrimidin-4-yl]amino]pyrimidin-2-yl]amino]phenyl]piperidine-4-carboxylate | 538.1 |
| 221 | 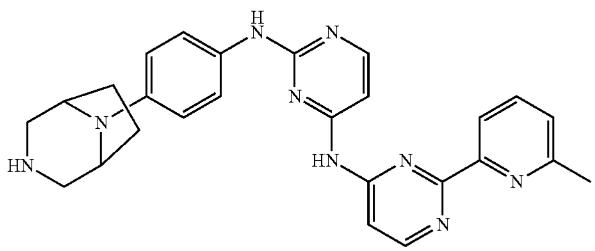 [SMILES: Cc1cccc(-c2nccc(Nc3ccnc(Nc4ccc(N5C6CCC5CNC6)cc4)n3)n2)n1] | N2-[4-(3,8-diazabicyclo[3.2.1]octan-8-yl)phenyl]-N4-[2-(6-methyl-2-pyridyl)pyrimidin-4-yl]pyrimidine-2,4-diamine | 466.1 |
| 222 | 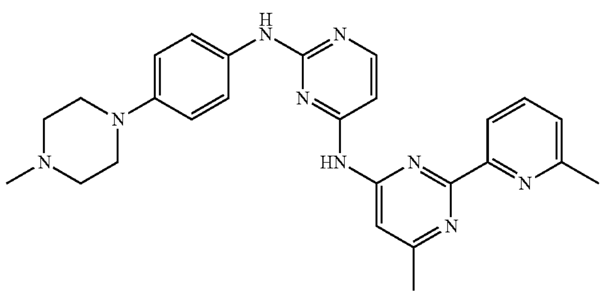 | N4-[6-methyl-2-(6-methyl-2-pyridyl)pyrimidin-4-yl]-N2-[4-(4-methylpiperazin-1-yl)phenyl]pyrimidine-2,4-diamine | 468.1 |
| 223 | 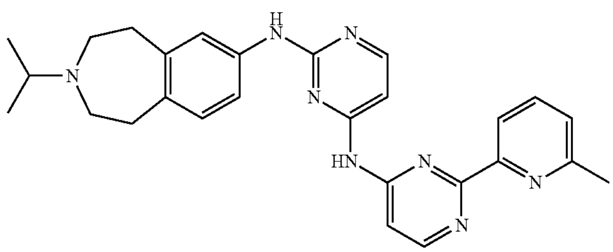 [SMILES: Cc1cccc(-c2nccc(Nc3ccnc(Nc4ccc5c(c4)CCN(C(C)C)CC5)n3)n2)n1] | N2-(3-isopropyl-1,2,4,5-tetrahydro-3-benzazepin-7-yl)-N4-[2-(6-methyl-2-pyridyl)pyrimidin-4-yl]pyrimidine-2,4-diamine | 467.3 |
| 224 | 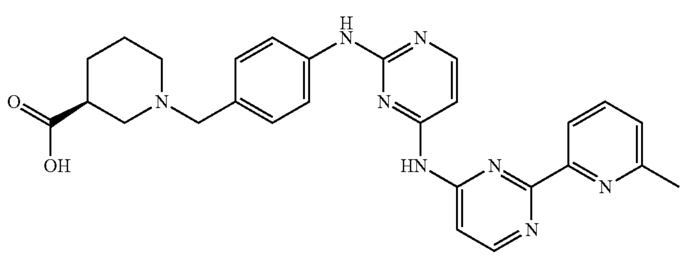 [SMILES: Cc1cccc(-c2nccc(Nc3ccnc(Nc4ccc(CN5CCC[C@H](C(=O)O)C5)cc4)n3)n2)n1] | (3S)-1-[[4-[[4-[[2-(6-methyl-2-pyridyl)pyrimidin-4-yl]amino]pyrimidin-2-yl]amino]phenyl]methyl]piperidine-3-carboxylic acid | 497.2 |
| 225 | 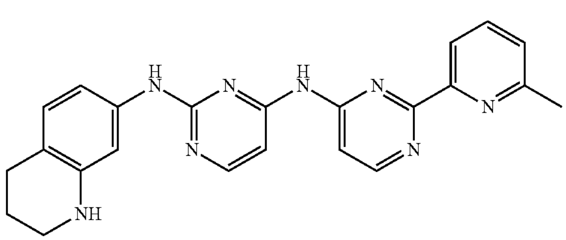 [SMILES: Cc1cccc(-c2nccc(Nc3ccnc(Nc4ccc5c(c4)NCCC5)n3)n2)n1] | N4-[2-(6-methyl-2-pyridyl)pyrimidin-4-yl]-N2-(1,2,3,4-tetrahydroquinolin-7-yl)pyrimidine-2,4-diamine | 411.2 |

TABLE 1-continued

| No. | Structure | Chemical Name | [M + H]+ |
|---|---|---|---|
| 226 | 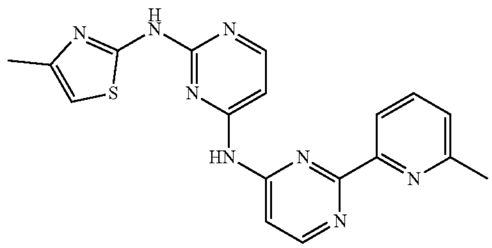 | N4-[2-(6-methyl-2-pyridyl)pyrimidin-4-yl]-N2-(4-methylthiazol-2-yl)pyrimidine-2,4-diamine | 377.0 |
| 227 | 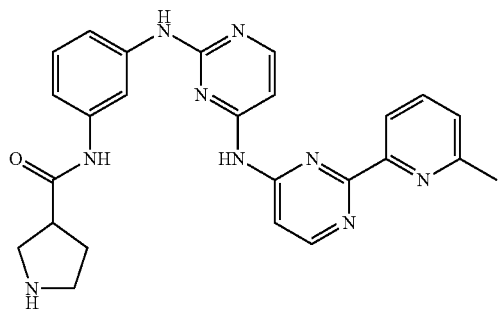 [SMILES: Cc1cccc(-c2nccc(Nc3ccnc(Nc4cccc(NC(=O)C5CCNC5)c4)n3)n2)n1] | N-[3-[[4-[[2-(6-methyl-2-pyridyl)pyrimidin-4-yl]amino]pyrimidin-2-yl]amino]phenyl]pyrrolidine-3-carboxamide | 468.1 |
| 228 | 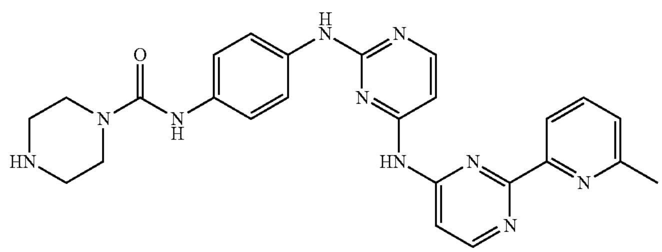 [SMILES: Cc1cccc(-c2nccc(Nc3ccnc(Nc4ccc(NC(=O)N5CCNCC5)cc4)n3)n2)n1] | N-[4-[[4-[[2-(6-methyl-2-pyridyl)pyrimidin-4-yl]amino]pyrimidin-2-yl]amino]phenyl]piperazine-1-carboxamide | 483.1 |
| 229 | 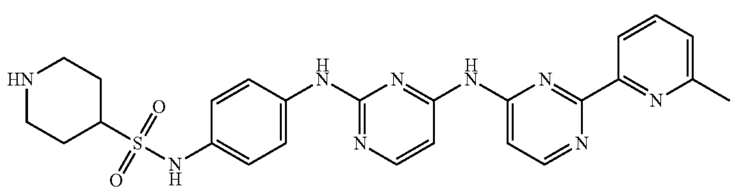 [SMILES: Cc1cccc(-c2nccc(Nc3ccnc(Nc4ccc(NS(=O)(=O)C5CCNCC5)cc4)n3)n2)n1] | N-[4-[[4-[[2-(6-methyl-2-pyridyl)pyrimidin-4-yl]amino]pyrimidin-2-yl]amino]phenyl]piperidine-4-sulfonamide | 518.2 |
| 230 | AND Enantiomer | [rac-(1R)-1-methylpropyl] 1-[4-[[4-[[2-(6-methyl-2-pyridyl)pyrimidin-4-yl]amino]pyrimidin-2-yl]amino]phenyl]piperazine-2-carboxylate | 540.2 |
| 231 | 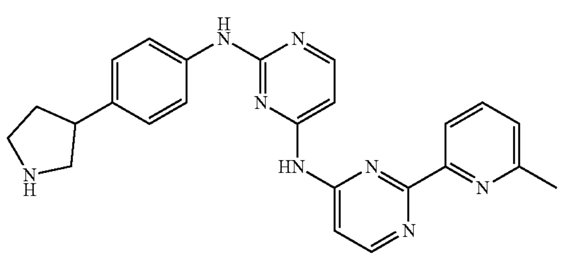 [SMILES: Cc1cccc(-c2nccc(Nc3ccnc(Nc4ccc(C5CCNC5)cc4)n3)n2)n1] | N4-[2-(6-methyl-2-pyridyl)pyrimidin-4-yl]-N2-(4-pyrrolidin-3-ylphenyl)pyrimidine-2,4-diamine | 425.1 |

TABLE 1-continued

| No. | Structure | Chemical Name | [M + H]+ |
|---|---|---|---|
| 232 | 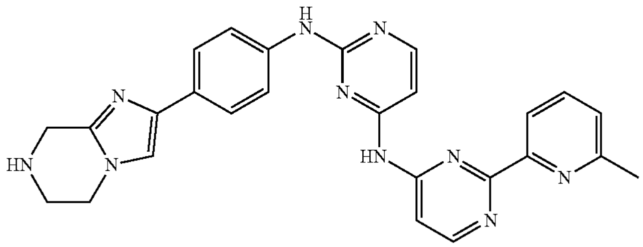 [SMILES: Cc1cccc(-c2nccc(Nc3ccnc(Nc4ccc(-c5cn6c(n5)CNCC6)cc4)n3)n2)n1] | N4-[2-(6-methyl-2-pyridyl)pyrimidin-4-yl]-N2-[4-(5,6,7,8-tetrahydroimidazo[1,2-a]pyrazin-2-yl)phenyl]pyrimidine-2,4-diamine | 477.2 |
| 233 | 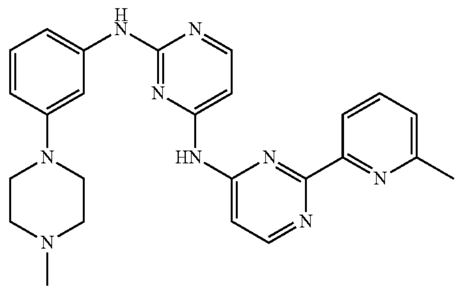 [SMILES: Cc1cccc(-c2nccc(Nc3ccnc(Nc4cccc(N5CCN(C)CC5)c4)n3)n2)n1] | N2-[3-(4-methylpiperazin-1-yl)phenyl]-N4-[2-(6-methyl-2-pyridyl)pyrimidin-4-yl]pyrimidine-2,4-diamine | 454.2 |
| 234 | 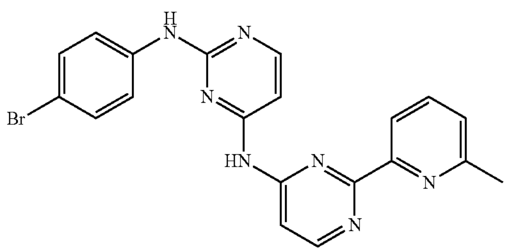 [SMILES: Cc1cccc(-c2nccc(Nc3ccnc(Nc4ccc(Br)cc4)n3)n2)n1] | N2-(4-bromophenyl)-N4-[2-(6-methyl-2-pyridyl)pyrimidin-4-yl]pyrimidine-2,4-diamine | 435.8 |
| 235 | 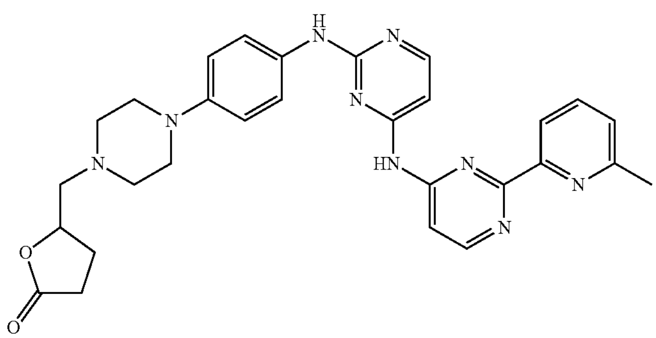 [SMILES: Cc1cccc(-c2nccc(Nc3ccnc(Nc4ccc(N5CCN(CC6CCC(=O)O6)CC5)cc4)n3)n2)n1] | 5-[[4-[4-[[4-[[2-(6-methyl-2-pyridyl)pyrimidin-4-yl]amino]pyrimidin-2-yl]amino]phenyl]piperazin-1-yl]methyl]tetrahydrofuran-2-one | 538.2 |
| 236 | 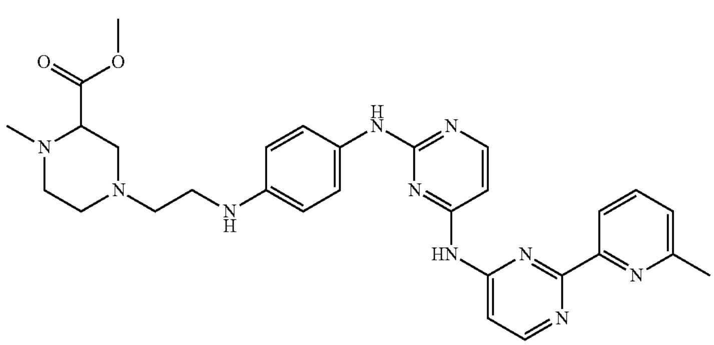 | methyl 1-methyl-4-[2-[4-[[4-[[2-(6-methyl-2-pyridyl)pyrimidin-4-yl]amino]pyrimidin-2-yl]amino]anilino]ethyl]piperazine-2-carboxylate | 555.1 |

TABLE 1-continued

| No. | Structure | Chemical Name | [M + H]+ |
|---|---|---|---|
| 237 | 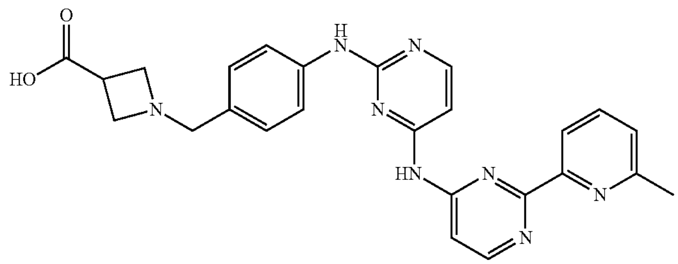 [SMILES: Cc1cccc(-c2nccc(Nc3ccnc(Nc4ccc(CN5CC(C(=O)O)C5)cc4)n3)n2)n1] | 1-[[4-[[4-[[2-(6-methyl-2-pyridyl)pyrimidin-4-yl]amino]pyrimidin-2-yl]amino]phenyl]methyl]azetidine-3-carboxylic acid | 469.2 |
| 238 | 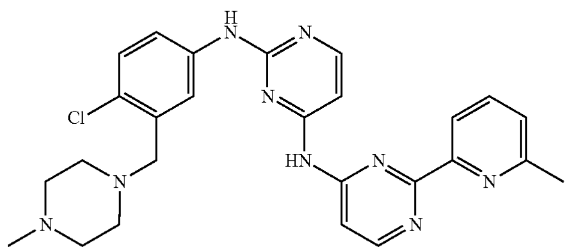 | N2-[4-chloro-3-[(4-methylpiperazin-1-yl)methyl]phenyl]-N4-[2-(6-methyl-2-pyridyl)pyrimidin-4-yl]pyrimidine-2,4-diamine | 502.1 |
| 239 | 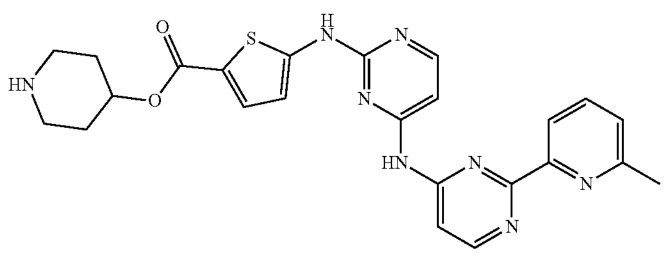 [SMILES: Cc1cccc(-c2nccc(Nc3ccnc(Nc4ccc(C(=O)OC5CCNCC5)s4)n3)n2)n1] | 4-piperidyl 5-[[4-[[2-(6-methyl-2-pyridyl)pyrimidin-4-yl]amino]pyrimidin-2-yl]amino]thiophene-2-carboxylate | 489.1 |
| 240 | 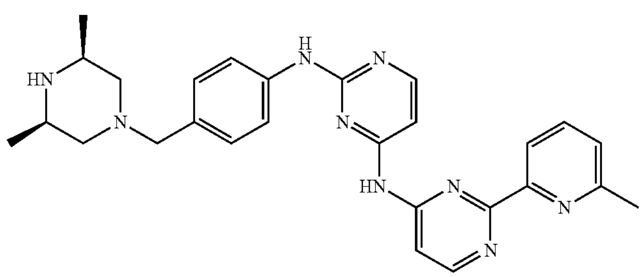 | N2-[4-[[(3R,5S)-3,5-dimethylpiperazin-1-yl]methyl]phenyl]-N4-[2-(6 methyl-2-pyridyl)pyrimidin-4-yl]pyrimidine-2,4-diamine | 482.2 |
| 241 | 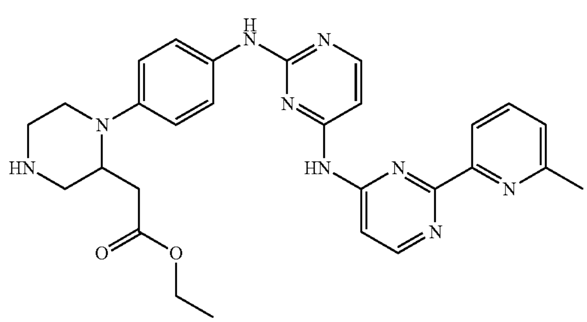 [SMILES: CCOC(=O)CC1CNCCN1c1ccc(Nc2nccc(Nc3ccnc(-c4cccc(C)n4)n3)n2)cc1] | ethyl 2-[1-[4-[[4-[[2-(6-methyl-2-pyridyl)pyrimidin-4-yl]amino]pyrimidin-2-yl]amino]phenyl]piperazin-2-yl]acetate | 526.4 |

TABLE 1-continued

| No. | Structure | Chemical Name | [M + H]+ |
|---|---|---|---|
| 242 | 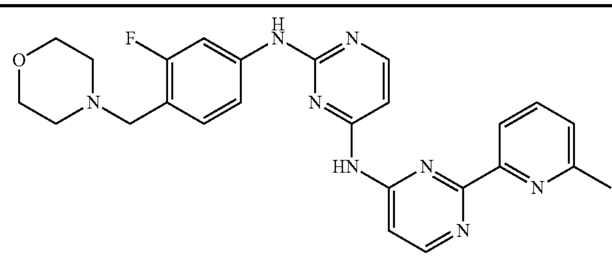 | N2-[3-fluoro-4-(morpholinomethyl)phenyl]-N4-[2-(6-methyl-2-pyridyl)pyrimidin-4-yl]pyrimidine-2,4-diamine | 473.2 |
| 243 | 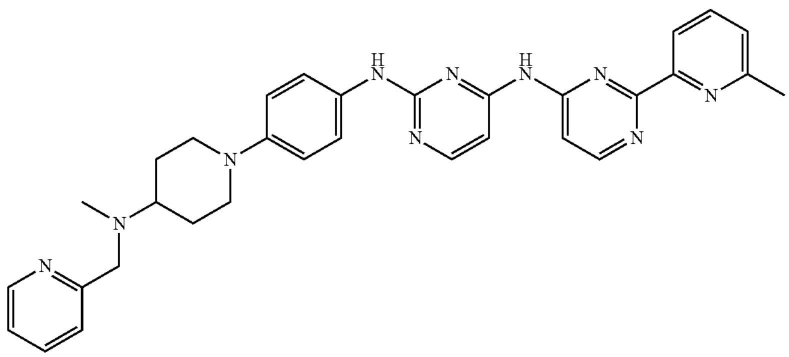 [SMILES: Cc1cccc(-c2nccc(Nc3ccnc(Nc4ccc(N5CCC(N(C)Cc6ccccn6)CC5)cc4)n3)n2)n1] | N2-[4-[4-[methyl(2-pyridylmethyl)amino]-1-piperidyl]phenyl]-N4-[2-(6-methyl-2-pyridyl)pyrimidin-4-yl]pyrimidine-2,4-diamine | 559.3 |
| 244 | 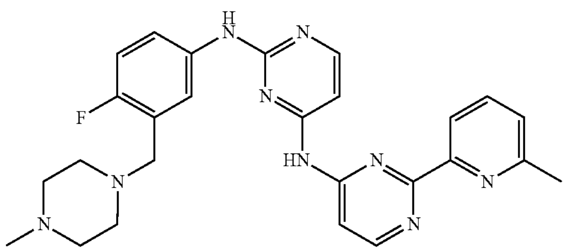 | N2-[4-fluoro-3-[(4-methylpiperazin-1-yl)methyl]phenyl]-N4-[2-(6-methyl-2-pyridyl)pyrimidin-4-yl]pyrimidine-2,4-diamine | 486.2 |
| 245 | 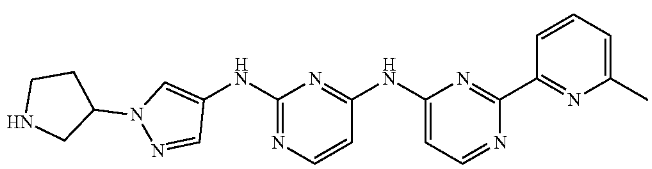 [SMILES: Cc1cccc(-c2nccc(Nc3ccnc(Nc4cnn(C5CCNC5)c4)n3)n2)n1] | N4-[2-(6-methyl-2-pyridyl)pyrimidin-4-yl]-N2-(1-pyrrolidin-3-ylpyrazol-4-yl)pyrimidine-2,4-diamine | 415.1 |
| 246 | 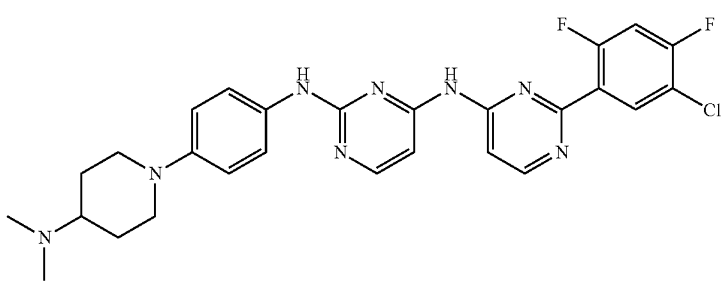 [SMILES: CN(C)C1CCN(c2ccc(Nc3nccc(Nc4ccnc(-c5cc(Cl)c(F)cc5F)n4)n3)cc2)CC1] | N4-[2-(5-chloro-2,4-difluoro-phenyl)pyrimidin-4-yl]-N2-[4-[4-(dimethylamino)-1-piperidyl]phenyl]pyrimidine-2,4-diamine | 538.1 |
| 247 | 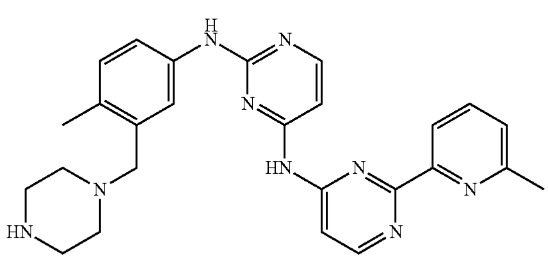 [SMILES: Cc1cccc(-c2nccc(Nc3ccnc(Nc4ccc(C)c(CN5CCNCC5)c4)n3)n2)n1] | N2-[4-methyl-3-(piperazin-1-ylmethyl)phenyl]-N4-[2-(6-methyl-2-pyridyl)pyrimidin-4-yl]pyrimidine-2,4-diamine | 468.2 |

TABLE 1-continued

| No. | Structure | Chemical Name | [M + H]+ |
|---|---|---|---|
| 248 | 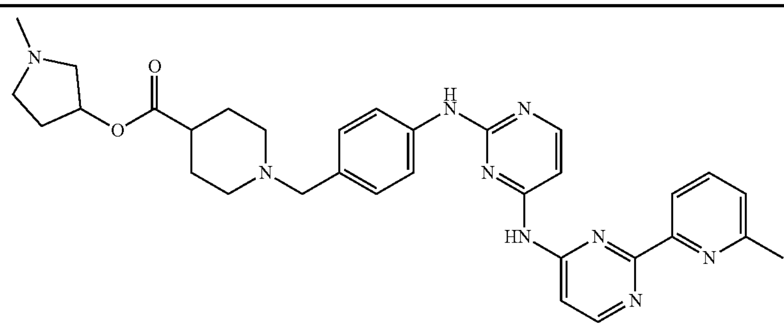 | (1-methylpyrrolidin-3-yl) 1-[[4-[[4-[[2-(6-methyl-2-pyridyl)pyrimidin-4-yl]amino]pyrimidin-2-yl]amino]phenyl]methyl]piperidine-4-carboxylate | 580.2 |
| 249 | 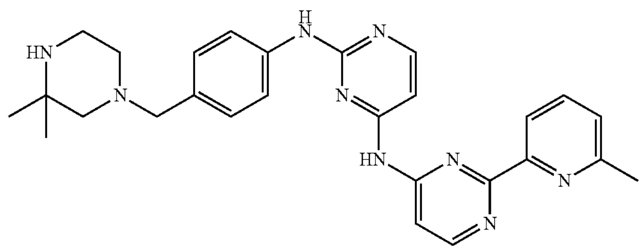 | N2-[4-[(3,3-dimethylpiperazin-1-yl)methyl]phenyl]-N4-[2-(6-methyl-2-pyridyl)pyrimidin-4-yl]pyrimidine-2,4-diamine | 482.3 |
| 250 | 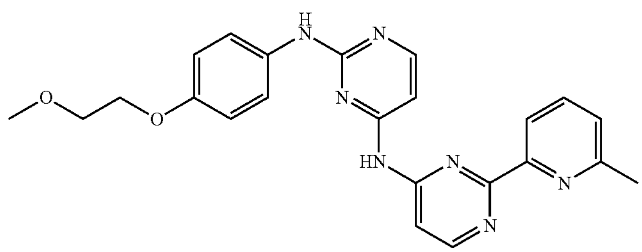 | N2-[4-(2-methoxyethoxy)phenyl]-N4-[2-(6-methyl-2-pyridyl)pyrimidin-4-yl]pyrimidine-2,4-diamine | 430.2 |
| 251 | 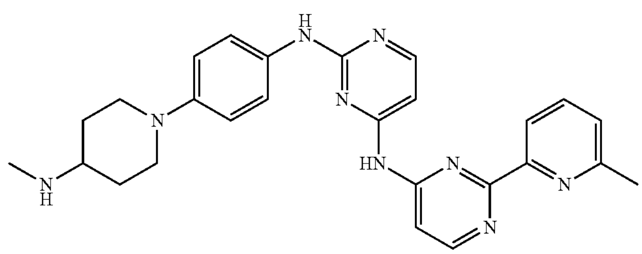 | N2-[4-[4-(methylamino)-1-piperidyl]phenyl]-N4-[2-(6-methyl-2-pyridyl)pyrimidin-4-yl]pyrimidine-2,4-diamine | 468.1 |
| 252 | 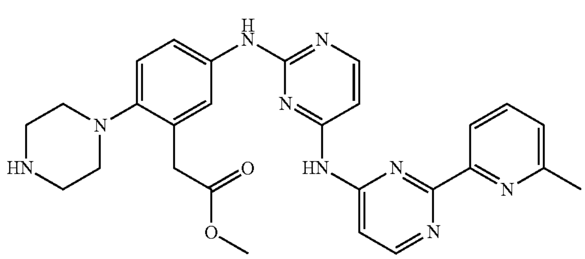 [SMILES: COC(=O)Cc1cc(Nc2nccc(Nc3ccnc(-c4cccc(C)n4)n3)n2)ccc1N1CCNCC1] | methyl 2-[5-[[4-[[2-(6-methyl-2-pyridyl)pyrimidin-4-yl]amino]pyrimidin-2-yl]amino]-2-piperazin-1-yl-phenyl]acetate | 512.4 |
| 253 | 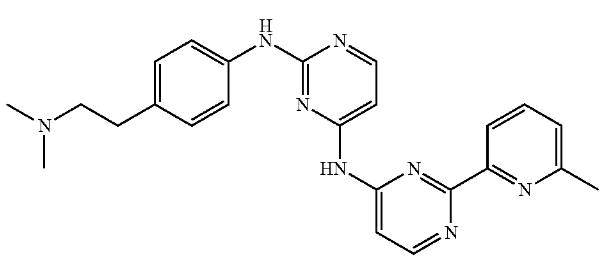 | N2-[4-[2-(dimethylamino)ethyl]phenyl]-N4-[2-(6-methyl-2-pyridyl)pyrimidin-4-yl]pyrimidine-2,4-diamine | 427.2 |

TABLE 1-continued

| No. | Structure | Chemical Name | [M + H]+ |
|---|---|---|---|
| 254 | 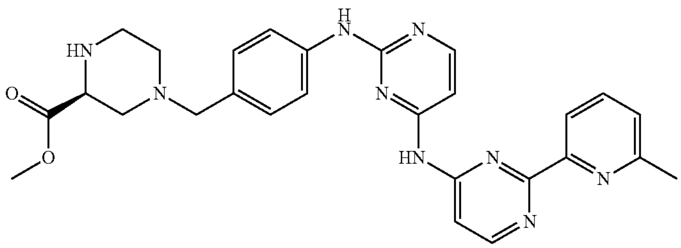 [SMILES: COC(=O)[C@@H]1CN(Cc2ccc(Nc3nccc(Nc4ccnc(-c5cccc(C)n5)n4)n3)cc2)CCN1] | methyl (2S)-4-[[4-[[4-[[2-(6-methyl-2-pyridyl)pyrimidin-4-yl]amino]pyrimidin-2-yl]amino]phenyl]methyl]piperazine-2-carboxylate | 512.2 |
| 255 | 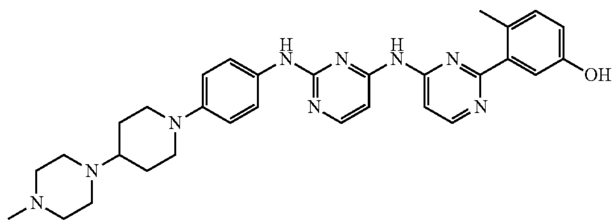 [SMILES: Cc1ccc(O)cc1-c1nccc(Nc2ccnc(Nc3ccc(N4CCC(N5CCN(C)CC5)CC4)cc3)n2)n1] | 4-methyl-3-[4-[[2-[4-[4-(4-methylpiperazin-1-yl)-1-piperidyl]anilino]pyrimidin-4-yl]amino]pyrimidin-2-yl]phenol | 552.2 |
| 256 | 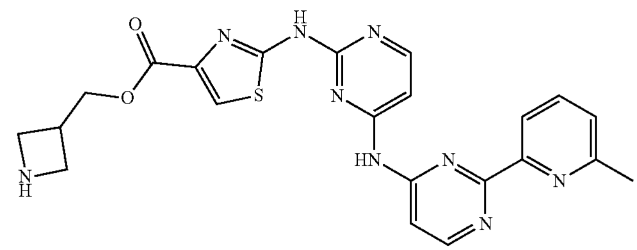 [SMILES: Cc1cccc(-c2nccc(Nc3ccnc(Nc4nc(C(=O)OCC5CNC5)cs4)n3)n2)n1] | azetidin-3-ylmethyl 2-[[4-[[2-(6-methyl-2-pyridyl)pyrimidin-4-yl]amino]pyrimidin-2-yl]amino]thiazole-4-carboxylate | 476.0 |
| 257 | 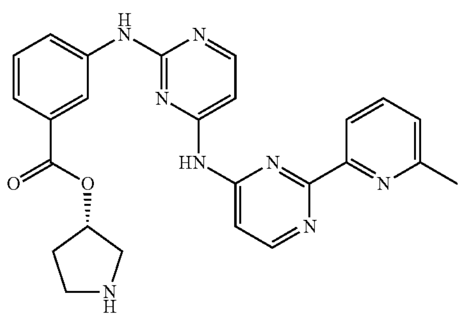 [SMILES: Cc1cccc(-c2nccc(Nc3ccnc(Nc4cccc(C(=O)O[C@H]5CCNC5)c4)n3)n2)n1] | [(3S)-pyrrolidin-3-yl] 3-[[4-[[2-(6-methyl-2-pyridyl)pyrimidin-4-yl]amino]pyrimidin-2-yl]amino]benzoate | 469.2 |
| 258 | 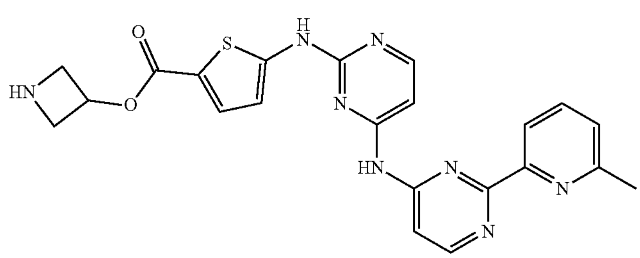 [SMILES: Cc1cccc(-c2nccc(Nc3ccnc(Nc4ccc(C(=O)OC5CNC5)s4)n3)n2)n1] | azetidin-3-yl 5-[[4-[[2-(6-methyl-2-pyridyl)pyrimidin-4-yl]amino]pyrimidin-2-yl]amino]thiophene-2-carboxylate | 461.1 |
| 259 | 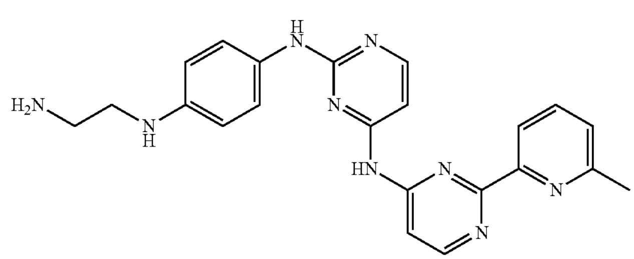 [SMILES: Cc1cccc(-c2nccc(Nc3ccnc(Nc4ccc(NCCN)cc4)n3)n2)n1] | N2-[4-(2-aminoethylamino)phenyl]-N4-[2-(6-methyl-2-pyridyl)pyrimidin-4-yl]pyrimidine-2,4-diamine | 414.2 |

TABLE 1-continued

| No. | Structure | Chemical Name | [M + H]+ |
|---|---|---|---|
| 260 | 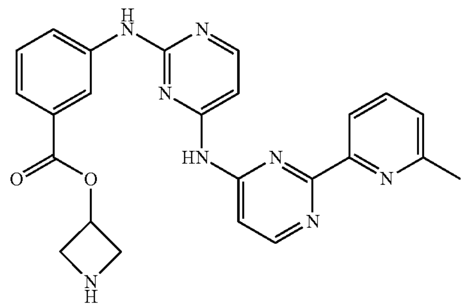 [SMILES: Cc1cccc(-c2nccc(Nc3ccnc(Nc4cccc(C(=O)OC5CNC5)c4)n3)n2)n1] | azetidin-3-yl 3-[[4-[[2-(6-methyl-2-pyridyl)pyrimidin-4-yl]amino]pyrimidin-2-yl]amino]benzoate | 455.1 |
| 261 | 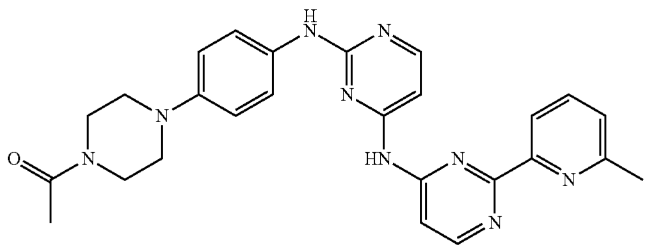 [SMILES: CC(=O)N1CCN(c2ccc(Nc3nccc(Nc4ccnc(-c5cccc(C)n5)n4)n3)cc2)CC1] | 1-[4-[4-[[4-[[2-(6-methyl-2-pyridyl)pyrimidin-4-yl]amino]pyrimidin-2-yl]amino]phenyl]piperazin-1-yl]ethanone | 482.2 |
| 262 | 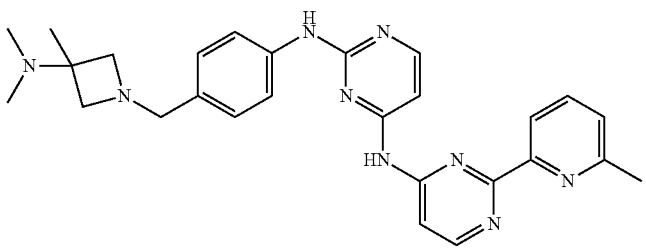 | N2-[4-[[3-(dimethylamino)-3-methyl-azetidin-1-yl]methyl]phenyl]-N4-[2-(6-methyl-2-pyridyl)pyrimidin-4-yl]pyrimidine-2,4-diamine | 482.2 |
| 263 | 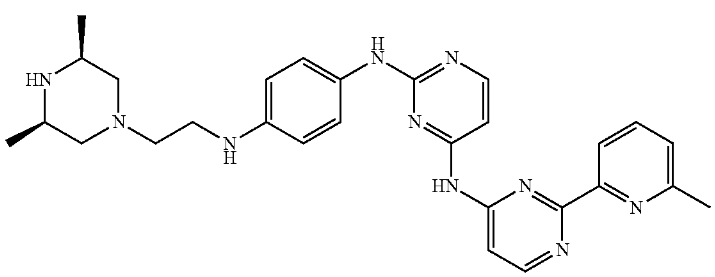 | N4-[2-(6-methyl-2-pyridyl)pyrimidin-4-yl]-N2-[4-[2-[rac-(3S,5R)-3,5-dimethylpiperazin-1-yl]ethylamino]phenyl]pyrimidine-2,4-diamine | 511.2 |
| 264 | 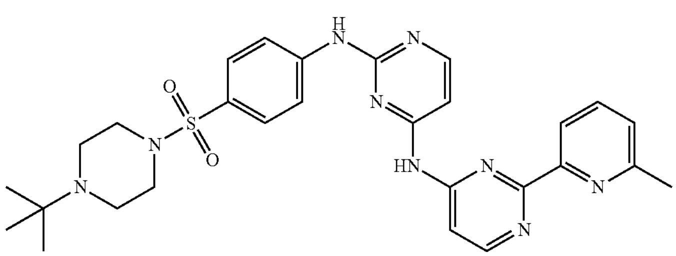 [SMILES: Cc1cccc(-c2nccc(Nc3ccnc(Nc4ccc(S(=O)(=O)N5CCN(C(C)(C)C)CC5)cc4)n3)n2)n1] | N2-[4-(4-tert-butylpiperazin-1-yl)sulfonylphenyl]-N4-[2-(6-methyl-2-pyridyl)pyrimidin-4-yl]pyrimidine-2,4-diamine | 560.1 |
| 265 | 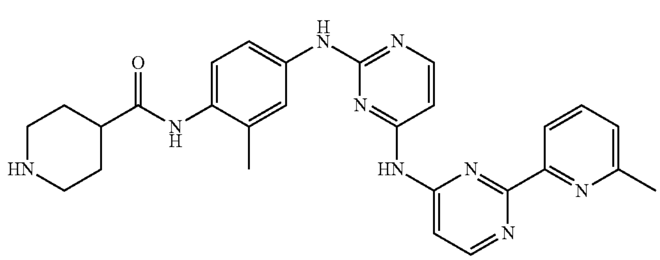 [SMILES: Cc1cccc(-c2nccc(Nc3ccnc(Nc4ccc(NC(=O)C5CCNCC5)c(C)c4)n3)n2)n1] | N-[2-methyl-4-[[4-[[2-(6-methyl-2-pyridyl)pyrimidin-4-yl]amino]pyrimidin-2-yl]amino]phenyl]piperidine-4-carboxamide | 496.1 |

TABLE 1-continued

| No. | Structure | Chemical Name | [M + H]⁺ |
|---|---|---|---|
| 266 | 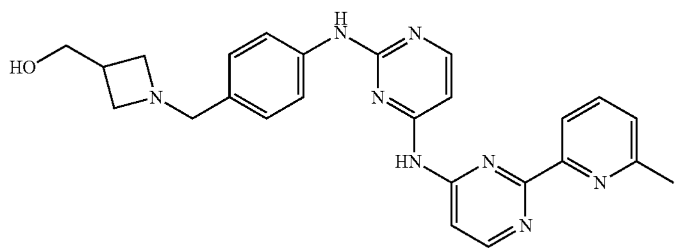 [SMILES: Cc1cccc(-c2nccc(Nc3ccnc(Nc4ccc(CN5CC(CO)C5)cc4)n3)n2)n1] | [1-[[4-[[4-[[2-(6-methyl-2-pyridyl)pyrimidin-4-yl]amino]pyrimidin-2-yl]amino]phenyl]methyl]azetidin-3-yl]methanol | 455.1 |
| 267 | 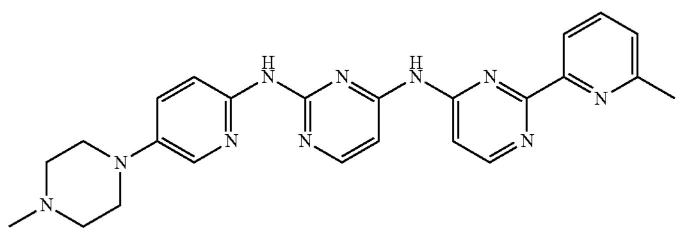 | N2-[5-(4-methylpiperazin-1-yl)-2-pyridyl]-N4-[2-(6-methyl-2-pyridyl)pyrimidin-4-yl]pyrimidine-2,4-diamine | 455.1 |
| 268 | 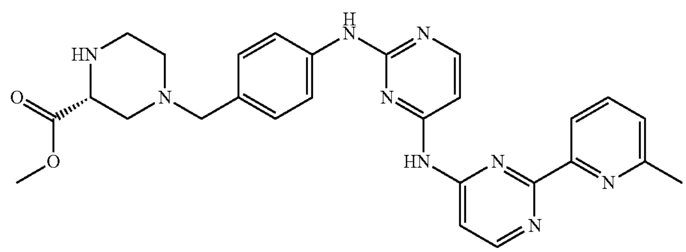 [SMILES: COC(=O)[C@H]1CN(Cc2ccc(Nc3nccc(Nc4ccnc(-c5cccc(C)n5)n4)n3)cc2)CCN1] | methyl (2R)-4-[[4-[[4-[[2-(6-methyl-2-pyridyl)pyrimidin-4-yl]amino]pyrimidin-2-yl]amino]phenyl]methyl]piperazine-2-carboxylate | 512.2 |
| 269 | 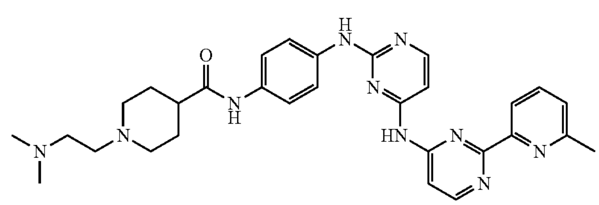 | 1-[2-(dimethylamino)ethyl]-N-[4-[[4-[[2-(6-methyl-2-pyridyl)pyrimidin-4-yl]amino]pyrimidin-2-yl]amino]phenyl]piperidine-4-carboxamide | 553.2 |
| 270 | 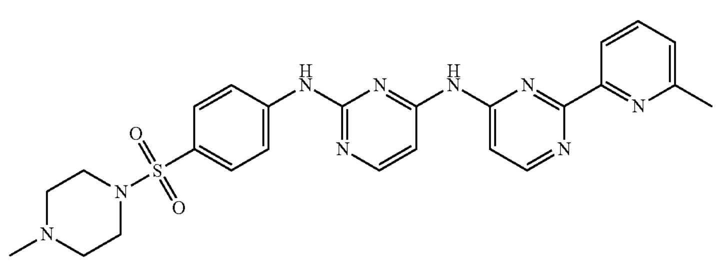 | N2-[4-(4-methylpiperazin-1-yl)sulfonylphenyl]-N4-[2-(6-methyl-2-pyridyl)pyrimidin-4-yl]pyrimidine-2,4-diamine | 518.2 |
| 271 | 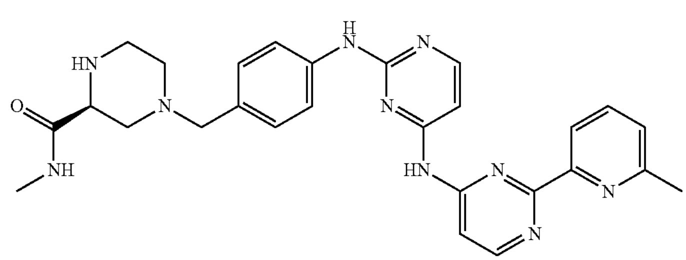 [SMILES: CNC(=O)[C@@H]1CN(Cc2ccc(Nc3nccc(Nc4ccnc(-c5cccc(C)n5)n4)n3)cc2)CCN1] | (2S)-N-methyl-4-[[4-[[4-[[2-(6-methyl-2-pyridyl)pyrimidin-4-yl]amino]pyrimidin-2-yl]amino]phenyl]methyl]piperazine-2-carboxamide | 511.1 |

TABLE 1-continued

| No. | Structure | Chemical Name | [M + H]+ |
|---|---|---|---|
| 272 | 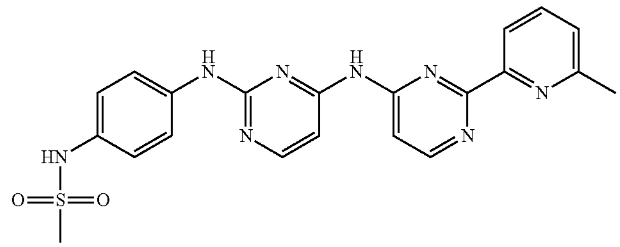 [SMILES: Cc1cccc(-c2nccc(Nc3ccnc(Nc4ccc(NS(C)(=O)=O)cc4)n3)n2)n1] | N-[4-[[4-[[2-(6-methyl-2-pyridyl)pyrimidin-4-yl]amino]pyrimidin-2-yl]amino]phenyl]methanesulfonamide | 449.1 |
| 273 | 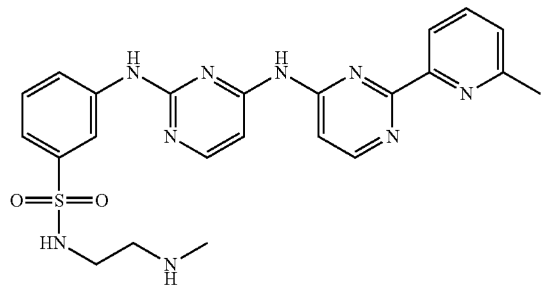 [SMILES: CNCCNS(=O)(=O)c1cccc(Nc2nccc(Nc3ccnc(-c4cccc(C)n4)n3)n2)c1] | N-[2-(methylamino)ethyl]-3-[[4-[[2-(6-methyl-2-pyridyl)pyrimidin-4-yl]amino]pyrimidin-2-yl]amino]benzenesulfonamide | 492.1 |
| 274 | AND Enantiomer | N4-[2-(6-methyl-2-pyridyl)pyrimidin-4-yl]-N2-[4-[methyl-[rac-(3R)-pyrrolidin-3-yl]amino]phenyl]pyrimidine-2,4-diamine | 454.1 |
| 275 | 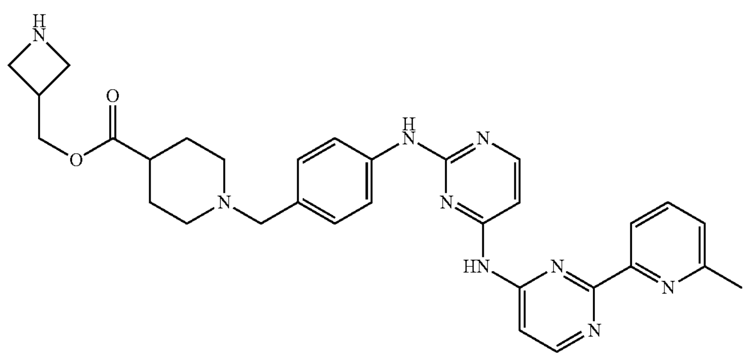 [SMILES: Cc1cccc(-c2nccc(Nc3ccnc(Nc4ccc(CN5CCC(C(=O)OCC6CNC6)CC5)cc4)n3)n2)n1] | azetidin-3-ylmethyl 1-[[4-[[4-[[2-(6-methyl-2-pyridyl)pyrimidin-4-yl]amino]pyrimidin-2-yl]amino]phenyl]methyl]piperidine-4-carboxylate | 566.1 |
| 276 | 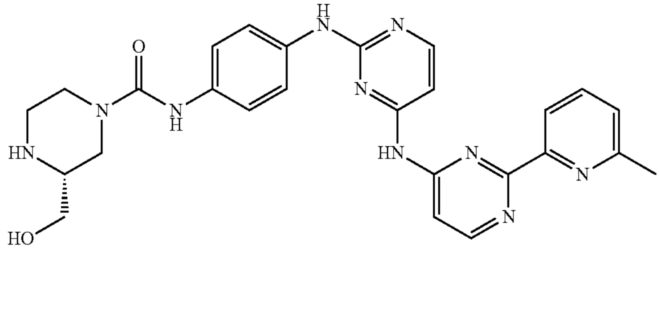 [SMILES: Cc1cccc(-c2nccc(Nc3ccnc(Nc4ccc(NC(=O)N5CCN[C@@H](CO)C5)cc4)n3)n2)n1] | (3R)-3-(hydroxymethyl)-N-[4-[[4-[[2-(6-methyl-2-pyridyl)pyrimidin-4-yl]amino]pyrimidin-2-yl]amino]phenyl]piperazine-1-carboxamide | 513.2 |

TABLE 1-continued

| No. | Structure | Chemical Name | [M + H]+ |
|---|---|---|---|
| 277 | 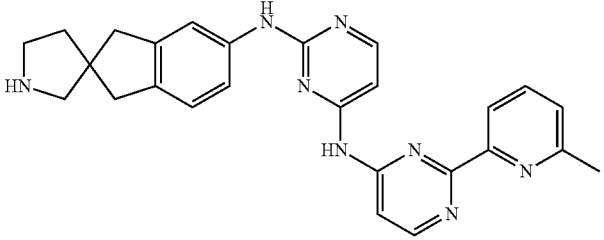 [SMILES: Cc1cccc(-c2nccc(Nc3ccnc(Nc4ccc5c(c4)CC4(CCNC4)C5)n3)n2)n1] | N4-[2-(6-methyl-2-pyridyl)pyrimidin-4-yl]-N2-spiro[indane-2,3'-pyrrolidine]-5-yl-pyrimidine-2,4-diamine | 451.1 |
| 278 | 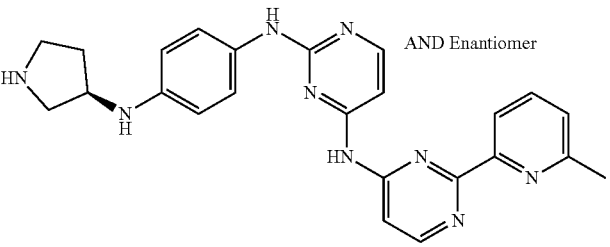 [SMILES: Cc1cccc(-c2nccc(Nc3ccnc(Nc4ccc(N[C@@H]5CCNC5)cc4)n3)n2)n1] AND Enantiomer | N4-[2-(6-methyl-2-pyridyl)pyrimidin-4-yl]-N2-[4-[[rac-(3R)-pyrrolidin-3-yl]amino]phenyl]pyrimidine-2,4-diamine | 440.1 |
| 279 | 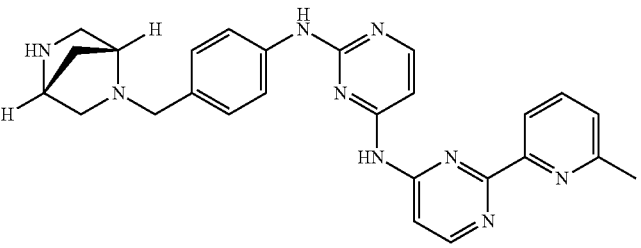 [SMILES: Cc1cccc(-c2nccc(Nc3ccnc(Nc4ccc(CN5C[C@H]6C[C@@H]5CN6)cc4)n3)n2)n1] | N2-[4-[[(1R,4R)-2,5-diazabicyclo[2.2.1]heptan-2-yl]methyl]phenyl]-N4-[2-(6-methyl-2-pyridyl)pyrimidin-4-yl]pyrimidine-2,4-diamine | 466.3 |
| 280 | 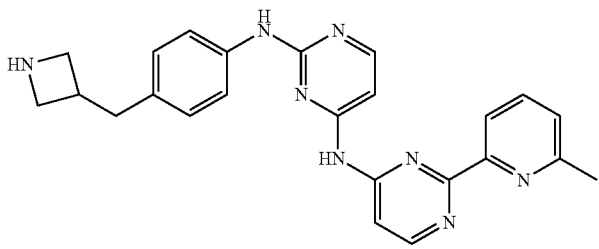 [SMILES: Cc1cccc(-c2nccc(Nc3ccnc(Nc4ccc(CC5CNC5)cc4)n3)n2)n1] | N2-[4-(azetidin-3-ylmethyl)phenyl]-N4-[2-(6-methyl-2-pyridyl)pyrimidin-4-yl]pyrimidine-2,4-diamine | 425.3 |
| 281 | 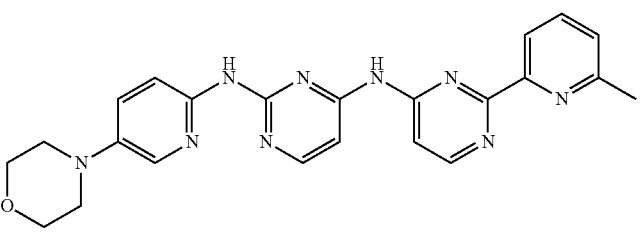 [SMILES: Cc1cccc(-c2nccc(Nc3ccnc(Nc4ccc(N5CCOCC5)cn4)n3)n2)n1] | N4-[2-(6-methyl-2-pyridyl)pyrimidin-4-yl]-N2-(5-morpholino-2-pyridyl)pyrimidine-2,4-diamine | 442.3 |

TABLE 1-continued

| No. | Structure | Chemical Name | [M + H]+ |
|---|---|---|---|
| 282 | 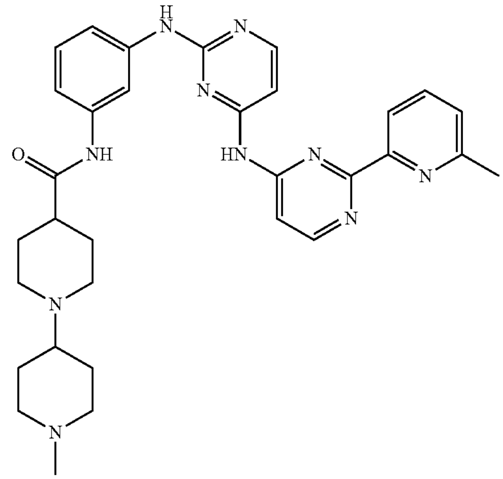 [SMILES: Cc1cccc(-c2nccc(Nc3ccnc(Nc4cccc(NC(=O)C5CCN(C6CCN(C)CC6)CC5)c4)n3)n2)n1] | 1-(1-methyl-4-piperidyl)-N-[3-[[4-[[2-(6-methyl-2-pyridyl)pyrimidin-4-yl]amino]pyrimidin-2-yl]amino]phenyl]piperidine-4-carboxamide | 579.2 |
| 283 | 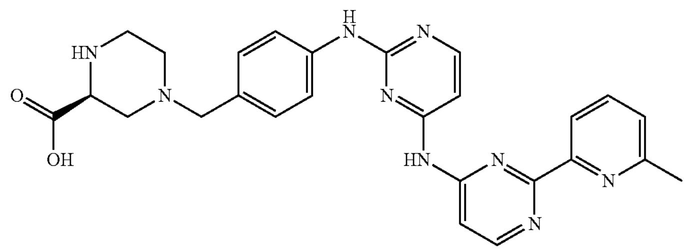 [SMILES: Cc1cccc(-c2nccc(Nc3ccnc(Nc4ccc(CN5CCN[C@H](C(=O)O)C5)cc4)n3)n2)n1] | (2S)-4-[[4-[[4-[[2-(6-methyl-2-pyridyl)pyrimidin-4-yl]amino]pyrimidin-2-yl]amino]phenyl]methyl]piperazine-2-carboxylic acid | 498.2 |
| 284 | 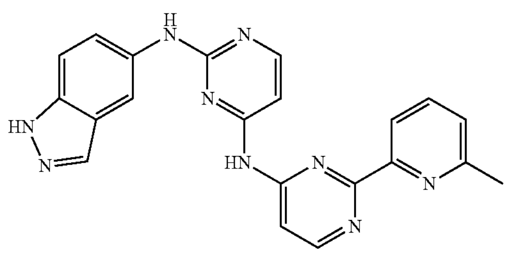 [SMILES: Cc1cccc(-c2nccc(Nc3ccnc(Nc4ccc5[nH]ncc5c4)n3)n2)n1] | N2-(1H-indazol-5-yl)-N4-[2-(6-methyl-2-pyridyl)pyrimidin-4-yl]pyrimidine-2,4-diamine | 396.0 |
| 285 | 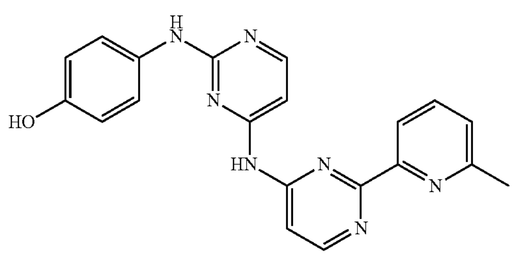 [SMILES: Cc1cccc(-c2nccc(Nc3ccnc(Nc4ccc(O)cc4)n3)n2)n1] | 4-[[4-[[2-(6-methyl-2-pyridyl)pyrimidin-4-yl]amino]pyrimidin-2-yl]amino]phenol | 372.2 |
| 286 | 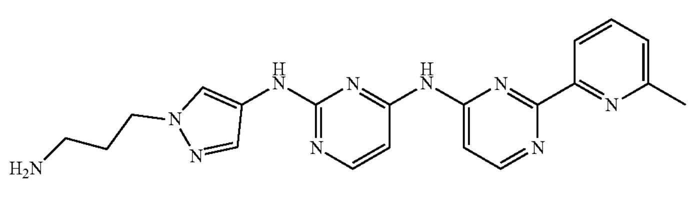 [SMILES: Cc1cccc(-c2nccc(Nc3ccnc(Nc4cnn(CCCN)c4)n3)n2)n1] | N2-[1-(3-aminopropyl)pyrazol-4-yl]-N4-[2-(6-methyl-2-pyridyl)pyrimidin-4-yl]pyrimidine-2,4-diamine | 403.2 |

TABLE 1-continued

| No. | Structure | Chemical Name | [M + H]+ |
|---|---|---|---|
| 287 | 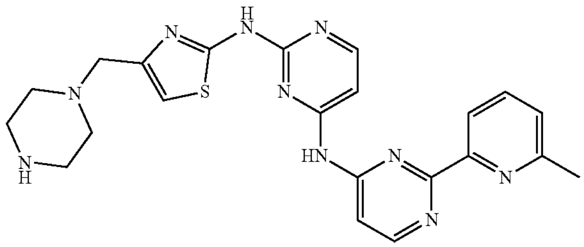 [SMILES: Cc1cccc(-c2nccc(Nc3ccnc(Nc4nc(CN5CCNCC5)cs4)n3)n2)n1] | N4-[2-(6-methyl-2-pyridyl)pyrimidin-4-yl]-N2-[4-(piperazin-1-ylmethyl)thiazol-2-yl]pyrimidine-2,4-diamine | 461.2 |
| 288 | 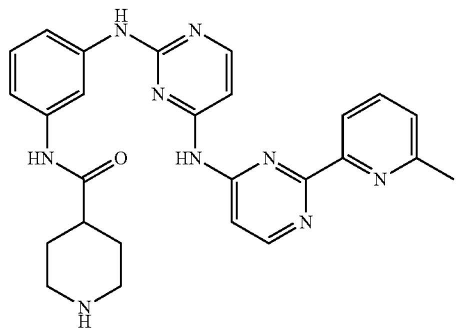 [SMILES: Cc1cccc(-c2nccc(Nc3ccnc(Nc4cccc(NC(=O)C5CCNCC5)c4)n3)n2)n1] | N-[3-[[4-[[2-(6-methyl-2-pyridyl)pyrimidin-4-yl]amino]pyrimidin-2-yl]amino]phenyl]piperidine-4-carboxamide | 482.2 |
| 289 | 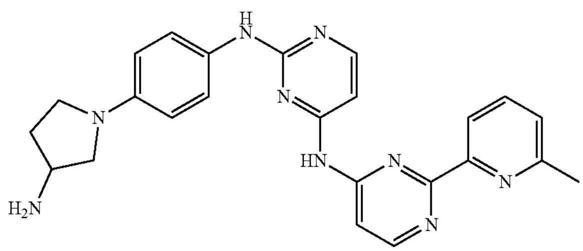 [SMILES: Cc1cccc(-c2nccc(Nc3ccnc(Nc4ccc(N5CCC(N)C5)cc4)n3)n2)n1] | N2-[4-(3-aminopyrrolidin-1-yl)phenyl]-N4-[2-(6-methyl-2-pyridyl)pyrimidin-4-yl]pyrimidine-2,4-diamine | 440.2 |
| 290 | 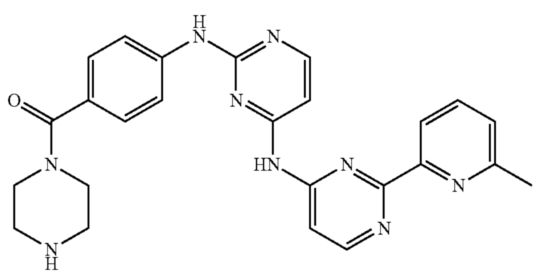 [SMILES: Cc1cccc(-c2nccc(Nc3ccnc(Nc4ccc(C(=O)N5CCNCC5)cc4)n3)n2)n1] | [4-[[4-[[2-(6-methyl-2-pyridyl)pyrimidin-4-yl]amino]pyrimidin-2-yl]amino]phenyl]-piperazin-1-yl-methanone | 468.1 |
| 291 | 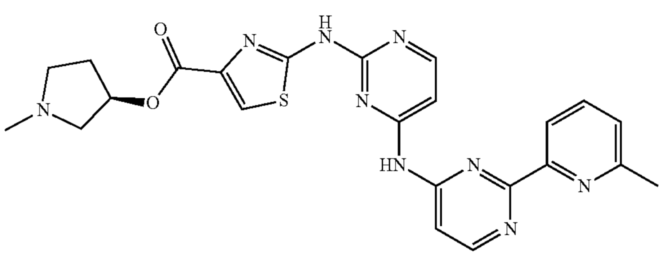 | [(3R)-1-methylpyrrolidin-3-yl] 2-[[4-[[2-(6-methyl-2-pyridyl)pyrimidin-4-yl]amino]pyrimidin-2-yl]amino]thiazole-4-carboxylate | 490.0 |

TABLE 1-continued

| No. | Structure | Chemical Name | [M + H]+ |
|---|---|---|---|
| 292 | 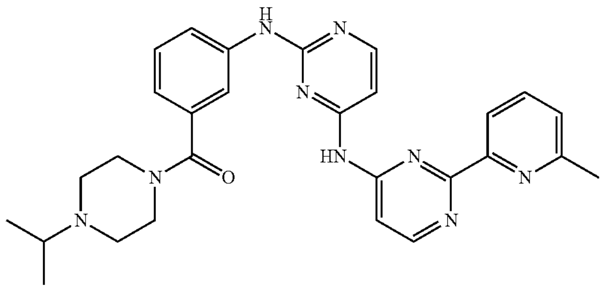 [SMILES: Cc1cccc(-c2nccc(Nc3ccnc(Nc4cccc(C(=O)N5CCN(C(C)C)CC5)c4)n3)n2)n1] | (4-isopropylpiperazin-1-yl)-[3-[[4-[[2-(6-methyl-2-pyridyl)pyrimidin-4-yl]amino]pyrimidin-2-yl]amino]phenyl]methanone | 510.1 |
| 293 | 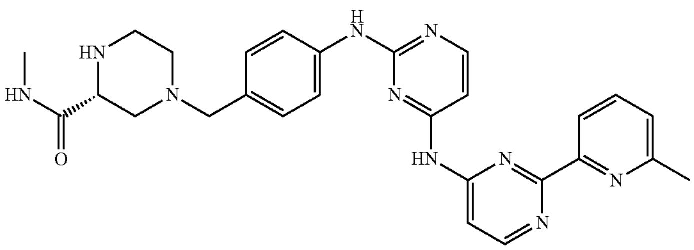 [SMILES: CNC(=O)[C@H]1CN(Cc2ccc(Nc3nccc(Nc4ccnc(-c5cccc(C)n5)n4)n3)cc2)CCN1] | (2R)-N-methyl-4-[[4-[[4-[[2-(6-methyl-2-pyridyl)pyrimidin-4-yl]amino]pyrimidin-2-yl]amino]phenyl]methyl]piperazine-2-carboxamide | 511.1 |
| 294 | 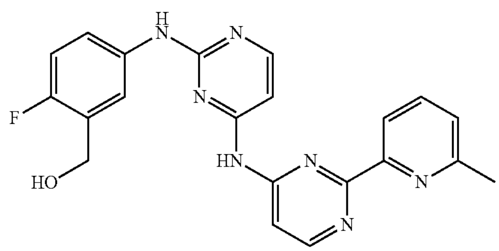 [SMILES: Cc1cccc(-c2nccc(Nc3ccnc(Nc4ccc(F)c(CO)c4)n3)n2)n1] | [2-fluoro-5-[[4-[[2-(6-methyl-2-pyridyl)pyrimidin-4-yl]amino]pyrimidin-2-yl]amino]phenyl]methanol | 404.2 |
| 295 | 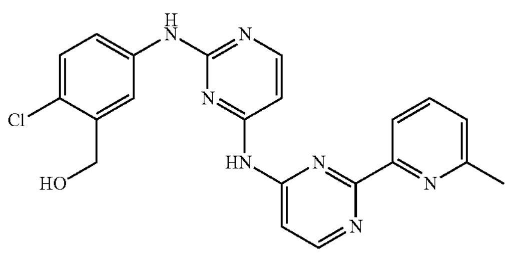 [SMILES: Cc1cccc(-c2nccc(Nc3ccnc(Nc4ccc(Cl)c(CO)c4)n3)n2)n1] | [2-chloro-5-[[4-[[2-(6-methyl-2-pyridyl)pyrimidin-4-yl]amino]pyrimidin-2-yl]amino]phenyl]methanol | 420.1 |
| 296 | 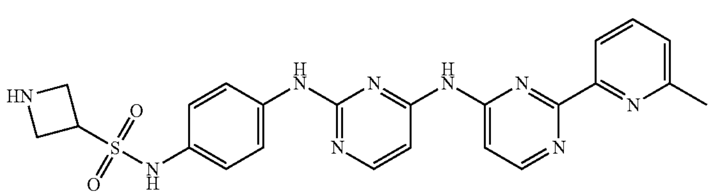 [SMILES: Cc1cccc(-c2nccc(Nc3ccnc(Nc4ccc(NS(=O)(=O)C5CNC5)cc4)n3)n2)n1] | N-[4-[[4-[[2-(6-methyl-2-pyridyl)pyrimidin-4-yl]amino]pyrimidin-2-yl]amino]phenyl]azetidine-3-sulfonamide | 490.1 |
| 297 | 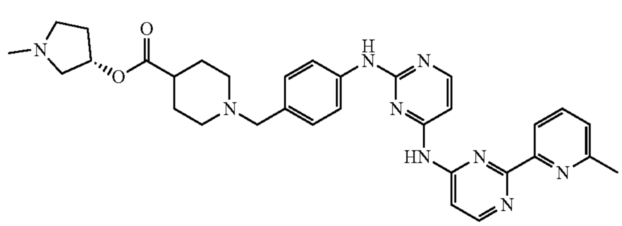 | [(3S)-1-methylpyrrolidin-3-yl] 1-[[4-[[4-[[2-(6-methyl-2-pyridyl)pyrimidin-4-yl]amino]pyrimidin-2-yl]amino]phenyl]methyl]piperidine-4-carboxylate | 580.2 |

TABLE 1-continued

| No. | Structure | Chemical Name | [M + H]+ |
|---|---|---|---|
| 298 | 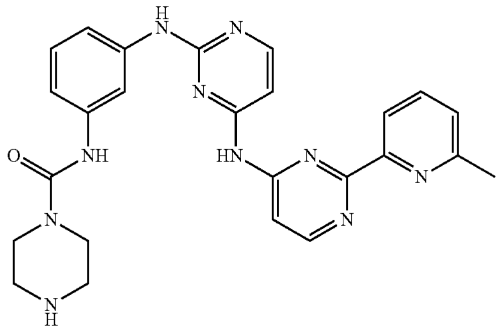 [SMILES: Cc1cccc(-c2nccc(Nc3ccnc(Nc4cccc(NC(=O)N5CCNCC5)c4)n3)n2)n1] | N-[3-[[4-[[2-(6-methyl-2-pyridyl)pyrimidin-4-yl]amino]pyrimidin-2-yl]amino]phenyl]piperazine-1-carboxamide | 483.1 |
| 299 | 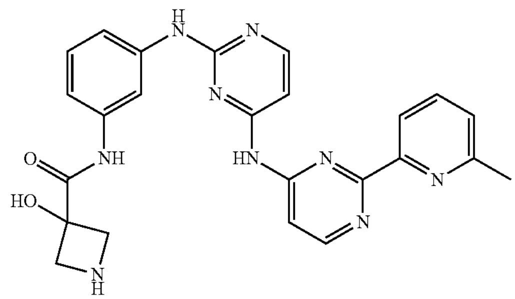 [SMILES: Cc1cccc(-c2nccc(Nc3ccnc(Nc4cccc(NC(=O)C5(O)CNC5)c4)n3)n2)n1] | 3-hydroxy-N-[3-[[4-[[2-(6-methyl-2-pyridyl)pyrimidin-4-yl]amino]pyrimidin-2-yl]amino]phenyl]azetidine-3-carboxamide | 470.0 |
| 300 | 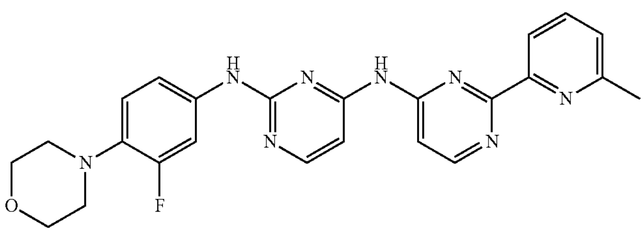 [SMILES: Cc1cccc(-c2nccc(Nc3ccnc(Nc4ccc(N5CCOCC5)c(F)c4)n3)n2)n1] | N2-(3-fluoro-4-morpholino-phenyl)-N4-[2-(6-methyl-2-pyridyl)pyrimidin-4-yl]pyrimidine-2,4-diamine | 459.1 |
| 301 | 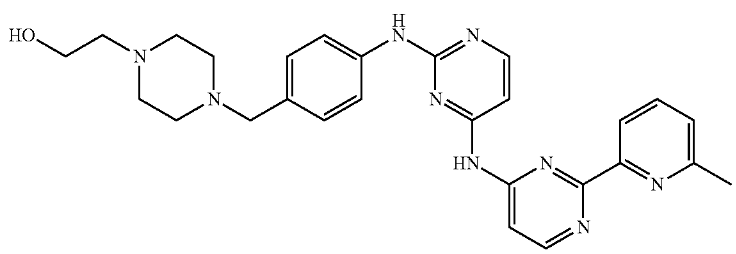 [SMILES: Cc1cccc(-c2nccc(Nc3ccnc(Nc4ccc(CN5CCN(CCO)CC5)cc4)n3)n2)n1] | 2-[4-[[4-[[4-[[2-(6-methyl-2-pyridyl)pyrimidin-4-yl]amino]pyrimidin-2-yl]amino]phenyl]methyl]piperazin-1-yl]ethanol | 498.2 |
| 302 | 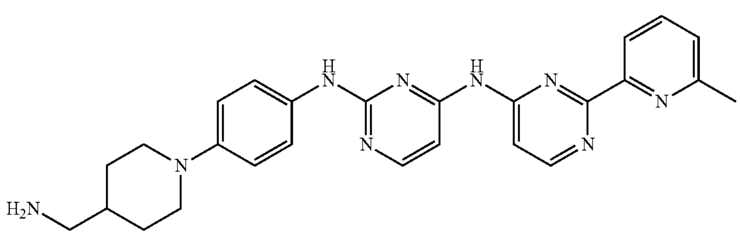 [SMILES: Cc1cccc(-c2nccc(Nc3ccnc(Nc4ccc(N5CCC(CN)CC5)cc4)n3)n2)n1] | N2-[4-[4-(aminomethyl)-1-piperidyl]phenyl]-N4-[2-(6-methyl-2-pyridyl)pyrimidin-4-yl]pyrimidine-2,4-diamine | 468.4 |
| 303 | 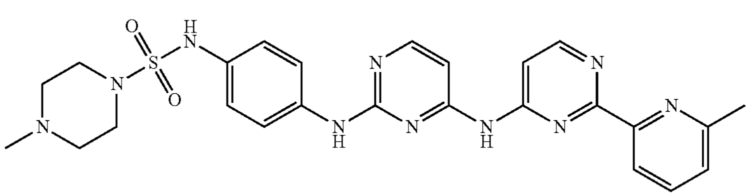 | 4-methyl-N-[4-[[4-[[2-(6-methyl-2-pyridyl)pyrimidin-4-yl]amino]pyrimidin-2-yl]amino]phenyl]piperazine-1-sulfonamide | 533.1 |

TABLE 1-continued

| No. | Structure | Chemical Name | [M + H]+ |
|---|---|---|---|
| 304 | 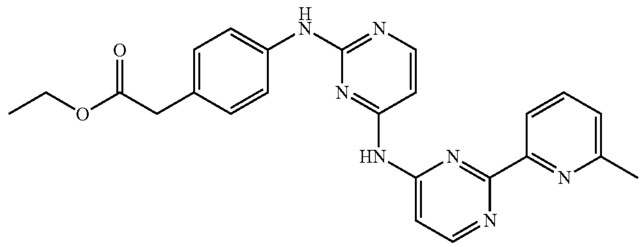 [SMILES: CCOC(=O)Cc1ccc(Nc2nccc(Nc3ccnc(-c4cccc(C)n4)n3)n2)cc1] | ethyl 2-[4-[[4-[[2-(6-methyl-2-pyridyl)pyrimidin-4-yl]amino]pyrimidin-2-yl]amino]phenyl]acetate | 442.1 |
| 305 | 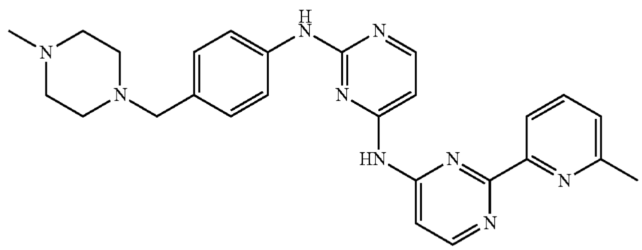 | N2-[4-[(4-methylpiperazin-1-yl)methyl]phenyl]-N4-[2-(6-methyl-2-pyridyl)pyrimidin-4-yl]pyrimidine-2,4-diamine | 468.1 |
| 306 | 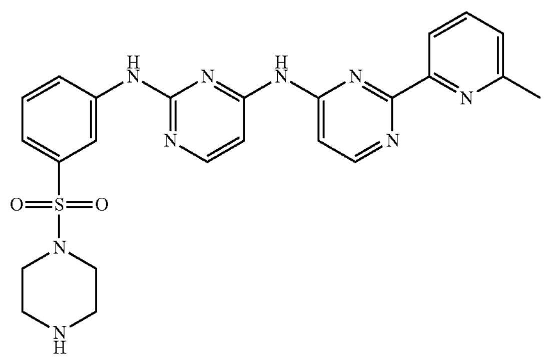 [SMILES: Cc1cccc(-c2nccc(Nc3ccnc(Nc4cccc(S(=O)(=O)N5CCNCC5)c4)n3)n2)n1] | N4-[2-(6-methyl-2-pyridyl)pyrimidin-4-yl]-N2-(3-piperazin-1-ylsulfonylphenyl)pyrimidine-2,4-diamine | 504.2 |
| 307 | 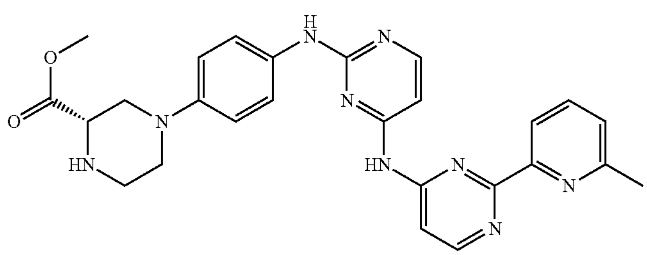 [SMILES: COC(=O)[C@@H]1CN(c2ccc(Nc3nccc(Nc4ccnc(-c5cccc(C)n5)n4)n3)cc2)CCN1] | methyl (2S)-4-[4-[[4-[[2-(6-methyl-2-pyridyl)pyrimidin-4-yl]amino]pyrimidin-2-yl]amino]phenyl]piperazine-2-carboxylate | 498.1 |
| 308 | 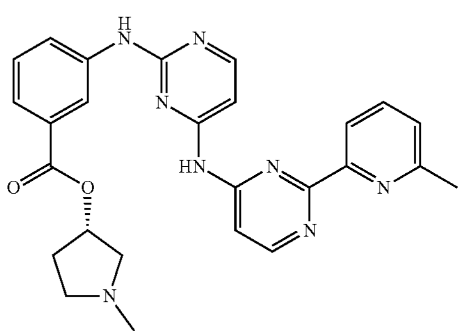 [SMILES: Cc1cccc(-c2nccc(Nc3ccnc(Nc4cccc(C(=O)O[C@H]5CCN(C)C5)c4)n3)n2)n1] | [(3S)-1-methylpyrrolidin-3-yl] 3-[[4-[[2-(6-methyl-2-pyridyl)pyrimidin-4-yl]amino]pyrimidin-2-yl]amino]benzoate | 483.1 |

TABLE 1-continued

| No. | Structure | Chemical Name | [M + H]+ |
|---|---|---|---|
| 309 | 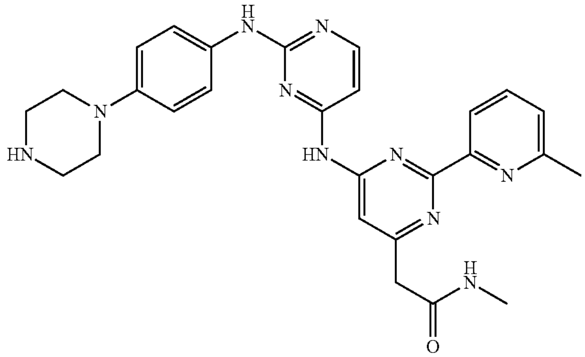 [SMILES: CNC(=O)Cc1cc(Nc2ccnc(Nc3ccc(N4CCNCC4)cc3)n2)nc(-c2cccc(C)n2)n1] | N-methyl-2-[2-(6-methyl-2-pyridyl)-6-[[2-(4-piperazin-1-ylanilino)pyrimidin-4-yl]amino]pyrimidin-4-yl]acetamide | 511.2 |
| 310 | 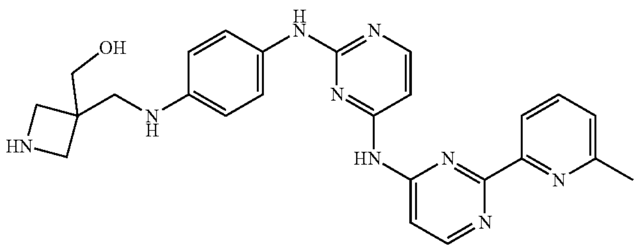 [SMILES: Cc1cccc(-c2nccc(Nc3ccnc(Nc4ccc(NCC5(CO)CNC5)cc4)n3)n2)n1] | [3-[[4-[[4-[[2-(6-methyl-2-pyridyl)pyrimidin-4-yl]amino]pyrimidin-2-yl]amino]anilino]methyl]azetidin-3-yl]methanol | 470.2 |
| 311 | 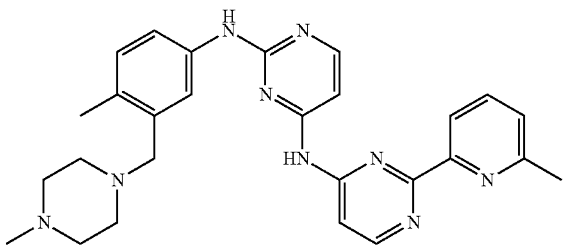 | N2-[4-methyl-3-[(4-methylpiperazin-1-yl)methyl]phenyl]-N4-[2-(6-methyl-2-pyridyl)pyrimidin-4-yl]pyrimidine-2,4-diamine | 482.2 |
| 312 | 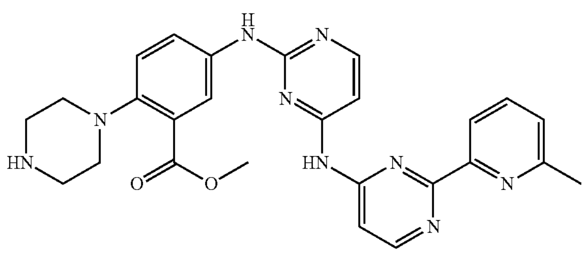 [SMILES: COC(=O)c1cc(Nc2nccc(Nc3ccnc(-c4cccc(C)n4)n3)n2)ccc1N1CCNCC1] | methyl 5-[[4-[[2-(6-methyl-2-pyridyl)pyrimidin-4-yl]amino]pyrimidin-2-yl]amino]-2-piperazin-1-yl-benzoate | 498.2 |
| 313 | 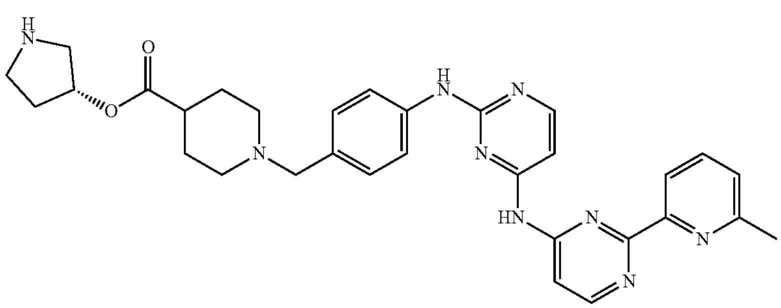 [SMILES: Cc1cccc(-c2nccc(Nc3ccnc(Nc4ccc(CN5CCC(C(=O)O[C@@H]6CCNC6)CC5)cc4)n3)n2)n1] | [(3R)-pyrrolidin-3-yl] 1-[[4-[[4-[[2-(6-methyl-2-pyridyl)pyrimidin-4-yl]amino]pyrimidin-2-yl]amino]phenyl]methyl]piperidine-4-carboxylate | 566.1 |

TABLE 1-continued

| No. | Structure | Chemical Name | [M + H]+ |
|---|---|---|---|
| 314 | 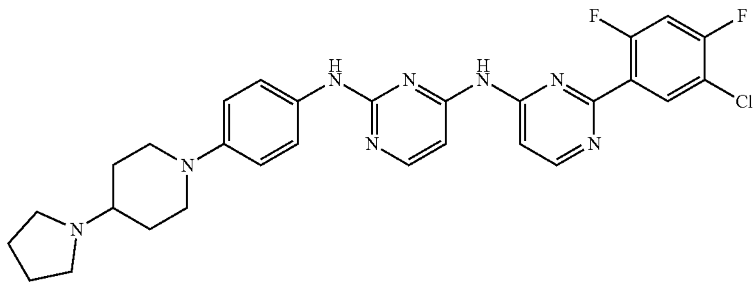 [SMILES: Fc1cc(F)c(-c2nccc(Nc3ccnc(Nc4ccc(N5CCC(N6CCCC6)CC5)cc4)n3)n2)cc1Cl] | N4-[2-(5-chloro-2,4-difluoro-phenyl)pyrimidin-4-yl]-N2-[4-(4-pyrrolidin-1-yl-1-piperidyl)phenyl]pyrimidine-2,4-diamine | 563.1 |
| 315 | 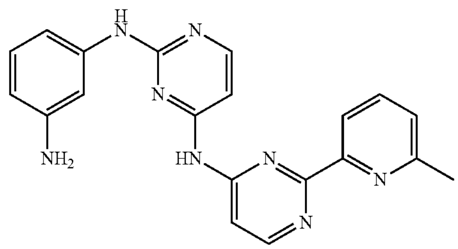 [SMILES: Cc1cccc(-c2nccc(Nc3ccnc(Nc4cccc(N)c4)n3)n2)n1] | N2-(3-aminophenyl)-N4-[2-(6-methyl-2-pyridyl)pyrimidin-4-yl]pyrimidine-2,4-diamine | 371.2 |
| 316 | 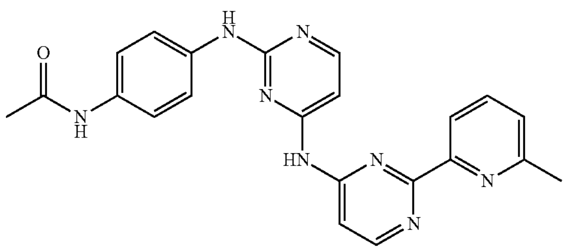 [SMILES: CC(=O)Nc1ccc(Nc2nccc(Nc3ccnc(-c4cccc(C)n4)n3)n2)cc1] | N-[4-[[4-[[2-(6-methyl-2-pyridyl)pyrimidin-4-yl]amino]pyrimidin-2-yl]amino]phenyl]acetamide | 413.1 |
| 317 | 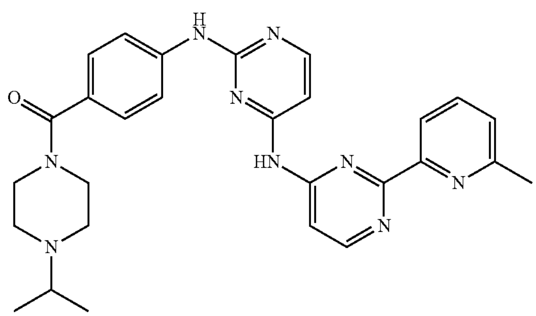 [SMILES: Cc1cccc(-c2nccc(Nc3ccnc(Nc4ccc(C(=O)N5CCN(C(C)C)CC5)cc4)n3)n2)n1] | (4-isopropylpiperazin-1-yl)-[4-[[4-[[2-(6-methyl-2-pyridyl)pyrimidin-4-yl]amino]pyrimidin-2-yl]amino]phenyl]methanone | 510.2 |
| 318 | 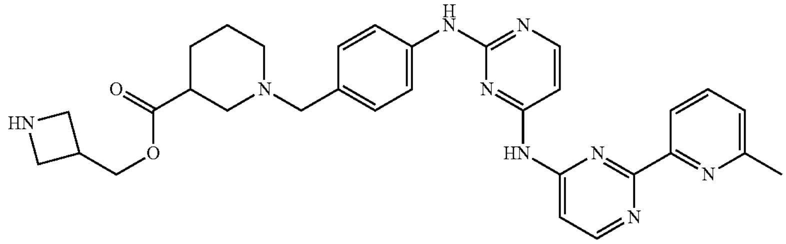 [SMILES: Cc1cccc(-c2nccc(Nc3ccnc(Nc4ccc(CN5CCCC(C(=O)OCC6CNC6)C5)cc4)n3)n2)n1] | azetidin-3-ylmethyl 1-[[4-[[4-[[2-(6-methyl-2-pyridyl)pyrimidin-4-yl]amino]pyrimidin-2-yl]amino]phenyl]methyl]piperidine-3-carboxylate | 566.2 |

TABLE 1-continued

| No. | Structure | Chemical Name | [M + H]+ |
|---|---|---|---|
| 319 | 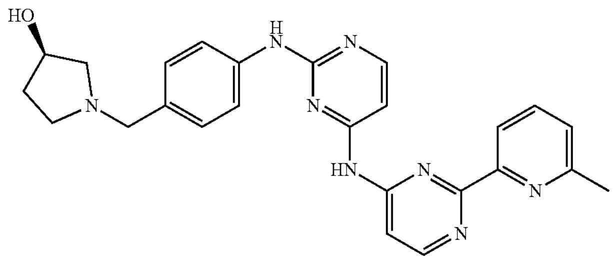 [SMILES: Cc1cccc(-c2nccc(Nc3ccnc(Nc4ccc(CN5CC[C@@H](O)C5)cc4)n3)n2)n1] | (3R)-1-[[4-[[4-[[2-(6-methyl-2-pyridyl)pyrimidin-4-yl]amino]pyrimidin-2-yl]amino]phenyl]methyl]pyrrolidin-3-ol | 455.1 |
| 320 | 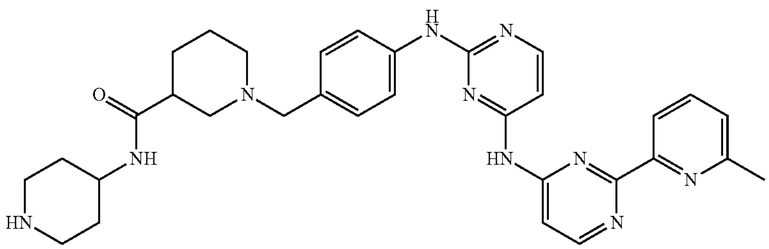 [SMILES: Cc1cccc(-c2nccc(Nc3ccnc(Nc4ccc(CN5CCCC(C(=O)NC6CCNCC6)C5)cc4)n3)n2)n1] | 1-[[4-[[4-[[2-(6-methyl-2-pyridyl)pyrimidin-4-yl]amino]pyrimidin-2-yl]amino]phenyl]methyl]-N-(4-piperidyl)piperidine-3-carboxamide | 579.3 |
| 321 | 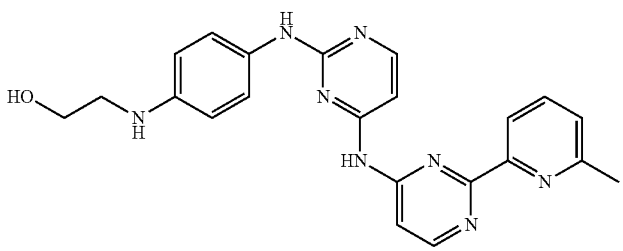 [SMILES: Cc1cccc(-c2nccc(Nc3ccnc(Nc4ccc(NCCO)cc4)n3)n2)n1] | 2-[4-[[4-[[2-(6-methyl-2-pyridyl)pyrimidin-4-yl]amino]pyrimidin-2-yl]amino]anilino]ethanol | 415.0 |
| 322 | 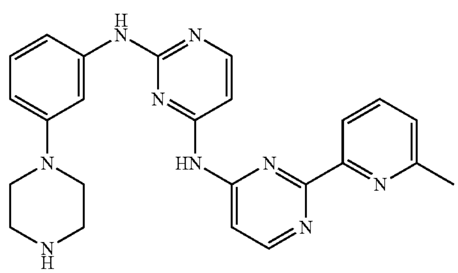 [SMILES: Cc1cccc(-c2nccc(Nc3ccnc(Nc4cccc(N5CCNCC5)c4)n3)n2)n1] | N4-[2-(6-methyl-2-pyridyl)pyrimidin-4-yl]-N2-(3-piperazin-1-ylphenyl)pyrimidine-2,4-diamine | 440.2 |
| 323 | 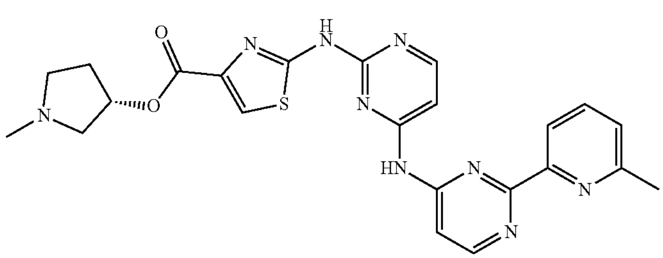 | [(3S)-1-methylpyrrolidin-3-yl] 2-[[4-[[2-(6-methyl-2-pyridyl)pyrimidin-4-yl]amino]pyrimidin-2-yl]amino]thiazole-4-carboxylate | 490.0 |
| 324 | 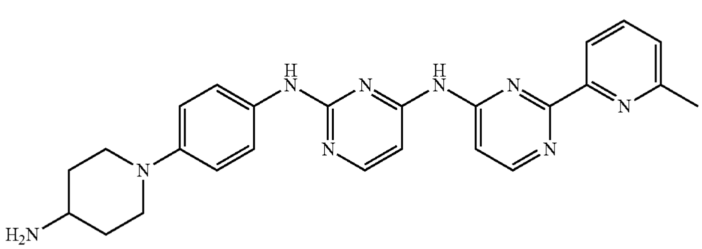 [SMILES: Cc1cccc(-c2nccc(Nc3ccnc(Nc4ccc(N5CCC(N)CC5)cc4)n3)n2)n1] | N2-[4-(4-amino-1-piperidyl)phenyl]-N4-[2-(6-methyl-2-pyridyl)pyrimidin-4-yl]pyrimidine-2,4-diamine | 454.1 |

TABLE 1-continued

| No. | Structure | Chemical Name | [M + H]+ |
|---|---|---|---|
| 325 | 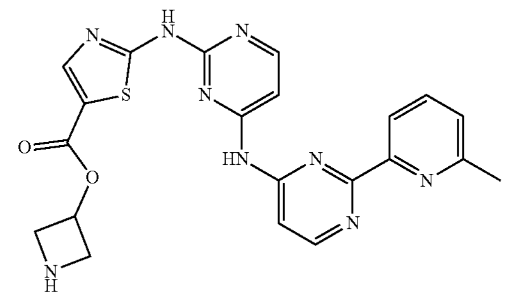 [SMILES: Cc1cccc(-c2nccc(Nc3ccnc(Nc4ncc(C(=O)OC5CNC5)s4)n3)n2)n1] | azetidin-3-yl 2-[[4-[[2-(6-methyl-2-pyridyl)pyrimidin-4-yl]amino]pyrimidin-2-yl]amino]thiazole-5-carboxylate | 462.0 |
| 326 | 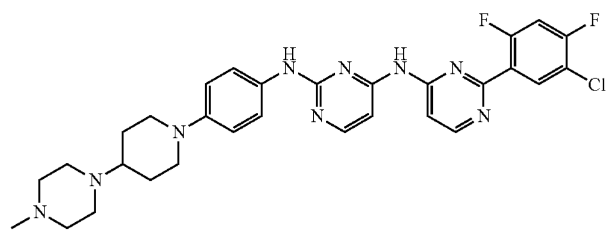 [SMILES: CN1CCN(C2CCN(c3ccc(Nc4nccc(Nc5ccnc(-c6cc(Cl)c(F)cc6F)n5)n4)cc3)CC2)CC1] | N4-[2-(5-chloro-2,4-difluoro-phenyl)pyrimidin-4-yl]-N2-[4-[4-(4-methylpiperazin-1-yl)-1-piperidyl]phenyl]pyrimidine-2,4-diamine | 592.2 |
| 327 | 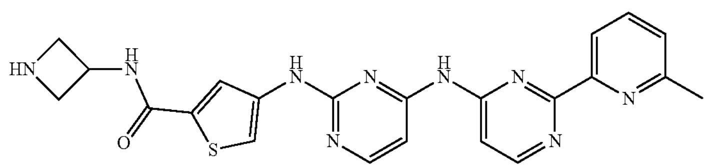 [SMILES: Cc1cccc(-c2nccc(Nc3ccnc(Nc4csc(C(=O)NC5CNC5)c4)n3)n2)n1] | N-(azetidin-3-yl)-4-[[4-[[2-(6-methyl-2-pyridyl)pyrimidin-4-yl]amino]pyrimidin-2-yl]amino]thiophene-2-carboxamide | 460.1 |
| 328 | 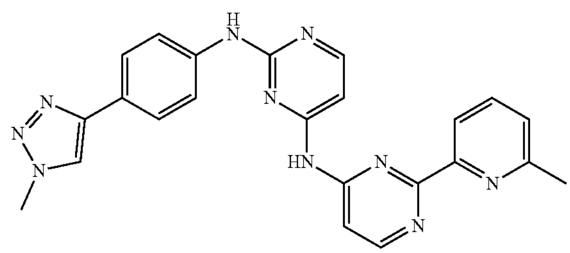 [SMILES: Cc1cccc(-c2nccc(Nc3ccnc(Nc4ccc(-c5cn(C)nn5)cc4)n3)n2)n1] | N4-[2-(6-methyl-2-pyridyl)pyrimidin-4-yl]-N2-[4-(1-methyltriazol-4-yl)phenyl]pyrimidine-2,4-diamine | 437.0 |
| 329 | 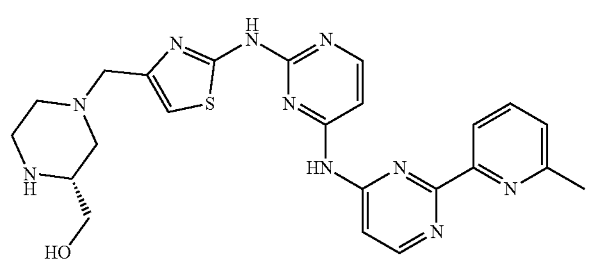 [SMILES: Cc1cccc(-c2nccc(Nc3ccnc(Nc4nc(CN5CCN[C@@H](CO)C5)cs4)n3)n2)n1] | [(2R)-4-[[2-[[4-[[2-(6-methyl-2-pyridyl)pyrimidin-4-yl]amino]pyrimidin-2-yl]amino]thiazol-4-yl]methyl]piperazin-2-yl]methanol | 491.1 |
| 330 | 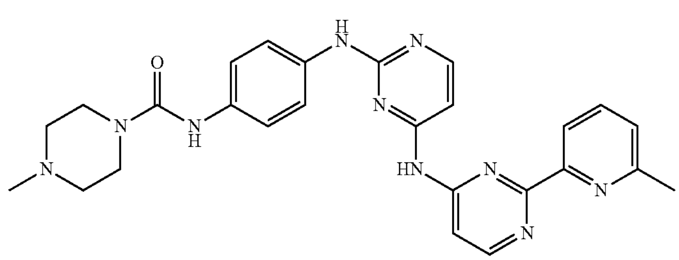 | 4-methyl-N-[4-[[4-[[2-(6-methyl-2-pyridyl)pyrimidin-4-yl]amino]pyrimidin-2-yl]amino]phenyl]piperazine-1-carboxamide | 497.2 |

TABLE 1-continued

| No. | Structure | Chemical Name | [M + H]+ |
|---|---|---|---|
| 331 | 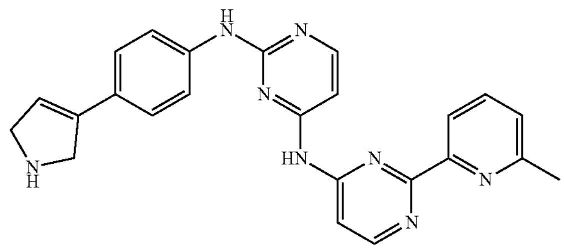 [SMILES: Cc1cccc(-c2nccc(Nc3ccnc(Nc4ccc(C5=CCNC5)cc4)n3)n2)n1] | N2-[4-(2,5-dihydro-1H-pyrrol-3-yl)phenyl]-N4-[2-(6-methyl-2-pyridyl)pyrimidin-4-yl]pyrimidine-2,4-diamine | 423.2 |
| 332 | 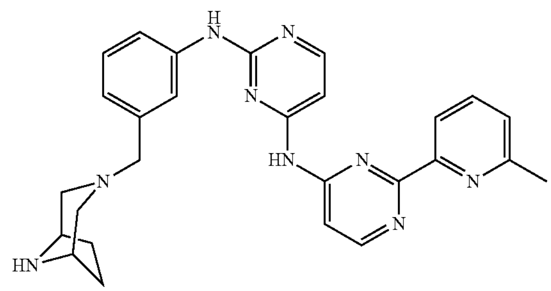 [SMILES: Cc1cccc(-c2nccc(Nc3ccnc(Nc4cccc(CN5CC6CCC(C5)N6)c4)n3)n2)n1] | N2-[3-(3,8-diazabicyclo[3.2.1]octan-3-ylmethyl)phenyl]-N4-[2-(6-methyl-2-pyridyl)pyrimidin-4-yl]pyrimidine-2,4-diamine | 480.2 |
| 333 | 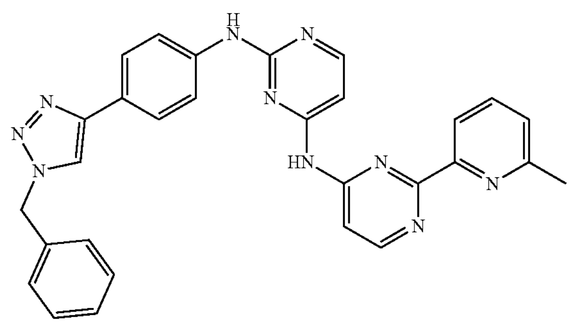 [SMILES: Cc1cccc(-c2nccc(Nc3ccnc(Nc4ccc(-c5cn(Cc6ccccc6)nn5)cc4)n3)n2)n1] | N2-[4-(1-benzyltriazol-4-yl)phenyl]-N4-[2-(6-methyl-2-pyridyl)pyrimidin-4-yl]pyrimidine-2,4-diamine | 513.0 |
| 334 | 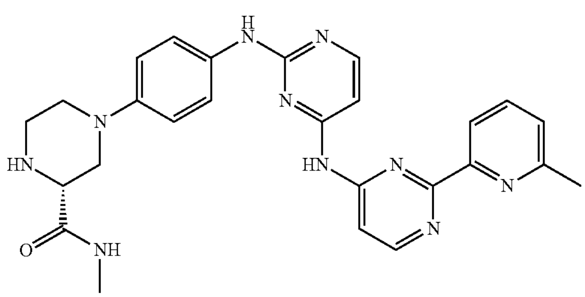 [SMILES: CNC(=O)[C@H]1CN(c2ccc(Nc3nccc(Nc4ccnc(-c5cccc(C)n5)n4)n3)cc2)CCN1] | (2R)-N-methyl-4-[4-[[4-[[2-(6-methyl-2-pyridyl)pyrimidin-4-yl]amino]pyrimidin-2-yl]amino]phenyl]piperazine-2-carboxamide | 497.1 |
| 335 | 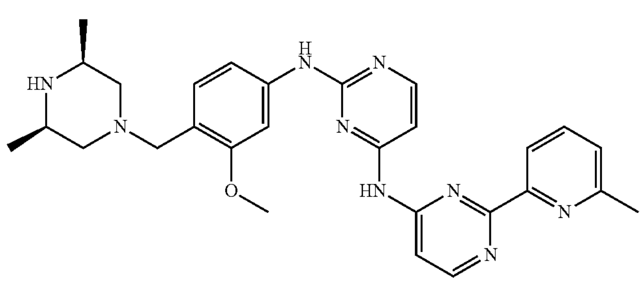 | N2-[3-methoxy-4-[[rac-(3S,5R)-3,5-dimethylpiperazin-1-yl]methyl]phenyl]-N4-[2-(6-methyl-2-pyridyl)pyrimidin-4-yl]pyrimidine-2,4-diamine | 512.3 |

TABLE 1-continued

| No. | Structure | Chemical Name | [M + H]+ |
|---|---|---|---|
| 336 | 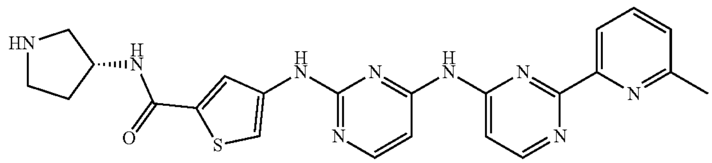 [SMILES: Cc1cccc(-c2nccc(Nc3ccnc(Nc4csc(C(=O)N[C@@H]5CCNC5)c4)n3)n2)n1] | 4-[[4-[[2-(6-methyl-2-pyridyl)pyrimidin-4-yl]amino]pyrimidin-2-yl]amino]-N-[(3R)-pyrrolidin-3-yl]thiophene-2-carboxamide | 474.2 |
| 337 | 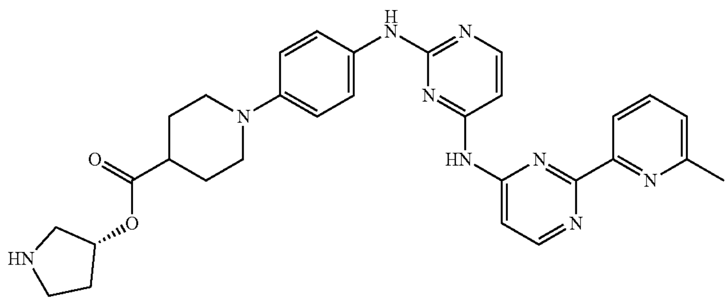 [SMILES: Cc1cccc(-c2nccc(Nc3ccnc(Nc4ccc(N5CCC(C(=O)O[C@@H]6CCNC6)CC5)cc4)n3)n2)n1] | [(3R)-pyrrolidin-3-yl] 1-[4-[[4-[[2-(6-methyl-2-pyridyl)pyrimidin-4-yl]amino]pyrimidin-2-yl]amino]phenyl]piperidine-4-carboxylate | 552.2 |
| 338 | 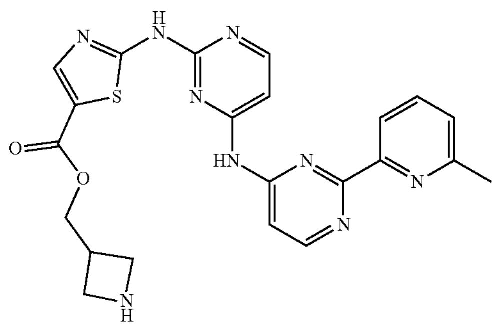 [SMILES: Cc1cccc(-c2nccc(Nc3ccnc(Nc4ncc(C(=O)OCC5CNC5)s4)n3)n2)n1] | azetidin-3-ylmethyl 2-[[4-[[2-(6-methyl-2-pyridyl)pyrimidin-4-yl]amino]pyrimidin-2-yl]amino]thiazole-5-carboxylate | 476.0 |
| 339 | 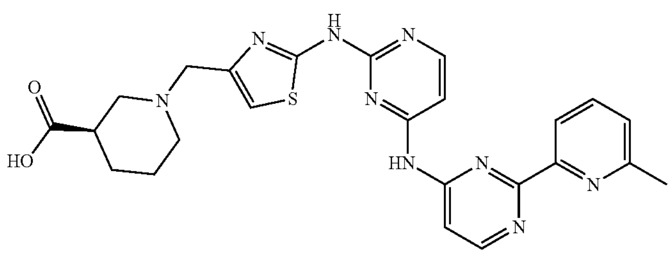 [SMILES: Cc1cccc(-c2nccc(Nc3ccnc(Nc4nc(CN5CCC[C@@H](C(=O)O)C5)cs4)n3)n2)n1] | (3R)-1-[[2-[[4-[[2-(6-methyl-2-pyridyl)pyrimidin-4-yl]amino]pyrimidin-2-yl]amino]thiazol-4-yl]methyl]piperidine-3-carboxylic acid | 504.2 |
| 340 | 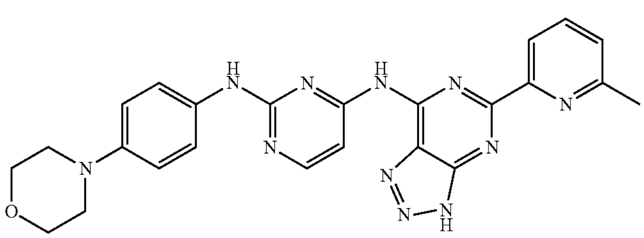 [SMILES: Cc1cccc(-c2nc(Nc3ccnc(Nc4ccc(N5CCOCC5)cc4)n3)c3nn[nH]c3n2)n1] | N4-[5-(6-methyl-2-pyridyl)-3H-triazolo[4,5-d]pyrimidin-7-yl]-N2-(4-morpholinophenyl)pyrimidine-2,4-diamine | 482.1 |
| 341 | 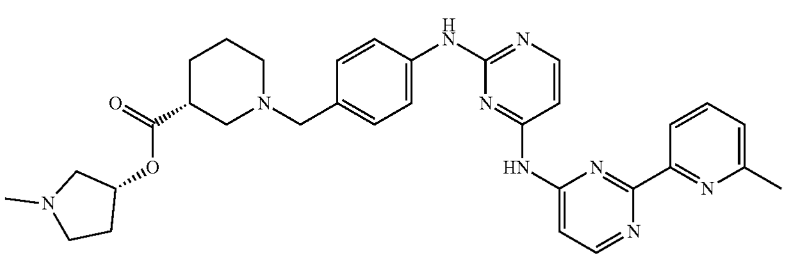 | [(3R)-1-methylpyrrolidin-3-yl] (3R)-1-[[4-[[4-[[2-(6-methyl-2-pyridyl)pyrimidin-4-yl]amino]pyrimidin-2-yl]amino]phenyl]methyl]piperidine-3-carboxylate | 580.3 |

TABLE 1-continued

| No. | Structure | Chemical Name | [M + H]+ |
|---|---|---|---|
| 342 | 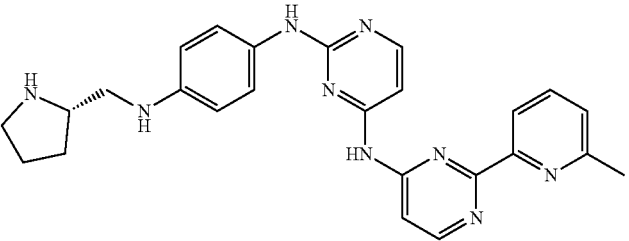 [SMILES: Cc1cccc(-c2nccc(Nc3ccnc(Nc4ccc(NC[C@@H]5CCCN5)cc4)n3)n2)n1] | N4-[2-(6-methyl-2-pyridyl)pyrimidin-4-yl]-N2-[4-[[(2S)-pyrrolidin-2-yl]methylamino]phenyl]pyrimidine-2,4-diamine | 454.2 |
| 343 | 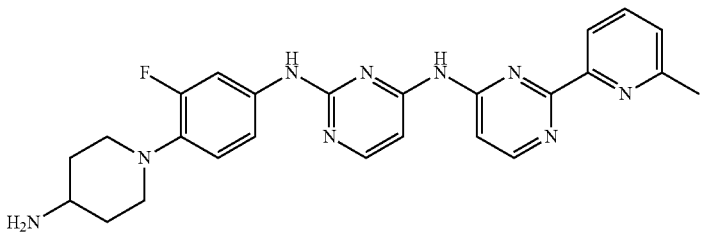 [SMILES: Cc1cccc(-c2nccc(Nc3ccnc(Nc4ccc(N5CCC(N)CC5)c(F)c4)n3)n2)n1] | N2-[4-(4-amino-1-piperidyl)-3-fluoro-phenyl]-N4-[2-(6-methyl-2-pyridyl)pyrimidin-4-yl]pyrimidine-2,4-diamine | 472.2 |
| 344 | 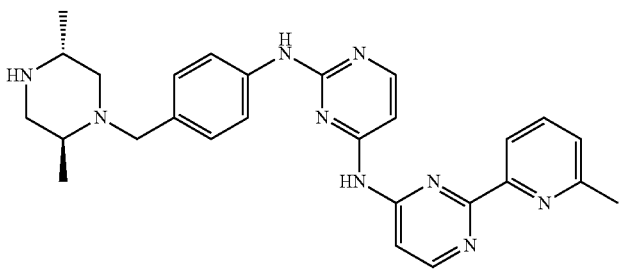 [SMILES: Cc1cccc(-c2nccc(Nc3ccnc(Nc4ccc(CN5C[C@@H](C)NC[C@@H]5C)cc4)n3)n2)n1] | N2-[4-[[(2S,5R)-2,5-dimethylpiperazin-1-yl]methyl]phenyl]-N4-[2-(6-methyl-2-pyridyl)pyrimidin-4-yl]pyrimidine-2,4-diamine | 482.2 |
| 345 | 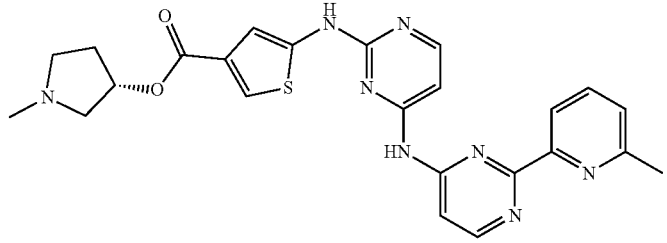 | [(3S)-1-methylpyrrolidin-3-yl] 5-[[4-[[2-(6-methyl-2-pyridyl)pyrimidin-4-yl]amino]pyrimidin-2-yl]amino]thiophene-3-carboxylate | 489.1 |
| 346 | 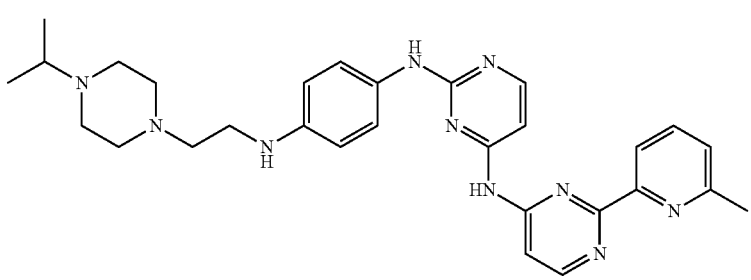 [SMILES: Cc1cccc(-c2nccc(Nc3ccnc(Nc4ccc(NCCN5CCN(C(C)C)CC5)cc4)n3)n2)n1] | N2-[4-[2-(4-isopropylpiperazin-1-yl)ethylamino]phenyl]-N4-[2-(6-methyl-2-pyridyl)pyrimidin-4-yl]pyrimidine-2,4-diamine | 525.2 |
| 347 | 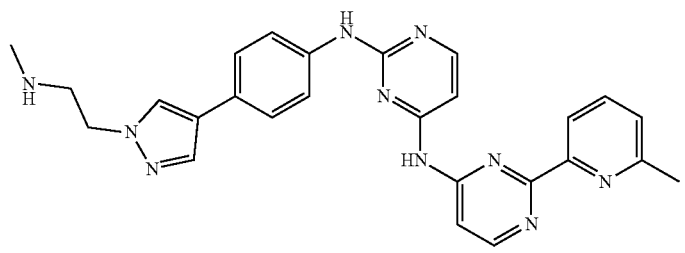 | N2-[4-[1-[2-(methylamino)ethyl]pyrazol-4-yl]phenyl]-N4-[2-(6-methyl-2-pyridyl)pyrimidin-4-yl]pyrimidine-2,4-diamine | 479.2 |

TABLE 1-continued

| No. | Structure | Chemical Name | [M + H]+ |
|---|---|---|---|
| 348 | 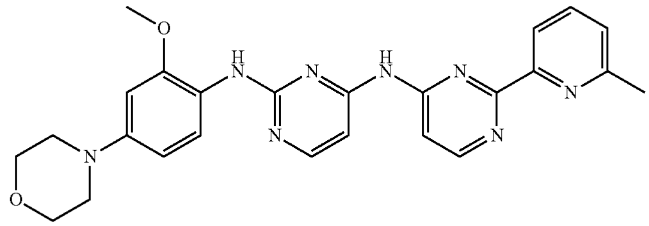 [SMILES: COc1cc(N2CCOCC2)ccc1Nc1nccc(Nc2ccnc(-c3cccc(C)n3)n2)n1] | N2-(2-methoxy-4-morpholino-phenyl)-N4-[2-(6-methyl-2-pyridyl)pyrimidin-4-yl]pyrimidine-2,4-diamine | 471.3 |
| 349 | 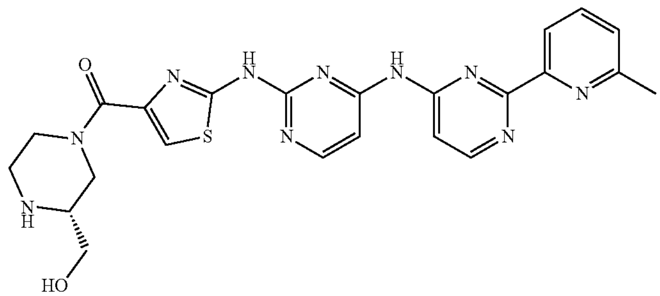 [SMILES: Cc1cccc(-c2nccc(Nc3ccnc(Nc4nc(C(=O)N5CCN[C@@H](CO)C5)cs4)n3)n2)n1] | [(3R)-3-(hydroxymethyl)piperazin-1-yl]-[2-[[4-[[2-(6-methyl-2-pyridyl)pyrimidin-4-yl]amino]pyrimidin-2-yl]amino]thiazol-4-yl]methanone | 505.0 |
| 350 | 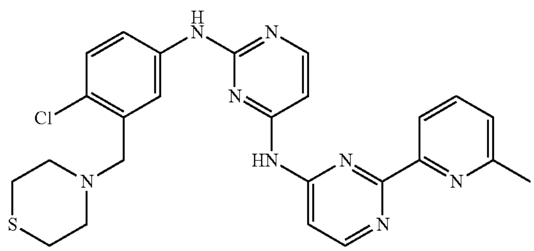 | N2-[4-chloro-3-(thiomorpholinomethyl)phenyl]-N4-[2-(6-methyl-2-pyridyl)pyrimidin-4-yl]pyrimidine-2,4-diamine | 505.2 |
| 351 | 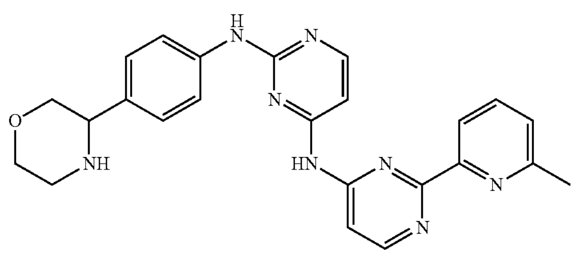 [SMILES: Cc1cccc(-c2nccc(Nc3ccnc(Nc4ccc(C5COCCN5)cc4)n3)n2)n1] | N4-[2-(6-methyl-2-pyridyl)pyrimidin-4-yl]-N2-(4-morpholin-3-ylphenyl)pyrimidine-2,4-diamine | 441.1 |
| 352 | 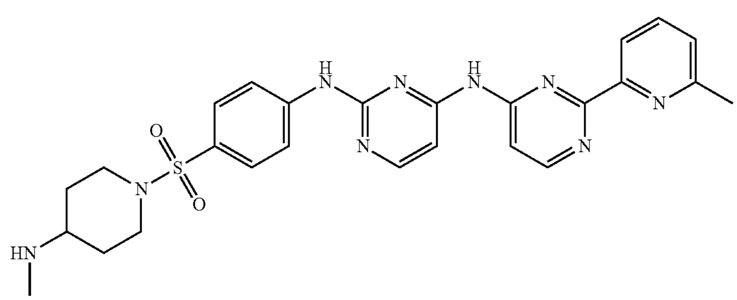 [SMILES: CNC1CCN(S(=O)(=O)c2ccc(Nc3nccc(Nc4ccnc(-c5cccc(C)n5)n4)n3)cc2)CC1] | N2-[4-[[4-(methylamino)-1-piperidyl]sulfonyl]phenyl]-N4-[2-(6-methyl-2-pyridyl)pyrimidin-4-yl]pyrimidine-2,4-diamine | 532.2 |
| 353 | 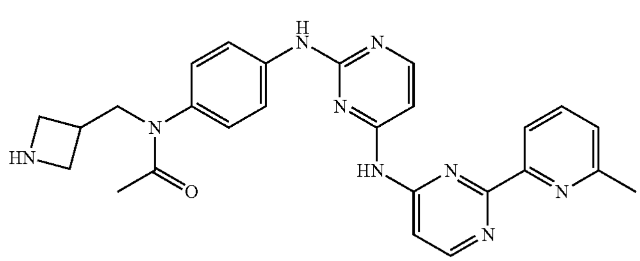 [SMILES: CC(=O)N(CC1CNC1)c1ccc(Nc2nccc(Nc3ccnc(-c4cccc(C)n4)n3)n2)cc1] | N-(azetidin-3-ylmethyl)-N-[4-[[4-[[2-(6-methyl-2-pyridyl)pyrimidin-4-yl]amino]pyrimidin-2-yl]amino]phenyl]acetamide | 482.3 |

TABLE 1-continued

| No. | Structure | Chemical Name | [M + H]+ |
|---|---|---|---|
| 354 | 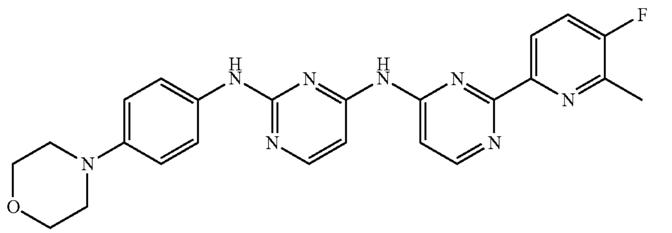 [SMILES: Cc1nc(-c2nccc(Nc3ccnc(Nc4ccc(N5CCOCC5)cc4)n3)n2)ccc1F] | N4-[2-(5-fluoro-6-methyl-2-pyridyl)pyrimidin-4-yl]-N2-(4-morpholinophenyl)pyrimidine-2,4-diamine | 459.2 |
| 355 | 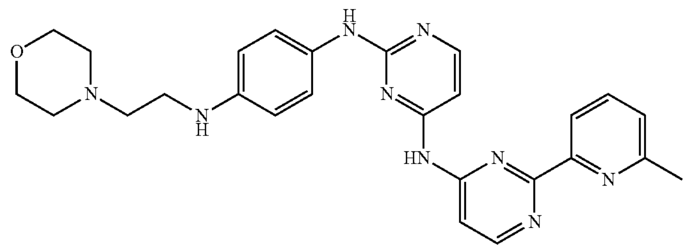 [SMILES: Cc1cccc(-c2nccc(Nc3ccnc(Nc4ccc(NCCN5CCOCC5)cc4)n3)n2)n1] | N4-[2-(6-methyl-2-pyridyl)pyrimidin-4-yl]-N2-[4-(2-morpholinoethylamino)phenyl]pyrimidine-2,4-diamine | 484.1 |
| 356 | 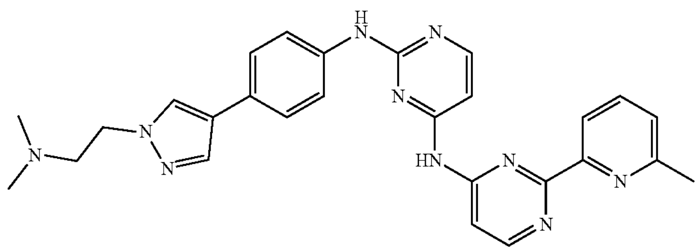 | N2-[4-[1-[2-(dimethylamino)ethyl]pyrazol-4-yl]phenyl]-N4-[2-(6-methyl-2-pyridyl)pyrimidin-4-yl]pyrimidine-2,4-diamine | 493.1 |
| 357 | 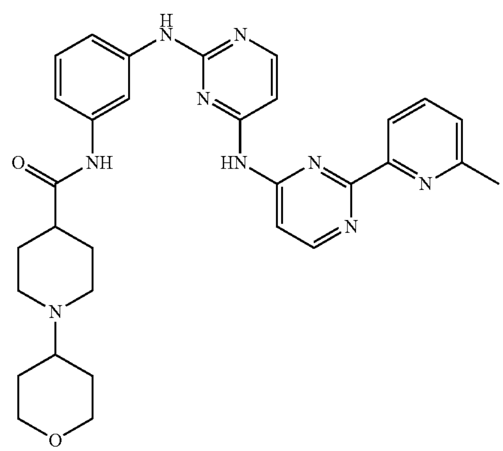 [SMILES: Cc1cccc(-c2nccc(Nc3ccnc(Nc4cccc(NC(=O)C5CCN(C6CCOCC6)CC5)c4)n3)n2)n1] | N-[3-[[4-[[2-(6-methyl-2-pyridyl)pyrimidin-4-yl]amino]pyrimidin-2-yl]amino]phenyl]-1-tetrahydropyran-4-yl-piperidine-4-carboxamide | 566.3 |
| 358 | 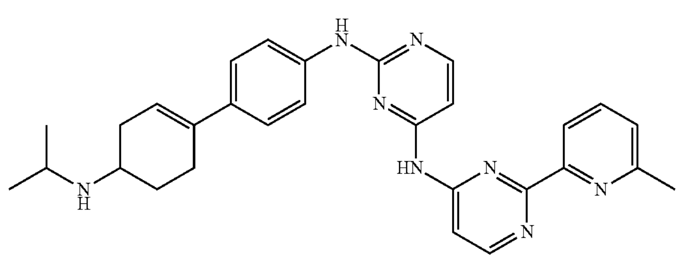 [SMILES: Cc1cccc(-c2nccc(Nc3ccnc(Nc4ccc(C5=CCC(NC(C)C)CC5)cc4)n3)n2)n1] | N2-[4-[4-(isopropylamino)cyclohexen-1-yl]phenyl]-N4-[2-(6-methyl-2-pyridyl)pyrimidin-4-yl]pyrimidine-2,4-diamine | 493.2 |

TABLE 1-continued

| No. | Structure | Chemical Name | [M + H]+ |
|---|---|---|---|
| 359 | 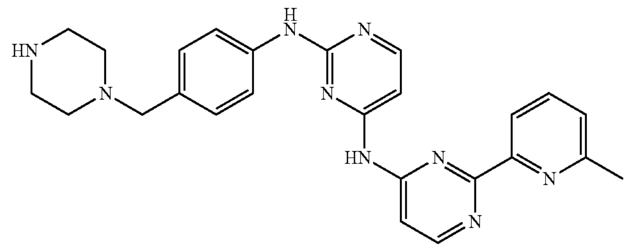 [SMILES: Cc1cccc(-c2nccc(Nc3ccnc(Nc4ccc(CN5CCNCC5)cc4)n3)n2)n1] | N4-[2-(6-methyl-2-pyridyl)pyrimidin-4-yl]-N2-[4-(piperazin-1-ylmethyl)phenyl]pyrimidine-2,4-diamine | 454.1 |
| 360 | 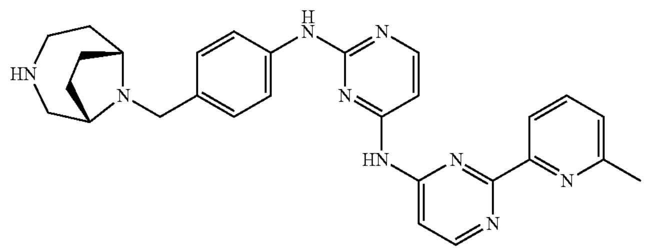 [SMILES: Cc1cccc(-c2nccc(Nc3ccnc(Nc4ccc(CN5[C@H]6CCNC[C@@H]5CC6)cc4)n3)n2)n1] | N4-[2-(6-methyl-2-pyridyl)pyrimidin-4-yl]-N2-[4-[[rac-(1S,6R)-3,9-diazabicyclo[4.2.1]nonan-9-yl]methyl]phenyl]pyrimidine-2,4-diamine | 494.2 |
| 361 | 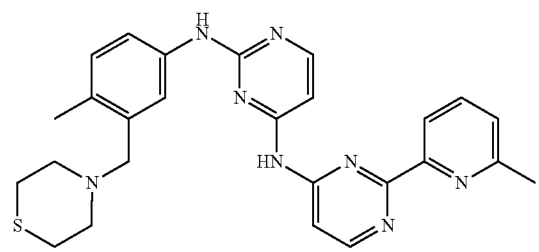 | N4-[2-(6-methyl-2-pyridyl)pyrimidin-4-yl]-N2-[4-methyl-3-(thiomorpholinomethyl)phenyl]pyrimidine-2,4-diamine | 485.1 |
| 362 | 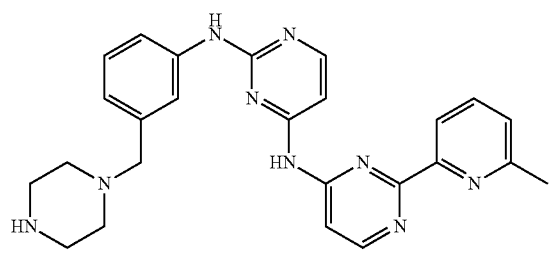 [SMILES: Cc1cccc(-c2nccc(Nc3ccnc(Nc4cccc(CN5CCNCC5)c4)n3)n2)n1] | N4-[2-(6-methyl-2-pyridyl)pyrimidin-4-yl]-N2-[3-(piperazin-1-ylmethyl)phenyl]pyrimidine-2,4-diamine | 454.2 |
| 363 | 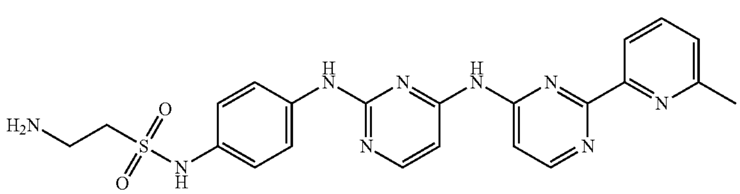 [SMILES: Cc1cccc(-c2nccc(Nc3ccnc(Nc4ccc(NS(=O)(=O)CCN)cc4)n3)n2)n1] | 2-amino-N-[4-[[4-[[2-(6-methyl-2-pyridyl)pyrimidin-4-yl]amino]pyrimidin-2-yl]amino]phenyl]ethanesulfonamide | 478.1 |
| 364 | 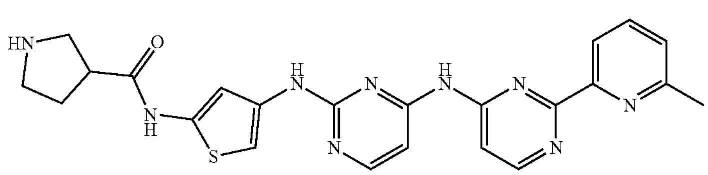 [SMILES: Cc1cccc(-c2nccc(Nc3ccnc(Nc4csc(NC(=O)C5CCNC5)c4)n3)n2)n1] | N-[4-[[4-[[2-(6-methyl-2-pyridyl)pyrimidin-4-yl]amino]pyrimidin-2-yl]amino]-2-thienyl]pyrrolidine-3-carboxamide | 474.0 |

TABLE 1-continued

| No. | Structure | Chemical Name | [M + H]+ |
|---|---|---|---|
| 365 | 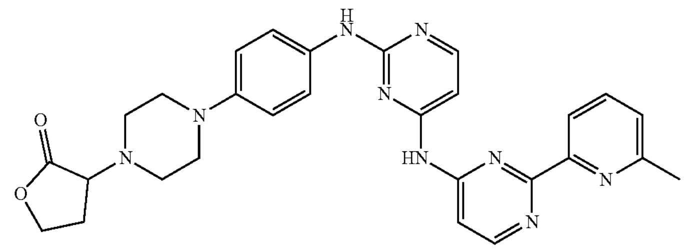 [SMILES: Cc1cccc(-c2nccc(Nc3ccnc(Nc4ccc(N5CCN(C6CCOC6=O)CC5)cc4)n3)n2)n1] | 3-[4-[4-[[4-[[2-(6-methyl-2-pyridyl)pyrimidin-4-yl]amino]pyrimidin-2-yl]amino]phenyl]piperazin-1-yl]tetrahydrofuran-2-one | 524.2 |
| 366 | 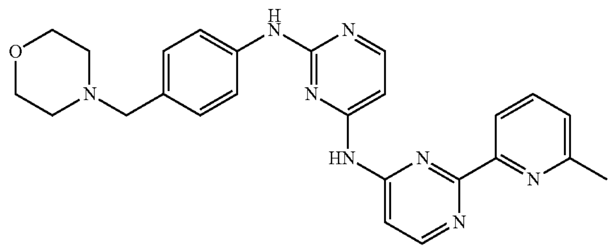 [SMILES: Cc1cccc(-c2nccc(Nc3ccnc(Nc4ccc(CN5CCOCC5)cc4)n3)n2)n1] | N4-[2-(6-methyl-2-pyridyl)pyrimidin-4-yl]-N2-[4-(morpholinomethyl)phenyl]pyrimidine-2,4-diamine | 455.2 |
| 367 | 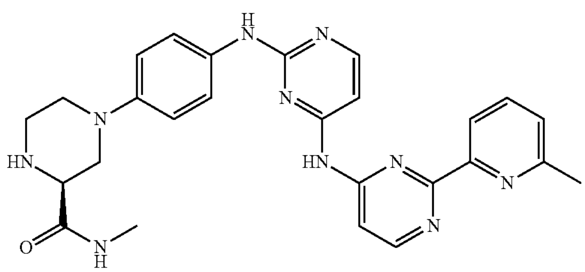 [SMILES: CNC(=O)[C@@H]1CN(c2ccc(Nc3nccc(Nc4ccnc(-c5cccc(C)n5)n4)n3)cc2)CCN1] | (2S)-N-methyl-4-[4-[[4-[[2-(6-methyl-2-pyridyl)pyrimidin-4-yl]amino]pyrimidin-2-yl]amino]phenyl]piperazine-2-carboxamide | 497.1 |
| 368 | 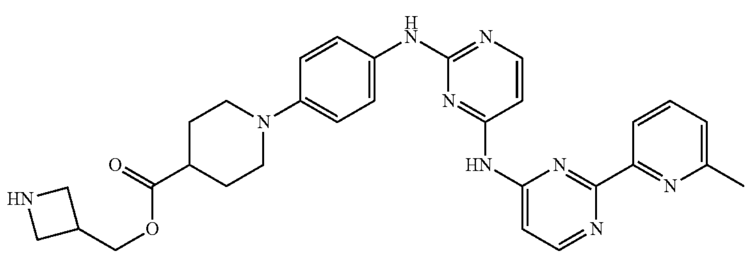 [SMILES: Cc1cccc(-c2nccc(Nc3ccnc(Nc4ccc(N5CCC(C(=O)OCC6CNC6)CC5)cc4)n3)n2)n1] | azetidin-3-ylmethyl 1-[4-[[4-[[2-(6-methyl-2-pyridyl)pyrimidin-4-yl]amino]pyrimidin-2-yl]amino]phenyl]piperidine-4-carboxylate | 552.1 |
| 369 | 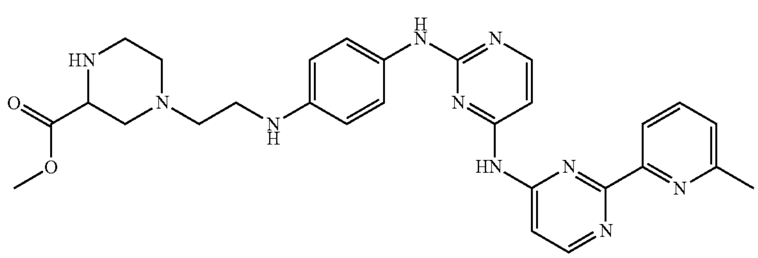 [SMILES: COC(=O)C1CN(CCNc2ccc(Nc3nccc(Nc4ccnc(-c5cccc(C)n5)n4)n3)cc2)CCN1] | methyl 4-[2-[4-[[4-[[2-(6-methyl-2-pyridyl)pyrimidin-4-yl]amino]pyrimidin-2-yl]amino]anilino]ethyl]piperazine-2-carboxylate | 541.2 |
| 370 | 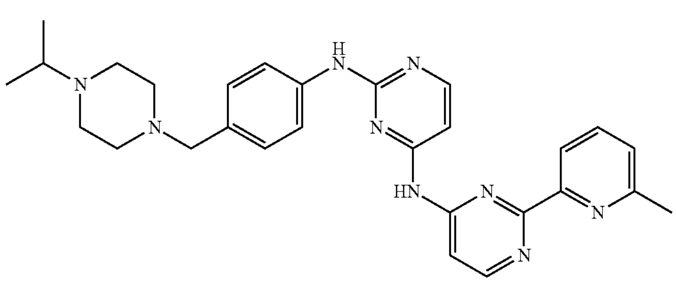 [SMILES: Cc1cccc(-c2nccc(Nc3ccnc(Nc4ccc(CN5CCN(C(C)C)CC5)cc4)n3)n2)n1] | N2-[4-[(4-isopropylpiperazin-1-yl)methyl]phenyl]-N4-[2-(6-methyl-2-pyridyl)pyrimidin-4-yl]pyrimidine-2,4-diamine | 496.1 |

TABLE 1-continued

| No. | Structure | Chemical Name | [M + H]+ |
|---|---|---|---|
| 371 | 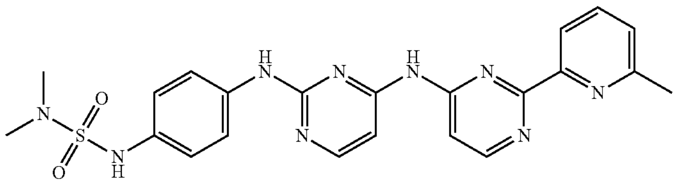 | 4-[[2-[4-(dimethylsulfamoylamino)anilino]pyrimidin-4-yl]amino]-2-(6-methyl-2-pyridyl)pyrimidine | 478.2 |
| 372 | 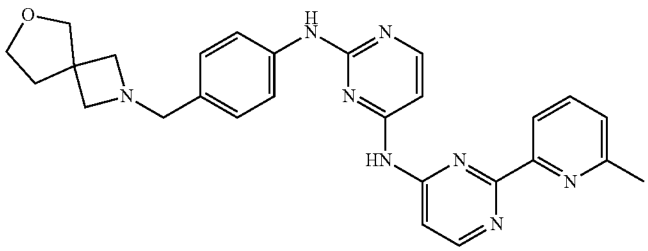 [SMILES: Cc1cccc(-c2nccc(Nc3ccnc(Nc4ccc(CN5CC6(CCOC6)C5)cc4)n3)n2)n1] | N4-[2-(6-methyl-2-pyridyl)pyrimidin-4-yl]-N2-[4-(6-oxa-2-azaspiro[3.4]octan-2-ylmethyl)phenyl]pyrimidine-2,4-diamine | 481.2 |
| 373 | 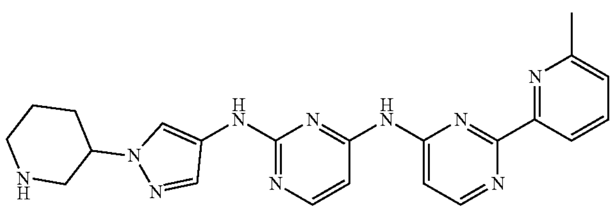 [SMILES: Cc1cccc(-c2nccc(Nc3ccnc(Nc4cnn(C5CCCNC5)c4)n3)n2)n1] | N4-[2-(6-methyl-2-pyridyl)pyrimidin-4-yl]-N2-[1-(3-piperidyl)pyrazol-4-yl]pyrimidine-2,4-diamine | 429.2 |
| 374 | 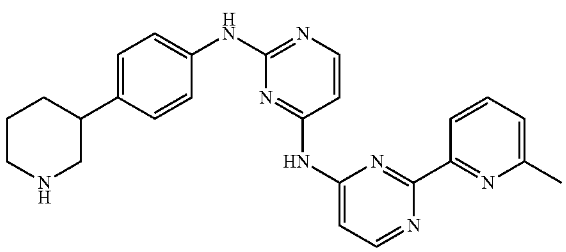 [SMILES: Cc1cccc(-c2nccc(Nc3ccnc(Nc4ccc(C5CCCNC5)cc4)n3)n2)n1] | N4-[2-(6-methyl-2-pyridyl)pyrimidin-4-yl]-N2-[4-(3-piperidyl)phenyl]pyrimidine-2,4-diamine | 439.2 |
| 375 | 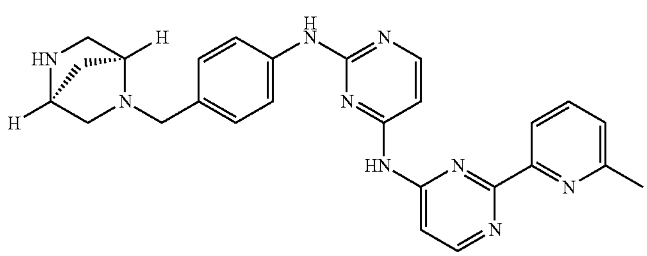 [SMILES: Cc1cccc(-c2nccc(Nc3ccnc(Nc4ccc(CN5C[C@@H]6C[C@H]5CN6)cc4)n3)n2)n1] | N2-[4-[[(1S,4S)-2,5-diazabicyclo[2.2.1]heptan-2-yl]methyl]phenyl]-N4-[2-(6-methyl-2-pyridyl)pyrimidin-4-yl]pyrimidine-2,4-diamine | 466.2 |
| 376 | 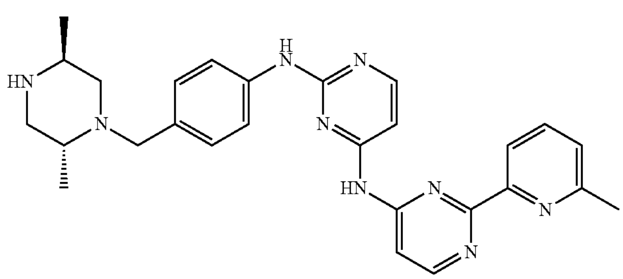 [SMILES: Cc1cccc(-c2nccc(Nc3ccnc(Nc4ccc(CN5C[C@H](C)NC[C@H]5C)cc4)n3)n2)n1] | N2-[4-[[(2R,5S)-2,5-dimethylpiperazin-1-yl]methyl]phenyl]-N4-[2-(6-methyl-2-pyridyl)pyrimidin-4-yl]pyrimidine-2,4-diamine | 482.2 |

TABLE 1-continued

| No. | Structure | Chemical Name | [M + H]+ |
|---|---|---|---|
| 377 | 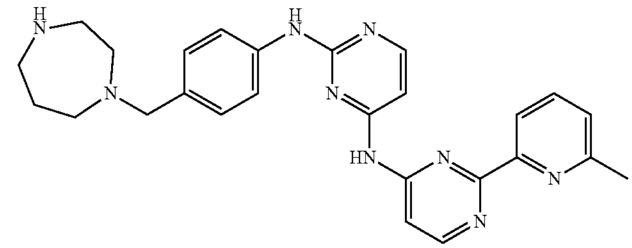 [SMILES: Cc1cccc(-c2nccc(Nc3ccnc(Nc4ccc(CN5CCCNCC5)cc4)n3)n2)n1] | N2-[4-(1,4-diazepan-1-ylmethyl)phenyl]-N4-[2-(6-methyl-2-pyridyl)pyrimidin-4-yl]pyrimidine-2,4-diamine | 468.1 |
| 378 | 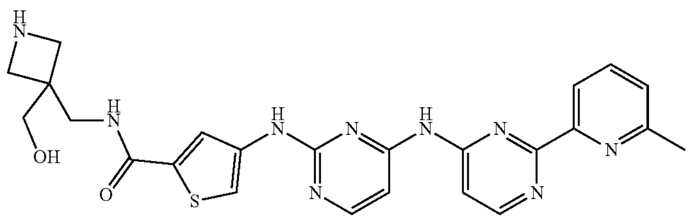 [SMILES: Cc1cccc(-c2nccc(Nc3ccnc(Nc4csc(C(=O)NCC5(CO)CNC5)c4)n3)n2)n1] | N-[[3-(hydroxymethyl)azetidin-3-yl]methyl]-4-[[4-[[2-(6-methyl-2-pyridyl)pyrimidin-4-yl]amino]pyrimidin-2-yl]amino]thiophene-2-carboxamide | 504.0 |
| 379 | 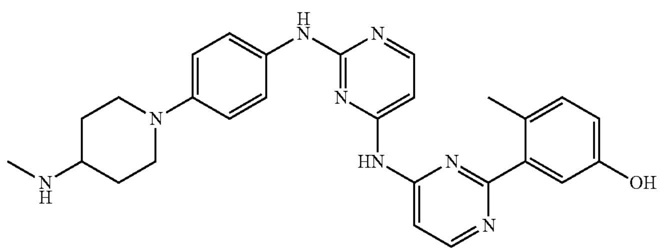 [SMILES: CNC1CCN(c2ccc(Nc3nccc(Nc4ccnc(-c5cc(O)ccc5C)n4)n3)cc2)CC1] | 4-methyl-3-[4-[[2-[4-[4-(methylamino)-1-piperidyl]anilino]pyrimidin-4-yl]amino]pyrimidin-2-yl]phenol | 483.1 |
| 380 | 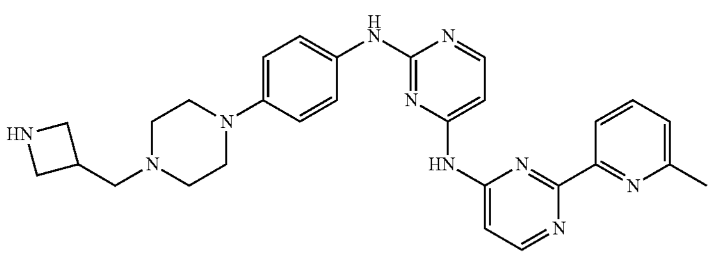 [SMILES: Cc1cccc(-c2nccc(Nc3ccnc(Nc4ccc(N5CCN(CC6CNC6)CC5)cc4)n3)n2)n1] | N2-[4-[4-(azetidin-3-ylmethyl)piperazin-1-yl]phenyl]-N4-[2-(6-methyl-2-pyridyl)pyrimidin-4-yl]pyrimidine-2,4-diamine | 509.2 |
| 381 | 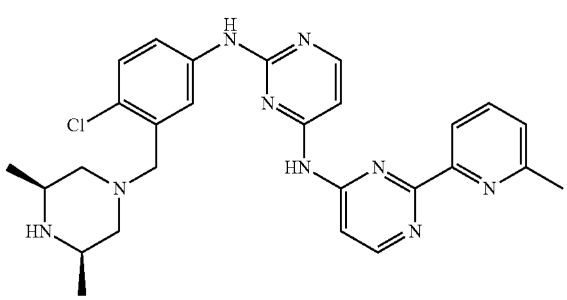 | N2-[4-chloro-3-[[rac-(3R,5S)-3,5-dimethylpiperazin-1-yl]methyl]phenyl]-N4-[2-(6-methyl-2-pyridyl)pyrimidin-4-yl]pyrimidine-2,4-diamine | 516.0 |
| 382 | AND Enantiomer | [rac-(1S)-1-methylpropyl] 4-[[4-[[4-[[2-(6-methyl-2-pyridyl)pyrimidin-4-yl]amino]pyrimidin-2-yl]amino]phenyl]methyl]piperazine-2-carboxylate | 554.6 |

TABLE 1-continued

| No. | Structure | Chemical Name | [M + H]+ |
|---|---|---|---|
| 383 | 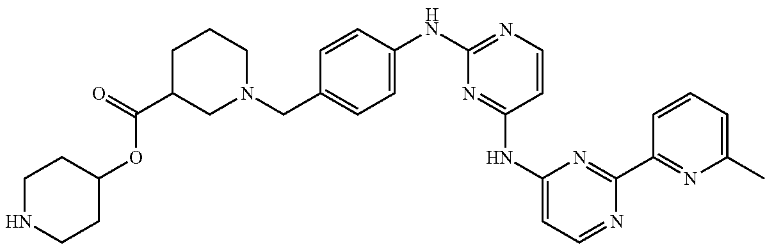 [SMILES: Cc1cccc(-c2nccc(Nc3ccnc(Nc4ccc(CN5CCCC(C(=O)OC6CCNCC6)C5)cc4)n3)n2)n1] | 4-piperidyl 1-[[4-[[4-[[2-(6-methyl-2-pyridyl)pyrimidin-4-yl]amino]pyrimidin-2-yl]amino]phenyl]methyl]piperidine-3-carboxylate | 580.2 |
| 384 | 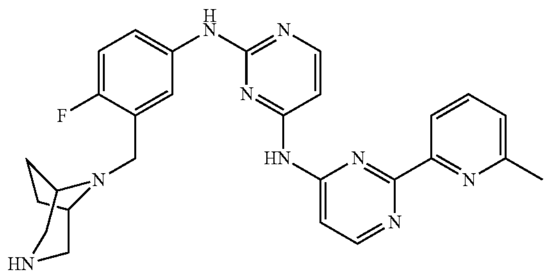 [SMILES: Cc1cccc(-c2nccc(Nc3ccnc(Nc4ccc(F)c(CN5C6CCC5CNC6)c4)n3)n2)n1] | N2-[3-(3,8-diazabicyclo[3.2.1]octan-8-ylmethyl)-4-fluoro-phenyl]-N4-[2-(6-methyl-2-pyridyl)pyrimidin-4-yl]pyrimidine-2,4-diamine | 498.1 |
| 385 | 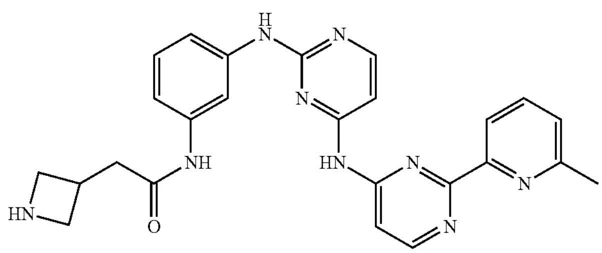 [SMILES: Cc1cccc(-c2nccc(Nc3ccnc(Nc4cccc(NC(=O)CC5CNC5)c4)n3)n2)n1] | 2-(azetidin-3-yl)-N-[3-[[4-[[2-(6-methyl-2-pyridyl)pyrimidin-4-yl]amino]pyrimidin-2-yl]amino]phenyl]acetamide | 468.1 |
| 386 | 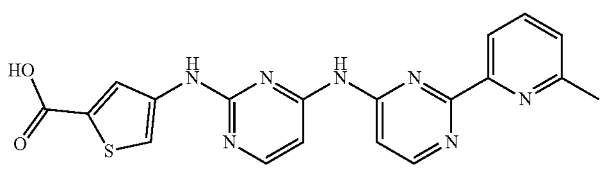 [SMILES: Cc1cccc(-c2nccc(Nc3ccnc(Nc4csc(C(=O)O)c4)n3)n2)n1] | 4-[[4-[[2-(6-methyl-2-pyridyl)pyrimidin-4-yl]amino]pyrimidin-2-yl]amino]thiophene-2-carboxylic acid | 406.0 |
| 387 | 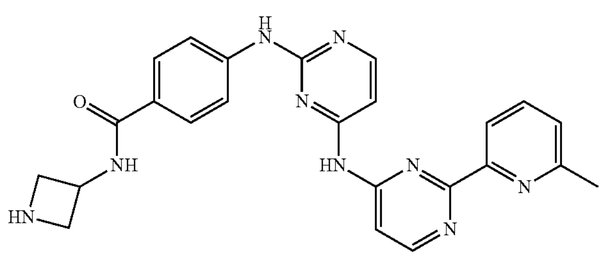 [SMILES: Cc1cccc(-c2nccc(Nc3ccnc(Nc4ccc(C(=O)NC5CNC5)cc4)n3)n2)n1] | N-(azetidin-3-yl)-4-[[4-[[2-(6-methyl-2-pyridyl)pyrimidin-4-yl]amino]pyrimidin-2-yl]amino]benzamide | 454.1 |
| 388 | 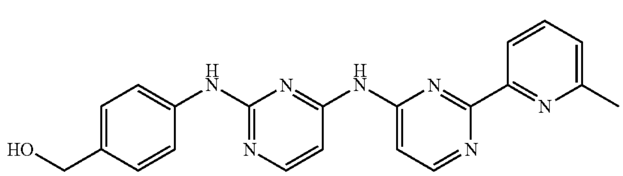 [SMILES: Cc1cccc(-c2nccc(Nc3ccnc(Nc4ccc(CO)cc4)n3)n2)n1] | [4-[[4-[[2-(6-methyl-2-pyridyl)pyrimidin-4-yl]amino]pyrimidin-2-yl]amino]phenyl]methanol | 386.1 |

TABLE 1-continued

| No. | Structure | Chemical Name | [M + H]+ |
|---|---|---|---|
| 389 | 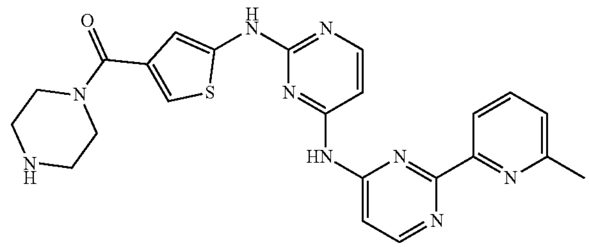 [SMILES: Cc1cccc(-c2nccc(Nc3ccnc(Nc4cc(C(=O)N5CCNCC5)cs4)n3)n2)n1] | [5-[[4-[[2-(6-methyl-2-pyridyl)pyrimidin-4-yl]amino]pyrimidin-2-yl]amino]-3-thienyl]-piperazin-1-yl-methanone | 474.2 |
| 390 | 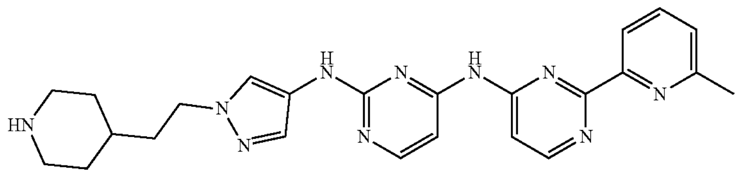 [SMILES: Cc1cccc(-c2nccc(Nc3ccnc(Nc4cnn(CCC5CCNCC5)c4)n3)n2)n1] | N4-[2-(6-methyl-2-pyridyl)pyrimidin-4-yl]-N2-[1-[2-(4-piperidyl)ethyl]pyrazol-4-yl]pyrimidine-2,4-diamine | 457.2 |
| 391 | 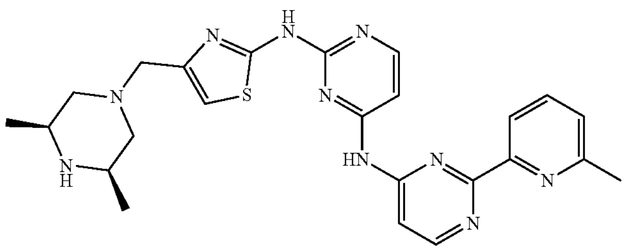 | N4-[2-(6-methyl-2-pyridyl)pyrimidin-4-yl]-N2-[4-[[rac-(3R,5S)-3,5-dimethylpiperazin-1-yl]methyl]thiazol-2-yl]pyrimidine-2,4-diamine | 489.1 |
| 392 | 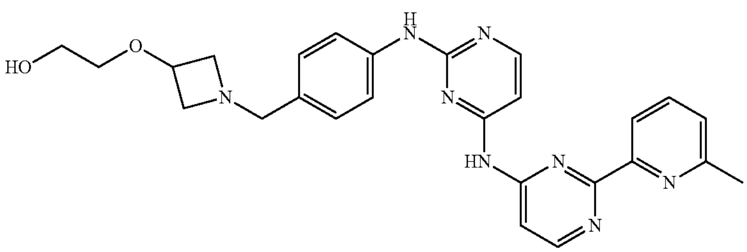 [SMILES: Cc1cccc(-c2nccc(Nc3ccnc(Nc4ccc(CN5CC(OCCO)C5)cc4)n3)n2)n1] | 2-[1-[[4-[[4-[[2-(6-methyl-2-pyridyl)pyrimidin-4-yl]amino]pyrimidin-2-yl]amino]phenyl]methyl]azetidin-3-yl]oxyethanol | 485.1 |
| 393 | 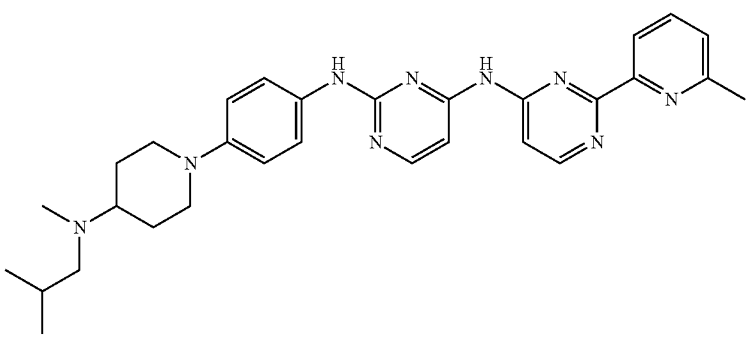 [SMILES: Cc1cccc(-c2nccc(Nc3ccnc(Nc4ccc(N5CCC(N(C)CC(C)C)CC5)cc4)n3)n2)n1] | N2-[4-[4-[isobutyl(methyl)amino]-1-piperidyl]phenyl]-N4-[2-(6-methyl-2-pyridyl)pyrimidin-4-yl]pyrimidine-2,4-diamine | 524.3 |
| 394 | 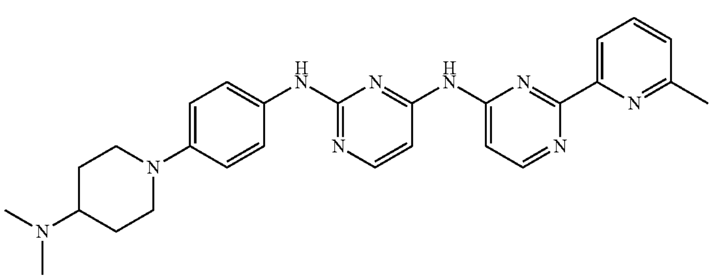 | N2-[4-[4-(dimethylamino)-1-piperidyl]phenyl]-N4-[2-(6-methyl-2-pyridyl)pyrimidin-4-yl]pyrimidine-2,4-diamine | 482.2 |

TABLE 1-continued

| No. | Structure | Chemical Name | [M + H]+ |
|---|---|---|---|
| 395 | 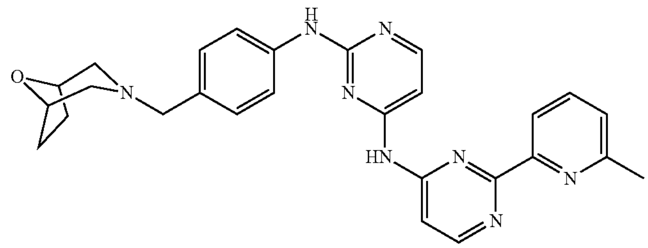 [SMILES: Cc1cccc(-c2nccc(Nc3ccnc(Nc4ccc(CN5CC6CCC(C5)O6)cc4)n3)n2)n1] | N4-[2-(6-methyl-2-pyridyl)pyrimidin-4-yl]-N2-[4-(8-oxa-3-azabicyclo[3.2.1]octan-3-ylmethyl)phenyl]pyrimidine-2,4-diamine | 481.2 |
| 396 | 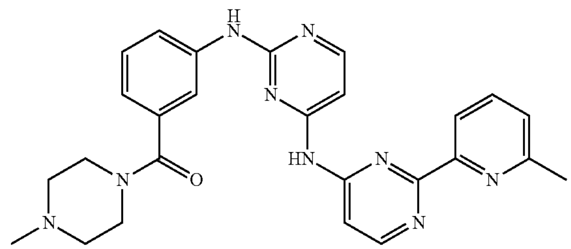 | (4-methylpiperazin-1-yl)-[3-[[4-[[2-(6-methyl-2-pyridyl)pyrimidin-4-yl]amino]pyrimidin-2-yl]amino]phenyl]methanone | 482.2 |
| 397 | 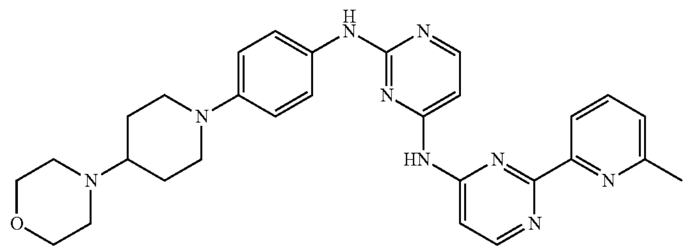 [SMILES: Cc1cccc(-c2nccc(Nc3ccnc(Nc4ccc(N5CCC(N6CCOCC6)CC5)cc4)n3)n2)n1] | N4-[2-(6-methyl-2-pyridyl)pyrimidin-4-yl]-N2-[4-(4-morpholino-1-piperidyl)phenyl]pyrimidine-2,4-diamine | 524.2 |
| 398 | 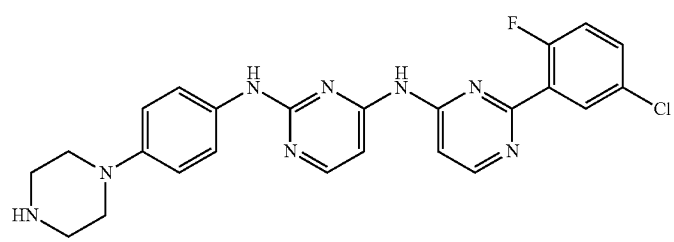 [SMILES: Fc1ccc(Cl)cc1-c1nccc(Nc2ccnc(Nc3ccc(N4CCNCC4)cc3)n2)n1] | N4-[2-(5-chloro-2-fluoro-phenyl)pyrimidin-4-yl]-N2-(4-piperazin-1-ylphenyl)pyrimidine-2,4-diamine | 477.1 |
| 399 | 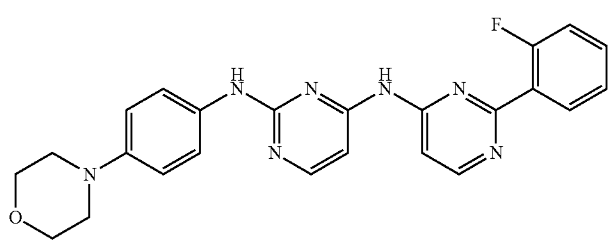 [SMILES: Fc1ccccc1-c1nccc(Nc2ccnc(Nc3ccc(N4CCOCC4)cc3)n2)n1] | N4-[2-(2-fluorophenyl)pyrimidin-4-yl]-N2-(4-morpholinophenyl)pyrimidine-2,4-diamine | 444.2 |
| 400 | 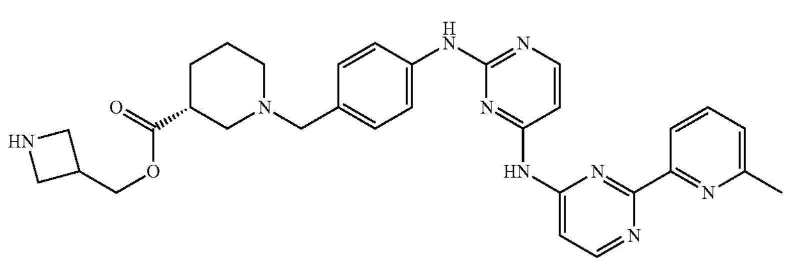 [SMILES: Cc1cccc(-c2nccc(Nc3ccnc(Nc4ccc(CN5CCC[C@@H](C(=O)OCC6CNC6)C5)cc4)n3)n2)n1] | azetidin-3-ylmethyl (3R)-1-[[4-[[4-[[2-(6-methyl-2-pyridyl)pyrimidin-4-yl]amino]pyrimidin-2-yl]amino]phenyl]methyl]piperidine-3-carboxylate | 566.1 |

TABLE 1-continued

| No. | Structure | Chemical Name | [M + H]+ |
|---|---|---|---|
| 401 | 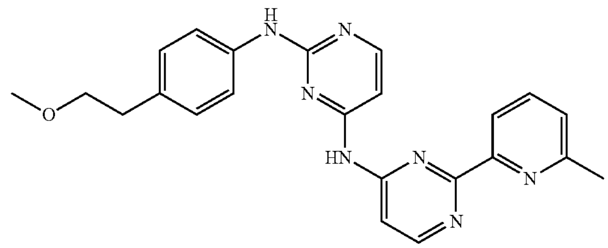 | N2-[4-(2-methoxyethyl)phenyl]-N4-[2-(6-methyl-2-pyridyl)pyrimidin-4-yl]pyrimidine-2,4-diamine | 414.1 |
| 402 | 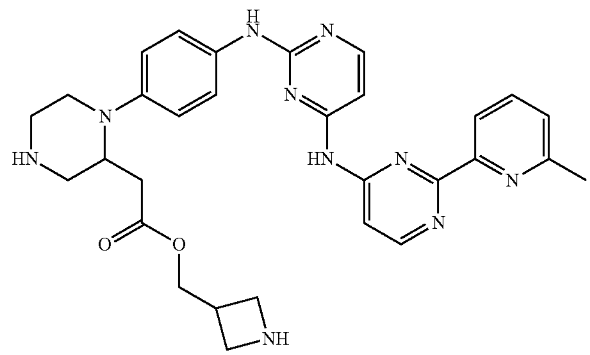 [SMILES: Cc1cccc(-c2nccc(Nc3ccnc(Nc4ccc(N5CCNCC5CC(=O)OCC5CNC5)cc4)n3)n2)n1] | azetidin-3-ylmethyl 2-[1-[4-[[4-[[2-(6-methyl-2-pyridyl)pyrimidin-4-yl]amino]pyrimidin-2-yl]amino]phenyl]piperazin-2-yl]acetate | 567.1 |
| 403 | 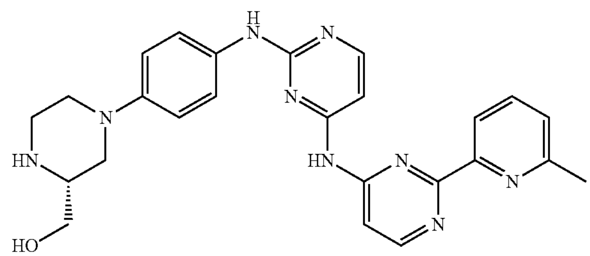 [SMILES: Cc1cccc(-c2nccc(Nc3ccnc(Nc4ccc(N5CCN[C@@H](CO)C5)cc4)n3)n2)n1] | [(2R)-4-[4-[[4-[[2-(6-methyl-2-pyridyl)pyrimidin-4-yl]amino]pyrimidin-2-yl]amino]phenyl]piperazin-2-yl]methanol | 470.1 |
| 404 | 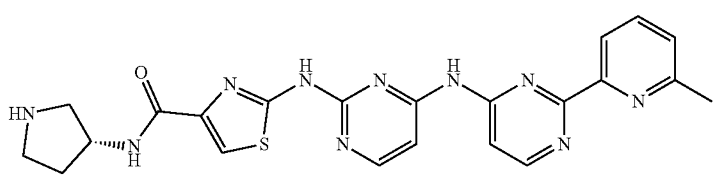 [SMILES: Cc1cccc(-c2nccc(Nc3ccnc(Nc4nc(C(=O)N[C@@H]5CCNC5)cs4)n3)n2)n1] | 2-[[4-[[2-(6-methyl-2-pyridyl)pyrimidin-4-yl]amino]pyrimidin-2-yl]amino]-N-[(3R)-pyrrolidin-3-yl]thiazole-4-carboxamide | 475.2 |
| 405 | 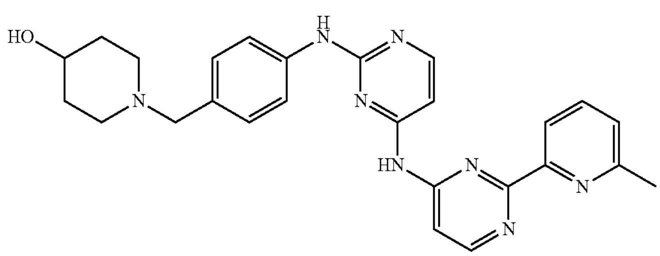 [SMILES: Cc1cccc(-c2nccc(Nc3ccnc(Nc4ccc(CN5CCC(O)CC5)cc4)n3)n2)n1] | 1-[[4-[[4-[[2-(6-methyl-2-pyridyl)pyrimidin-4-yl]amino]pyrimidin-2-yl]amino]phenyl]methyl]piperidin-4-ol | 469.1 |
| 406 | 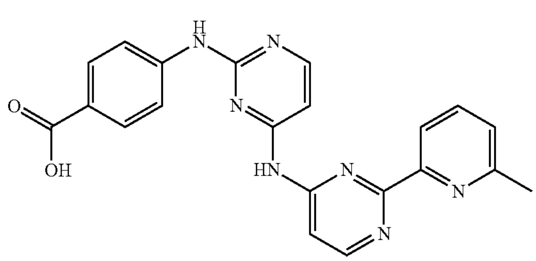 [SMILES: Cc1cccc(-c2nccc(Nc3ccnc(Nc4ccc(C(=O)O)cc4)n3)n2)n1] | 4-[[4-[[2-(6-methyl-2-pyridyl)pyrimidin-4-yl]amino]pyrimidin-2-yl]amino]benzoic acid | 399.9 |

TABLE 1-continued

| No. | Structure | Chemical Name | [M + H]+ |
|---|---|---|---|
| 407 | 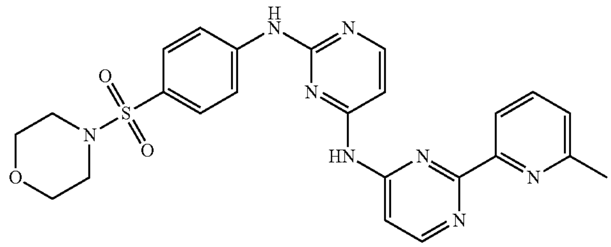 [SMILES: Cc1cccc(-c2nccc(Nc3ccnc(Nc4ccc(S(=O)(=O)N5CCOCC5)cc4)n3)n2)n1] | N4-[2-(6-methyl-2-pyridyl)pyrimidin-4-yl]-N2-(4-morpholinosulfonylphenyl)pyrimidine-2,4-diamine | 505.1 |
| 408 | 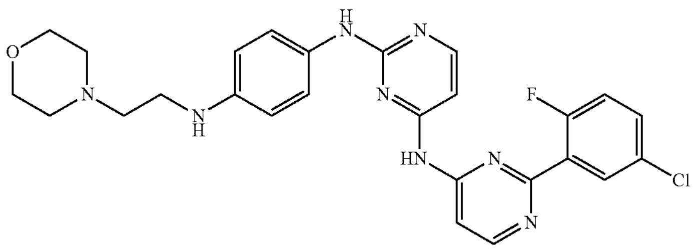 [SMILES: Fc1ccc(Cl)cc1-c1nccc(Nc2ccnc(Nc3ccc(NCCN4CCOCC4)cc3)n2)n1] | N4-[2-(5-chloro-2-fluoro-phenyl)pyrimidin-4-yl]-N2-[4-(2-morpholinoethylamino)phenyl]pyrimidine-2,4-diamine | 521.1 |
| 409 | 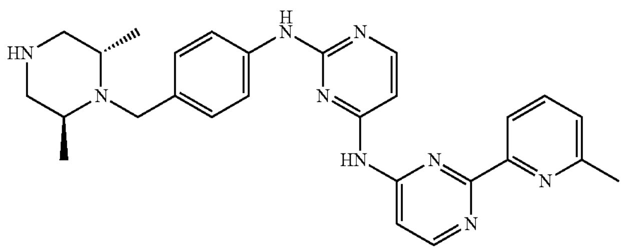 [SMILES: Cc1cccc(-c2nccc(Nc3ccnc(Nc4ccc(CN5[C@@H](C)CNC[C@@H]5C)cc4)n3)n2)n1] | N2-[4-[[(2S,6S)-2,6-dimethylpiperazin-1-yl]methyl]phenyl]-N4-[2-(6-methyl-2-pyridyl)pyrimidin-4-yl]pyrimidine-2,4-diamine | 482.2 |
| 410 | 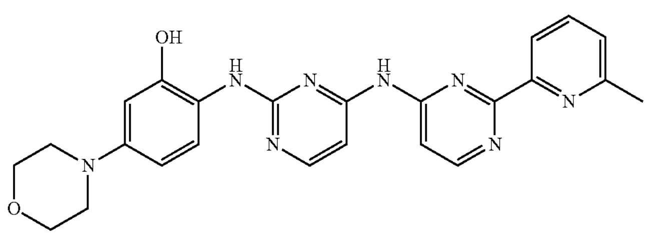 [SMILES: Cc1cccc(-c2nccc(Nc3ccnc(Nc4ccc(N5CCOCC5)cc4O)n3)n2)n1] | 2-[[4-[[2-(6-methyl-2-pyridyl)pyrimidin-4-yl]amino]pyrimidin-2-yl]amino]-5-morpholino-phenol | 457.2 |
| 411 | 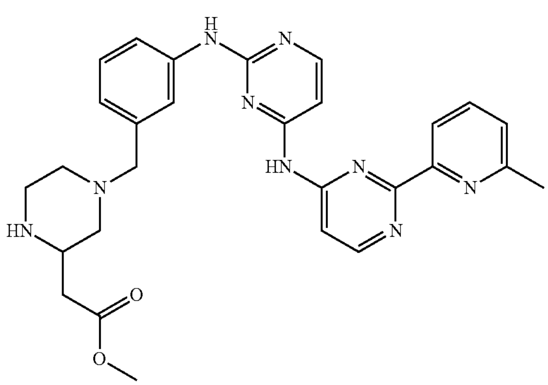 [SMILES: COC(=O)CC1CN(Cc2cccc(Nc3nccc(Nc4ccnc(-c5cccc(C)n5)n4)n3)c2)CCN1] | methyl 2-[4-[[3-[[4-[[2-(6-methyl-2-pyridyl)pyrimidin-4-yl]amino]pyrimidin-2-yl]amino]phenyl]methyl]piperazin-2-yl]acetate | 526.2 |

TABLE 1-continued

| No. | Structure | Chemical Name | [M + H]+ |
|---|---|---|---|
| 412 | 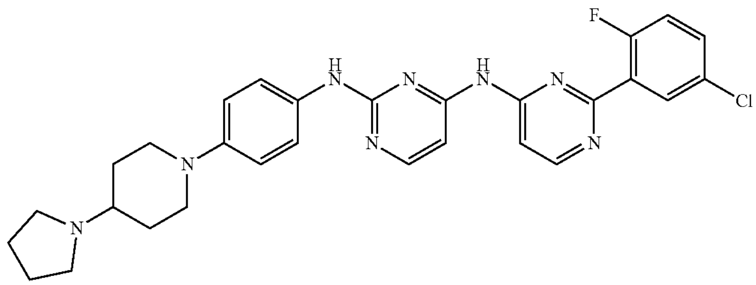 [SMILES: Fc1ccc(Cl)cc1-c1nccc(Nc2ccnc(Nc3ccc(N4CCC(N5CCCC5)CC4)cc3)n2)n1] | N4-[2-(5-chloro-2-fluoro-phenyl)pyrimidin-4-yl]-N2-[4-(4-pyrrolidin-1-yl-1-piperidyl)phenyl]pyrimidine-2,4-diamine | 545.1 |
| 413 | 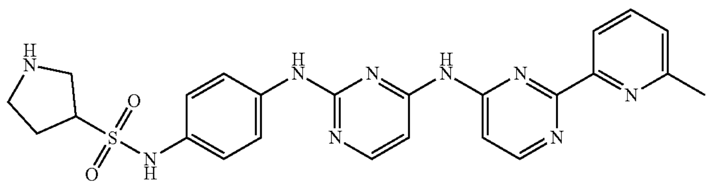 [SMILES: Cc1cccc(-c2nccc(Nc3ccnc(Nc4ccc(NS(=O)(=O)C5CCNC5)cc4)n3)n2)n1] | N-[4-[[4-[[2-(6-methyl-2-pyridyl)pyrimidin-4-yl]amino]pyrimidin-2-yl]amino]phenyl]pyrrolidine-3-sulfonamide | 504.1 |
| 414 | 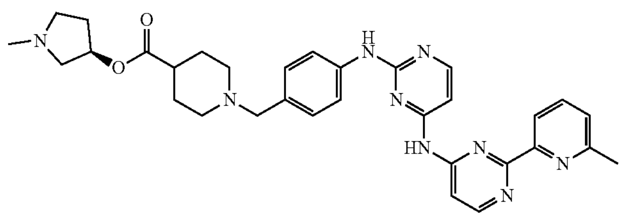 | [(3R)-1-methylpyrrolidin-3-yl] 1-[[4-[[4-[[2-(6-methyl-2-pyridyl)pyrimidin-4-yl]amino]pyrimidin-2-yl]amino]phenyl]methyl]piperidine-4-carboxylate | 580.3 |
| 415 | 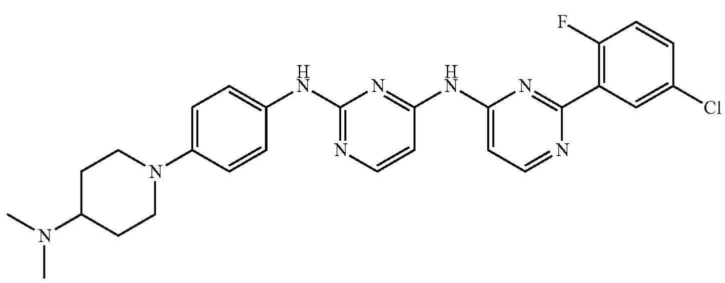 [SMILES: CN(C)C1CCN(c2ccc(Nc3nccc(Nc4ccnc(-c5cc(Cl)ccc5F)n4)n3)cc2)CC1] | N4-[2-(5-chloro-2-fluoro-phenyl)pyrimidin-4-yl]-N2-[4-[4-(dimethylamino)-1-piperidyl]phenyl]pyrimidine-2,4-diamine | 520.1 |
| 416 | 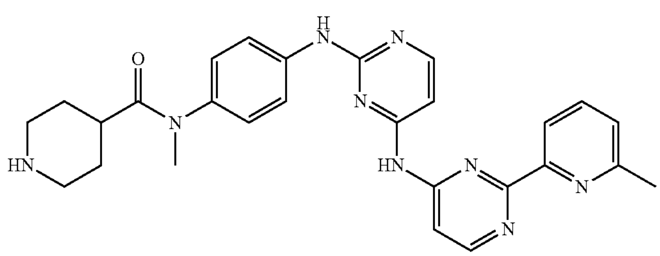 [SMILES: Cc1cccc(-c2nccc(Nc3ccnc(Nc4ccc(N(C)C(=O)C5CCNCC5)cc4)n3)n2)n1] | N-methyl-N-[4-[[4-[[2-(6-methyl-2-pyridyl)pyrimidin-4-yl]amino]pyrimidin-2-yl]amino]phenyl]piperidine-4-carboxamide | 496.2 |
| 417 | 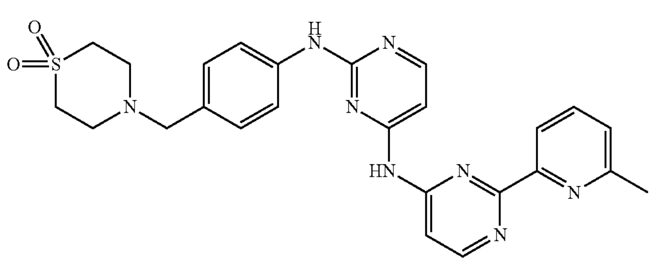 [SMILES: Cc1cccc(-c2nccc(Nc3ccnc(Nc4ccc(CN5CCS(=O)(=O)CC5)cc4)n3)n2)n1] | N2-[4-[(1,1-dioxo-1,4-thiazinan-4-yl)methyl]phenyl]-N4-[2-(6-methyl-2-pyridyl)pyrimidin-4-yl]pyrimidine-2,4-diamine | 503.1 |

TABLE 1-continued

| No. | Structure | Chemical Name | [M + H]+ |
|---|---|---|---|
| 418 | 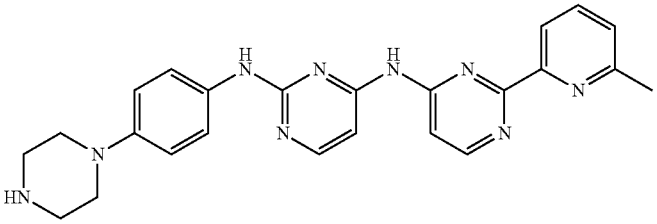 [SMILES: Cc1cccc(-c2nccc(Nc3ccnc(Nc4ccc(N5CCNCC5)cc4)n3)n2)n1] | N4-[2-(6-methyl-2-pyridyl)pyrimidin-4-yl]-N2-(4-piperazin-1-ylphenyl)pyrimidine-2,4-diamine | 440.2 |
| 419 | 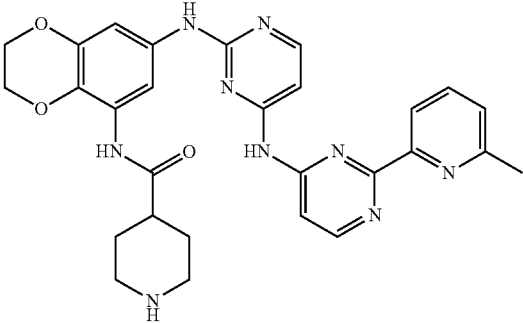 [SMILES: Cc1cccc(-c2nccc(Nc3ccnc(Nc4cc(NC(=O)C5CCNCC5)c5c(c4)OCCO5)n3)n2)n1] | N-[7-[[4-[[2-(6-methyl-2-pyridyl)pyrimidin-4-yl]amino]pyrimidin-2-yl]amino]-2,3-dihydro-1,4-benzodioxin-5-yl]piperidine-4-carboxamide | 540.2 |
| 420 | 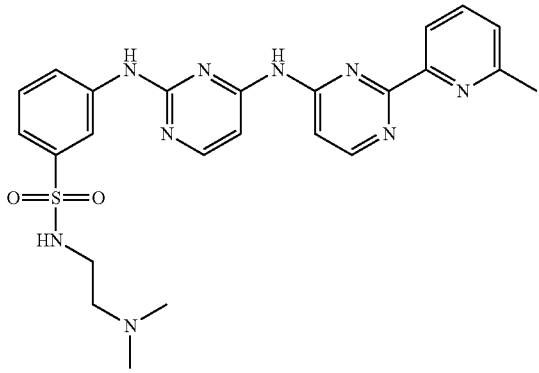 [SMILES: Cc1cccc(-c2nccc(Nc3ccnc(Nc4cccc(S(=O)(=O)NCCN(C)C)c4)n3)n2)n1] | N-[2-(dimethylamino)ethyl]-3-[[4-[[2-(6-methyl-2-pyridyl)pyrimidin-4-yl]amino]pyrimidin-2-yl]amino]benzenesulfonamide | 506.2 |
| 421 | 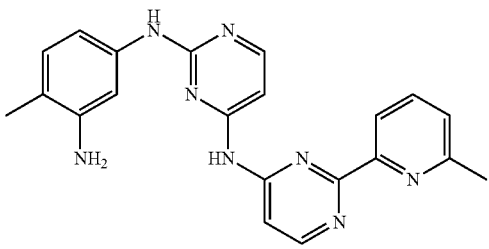 | N2-(3-amino-4-methyl-phenyl)-N4-[2-(6-methyl-2-pyridyl)pyrimidin-4-yl]pyrimidine-2,4-diamine | 385.1 |
| 422 | 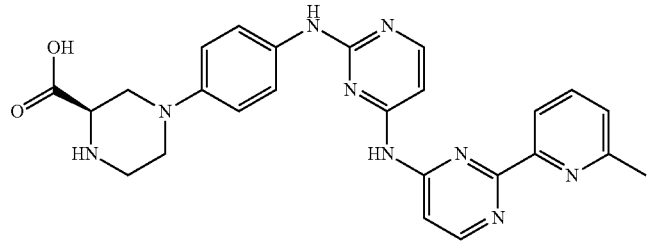 [SMILES: Cc1cccc(-c2nccc(Nc3ccnc(Nc4ccc(N5CCN[C@@H](C(=O)O)C5)cc4)n3)n2)n1] | (2R)-4-[4-[[4-[[2-(6-methyl-2-pyridyl)pyrimidin-4-yl]amino]pyrimidin-2-yl]amino]phenyl]piperazine-2-carboxylic acid | 484.1 |

TABLE 1-continued

| No. | Structure | Chemical Name | [M + H]+ |
|---|---|---|---|
| 423 | 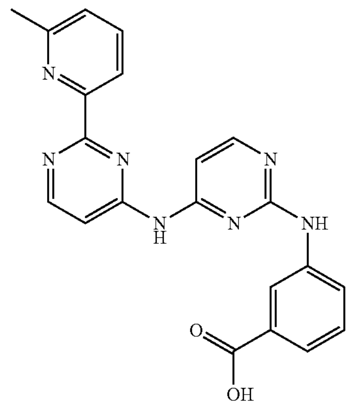 [SMILES: Cc1cccc(-c2nccc(Nc3ccnc(Nc4cccc(C(=O)O)c4)n3)n2)n1] | 3-[[4-[[2-(6-methyl-2-pyridyl)pyrimidin-4-yl]amino]pyrimidin-2-yl]amino]benzoic acid | 399.9 |
| 424 | 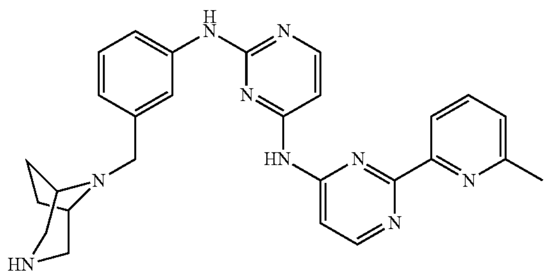 [SMILES: Cc1cccc(-c2nccc(Nc3ccnc(Nc4cccc(CN5C6CCC5CNC6)c4)n3)n2)n1] | N2-[3-(3,8-diazabicyclo[3.2.1]octan-8-ylmethyl)phenyl]-N4-[2-(6-methyl-2-pyridyl)pyrimidin-4-yl]pyrimidine-2,4-diamine | 480.2 |
| 425 | 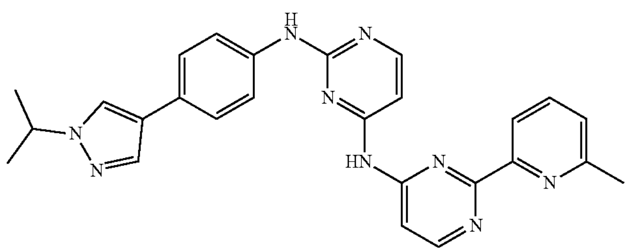 [SMILES: Cc1cccc(-c2nccc(Nc3ccnc(Nc4ccc(-c5cnn(C(C)C)c5)cc4)n3)n2)n1] | N2-[4-(1-isopropylpyrazol-4-yl)phenyl]-N4-[2-(6-methyl-2-pyridyl)pyrimidin-4-yl]pyrimidine-2,4-diamine | 464.2 |
| 426 | 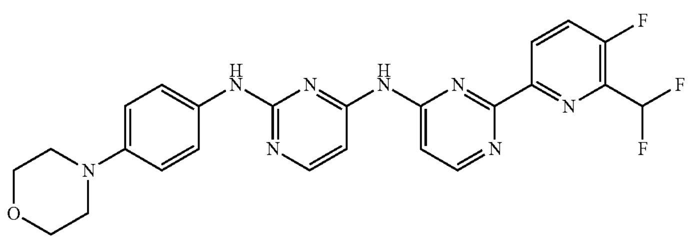 [SMILES: Fc1ccc(-c2nccc(Nc3ccnc(Nc4ccc(N5CCOCC5)cc4)n3)n2)nc1C(F)F] | N4-[2-[6-(difluoromethyl)-5-fluoro-2-pyridyl]pyrimidin-4-yl]-N2-(4-morpholinophenyl)pyrimidine-2,4-diamine | 495.0 |
| 427 | 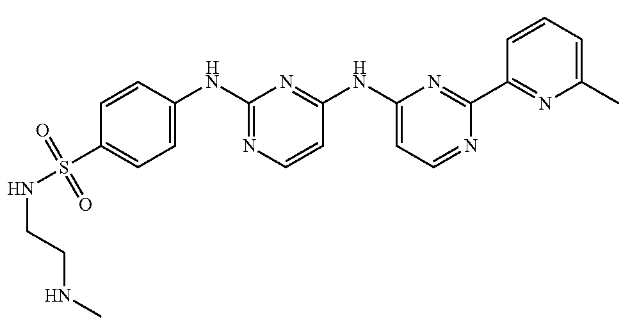 [SMILES: CNCCNS(=O)(=O)c1ccc(Nc2nccc(Nc3ccnc(-c4cccc(C)n4)n3)n2)cc1] | N-[2-(methylamino)ethyl]-4-[[4-[[2-(6-methyl-2-pyridyl)pyrimidin-4-yl]amino]pyrimidin-2-yl]amino]benzenesulfonamide | 492.2 |

TABLE 1-continued

| No. | Structure | Chemical Name | [M + H]+ |
|---|---|---|---|
| 428 | 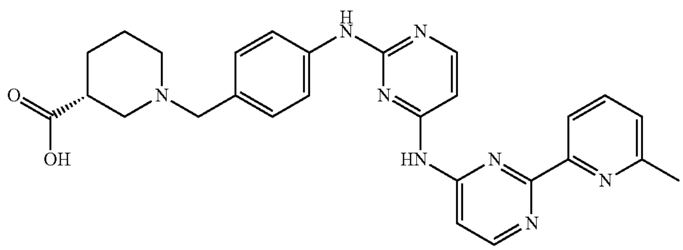 [SMILES: Cc1cccc(-c2nccc(Nc3ccnc(Nc4ccc(CN5CCC[C@@H](C(=O)O)C5)cc4)n3)n2)n1] | (3R)-1-[[4-[[4-[[2-(6-methyl-2-pyridyl)pyrimidin-4-yl]amino]pyrimidin-2-yl]amino]phenyl]methyl]piperidine-3-carboxylic acid | 497.2 |
| 429 | 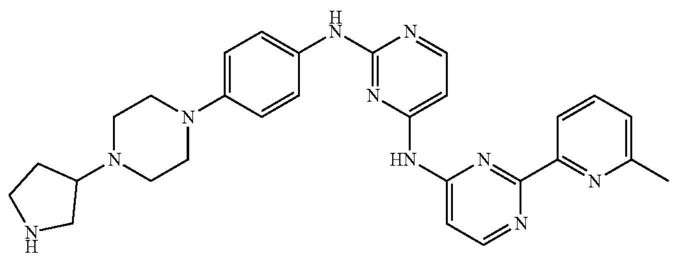 [SMILES: Cc1cccc(-c2nccc(Nc3ccnc(Nc4ccc(N5CCN(C6CCNC6)CC5)cc4)n3)n2)n1] | N4-[2-(6-methyl-2-pyridyl)pyrimidin-4-yl]-N2-[4-(4-pyrrolidin-3-ylpiperazin-1-yl)phenyl]pyrimidine-2,4-diamine | 509.2 |
| 430 | 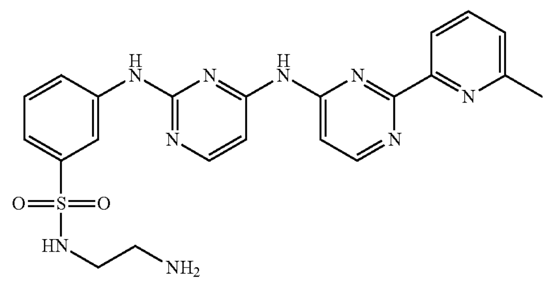 [SMILES: Cc1cccc(-c2nccc(Nc3ccnc(Nc4cccc(S(=O)(=O)NCCN)c4)n3)n2)n1] | N-(2-aminoethyl)-3-[[4-[[2-(6-methyl-2-pyridyl)pyrimidin-4-yl]amino]pyrimidin-2-yl]amino]benzenesulfonamide | 478.1 |
| 431 | 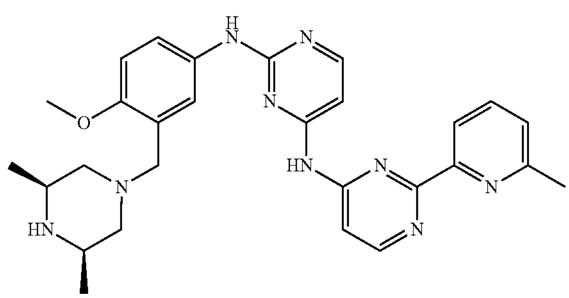 | N2-[4-methoxy-3-[[rac-(3R,5S)-3,5-dimethylpiperazin-1-yl]methyl]phenyl]-N4-[2-(6-methyl-2-pyridyl)pyrimidin-4-yl]pyrimidine-2,4-diamine | 512.2 |
| 432 | 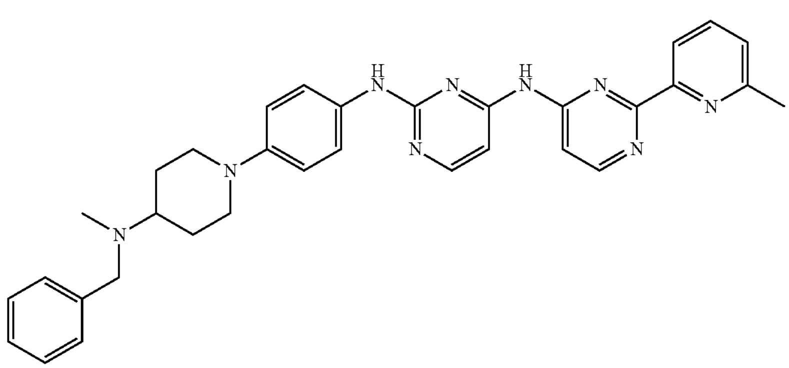 [SMILES: Cc1cccc(-c2nccc(Nc3ccnc(Nc4ccc(N5CCC(N(C)Cc6ccccc6)CC5)cc4)n3)n2)n1] | N2-[4-[4-[benzyl(methyl)amino]-1-piperidyl]phenyl]-N4-[2-(6-methyl-2-pyridyl)pyrimidin-4-yl]pyrimidine-2,4-diamine | 558.2 |

TABLE 1-continued

| No. | Structure | Chemical Name | [M + H]⁺ |
|---|---|---|---|
| 433 | 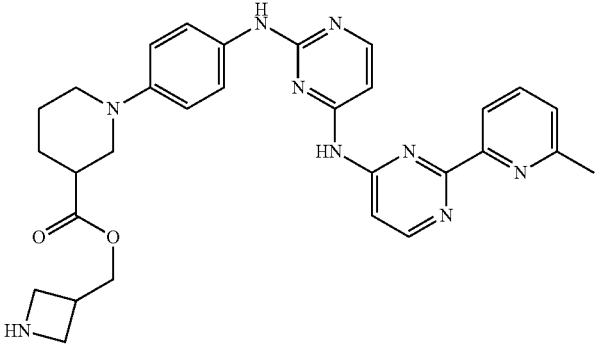 [SMILES: Cc1cccc(-c2nccc(Nc3ccnc(Nc4ccc(N5CCCC(C(=O)OCC6CNC6)C5)cc4)n3)n2)n1] | azetidin-3-ylmethyl 1-[4-[[4-[[2-(6-methyl-2-pyridyl)pyrimidin-4-yl]amino]pyrimidin-2-yl]amino]phenyl]piperidine-3-carboxylate | 552.2 |
| 434 | 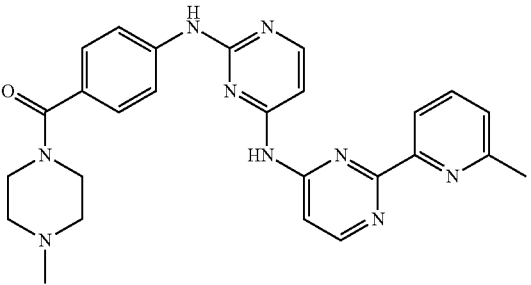 [SMILES: Cc1cccc(-c2nccc(Nc3ccnc(Nc4ccc(C(=O)N5CCN(C)CC5)cc4)n3)n2)n1] | (4-methylpiperazin-1-yl)-[4-[[4-[[2-(6-methyl-2-pyridyl)pyrimidin-4-yl]amino]pyrimidin-2-yl]amino]phenyl]methanone | 482.2 |
| 435 | 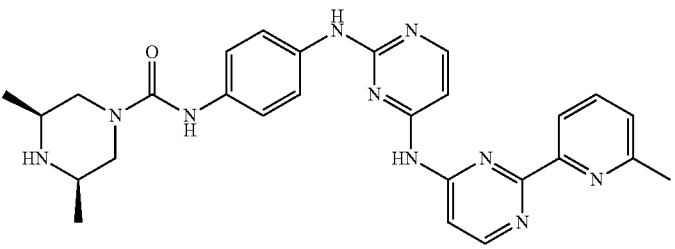 | rac-(3S,5R)-3,5-dimethyl-N-[4-[[4-[[2-(6-methyl-2-pyridyl)pyrimidin-4-yl]amino]pyrimidin-2-yl]amino]phenyl]piperazine-1-carboxamide | 511.3 |
| 436 | 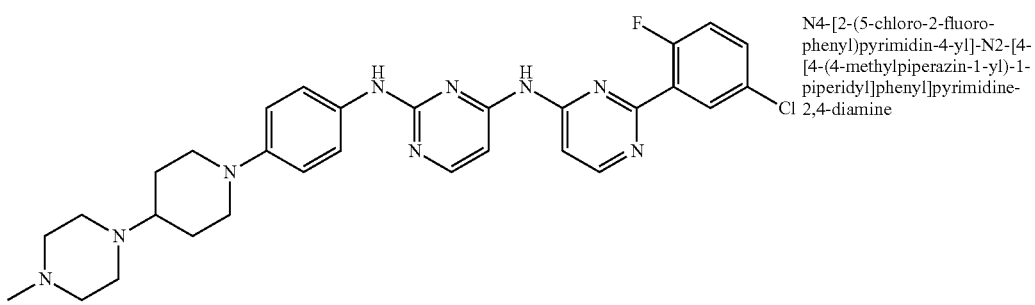 | N4-[2-(5-chloro-2-fluoro-phenyl)pyrimidin-4-yl]-N2-[4-[4-(4-methylpiperazin-1-yl)-1-piperidyl]phenyl]pyrimidine-2,4-diamine | 574.2 |
| 437 | 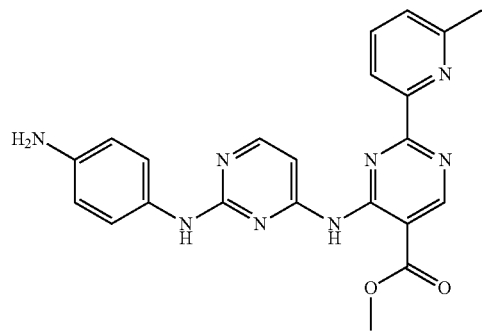 [SMILES: COC(=O)c1cnc(-c2cccc(C)n2)nc1Nc1ccnc(Nc2ccc(N)cc2)n1] | methyl 4-[[2-(4-aminoanilino)pyrimidin-4-yl]amino]-2-(6-methyl-2-pyridyl)pyrimidine-5-carboxylate | 429.0 |

TABLE 1-continued

| No. | Structure | Chemical Name | [M + H]+ |
|---|---|---|---|
| 438 | 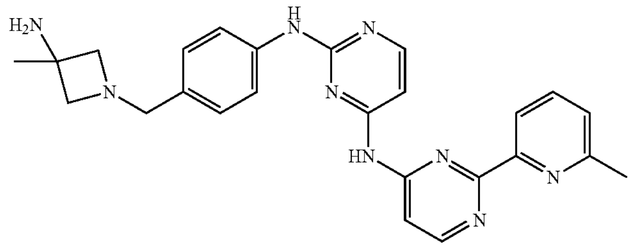 | N2-[4-[(3-amino-3-methyl-azetidin-1-yl)methyl]phenyl]-N4-[2-(6-methyl-2-pyridyl)pyrimidin-4-yl]pyrimidine-2,4-diamine | 454.2 |
| 439 | 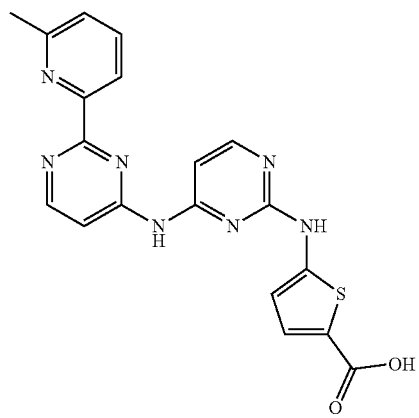 [SMILES: Cc1cccc(-c2nccc(Nc3ccnc(Nc4ccc(C(=O)O)s4)n3)n2)n1] | 5-[[4-[[2-(6-methyl-2-pyridyl)pyrimidin-4-yl]amino]pyrimidin-2-yl]amino]thiophene-2-carboxylic acid | 406.3 |
| 440 | 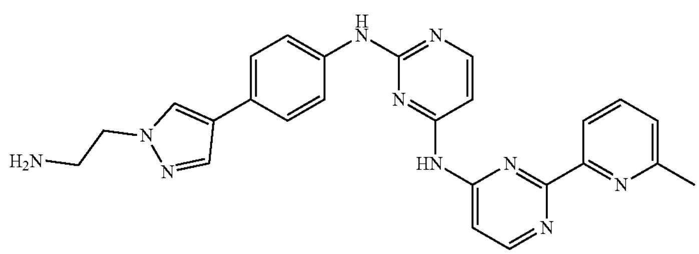 [SMILES: Cc1cccc(-c2nccc(Nc3ccnc(Nc4ccc(-c5cnn(CCN)c5)cc4)n3)n2)n1] | N2-[4-[1-(2-aminoethyl)pyrazol-4-yl]phenyl]-N4-[2-(6-methyl-2-pyridyl)pyrimidin-4-yl]pyrimidine-2,4-diamine | 465.1 |
| 441 | 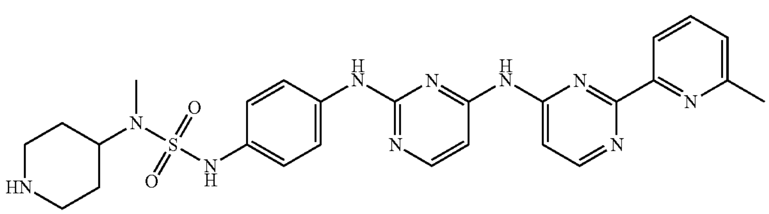 [SMILES: Cc1cccc(-c2nccc(Nc3ccnc(Nc4ccc(NS(=O)(=O)N(C)C5CCNCC5)cc4)n3)n2)n1] | 4-[[2-[4-[[methyl(4-piperidyl)sulfamoyl]amino]anilino]pyrimidin-4-yl]amino]-2-(6-methyl-2-pyridyl)pyrimidine | 547.1 |
| 442 | 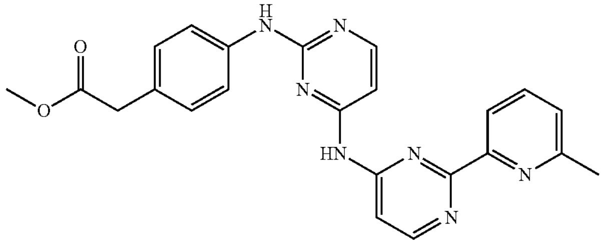 | methyl 2-[4-[[4-[[2-(6-methyl-2-pyridyl)pyrimidin-4-yl]amino]pyrimidin-2-yl]amino]phenyl]acetate | 428.1 |

TABLE 1-continued

| No. | Structure | Chemical Name | [M + H]+ |
|---|---|---|---|
| 443 | 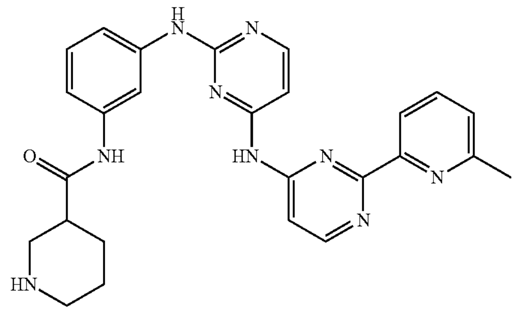 [SMILES: Cc1cccc(-c2nccc(Nc3ccnc(Nc4cccc(NC(=O)C5CCCNC5)c4)n3)n2)n1] | N-[3-[[4-[[2-(6-methyl-2-pyridyl)pyrimidin-4-yl]amino]pyrimidin-2-yl]amino]phenyl]piperidine-3-carboxamide | 482.1 |
| 444 | 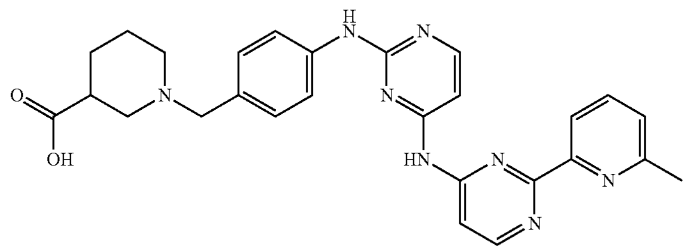 [SMILES: Cc1cccc(-c2nccc(Nc3ccnc(Nc4ccc(CN5CCCC(C(=O)O)C5)cc4)n3)n2)n1] | 1-[[4-[[4-[[2-(6-methyl-2-pyridyl)pyrimidin-4-yl]amino]pyrimidin-2-yl]amino]phenyl]methyl]piperidine-3-carboxylic acid | 497.1 |
| 445 | 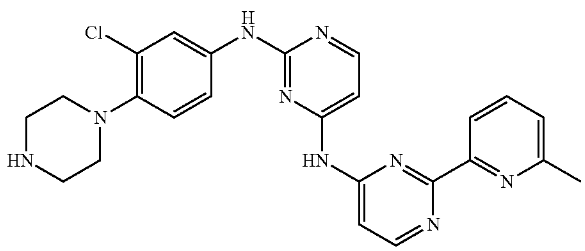 [SMILES: Cc1cccc(-c2nccc(Nc3ccnc(Nc4ccc(N5CCNCC5)c(Cl)c4)n3)n2)n1] | N2-(3-chloro-4-piperazin-1-yl-phenyl)-N4-[2-(6-methyl-2-pyridyl)pyrimidin-4-yl]pyrimidine-2,4-diamine | 474.1 |
| 446 | 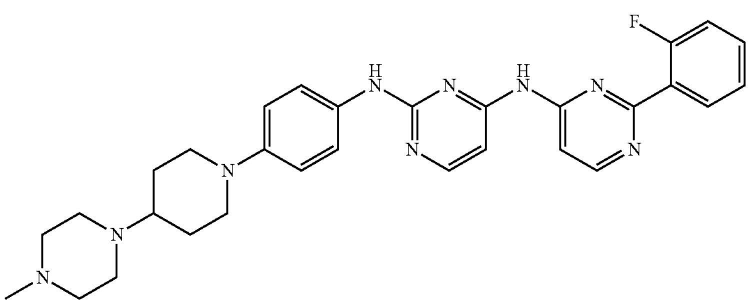 [SMILES: CN1CCN(C2CCN(c3ccc(Nc4nccc(Nc5ccnc(-c6ccccc6F)n5)n4)cc3)CC2)CC1] | N4-[2-(2-fluorophenyl)pyrimidin-4-yl]-N2-[4-[4-(4-methylpiperazin-1-yl)-1-piperidyl]phenyl]pyrimidine-2,4-diamine | 540.3 |
| 447 | 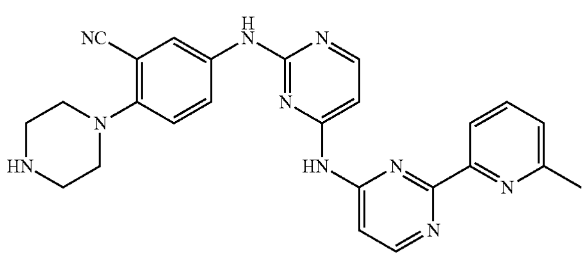 | 5-[[4-[[2-(6-methyl-2-pyridyl)pyrimidin-4-yl]amino]pyrimidin-2-yl]amino]-2-piperazin-1-yl-benzonitrile | 465.2 |

TABLE 1-continued

| No. | Structure | Chemical Name | [M + H]+ |
|---|---|---|---|
| 448 | 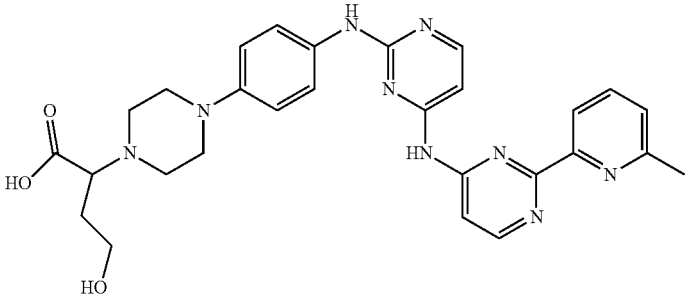 [SMILES: Cc1cccc(-c2nccc(Nc3ccnc(Nc4ccc(N5CCN(C(CCO)C(=O)O)CC5)cc4)n3)n2)n1] | 4-hydroxy-2-[4-[4-[[4-[[2-(6-methyl-2-pyridyl)pyrimidin-4-yl]amino]pyrimidin-2-yl]amino]phenyl]piperazin-1-yl]butanoic acid | 542.2 |
| 449 | 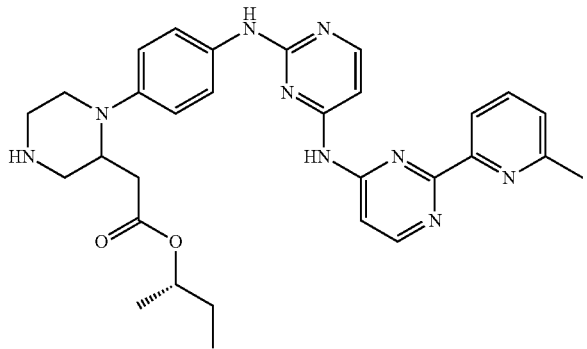 [SMILES: CC[C@H](C)OC(=O)CC1CNCCN1c1ccc(Nc2nccc(Nc3ccnc(-c4cccc(C)n4)n3)n2)cc1] | [(1S)-1-methylpropyl] 2-[1-[4-[[4-[[2-(6-methyl-2-pyridyl)pyrimidin-4-yl]amino]pyrimidin-2-yl]amino]phenyl]piperazin-2-yl]acetate | 554.5 |
| 450 | 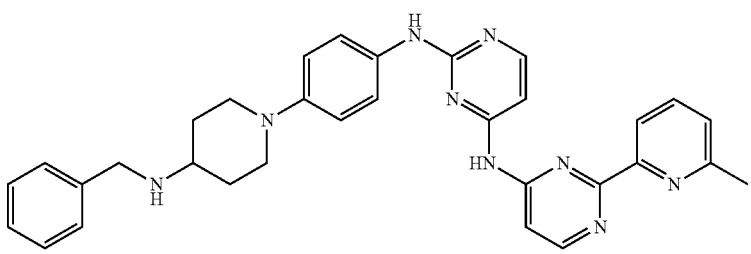 [SMILES: Cc1cccc(-c2nccc(Nc3ccnc(Nc4ccc(N5CCC(NCc6ccccc6)CC5)cc4)n3)n2)n1] | N2-[4-[4-(benzylamino)-1-piperidyl]phenyl]-N4-[2-(6-methyl-2-pyridyl)pyrimidin-4-yl]pyrimidine-2,4-diamine | 544.3 |
| 451 | 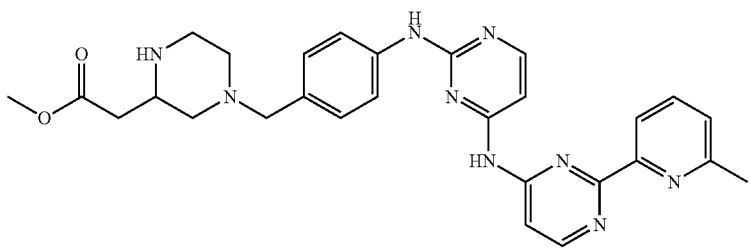 | methyl 2-[4-[[4-[[4-[[2-(6-methyl-2-pyridyl)pyrimidin-4-yl]amino]pyrimidin-2-yl]amino]phenyl]methyl]piperazin-2-yl]acetate | 526.2 |
| 452 | 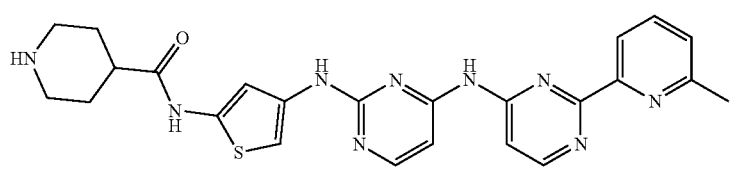 [SMILES: Cc1cccc(-c2nccc(Nc3ccnc(Nc4csc(NC(=O)C5CCNCC5)c4)n3)n2)n1] | N-[4-[[4-[[2-(6-methyl-2-pyridyl)pyrimidin-4-yl]amino]pyrimidin-2-yl]amino]-2-thienyl]piperidine-4-carboxamide | 488.0 |

TABLE 1-continued

| No. | Structure | Chemical Name | [M + H]+ |
|---|---|---|---|
| 453 | 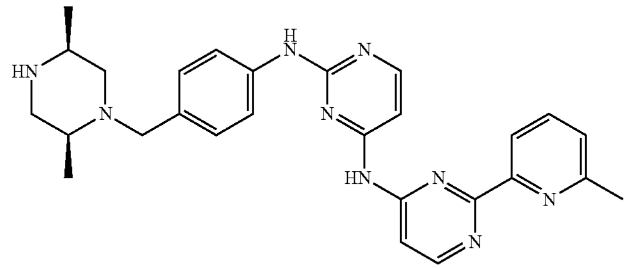 [SMILES: Cc1cccc(-c2nccc(Nc3ccnc(Nc4ccc(CN5C[C@H](C)NC[C@@H]5C)cc4)n3)n2)n1] | N2-[4-[[(2S,5S)-2,5-dimethylpiperazin-1-yl]methyl]phenyl]-N4-[2-(6-methyl-2-pyridyl)pyrimidin-4-yl]pyrimidine-2,4-diamine | 482.2 |
| 454 | 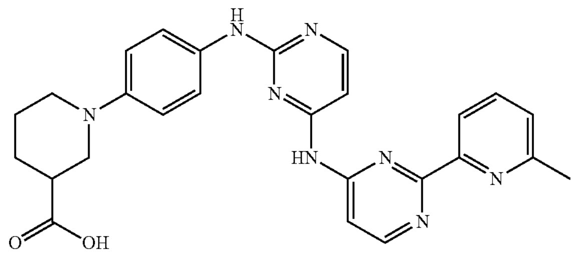 [SMILES: Cc1cccc(-c2nccc(Nc3ccnc(Nc4ccc(N5CCCC(C(=O)O)C5)cc4)n3)n2)n1] | 1-[4-[[4-[[2-(6-methyl-2-pyridyl)pyrimidin-4-yl]amino]pyrimidin-2-yl]amino]phenyl]piperidine-3-carboxylic acid | 483.1 |
| 455 | 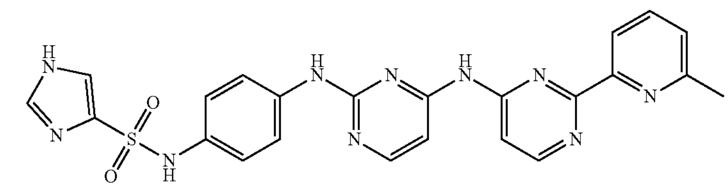 [SMILES: Cc1cccc(-c2nccc(Nc3ccnc(Nc4ccc(NS(=O)(=O)c5c[nH]cn5)cc4)n3)n2)n1] | N-[4-[[4-[[2-(6-methyl-2-pyridyl)pyrimidin-4-yl]amino]pyrimidin-2-yl]amino]phenyl]-1H-imidazole-4-sulfonamide | 501.0 |
| 456 | AND Enantiomer | 1-[[4-[[4-[[2-(6-methyl-2-pyridyl)pyrimidin-4-yl]amino]pyrimidin-2-yl]amino]phenyl]methyl]-N-[rac-(3R)-pyrrolidin-3-yl]piperidine-3-carboxamide | 565.2 |
| 457 | 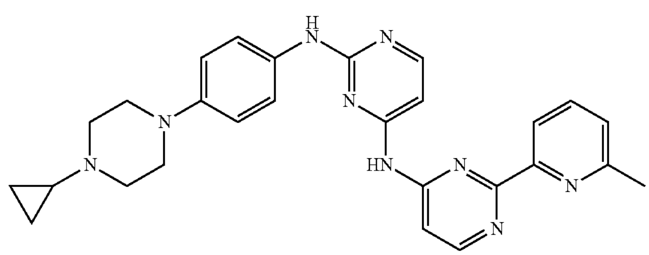 [SMILES: Cc1cccc(-c2nccc(Nc3ccnc(Nc4ccc(N5CCN(C6CC6)CC5)cc4)n3)n2)n1] | N2-[4-(4-cyclopropylpiperazin-1-yl)phenyl]-N4-[2-(6-methyl-2-pyridyl)pyrimidin-4-yl]pyrimidine-2,4-diamine | 480.2 |
| 458 | 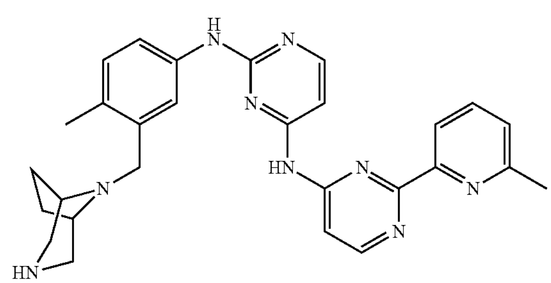 [SMILES: Cc1cccc(-c2nccc(Nc3ccnc(Nc4ccc(C)c(CN5C6CCC5CNC6)c4)n3)n2)n1] | N2-[3-(3,8-diazabicyclo[3.2.1]octan-8-ylmethyl)-4-methyl-phenyl]-N4-[2-(6-methyl-2-pyridyl)pyrimidin-4-yl]pyrimidine-2,4-diamine | 494.1 |

TABLE 1-continued

| No. | Structure | Chemical Name | [M + H]+ |
|---|---|---|---|
| 459 | 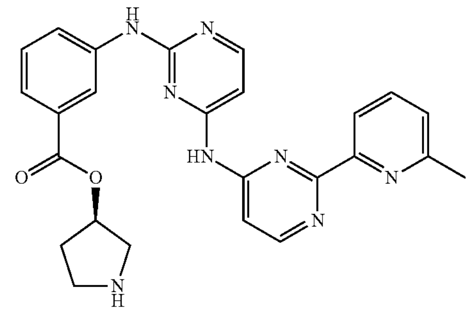 [SMILES: Cc1cccc(-c2nccc(Nc3ccnc(Nc4cccc(C(=O)O[C@@H]5CCNC5)c4)n3)n2)n1] | [(3R)-pyrrolidin-3-yl] 3-[[4-[[2-(6-methyl-2-pyridyl)pyrimidin-4-yl]amino]pyrimidin-2-yl]amino]benzoate | 469.1 |
| 460 | 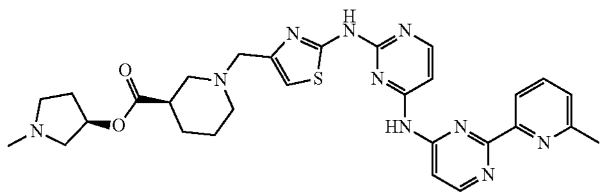 | [(3R)-1-methylpyrrolidin-3-yl] (3R)-1-[[2-[[4-[[2-(6-methyl-2-pyridyl)pyrimidin-4-yl]amino]pyrimidin-2-yl]amino]thiazol-4-yl]methyl]piperidine-3-carboxylate | 587.2 |
| 461 | 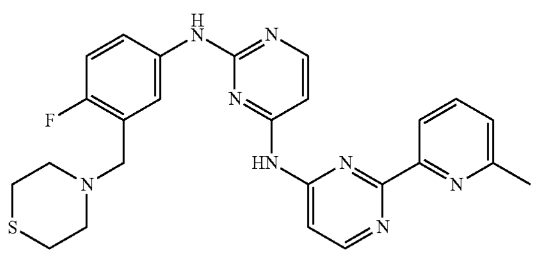 [SMILES: Cc1cccc(-c2nccc(Nc3ccnc(Nc4ccc(F)c(CN5CCSCC5)c4)n3)n2)n1] | N2-[4-fluoro-3-(thiomorpholinomethyl)phenyl]-N4-[2-(6-methyl-2-pyridyl)pyrimidin-4-yl]pyrimidine-2,4-diamine | 489.2 |
| 462 | 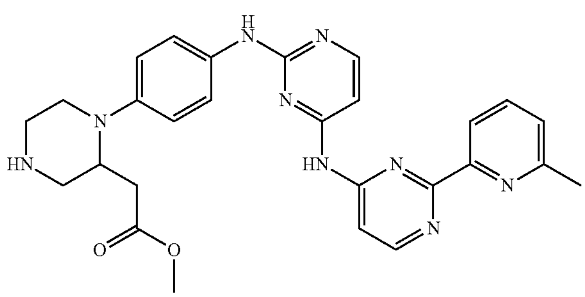 [SMILES: COC(=O)CC1CNCCN1c1ccc(Nc2nccc(Nc3ccnc(-c4cccc(C)n4)n3)n2)cc1] | methyl 2-[1-[4-[[4-[[2-(6-methyl-2-pyridyl)pyrimidin-4-yl]amino]pyrimidin-2-yl]amino]phenyl]piperazin-2-yl]acetate | 512.4 |
| 463 | 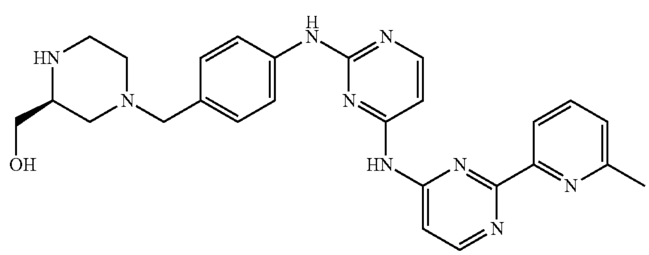 [SMILES: Cc1cccc(-c2nccc(Nc3ccnc(Nc4ccc(CN5CCN[C@H](CO)C5)cc4)n3)n2)n1] | [(2S)-4-[[4-[[4-[[2-(6-methyl-2-pyridyl)pyrimidin-4-yl]amino]pyrimidin-2-yl]amino]phenyl]methyl]piperazin-2-yl]methanol | 484.1 |
| 464 | 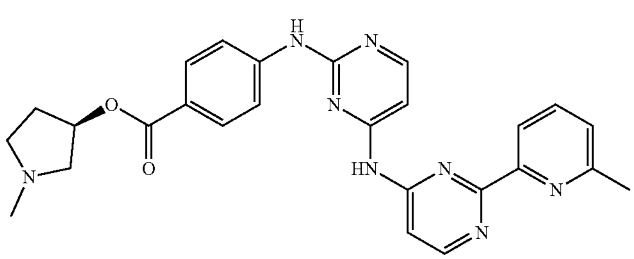 [SMILES: Cc1cccc(-c2nccc(Nc3ccnc(Nc4ccc(C(=O)O[C@@H]5CCN(C)C5)cc4)n3)n2)n1] | [(3R)-1-methylpyrrolidin-3-yl] 4-[[4-[[2-(6-methyl-2-pyridyl)pyrimidin-4-yl]amino]pyrimidin-2-yl]amino]benzoate | 483.0 |

TABLE 1-continued

| No. | Structure | Chemical Name | [M + H]+ |
|---|---|---|---|
| 465 | 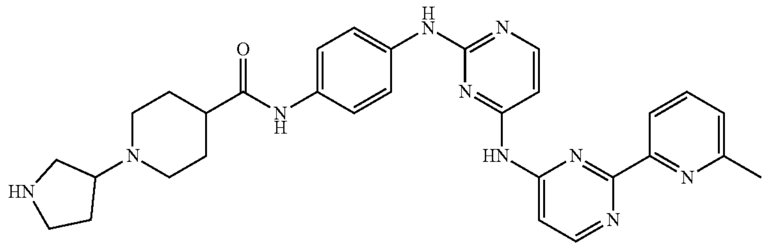 [SMILES: Cc1cccc(-c2nccc(Nc3ccnc(Nc4ccc(NC(=O)C5CCN(C6CCNC6)CC5)cc4)n3)n2)n1] | N-[4-[[4-[[2-(6-methyl-2-pyridyl)pyrimidin-4-yl]amino]pyrimidin-2-yl]amino]phenyl]-1-pyrrolidin-3-yl-piperidine-4-carboxamide | 551.2 |
| 466 | 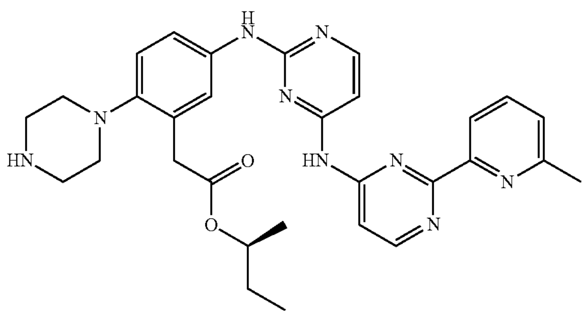 [SMILES: CC[C@H](C)OC(=O)Cc1cc(Nc2nccc(Nc3ccnc(-c4cccc(C)n4)n3)n2)ccc1N1CCNCC1] | [(1S)-1-methylpropyl] 2-[5-[[4-[[2-(6-methyl-2-pyridyl)pyrimidin-4-yl]amino]pyrimidin-2-yl]amino]-2-piperazin-1-yl-phenyl]acetate | 554.4 |
| 467 | 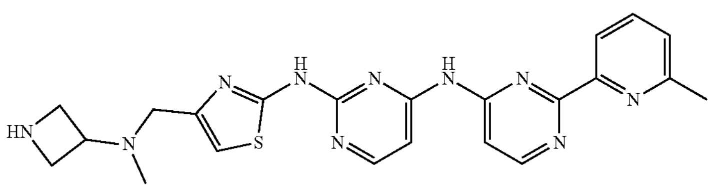 [SMILES: Cc1cccc(-c2nccc(Nc3ccnc(Nc4nc(CN(C)C5CNC5)cs4)n3)n2)n1] | N2-[4-[[azetidin-3-yl(methyl)amino]methyl]thiazol-2-yl]-N4-[2-(6-methyl-2-pyridyl)pyrimidin-4-yl]pyrimidine-2,4-diamine | 461.0 |
| 468 | 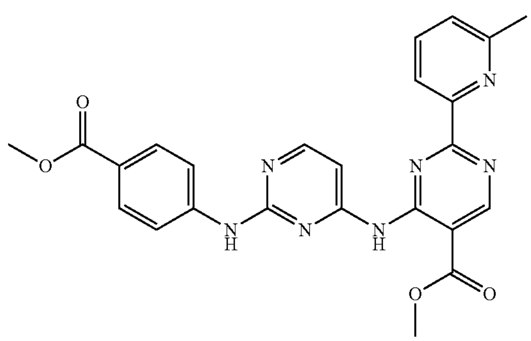 | methyl 4-[[2-(4-methoxycarbonylanilino)pyrimidin-4-yl]amino]-2-(6-methyl-2-pyridyl)pyrimidine-5-carboxylate | 472.0 |
| 469 | 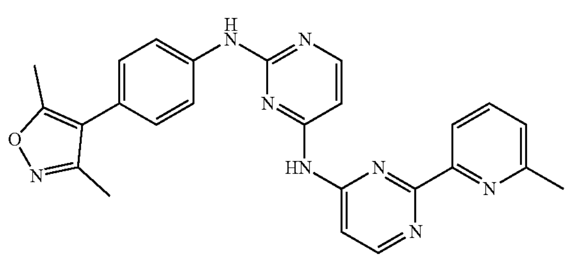 [SMILES: Cc1cccc(-c2nccc(Nc3ccnc(Nc4ccc(-c5c(C)noc5C)cc4)n3)n2)n1] | N2-[4-(3,5-dimethylisoxazol-4-yl)phenyl]-N4-[2-(6-methyl-2-pyridyl)pyrimidin-4-yl]pyrimidine-2,4-diamine | 451.1 |

TABLE 1-continued

| No. | Structure | Chemical Name | [M + H]+ |
|---|---|---|---|
| 470 | 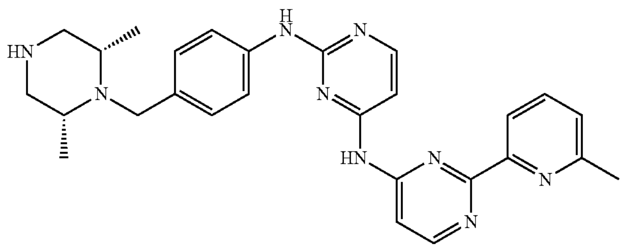 [SMILES: Cc1cccc(-c2nccc(Nc3ccnc(Nc4ccc(CN5[C@H](C)CNC[C@@H]5C)cc4)n3)n2)n1] | N2-[4-[[(2R,6S)-2,6-dimethylpiperazin-1-yl]methyl]phenyl]-N4-[2-(6-methyl-2-pyridyl)pyrimidin-4-yl]pyrimidine-2,4-diamine | 482.2 |
| 471 | 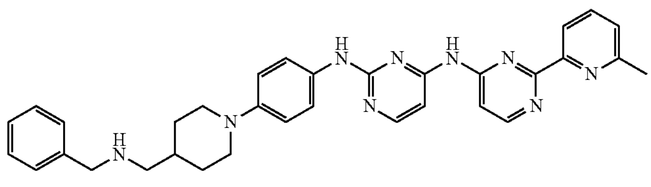 [SMILES: Cc1cccc(-c2nccc(Nc3ccnc(Nc4ccc(N5CCC(CNCc6ccccc6)CC5)cc4)n3)n2)n1] | N2-[4-[4-[(benzylamino)methyl]-1-piperidyl]phenyl]-N4-[2-(6-methyl-2-pyridyl)pyrimidin-4-yl]pyrimidine-2,4-diamine | 558.1 |
| 472 | 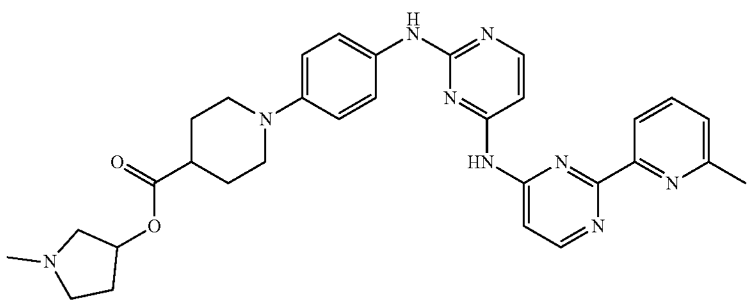 | (1-methylpyrrolidin-3-yl) 1-[4-[[4-[[2-(6-methyl-2-pyridyl)pyrimidin-4-yl]amino]pyrimidin-2-yl]amino]phenyl]piperidine-4-carboxylate | 566.2 |
| 473 | 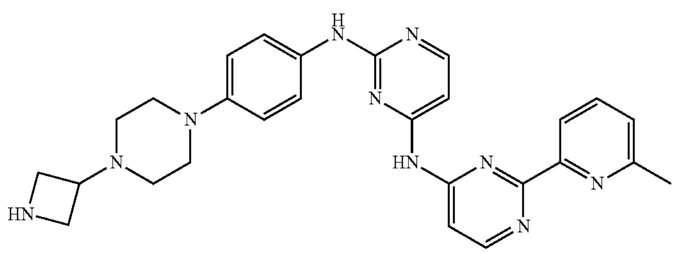 [SMILES: Cc1cccc(-c2nccc(Nc3ccnc(Nc4ccc(N5CCN(C6CNC6)CC5)cc4)n3)n2)n1] | N2-[4-[4-(azetidin-3-yl)piperazin-1-yl]phenyl]-N4-[2-(6-methyl-2-pyridyl)pyrimidin-4-yl]pyrimidine-2,4-diamine | 495.1 |
| 474 | 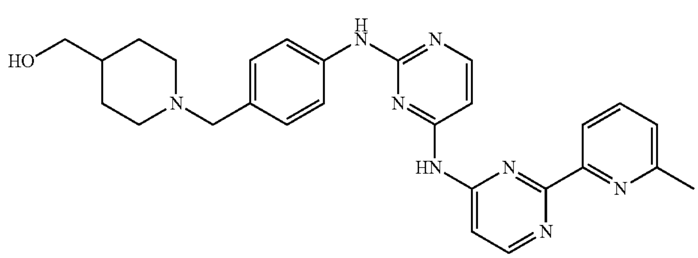 [SMILES: Cc1cccc(-c2nccc(Nc3ccnc(Nc4ccc(CN5CCC(CO)CC5)cc4)n3)n2)n1] | [1-[[4-[[4-[[2-(6-methyl-2-pyridyl)pyrimidin-4-yl]amino]pyrimidin-2-yl]amino]phenyl]methyl]-4-piperidyl]methanol | 483.1 |
| 475 | 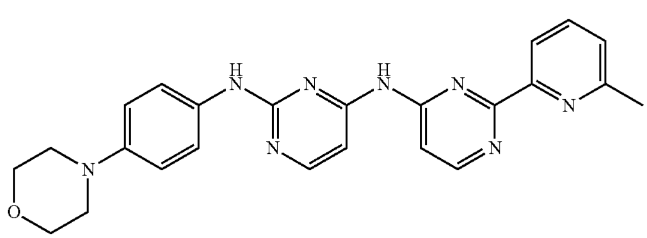 [SMILES: Cc1cccc(-c2nccc(Nc3ccnc(Nc4ccc(N5CCOCC5)cc4)n3)n2)n1] | N4-[2-(6-methyl-2-pyridyl)pyrimidin-4-yl]-N2-(4-morpholinophenyl)pyrimidine-2,4-diamine | 441.4 |

TABLE 1-continued

| No. | Structure | Chemical Name | [M + H]+ |
|---|---|---|---|
| 476 | 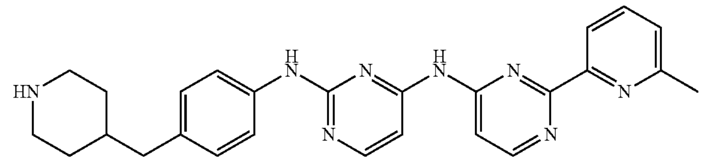 [SMILES: Cc1cccc(-c2nccc(Nc3ccnc(Nc4ccc(CC5CCNCC5)cc4)n3)n2)n1] | N4-[2-(6-methyl-2-pyridyl)pyrimidin-4-yl]-N2-[4-(4-piperidylmethyl)phenyl]pyrimidine-2,4-diamine | 453.2 |
| 477 | 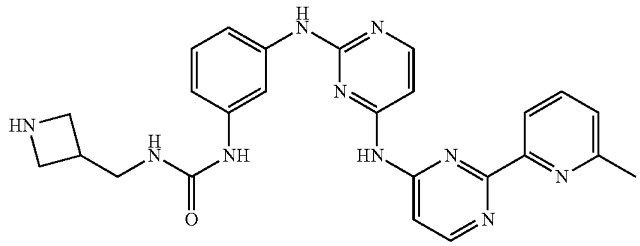 [SMILES: Cc1cccc(-c2nccc(Nc3ccnc(Nc4cccc(NC(=O)NCC5CNC5)c4)n3)n2)n1] | 1-(azetidin-3-ylmethyl)-3-[3-[[4-[[2-(6-methyl-2-pyridyl)pyrimidin-4-yl]amino]pyrimidin-2-yl]amino]phenyl]urea | 483.1 |
| 478 | 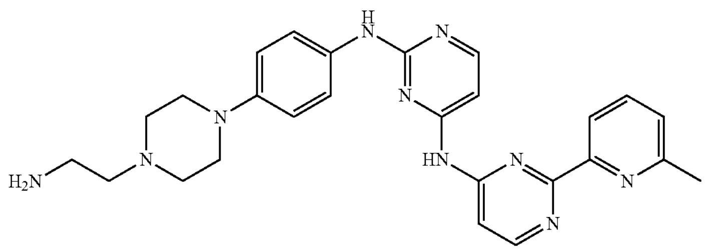 [SMILES: Cc1cccc(-c2nccc(Nc3ccnc(Nc4ccc(N5CCN(CCN)CC5)cc4)n3)n2)n1] | N2-[4-[4-(2-aminoethyl)piperazin-1-yl]phenyl]-N4-[2-(6-methyl-2-pyridyl)pyrimidin-4-yl]pyrimidine-2,4-diamine | 483.3 |
| 479 | 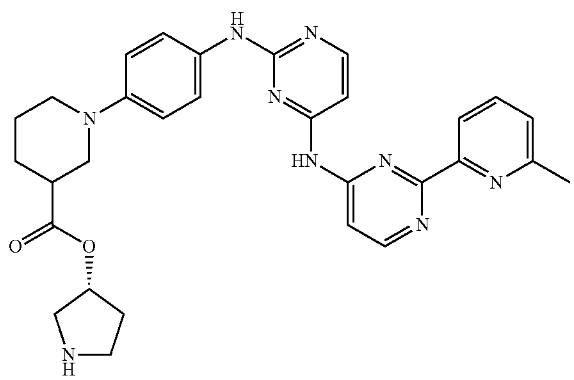 [SMILES: Cc1cccc(-c2nccc(Nc3ccnc(Nc4ccc(N5CCCC(C(=O)O[C@@H]6CCNC6)C5)cc4)n3)n2)n1] | [(3R)-pyrrolidin-3-yl] 1-[4-[[4-[[2-(6-methyl-2-pyridyl)pyrimidin-4-yl]amino]pyrimidin-2-yl]amino]phenyl]piperidine-3-carboxylate | 552.2 |
| 480 | 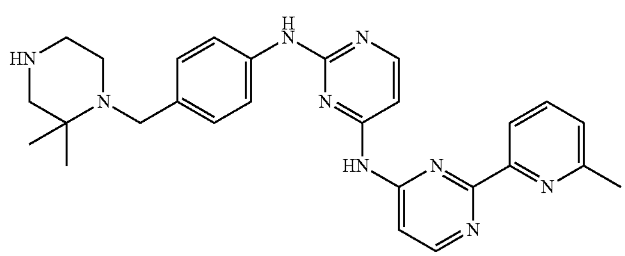 [SMILES: Cc1cccc(-c2nccc(Nc3ccnc(Nc4ccc(CN5CCNCC5(C)C)cc4)n3)n2)n1] | N2-[4-[(2,2-dimethylpiperazin-1-yl)methyl]phenyl]-N4-[2-(6-methyl-2-pyridyl)pyrimidin-4-yl]pyrimidine-2,4-diamine | 482.2 |
| 481 | 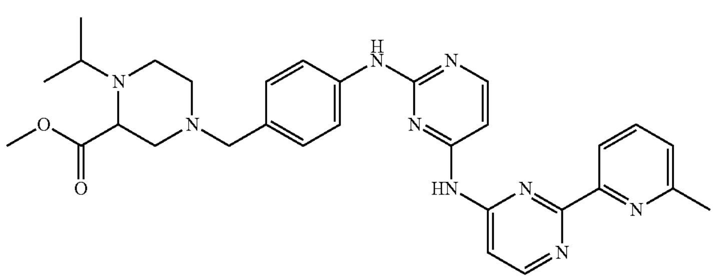 | methyl 1-isopropyl-4-[[4-[[4-[[2-(6-methyl-2-pyridyl)pyrimidin-4-yl]amino]pyrimidin-2-yl]amino]phenyl]methyl]piperazine-2-carboxylate | 554.2 |

TABLE 1-continued

| No. | Structure | Chemical Name | [M + H]+ |
|---|---|---|---|
| 482 | 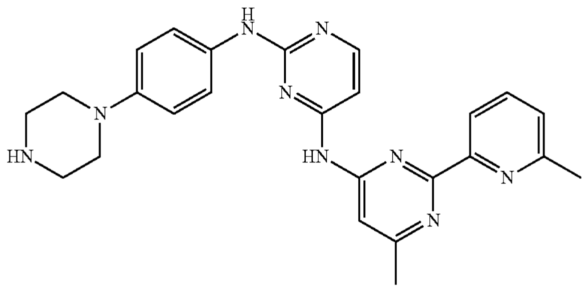 [SMILES: Cc1cccc(-c2nc(C)cc(Nc3ccnc(Nc4ccc(N5CCNCC5)cc4)n3)n2)n1] | N4-[6-methyl-2-(6-methyl-2-pyridyl)pyrimidin-4-yl]-N2-(4-piperazin-1-ylphenyl)pyrimidine-2,4-diamine | 454.2 |
| 483 | 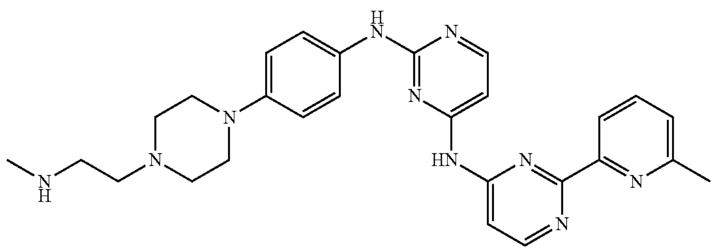 | N2-[4-[4-[2-(methylamino)ethyl]piperazin-1-yl]phenyl]-N4-[2-(6-methyl-2-pyridyl)pyrimidin-4-yl]pyrimidine-2,4-diamine | 497.2 |
| 484 | 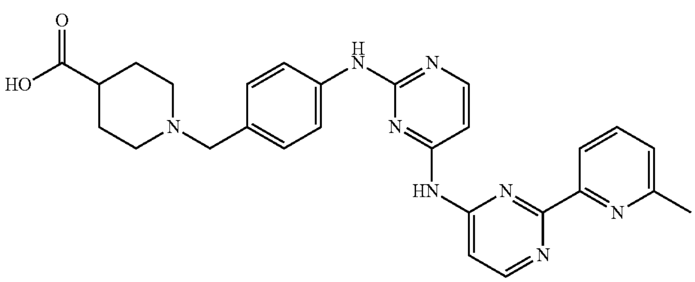 [SMILES: Cc1cccc(-c2nccc(Nc3ccnc(Nc4ccc(CN5CCC(C(=O)O)CC5)cc4)n3)n2)n1] | 1-[[4-[[4-[[2-(6-methyl-2-pyridyl)pyrimidin-4-yl]amino]pyrimidin-2-yl]amino]phenyl]methyl]piperidine-4-carboxylic acid | 497.1 |
| 485 | 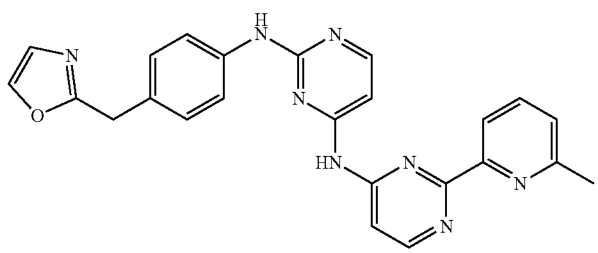 [SMILES: Cc1cccc(-c2nccc(Nc3ccnc(Nc4ccc(Cc5ncco5)cc4)n3)n2)n1] | N4-[2-(6-methyl-2-pyridyl)pyrimidin-4-yl]-N2-[4-(oxazol-2-ylmethyl)phenyl]pyrimidine-2,4-diamine | 437.1 |
| 486 | 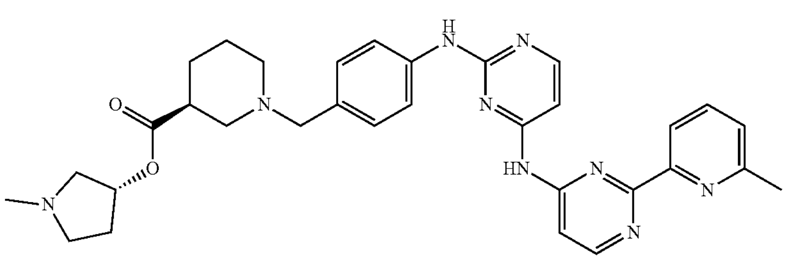 | [(3R)-1-methylpyrrolidin-3-yl] (3S)-1-[[4-[[4-[[2-(6-methyl-2-pyridyl)pyrimidin-4-yl]amino]pyrimidin-2-yl]amino]phenyl]methyl]piperidine-3-carboxylate | 580.3 |

TABLE 1-continued

| No. | Structure | Chemical Name | [M + H]+ |
|---|---|---|---|
| 487 | 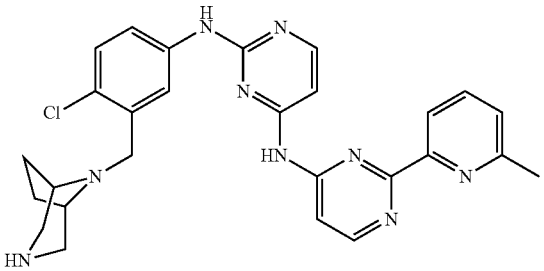 | N2-[4-chloro-3-(3,8-diazabicyclo[3.2.1]octan-8-ylmethyl)phenyl]-N4-[2-(6-methyl-2-pyridyl)pyrimidin-4-yl]pyrimidine-2,4-diamine | 514.0 |
| 488 | 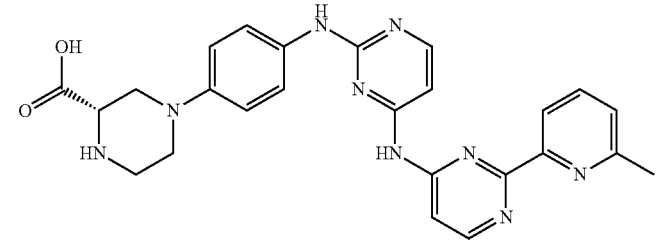 [SMILES: Cc1cccc(-c2nccc(Nc3ccnc(Nc4ccc(N5CCN[C@H](C(=O)O)C5)cc4)n3)n2)n1] | (2S)-4-[4-[[4-[[2-(6-methyl-2-pyridyl)pyrimidin-4-yl]amino]pyrimidin-2-yl]amino]phenyl]piperazine-2-carboxylic acid | 484.1 |
| 489 | 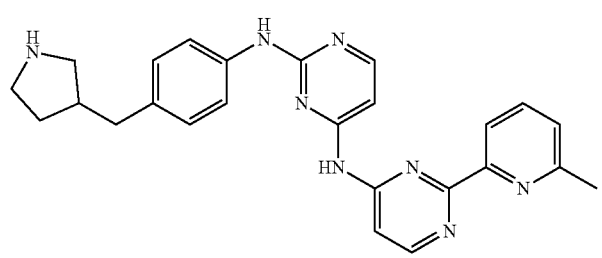 [SMILES: Cc1cccc(-c2nccc(Nc3ccnc(Nc4ccc(CC5CCNC5)cc4)n3)n2)n1] | N4-[2-(6-methyl-2-pyridyl)pyrimidin-4-yl]-N2-[4-(pyrrolidin-3-ylmethyl)phenyl]pyrimidine-2,4-diamine | 439.2 |
| 490 | 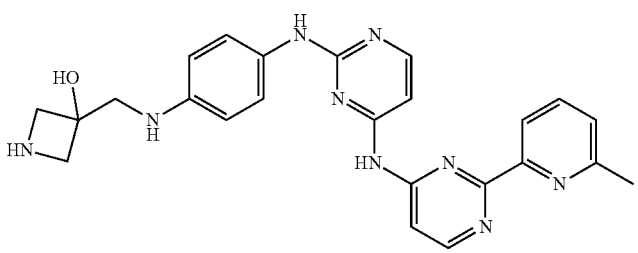 [SMILES: Cc1cccc(-c2nccc(Nc3ccnc(Nc4ccc(NCC5(O)CNC5)cc4)n3)n2)n1] | 3-[[4-[[4-[[2-(6-methyl-2-pyridyl)pyrimidin-4-yl]amino]pyrimidin-2-yl]amino]anilino]methyl]azetidin-3-ol | 456.2 |
| 491 | 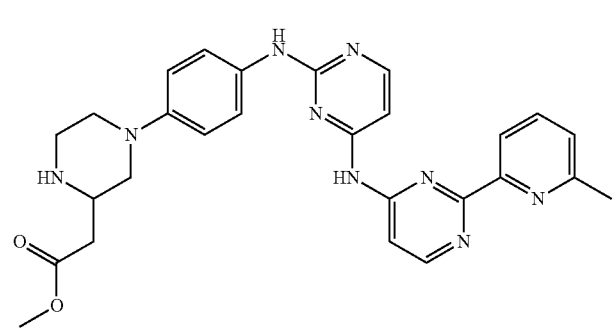 [SMILES: COC(=O)CC1CN(c2ccc(Nc3nccc(Nc4ccnc(-c5cccc(C)n5)n4)n3)cc2)CCN1] | methyl 2-[4-[4-[[4-[[2-(6-methyl-2-pyridyl)pyrimidin-4-yl]amino]pyrimidin-2-yl]amino]phenyl]piperazin-2-yl]acetate | 512.2 |
| 492 | 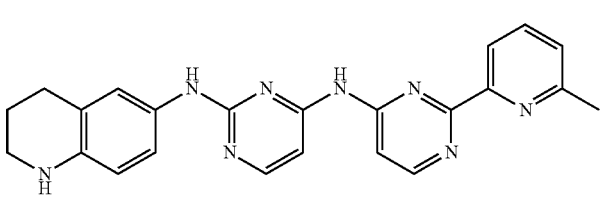 [SMILES: Cc1cccc(-c2nccc(Nc3ccnc(Nc4ccc5c(c4)CCCN5)n3)n2)n1] | N4-[2-(6-methyl-2-pyridyl)pyrimidin-4-yl]-N2-(1,2,3,4-tetrahydroquinolin-6-yl)pyrimidine-2,4-diamine | 411.2 |

TABLE 1-continued

| No. | Structure | Chemical Name | [M + H]+ |
|---|---|---|---|
| 493 | 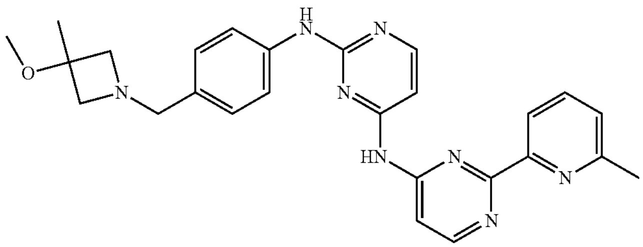 | N2-[4-[(3-methoxy-3-methyl-azetidin-1-yl)methyl]phenyl]-N4-[2-(6-methyl-2-pyridyl)pyrimidin-4-yl]pyrimidine-2,4-diamine | 469.1 |
| 494 | 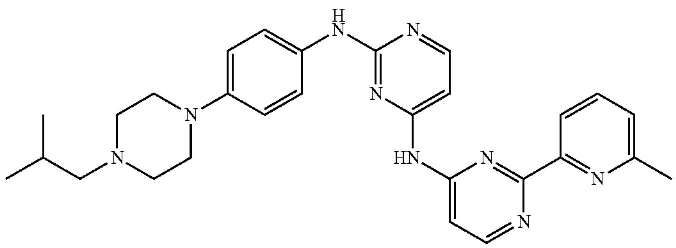 [SMILES: Cc1cccc(-c2nccc(Nc3ccnc(Nc4ccc(N5CCN(CC(C)C)CC5)cc4)n3)n2)n1] | N2-[4-(4-isobutylpiperazin-1-yl)phenyl]-N4-[2-(6-methyl-2-pyridyl)pyrimidin-4-yl]pyrimidine-2,4-diamine | 496.2 |
| 495 | 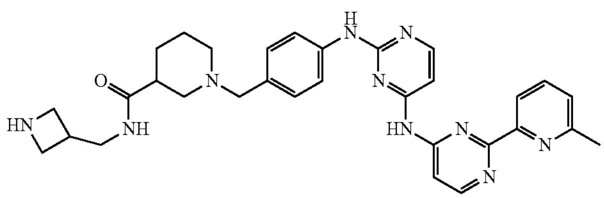 [SMILES: Cc1cccc(-c2nccc(Nc3ccnc(Nc4ccc(CN5CCCC(C(=O)NCC6CNC6)C5)cc4)n3)n2)n1] | N-(azetidin-3-ylmethyl)-1-[[4-[[4-[[2-(6-methyl-2-pyridyl)pyrimidin-4-yl]amino]pyrimidin-2-yl]amino]phenyl]methyl]piperidine-3-carboxamide | 565.3 |
| 496 | 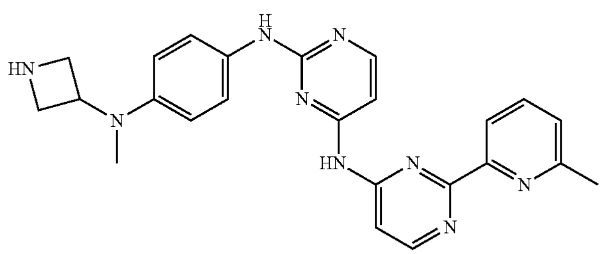 [SMILES: Cc1cccc(-c2nccc(Nc3ccnc(Nc4ccc(N(C)C5CNC5)cc4)n3)n2)n1] | N2-[4-[azetidin-3-yl(methyl)amino]phenyl]-N4-[2-(6-methyl-2-pyridyl)pyrimidin-4-yl]pyrimidine-2,4-diamine | 440.1 |
| 497 | 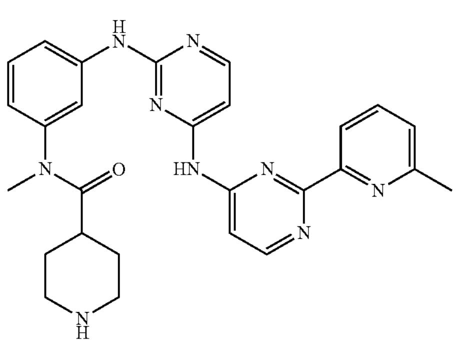 [SMILES: Cc1cccc(-c2nccc(Nc3ccnc(Nc4cccc(N(C)C(=O)C5CCNCC5)c4)n3)n2)n1] | N-methyl-N-[3-[[4-[[2-(6-methyl-2-pyridyl)pyrimidin-4-yl]amino]pyrimidin-2-yl]amino]phenyl]piperidine-4-carboxamide | 496.2 |

TABLE 1-continued

| No. | Structure | Chemical Name | [M + H]+ |
|---|---|---|---|
| 498 | 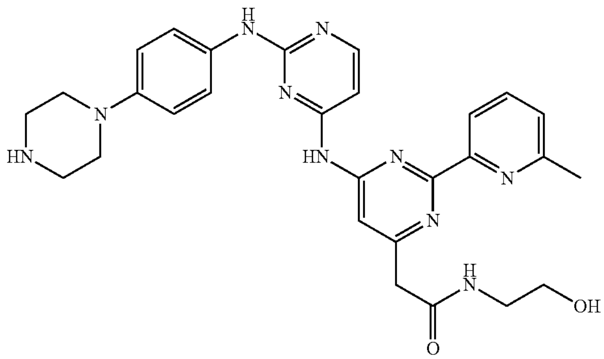 [SMILES: Cc1cccc(-c2nc(CC(=O)NCCO)cc(Nc3ccnc(Nc4ccc(N5CCNCC5)cc4)n3)n2)n1] | N-(2-hydroxyethyl)-2-[2-[2-(6-methyl-2-pyridyl)-6-[[2-(4-piperazin-1-ylanilino)pyrimidin-4-yl]amino]pyrimidin-4-yl]acetamide | 541.1 |
| 499 | 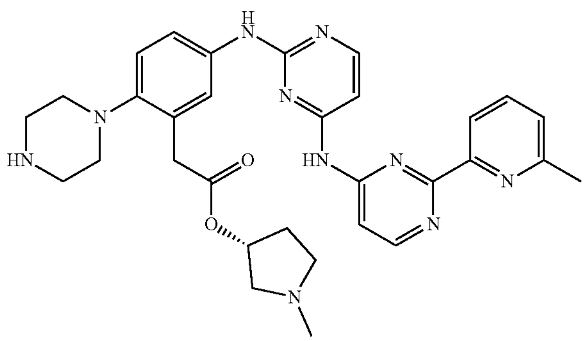 [SMILES: Cc1cccc(-c2nccc(Nc3ccnc(Nc4ccc(N5CCNCC5)c(CC(=O)O[C@@H]5CCN(C)C5)c4)n3)n2)n1] | [(3R)-1-methylpyrrolidin-3-yl] 2-[5-[[4-[[2-(6-methyl-2-pyridyl)pyrimidin-4-yl]amino]pyrimidin-2-yl]amino]-2-piperazin-1-yl-phenyl]acetate | 581.1 |
| 500 | 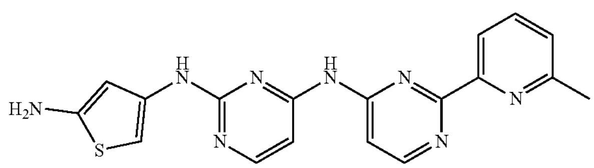 [SMILES: Cc1cccc(-c2nccc(Nc3ccnc(Nc4csc(N)c4)n3)n2)n1] | N2-(5-amino-3-thienyl)-N4-[2-(6-methyl-2-pyridyl)pyrimidin-4-yl]pyrimidine-2,4-diamine | 377.1 |
| 501 | 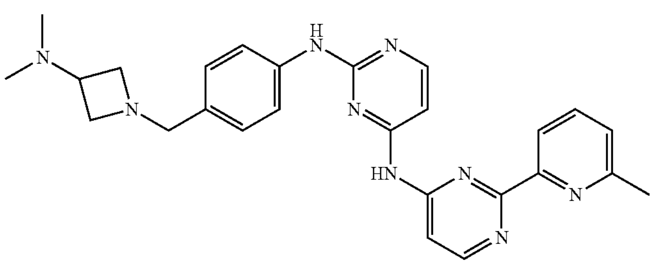 | N2-[4-[[3-(dimethylamino)azetidin-1-yl]methyl]phenyl]-N4-[2-(6-methyl-2-pyridyl)pyrimidin-4-yl]pyrimidine-2,4-diamine | 468.3 |
| 502 | 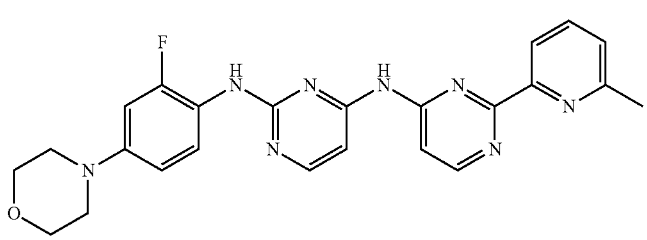 [SMILES: Cc1cccc(-c2nccc(Nc3ccnc(Nc4ccc(N5CCOCC5)cc4F)n3)n2)n1] | N2-(2-fluoro-4-morpholino-phenyl)-N4-[2-(6-methyl-2-pyridyl)pyrimidin-4-yl]pyrimidine-2,4-diamine | 459.1 |

TABLE 1-continued

| No. | Structure | Chemical Name | [M + H]+ |
|---|---|---|---|
| 503 | 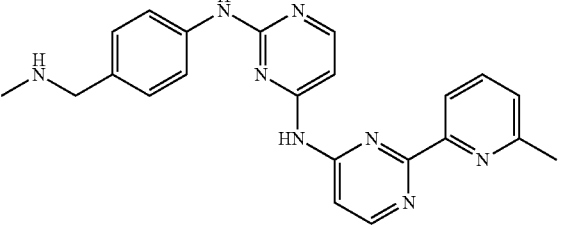 | N2-[4-(methylaminomethyl)phenyl]-N4-[2-(6-methyl-2-pyridyl)pyrimidin-4-yl]pyrimidine-2,4-diamine | 399.2 |
| 504 | 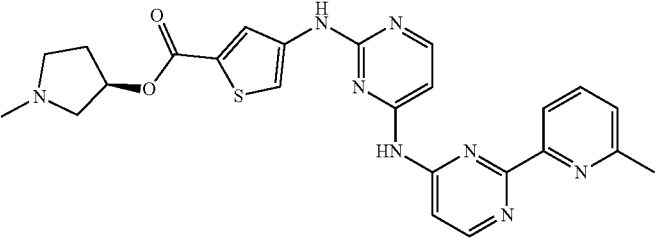 | [(3R)-1-methylpyrrolidin-3-yl] 4-[[4-[[2-(6-methyl-2-pyridyl)pyrimidin-4-yl]amino]pyrimidin-2-yl]amino]thiophene-2-carboxylate | 489.0 |
| 505 | 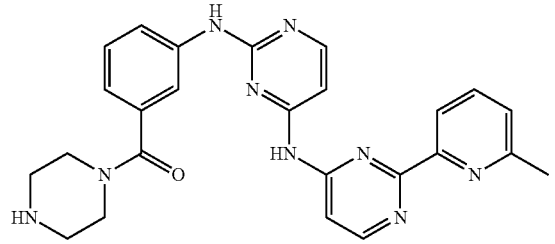 [SMILES: Cc1cccc(-c2nccc(Nc3ccnc(Nc4cccc(C(=O)N5CCNCC5)c4)n3)n2)n1] | [3-[[4-[[2-(6-methyl-2-pyridyl)pyrimidin-4-yl]amino]pyrimidin-2-yl]amino]phenyl]-piperazin-1-yl-methanone | 468.1 |
| 506 | 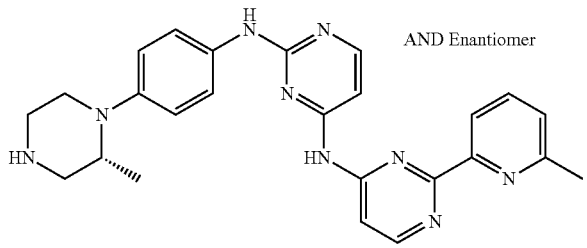 [SMILES: Cc1cccc(-c2nccc(Nc3ccnc(Nc4ccc(N5CCNC[C@H]5C)cc4)n3)n2)n1] AND Enantiomer | N4-[2-(6-methyl-2-pyridyl)pyrimidin-4-yl]-N2-[4-[rac-(2R)-2-methylpiperazin-1-yl]phenyl]pyrimidine-2,4-diamine | 454.1 |
| 507 | 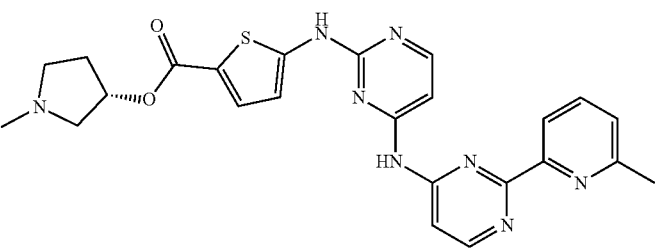 | [(3S)-1-methylpyrrolidin-3-yl] 5-[[4-[[2-(6-methyl-2-pyridyl)pyrimidin-4-yl]amino]pyrimidin-2-yl]amino]thiophene-2-carboxylate | 489.1 |
| 508 | 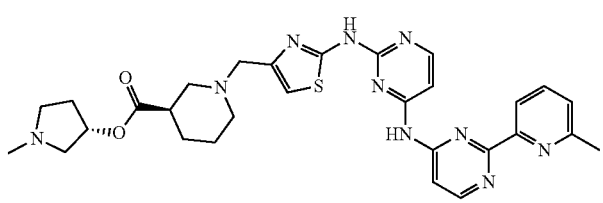 | [(3S)-1-methylpyrrolidin-3-yl] (3R)-1-[[2-[[4-[[2-(6-methyl-2-pyridyl)pyrimidin-4-yl]amino]pyrimidin-2-yl]amino]thiazol-4-yl]methyl]piperidine-3-carboxylate | 587.1 |

TABLE 1-continued

| No. | Structure | Chemical Name | [M + H]+ |
|---|---|---|---|
| 509 | 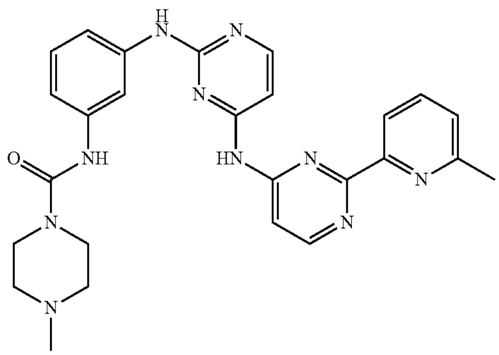 [SMILES: Cc1cccc(-c2nccc(Nc3ccnc(Nc4cccc(NC(=O)N5CCN(C)CC5)c4)n3)n2)n1] | 4-methyl-N-[3-[[4-[[2-(6-methyl-2-pyridyl)pyrimidin-4-yl]amino]pyrimidin-2-yl]amino]phenyl]piperazine-1-carboxamide | 497.1 |
| 510 | 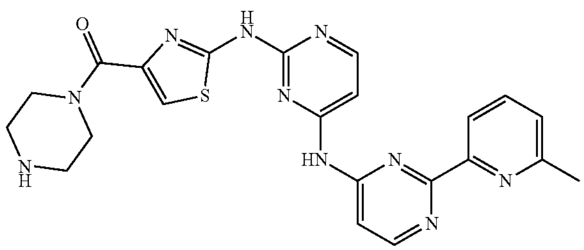 [SMILES: Cc1cccc(-c2nccc(Nc3ccnc(Nc4nc(C(=O)N5CCNCC5)cs4)n3)n2)n1] | [2-[[4-[[2-(6-methyl-2-pyridyl)pyrimidin-4-yl]amino]pyrimidin-2-yl]amino]thiazol-4-yl]-piperazin-1-yl-methanone | 475.0 |
| 511 | 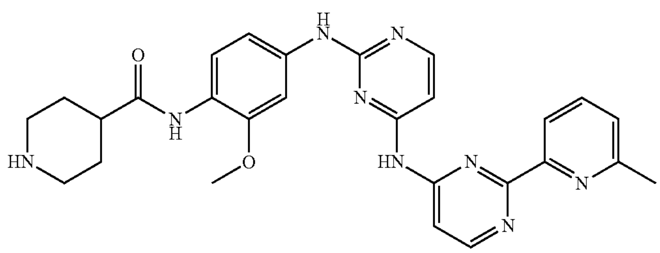 [SMILES: COc1cc(Nc2nccc(Nc3ccnc(-c4cccc(C)n4)n3)n2)ccc1NC(=O)C1CCNCC1] | N-[2-methoxy-4-[[4-[[2-(6-methyl-2-pyridyl)pyrimidin-4-yl]amino]pyrimidin-2-yl]amino]phenyl]piperidine-4-carboxamide | 512.2 |
| 512 | 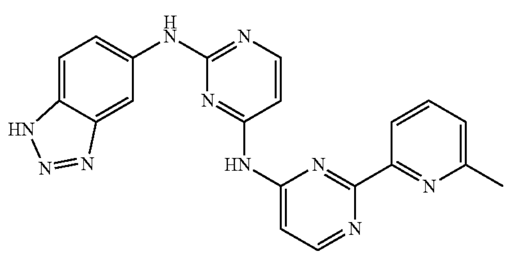 [SMILES: Cc1cccc(-c2nccc(Nc3ccnc(Nc4ccc5[nH]nnc5c4)n3)n2)n1] | N2-(1H-benzotriazol-5-yl)-N4-[2-(6-methyl-2-pyridyl)pyrimidin-4-yl]pyrimidine-2,4-diamine | 397.1 |
| 513 | 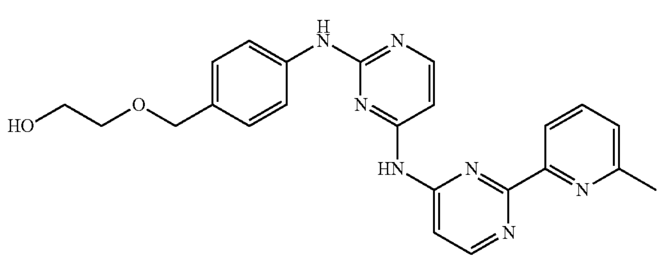 [SMILES: Cc1cccc(-c2nccc(Nc3ccnc(Nc4ccc(COCCO)cc4)n3)n2)n1] | 2-[[4-[[4-[[2-(6-methyl-2-pyridyl)pyrimidin-4-yl]amino]pyrimidin-2-yl]amino]phenyl]methoxy]ethanol | 430.2 |

TABLE 1-continued

| No. | Structure | Chemical Name | [M + H]+ |
|---|---|---|---|
| 514 | 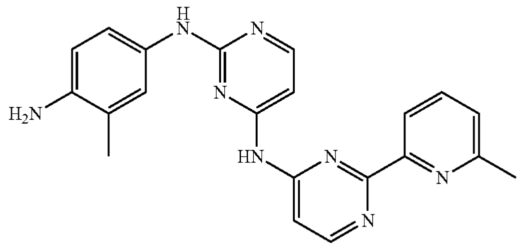 [SMILES: Cc1cccc(-c2nccc(Nc3ccnc(Nc4ccc(N)c(C)c4)n3)n2)n1] | N2-(4-amino-3-methyl-phenyl)-N4-[2-(6-methyl-2-pyridyl)pyrimidin-4-yl]pyrimidine-2,4-diamine | 385.1 |
| 515 | 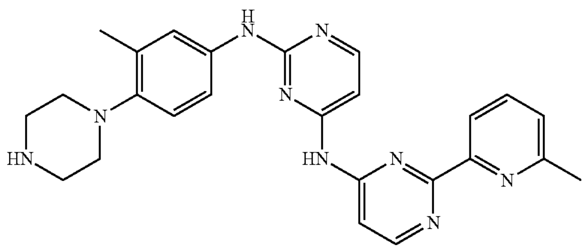 [SMILES: Cc1cccc(-c2nccc(Nc3ccnc(Nc4ccc(N5CCNCC5)c(C)c4)n3)n2)n1] | N2-(3-methyl-4-piperazin-1-yl-phenyl)-N4-[2-(6-methyl-2-pyridyl)pyrimidin-4-yl]pyrimidine-2,4-diamine | 454.1 |
| 516 | 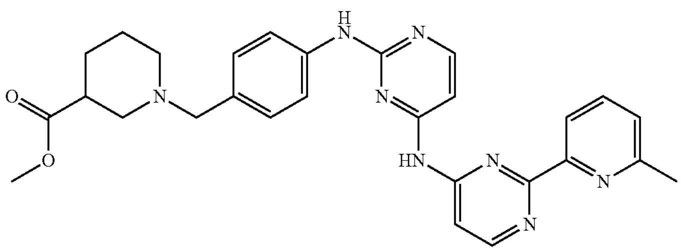 [SMILES: COC(=O)C1CCCN(Cc2ccc(Nc3nccc(Nc4ccnc(-c5cccc(C)n5)n4)n3)cc2)C1] | methyl 1-[[4-[[4-[[2-(6-methyl-2-pyridyl)pyrimidin-4-yl]amino]pyrimidin-2-yl]amino]phenyl]methyl]piperidine-3-carboxylate | 511.1 |
| 517 | 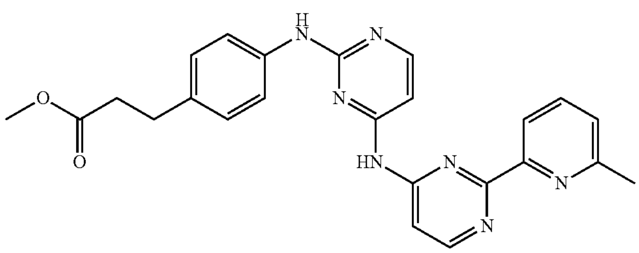 | methyl 3-[4-[[4-[[2-(6-methyl-2-pyridyl)pyrimidin-4-yl]amino]pyrimidin-2-yl]amino]phenyl]propanoate | 442.1 |
| 518 | 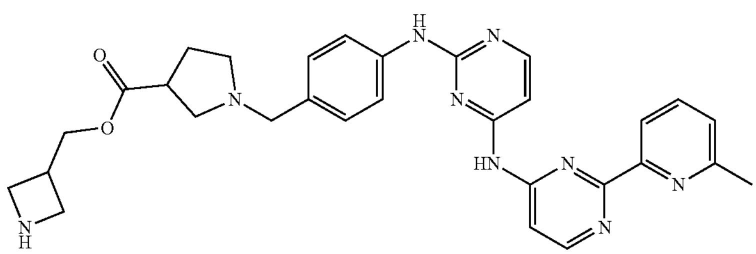 [SMILES: Cc1cccc(-c2nccc(Nc3ccnc(Nc4ccc(CN5CCC(C(=O)OCC6CNC6)C5)cc4)n3)n2)n1] | azetidin-3-ylmethyl 1-[[4-[[4-[[2-(6-methyl-2-pyridyl)pyrimidin-4-yl]amino]pyrimidin-2-yl]amino]phenyl]methyl]pyrrolidine-3-carboxylate | 552.1 |
| 519 | 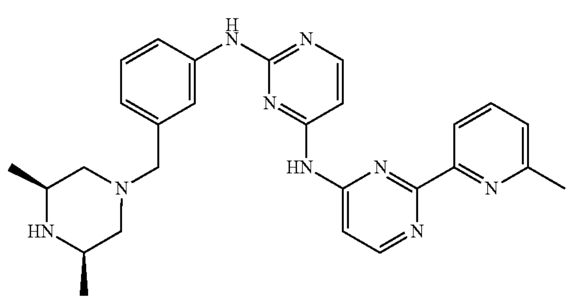 | N4-[2-(6-methyl-2-pyridyl)pyrimidin-4-yl]-N2-[3-[[rac-(3R,5S)-3,5-dimethylpiperazin-1-yl]methyl]phenyl]pyrimidine-2,4-diamine | 482.1 |

TABLE 1-continued

| No. | Structure | Chemical Name | [M + H]+ |
|---|---|---|---|
| 520 | 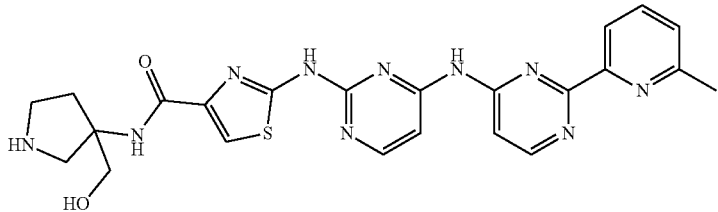 [SMILES: Cc1cccc(-c2nccc(Nc3ccnc(Nc4nc(C(=O)NC5(CO)CCNC5)cs4)n3)n2)n1] | N-[3-(hydroxymethyl)pyrrolidin-3-yl]-2-[[4-[[2-(6-methyl-2-pyridyl)pyrimidin-4-yl]amino]pyrimidin-2-yl]amino]thiazole-4-carboxamide | 505.1 |
| 521 | 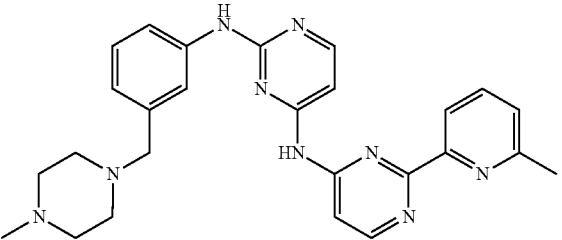 | N2-[3-[(4-methylpiperazin-1-yl)methyl]phenyl]-N4-[2-(6-methyl-2-pyridyl)pyrimidin-4-yl]pyrimidine-2,4-diamine | 468.2 |
| 522 | 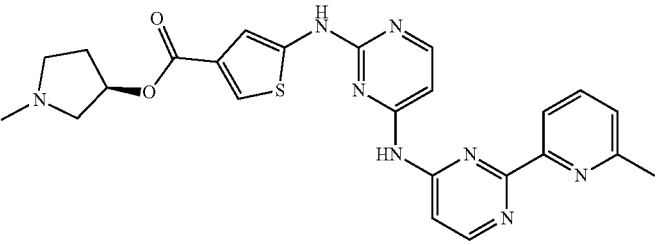 | [(3R)-1-methylpyrrolidin-3-yl] 5-[[4-[[2-(6-methyl-2-pyridyl)pyrimidin-4-yl]amino]pyrimidin-2-yl]amino]thiophene-3-carboxylate | 489.2 |
| 523 | 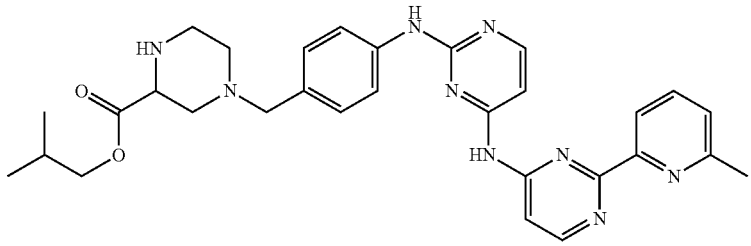 [SMILES: Cc1cccc(-c2nccc(Nc3ccnc(Nc4ccc(CN5CCNC(C(=O)OCC(C)C)C5)cc4)n3)n2)n1] | isobutyl 4-[[4-[[4-[[2-(6-methyl-2-pyridyl)pyrimidin-4-yl]amino]pyrimidin-2-yl]amino]phenyl]methyl]piperazine-2-carboxylate | 554.2 |
| 524 | 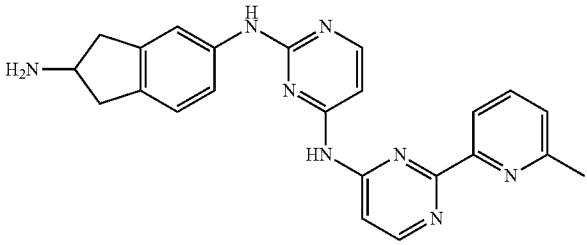 [SMILES: Cc1cccc(-c2nccc(Nc3ccnc(Nc4ccc5c(c4)CC(N)C5)n3)n2)n1] | N2-(2-aminoindan-5-yl)-N4-[2-(6-methyl-2-pyridyl)pyrimidin-4-yl]pyrimidine-2,4-diamine | 411.1 |
| 525 | 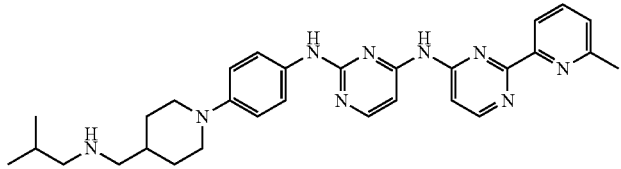 [SMILES: Cc1cccc(-c2nccc(Nc3ccnc(Nc4ccc(N5CCC(CNCC(C)C)CC5)cc4)n3)n2)n1] | N2-[4-[4-[(isobutylamino)methyl]-1-piperidyl]phenyl]-N4-[2-(6-methyl-2-pyridyl)pyrimidin-4-yl]pyrimidine-2,4-diamine | 524.1 |

| No. | Structure | Chemical Name | [M + H]+ |
|---|---|---|---|
| 526 | 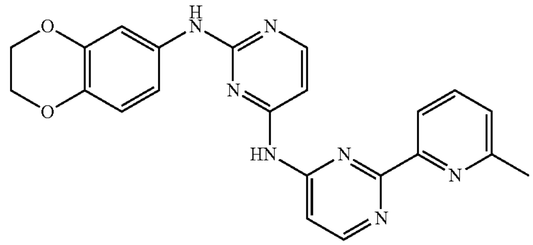 [SMILES: Cc1cccc(-c2nccc(Nc3ccnc(Nc4ccc5c(c4)OCCO5)n3)n2)n1] | N2-(2,3-dihydro-1,4-benzodioxin-6-yl)-N4-[2-(6-methyl-2-pyridyl)pyrimidin-4-yl]pyrimidine-2,4-diamine | 414.1 |
| 527 | 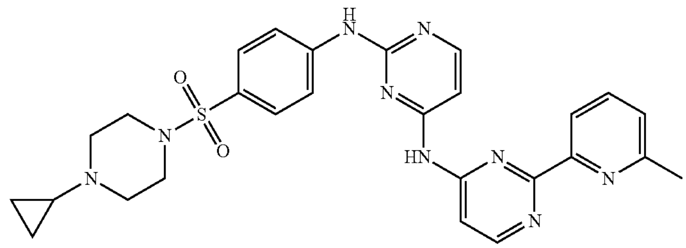 [SMILES: Cc1cccc(-c2nccc(Nc3ccnc(Nc4ccc(S(=O)(=O)N5CCN(C6CC6)CC5)cc4)n3)n2)n1] | N2-[4-(4-cyclopropylpiperazin-1-yl)sulfonylphenyl]-N4-[2-(6-methyl-2-pyridyl)pyrimidin-4-yl]pyrimidine-2,4-diamine | 544.0 |
| 528 | AND Enantiomer | N4-[2-(6-methyl-2-pyridyl)pyrimidin-4-yl]-N2-[4-[rac-(3S)-3-methylpiperazin-1-yl]phenyl]pyrimidine-2,4-diamine | 454.1 |
| 529 | 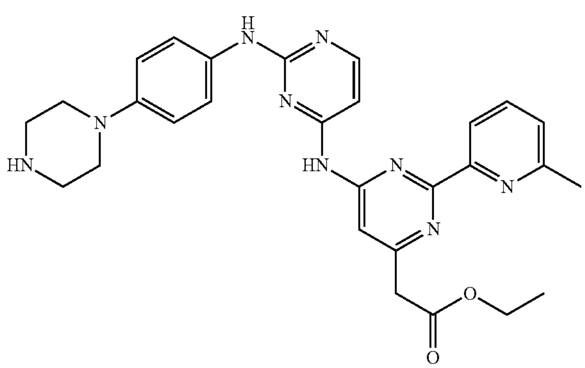 [SMILES: CCOC(=O)Cc1cc(Nc2ccnc(Nc3ccc(N4CCNCC4)cc3)n2)nc(-c2cccc(C)n2)n1] | ethyl 2-[2-(6-methyl-2-pyridyl)-6-[[2-(4-piperazin-1-ylanilino)pyrimidin-4-yl]amino]pyrimidin-4-yl]acetate | 526.1 |
| 530 | 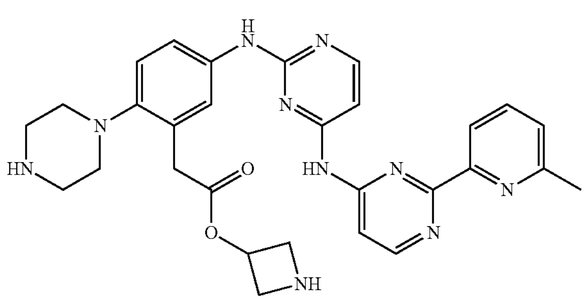 [SMILES: Cc1cccc(-c2nccc(Nc3ccnc(Nc4ccc(N5CCNCC5)c(CC(=O)OC5CNC5)c4)n3)n2)n1] | azetidin-3-yl 2-[5-[[4-[[2-(6-methyl-2-pyridyl)pyrimidin-4-yl]amino]pyrimidin-2-yl]amino]-2-piperazin-1-yl-phenyl]acetate | 553.1 |

TABLE 1-continued

| No. | Structure | Chemical Name | [M + H]+ |
|---|---|---|---|
| 531 | 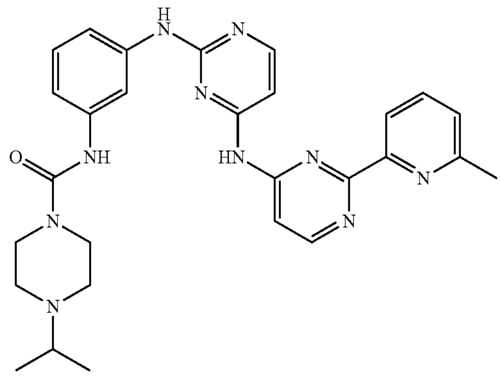 [SMILES: Cc1cccc(-c2nccc(Nc3ccnc(Nc4cccc(NC(=O)N5CCN(C(C)C)CC5)c4)n3)n2)n1] | 4-isopropyl-N-[3-[[4-[[2-(6-methyl-2-pyridyl)pyrimidin-4-yl]amino]pyrimidin-2-yl]amino]phenyl]piperazine-1-carboxamide | 525.2 |
| 532 | 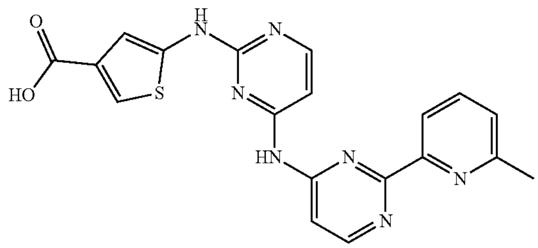 [SMILES: Cc1cccc(-c2nccc(Nc3ccnc(Nc4cc(C(=O)O)cs4)n3)n2)n1] | 5-[[4-[[2-(6-methyl-2-pyridyl)pyrimidin-4-yl]amino]pyrimidin-2-yl]amino]thiophene-3-carboxylic acid | 406.2 |
| 533 | 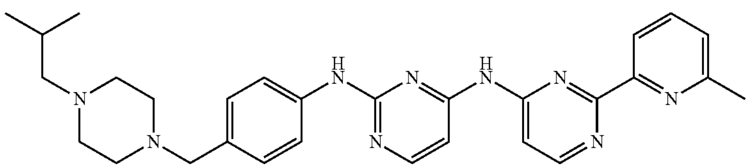 [SMILES: Cc1cccc(-c2nccc(Nc3ccnc(Nc4ccc(CN5CCN(CC(C)C)CC5)cc4)n3)n2)n1] | N2-[4-[(4-isobutylpiperazin-1-yl)methyl]phenyl]-N4-[2-(6-methyl-2-pyridyl)pyrimidin-4-yl]pyrimidine-2,4-diamine | 510.3 |
| 534 | 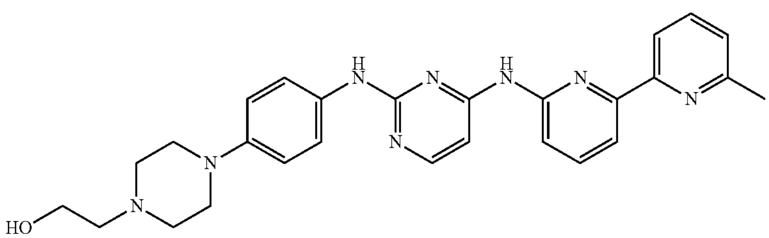 [SMILES: Cc1cccc(-c2cccc(Nc3ccnc(Nc4ccc(N5CCN(CCO)CC5)cc4)n3)n2)n1] | 2-[4-[4-[[4-[[2-(6-methyl-2-pyridyl)pyrimidin-4-yl]amino]pyrimidin-2-yl]amino]phenyl]piperazin-1-yl]ethanol | 484.3 |
| 535 | 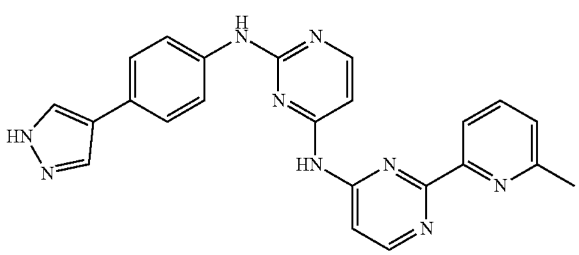 [SMILES: Cc1cccc(-c2nccc(Nc3ccnc(Nc4ccc(-c5cn[nH]c5)cc4)n3)n2)n1] | N4-[2-(6-methyl-2-pyridyl)pyrimidin-4-yl]-N2-[4-(1H-pyrazol-4-yl)phenyl]pyrimidine-2,4-diamine | 422.0 |
| 536 | 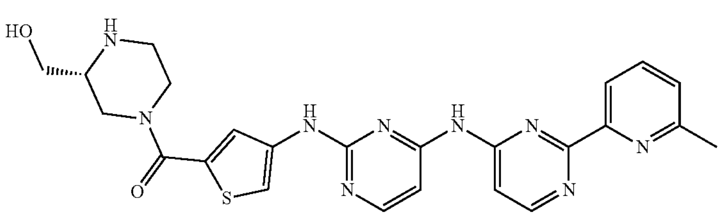 [SMILES: Cc1cccc(-c2nccc(Nc3ccnc(Nc4csc(C(=O)N5CCN[C@@H](CO)C5)c4)n3)n2)n1] | [(3R)-3-(hydroxymethyl)piperazin-1-yl]-[4-[[4-[[2-(6-methyl-2-pyridyl)pyrimidin-4-yl]amino]pyrimidin-2-yl]amino]-2-thienyl]methanone | 504.1 |

TABLE 1-continued

| No. | Structure | Chemical Name | [M + H]+ |
|---|---|---|---|
| 537 | 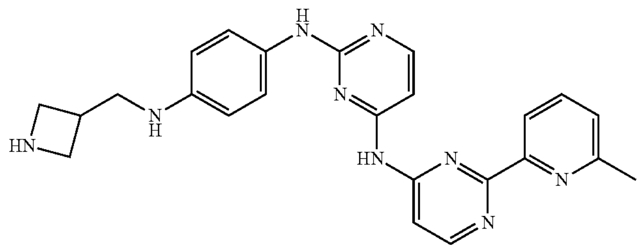 | N2-[4-(azetidin-3-ylmethylamino)phenyl]-N4-[2-(6-methyl-2-pyridyl)pyrimidin-4-yl]pyrimidine-2,4-diamine | 440.2 |
| 538 | 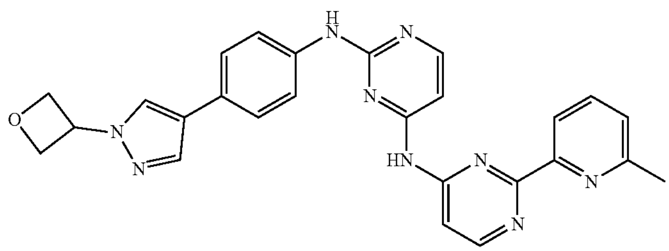 [SMILES: Cc1cccc(-c2nccc(Nc3ccnc(Nc4ccc(-c5cnn(C6COC6)c5)cc4)n3)n2)n1] | N4-[2-(6-methyl-2-pyridyl)pyrimidin-4-yl]-N2-[4-[1-(oxetan-3-yl)pyrazol-4-yl]phenyl]pyrimidine-2,4-diamine | 478.1 |
| 539 | 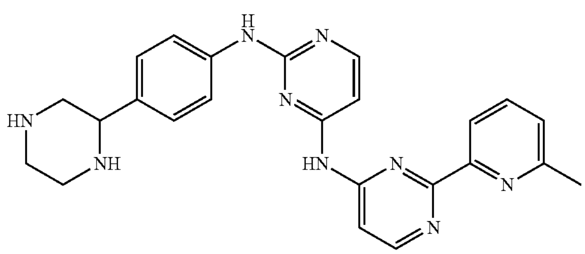 [SMILES: Cc1cccc(-c2nccc(Nc3ccnc(Nc4ccc(C5CNCCN5)cc4)n3)n2)n1] | N4-[2-(6-methyl-2-pyridyl)pyrimidin-4-yl]-N2-(4-piperazin-2-ylphenyl)pyrimidine-2,4-diamine | 440.1 |
| 540 | 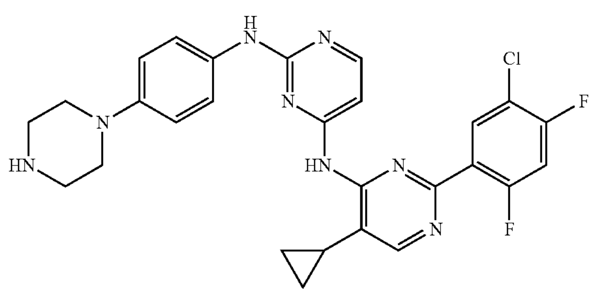 [SMILES: Fc1cc(F)c(-c2ncc(C3CC3)c(Nc3ccnc(Nc4ccc(N5CCNCC5)cc4)n3)n2)cc1Cl] | N4-[2-(5-chloro-2,4-difluoro-phenyl)-5-cyclopropyl-pyrimidin-4-yl]-N2-(4-piperazin-1-ylphenyl)pyrimidine-2,4-diamine | 535.1 |
| 541 | 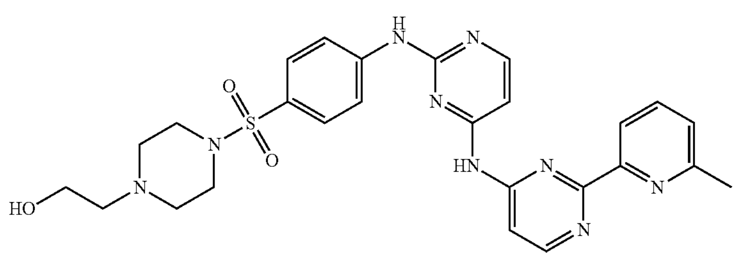 [SMILES: Cc1cccc(-c2nccc(Nc3ccnc(Nc4ccc(S(=O)(=O)N5CCN(CCO)CC5)cc4)n3)n2)n1] | 2-[4-[4-[[4-[[2-(6-methyl-2-pyridyl)pyrimidin-4-yl]amino]pyrimidin-2-yl]amino]phenyl]sulfonylpiperazin-1-yl]ethanol | 458.0 |
| 542 | 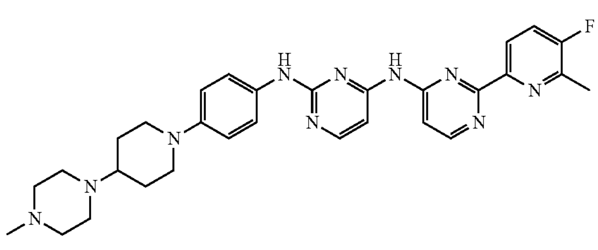 [SMILES: Cc1nc(-c2nccc(Nc3ccnc(Nc4ccc(N5CCC(N6CCN(C)CC6)CC5)cc4)n3)n2)ccc1F] | N4-[2-(5-fluoro-6-methyl-2-pyridyl)pyrimidin-4-yl]-N2-[4-[4-(4-methylpiperazin-1-yl)-1-piperidyl]phenyl]pyrimidine-2,4-diamine | 555.3 |

TABLE 1-continued

| No. | Structure | Chemical Name | [M + H]+ |
|---|---|---|---|
| 543 | 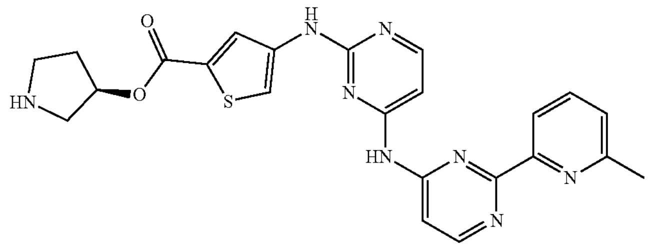 [SMILES: Cc1cccc(-c2nccc(Nc3ccnc(Nc4csc(C(=O)O[C@@H]5CCNC5)c4)n3)n2)n1] | [(3R)-pyrrolidin-3-yl] 4-[[4-[[2-(6-methyl-2-pyridyl)pyrimidin-4-yl]amino]pyrimidin-2-yl]amino]thiophene-2-carboxylate | 475.2 |
| 544 | 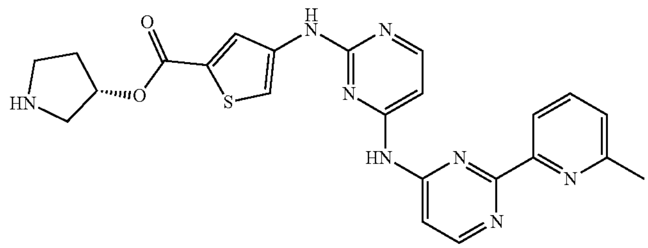 [SMILES: Cc1cccc(-c2nccc(Nc3ccnc(Nc4csc(C(=O)O[C@H]5CCNC5)c4)n3)n2)n1] | [(3S)-pyrrolidin-3-yl] 4-[[4-[[2-(6-methyl-2-pyridyl)pyrimidin-4-yl]amino]pyrimidin-2-yl]amino]thiophene-2-carboxylate | 475.1 |
| 545 | 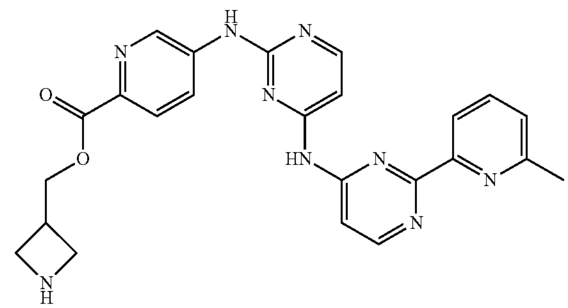 [SMILES: Cc1cccc(-c2nccc(Nc3ccnc(Nc4ccc(C(=O)OCC5CNC5)nc4)n3)n2)n1] | azetidin-3-ylmethyl 5-[[4-[[2-(6-methyl-2-pyridyl)pyrimidin-4-yl]amino]pyrimidin-2-yl]amino]pyridine-2-carboxylate | 470.1 |
| 546 | 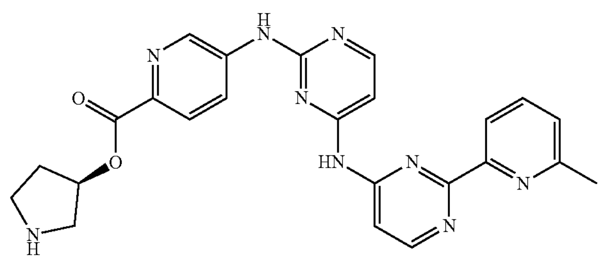 [SMILES: Cc1cccc(-c2nccc(Nc3ccnc(Nc4ccc(C(=O)O[C@@H]5CCNC5)nc4)n3)n2)n1] | [(3R)-pyrrolidin-3-yl] 5-[[4-[[2-(6-methyl-2-pyridyl)pyrimidin-4-yl]amino]pyrimidin-2-yl]amino]pyridine-2-carboxylate | 470.1 |
| 547 | 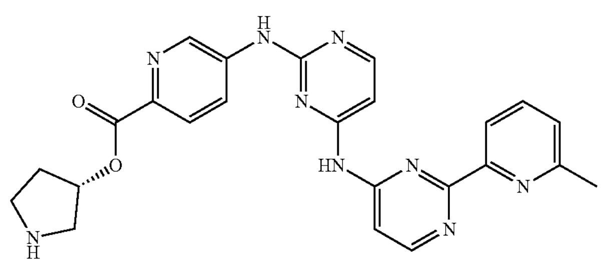 [SMILES: Cc1cccc(-c2nccc(Nc3ccnc(Nc4ccc(C(=O)O[C@H]5CCNC5)nc4)n3)n2)n1] | [(3S)-pyrrolidin-3-yl] 5-[[4-[[2-(6-methyl-2-pyridyl)pyrimidin-4-yl]amino]pyrimidin-2-yl]amino]pyridine-2-carboxylate | 470.1 |

TABLE 1-continued

| No. | Structure | Chemical Name | [M + H]+ |
|---|---|---|---|
| 548 | 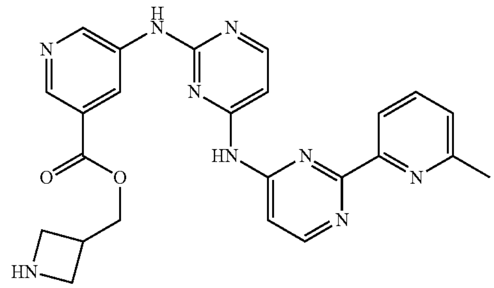 [SMILES: Cc1cccc(-c2nccc(Nc3ccnc(Nc4cncc(C(=O)OCC5CNC5)c4)n3)n2)n1] | azetidin-3-ylmethyl 5-[[4-[[2-(6-methyl-2-pyridyl)pyrimidin-4-yl]amino]pyrimidin-2-yl]amino]pyridine-3-carboxylate | 470.1 |
| 549 | 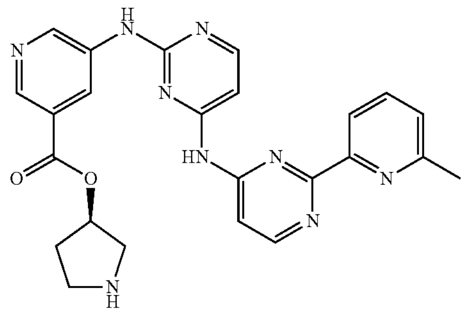 [SMILES: Cc1cccc(-c2nccc(Nc3ccnc(Nc4cncc(C(=O)O[C@@H]5CCNC5)c4)n3)n2)n1] | [(3R)-pyrrolidin-3-yl] 5-[[4-[[2-(6-methyl-2-pyridyl)pyrimidin-4-yl]amino]pyrimidin-2-yl]amino]pyridine-3-carboxylate | 470.1 |
| 550 | 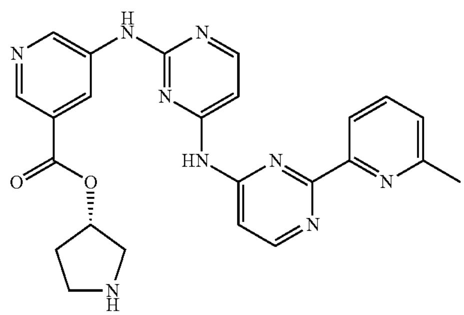 [SMILES: Cc1cccc(-c2nccc(Nc3ccnc(Nc4cncc(C(=O)O[C@H]5CCNC5)c4)n3)n2)n1] | [(3S)-pyrrolidin-3-yl] 5-[[4-[[2-(6-methyl-2-pyridyl)pyrimidin-4-yl]amino]pyrimidin-2-yl]amino]pyridine-3-carboxylate | 470.2 |
| 551 | 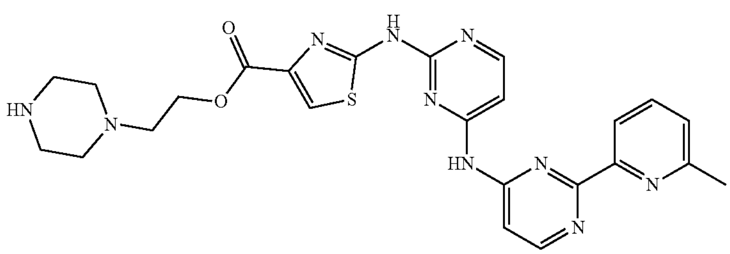 [SMILES: Cc1cccc(-c2nccc(Nc3ccnc(Nc4nc(C(=O)OCCN5CCNCC5)cs4)n3)n2)n1] | 2-piperazin-1-ylethyl 2-[[4-[[2-(6-methyl-2-pyridyl)pyrimidin-4-yl]amino]pyrimidin-2-yl]amino]thiazole-4-carboxylate | 519.2 |
| 552 | 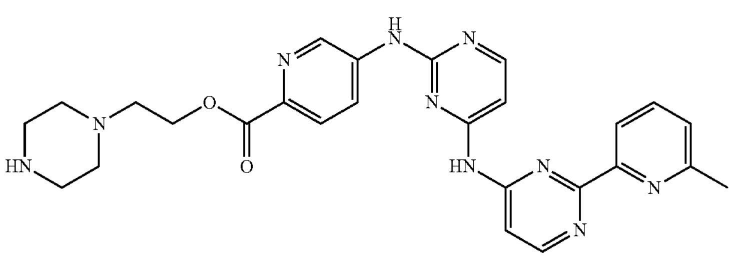 [SMILES: Cc1cccc(-c2nccc(Nc3ccnc(Nc4ccc(C(=O)OCCN5CCNCC5)nc4)n3)n2)n1] | 2-piperazin-1-ylethyl 5-[[4-[[2-(6-methyl-2-pyridyl)pyrimidin-4-yl]amino]pyrimidin-2-yl]amino]pyridine-2-carboxylate | 513.2 |

TABLE 1-continued

| No. | Structure | Chemical Name | [M + H]+ |
|---|---|---|---|
| 553 | 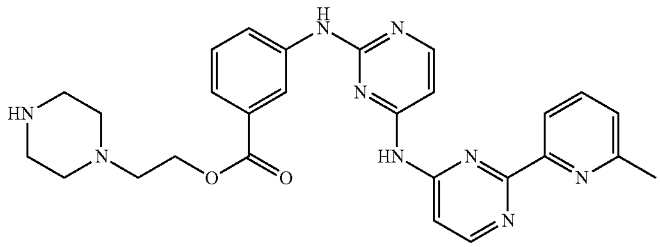 [SMILES: Cc1cccc(-c2nccc(Nc3ccnc(Nc4cccc(C(=O)OCCN5CCNCC5)c4)n3)n2)n1] | 2-piperazin-1-ylethyl 3-[[4-[[2-(6-methyl-2-pyridyl)pyrimidin-4-yl]amino]pyrimidin-2-yl]amino]benzoate | 512.2 |
| 554 | 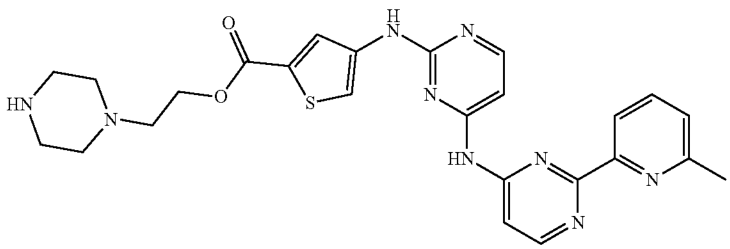 [SMILES: Cc1cccc(-c2nccc(Nc3ccnc(Nc4csc(C(=O)OCCN5CCNCC5)c4)n3)n2)n1] | 2-piperazin-1-ylethyl 4-[[4-[[2-(6-methyl-2-pyridyl)pyrimidin-4-yl]amino]pyrimidin-2-yl]amino]thiophene-2-carboxylate | 518.1 |
| 555 | 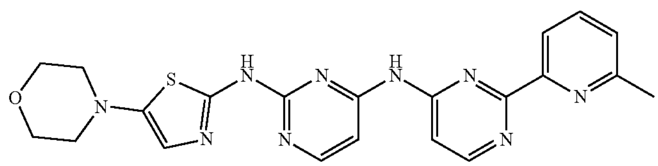 [SMILES: Cc1cccc(-c2nccc(Nc3ccnc(Nc4ncc(N5CCOCC5)s4)n3)n2)n1] | N4-[2-(6-methyl-2-pyridyl)pyrimidin-4-yl]-N2-(5-morpholinothiazol-2-yl)pyrimidine-2,4-diamine | 448.2 |
| 556 | 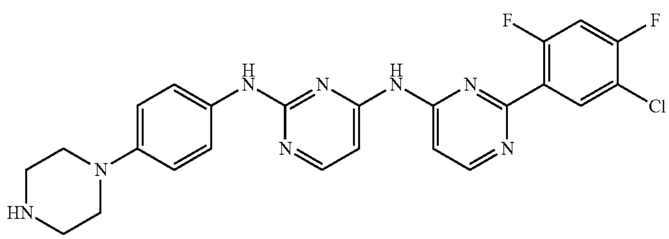 [SMILES: Fc1cc(F)c(-c2nccc(Nc3ccnc(Nc4ccc(N5CCNCC5)cc4)n3)n2)cc1Cl] | N4-[2-(5-chloro-2,4-difluoro-phenyl)pyrimidin-4-yl]-N2-(4-piperazin-1-ylphenyl)pyrimidine-2,4-diamine | 495.1 |
| 557 | 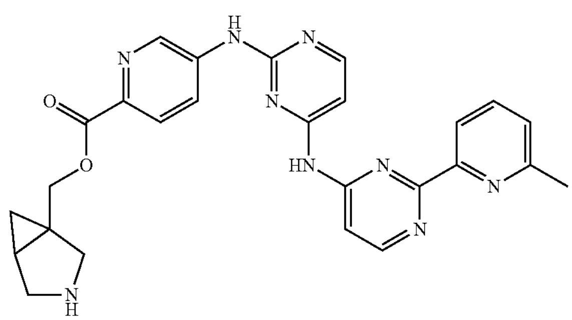 [SMILES: Cc1cccc(-c2nccc(Nc3ccnc(Nc4ccc(C(=O)OCC56CNCC5C6)nc4)n3)n2)n1] | 3-azabicyclo[3.1.0]hexan-1-ylmethyl 5-[[4-[[2-(6-methyl-2-pyridyl)pyrimidin-4-yl]amino]pyrimidin-2-yl]amino]pyridine-2-carboxylate | 496.2 |
| 558 | 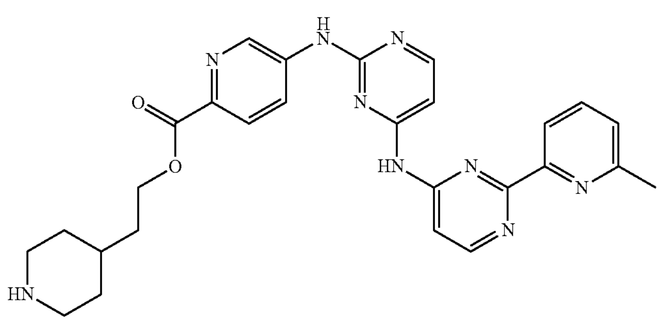 [SMILES: Cc1cccc(-c2nccc(Nc3ccnc(Nc4ccc(C(=O)OCCC5CCNCC5)nc4)n3)n2)n1] | 2-(4-piperidyl)ethyl 5-[[4-[[2-(6-methyl-2-pyridyl)pyrimidin-4-yl]amino]pyrimidin-2-yl]amino]pyridine-2-carboxylate | 512.3 |

TABLE 1-continued

| No. | Structure | Chemical Name | [M + H]+ |
|---|---|---|---|
| 559 | 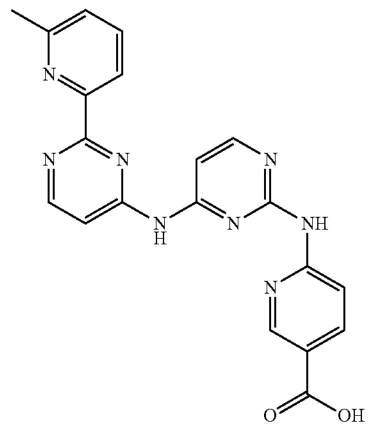 [SMILES: Cc1cccc(-c2nccc(Nc3ccnc(Nc4ccc(C(=O)O)cn4)n3)n2)n1] | 6-[[4-[[2-(6-methyl-2-pyridyl)pyrimidin-4-yl]amino]pyrimidin-2-yl]amino]pyridine-3-carboxylic acid | 401.1 |
| 560 | 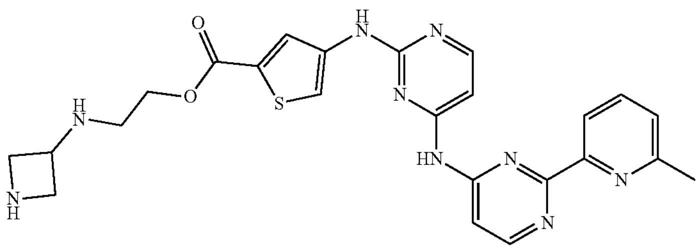 [SMILES: Cc1cccc(-c2nccc(Nc3ccnc(Nc4csc(C(=O)OCCNC5CNC5)c4)n3)n2)n1] | 2-(azetidin-3-ylamino)ethyl 4-[[4-[[2-(6-methyl-2-pyridyl)pyrimidin-4-yl]amino]pyrimidin-2-yl]amino]thiophene-2-carboxylate | 504.1 |
| 561 | 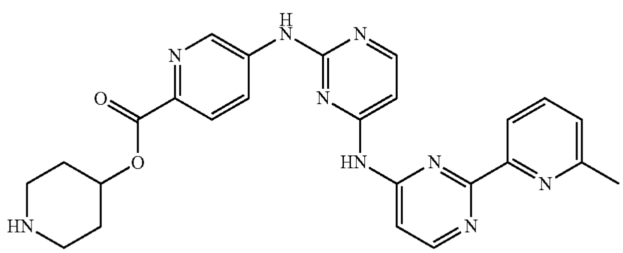 [SMILES: Cc1cccc(-c2nccc(Nc3ccnc(Nc4ccc(C(=O)OC5CCNCC5)nc4)n3)n2)n1] | 4-piperidyl 5-[[4-[[2-(6-methyl-2-pyridyl)pyrimidin-4-yl]amino]pyrimidin-2-yl]amino]pyridine-2-carboxylate | 484.2 |
| 562 | 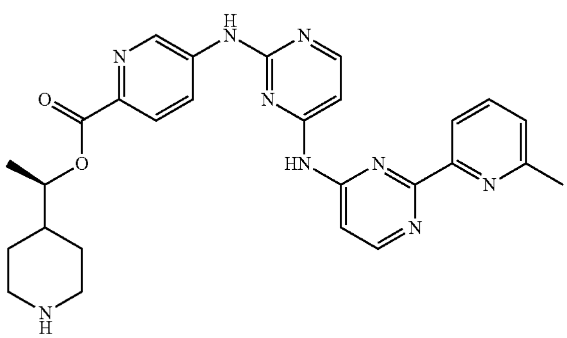 [SMILES: Cc1cccc(-c2nccc(Nc3ccnc(Nc4ccc(C(=O)O[C@H](C)C5CCNCC5)nc4)n3)n2)n1] | [(1R)-1-(4-piperidyl)ethyl] 5-[[4-[[2-(6-methyl-2-pyridyl)pyrimidin-4-yl]amino]pyrimidin-2-yl]amino]pyridine-2-carboxylate | 512.2 |
| 563 | 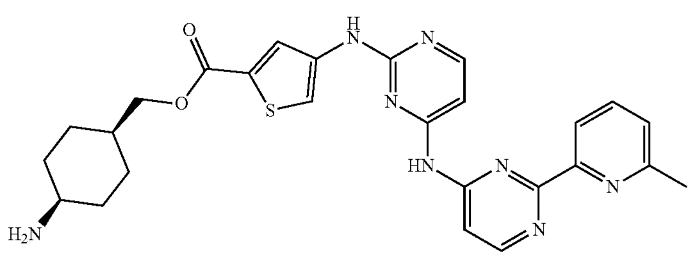 [SMILES: Cc1cccc(-c2nccc(Nc3ccnc(Nc4csc(C(=O)OC[C@H]5CC[C@@H](N)CC5)c4)n3)n2)n1] | (4-aminocyclohexyl)methyl 4-[[4-[[2-(6-methyl-2-pyridyl)pyrimidin-4-yl]amino]pyrimidin-2-yl]amino]thiophene-2-carboxylate | 517.1 |

TABLE 1-continued

| No. | Structure | Chemical Name | [M + H]+ |
|---|---|---|---|
| 564 | 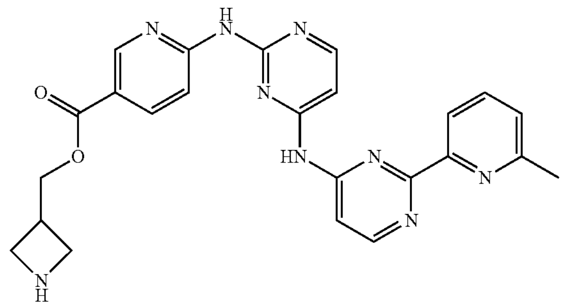 [SMILES: Cc1cccc(-c2nccc(Nc3ccnc(Nc4ccc(C(=O)OCC5CNC5)cn4)n3)n2)n1] | azetidin-3-ylmethyl 6-[[4-[[2-(6-methyl-2-pyridyl)pyrimidin-4-yl]amino]pyrimidin-2-yl]amino]pyridine-3-carboxylate | 470.2 |
| 565 | 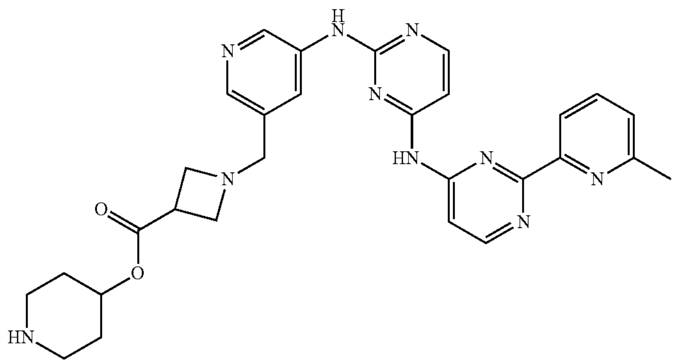 [SMILES: Cc1cccc(-c2nccc(Nc3ccnc(Nc4cncc(CN5CC(C(=O)OC6CCNCC6)C5)c4)n3)n2)n1] | 4-piperidyl 1-[[5-[[4-[[2-(6-methyl-2-pyridyl)pyrimidin-4-yl]amino]pyrimidin-2-yl]amino]-3-pyridyl]methyl]azetidine-3-carboxylate | 553.2 |
| 566 | 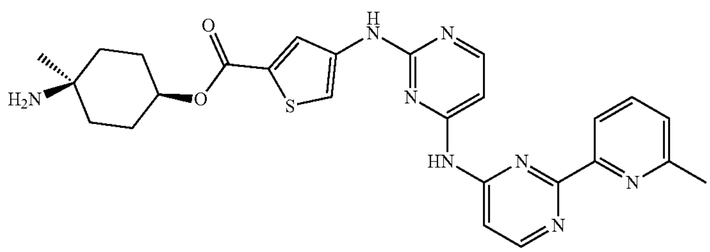 [SMILES: Cc1cccc(-c2nccc(Nc3ccnc(Nc4csc(C(=O)O[C@H]5CC[C@@](C)(N)CC5)c4)n3)n2)n1] | (4-amino-4-methyl-cyclohexyl) 4-[[4-[[2-(6-methyl-2-pyridyl)pyrimidin-4-yl]amino]pyrimidin-2-yl]amino]thiophene-2-carboxylate | 517.1 |
| 567 | 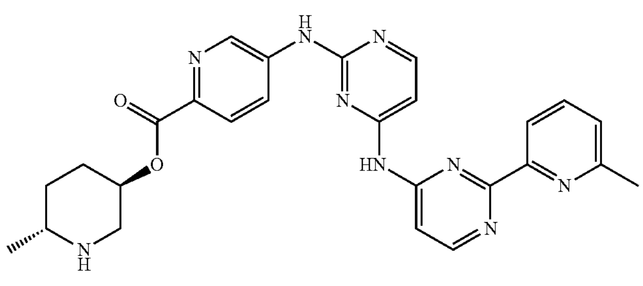 | [(3R,6R)-6-methyl-3-piperidyl] 5-[[4-[[2-(6-methyl-2-pyridyl)pyrimidin-4-yl]amino]pyrimidin-2-yl]amino]pyridine-2-carboxylate | 498.2 |
| 568 | 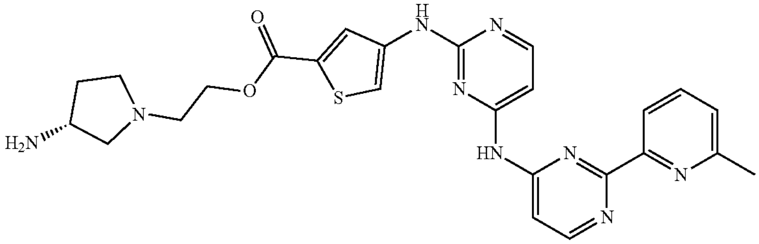 [SMILES: Cc1cccc(-c2nccc(Nc3ccnc(Nc4csc(C(=O)OCCN5CC[C@@H](N)C5)c4)n3)n2)n1] | 2-[(3R)-3-aminopyrrolidin-1-yl]ethyl 4-[[4-[[2-(6-methyl-2-pyridyl)pyrimidin-4-yl]amino]pyrimidin-2-yl]amino]thiophene-2-carboxylate | 518.1 |

TABLE 1-continued

| No. | Structure | Chemical Name | [M + H]+ |
|---|---|---|---|
| 569 | 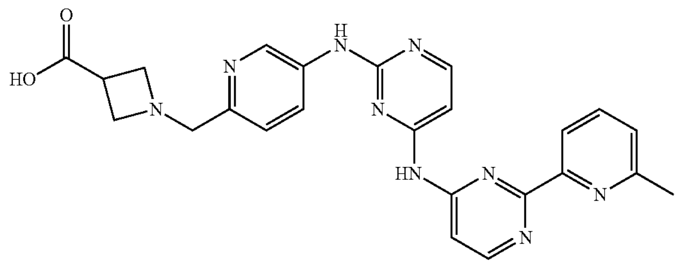 [SMILES: Cc1cccc(-c2nccc(Nc3ccnc(Nc4ccc(CN5CC(C(=O)O)C5)nc4)n3)n2)n1] | 1-[[5-[[4-[[2-(6-methyl-2-pyridyl)pyrimidin-4-yl]amino]pyrimidin-2-yl]amino]-2-pyridyl]methyl]azetidine-3-carboxylic acid | 470.1 |
| 570 | 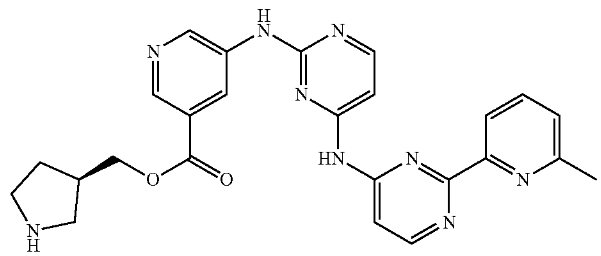 [SMILES: Cc1cccc(-c2nccc(Nc3ccnc(Nc4cncc(C(=O)OC[C@@H]5CCNC5)c4)n3)n2)n1] | [(3R)-pyrrolidin-3-yl]methyl 5-[[4-[[2-(6-methyl-2-pyridyl)pyrimidin-4-yl]amino]pyrimidin-2-yl]amino]pyridine-3-carboxylate | 484.2 |
| 571 | 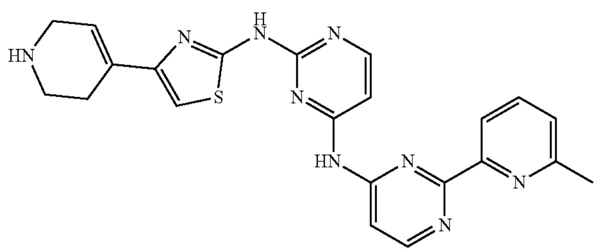 [SMILES: Cc1cccc(-c2nccc(Nc3ccnc(Nc4nc(C5=CCNCC5)cs4)n3)n2)n1] | N4-[2-(6-methyl-2-pyridyl)pyrimidin-4-yl]-N2-[4-(1,2,3,6-tetrahydropyridin-4-yl)thiazol-2-yl]pyrimidine-2,4-diamine | 444.2 |
| 572 | 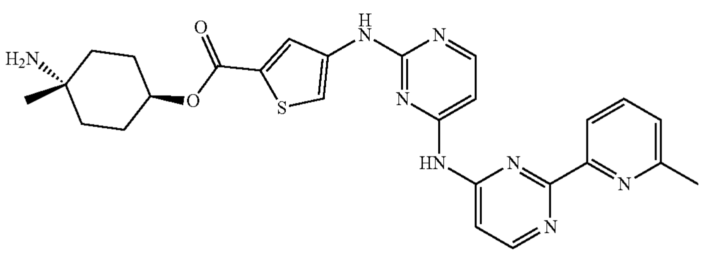 | (4-amino-4-methyl-cyclohexyl) 4-[[4-[[2-(6-methyl-2-pyridyl)pyrimidin-4-yl]amino]pyrimidin-2-yl]amino]thiophene-2-carboxylate | 517.2 |
| 573 | 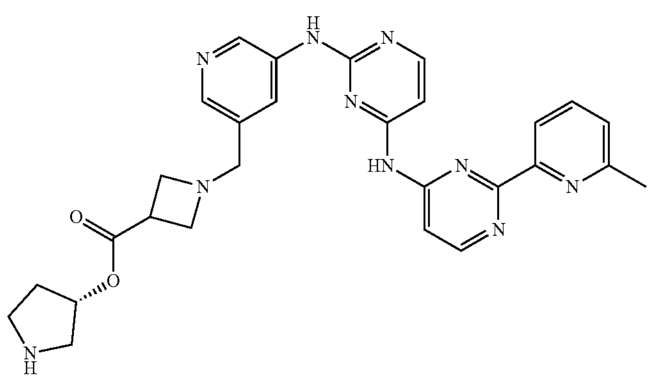 [SMILES: Cc1cccc(-c2nccc(Nc3ccnc(Nc4cncc(CN5CC(C(=O)O[C@H]6CCNC6)C5)c4)n3)n2)n1] | [(3S)-pyrrolidin-3-yl] 1-[[5-[[4-[[2-(6-methyl-2-pyridyl)pyrimidin-4-yl]amino]pyrimidin-2-yl]amino]-3-pyridyl]methyl]azetidine-3-carboxylate | 539.2 |

TABLE 1-continued

| No. | Structure | Chemical Name | [M + H]+ |
|---|---|---|---|
| 574 | 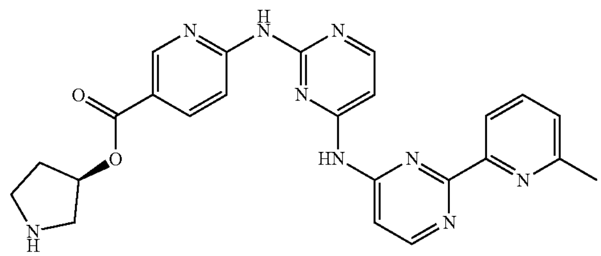 [SMILES: Cc1cccc(-c2nccc(Nc3ccnc(Nc4ccc(C(=O)O[C@@H]5CCNC5)cn4)n3)n2)n1] | [(3R)-pyrrolidin-3-yl] 6-[[4-[[2-(6-methyl-2-pyridyl)pyrimidin-4-yl]amino]pyrimidin-2-yl]amino]pyridine-3-carboxylate | 470.2 |
| 575 | 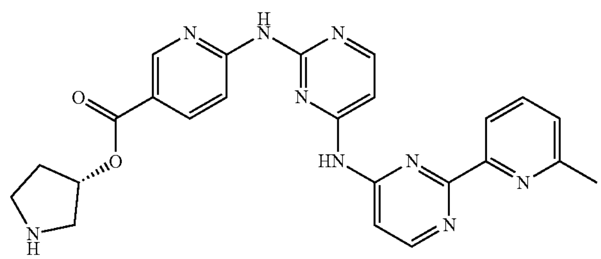 [SMILES: Cc1cccc(-c2nccc(Nc3ccnc(Nc4ccc(C(=O)O[C@H]5CCNC5)cn4)n3)n2)n1] | [(3S)-pyrrolidin-3-yl] 6-[[4-[[2-(6-methyl-2-pyridyl)pyrimidin-4-yl]amino]pyrimidin-2-yl]amino]pyridine-3-carboxylate | 470.1 |
| 576 | 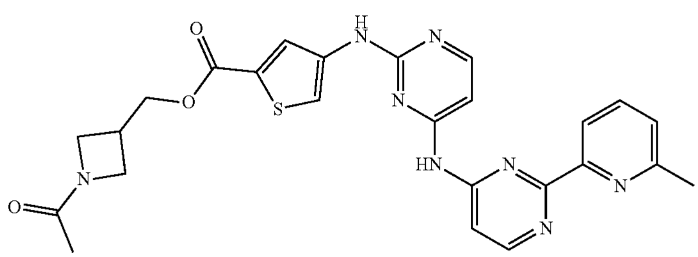 [SMILES: CC(=O)N1CC(COC(=O)c2cc(Nc3nccc(Nc4ccnc(-c5cccc(C)n5)n4)n3)cs2)C1] | (1-acetylazetidin-3-yl)methyl 4-[[4-[[2-(6-methyl-2-pyridyl)pyrimidin-4-yl]amino]pyrimidin-2-yl]amino]thiophene-2-carboxylate | 517.1 |
| 577 | 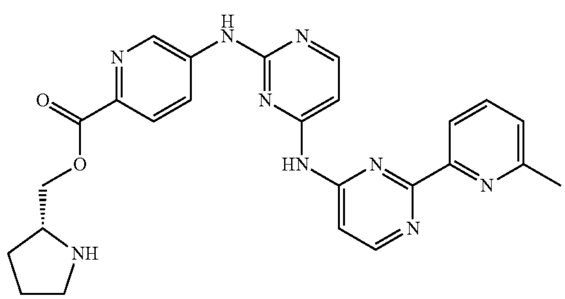 [SMILES: Cc1cccc(-c2nccc(Nc3ccnc(Nc4ccc(C(=O)OC[C@H]5CCCN5)nc4)n3)n2)n1] | [(2R)-pyrrolidin-2-yl]methyl 5-[[4-[[2-(6-methyl-2-pyridyl)pyrimidin-4-yl]amino]pyrimidin-2-yl]amino]pyridine-2-carboxylate | 484.1 |
| 578 | 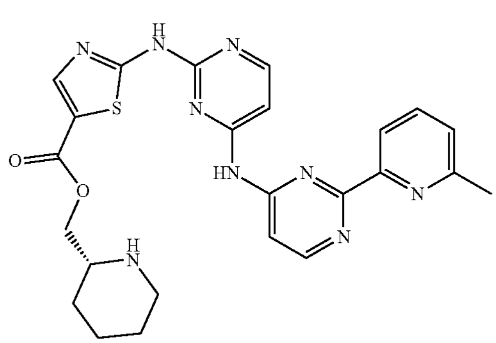 [SMILES: Cc1cccc(-c2nccc(Nc3ccnc(Nc4ncc(C(=O)OC[C@H]5CCCCN5)s4)n3)n2)n1] | [(2R)-2-piperidyl]methyl 2-[[4-[[2-(6-methyl-2-pyridyl)pyrimidin-4-yl]amino]pyrimidin-2-yl]amino]thiazole-5-carboxylate | 504.1 |

TABLE 1-continued

| No. | Structure | Chemical Name | [M + H]+ |
|---|---|---|---|
| 579 | 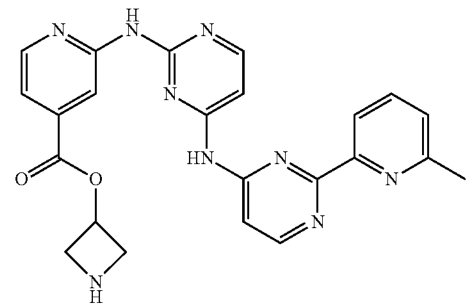 [SMILES: Cc1cccc(-c2nccc(Nc3ccnc(Nc4cc(C(=O)OC5CNC5)ccn4)n3)n2)n1] | azetidin-3-yl 2-[[4-[[2-(6-methyl-2-pyridyl)pyrimidin-4-yl]amino]pyrimidin-2-yl]amino]pyridine-4-carboxylate | 456.1 |
| 580 | 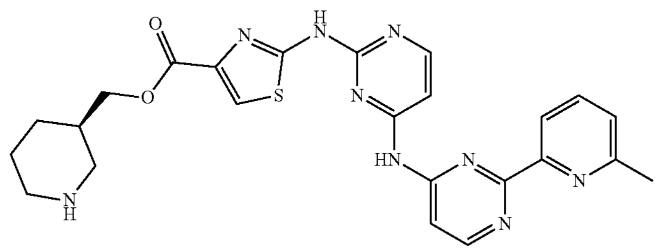 [SMILES: Cc1cccc(-c2nccc(Nc3ccnc(Nc4nc(C(=O)OC[C@@H]5CCCNC5)cs4)n3)n2)n1] | [(3R)-3-piperidyl]methyl 2-[[4-[[2-(6-methyl-2-pyridyl)pyrimidin-4-yl]amino]pyrimidin-2-yl]amino]thiazole-4-carboxylate | 504.2 |
| 581 | 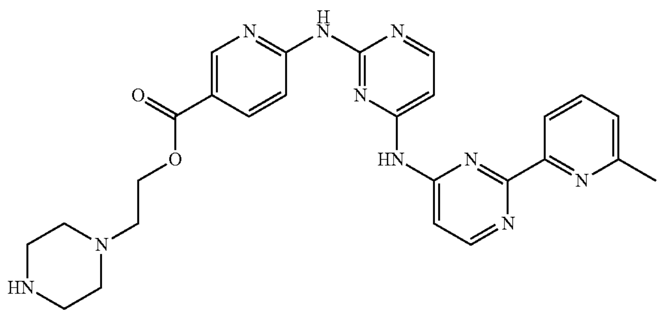 [SMILES: Cc1cccc(-c2nccc(Nc3ccnc(Nc4ccc(C(=O)OCCN5CCNCC5)cn4)n3)n2)n1] | 2-piperazin-1-ylethyl 6-[[4-[[2-(6-methyl-2-pyridyl)pyrimidin-4-yl]amino]pyrimidin-2-yl]amino]pyridine-3-carboxylate | 513.2 |
| 582 | 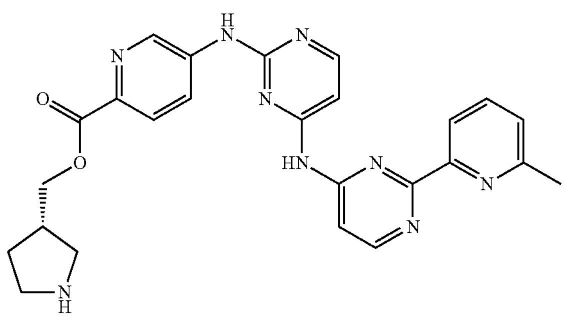 [SMILES: Cc1cccc(-c2nccc(Nc3ccnc(Nc4ccc(C(=O)OC[C@H]5CCNC5)nc4)n3)n2)n1] | [(3S)-pyrrolidin-3-yl]methyl 5-[[4-[[2-(6-methyl-2-pyridyl)pyrimidin-4-yl]amino]pyrimidin-2-yl]amino]pyridine-2-carboxylate | 484.3 |
| 583 | 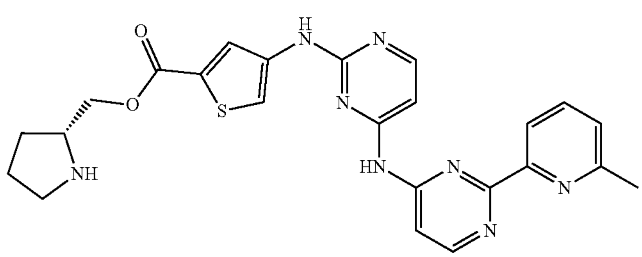 [SMILES: Cc1cccc(-c2nccc(Nc3ccnc(Nc4csc(C(=O)OC[C@H]5CCCN5)c4)n3)n2)n1] | [(2R)-pyrrolidin-2-yl]methyl 4-[[4-[[2-(6-methyl-2-pyridyl)pyrimidin-4-yl]amino]pyrimidin-2-yl]amino]thiophene-2-carboxylate | 489.1 |

TABLE 1-continued

| No. | Chemical Name | [M + H]⁺ |
|---|---|---|
| 584 | [(3R)-pyrrolidin-3-yl]methyl 5-[[4-[[2-(6-methyl-2-pyridyl)pyrimidin-4-yl]amino]pyrimidin-2-yl]amino]pyridine-2-carboxylate | 484.1 |
| 585 | 4-[[4-[[2-(6-methyl-2-pyridyl)pyrimidin-4-yl]amino]pyrimidin-2-yl]amino]thiazole-2-carboxylic acid | 407.1 |
| 586 | [(2R)-2-piperidyl]methyl 2-[[4-[[2-(6-methyl-2-pyridyl)pyrimidin-4-yl]amino]pyrimidin-2-yl]amino]thiazole-4-carboxylate | 504.3 |
| 587 | 4-piperidylmethyl 5-[[4-[[2-(6-methyl-2-pyridyl)pyrimidin-4-yl]amino]pyrimidin-2-yl]amino]pyridine-2-carboxylate | 498.1 |
| 588 | [(2R)-2-piperidyl]methyl 4-[[4-[[2-(6-methyl-2-pyridyl)pyrimidin-4-yl]amino]pyrimidin-2-yl]amino]thiophene-2-carboxylate | 503.1 |

TABLE 1-continued

| No. | Chemical Name | [M + H]+ |
|---|---|---|
| 589 | 2-[(3R,5S)-3,5-dimethylpiperazin-1-yl]ethyl 5-[[4-[[2-(6-methyl-2-pyridyl)pyrimidin-4-yl]amino]pyrimidin-2-yl]amino]pyridine-2-carboxylate | 541.2 |
| 590 | (4-aminocyclohexyl)methyl 4-[[4-[[2-(6-methyl-2-pyridyl)pyrimidin-4-yl]amino]pyrimidin-2-yl]amino]thiophene-2-carboxylate | 517.2 |
| 591 | 4-piperidyl 4-[[4-[[2-(6-methyl-2-pyridyl)pyrimidin-4-yl]amino]pyrimidin-2-yl]amino]thiophene-2-carboxylate | 488.9 |
| 592 | [(2R)-pyrrolidin-2-yl]methyl 2-[[4-[[2-(6-methyl-2-pyridyl)pyrimidin-4-yl]amino]pyrimidin-2-yl]amino]thiazole-5-carboxylate | 490.1 |
| 593 | [(2R)-pyrrolidin-2-yl]methyl 2-[[4-[[2-(6-methyl-2-pyridyl)pyrimidin-4-yl]amino]pyrimidin-2-yl]amino]thiazole-4-carboxylate | 490.1 |

TABLE 1-continued

| No. | Structure | Chemical Name | [M + H]+ |
|---|---|---|---|
| 594 | 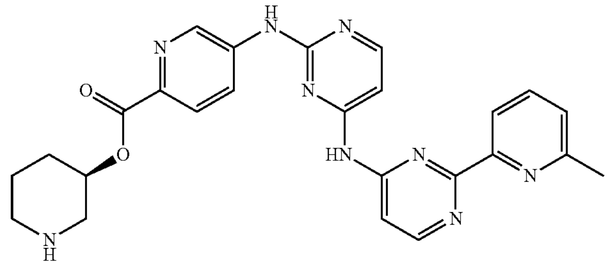 [SMILES: Cc1cccc(-c2nccc(Nc3ccnc(Nc4ccc(C(=O)O[C@@H]5CCCNC5)nc4)n3)n2)n1] | [(3R)-3-piperidyl] 5-[[4-[[2-(6-methyl-2-pyridyl)pyrimidin-4-yl]amino]pyrimidin-2-yl]amino]pyridine-2-carboxylate | 484.1 |
| 595 | 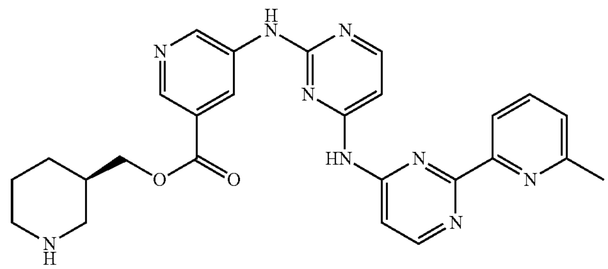 [SMILES: Cc1cccc(-c2nccc(Nc3ccnc(Nc4cncc(C(=O)OC[C@@H]5CCCNC5)c4)n3)n2)n1] | (3R)-3-piperidyl]methyl 5-[[4-[[2-(6-methyl-2-pyridyl)pyrimidin-4-yl]amino]pyrimidin-2-yl]amino]pyridine-3-carboxylate | 498.1 |
| 596 | 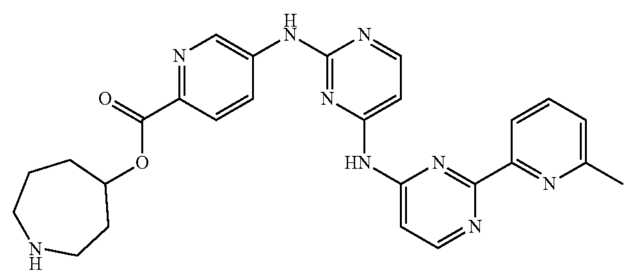 [SMILES: Cc1cccc(-c2nccc(Nc3ccnc(Nc4ccc(C(=O)OC5CCCNCC5)nc4)n3)n2)n1] | azepan-4-yl 5-[[4-[[2-(6-methyl-2-pyridyl)pyrimidin-4-yl]amino]pyrimidin-2-yl]amino]pyridine-2-carboxylate | 498.2 |
| 597 | 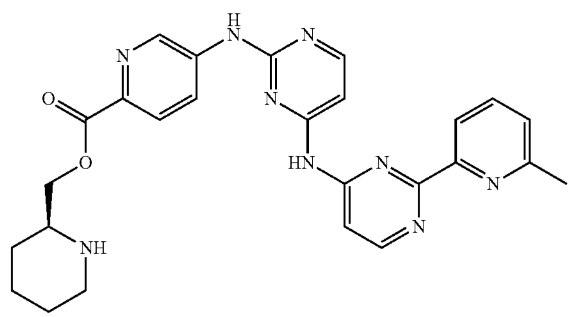 [SMILES: Cc1cccc(-c2nccc(Nc3ccnc(Nc4ccc(C(=O)OC[C@@H]5CCCCN5)nc4)n3)n2)n1] | [(2S)-2-piperidyl]methyl 5-[[4-[[2-(6-methyl-2-pyridyl)pyrimidin-4-yl]amino]pyrimidin-2-yl]amino]pyridine-2-carboxylate | 498.1 |
| 598 | 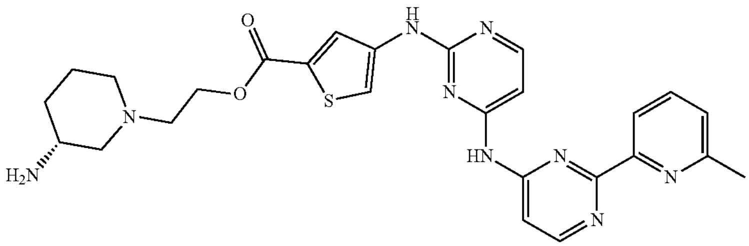 [SMILES: Cc1cccc(-c2nccc(Nc3ccnc(Nc4csc(C(=O)OCCN5CCC[C@@H](N)C5)c4)n3)n2)n1] | 2-[(3R)-3-amino-1-piperidyl]ethyl 4-[[4-[[2-(6-methyl-2-pyridyl)pyrimidin-4-yl]amino]pyrimidin-2-yl]amino]thiophene-2-carboxylate | 532.1 |

TABLE 1-continued

| No. | Structure | Chemical Name | [M + H]+ |
|---|---|---|---|
| 599 | 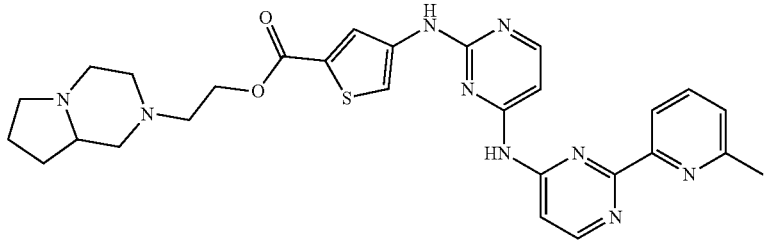 [SMILES: Cc1cccc(-c2nccc(Nc3ccnc(Nc4csc(C(=O)OCCN5CCN6CCCC6C5)c4)n3)n2)n1] | 2-(3,4,6,7,8,8a-hexahydro-1H-pyrrolo[1,2-a]pyrazin-2-yl)ethyl 4-[[4-[[2-(6-methyl-2-pyridyl)pyrimidin-4-yl]amino]pyrimidin-2-yl]amino]thiophene-2-carboxylate | 558.2 |
| 600 | 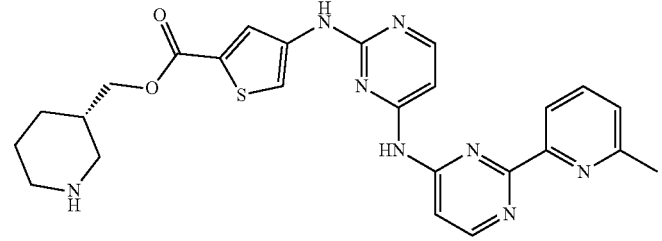 [SMILES: Cc1cccc(-c2nccc(Nc3ccnc(Nc4csc(C(=O)OC[C@H]5CCCNC5)c4)n3)n2)n1] | [(3S)-3-piperidyl]methyl 4-[[4-[[2-(6-methyl-2-pyridyl)pyrimidin-4-yl]amino]pyrimidin-2-yl]amino]thiophene-2-carboxylate | 503.1 |
| 601 | 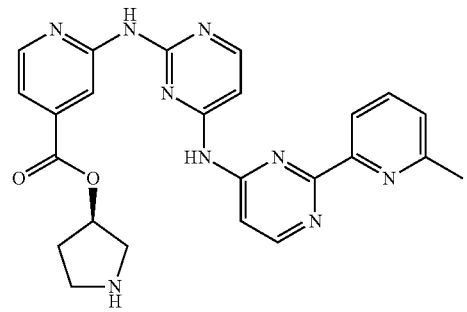 [SMILES: Cc1cccc(-c2nccc(Nc3ccnc(Nc4cc(C(=O)O[C@@H]5CCNC5)ccn4)n3)n2)n1] | [(3R)-pyrrolidin-3-yl] 2-[[4-[[2-(6-methyl-2-pyridyl)pyrimidin-4-yl]amino]pyrimidin-2-yl]amino]pyridine-4-carboxylate | 470.1 |
| 602 | 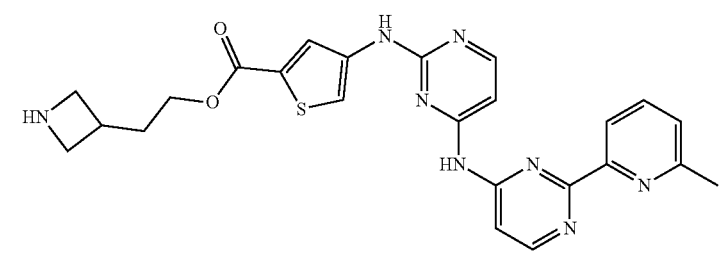 [SMILES: Cc1cccc(-c2nccc(Nc3ccnc(Nc4csc(C(=O)OCCC5CNC5)c4)n3)n2)n1] | 2-(azetidin-3-yl)ethyl 4-[[4-[[2-(6-methyl-2-pyridyl)pyrimidin-4-yl]amino]pyrimidin-2-yl]amino]thiophene-2-carboxylate | 489.1 |
| 603 | 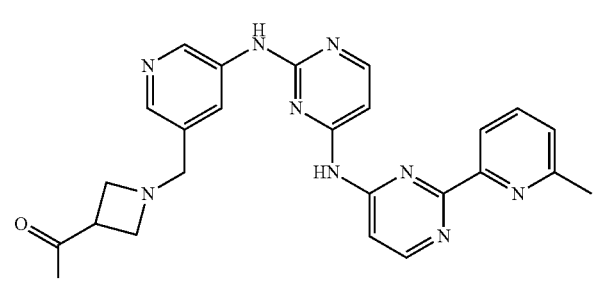 | 1-[[5-[[4-[[2-(6-methyl-2-pyridyl)pyrimidin-4-yl]amino]pyrimidin-2-yl]amino]-3-pyridyl]methyl]azetidine-3-carboxylic acid | 470.1 |

TABLE 1-continued

| No. | Structure | Chemical Name | [M + H]+ |
|---|---|---|---|
| 604 | 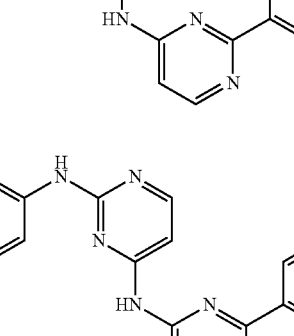 | N2-[5-[(3R,5S)-3,5-dimethylpiperazin-1-yl]thiazol-2-yl]-N4-[2-(6-methyl-2-pyridyl)pyrimidin-4-yl]pyrimidine-2,4-diamine | 475.1 |
| 605 | 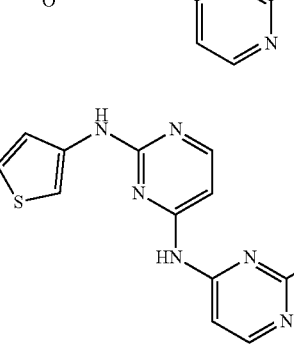 | [(2R)-morpholin-2-yl]methyl 5-[[4-[[2-(6-methyl-2-pyridyl)pyrimidin-4-yl]amino]pyrimidin-2-yl]amino]pyridine-2-carboxylate | 500.1 |
| 606 | 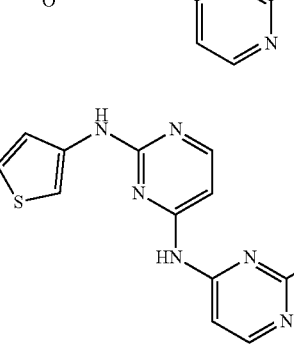 | 4-piperidylmethyl 5-[[4-[[2-(6-methyl-2-pyridyl)pyrimidin-4-yl]amino]pyrimidin-2-yl]amino]pyridine-3-carboxylate | 498.2 |
| 607 | 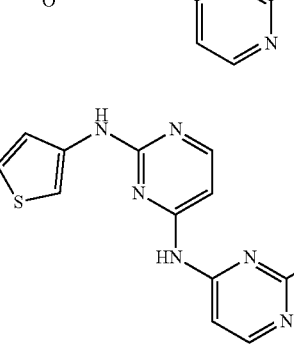 | 4-piperidylmethyl 4-[[4-[[2-(6-methyl-2-pyridyl)pyrimidin-4-yl]amino]pyrimidin-2-yl]amino]thiophene-2-carboxylate | 503.1 |
| 608 | 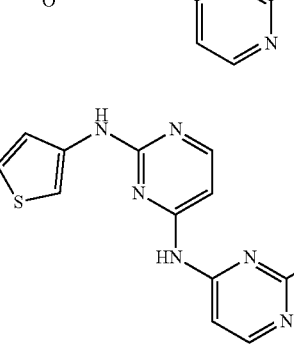 | azetidin-3-ylmethyl 2-[[4-[[2-(6-methyl-2-pyridyl)pyrimidin-4-yl]amino]pyrimidin-2-yl]amino]pyridine-4-carboxylate | 470.1 |

TABLE 1-continued

| No. | Structure | Chemical Name | [M + H]+ |
|---|---|---|---|
| 609 | 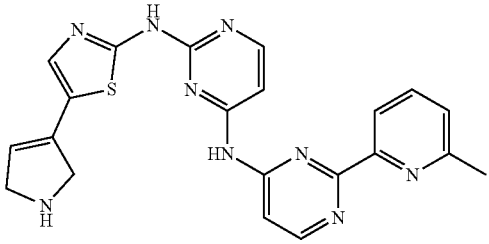 [SMILES: Cc1cccc(-c2nccc(Nc3ccnc(Nc4ncc(C5=CCNC5)s4)n3)n2)n1] | N2-[5-(2,5-dihydro-1H-pyrrol-3-yl)thiazol-2-yl]-N4-[2-(6-methyl-2-pyridyl)pyrimidin-4-yl]pyrimidine-2,4-diamine | 430.2 |
| 610 | 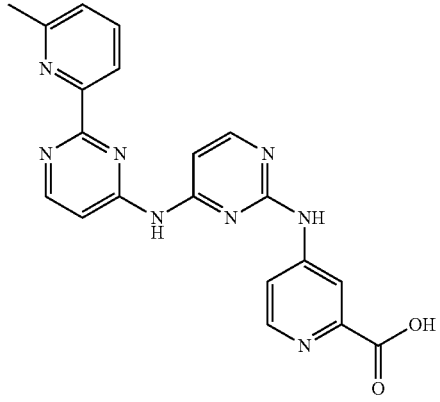 [SMILES: Cc1cccc(-c2nccc(Nc3ccnc(Nc4ccnc(C(=O)O)c4)n3)n2)n1] | 4-[[4-[[2-(6-methyl-2-pyridyl)pyrimidin-4-yl]amino]pyrimidin-2-yl]amino]pyridine-2-carboxylic acid | 401.2 |
| 611 | 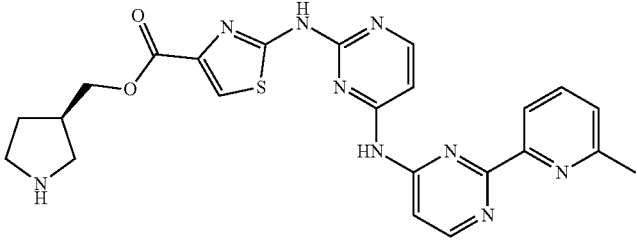 [SMILES: Cc1cccc(-c2nccc(Nc3ccnc(Nc4nc(C(=O)OC[C@@H]5CCNC5)cs4)n3)n2)n1] | [(3R)-pyrrolidin-3-yl]methyl 2-[[4-[[2-(6-methyl-2-pyridyl)pyrimidin-4-yl]amino]pyrimidin-2-yl]amino]thiazole-4-carboxylate | 490.1 |
| 612 | 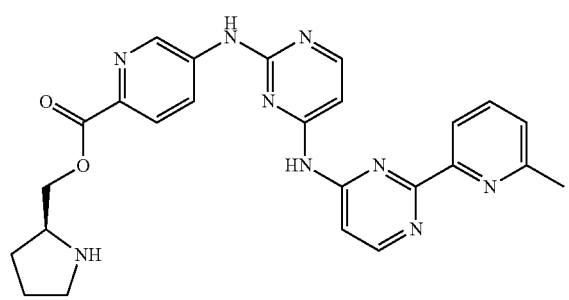 [SMILES: Cc1cccc(-c2nccc(Nc3ccnc(Nc4ccc(C(=O)OC[C@@H]5CCCN5)nc4)n3)n2)n1] | [(2S)-pyrrolidin-2-yl]methyl 5-[[4-[[2-(6-methyl-2-pyridyl)pyrimidin-4-yl]amino]pyrimidin-2-yl]amino]pyridine-2-carboxylate | 484.1 |
| 613 | 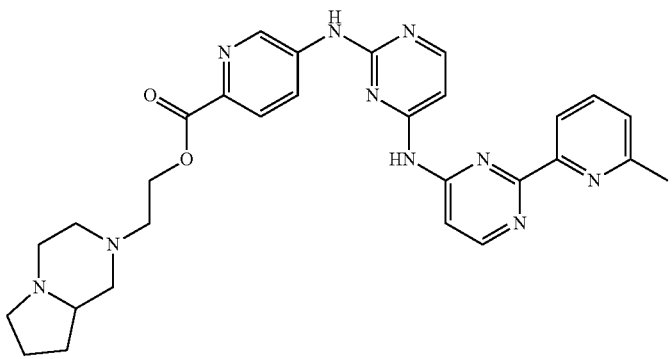 [SMILES: Cc1cccc(-c2nccc(Nc3ccnc(Nc4ccc(C(=O)OCCN5CCN6CCCC6C5)nc4)n3)n2)n1] | 2-(3,4,6,7,8,8a-hexahydro-1H-pyrrolo[1,2-a]pyrazin-2-yl)ethyl 5-[[4-[[2-(6-methyl-2-pyridyl)pyrimidin-4-yl]amino]pyrimidin-2-yl]amino]pyridine-2-carboxylate | 553.0 |

TABLE 1-continued

| No. | Structure | Chemical Name | [M + H]+ |
|---|---|---|---|
| 614 | 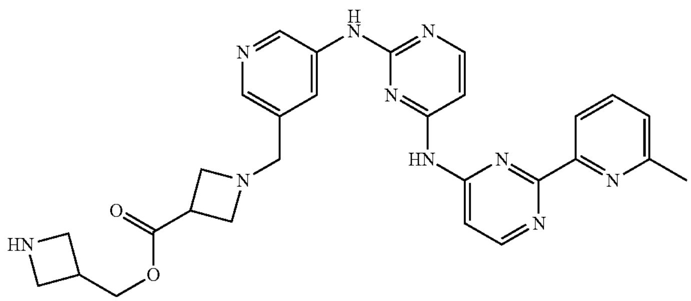 [SMILES: Cc1cccc(-c2nccc(Nc3ccnc(Nc4cncc(CN5CC(C(=O)OCC6CNC6)C5)c4)n3)n2)n1] | azetidin-3-ylmethyl 1-[[5-[[4-[[2-(6-methyl-2-pyridyl)pyrimidin-4-yl]amino]pyrimidin-2-yl]amino]-3-pyridyl]methyl]azetidine-3-carboxylate | 539.2 |
| 615 | 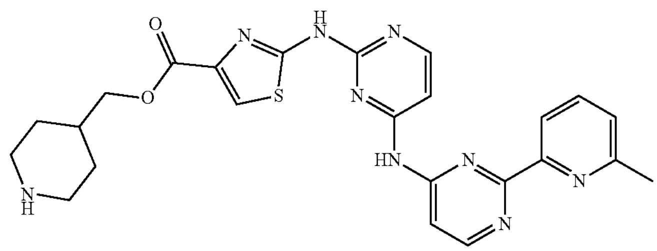 [SMILES: Cc1cccc(-c2nccc(Nc3ccnc(Nc4nc(C(=O)OCC5CCNCC5)cs4)n3)n2)n1] | 4-piperidylmethyl 2-[[4-[[2-(6-methyl-2-pyridyl)pyrimidin-4-yl]amino]pyrimidin-2-yl]amino]thiazole-4-carboxylate | 504.3 |
| 616 | 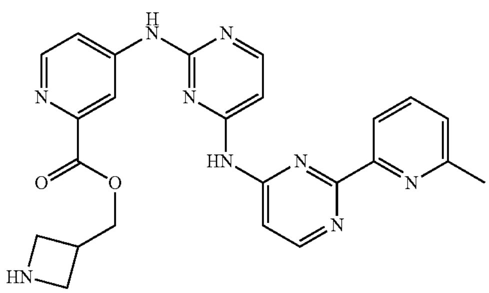 [SMILES: Cc1cccc(-c2nccc(Nc3ccnc(Nc4ccnc(C(=O)OCC5CNC5)c4)n3)n2)n1] | azetidin-3-ylmethyl 4-[[4-[[2-(6-methyl-2-pyridyl)pyrimidin-4-yl]amino]pyrimidin-2-yl]amino]pyridine-2-carboxylate | 470.1 |
| 617 | 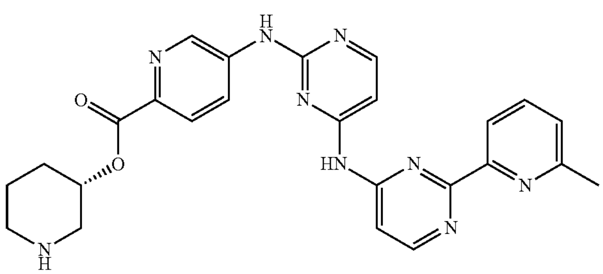 [SMILES: Cc1cccc(-c2nccc(Nc3ccnc(Nc4ccc(C(=O)O[C@H]5CCCNC5)nc4)n3)n2)n1] | [(3S)-3-piperidyl] 5-[[4-[[2-(6-methyl-2-pyridyl)pyrimidin-4-yl]amino]pyrimidin-2-yl]amino]pyridine-2-carboxylate | 484.4 |
| 618 | 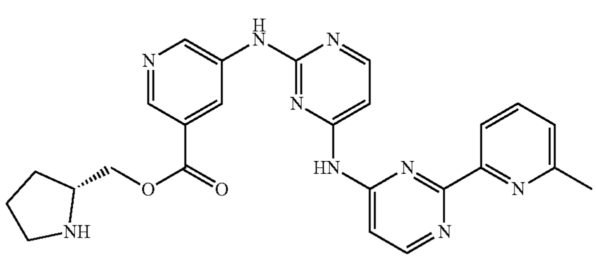 [SMILES: Cc1cccc(-c2nccc(Nc3ccnc(Nc4cncc(C(=O)OC[C@H]5CCCN5)c4)n3)n2)n1] | [(2R)-pyrrolidin-2-yl]methyl 5-[[4-[[2-(6-methyl-2-pyridyl)pyrimidin-4-yl]amino]pyrimidin-2-yl]amino]pyridine-3-carboxylate | 484.1 |

TABLE 1-continued

| No. | Structure | Chemical Name | [M + H]+ |
|---|---|---|---|
| 619 | 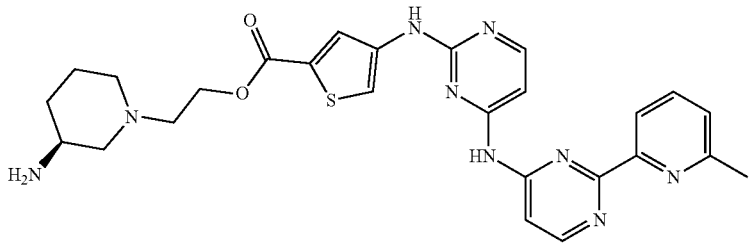 [SMILES: Cc1cccc(-c2nccc(Nc3ccnc(Nc4csc(C(=O)OCCN5CCC[C@H](N)C5)c4)n3)n2)n1] | 2-[(3S)-3-amino-1-piperidyl]ethyl 4-[[4-[[2-(6-methyl-2-pyridyl)pyrimidin-4-yl]amino]pyrimidin-2-yl]amino]thiophene-2-carboxylate | 532.1 |
| 620 | 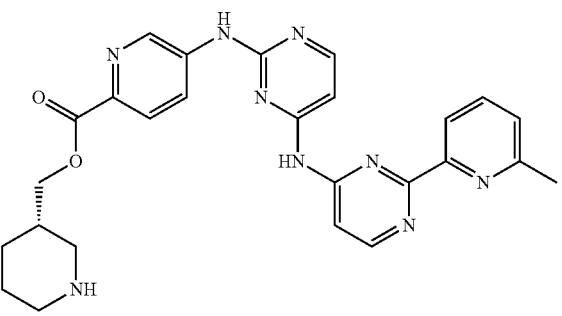 [SMILES: Cc1cccc(-c2nccc(Nc3ccnc(Nc4ccc(C(=O)OC[C@H]5CCCNC5)nc4)n3)n2)n1] | [(3S)-3-piperidyl]methyl 5-[[4-[[2-(6-methyl-2-pyridyl)pyrimidin-4-yl]amino]pyrimidin-2-yl]amino]pyridine-2-carboxylate | 498.2 |
| 621 | 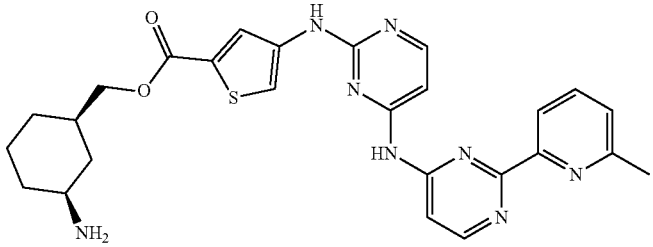 [SMILES: Cc1cccc(-c2nccc(Nc3ccnc(Nc4csc(C(=O)OC[C@@H]5CCC[C@H](N)C5)c4)n3)n2)n1] | [(1R,3S)-3-aminocyclohexyl]methyl 4-[[4-[[2-(6-methyl-2-pyridyl)pyrimidin-4-yl]amino]pyrimidin-2-yl]amino]thiophene-2-carboxylate | 517.1 |
| 622 | 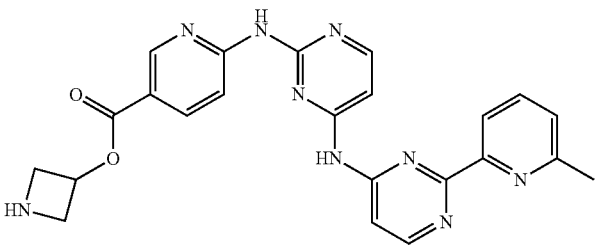 [SMILES: Cc1cccc(-c2nccc(Nc3ccnc(Nc4ccc(C(=O)OC5CNC5)cn4)n3)n2)n1] | azetidin-3-yl 6-[[4-[[2-(6-methyl-2-pyridyl)pyrimidin-4-yl]amino]pyrimidin-2-yl]amino]pyridine-3-carboxylate | 456.1 |
| 623 | 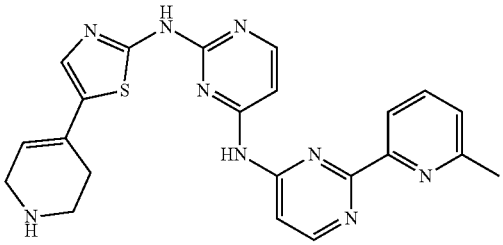 [SMILES: Cc1cccc(-c2nccc(Nc3ccnc(Nc4ncc(C5=CCNCC5)s4)n3)n2)n1] | N4-[2-(6-methyl-2-pyridyl)pyrimidin-4-yl]-N2-[5-(1,2,3,6-tetrahydropyridin-4-yl)thiazol-2-yl]pyrimidine-2,4-diamine | 444.3 |

TABLE 1-continued

| No. | Structure | Chemical Name | [M + H]⁺ |
|---|---|---|---|
| 624 | 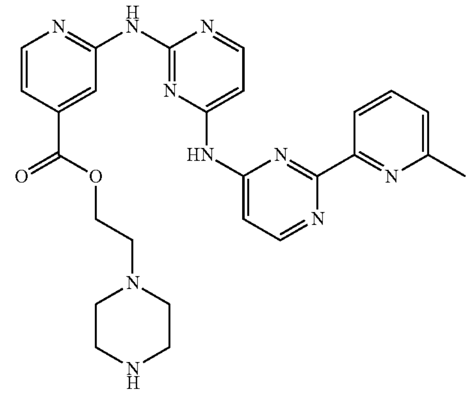 [SMILES: Cc1cccc(-c2nccc(Nc3ccnc(Nc4cc(C(=O)OCCN5CCNCC5)ccn4)n3)n2)n1] | 2-piperazin-1-ylethyl 2-[[4-[[2-(6-methyl-2-pyridyl)pyrimidin-4-yl]amino]pyrimidin-2-yl]amino]pyridine-4-carboxylate | 513.2 |
| 625 | 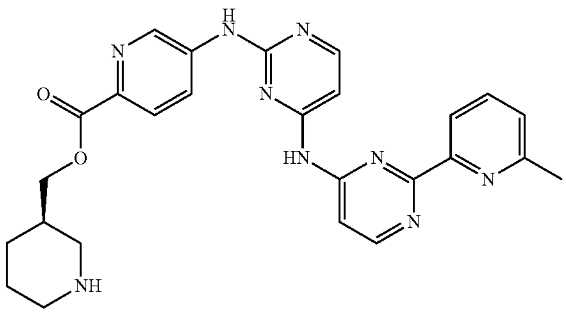 [SMILES: Cc1cccc(-c2nccc(Nc3ccnc(Nc4ccc(C(=O)OC[C@@H]5CCCNC5)nc4)n3)n2)n1] | [(3R)-3-piperidyl]methyl 5-[[4-[[2-(6-methyl-2-pyridyl)pyrimidin-4-yl]amino]pyrimidin-2-yl]amino]pyridine-2-carboxylate | 498.1 |
| 626 | 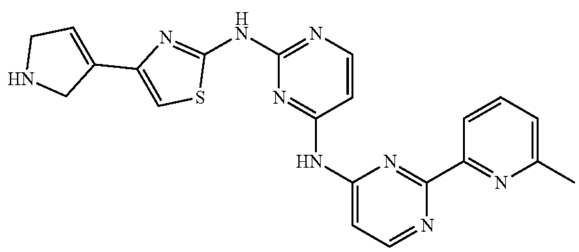 [SMILES: Cc1cccc(-c2nccc(Nc3ccnc(Nc4nc(C5=CCNC5)cs4)n3)n2)n1] | N2-[4-(2,5-dihydro-1H-pyrrol-3-yl)thiazol-2-yl]-N4-[2-(6-methyl-2-pyridyl)pyrimidin-4-yl]pyrimidine-2,4-diamine | 430.2 |
| 627 | 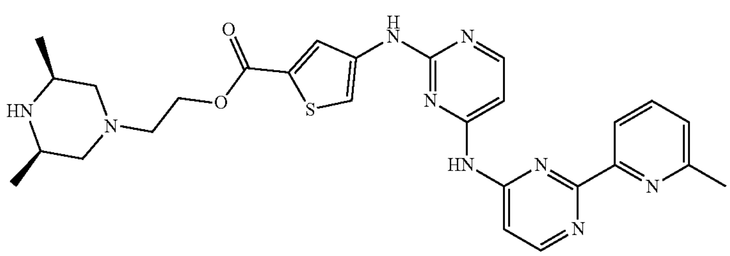 | 2-[(3S,5R)-3,5-dimethylpiperazin-1-yl]ethyl 4-[[4-[[2-(6-methyl-2-pyridyl)pyrimidin-4-yl]amino]pyrimidin-2-yl]amino]thiophene-2-carboxylate | 546.1 |
| 628 | 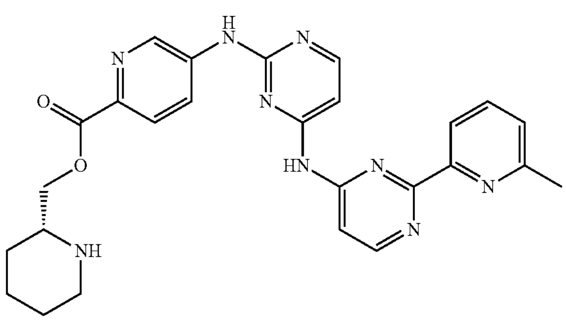 [SMILES: Cc1cccc(-c2nccc(Nc3ccnc(Nc4ccc(C(=O)OC[C@H]5CCCCN5)nc4)n3)n2)n1] | [(2R)-2-piperidyl]methyl 5-[[4-[[2-(6-methyl-2-pyridyl)pyrimidin-4-yl]amino]pyrimidin-2-yl]amino]pyridine-2-carboxylate | 498.2 |

TABLE 1-continued

| No. | Structure | Chemical Name | [M + H]+ |
|---|---|---|---|
| 629 | 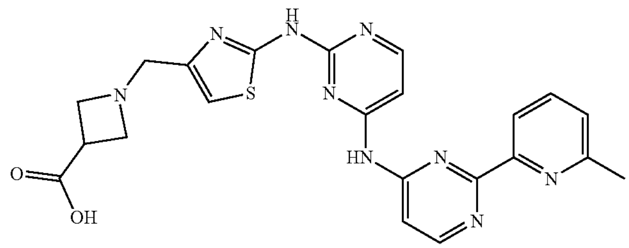 [SMILES: Cc1cccc(-c2nccc(Nc3ccnc(Nc4nc(CN5CC(C(=O)O)C5)cs4)n3)n2)n1] | 1-[[2-[[4-[[2-(6-methyl-2-pyridyl)pyrimidin-4-yl]amino]pyrimidin-2-yl]amino]thiazol-4-yl]methyl]azetidine-3-carboxylic acid | 476.1 |
| 630 | 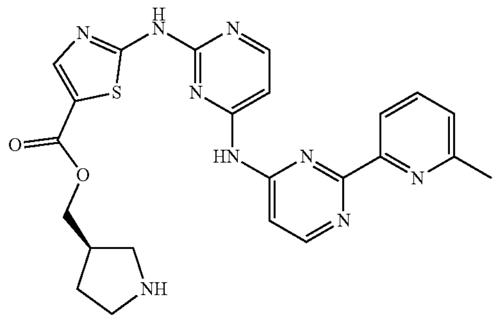 [SMILES: Cc1cccc(-c2nccc(Nc3ccnc(Nc4ncc(C(=O)OC[C@@H]5CCNC5)s4)n3)n2)n1] | [(3R)-pyrrolidin-3-yl]methyl 2-[[4-[[2-(6-methyl-2-pyridyl)pyrimidin-4-yl]amino]pyrimidin-2-yl]amino]thiazole-5-carboxylate | 490.1 |
| 631 | 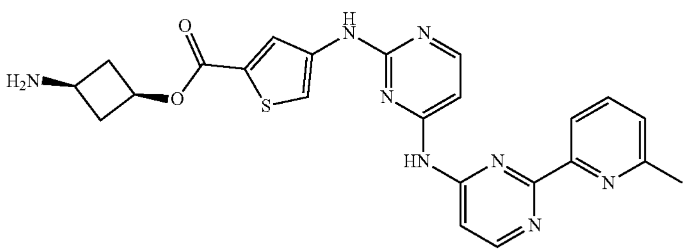 [SMILES: Cc1cccc(-c2nccc(Nc3ccnc(Nc4csc(C(=O)O[C@H]5C[C@@H](N)C5)c4)n3)n2)n1] | (3-aminocyclobutyl) 4-[[4-[[2-(6-methyl-2-pyridyl)pyrimidin-4-yl]amino]pyrimidin-2-yl]amino]thiophene-2-carboxylate | 475.1 |
| 632 | 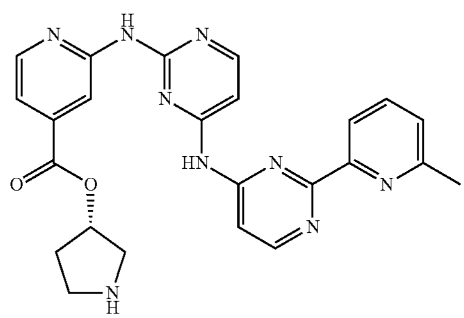 [SMILES: Cc1cccc(-c2nccc(Nc3ccnc(Nc4cc(C(=O)O[C@H]5CCNC5)ccn4)n3)n2)n1] | [(3S)-pyrrolidin-3-yl] 2-[[4-[[2-(6-methyl-2-pyridyl)pyrimidin-4-yl]amino]pyrimidin-2-yl]amino]pyridine-4-carboxylate | 470.1 |
| 633 | 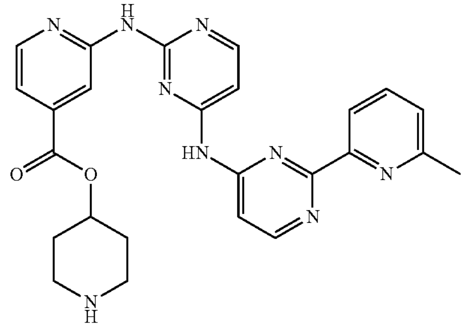 [SMILES: Cc1cccc(-c2nccc(Nc3ccnc(Nc4cc(C(=O)OC5CCNCC5)ccn4)n3)n2)n1] | 4-piperidyl 2-[[4-[[2-(6-methyl-2-pyridyl)pyrimidin-4-yl]amino]pyrimidin-2-yl]amino]pyridine-4-carboxylate | 484.1 |

TABLE 1-continued

| No. | Structure | Chemical Name | [M + H]+ |
|---|---|---|---|
| 634 | 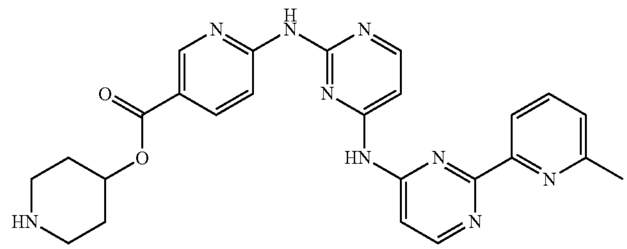 [SMILES: Cc1cccc(-c2nccc(Nc3ccnc(Nc4ccc(C(=O)OC5CCNCC5)cn4)n3)n2)n1] | 4-piperidyl 6-[[4-[[2-(6-methyl-2-pyridyl)pyrimidin-4-yl]amino]pyrimidin-2-yl]amino]pyridine-3-carboxylate | 484.2 |
| 635 | 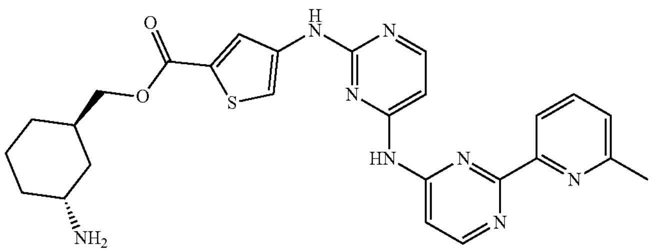 [SMILES: Cc1cccc(-c2nccc(Nc3ccnc(Nc4csc(C(=O)OC[C@@H]5CCC[C@@H](N)C5)c4)n3)n2)n1] | [(1R,3R)-3-aminocyclohexyl]methyl 4-[[4-[[2-(6-methyl-2-pyridyl)pyrimidin-4-yl]amino]pyrimidin-2-yl]amino]thiophene-2-carboxylate | 517.1 |
| 636 | 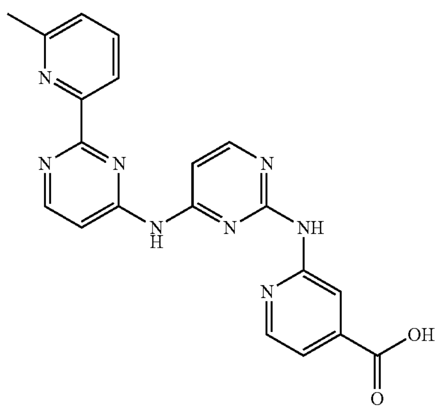 [SMILES: Cc1cccc(-c2nccc(Nc3ccnc(Nc4cc(C(=O)O)ccn4)n3)n2)n1] | 2-[[4-[[2-(6-methyl-2-pyridyl)pyrimidin-4-yl]amino]pyrimidin-2-yl]amino]pyridine-4-carboxylic acid | 401.2 |
| 637 | 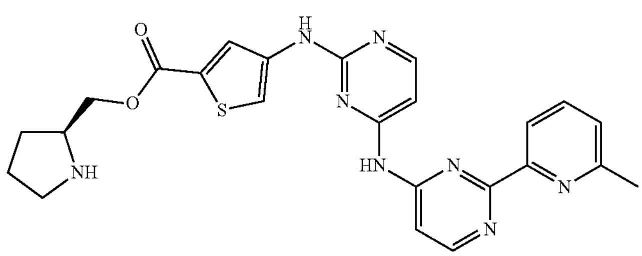 [SMILES: Cc1cccc(-c2nccc(Nc3ccnc(Nc4csc(C(=O)OC[C@@H]5CCCN5)c4)n3)n2)n1] | [(2S)-pyrrolidin-2-yl]methyl 4-[[4-[[2-(6-methyl-2-pyridyl)pyrimidin-4-yl]amino]pyrimidin-2-yl]amino]thiophene-2-carboxylate | 489.1 |
| 638 | 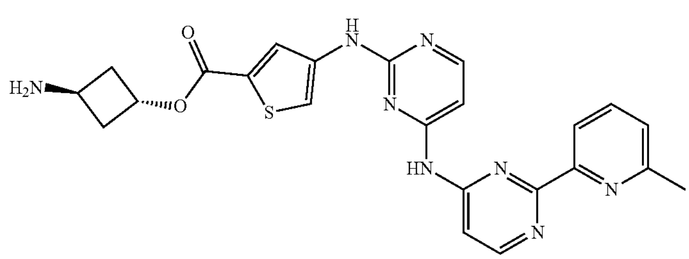 [SMILES: Cc1cccc(-c2nccc(Nc3ccnc(Nc4csc(C(=O)O[C@H]5C[C@H](N)C5)c4)n3)n2)n1] | (3-aminocyclobutyl) 4-[[4-[[2-(6-methyl-2-pyridyl)pyrimidin-4-yl]amino]pyrimidin-2-yl]amino]thiophene-2-carboxylate | 475.1 |

TABLE 1-continued

| No. | Structure | Chemical Name | [M + H]+ |
|---|---|---|---|
| 639 | 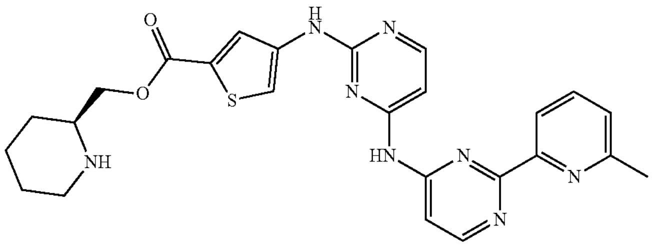 [SMILES: Cc1cccc(-c2nccc(Nc3ccnc(Nc4csc(C(=O)OC[C@@H]5CCCCN5)c4)n3)n2)n1] | [(2S)-2-piperidyl]methyl 4-[[4-[[2-(6-methyl-2-pyridyl)pyrimidin-4-yl]amino]pyrimidin-2-yl]amino]thiophene-2-carboxylate | 503.1 |
| 640 | 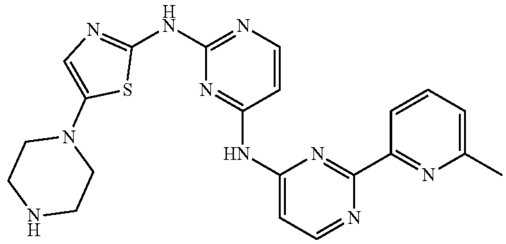 [SMILES: Cc1cccc(-c2nccc(Nc3ccnc(Nc4ncc(N5CCNCC5)s4)n3)n2)n1] | N4-[2-(6-methyl-2-pyridyl)pyrimidin-4-yl]-N2-(5-piperazin-1-ylthiazol-2-yl)pyrimidine-2,4-diamine | 447.2 |
| 641 | 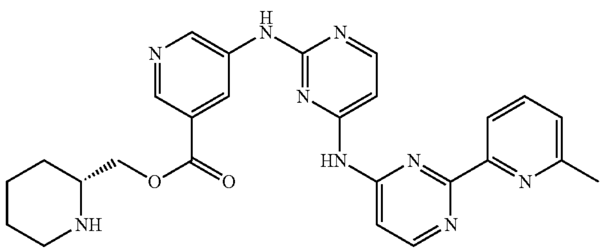 [SMILES: Cc1cccc(-c2nccc(Nc3ccnc(Nc4cncc(C(=O)OC[C@H]5CCCCN5)c4)n3)n2)n1] | [(2R)-2-piperidyl]methyl 5-[[4-[[2-(6-methyl-2-pyridyl)pyrimidin-4-yl]amino]pyrimidin-2-yl]amino]pyridine-3-carboxylate | 498.2 |
| 642 | 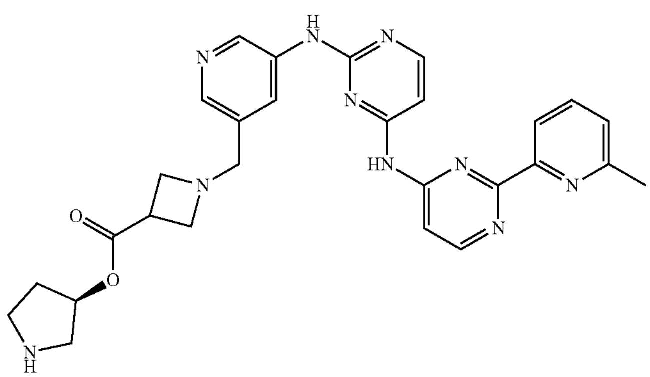 [SMILES: Cc1cccc(-c2nccc(Nc3ccnc(Nc4cncc(CN5CC(C(=O)O[C@@H]6CCNC6)C5)c4)n3)n2)n1] | [(3R)-pyrrolidin-3-yl] 1-[[5-[[4-[[2-(6-methyl-2-pyridyl)pyrimidin-4-yl]amino]pyrimidin-2-yl]amino]-3-pyridyl]methyl]azetidine-3-carboxylate | 539.2 |

In some embodiments, exemplary compounds may include, but are not limited to, a compound or salt thereof selected from Table 2.

TABLE 2

| No. | Structure | Chemical Name | [M + H]+ |
|---|---|---|---|
| 1000 | 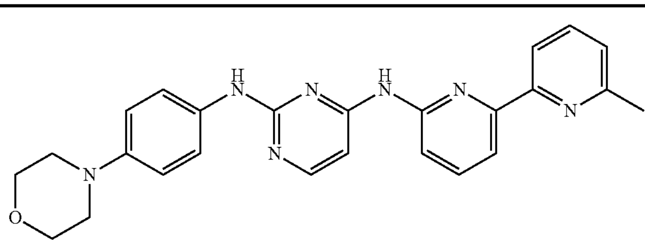 | N4-[6-(6-methyl-2-pyridyl)-2-pyridyl]-N2-(4-morpholinophenyl)pyrimidine-2,4-diamine | 440.1 |

TABLE 2-continued

| No. | Structure | Chemical Name | [M + H]+ |
|---|---|---|---|
| 1001 | 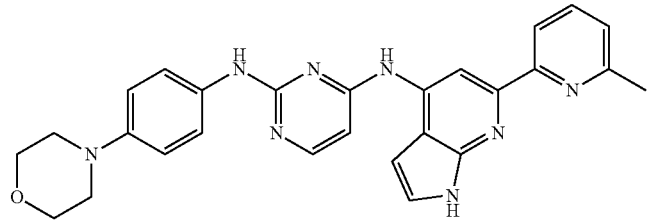 [SMILES: Cc1cccc(-c2cc(Nc3ccnc(Nc4ccc(N5CCOCC5)cc4)n3)c3cc[nH]c3n2)n1] | N4-[6-(6-methyl-2-pyridyl)-1H-pyrrolo[2,3-b]pyridin-4-yl]-N2-(4-morpholinophenyl)pyrimidine-2,4-diamine | 479.3 |
| 1002 | 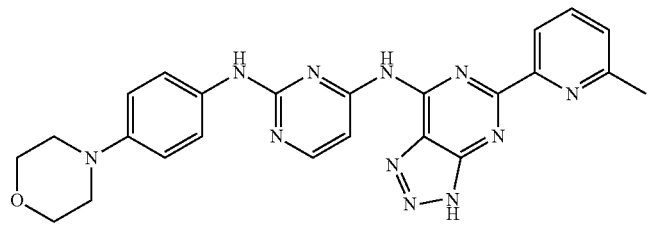 [SMILES: Cc1cccc(-c2nc(Nc3ccnc(Nc4ccc(N5CCOCC5)cc4)n3)c3nn[nH]c3n2)n1] | N4-[5-(6-methyl-2-pyridyl)-3H-triazolo[4,5-d]pyrimidin-7-yl]-N2-(4-morpholinophenyl)pyrimidine-2,4-diamine | 482.1 |
| 1003 | 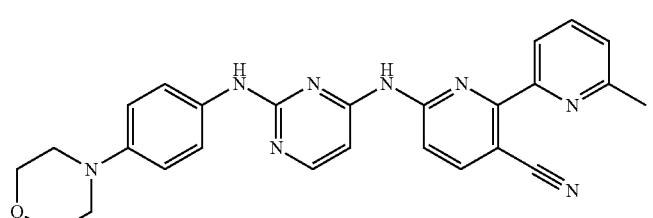 | 2-(6-methyl-2-pyridyl)-6-[[2-(4-morpholinoanilino)pyrimidin-4-yl]amino]pyridine-3-carbonitrile | 465.2 |
| 1004 | 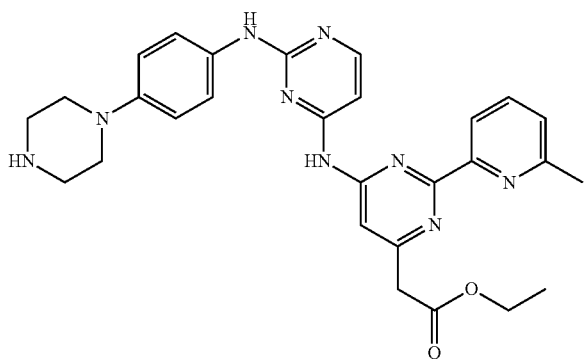 [SMILES: CCOC(=O)Cc1cc(Nc2ccnc(Nc3ccc(N4CCNCC4)cc3)n2)nc(-c2cccc(C)n2)n1] | ethyl 2-[2-(6-methyl-2-pyridyl)-6-[[2-(4-piperazin-1-ylanilino)pyrimidin-4-yl]amino]pyrimidin-4-yl]acetate | 526.1 |
| 1005 | 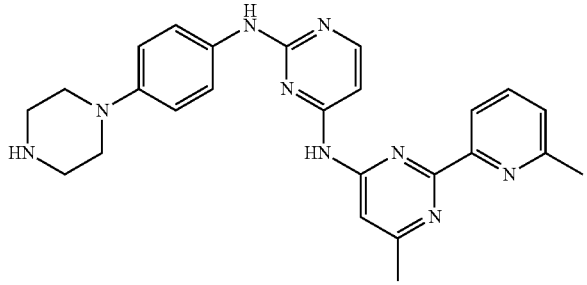 [SMILES: Cc1cccc(-c2nc(C)cc(Nc3ccnc(Nc4ccc(N5CCNCC5)cc4)n3)n2)n1] | N4-[6-methyl-2-(6-methyl-2-pyridyl)pyrimidin-4-yl]-N2-(4-piperazin-1-ylphenyl)pyrimidine-2,4-diamine | 454.2 |

TABLE 2-continued

| No. | Structure | Chemical Name | [M + H]⁺ |
|---|---|---|---|
| 1006 | 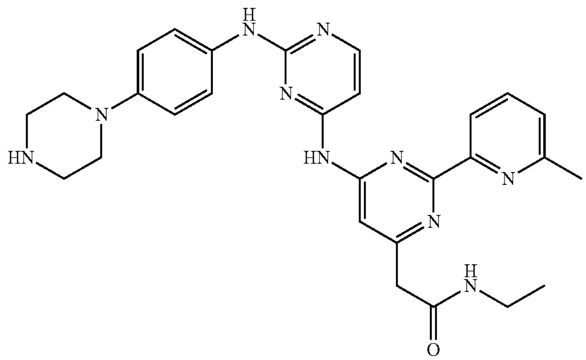 [SMILES: CCNC(=O)Cc1cc(Nc2ccnc(Nc3ccc(N4CCNCC4)cc3)n2)nc(-c2cccc(C)n2)n1] | N-ethyl-2-[2-(6-methyl-2-pyridyl)-6-[[2-(4-piperazin-1-ylanilino)pyrimidin-4-yl]amino]pyrimidin-4-yl]acetamide | 525.1 |
| 1007 | 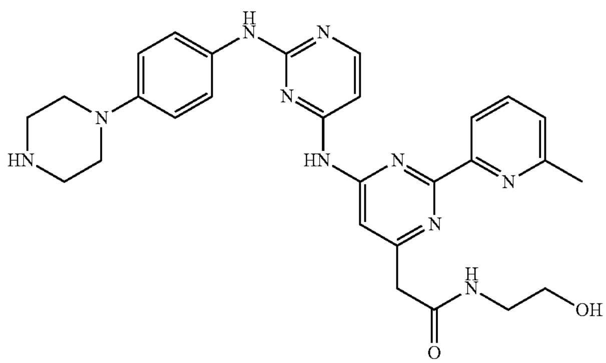 [SMILES: Cc1cccc(-c2nc(CC(=O)NCCO)cc(Nc3ccnc(Nc4ccc(N5CCNCC5)cc4)n3)n2)n1] | N-(2-hydroxyethyl)-2-[2-(6-methyl-2-pyridyl)-6-[[2-(4-piperazin-1-ylanilino)pyrimidin-4-yl]amino]pyrimidin-4-yl]acetamide | 541.1 |
| 1008 | 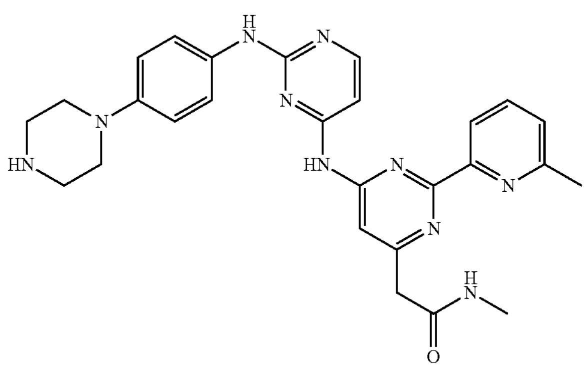 [SMILES: CNC(=O)Cc1cc(Nc2ccnc(Nc3ccc(N4CCNCC4)cc3)n2)nc(-c2cccc(C)n2)n1] | N-methyl-2-[2-(6-methyl-2-pyridyl)-6-[[2-(4-piperazin-1-ylanilino)pyrimidin-4-yl]amino]pyrimidin-4-yl]acetamide | 511.2 |
| 1009 | 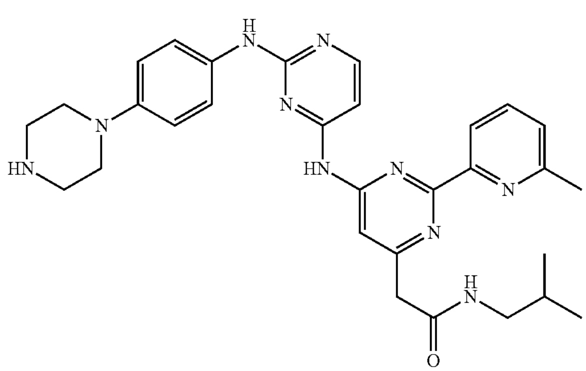 [SMILES: Cc1cccc(-c2nc(CC(=O)NCC(C)C)cc(Nc3ccnc(Nc4ccc(N5CCNCC5)cc4)n3)n2)n1] | N-isobutyl-2-[2-(6-methyl-2-pyridyl)-6-[[2-(4-piperazin-1-ylanilino)pyrimidin-4-yl]amino]pyrimidin-4-yl]acetamide | 553.2 |

TABLE 2-continued

| No. | Structure | Chemical Name | [M + H]⁺ |
|---|---|---|---|
| 1010 | 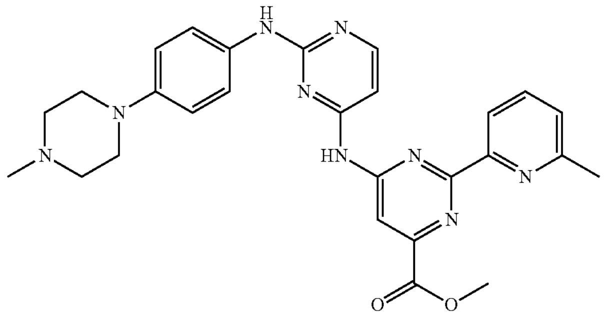 | methyl 6-[[2-[4-(4-methylpiperazin-1-yl)anilino]pyrimidin-4-yl]amino]-2-(6-methyl-2-pyridyl)pyrimidine-4-carboxylate | 512.2 |
| 1011 | 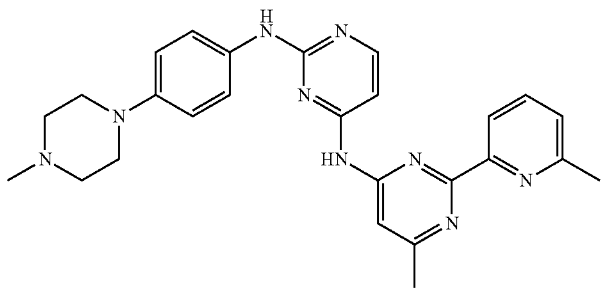 | N4-[6-methyl-2-(6-methyl-2-pyridyl)pyrimidin-4-yl]-N2-[4-(4-methylpiperazin-1-yl)phenyl]pyrimidine-2,4-diamine | 468.1 |
| 1012 | 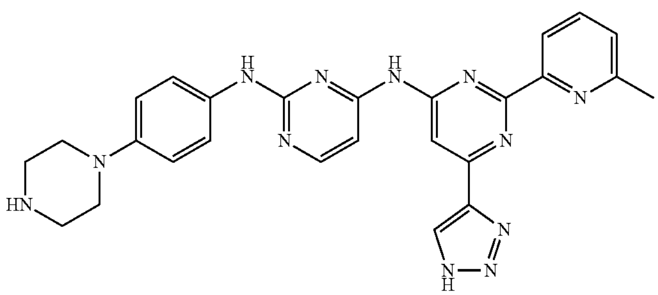 [SMILES: Cc1cccc(-c2nc(Nc3ccnc(Nc4ccc(N5CCNCC5)cc4)n3)cc(-c3c[nH]nn3)n2)n1] | N4-[2-(6-methyl-2-pyridyl)-6-(1H-triazol-4-yl)pyrimidin-4-yl]-N2-(4-piperazin-1-ylphenyl)pyrimidine-2,4-diamine | 507.2 |
| 1013 | 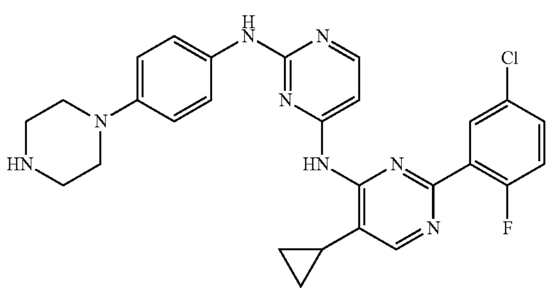 [SMILES: Fc1ccc(Cl)cc1-c1ncc(C2CC2)c(Nc2ccnc(Nc3ccc(N4CCNCC4)cc3)n2)n1] | N4-[2-(5-chloro-2-fluoro-phenyl)-5-cyclopropyl-pyrimidin-4-yl]-N2-(4-piperazin-1-ylphenyl)pyrimidine-2,4-diamine | 517.1 |
| 1014 | 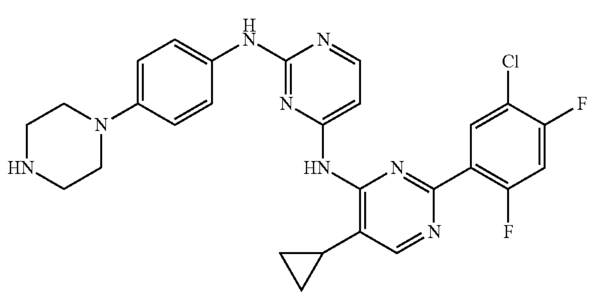 [SMILES: Fc1cc(F)c(-c2ncc(C3CC3)c(Nc3ccnc(Nc4ccc(N5CCNCC5)cc4)n3)n2)cc1Cl] | N4-[2-(5-chloro-2,4-difluoro-phenyl)-5-cyclopropyl-pyrimidin-4-yl]-N2-(4-piperazin-1-ylphenyl)pyrimidine-2,4-diamine | 535.1 |

TABLE 2-continued

| No. | Structure | Chemical Name | [M + H]+ |
|---|---|---|---|
| 1015 | 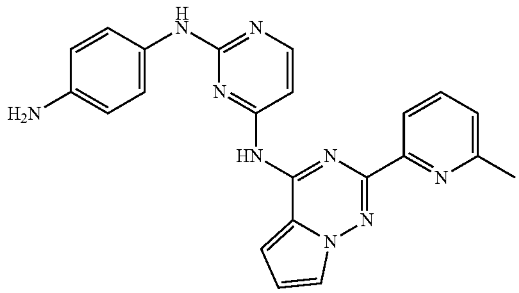 [SMILES: Cc1cccc(-c2nc(Nc3ccnc(Nc4ccc(N)cc4)n3)c3cccn3n2)n1] | N2-(4-aminophenyl)-N4-[2-(6-methyl-2-pyridyl)pyrrolo[2,1-f][1,2,4]triazin-4-yl]pyrimidine-2,4-diamine | 410.1 |
| 1016 | 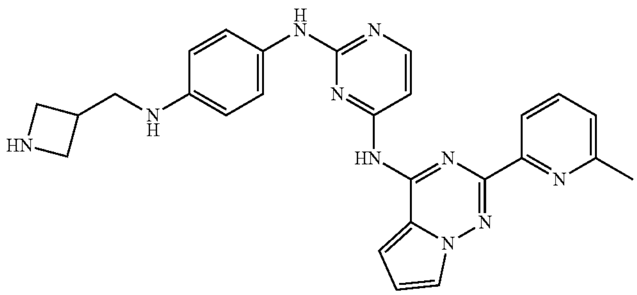 [SMILES: Cc1cccc(-c2nc(Nc3ccnc(Nc4ccc(NCC5CNC5)cc4)n3)c3cccn3n2)n1] | N2-[4-(azetidin-3-ylmethylamino)phenyl]-N4-[2-(6-methyl-2-pyridyl)pyrrolo[2,1-f][1,2,4]triazin-4-yl]pyrimidine-2,4-diamine | 479.1 |
| 1017 | 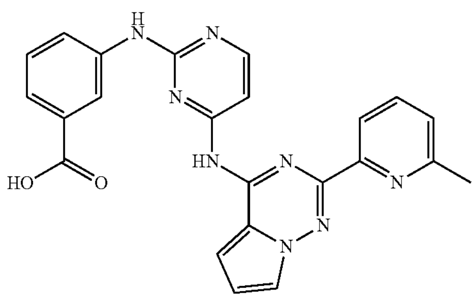 [SMILES: Cc1cccc(-c2nc(Nc3ccnc(Nc4cccc(C(=O)O)c4)n3)c3cccn3n2)n1] | 3-[[4-[[2-(6-methyl-2-pyridyl)pyrrolo[2,1-f][1,2,4]triazin-4-yl]amino]pyrimidin-2-yl]amino]benzoic acid | 439.1 |
| 1018 | 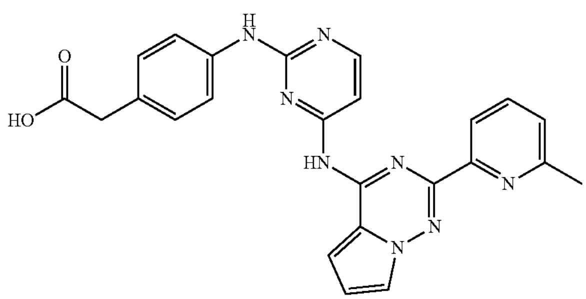 [SMILES: Cc1cccc(-c2nc(Nc3ccnc(Nc4ccc(CC(=O)O)cc4)n3)c3cccn3n2)n1] | 2-[4-[[4-[[2-(6-methyl-2-pyridyl)pyrrolo[2,1-f][1,2,4]triazin-4-yl]amino]pyrimidin-2-yl]amino]phenyl]acetic acid | 453.2 |
| 1019 | 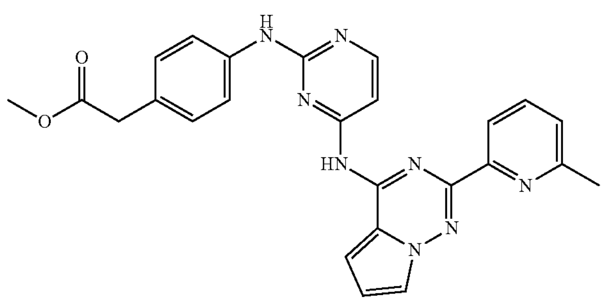 | methyl 2-[4-[[4-[[2-(6-methyl-2-pyridyl)pyrrolo[2,1-f][1,2,4]triazin-4-yl]amino]pyrimidin-2-yl]amino]phenyl]acetate | 467.1 |

TABLE 2-continued

| No. | Structure | Chemical Name | [M + H]+ |
|---|---|---|---|
| 1020 | 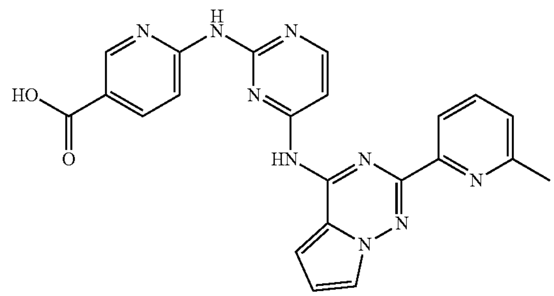 [SMILES: Cc1cccc(-c2nc(Nc3ccnc(Nc4ccc(C(=O)O)cn4)n3)c3cccn3n2)n1] | 6-[[4-[[2-(6-methyl-2-pyridyl)pyrrolo[2,1-f]]1,2,4]triazin-4-yl]amino]pyrimidin-2-yl]amino]pyridine-3-carboxylic acid | 440.0 |
| 1021 | 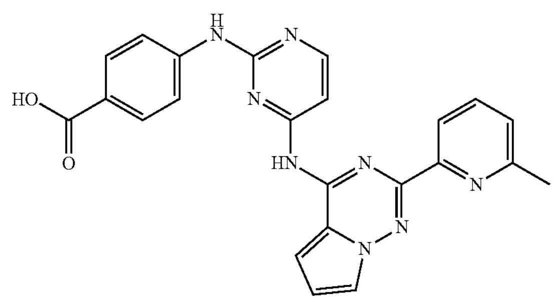 [SMILES: Cc1cccc(-c2nc(Nc3ccnc(Nc4ccc(C(=O)O)cc4)n3)c3cccn3n2)n1] | 4-[[4-[[2-(6-methyl-2-pyridyl)pyrrolo[2,1-f][1,2,4]triazin-4-yl]amino]pyrimidin-2-yl]amino]benzoic acid | 439.1 |
| 1022 | 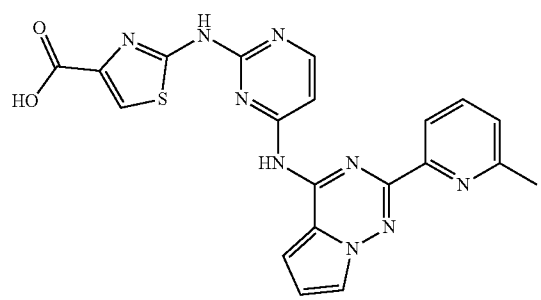 [SMILES: Cc1cccc(-c2nc(Nc3ccnc(Nc4nc(C(=O)O)cs4)n3)c3cccn3n2)n1] | 2-[[4-[[2-(6-methyl-2-pyridyl)pyrrolo[2,1-f][1,2,4]triazin-4-yl]amino]pyrimidin-2-yl]amino]thiazole-4-carboxylic acid | 446.0 |
| 1023 | 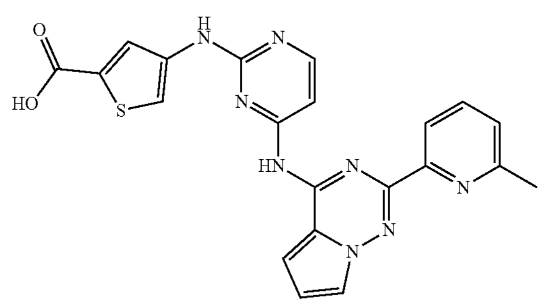 [SMILES: Cc1cccc(-c2nc(Nc3ccnc(Nc4csc(C(=O)O)c4)n3)c3cccn3n2)n1] | 4-[[4-[[2-(6-methyl-2-pyridyl)pyrrolo[2,1-f][1,2,4]triazin-4-yl]amino]pyrimidin-2-yl]amino]thiophene-2-carboxylic acid | 445.0 |
| 1024 | 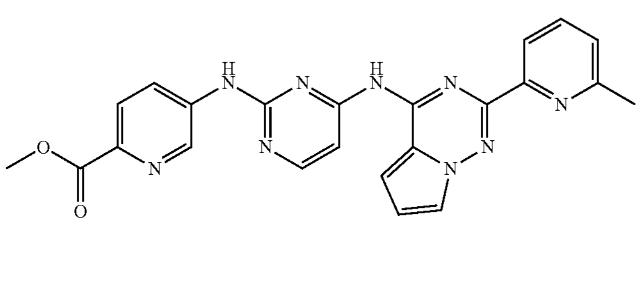 | methyl 5-[[4-[[2-(6-methyl-2-pyridyl)pyrrolo[2,1-f][1,2,4]triazin-4-yl]amino]pyrimidin-2-yl]amino]pyridine-2-carboxylate | 454.0 |

TABLE 2-continued

| No. | Structure | Chemical Name | [M + H]+ |
|---|---|---|---|
| 1025 | 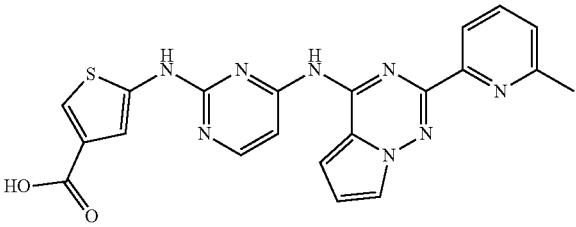 [SMILES: Cc1cccc(-c2nc(Nc3ccnc(Nc4cc(C(=O)O)cs4)n3)c3cccn3n2)n1] | 5-[[4-[[2-(6-methyl-2-pyridyl)pyrrolo[2,1-f][1,2,4]triazin-4-yl]amino]pyrimidin-2-yl]amino]thiophene-3-carboxylic acid | 444.9 |
| 1026 | 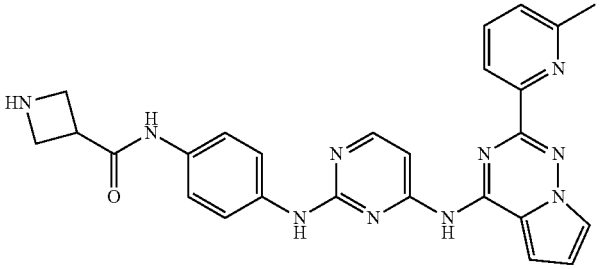 [SMILES: Cc1cccc(-c2nc(Nc3ccnc(Nc4ccc(NC(=O)C5CNC5)cc4)n3)c3cccn3n2)n1] | N-[4-[[4-[[2-(6-methyl-2-pyridyl)pyrrolo[2,1-f][1,2,4]triazin-4-yl]amino]pyrimidin-2-yl]amino]phenyl]azetidine-3-carboxamide | 493.1 |
| 1027 | 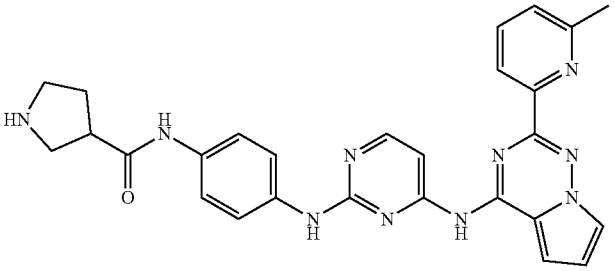 [SMILES: Cc1cccc(-c2nc(Nc3ccnc(Nc4ccc(NC(=O)C5CCNC5)cc4)n3)c3cccn3n2)n1] | N-[4-[[4-[[2-(6-methyl-2-pyridyl)pyrrolo[2,1-f][1,2,4]triazin-4-yl]amino]pyrimidin-2-yl]amino]phenyl]pyrrolidine-3-carboxamide | 507.1 |
| 1028 | 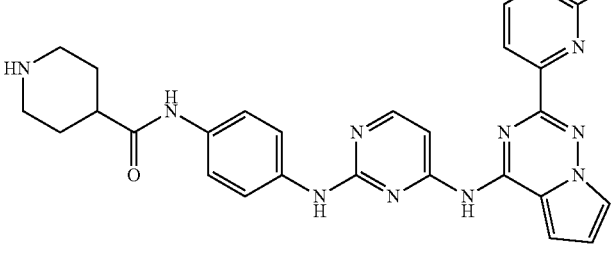 | N-[4-[[4-[[2-(6-methyl-2-pyridyl)pyrrolo[2,1-f][1,2,4]triazin-4-yl]amino]pyrimidin-2-yl]amino]phenyl]piperidine-4-carboxamide | 521.2 |
| 1029 | 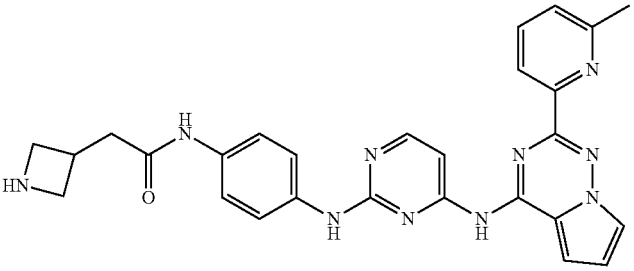 [SMILES: Cc1cccc(-c2nc(Nc3ccnc(Nc4ccc(NC(=O)CC5CNC5)cc4)n3)c3cccn3n2)n1] | 2-(azetidin-3-yl)-N-[4-[[4-[[2-(6-methyl-2-pyridyl)pyrrolo[2,1-f][1,2,4]triazin-4-yl]amino]pyrimidin-2-yl]amino]phenyl]acetamide | 507.1 |

TABLE 2-continued

| No. | Structure | Chemical Name | [M + H]+ |
|---|---|---|---|
| 1030 | 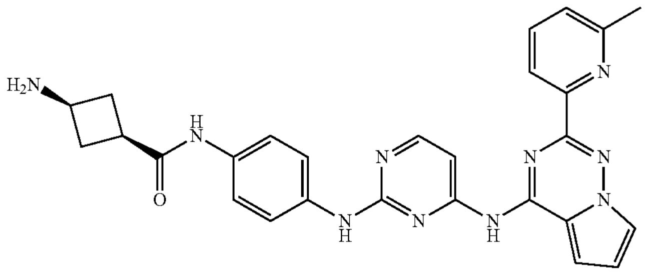 [SMILES: Cc1cccc(-c2nc(Nc3ccnc(Nc4ccc(NC(=O)[C@H]5C[C@@H](N)C5)cc4)n3)c3cccn3n2)n1] | 3-amino-N-[4-[[4-[[2-(6-methyl-2-pyridyl)pyrrolo[2,1-f][1,2,4]triazin-4-yl]amino]pyrimidin-2-yl]amino]phenyl]cyclobutanecarboxamide | 507.1 |
| 1031 | 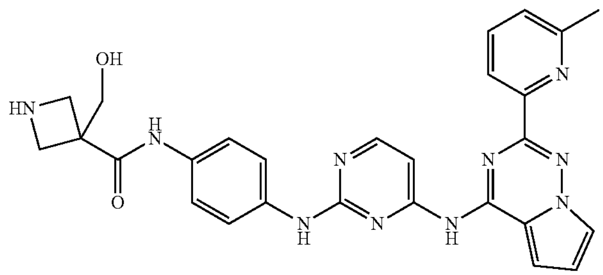 [SMILES: Cc1cccc(-c2nc(Nc3ccnc(Nc4ccc(NC(=O)C5(CO)CNC5)cc4)n3)c3cccn3n2)n1] | 3-(hydroxymethyl)-N-[4-[[4-[[2-(6-methyl-2-pyridyl)pyrrolo[2,1-f][1,2,4]triazin-4-yl]amino]pyrimidin-2-yl]amino]phenyl]azetidine-3-carboxamide | 523.1 |
| 1032 | 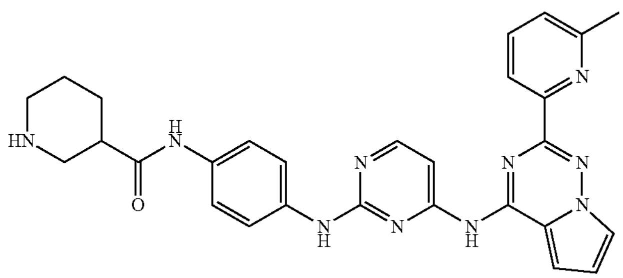 [SMILES: Cc1cccc(-c2nc(Nc3ccnc(Nc4ccc(NC(=O)C5CCCNC5)cc4)n3)c3cccn3n2)n1] | N-[4-[[4-[[2-(6-methyl-2-pyridyl)pyrrolo[2,1-f][1,2,4]triazin-4-yl]amino]pyrimidin-2-yl]amino]phenyl]piperidine-3-carboxamide | 521.2 |
| 1033 | 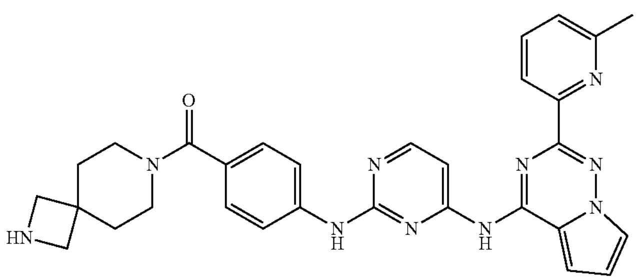 [SMILES: Cc1cccc(-c2nc(Nc3ccnc(Nc4ccc(C(=O)N5CCC6(CC5)CNC6)cc4)n3)c3cccn3n2)n1] | 2,7-diazaspiro[3.5]nonan-7-yl-[4-[[4-[[2-(6-methyl-2-pyridyl)pyrrolo[2,1-f][1,2,4]triazin-4-yl]amino]pyrimidin-2-yl]amino]phenyl]methanone | 547.1 |
| 1034 | 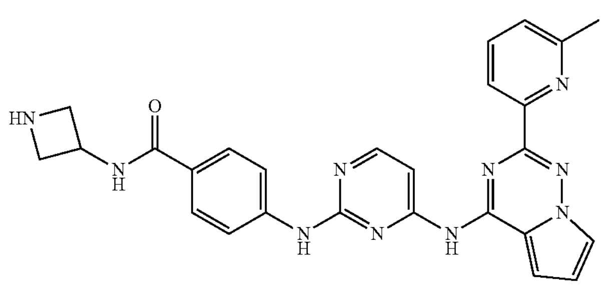 [SMILES: Cc1cccc(-c2nc(Nc3ccnc(Nc4ccc(C(=O)NC5CNC5)cc4)n3)c3cccn3n2)n1] | N-(azetidin-3-yl)-4-[[4-[[2-(6-methyl-2-pyridyl)pyrrolo[2,1-f][1,2,4]triazin-4-yl]amino]pyrimidin-2-yl]amino]benzamide | 493.0 |

TABLE 2-continued

| No. | Structure | Chemical Name | [M + H]+ |
|---|---|---|---|
| 1035 | 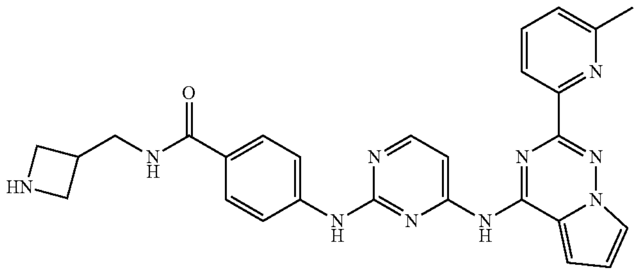 | N-(azetidin-3-ylmethyl)-4-[[4-[[2-(6-methyl-2-pyridyl)pyrrolo[2,1-f][1,2,4]triazin-4-yl]amino]pyrimidin-2-yl]amino]benzamide | 507.1 |
| 1036 | 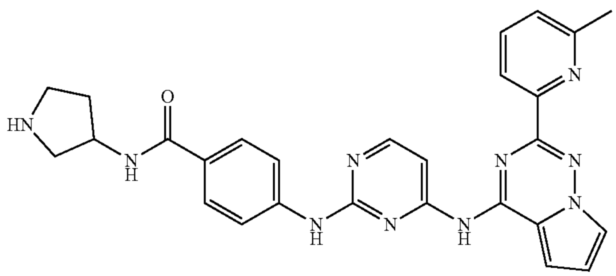 [SMILES: Cc1cccc(-c2nc(Nc3ccnc(Nc4ccc(C(=O)NC5CCNC5)cc4)n3)c3cccn3n2)n1] | 4-[[4-[[2-(6-methyl-2-pyridyl)pyrrolo[2,1-f][1,2,4]triazin-4-yl]amino]pyrimidin-2-yl]amino]-N-pyrrolidin-3-yl-benzamide | 507.1 |
| 1037 | 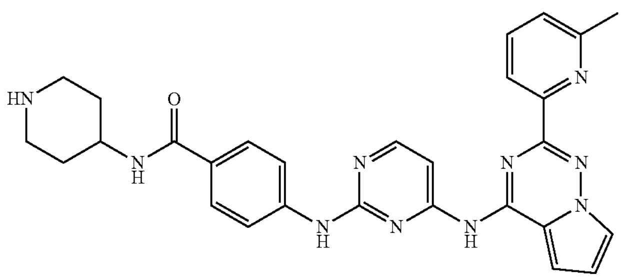 [SMILES: Cc1cccc(-c2nc(Nc3ccnc(Nc4ccc(C(=O)NC5CCNCC5)cc4)n3)c3cccn3n2)n1] | 4-[[4-[[2-(6-methyl-2-pyridyl)pyrrolo[2,1-f][1,2,4]triazin-4-yl]amino]pyrimidin-2-yl]amino]-N-(4-piperidyl)benzamide | 521.1 |
| 1038 | 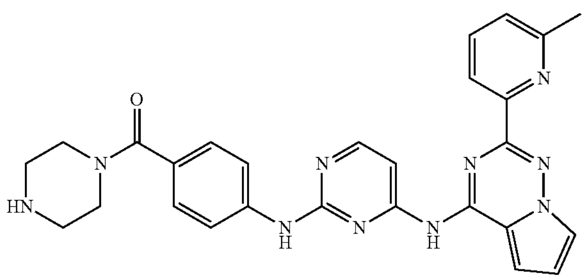 [SMILES: Cc1cccc(-c2nc(Nc3ccnc(Nc4ccc(C(=O)N5CCNCC5)cc4)n3)c3cccn3n2)n1] | [4-[[4-[[2-(6-methyl-2-pyridyl)pyrrolo[2,1-f][1,2,4]triazin-4-yl]amino]pyrimidin-2-yl]amino]phenyl]-piperazin-1-yl-methanone | 507.0 |
| 1039 | 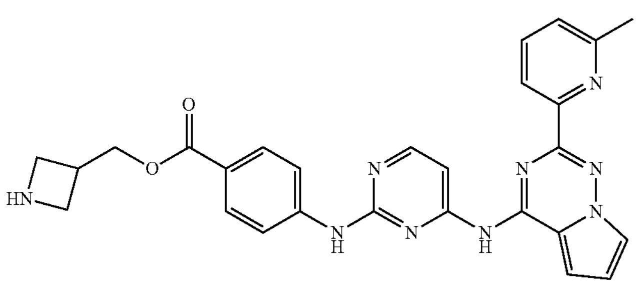 [SMILES: Cc1cccc(-c2nc(Nc3ccnc(Nc4ccc(C(=O)OCC5CNC5)cc4)n3)c3cccn3n2)n1] | azetidin-3-ylmethyl 4-[[4-[[2-(6-methyl-2-pyridyl)pyrrolo[2,1-f][1,2,4]triazin-4-yl]amino]pyrimidin-2-yl]amino]benzoate | 508.1 |

TABLE 2-continued

| No. | Structure | Chemical Name | [M + H]+ |
|---|---|---|---|
| 1040 | 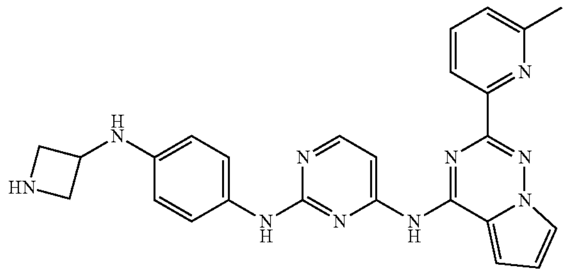 [SMILES: Cc1cccc(-c2nc(Nc3ccnc(Nc4ccc(NC5CNC5)cc4)n3)c3cccn3n2)n1] | N2-[4-(azetidin-3-ylamino)phenyl]-N4-[2-(6-methyl-2-pyridyl)pyrrolo[2,1-f][1,2,4]triazin-4-yl]pyrimidine-2,4-diamine | 465.1 |
| 1041 | 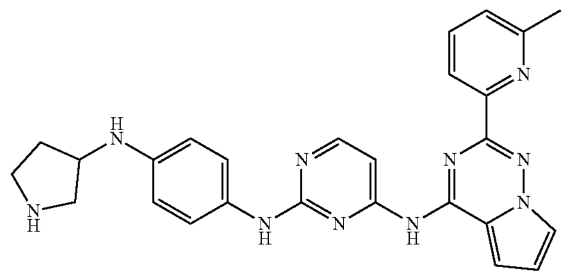 [SMILES: Cc1cccc(-c2nc(Nc3ccnc(Nc4ccc(NC5CCNC5)cc4)n3)c3cccn3n2)n1] | N4-[2-(6-methyl-2-pyridyl)pyrrolo[2,1-f][1,2,4]triazin-4-yl]-N2-[4-(pyrrolidin-3-ylamino)phenyl]pyrimidine-2,4-diamine | 479.1 |
| 1042 | 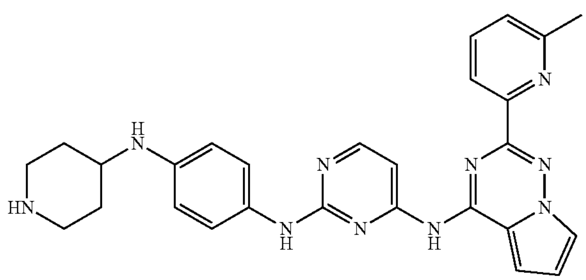 [SMILES: Cc1cccc(-c2nc(Nc3ccnc(Nc4ccc(NC5CCNCC5)cc4)n3)c3cccn3n2)n1] | N4-[2-(6-methyl-2-pyridyl)pyrrolo[2,1-f][1,2,4]triazin-4-yl]-N2-[4-(4-piperidylamino)phenyl]pyrimidine-2,4-diamine | 493.1 |
| 1043 | 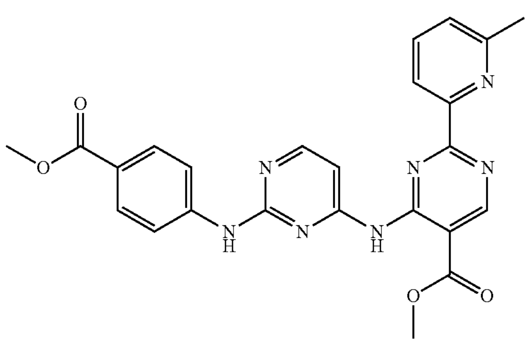 | methyl 4-[[2-(4-methoxycarbonylanilino)pyrimidin-4-yl]amino]-2-(6-methyl-2-pyridyl)pyrimidine-5-carboxylate | 472.0 |
| 1044 | 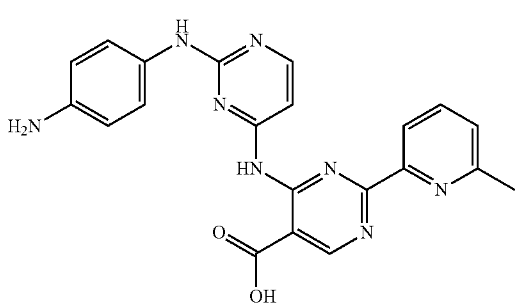 [SMILES: Cc1cccc(-c2ncc(C(=O)O)c(Nc3ccnc(Nc4ccc(N)cc4)n3)n2)n1] | 4-[[2-(4-aminoanilino)pyrimidin-4-yl]amino]-2-(6-methyl-2-pyridyl)pyrimidine-5-carboxylic acid | 415.0 |

TABLE 2-continued

| No. | Structure | Chemical Name | [M + H]⁺ |
|---|---|---|---|
| 1045 | 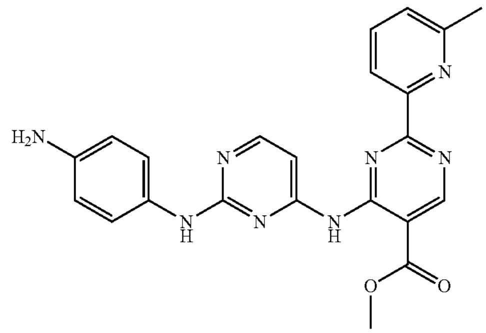 [SMILES: COC(=O)c1cnc(-c2cccc(C)n2)nc1Nc1ccnc(Nc2ccc(N)cc2)n1] | methyl 4-[[2-(4-aminoanilino)pyrimidin-4-yl]amino]-2-(6-methyl-2-pyridyl)pyrimidine-5-carboxylate | 429.0 |

Methods

In some aspects, the present disclosure provides a method of inhibiting TGFβ signaling, comprising contacting a cell with an effective amount of a compound disclosed herein, such as a compound of Formula (I), (I'), (I-A), (I'-A), (I-B), (I'-B), (I-C), (I'-C), (I-D), (I'-D), (I-E) or (I'-E). In some embodiments, the present disclosure provides a method of inhibiting ALK5, comprising contacting ALK5 with an effective amount of a compound disclosed herein. Inhibition of ALK5 or TGFβ signaling can be assessed by a variety of methods known in the art. Non-limiting examples include a showing of (a) a decrease in kinase activity of ALK5; (b) a decrease in binding affinity between the TGFβ/TGFβ-RII complex and ALK5; (c) a decrease in the levels of phosphorylated intracellular signaling molecules downstream in the TGFβ signaling pathway, such as a decrease in pSMAD2 or pSMAD3 levels; (d) a decrease in binding of ALK5 to downstream signaling molecules, such as SMAD2 and SMAD3; and/or (e) an increase in ATP levels or a decrease in ADP levels. Kits and commercially available assays can be utilized for determining one or more of the above.

In some aspects, the present disclosure provides a method of treating an ALK5-mediated disease or condition in a subject, comprising administering to the subject a therapeutically effective amount of a compound disclosed herein. In some embodiments, the disease or condition is selected from fibrosis and cancer. In some embodiments, the disease or condition is pulmonary fibrosis, such as idiopathic pulmonary fibrosis or virus-induced fibrosis. In some embodiments, the disease or condition is intestinal fibrosis. In some embodiments, the disease or condition is alopecia. In some embodiments, the disease is a neurodegenerative disease, such as Alzheimer's disease. In some embodiments, the present disclosure provides a method of reversing symptoms of aging. For example, the method may enhance neurogenesis, reduce neuroinflammation, improve cognitive performance, regenerate liver tissue, and reduce p16 levels.

In some aspects, the present disclosure provides a method of treating fibrosis, comprising administering to a patient an effective amount of a compound disclosed herein. In some embodiments, the fibrosis is mediated by ALK5. In some embodiments, the fibrosis is selected from systemic sclerosis, systemic fibrosis, organ-specific fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis. In some embodiments, the fibrosis is pulmonary fibrosis, such as idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis or chemotherapy-induced lung fibrosis. In some embodiments, the fibrosis is idiopathic pulmonary fibrosis (IPF). In some embodiments, the fibrosis is TGF-β-mediated pulmonary fibrosis. In some embodiments, the patient has been diagnosed with acute respiratory distress syndrome (ARDS). In some embodiments, the fibrosis is acute fibrosis. In some embodiments, the fibrosis is chronic fibrosis.

In some aspects, the present disclosure provides a method of treating pulmonary fibrosis induced by a viral infection, comprising administering to a patient an effective amount of a compound disclosed herein. The pulmonary fibrosis may be induced by an erythrovirus, a dependovirus, a papillomavirus, a polyomavirus, a mastadenovirus, an alphaherpesvirinae, a varicellovirus, a gammaherpesvirinae, a betaherpesvirinae, a roseolovirus, an orthopoxvirus, a parapoxvirus, a molluscipoxvirus, an orthohepadnavirus, an enterovirus, a rhinovirus, a hepatovirus, an aphthovirus, a calicivirus, an astrovirus, an alphavirus, a rubivirus, a flavivirus, a Hepatitis C virus, a reovirus, an orbivirus, a rotavirus, an influenzavirus A, an influenzavirus B, an influenzavirus C, a paramyxovirus, a morbillivirus, a rubulavirus, a pneumovirus, a vesiculovirus, a lyssavirus, a bunyavirus, a hantavirus, a nairovirus, a phlebovirus, a coronavirus, an arenavirus, a BLV-HTLV-retrovirus, a lentivirinae, a spumavinnae or a filovirus. In some embodiments, the fibrosis is virus-induced fibrosis, such as virus-induced pulmonary fibrosis. In some embodiments, the fibrosis is selected from EBV-induced pulmonary fibrosis, CMV-induced pulmonary fibrosis, herpesvirus-induced pulmonary fibrosis and coronavirus-induced pulmonary fibrosis. In some embodiments, the fibrosis is selected from EBV-induced pulmonary fibrosis, CMV-induced pulmonary fibrosis, HHV-6-induced pulmonary fibrosis, HHV-7-induced pulmonary fibrosis, HHV-8-induced pulmonary fibrosis, H5N1 virus-induced pulmonary fibrosis, SARS-CoV-induced pulmonary fibrosis, MERS-CoV-induced pulmonary fibrosis and SARS-CoV-2-induced pulmonary fibrosis. In some embodiments, the pulmonary fibrosis is coronavirus-induced pulmonary fibrosis. In some embodiments, the pulmonary fibrosis is SARS-CoV-2-induced pulmonary fibrosis. In some embodiments, the pulmonary fibrosis is COVID-19-induced pulmonary fibrosis.

In some aspects, the present disclosure provides a method of treating acute lung injury (ALI), comprising administering to a patient an effective amount of a compound disclosed herein. In some embodiments, the present disclosure provides a method of treating acute respiratory distress syndrome (ARDS), comprising administering to a patient an effective amount of a compound disclosed herein. The ARDS may be in the early acute injury phase or the fibroproliferative phase. In some embodiments, the ARDS is fibroproliferative ARDS. In some embodiments, the present disclosure provides a method of treating fibrosis resulting from ARDS, comprising administering to a patient an effective amount of a compound disclosed herein. The fibrosis resulting from ARDS may be pulmonary fibrosis. In some embodiments, the present disclosure provides a method of treating fibrosis resulting from ALI, comprising administering to a patient an effective amount of a compound disclosed herein. The fibrosis resulting from ALI may be pulmonary fibrosis.

In some aspects, the present disclosure provides a method of treating intestinal fibrosis, comprising administering to a patient an effective amount of a compound disclosed herein. In some embodiments, the intestinal fibrosis is mediated by ALK5. In some embodiments, the compound is administered in an amount effective to delay progression of, reduce the incidence of, or reduce the degree of one or more characteristics associated with intestinal fibrosis. In some embodiments, the compound is administered, either in a single dose or over multiple doses, in an amount effective to reverse established fibrosis.

In some aspects, the present disclosure provides a method of treating cancer, comprising administering to a patient an effective amount of a compound disclosed herein. In some embodiments, the cancer is mediated by ALK5. In some embodiments, the cancer is selected from breast cancer, colon cancer, prostate cancer, lung cancer, hepatocellular carcinoma, glioblastoma, melanoma and pancreatic cancer. In some embodiments, the cancer is lung cancer, such as non-small cell lung cancer. In some aspects, the present disclosure provides a method of treating cancer, such as non-small cell lung cancer, comprising administering to a patient an effective amount of a compound disclosed herein and an immunotherapeutic agent. In some embodiments, the cancer is stage III non-small cell lung cancer. In some embodiments, the method further comprises administering radiation to the patient. In some embodiments, the immunotherapeutic agent is a PD-1 inhibitor or a CTLA-4 inhibitor. In some embodiments, the immunotherapeutic agent is selected from atezolizumab, avelumab, nivolumab, pembrolizumab, durvalumab, BGB-A317, tremelimumab and ipilimumab. In some embodiments, the immunotherapeutic agent is selected from pembrolizumab and durvalumab.

The compounds described herein, including compounds of Formula (I), (I'), (I-A), (I'-A), (I-B), (I'-B), (I-C), (I'-C), (I-D), (I'-D), (I-E) or (I'-E), are ALK5 inhibitors that limit the activity of TGFβ. TGFβ is one of several factors involved in the initiation and development of fibrotic diseases throughout the body. As such, the compounds of the disclosure are expected to be useful for the treatment, prevention and/or reduction of fibrosis in a patient by administering a therapeutically effective amount of a compound disclosed herein. By inhibiting ALK5, the compound is expected to potentiate the formation of fibrosis in areas of the body that suffer from excessive deposition of the extracellular matrix. Those areas are described below.

Systemic Fibrotic Diseases

Systemic sclerosis (SSc) is an autoimmune disorder that affects the skin and internal organs and results in autoantibody production, vascular endothelial activation of small blood vessels, and tissue fibrosis as a result of fibroblast dysfunction. Transforming growth factor β (TGF-β) has been identified as a regulator of pathological fibrogenesis in SSc (Ayers, N. B., et al., *Journal of Biomedical Research*, 2018, 32(1), pp. 3-12). According to the authors, "understanding the essential role TGF-β pathways play in the pathology of systemic sclerosis could provide a potential outlet for treatment and a better understanding of this severe disease." In some embodiments, the present disclosure provides a method of treating SSc, comprising administering to a subject an effective amount of a compound disclosed herein.

Multifocal fibrosclerosis (MF) and idiopathic multifocal fibrosclerosis (IMF) are disorders characterized by fibrous lesions at varying sites and include retroperitoneal fibrosis, mediastinal fibrosis and Riedel's thyroiditis. Both multifocal fibrosclerosis and idiopathic multifocal fibrosclerosis are considered to be an outcome of $IgG_4$-associated fibrosis/disease and TGF-β is believed to be one factor involved in the initiation and development of fibrosis (Pardali, E., et. al., *Int. J. Mol. Sci.*, 18, 2157, pp. 1-22). In some embodiments, the present disclosure provides a method of treating multifocal fibrosclerosis or idiopathic multifocal fibrosclerosis, comprising administering to a subject an effective amount of a compound disclosed herein.

In some embodiments, the present disclosure provides a method of treating nephrogenic systemic fibrosis, comprising administering to a subject an effective amount of a compound disclosed herein. Nephrogenic systemic fibrosis is a rare disease occurring mainly in people with advanced kidney failure with or without dialysis. In a study performed by Kelly et al. (*J. Am. Acad. Dermatol.*, 2008, 58, 6, pp. 1025-1030), it was shown that TGF-β, as well as Smad 2/3, appear to be associated with fibrosis seen in nephrogenic systemic fibrosis.

Sclerodermatous graft-versus-host disease (GVHD) is a prevalent complication of allogeneic hematopoietic stem cell graft appearing two to three months after allogeneic bone marrow transplantation. The disease results in production of autoantibodies and fibrosis of skin and inner organs. Using a murine cutaneous GVHD model, it has been shown that progression of early skin and lung disease can be inhibited with TGF-β neutralizing antibodies (McCormick, L. L., et al., *J. Immunol.*, 1999, 163, pp. 5693-5699). In some embodiments, the present disclosure provides a method of treating sclerodermatous GVHD, comprising administering to a subject an effective amount of a compound disclosed herein.

Organ-Specific Fibrotic Diseases

Cardiac fibrosis refers to the abnormal thickening of heart valves due to the abnormal proliferation of cardiac fibroblasts resulting in excess deposition of ECM in heart muscle. Fibroblasts secrete collagen, which serves as structural support for the heart. However, when collagen is excessively secreted in the heart, wall and valve thickening can result in tissue build-up on the tricuspid and pulmonary valves. This in turn causes loss of flexibility and ultimately valvular dysfunction leading to heart failure. A specific type of cardiac fibrosis is hypertension-associated cardiac fibrosis as described by J. Diez (*J. Clin. Hypertens.*, 2007, July 9(7), pp. 546-550). According to Diez, changes in the composition of cardiac tissue develop in hypertensive patients with left ventricular hypertrophy and lead to structural remodeling of the heart tissue. One change relates to the disruption of the equilibrium between the synthesis and degradation of collagen types I and III molecules, resulting in excessive accumulation of collagen fibers in the heart tissue. Other types of cardiac fibrosis include post-myocardial infarction and Chagas disease-induced myocardial fibrosis. In Chagas disease, transforming growth factor β1 (TGF-β1) has been implicated in Chagas disease physiopathology, where animal models suggest that the TGF-β1-pathway is up-regulated during infection (Araujo-Jorge, T. C., et al., *Clin. Pharmacol. Ther.*, 2012, 92(5), pp. 613-621; Curvo, E., *Mem Inst Oswaldo Cruz*, 2018, Vol. 113(4), e170440, pp. 1-8). In some embodiments, the present disclosure provides a method of treating various forms of cardiac fibrosis, such as hypertension-associated cardiac fibrosis, post-myocardial infarction or Chagas disease-induced myocardial fibrosis, comprising administering to a subject an effective amount of a compound disclosed herein.

Renal fibrosis encompasses a variety of disorders associated with the aberrant expression and activity of TGF-β, including, but not limited to, diabetic and hypertensive nephropathy, urinary tract obstruction-induced kidney fibrosis, inflammatory/autoimmune-induced kidney fibrosis, aristolochic acid nephropathy, progressive kidney fibrosis, and polysystic kidney disease. As discussed above, fibrosis involves an excess accumulation of the ECM, which in turn causes loss of function when normal tissue is replaced with scar tissue (Wynn, T. A., J Clin Invest., 2007, 117, pp. 524-529). As early as 2005, ALK5 inhibitors were being studied in models for renal disease (Laping, N. J., *Current Opinion in Pharmacology*, 2003, 3, pp. 204-208). In some embodiments, the present disclosure provides a method of treating renal fibrosis, comprising administering to a subject an effective amount of a compound disclosed herein.

One fibrotic disease that has been particularly difficult to treat is idiopathic pulmonary fibrosis (IPF). IPF is a chronic, progressive and fatal fibrotic lung disease with survival only improved by lung transplantation. Current oral therapies such as nintedanib and pirfenidone have been shown to slow the progression of the disease, but have adverse effects that lead to discontinuation and lack of compliance by the patient. Although there are other therapies in development targeting various pathways, an unmet need remains for patients with IPF.

Although ALK5 is an important and known component in the fibrotic disease pathway, the efficacy of ALK5 inhibitors in IPF have not been realized due to systemic adverse effects, especially in the heart. Thus, one of the goals of this disclosure is to develop ALK5 inhibitors with high lung selectivity and rapid clearance. One preferred embodiment of this disclosure is to treat patients with idiopathic pulmonary fibrosis with a compound described herein, for example, by once or twice daily administration of inhalable ALK5 inhibitor having minimal systemic exposure. The inhaled ALK5 inhibitor may be administered as a monotherapy or co-dosed with other orally available IPF therapies. In some embodiments, the present disclosure provides a method of treating idiopathic pulmonary fibrosis, comprising administering to a subject an effective amount of a compound disclosed herein. In some embodiments, the compound is administered by inhalation.

Familial pulmonary fibrosis is a hereditary disease where two or more family members have confirmed IPF. In some embodiments, the present disclosure provides a method of treating familial pulmonary fibrosis, comprising administering to a subject an effective amount of a compound disclosed herein.

Pulmonary fibrosis is a typical clinical feature associated with viral infection, such as SARS and COVID-19. SARS-mediated TGF-β signaling has been shown to promote fibrosis and block apoptosis of SARS-CoV-infected host cells (Zhao, X. et al., *J. Biol. Chem.*, 2008, 283(6), pp. 3272-3280). Increased TGF-β expression was similarly observed in patients infected with SARS-CoV-2, ultimately leading to the development of pulmonary fibrosis. TGF-β signaling mediated by SARS-CoV-2 can promote fibroblast proliferation and myofibroblast differentiation and block host cell apoptosis. (Xiong, Y. et al., *Emerging Microbes & Infections*, 2020, 9(1), pp. 761-770). Compounds of the present disclosure are expected to inhibit increased TGF-β signaling mediated by viral infection and prevent, halt, slow or reverse the progression of pulmonary fibrosis associated with the infection. Accordingly, in some embodiments, the present disclosure provides a method of treating pulmonary fibrosis induced by a viral infection, comprising administering to a subject an effective amount of a compound disclosed herein. In some embodiments, the pulmonary fibrosis is induced by SARS-CoV or SARS-CoV-2. In some embodiments, the compound is administered by inhalation.

Chronic lung disease, such as interstitial lung disease (ILD), chronic obstructive pulmonary disease (COPD) and idiopathic pulmonary fibrosis (IPF), may lead to pulmonary hypertension (PH). Pulmonary hypertension is a progressive disease characterized by high blood pressure in the lungs. The World Health Organization (WHO) has defined five classifications of PH (WHO Group I: Pulmonary arterial hypertension (PAH); WHO Group II: Pulmonary hypertension due to left heart disease; WHO Group III: Pulmonary hypertension due to lung disease and/or hypoxia; WHO Group IV: Chronic thromboembolic pulmonary hypertension (CTEPH); and WHO Group V: Pulmonary hypertension with unclear multifactorial mechanisms). TGF-β signaling has been implicated in the pathogenesis of PH. Moreover, inhibition of ALK5 in a monocrotaline (MCT) model of severe PH was shown to attenuate the development of PH and reduce pulmonary vascular remodeling in a dose-dependent manner, namely by reducing RV systolic pressure, reducing RV diastolic pressure, increasing cardiac output and reducing RV hypertrophy (Zaiman, A. L.; et al., *Am. J. Respir. Crit. Care Med.*, 2008, 177, pp. 896-905). Compounds of the present disclosure are expected to inhibit TGF-β signaling in lung tissue and prevent, halt, slow or reverse the progression of PH, particularly in WHO Group III PH. Accordingly, in some embodiments, the present disclosure provides a method of treating pulmonary hypertension, comprising administering to a subject an effective amount of a compound disclosed herein. The pulmonary hypertension may be WHO Group III pulmonary hypertension, such as pulmonary fibrosis-related pulmonary hypertension (PH-PF) or interstitial lung disease-related pulmonary hypertension (PH-ILD). In some embodiments, the compound is administered by inhalation.

Other types of interstitial lung diseases include, but are not limited to, (1) interstitial pneumonia caused by bacteria, viruses, or fungi; (2) nonspecific interstitial pneumonitis usually associated with autoimmune conditions such as rheumatoid arthritis or scleroderma; (3) hypersensitivity pneumonitis caused by inhalation of dust, mold, or other irritants; (4) cryptogenic organizing pneumonia; (5) acute interstitial pneumonitis; (6) desquamative interstitial pneumonitis; (7) sarcoidosis; (8) drug-induced interstitial lung disease; and (9) progressive fibrosing interstitial lung disease (PF-ILD). In some embodiments, the present disclosure provides a method of treating an interstitial lung disease, comprising administering to a subject an effective amount of a compound disclosed herein.

Both transforming growth factor (TGF)-beta(1) and activin-A have been implicated in airway remodeling in asthma (Kariyawasam, H. H., *J Allergy Clin Immunol.*, 2009, September, 124(3), pp. 454-462). In some embodiments, the present disclosure provides a method of treating asthma, comprising administering to a subject an effective amount of a compound disclosed herein.

Chronic obstructive pulmonary disease (COPD) is a pulmonary disorder characterized by a poorly reversible and progressive airflow limitation caused by airway inflammation and emphysema, whereas IPF is associated with impaired diffusion capacity (Chilosi, M., et al., *Respir. Res.*, 2012, 13(1), 3, pp. 1-9). Both diseases, however, demonstrate a progressive loss of alveolar parenchyma leading to severe impairment of respiratory function. Fibrosis associated with emphysema is known and research has demonstrated TGF-β1 involvement in chronic sinus disease, pulmonary fibrosis, asthma, and COPD (Yang, Y. C., et al., *Allergy*, 2012, 67, pp. 1193-1202). In some embodiments, the present disclosure provides a method of treating COPD, comprising administering to a subject an effective amount of a compound disclosed herein.

Other types of lung injury that result in fibrosis include silica-induced pneumoconiosis (silicosis), asbestos-induced pulmonary fibrosis (asbestosis), and chemotherapeutic agent-induced pulmonary fibrosis. In some embodiments, the present disclosure provides a method of treating injury-induced fibrosis, comprising administering to a subject an effective amount of a compound disclosed herein.

In some embodiments, the present disclosure provides a method of treating liver fibrosis, comprising administering to a subject an effective amount of a compound disclosed herein. Fibrosis develops in the liver when it is repeatedly or continuously damaged, for example, in patients with chronic hepatitis. TGF-β signaling participates in all stages of disease progression, from initial liver injury through inflammation and fibrosis, to cirrhosis and cancer (Fabregat, I., et al., *The FEBS J.*, 2016, 283(12), pp. 2219-2232).

A related condition involves fibrosis resulting from idiopathic non-cirrhotic portal hypertension (INCPH). This disease is of uncertain etiology characterized by periportal fibrosis and involvement of small and medium branches of the portal vein. According to Nakanuma et al., small portal veins and skin findings are similar between patients with scleroderma and INCPH (Nakanuma, Y., *Hepatol. Res.*, 2009, 39, pp. 1023-1031). Transforming growth factor-β (TGF-β) and connective tissue growth factor, which are fibrosis-related and vascular endothelial growth factors, respectively, increase in serum, skin, and the portal vein, suggesting that these could be mechanisms of the portal vein occlusion in INCPH. Moreover, endothelial mesenchymal transition (EndMT) theory was proposed by Kitao et al. based on these findings (Kitao, A., et al., *Am. J. Pathol.*, 2009, 175, pp. 616-626). The increase of TGF-β in sera may act as a potent inducer of EndMT. In some embodiments, the present disclosure provides a method of treating INCPH, comprising administering to a subject an effective amount of a compound disclosed herein.

Other types of liver fibrosis include alcoholic and non-alcoholic liver fibrosis, hepatitis C-induced liver fibrosis, primary biliary cirrhosis or cholangitis, and parasite-induced liver fibrosis (schistosomiasis). In some embodiments, the present disclosure provides a method of treating alcoholic liver fibrosis, non-alcoholic liver fibrosis, hepatitis C-induced liver fibrosis, primary biliary cirrhosis, primary biliary cholangitis, or parasite-induced liver fibrosis (schistosomiasis), comprising administering to a subject an effective amount of a compound disclosed herein.

Primary biliary cholangitis (PBC) and primary sclerosing cholangitis (PSC) are two types of chronic liver disease that often lead to cirrhosis and liver failure. Liver biopsies of patients with PBC or PSC typically reveal inflammation and fibrosis. Inhibition of integrin αvβ6, which has been shown to bind to and activate TGFβ1 on epithelial cells, suppresses biliary fibrosis in rodents. (Peng, Z-W., et al., *Hepatology*, 2016, 63, pp. 217-232). Accordingly, inhibition of the TGF-β pathway is also expected to suppress fibrotic processes in both PBC and PSC. Compounds of the present disclosure are expected to inhibit TGF-β signaling in liver tissue and prevent, halt, slow or reverse the progression of PBC and PSC. Thus, in some embodiments, the present disclosure provides a method of treating primary biliary cholangitis or primary sclerosing cholangitis, comprising administering to a subject an effect amount of a compound described herein. In some embodiments, the present disclosure provides a method of treating liver fibrosis, optionally in a subject that suffers from PBC or PSC, comprising administering to the subject an effective amount of a compound described herein.

Fibrotic skin conditions include, but are not limited to, hypertrophic scarring, keloids, and localized or systemic sclerosis (scleroderma). As discussed previously, TGF-β is a potent stimulus of connective tissue accumulation and has been implicated in the pathogenesis of scleroderma and other fibrotic disorders (Lakos, G., et al., *Am. J. Pathol.*, 2004, 165(1), pp. 203-217). Lakos et. al. demonstrated that Smad3 functions as a key intracellular signal transducer for profibrotic TGF-β responses in normal skin fibroblasts and found that the targeted disruption of TGF-β/Smad3 signaling modulated skin fibrosis in the mouse model of scleroderma. In some embodiments, the present disclosure provides a method of treating skin fibrosis, comprising administering to a subject an effective amount of a compound disclosed herein.

Intestinal fibrosis is a common complication of inflammatory bowel disease (IBD) and is a serious clinical problem. TGF-β has been implicated as a major driving factor of intestinal fibrosis. Moreover, TGF-β1 signaling contributes to stricture formation in fibrostenotic Crohn's disease by inducing insulin-like growth factor I (IGF-I) and mechano-growth factor (MGF) production in intestinal smooth muscle. (Latella, G., Rieder, F., *Curr. Opin. Gastroenterol.*, 2017, 33(4), pp. 239-245). Inhibition of TGF-β signaling could thus slow, halt or reverse the progression of fibrosis in the intestine. However, adverse side effects of concern to patients with IBD—such as inflammation and neoplasia—would likely result from systemic inhibition of TGF-β signaling. One goal of the present disclosure is to develop ALK5 inhibitors with high selectivity for the gastrointestinal tract and rapid clearance. In some embodiments, the present disclosure provides a method of treating intestinal fibrosis, comprising administering to a subject an effective amount of a compound described herein, for example, by once or twice daily administration of an oral ALK5 inhibitor having minimal systemic exposure. In some embodiments, the subject suffers from inflammatory bowel disease, such as Crohn's disease or colitis. The degree of therapeutic efficacy may be with respect to a starting condition of the subject (e.g., a baseline Mayo score, baseline Lichtiger score, or severity or incidence of one or more symptoms), or with respect to a reference population (e.g., an untreated population, or a population treated with a different agent). Severity of intestinal fibrosis may be assessed using any suitable method, such as delayed enhancement MRI, ultrasound elastography, shear wave elastography, magnetization MRI, or by the direct detection of macromolecules such as collagen. Preferably, treatment with a compound of the present disclosure reduces the severity of the fibrosis, such as from severe fibrosis to moderate or mild fibrosis. In some embodiments, the treatment increases intestinal tissue elasticity, reduces tissue stiffness, and/or reduces collagen levels. In some embodiments, the treatment prevents myofibroblast accumulation, inhibits expression of pro-fibrotic factors, and/or inhibits accumulation of fibrotic tissue.

Other types of organ-specific fibrosis or fibrotic diseases involving the TGF-β pathway include, but are not limited to, radiation-induced fibrosis (various organs), bladder fibrosis, intestinal fibrosis, peritoneal sclerosis, diffuse fasciitis, Dupuytren's disease, myelofibrosis, oral submucous fibrosis, and retinal fibrosis. In some embodiments, the present disclosure provides a method of treating radiation-induced fibrosis, bladder fibrosis, intestinal fibrosis, peritoneal sclerosis, diffuse fasciitis, Dupuytren's disease, myelofibrosis, oral submucous fibrosis, or retinal fibrosis, comprising administering to a subject an effective amount of a compound disclosed herein.

Although one of the goals of this disclosure is to treat fibrotic and pulmonary diseases locally or in a targeted way, the compounds described herein may also be used to treat patients systemically. Diseases that may be treated systemically, include, for example, oncologic diseases such as glioblastoma, pancreatic cancer and hepatocellular carcinoma, breast cancer metastasized to lungs, non-small cell lung cancer, small cell lung cancer, cystic fibrosis, and metastasis of other forms of primary cancer subtypes. Some of the forgoing diseases may also be treated locally as well.

Other fibrotic diseases that compounds disclosed herein may treat include angioedema, anti-aging, and alopecia. Alopecia includes alopecia totalis, alopecia universalis, androgenetic alopecia, alopecia areata, diffuse alopecia, postpartum alopecia, and traction alopecia.

Other Indications

In certain aspects, the present disclosure provides a method of reversing one or more symptoms of aging, comprising administering to a subject an ALK5 inhibitor. The method may further comprise administering an activator of the MAPK pathway, such as oxytocin. The method may be effective in one or more of enhancing neurogenesis in the hippocampus, reducing neuroinflammation, improving cognitive ability, reducing liver adiposity, reducing liver fibrosis, and decreasing the number of p16$^+$ cells. In some embodiments, a method described herein increases stem cell activity. The increase in stem cell activity may allow the subject to generate new muscle fibers and/or to form new neurons in the hippocampus. Treatment with an ALK5 inhibitor, such as a compound described herein, may prevent or slow the onset of age-related diseases, such as Alzheimer's disease. (see Mehdipour, M. et al. *Aging* 2018, 10, 5628-5645).

Pharmaceutical Compositions

In some aspects, the present disclosure provides a pharmaceutical composition. The pharmaceutical composition may comprise a compound disclosed herein, such as a compound of Formula (I), (I'), (I-A), (I'-A), (I-B), (I'-B), (I-C), (I'-C), (I-D), (I'-D), (I-E) or (I'-E), and a pharmaceutically acceptable carrier. In some embodiments, the pharmaceutical composition is formulated for oral administration. In some embodiments, the pharmaceutical composition is formulated for inhalation. In some embodiments, the pharmaceutical composition comprises a compound disclosed herein and an additional therapeutic agent. Non-limiting examples of such therapeutic agents are described herein below.

Pharmaceutical compositions typically include at least one pharmaceutically acceptable carrier, diluent or excipient and at least one compound of Formula (I), (I'), (I-A), (I'-A), (I-B), (I'-B), (I-C), (I'-C), (I-D), (I'-D), (I-E) or (I'-E), or a compound provided in Table 1 or 2—described herein as the active agent. The active agent may be provided in any form suitable for the particular mode of administration, such as a free base, a free acid, or a pharmaceutically acceptable salt. Additionally, the methods and pharmaceutical compositions of the present disclosure include the use of N-oxides, crystalline forms (e.g., polymorphs), as well as metabolites of these compounds having similar activity. All tautomers of the compounds described herein are included within the scope of the present disclosure. Additionally, the compounds described herein encompass unsolvated as well as solvated forms with pharmaceutically acceptable solvents such as water, ethanol and the like.

Suitable routes of administration include, but are not limited to, oral, intravenous, rectal, vaginal, aerosol, pulmonary, nasal, transmucosal, topical, transdermal, otic, ocular, and parenteral modes of administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound described herein is administered in a local rather than systemic manner, for example, via injection of the compound directly into an organ, often in a depot preparation or sustained release formulation. In some embodiments, a long acting formulation is administered by implantation (e.g., subcutaneously or intramuscularly) or by intramuscular injection. In some embodiments, a compound described herein is provided in the form of a rapid release formulation, an extended release formulation, or an intermediate release formulation. In some embodiments, a compound described herein is provided in the form of a nebulized formulation. In some embodiments, a compound described herein is administered locally to the lungs by inhalation.

Compounds of the present disclosure are effective over a wide dosage range. For example, in the treatment of adult humans, dosages from 0.01 to 1000 mg, 0.5 to 100 mg, 1 to 50 mg, or from 5 to 40 mg per day may be administered to a subject in need thereof. The exact dosage will depend upon the route of administration, the form in which the compound is administered, the subject to be treated, the body weight of the subject to be treated, and the preference and experience of the attending physician.

A compound of the present disclosure may be administered in a single dose. In some embodiments, a compound of the disclosure is administered in multiple doses, such as about once, twice, three times, four times, five times, six times, or more than six times per day. In some embodiments, dosing is about once a month, once every two weeks, once a week, or once every other day. In some embodiments, a compound of the disclosure and an additional therapeutic agent are administered together about once per day to about 6 times per day. In some embodiments, the administration continues for more than about 6, 10, 14, 28 days, two months, six months, or more than about one year. In some embodiments, a dosing schedule is maintained as long as necessary. A compound of the present disclosure may be administered chronically on an ongoing basis, e.g., for the treatment of chronic effects.

Pharmaceutical compositions of the present disclosure typically contain a therapeutically effective amount of a compound of the present disclosure. Those skilled in the art will recognize, however, that a pharmaceutical composition may contain more than a therapeutically effective amount, e.g., bulk compositions, or less than a therapeutically effective amount, e.g., individual unit doses designed for co-administration to achieve a therapeutically effective amount.

Typically, pharmaceutical compositions of the present disclosure contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions of the present disclosure. The choice of a particular carrier or excipient, or combinations of carriers or excipients, will depend on the mode of administration being used to treat a particular patient or type of medical condition or disease state. Additionally, the carriers or excipients used in the pharmaceutical compositions of this disclosure may be commercially-available. Conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In one aspect, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and a micronized form of a compound disclosed herein. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

A pharmaceutical composition of the present disclosure may be administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed, including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is a hydrofluoroalkane. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of the present disclosure; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

A pharmaceutical composition of the present disclosure may be administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 µg/mL to about 20 mg/mL of a compound of the present disclosure and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat® Softmist™ Inhalaler (Boehringer Ingelheim); the AERx® Pulmonary Delivery System (Aradigm Corp.); the PARI LC Plus® Reusable Nebulizer or PARI eFlow® rapid Nebulizer System (Pari GmbH); and the like.

A pharmaceutical composition of the present disclosure may be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form, the pharmaceutical compositions of the disclosure will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the present pharmaceutical compositions.

Alternative formulations may include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present disclosure.

Dry Powder Composition

A micronized compound of the present disclosure (1 g) is blended with milled lactose (25 g). This blended mixture is then loaded into individual blisters of a peelable blister pack in an amount sufficient to provide between about 0.1 mg to about 4 mg of the compound per dose. The contents of the blisters are administered using a dry powder inhaler.

Dry Powder Composition

A micronized compound of the present disclosure (1 g) is blended with milled lactose (20 g) to form a bulk composition having a weight ratio of compound to milled lactose of 1:20. The blended composition is packed into a dry powder inhalation device capable of delivering between about 0.1 mg to about 4 mg of the compound per dose.

Metered-Dose Inhaler Composition

A micronized compound of the present disclosure (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 0.1 mg to about 4 mg of the compound per dose when administered by the metered dose inhaler.

Nebulizer Composition

A representative nebulizer composition is as follows. A compound of the present disclosure (2 g of free-base equivalents) is dissolved in a solution containing 80 mL reverse-osmosis water, 0.1-1% by weight of anhydrous citric acid, and 0.5-1.5 equivalents of hydrochloric acid, followed by addition of sodium hydroxide to adjust the pH to 3.5 to 5.5. Thereafter, between 4-6% by weight of D-mannitol is added and solution q.s. to 100 mL. The solution is then filtered through a 0.2 µm filter and stored at room temperature prior to use. The solution is administered using a nebulizer device that provides about 0.1 mg to about 4 mg of the compound per dose.

Kits

In certain aspects, the present disclosure provides a kit comprising one or more unit doses of a compound or pharmaceutical composition described herein, optionally wherein the kit further comprises instructions for using the compound or pharmaceutical composition. In some embodiments, the kit comprises a carrier, package, or container that is compartmentalized to receive one or more containers, such as vials, tubes, and the like, each of the container(s) comprising one of the separate elements to be used in a method described herein. Suitable containers include, for example, bottles, vials, syringes, and test tubes. The containers may be formed from a variety of materials, such as glass or plastic.

The articles of manufacture provided herein may contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) may include one or more compounds described herein, optionally in a composition or in combination with another agent as disclosed herein. The container(s) may optionally have a sterile access port (for example, the container is an intravenous solution bag or a vial having a stopper pierceable by a hypodermic injection needle). Such kits may optionally comprise a compound with an identifying description or label or instructions relating to its use in the methods described herein.

In some embodiments, a kit includes one or more containers, each with one or more of various materials (such as reagents, optionally in concentrated form, and/or devices) desirable from a commercial and user standpoint for use of a compound described herein. Nonlimiting examples of such materials include, but are not limited to, buffers, diluents, filters, needles, syringes, carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded, or etched onto the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack may contain metal or plastic foil, such as a blister pack. In some embodiments, the pack or dispenser device is accompanied by instructions for administration. Optionally, the pack or dispenser is accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Combination Therapy

The compounds and pharmaceutical compositions of the disclosure may be used in combination with one or more therapeutic agents which act by the same mechanism or by a different mechanism to treat a disease. The one or more agents may be administered sequentially or simultaneously, in separate compositions or in the same composition. Useful classes of agents for combination therapy include, but are not limited to, compounds used to treat cardiac, kidney, pulmonary, liver, skin, immunological and oncological conditions.

In practicing any of the subject methods, an ALK5 inhibitor and a second therapeutic agent can be administered sequentially, wherein the two agents are introduced into a subject at two different time points. The two time points can be separated by more than 2 hours, 1 or more days, 1 or more weeks, 1 or more months, or according to any intermittent regimen schedule disclosed herein.

In some embodiments, the ALK5 inhibitor and the second therapeutic agent are administered simultaneously. The two agents may form part of the same composition, or the two agents may be provided in one or more unit doses.

In some embodiments, the ALK5 inhibitor or the second therapeutic agent are administered parenterally, orally, inhalatively, intraperitoneally, intravenously, intraarterially, transdermally, intramuscularly, liposomally, via local delivery by catheter or stent, subcutaneously, intraadiposally, or intrathecally. As used herein, a therapeutically effective amount of a combination of an ALK5 inhibitor and a second therapeutic agent refers to a combination of an ALK5 inhibitor and a second therapeutic agent, wherein the combination is sufficient to affect the intended application, including but not limited to, disease treatment, as defined herein. Also contemplated in the subject methods is the use of a sub-therapeutic amount of an ALK5 inhibitor and a second therapeutic agent in combination for treating an intended disease condition. The individual components of the combination, though present in sub-therapeutic amounts, synergistically yield an efficacious effect and/or reduced a side effect in an intended application.

The amount of the ALK5 inhibitor and the second therapeutic agent administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring an immune response and/or the inhibition of biological effects of ALK5 can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with an ALK5 inhibitor and a second therapeutic agent may be monitored to determine the effectiveness of treatment, and the treatment regimen may be adjusted based on the subject's physiological response to treatment. For example, if inhibition of a biological effect of ALK5 inhibition is above or below a threshold, the dosing amount or frequency may be decreased or increased, respectively. Alternatively, the treatment regimen may be adjusted with respect to an immune response. The methods can further comprise continuing the therapy if the therapy is determined to be efficacious. The methods can comprise maintaining, tapering, reducing, or stopping the administered amount of a compound or compounds in the therapy if the therapy is determined to be efficacious. The methods can comprise increasing the administered amount of a compound or compounds in the therapy if it is determined not to be efficacious. Alternatively, the methods can comprise stopping therapy if it is determined not to be efficacious. In some embodiments, treatment with an ALK5 inhibitor and a second therapeutic agent is discontinued if inhibition of the biological effect is above or below a threshold, such as in a lack of response or an adverse reaction. The biological effect may be a change in any of a variety of physiological indicators.

Specific agents that may be used in combination with the compounds disclosed herein include, but are not limited to, OFEV® (nintedanib) and Esbriet® (pirfenidone). In some embodiments, a compound disclosed herein is administered in combination with pirfenidone, optionally wherein the pirfenidone is administered by inhalation. In some embodiments, the present disclosure provides a method of treating fibrosis, such as idiopathic pulmonary fibrosis, in a subject, comprising administering to the subject an ALK5 inhibitor, such as a compound disclosed in Table 1, and nintedanib or pirfenidone. In some embodiments, the present disclosure provides a method of treating cancer, such as lung cancer, in a subject, comprising administering to the subject an ALK5 inhibitor, such as a compound disclosed in Table 1, and nintedanib or pirfenidone.

In some embodiments, the present disclosure provides a method for treating a proliferative disorder (e.g., lung cancer) in a subject in need thereof, comprising administering to said subject an ALK5 inhibitor and an immunotherapeutic agent. TGF-β has been shown to regulate lymphocyte differentiation, suppress T cell proliferation and to enhance tumor growth. Moreover, TGF-β has been shown to prevent optimal activation of the immune system in immunotherapy-resistant patients (see Löffek, S. *J. Oncolo.* 2018, 1-9; incorporated herein by reference in its entirety). Not wishing to be bound by any particular theory, the present inventors expect that inhibition of ALK5 may enhance the efficacy of a particular immunotherapy. As such, treatment with an immunotherapeutic agent, such as durvalumab or pembrolizumab, and an ALK5 inhibitor, such as a compound of the present disclosure, is expected to improve the clinical outcome of a subject with cancer, such as a subject with non-small cell lung cancer. The combination is expected to produce a synergistic effect. A synergistic combination is also expected for a triple combination of radiation therapy, immunotherapy, and ALK5 inhibition. In addition, the ALK5 inhibitor, even when administered locally (e.g., to the lung by inhalation), may stimulate both local and systemic immune responses, allowing for the treatment of primary or metastatic tumors in tissues beyond the site of the local delivery. For example, an inhaled ALK5 inhibitor may be administered in combination with an immunotherapeutic agent to treat melanoma, renal cell carcinoma, colon cancer, or breast cancer.

In some embodiments, the ALK5 inhibitor and the immunotherapeutic agent are administered sequentially or simultaneously. In some embodiments, the ALK5 inhibitor and the immunotherapeutic agent are more effective in treating the proliferative disorder than either agent alone. In some embodiments, the ALK5 inhibitor and the immunotherapeutic agent yield a synergistic effect in treating the proliferative disorder. The synergistic effect may be a therapeutic effect that is greater than either agent used alone in comparable amounts under comparable conditions. The synergistic effect may be a therapeutic effect that is greater than results expected by adding the effects of each agent alone. In some embodiments, the proliferative disorder is a cancer condition. In some embodiments, the cancer condition is lung cancer, such as non-small cell lung cancer.

The term "immunotherapeutic agent" refers to any agent that induces, enhances, suppresses or otherwise modifies an immune response. This includes the administration of an active agent to, or any type of intervention or process performed on, the subject, with the objective of modifying an immune response. An immunotherapeutic agent may, for example, increase or enhance the effectiveness or potency of an existing immune response in a subject, for example, by stimulating mechanisms that enhance the endogenous host immune response or overcoming mechanisms that suppress the endogenous host immune response.

"Immune response" refers to the action of a cell of the immune system including, for example, B lymphocytes, T lymphocytes, natural killer (NK) cells, macrophages, eosinophils, mast cells, myeloid-derived suppressor cells, dendritic cells and neutrophils and soluble macromolecules produced by any of these cells or the liver (including antibodies, cytokines and complement), that results in selective targeting, binding to, damage to, destruction of, and/or elimination of invading pathogens, cells or tissues infected with pathogens, cancerous or other abnormal cells, or, in cases of autoimmunity or pathological inflammation, normal human cells or tissues, from the body of a subject.

In one embodiment, an immunotherapeutic agent may comprise a PD-1 inhibitor. In another embodiment, an immunotherapeutic agent may comprise a CTLA-4 inhibitor. In still another embodiment, an immunotherapeutic agent may comprise a B7 inhibitor.

Exemplary PD-1 inhibitors: A PD-1 inhibitor suitable for use in the subject methods can be selected from a variety of types of molecules. For example, the PD-1 inhibitor can be a biological or chemical compound, such as an organic or inorganic molecule, peptide, peptide mimetic, antibody or an antigen-binding fragment of an antibody. Some exemplary classes of agents suitable for use in the subject methods are detailed in the sections below. A PD-1 inhibitor for use in the present disclosure can be any PD-1 inhibitor that is known in the art, and can include any entity that, upon administration to a patient, results in inhibition of the PD-1 pathway in the patient. A PD-1 inhibitor can inhibit PD-1 by any biochemical mechanism, including disruption of any one or more of PD-1/PD-L1, PD1/PD-L2 and PD-L1/CD80 interactions.

In some embodiments, the PD-1 inhibitor is a molecule that inhibits the binding of PD-1 to its ligand binding partners. In a specific aspect, the PD-1 ligand binding partners are PD-L1 and/or PD-L2. In another embodiment, a PD-1 inhibitor is a molecule that inhibits the binding of PD-L1 to its binding partners. In a specific aspect, PD-L1 binding partners are PD1 and/or CD80. In another embodiment, the PD-1 inhibitor is a molecule that inhibits the binding of PD-L2 to its binding partners. In a specific aspect, a PD-L2 binding partner is PD1. The inhibitor may be an antibody, an antigen binding fragment thereof, an immunoadhesin, a fusion protein or oligopeptide.

In some embodiments, the PD-1 inhibitor is an anti-PD-1 antibody. In some further embodiments, the anti-PD-1 antibody is capable of inhibiting binding between PD-1 and PD-L1. In another embodiment, the anti-PD-1 antibody is capable of inhibiting binding between PD-1 and PD-L2. In some embodiments, the PD-1 inhibitor is an anti-PD-L1 antibody. In some embodiments, the anti-PD-L1 antibody is capable of inhibiting binding between PD-L1 and PD-1 and/or between PD-L1 and CD80. In some embodiments, the PD-1 inhibitor is an anti-PD-L2 antibody. In some further embodiments, the anti-PD-L2 antibody is capable of inhibiting binding between PD-1 and PD-L2. In yet another embodiment, the PD-1 inhibitor is nivolumab or pembrolizumab. In some embodiments, the PD-1 inhibitor is selected from atezolizumab, avelumab, nivolumab, pembrolizumab, durvalumab and BGB-A317.

Inhibition of the PD-1 pathway can enhance the immune response to cancerous cells in a patient. The interaction between PD-1 and PD-L1 impairs T cell response as manifested by a decrease in tumor-infiltrating lymphocytes (TILs) and a decrease in T-cell receptor mediated proliferation, resulting in T cell anergy, exhaustion or apoptosis, and immune evasion by the cancerous cells. This immune suppression can be reversed by inhibiting the local interaction between PD-L1 and PD-1 using a PD-1 inhibitor, including, for example, an anti-PD-1 and/or an anti-PD-L1 Ab. A PD-1 inhibitor may improve or restore antitumor T-cell functions.

Anti-PD-1 antibodies suitable for use in the disclosure can be generated using methods well known in the art. Exemplary PD-1 inhibitors include, but are not limited to: nivolumab (BMS936558), pembrolizumab (MK-3475), pidilizumab (CT-011), AMP-224, AMP-514, BMS-936559, RG7446 (MPDL3280A), MDX-1106 (Medarex Inc.), MSB0010718C, MED14736, and HenGrui mAB005 (WO 15/085847). Further PD-1 antibodies and other PD-1 inhibitors include those described in WO 04/056875, WO 06/121168, WO 07/005874, WO 08/156712, WO 09/014708, WO 09/114335, WO 09/101611, WO 10/036959, WO 10/089411, WO 10/027827, WO 10/077634, WO 11/066342, WO 12/145493, WO 13/019906, WO 13/181452, WO 14/022758, WO 14/100079, WO 14/206107, WO 15/036394, WO 15/085847, WO 15/112900, WO 15/112805, WO 15/112800, WO 15/109124, WO 15/061668, WO 15/048520, WO 15/044900, WO 15/036927, WO 15/035606; U. S. Pub. No. 2015/0071910; and U.S. Pat. Nos. 7,488,802; 7,521,051; 7,595,048; 7,722, 868; 7,794, 710; 8,008,449; 8,354,509; 8,383,796; 8,652,465; and 8,735,553; all of which are incorporated herein by reference. Some anti-PD-1 antibodies are commercially available, for example from ABCAM (AB137132), BIOLEGEND (EH12.2H7, RMP 1-14) and AFFYMETRIX EBIOSCIENCE (J105, J116, M1H4).

Exemplary CTLA-4 inhibitors: A CTLA-4 inhibitor suitable for use in the subject methods can be selected from a variety of types of molecules. For example, the CTLA-4 inhibitor can be a biological or chemical compound, such as an organic or inorganic molecule, peptide, peptide mimetic, antibody or an antigen-binding fragment of an antibody. Some exemplary classes of agents suitable for use in the subject methods are detailed in the sections below. A CTLA-4 inhibitor for use in the present disclosure can be any CTLA-4 inhibitor that is known in the art, and can include any entity that, upon administration to a patient, results in inhibition of the CTLA-4 pathway in the patient. A CTLA-4 inhibitor can inhibit CTLA-4 by any biochemical mechanism, including disruption of either one or both of CTLA-4/CD80 and CTLA-4/CD86 interactions.

In some embodiments, the CTLA-4 inhibitor is a molecule that inhibits the binding of CTLA-4 to its ligand binding partners. In a specific aspect, the CTLA-4 ligand binding partners are CD80 and/or CD86. In another embodiment, a CTLA-4 inhibitor is a molecule that inhibits the binding of CD80 to its binding partners. In a specific aspect, a CD80 binding partner is CTLA-4. In another embodiment, the CTLA-4 inhibitor is a molecule that inhibits the binding of CD86 to its binding partners. In a specific aspect, a CD86 binding partner is CTLA-4. The inhibitor may be an antibody, an antigen binding fragment thereof, an immunoadhesin, a fusion protein or oligopeptide.

In some embodiments, the CTLA-4 inhibitor is an anti-CTLA-4 antibody. In some further embodiments, the anti-CTLA-4 antibody is capable of inhibiting binding between CTLA-4 and CD80. In another embodiment, the anti-CTLA-4 antibody is capable of inhibiting binding between CTLA-4 and CD86. In some embodiments, the CTLA-4 inhibitor is an anti-CD80 antibody. In some embodiments, the anti-CD80 antibody is capable of inhibiting binding between CTLA-4 and CD80. In some embodiments, the CTLA-4 inhibitor is an anti-CD86 antibody. In some further embodiments, the anti-CD86 antibody is capable of inhibiting binding between CTLA-4 and CD86. In yet another embodiment, the CTLA-4 inhibitor is tremelimumab or ipilimumab.

Inhibition of the CTLA-4 pathway can enhance the immune response to cancerous cells in a patient. The interaction between CTLA-4 and one of its natural ligands, CD80 and CD86, delivers a negative regulatory signal to T cells. This immune suppression can be reversed by inhibiting the local interaction between CD80 or CD86 and CTLA-4 using a CTLA-4 inhibitor, including, for example, an anti-CTLA-4 Ab, anti-CD80 Ab or an antiCD86 Ab. A CTLA-4 inhibitor may improve or restore antitumor T-cell functions.

Anti-CTLA-4 antibodies suitable for use in the disclosure can be generated using methods well known in the art. Exemplary CTLA-4 inhibitors include but are not limited to tremelimumab and ipilimumab (also known as 10D1 or MDX-010). Further CTLA-4 antibodies and other CTLA-4 inhibitors include those described in WO 98/042752, WO 00/037504, WO 01/014424 and WO 04/035607; U.S. Pub. Nos. 2002/0039581, 2002/086014 and 2005/0201994; U.S. Pat. Nos. 5,811,097; 5,855,887; 5,977,318; 6,051,227; 6,207, 156; 6,682,736; 6,984,720; 7, 109,003; 7, 132,281; 7,605,238; 8, 143,379; 8,318,916; 8,435,516; 8,784,815; and 8,883,984; EP Pat. No. 1212422; Hurwitz et al., PNAS 1998, 95(17): 10067-10071; Camacho et al., J Clin Oncology 2004, 22(145): abstract no. 2505 (antibody CP675206); and Mokyr, et al., Cancer Research 1998, 58:5301-5304; each of which is incorporated herein by reference.

Also provided herein is a pharmaceutical composition comprising a compound of the disclosure or a pharmaceutically acceptable salt thereof and one or more other therapeutic agents. The therapeutic agent may be selected from the classes of agents specified above and from the lists of specific agents described above. In some embodiments, the pharmaceutical composition is suitable for delivery to the lungs. In some embodiments, the pharmaceutical composition is suitable for inhaled or nebulized administration. In some embodiments, the pharmaceutical composition is a dry powder or a liquid composition.

Further, in a method aspect, the disclosure provides a method of treating a disease or disorder in a mammal comprising administering to the mammal a compound of the disclosure or a pharmaceutically acceptable salt thereof and one or more other therapeutic agents.

When used in combination therapy, the agents may be formulated in a single pharmaceutical composition, or the agents may be provided in separate compositions that are administered simultaneously or at separate times, by the same or by different routes of administration. Such compositions can be packaged separately or may be packaged together as a kit. The two or more therapeutic agents in the kit may be administered by the same route of administration or by different routes of administration.

EXAMPLES

The following examples are given for the purpose of illustrating various embodiments of the disclosure and are not meant to limit the present disclosure in any fashion. The present examples, along with the methods and compositions described herein, are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

The following abbreviations have the following meanings unless otherwise indicated and any other abbreviations used herein and not defined have their standard, generally accepted meaning:

AcOH=acetic acid
AcONa=sodium acetate
ACN=acetonitrile
Atm=atmosphere
BINAP=(±)-2,2'-bis(diphenylphosphino)-1,1'-binaphthalene
Boc$_2$O=di-tert-butyl dicarbonate
(Bpin)$_2$=bis(pinacolato)diboron
BrettPhos=2-(dicyclohexylphosphino)3,6-dimethoxy-2', 4',6'-triisopropyl-1,1'-biphenyl
BrettPhos Pd G4=N-substituted 2-aminobiphenylpalladium methanesulfonate precatalyst
BSA=bovine serum albumin, Fraction V
Cp*RuCl(PPh$_3$)$_2$=pentamethylcyclopentadienylbis (triphenylphosphine)ruthenium(II) chloride
d=day(s)
DAST=diethylaminosulfur trifluoride
DCC=N,N'-dicyclohexylcarbodiimide
DCE=1,2-dichloroethane
DCM=dichloromethane or methylene chloride DHP=dihydropyran
DIAD=diisopropyl azodicarboxylate
DIBAH=diisobutylaluminium hydride
DIPEA or DIEA=N,N-diisopropylethylamine
DMA or DMAc=dimethylacetamide
DMAP=4-dimethylaminopyridine
DMEDA=1,2-bis(methylamino)ethane
DMF=N,N-dimethylformamide
DMP=Dess-Martin periodinane
DMSO=dimethyl sulfoxide
DPPA=diphenylphosphoryl azide
DPPF=1,1'-bis(diphenylphosphino)ferrocene
DTT=dithiothreitol
EDCI=N-ethyl-N'-(3-dimethylaminopropyl) carbodiimide hydrochloride
EDTA=ethylenediaminetetraacetic acid
EGTA=ethylene glycol-bis(O-aminoethyl ether)-N,N,N',N'-tetraacetic acid
EtOH=ethanol
EtOAc or EA=ethyl acetate
g=gram(s)
h=hour(s)
HATU=N,N,N,N'-tetramethyl-O-(7-azabenzotriazol-1-yl)uronium hexafluorophosphate
HEPES=4-(2-hyrdroxyethyl)-1-piperazine ethanesulfonic acid
HOBT=hydroxybenzotriazole
i-PrOBPin=2-isopropyl-4,4,5,5-tetramethyl-1,3,2-dioxaborolane
IPA or i-PrOH=isopropyl alcohol
KHMDS=potassium bis(trimethylsilyl)amide
LAH=lithium aluminum hydride
LDA=lithium diisopropylamide
LiHDMS=hexamethyldisilazane lithium salt
m-CPBA=meta-chloroperoxybenzoic acid
MeCN=acetonitrile
MeOH=methanol
min=minute(s)
MTBE=methyl tert-butyl ether
NaHDMS=hexamethyldisilazane sodium salt
NBS=N-bromosuccinimide
n-BuLi=n-butyl lithium
Pd(dppf)Cl$_2$=[1,1'-bis(diphenylphosphino)ferrocene]-dichloropalladium(II)
Pd(OAc)$_2$=palladium(II) acetate
Pd(PPh$_3$)$_4$=tetrakis(triphenylphosphine)palladium(0)
Pd/C=palladium on activated carbon, 10% loading
Pd$_2$(dba)$_3$=tris(dibenzylideneacetone)dipalladium(0)
PE=petroleum ether
PhN$_2$=benzene diazonium ion
PTSA=p-toluenesulfonic acid
RT, rt, or r.t.=room temperature
RuPhos=2-dicyclohexylphosphino-2',6'-diisopropoxybiphenyl
RuPhos Pd G2=chloro(2-dicyclohexylphosphino-2',6'-diisopropoxy-1,1'-biphenyl)[2-(2'-amino-1,1'-biphenyl)]palladium(II)
RuPhos Pd G4=ligand for Buchwald 4$^{th}$ generation Palladacycle
SEMCI=2-(trimethylsilyl)ethoxymethyl chloride
SiO$_2$=silicon dioxide or silica
SPhos Pd G3=(2-dicyclohexylphosphino-2',6'-dimethoxybiphenyl) [2-(2'-amino-1,1'-biphenyl)]palladium(II) methanesulfonate
STAB=sodium triacetoxyborohydride
TBAB=tetrabutylammonium bromide
TBSCl=tert-butyldimethylchlorosilane
t-BuOK=potassium tert-butoxide
t-BuONa=sodium tert-butoxide
TEA, Et$_3$N=triethylamine
TFA=trifluoroacetic acid
TFAA=trifluoroacetic anhydride
THF=tetrahydrofuran
TMS=tetramethylsilane
TosCl=p-toluenesulfonyl chloride
Tris-HCl=tris(hydroxymethyl)aminomethane hydrochloride
Tween-20=polyoxyethylene sorbitan monolaurate
Xantphos=4,5-bis(diphenylphosphino)-9,9-dimethylxanthene
XPhos Pd G4=Buchwald 4$^{th}$ generation palladacycle Unless noted otherwise, all materials, such as reagents, starting materials and solvents, were purchased from commercial suppliers, such as Sigma-Aldrich, Fluka Riedel-de Haën, and the like, and were used without further purification.

Reactions were run under nitrogen atmosphere, unless noted otherwise. The progress of reactions was monitored by thin layer chromatography (TLC), analytical high performance liquid chromatography (anal. HPLC), and mass spectrometry, the details of which are given in specific examples.

Reactions were worked up as described specifically in each preparation; commonly, reaction mixtures were purified by extraction and other purification methods such as temperature- and solvent-dependent crystallization, and precipitation. In addition, reaction mixtures were routinely purified by preparative HPLC, typically using Microsorb C18 and Microsorb BDS column packings and conventional eluents. Progress of reactions was typically monitored by liquid chromatography mass spectrometry (LCMS). Characterization of isomers was typically done by Nuclear Overhauser effect spectroscopy (NOE). Characterization of reaction products was routinely carried out by mass spectrometry and/or $^1$H-NMR spectroscopy. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Example 1: Synthesis of N4-(2-(6-methylpyridin-2-yl)pyrimidin-4-yl)-N2-(4-morpholinophenyl)pyrimidine-2,4-diamine (475)

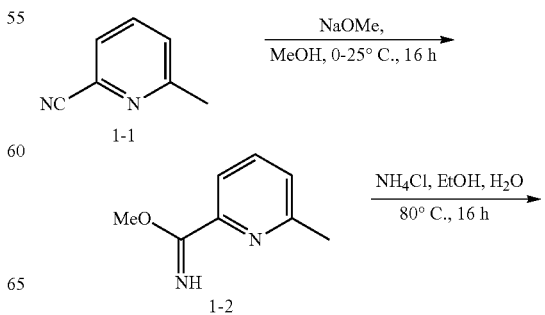

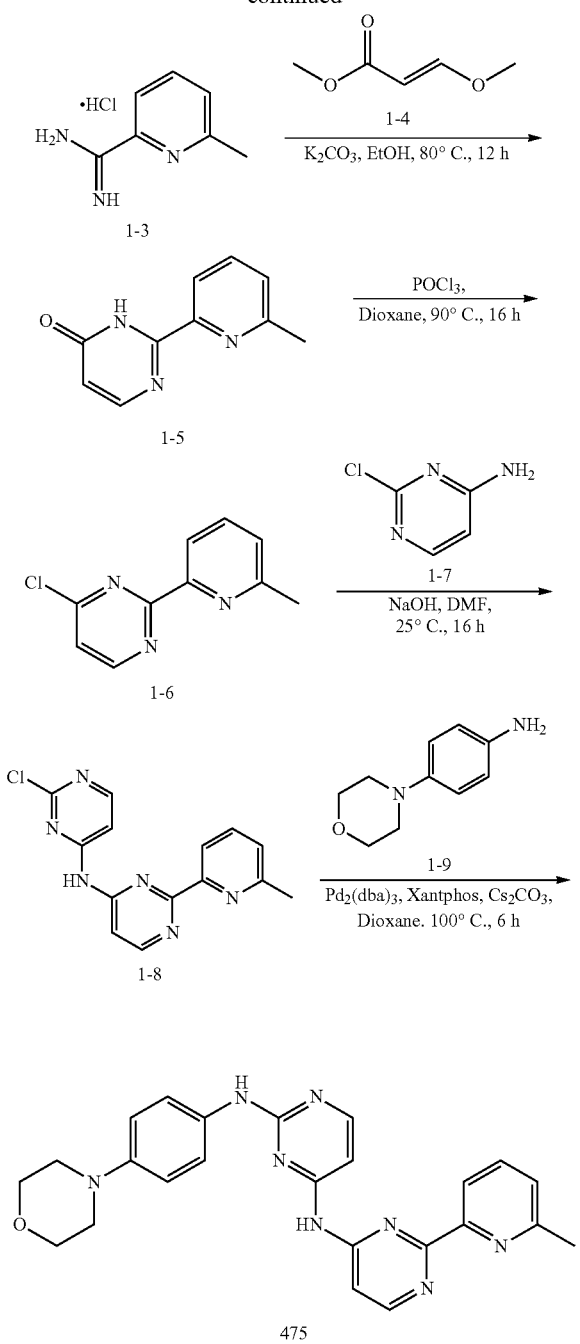

Step A: Preparation of methyl 6-methylpicolinimidate (1-2). To a solution of 1-1 (50.0 g, 423.3 mmol) in MeOH (300 ml) was added 25% NaOMe in MeOH (100 ml, 465 mmol) at 0° C. Then the reaction was stirred at 25° C. for 16 h. The reaction mixture was concentrated in vacuum and the crude residue was dissolved in EtOAc. Brine was added to the solution and white solid precipitation was observed. The suspension was filtered and the organic layer of filtrate was separated. The organic phase was washed with brine, dried over sodium sulfate, filtered and concentrated to give the crude residue 1-2 (58.0 g). The crude product was used directly in the next step without further purification. [M+H]$^+$ calcd for $C_8H_{10}N_2O$ 150.18, found 151.05.

Step B: Preparation of 6-methylpicolinimidamide hydrogen chloride (1-3). To a solution of 1-2 (58.0 g, 386.6 mmol) in EtOH (250 ml) and H$_2$O (25 ml) was added NH$_4$Cl (22.9 g, 425.02 mmol) and the reaction was stirred at 80° C. for 16 h. The reaction was concentrated to dryness. The crude residue was triturated in EtOAc and then filtered to remove non-polar impurities. The solid precipitate was treated with excess EtOH and filtered. The filtrate was concentrated to obtain an HCl salt of the desired product 1-3 (55.0 g). The crude product was used directly in the next step without further purification. [M+H]$^+$ calcd for $C_7H_9N_3$ 135.17, found 136.10.

Step C: Preparation of 2-(6-methylpyridin-2-yl)pyrimidin-4(3H)-one (1-5). To a solution of 1-3 (55.0 g, 407.4 mmol) and 1-4 (46.4 ml, 427.7 mmol) in EtOH (385 ml) was added K$_2$CO$_3$ (112.4 g, 814.8 mmol). The reaction was stirred at 80° C. for 16 h. The reaction was cooled to 25° C., filtered through a pad of Celite and concentrated to give crude product. The crude product was acidified with 4N HCl and triturated with EtOAc, then filtered to give an HCl salt of 1-5 (65.0 g). The crude product was used directly in the next step without further purification. [M+H]$^+$ calcd for $C_{10}H_9N_3O$ 187.20, found 187.17.

Step D: Preparation of 4-chloro-2-(6-methylpyridin-2-yl)pyrimidine (1-6). To a solution of 1-5 (10.0 g, 53.41 mmol, HCl salt) in 1,4-dioxane (70 ml) was added POCl$_3$ (15.0 ml, 160.25 mmol). The reaction was stirred at 90° C. for 16 h, then concentrated to dryness. The crude residue was poured onto ice-cold water. The pH was adjusted to 8 by saturated NaHCO$_3$. The mixture was then extracted with EtOAc. The organic phase was dried over sodium sulfate and concentrated to give crude product. The crude residue was triturated in pentane and filtered to give 1-6 (5.0 g). The crude product was used directly in the next step without further purification. [M+H]$^+$ calcd for $C_{10}H_8ClN_3$ 205.65, found 206.09.

Step E: Preparation of 2-chloro-N-(2-(6-methylpyridin-2-yl)pyrimidin-4-yl)pyrimidin-4-amine (1-8). To a solution of 1-6 (3.0 g, 14.63 mmol) and 1-7 (2.26 g, 17.56 mmol) in DMF (15 ml) was added solid crushed NaOH (1.17 g, 29.26 mmol) at 0° C. The reaction was stirred at 25° C. for 16 h. The reaction was poured onto ice-cold water and the solid precipitated. The solid was collected by filtration and dried. The crude residue was triturated with ether and ACN to give 1-8 (3.5 g). The crude product was used directly in the next step without further purification. [M+H]$^+$ calcd for $C_{14}H_{11}ClN_6$ 298.73, found 298.94.

Step F: Preparation of N4-(2-(6-methylpyridin-2-yl)pyrimidin-4-yl)-N2-(4-morpholinophenyl)pyrimidine-2,4-diamine (475). To a solution of 1-8 (250 mg, 0.84 mmol) in 1,4-dioxane (10 ml) was added 1-9 (298 mg, 1.67 mmol), Pd$_2$(dba)$_3$ (77 mg, 0.08 mmol), Xantphos (48 mg, 0.08 mmol), Cs$_2$CO$_3$ (545 mg, 1.67 mmol) and the resulting mixture was heated at 100° C. for 6 h under N$_2$. The reaction mixture was concentrated in vacuum. The residue was purified by preparative HPLC chromatography using a gradient (25 to 55%) of acetonitrile in water with 0.05% ammonia hydroxide to obtain the title compound as a white solid (62 mg). [M+H]$^+$ calcd for $C_{24}H_{24}N_8O$ 440.51, found 441.4.

Example 2: Synthesis of N4-(2-(6-methylpyridin-2-yl)pyrimidin-4-yl)-N2-(4-(piperazin-1-yl)phenyl)pyrimidine-2,4-diamine (418)

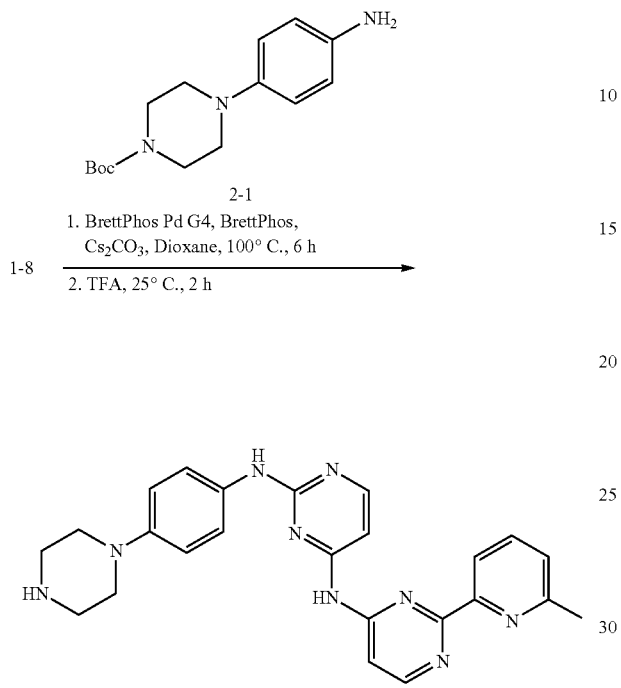

A vial of 1-8 (20 mg, 0.067 mmol), 2-1 (30 mg, 0.100 mmol), cesium carbonate (32.7 mg, 0.100 mmol), BrettPhos (3.59 mg, 6.69 µmol), and BrettPhos Pd G4 (6.16 mg, 6.69 µmol) in degassed 1,4-dioxane (1 ml) was heated at 110° C. for 16 h. The reaction mixture was concentrated in vacuum. TFA (1 ml) and DCM (1 ml) were added to the residue and stirred at 25° C. for 2 h. TFA was removed in vacuum and the residue was purified by preparative HPLC chromatography using a gradient (2 to 30%) of acetonitrile in water with 0.05% trifluoroacetic acid to yield a TFA salt of the title compound (27.2 mg). [M+H]$^+$ calcd for $C_{24}H_{25}N_9$ 439.53, found 440.2.

Example 3: Synthesis of N4-(2-(6-methylpyridin-2-yl)pyrimidin-4-yl)-N2-(5-(piperazin-1-yl)pyridin-2-yl)pyrimidine-2,4-diamine (121)

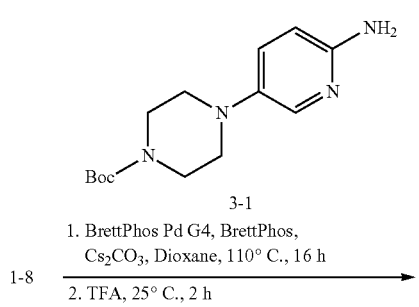

A vial of 1-8 (20 mg, 0.067 mmol), 3-1 (30 mg, 0.100 mmol), cesium carbonate (32.7 mg, 0.100 mmol), BrettPhos (3.59 mg, 6.69 µmol), and BrettPhos Pd G4 (6.16 mg, 6.69 µmol) in degassed 1,4-dioxane (1 ml) was heated at 110° C. for 16 h. The reaction mixture was concentrated in vacuum. TFA (1 ml) and DCM (1 ml) were added to the residue and stirred at 25° C. for 2 h. TFA was removed in vacuum and the residue was purified by preparative HPLC chromatography using a gradient (2 to 30%) of acetonitrile in water with 0.05% trifluoroacetic acid to yield a TFA salt of the title compound (28.6 mg). [M+H]$^+$ calcd for $C_{23}H_{24}N_{10}$ 440.52, found 441.3.

Example 4: Synthesis of N4-(2-(6-methylpyridin-2-yl)pyrimidin-4-yl)-N2-(2-(piperazin-1-yl)pyrimidin-5-yl)pyrimidine-2,4-diamine (86)

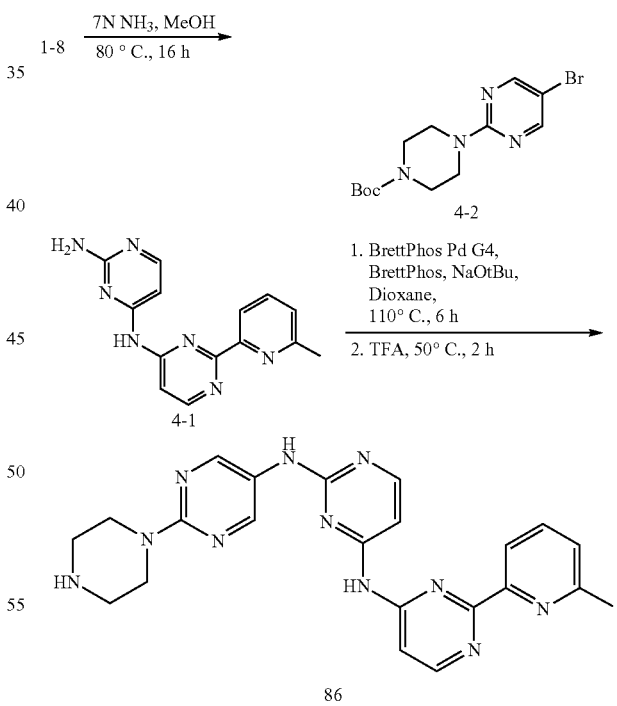

Step A: Preparation of N4-(2-(6-methylpyridin-2-yl)pyrimidin-4-yl)pyrimidine-2,4-diamine (4-1). To a vial of 1-8 (238 mg, 0.797 mmol) was added ammonia solution (7N in MeOH) (4 ml, 28.0 mmol). The resulting suspension was heated at 80° C. for 16 h. The reaction mixture was concentrated in vacuum. The crude residue was purified by silica-gel chromatography using a gradient (0 to 15%) of MeOH in DCM to give 4-1 (108 mg) as a brown solid. [M+H]+ calcd for $C_{13}H_{13}N_7$ 279.31, found 280.0.

Step B: Preparation of N4-(2-(6-methylpyridin-2-yl)pyrimidin-4-yl)-N2-(2-(piperazin-1-yl)pyrimidin-5-yl)pyrimidine-2,4-diamine (86). A vial of 4-1 (24.41 mg, 0.087 mmol), 4-2 (20 mg, 0.058 mmol), sodium tert-butoxide (11.20 mg, 0.117 mmol), BrettPhos (6.26 mg, 0.012 mmol), and BrettPhos Pd G4 (10.73 mg, 0.012 mmol) in degassed 1,4-dioxane (1 ml) was heated at 110° C. for 1 h. The reaction mixture was concentrated in vacuum. TFA (1 ml) was added to the residue and heated at 50° C. for 2 h. TFA was removed in vacuum and the residue was purified by preparative HPLC chromatography using a gradient (2 to 60%) of acetonitrile in water with 0.05% trifluoroacetic acid to yield a TFA salt of the title compound (17.2 mg). [M+H]+ calcd for $C_{22}H_{23}N_{11}$ 441.50, found 442.2.

Example 5: Synthesis of (R)-(4-(4-((4-((2-(6-methylpyridin-2-yl)pyrimidin-4-yl)amino)pyrimidin-2-yl)amino)phenyl)piperazin-2-yl)methanol (403)

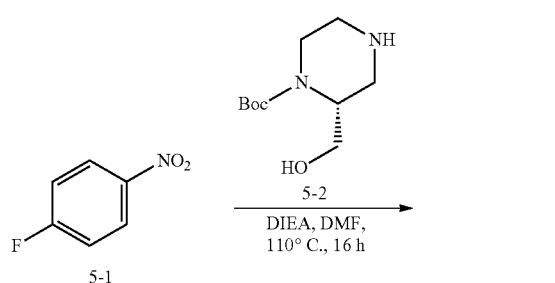

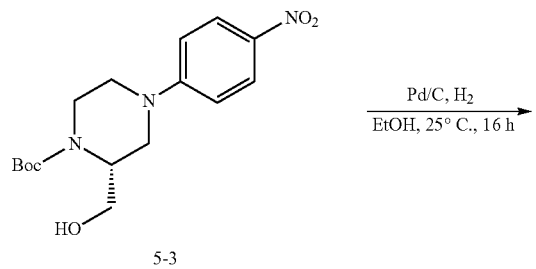

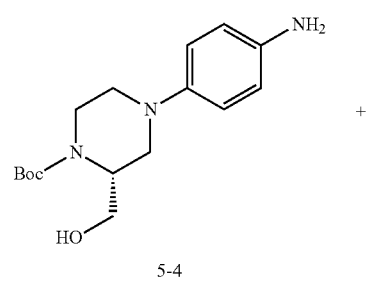

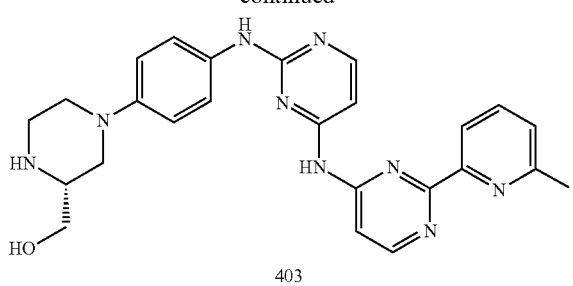

403

Step A: Preparation of tert-butyl (R)-2-(hydroxymethyl)-4-(4-nitrophenyl)piperazine-1-carboxylate (5-3). A solution of 5-1 (98 mg, 0.694 mmol), 5-2 (150 mg, 0.694 mmol), and DIPEA (1.21 ml, 6.94 mmol) in DMF (3 ml) was heated at 110° C. for 16 h. The reaction was concentrated in vacuum. The crude residue was purified by silica-gel chromatography using a gradient (0 to 15%) of MeOH in DCM to give 5-3 (157 mg) as an orange oil. [M+H]+ calcd for $C_{16}H_{23}N_3O_5$ 337.38, found 338.4.

Step B: Preparation of tert-butyl (R)-4-(4-aminophenyl)-2-(hydroxymethyl)piperazine-1-carboxylate (5-4). A solution of 5-3 (157 mg, 0.465 mmol) was taken up in ethanol (3 ml), and Pd/C (9.90 mg, 9.31 μmol) was added and the reaction mixture was purged under an atmosphere of $H_2$ and stirred at 25° C. for 16 h. The reaction mixture was filtered through a pad of Celite and concentrated in vacuum and the crude residue 5-4 (140 mg) was used directly in the next step. [M+H]+ calcd for $C_{16}H_{25}N_3O_3$ 307.40, found 308.0.

Step C: Preparation of (R)-(4-(4-((4-((2-(6-methylpyridin-2-yl)pyrimidin-4-yl)amino)pyrimidin-2-yl)amino)phenyl)piperazin-2-yl)methanol (403). A vial of 1-8 (25 mg, 0.084 mmol), 5-4 (25.7 mg, 0.084 mmol), cesium carbonate (35.4 mg, 0.109 mmol), BrettPhos (2.25 mg, 4.18 μmol), and BrettPhos Pd G4 (3.85 mg, 4.18 μmol) in degassed 1,4-dioxane (1.5 ml) was heated to 110° C. for 16 h. The reaction mixture was concentrated in vacuum. TFA (226 μl) and DCM (118 μl) were added to the residue and stirred at 45° C. for 30 min. TFA was removed in vacuum and the residue was purified by preparative HPLC chromatography using a gradient (2 to 60%) of acetonitrile in water with 0.05% trifluoroacetic acid to yield a TFA salt of the title compound (10.2 mg). [M+H]+ calcd for $C_{25}H_{27}N_9O$ 469.55, found 470.1.

Example 6: Synthesis of N2-(4-((azetidin-3-ylmethyl)amino)phenyl)-N4-(2-(6-methylpyridin-2-yl)pyrimidin-4-yl)pyrimidine-2,4-diamine (537)

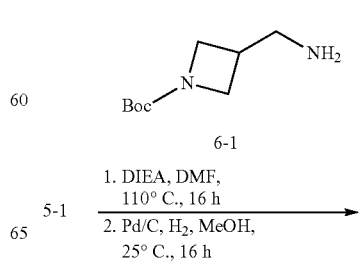

-continued

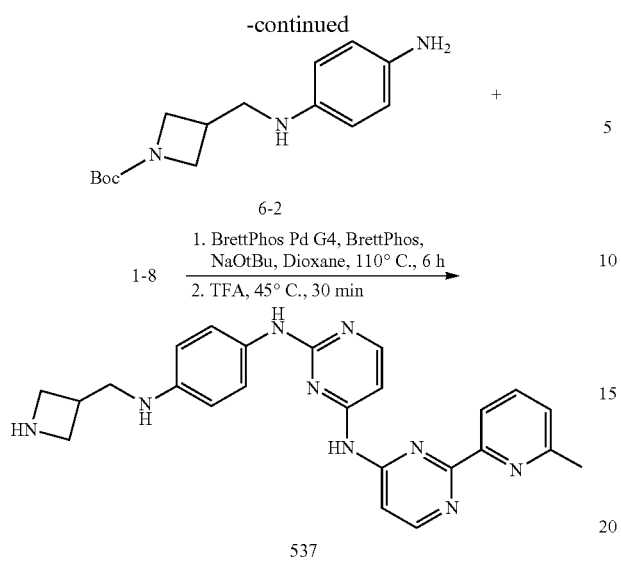

Step A: Preparation of tert-butyl 3-(((4-aminophenyl)amino)methyl)azetidine-1-carboxylate (6-2). A solution of 5-1 (65 mg, 0.461 mmol), 6-1 (86 mg, 0.461 mmol), and DIPEA (805 µl, 4.61 mmol) in DMF (1 ml) was heated at 110° C. for 16 h. The reaction was concentrated in vacuum. The crude product was purified by silica-gel chromatography using a gradient (0 to 60%) of EtOAc in Hexanes to give tert-butyl 3-(((4-nitrophenyl)amino)methyl)azetidine-1-carboxylate (53 mg, 37% yield) as an orange oil. [M+H]$^+$ calcd for $C_{15}H_{21}N_3O_4$ 307.35, found 308.6. The orange oil (53 mg, 0.172 mmol) was taken up in ethanol (3 ml), and Pd/C (2.42 mg, 0.017 mmol) was added and the reaction mixture was purged under an atmosphere of H$_2$ and stirred at 25° C. for 16 h. The reaction mixture was filtered through a pad of Celite and concentrated in vacuum to provide 6-2 as a crude residue (44 mg, 92% yield), used directly in the next step without further purification. [M+H]$^+$ calcd for $C_{15}H_{23}N_3O_2$ 277.37, found 277.2.

Step B: Preparation of N2-(4-((azetidin-3-ylmethyl)amino)phenyl)-N4-(2-(6-methylpyridin-2-yl)pyrimidin-4-yl)pyrimidine-2,4-diamine (537). A vial of 1-8 (48 mg, 0.162 mmol), 6-2 (44 mg, 0.159 mmol), cesium carbonate (211 mg, 0.647 mmol), BrettPhos (35 mg, 0.065 mmol), and BrettPhos Pd G4 (60 mg, 0.065 mmol) in degassed 1,4-dioxane (1.62 ml) was heated at 110° C. for 16 h. The reaction mixture was concentrated in vacuum. TFA (1.24 ml) and DCM (1.04 ml) were added to the residue and stirred at 45° C. for 30 min. TFA was removed in vacuum and the residue was purified by preparative HPLC chromatography using a gradient (5 to 75%) of acetonitrile in water with 0.05% trifluoroacetic acid to yield a TFA salt of the title compound (10.7 mg). [M+H]$^+$ calcd for $C_{24}H_{25}N_9$ 439.53, found 440.1.

Example 7: Synthesis of N2-(4-((azetidin-3-ylmethyl)(methyl)amino)phenyl)-N4-(2-(6-methylpyridin-2-yl)pyrimidin-4-yl)pyrimidine-2,4-diamine (202)

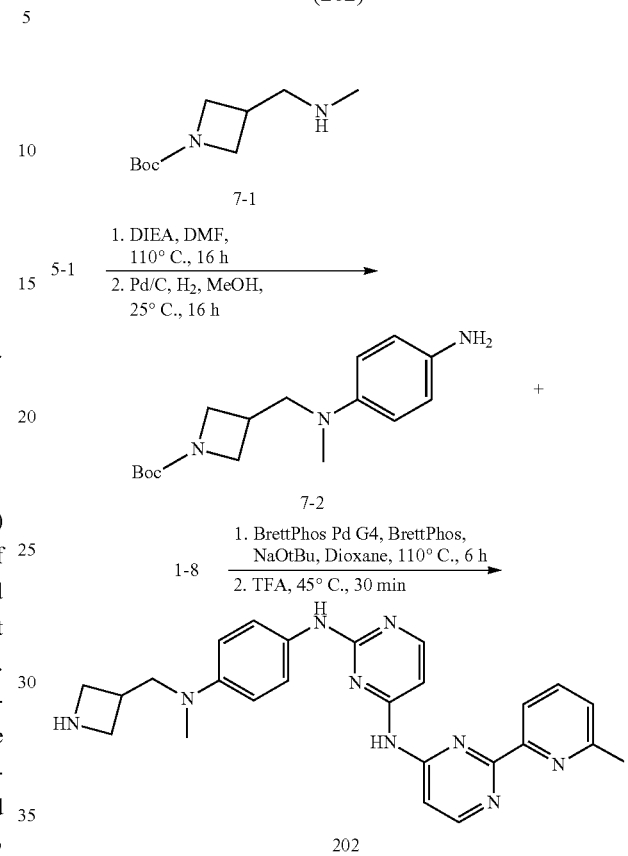

Step A: Preparation of tert-butyl 3-(((4-aminophenyl)(methyl)amino)methyl)azetidine-1-carboxylate (7-2). A solution of 5-1 (65 mg, 0.461 mmol), 7-1 (92 mg, 0.461 mmol), and DIPEA (805 µl, 4.61 mmol) in DMF (1 ml) was heated at 110° C. for 16 h. The reaction was concentrated in vacuum. The crude product was purified by silica-gel chromatography using a gradient (0 to 60%) of EtOAc in Hexanes to give tert-butyl 3-((methyl(4-nitrophenyl)amino)methyl)azetidine-1-carboxylate (118 mg, 80% yield) as an orange oil. [M+H]$^+$ calcd for $C_{16}H_{23}N_3O_4$ 321.38, found 322.2. The orange oil (118 mg, 0.367 mmol) was taken up in ethanol (3 ml), and Pd/C (2.42 mg, 0.017 mmol) was added and the reaction mixture was purged under an atmosphere of H$_2$ and stirred at 25° C. for 16 h. The reaction mixture was filtered through a pad of Celite and concentrated in vacuum, and the crude residue 7-2 (113 mg) was used directly in the next step. [M+H]$^+$ calcd for $C_{16}H_{25}N_3O_2$ 291.40, found 291.2.

Step B: Preparation of N2-(4-((azetidin-3-ylmethyl)(methyl)amino)phenyl)-N4-(2-(6-methylpyridin-2-yl)pyrimidin-4-yl)pyrimidine-2,4-diamine (202). A vial of 1-8 (97 mg, 0.323 mmol), 7-2 (113 mg, 0.159 mmol), cesium carbonate (211 mg, 0.647 mmol), BrettPhos (35 mg, 0.065 mmol), and BrettPhos Pd G4 (60 mg, 0.065 mmol) in degassed 1,4-dioxane (1.62 ml) was heated at 110° C. for 16 h. The reaction mixture was concentrated in vacuum. TFA (1.24 ml) and DCM (1.04 ml) were added to the residue and heated at 45° C. for 30 min. TFA was removed in vacuum and the residue was purified by preparative HPLC chromatography using a gradient (5 to 75%) of acetonitrile in water with 0.05% trifluoroacetic acid to yield a TFA salt of the title compound (45.5 mg). [M+H]+ calcd for $C_{25}H_{27}N_9$ 453.55, found 454.2.

Example 8: Synthesis of (R)—N4-(2-(6-methylpyridin-2-yl)pyrimidin-4-yl)-N2-(4-(pyrrolidin-3-ylamino)phenyl)pyrimidine-2,4-diamine (278)

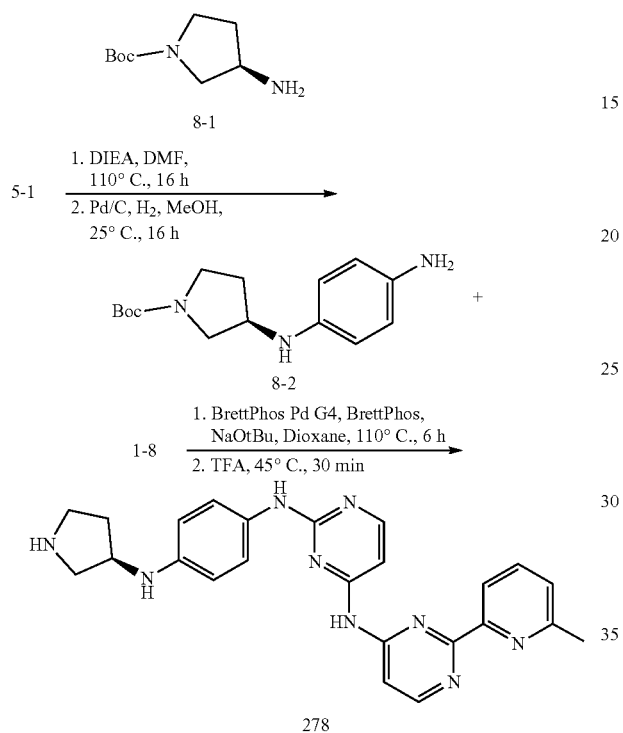

Step A: Preparation of tert-butyl (R)-3-((4-aminophenyl)amino)pyrrolidine-1-carboxylate (8-2). A solution of 5-1 (100 mg, 0.709 mmol), 8-1 (132 mg, 0.709 mmol), and DIPEA (1.24 ml, 7.09 mmol) in DMF (3 ml) was heated at 110° C. for 16 h. The reaction was concentrated in vacuum. The crude product was purified by silica-gel chromatography using a gradient (0 to 60%) of EtOAc in Hexanes to give tert-butyl (R)-3-((4-nitrophenyl)amino)pyrrolidine-1-carboxylate (130 mg, 60% yield) as a yellow oil. [M+H]+ calcd for $C_{15}H_{21}N_3O_4$ 307.35, found 308.5. The yellow oil (130 mg, 0.423 mmol) was taken up in ethanol (3 mL), Pd/C (4.55 mg, 0.032 mmol) was added and the reaction mixture was purged under an atmosphere of $H_2$ and stirred at 25° C. for 16 h. The reaction mixture was filtered through a pad of Celite and concentrated in vacuum to afford the crude residue 8-2 (100 mg), used directly in the next step without further purification. [M+H]+ calcd for $C_{15}H_{23}N_3O_2$ 277.37, found 277.3.

Step B: Preparation of (R)—N4-(2-(6-methylpyridin-2-yl)pyrimidin-4-yl)-N2-(4-(pyrrolidin-3-ylamino)phenyl)pyrimidine-2,4-diamine (278). A vial of 1-8 (45 mg, 0.151 mmol), 8-2 (50.1 mg, 0.181 mmol), cesium carbonate (98 mg, 0.301 mmol), BrettPhos (8.09 mg, 0.015 mmol), and BrettPhos Pd G4 (13.87 mg, 0.015 mmol) in degassed 1,4-dioxane (4 ml) was heated at 110° C. for 16 h. The reaction mixture was concentrated in vacuum. TFA (580 µl) and DCM (485 µl) were added to the residue and the resulting mixture heated at 45° C. for 30 min. TFA was removed in vacuum and the residue was purified by preparative HPLC chromatography using a gradient (5 to 75%) of acetonitrile in water with 0.05% trifluoroacetic acid to yield a TFA salt of the title compound (30.7 mg). [M+H]+ calcd for $C_{24}H_{25}N_9$ 439.53, found 440.1.

Example 9: Synthesis of 4-((4-((2-(6-methylpyridin-2-yl)pyrimidin-4-yl)amino)pyrimidin-2-yl)amino)benzenesulfonamide (108)

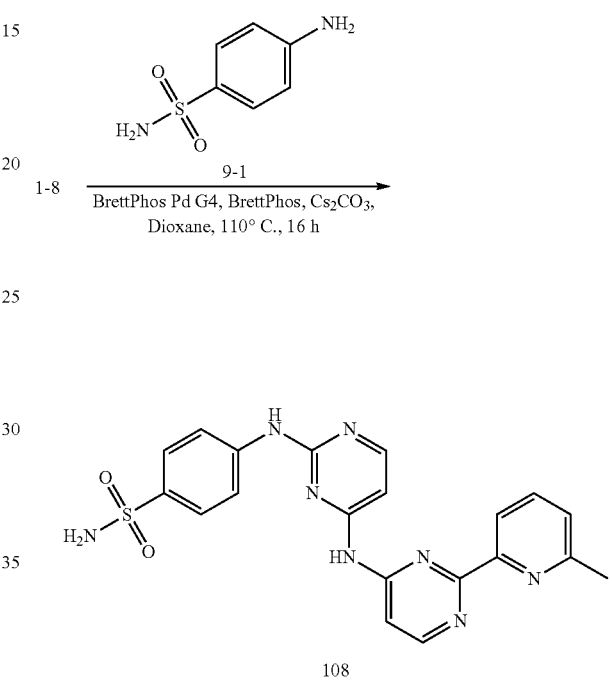

A vial of 1-8 (30 mg, 0.100 mmol), 9-1 (21 mg, 0.121 mmol), cesium carbonate (42.5 mg, 0.131 mmol), BrettPhos (2.70 mg, 5.02 µmol), and BrettPhos Pd G4 (4.62 mg, 5.02 µmol) in degassed 1,4-dioxane (1 ml) was heated at 110° C. for 16 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (12.7 mg). [M+H]+ calcd for $C_{20}H_{18}N_8O_2S$ 434.48, found 435.0.

Example 10: Synthesis of N4-(2-(6-methylpyridin-2-yl)pyrimidin-4-yl)-N2-(5-morpholinothiazol-2-yl)pyrimidine-2,4-diamine (555)

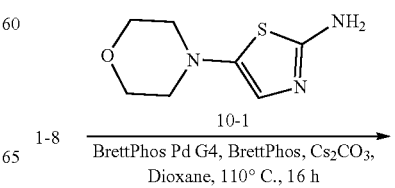

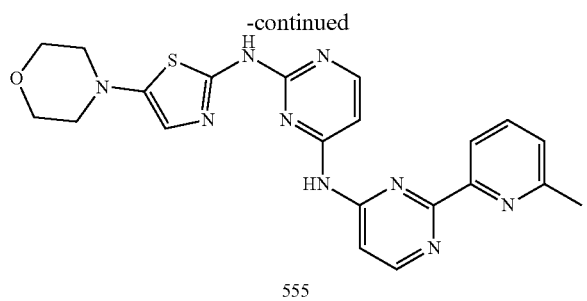

555

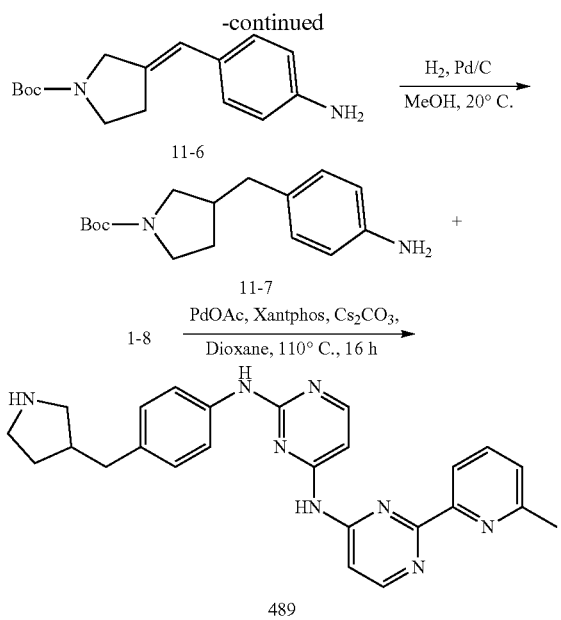

489

A vial of 1-8 (20 mg, 0.067 mmol), 10-1 (24.8 mg, 0.134 mmol), cesium carbonate (43.6 mg, 0.134 mmol), BrettPhos (7.19 mg, 0.013 mmol), and BrettPhos Pd G4 (12.33 mg, 0.013 mmol) in degassed 1,4-dioxane (1 ml) was heated at 110° C. for 16 h. The reaction mixture was concentrated in vacuum and the residue was purified by preparative HPLC chromatography using a gradient (5 to 65%) of acetonitrile in water with 0.05% trifluoroacetic acid to yield a TFA salt of the title compound (7.7 mg). [M+H]+ calcd for $C_{21}H_{21}N_9OS$ 447.52, found 448.2.

Example 11: Synthesis of N4-(2-(6-methylpyridin-2-yl)pyrimidin-4-yl)-N2-(4-(pyrrolidin-3-ylmethyl)phenyl)pyrimidine-2,4-diamine (489)

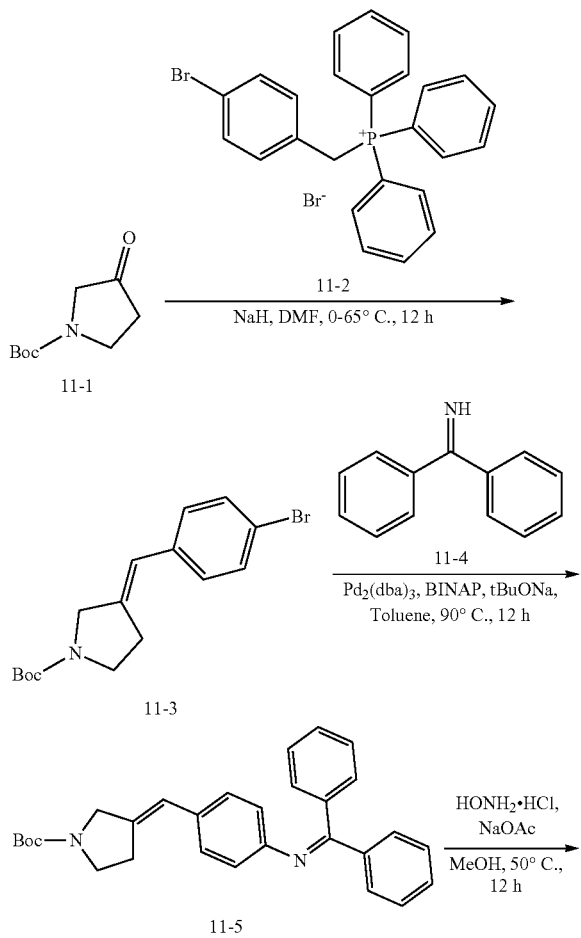

Step A: Preparation of tert-butyl (E)-3-(4-bromobenzylidene)pyrrolidine-1-carboxylate (11-3). To a solution of 11-1 (2.0 g, 10.8 mmol) in DMF (40 ml) was added NaH (561 mg, 14.0 mmol) at 0° C. The reaction mixture was stirred at 0° C. for 30 min, then 11-2 (6.1 g, 11.9 mmol) in DMF (10 ml) was added. The reaction mixture was heated at 65° C. for 12 h. The mixture was poured into $H_2O$ (400 mL), the white suspension was extracted with EA (200 mL×3), the combined organic phase was washed with sat. NaCl (200 mL×3), dried over solid $Na_2SO_4$, and concentrated under reduced pressure. The residue was purified by silica-gel column chromatography using a gradient (0 to 5%) of EtOAc in PE to give 11-3 (800 mg) as colorless oil.

Step B: Preparation of tert-butyl (E)-3-(4-((diphenylmethylene)amino)benzylidene)pyrrolidine-1-carboxylate (11-5). To a mixture of 11-3 (800 mg, 2.36 mmol), 11-4 (472 mg, 3.60 mmol) and tBuONa (364 mg, 3.78 mmol) in toluene (15 ml) was added $Pd_2(dba)_3$ (65 mg, 0.071 mmol) and BINAP (147 mg, 0.236 mmol) under $N_2$ atmosphere. The reaction mixture was degassed with $N_2$ several times, then heated at 90° C. for 4 h. The reaction mixture was concentrated under reduced pressure. The residue was purified by silica-gel column chromatography using a gradient (0 to 10%) of EtOAc in PE to give 11-5 (800 mg) as yellow oil.

Step C: Preparation of tert-butyl (E)-3-(4-aminobenzylidene)pyrrolidine-1-carboxylate (11-6). To a mixture of 11-5 (800 mg, 1.31 mmol) in MeOH (10 ml) under $N_2$ atmosphere was added $HONH_2$—HCl (200 mg, 2.89 mmol) and NaOAc (323 mg, 3.94 mmol). The reaction mixture was heated at 50° C. for 12 h. The reaction mixture was diluted with $H_2O$ (10 ml) and the product extracted in EtOAc (10 ml×3), the combined organic layer was dried over $Na_2SO_4$ and concentrated under reduced pressure. The residue was purified by preparative HPLC chromatography using a gradient (30 to 60%) of acetonitrile in water with 0.225% formic acid to give to give 11-6 (150 mg) as light yellow oil. [M+H]+ calcd for $C_{16}H_{22}N_2O_2$ 274.36, found 275.2.

Step D: Preparation of tert-butyl 3-(4-aminobenzyl)pyrrolidine-1-carboxylate (11-7). To a solution of 11-6 (250 mg, 0.911 mmol) in MeOH (15 ml) was added Pd/C (30 mg, 10%). The reaction mixture was degassed with $H_2$ several times, then stirred at 20° C. for 1 h. The reaction mixture was filtered through a pad of Celite and the filtrate was concentrated under reduced pressure. The residue was purified by preparative HPLC chromatography using a gradient (23 to 53%) of acetonitrile in water with 0.225% formic acid to give 11-7 (100 mg) as a yellow solid. [M+Na]$^+$ calcd for $C_{16}H_{24}N_2O_2$ 299.37, found 299.2.

Step E: Preparation of N4-(2-(6-methylpyridin-2-yl)pyrimidin-4-yl)-N2-(4-(pyrrolidin-3-ylmethyl)phenyl)pyrimidine-2,4-diamine (489). A vial of 1-8 (30 mg, 0.100 mmol), 11-7 (33.3 mg, 0.121 mmol), cesium carbonate (65.4 mg, 0.201 mmol), Xantphos (11.62 mg, 0.020 mmol), and Pd(OAc)$_2$ (4.51 mg, 0.020 mmol) in degassed 1,4-dioxane (1 ml) was heated at 110° C. for 16 h. The reaction mixture was concentrated in vacuum and the residue was purified by preparative HPLC chromatography using a gradient (2 to 50%) of acetonitrile in water with 0.05% trifluoroacetic acid to yield a TFA salt of the title compound (24.9 mg). [M+H]$^+$ calcd for $C_{25}H_{26}N_8$ 438.54, found 439.2.

Example 12: Synthesis of N2-(3-isopropyl-2,3,4,5-tetrahydro-1H-benzo[d]azepin-7-yl)-N4-(2-(6-methylpyridin-2-yl)pyrimidin-4-yl)pyrimidine-2,4-diamine (223)

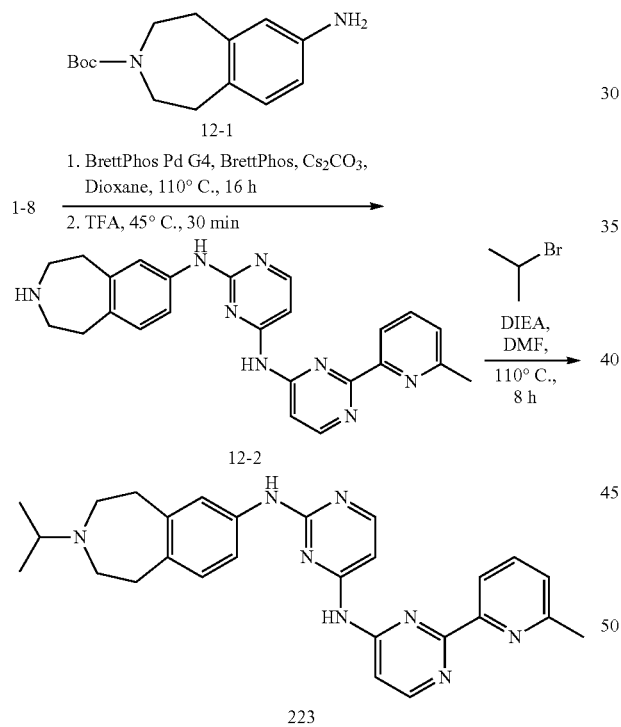

Step A: Preparation of N4-(2-(6-methylpyridin-2-yl)pyrimidin-4-yl)-N2-(2,3,4,5-tetrahydro-1H-benzo[d]azepin-7-yl)pyrimidine-2,4-diamine (12-2). A vial of 1-8 (35 mg, 0.117 mmol), 12-1 (46.1 mg, 0.176 mmol), cesium carbonate (76 mg, 0.234 mmol), BrettPhos (12.58 mg, 0.023 mmol), and BrettPhos Pd G4 (21.57 mg, 0.023 mmol) in degassed 1,4-dioxane (586 µl) was heated at 110° C. for 16 h. The reaction mixture was concentrated in vacuum. TFA (468 µl) and DCM (348 µl) were added to the residue and heated at 45° C. for 30 min. TFA was removed in vacuum and the residue was purified by preparative HPLC chromatography using a gradient (2 to 30%) of acetonitrile in water with 0.05% trifluoroacetic acid to yield a TFA salt of the title compound (76 mg). [M+H]$^+$ calcd for $C_{24}H_{24}N_8$ 424.51, found 425.1.

Step B: Preparation of N2-(3-isopropyl-2,3,4,5-tetrahydro-1H-benzo[d]azepin-7-yl)-N4-(2-(6-methylpyridin-2-yl)pyrimidin-4-yl)pyrimidine-2,4-diamine (223). A vial of 12-2 (18 mg, 0.028 mmol), 2-bromopropane (10.18 mg, 0.083 mmol), and DIEA (48.2 µl, 0.276 mmol) in DMF (276 µl) was heated at 110° C. for 8 h. The reaction mixture was concentrated in vacuum and the residue was purified by preparative HPLC chromatography using a gradient (2 to 60%) of acetonitrile in water with 0.05% trifluoroacetic acid to yield a TFA salt of the title compound (2.3 mg). [M+H]$^+$ calcd for $C_{27}H_{30}N_8$ 466.59, found 467.3.

Example 13: Synthesis of N4-(2-(6-methylpyridin-2-yl)pyrimidin-4-yl)-N2-(1,2,3,4-tetrahydroisoquinolin-7-yl)pyrimidine-2,4-diamine (175)

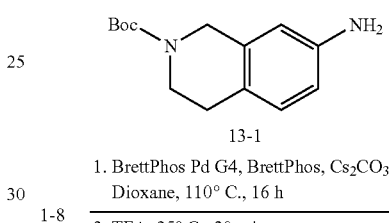

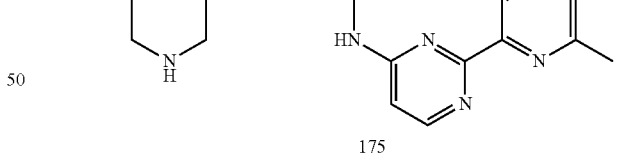

A vial of 1-8 (25 mg, 0.075 mmol), 13-1 (28 mg, 0.112 mmol), cesium carbonate (48.6 mg, 0.149 mmol), BrettPhos (8.01 mg, 0.015 mmol), and BrettPhos Pd G4 (13.73 mg, 0.015 mmol) in degassed 1,4-dioxane (1 ml) was heated at 110° C. for 16 h. The reaction mixture was concentrated in vacuum. TFA (1 ml) and DCM (1 ml) were added to the residue and stirred at 25° C. for 1 h. TFA was removed in vacuum and the residue was purified by preparative HPLC chromatography using a gradient (5 to 65%) of acetonitrile in water with 0.05% trifluoroacetic acid to yield a TFA salt of the title compound (16.7 mg). [M+H]$^+$ calcd for $C_{23}H_{22}N_8$ 410.49, found 411.1.

Example 14: Synthesis of N2-(4-(3,8-diazabicyclo[3.2.1]octan-8-yl)phenyl)-N4-(2-(6-methylpyridin-2-yl)pyrimidin-4-yl)pyrimidine-2,4-diamine (221)

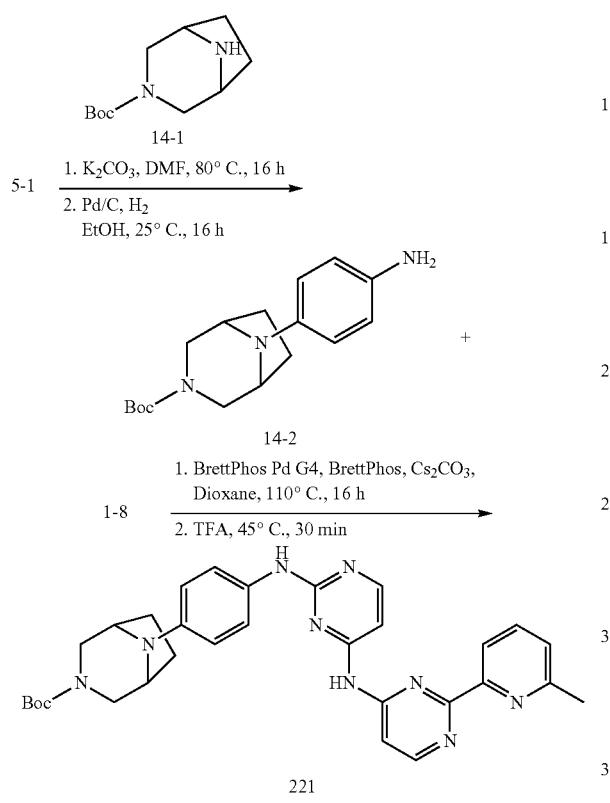

Step A: Preparation of tert-butyl 8-(4-aminophenyl)-3,8-diazabicyclo[3.2.1]octane-3-carboxylate (14-2). A solution of 5-1 (75 mg, 0.532 mmol), 14-1 (124 mg, 0.585 mmol), and potassium carbonate (147 mg, 1.063 mmol) in DMF (1.77 ml) was heated at 80° C. for 16 h. The reaction was concentrated in vacuum. The crude product was purified by silica-gel chromatography using a gradient (0 to 15%) of MeOH in DCM with 2.5% triethylamine to give tert-butyl 8-(4-nitrophenyl)-3,8-diazabicyclo[3.2.1]octane-3-carboxylate (68 mg, 39% yield) as an orange solid. [M+H]$^+$ calcd for $C_{17}H_{23}N_3O_4$ 333.39, found 334.0. The orange solid (68 mg, 0.204 mmol) was taken up in ethanol (1.61 ml), and Pd/C (51.4 mg, 0.097 mmol) was added and the reaction mixture was purged under an atmosphere of $H_2$ and stirred at 25° C. for 16 h. The reaction mixture was filtered through a pad of Celite and concentrated in vacuum to give the crude residue 14-2 (55 mg), used directly in the next step. [M+H]$^+$ calcd for $C_{15}H_{25}N_3O_2$ 303.41, found 304.0.

Step B: Preparation of N2-(4-(3,8-diazabicyclo[3.2.1]octan-8-yl)phenyl)-N4-(2-(6-methylpyridin-2-yl)pyrimidin-4-yl)pyrimidine-2,4-diamine (221). A vial of 1-8 (25 mg, 0.084 mmol), 14-2 (25.4 mg, 0.084 mmol), cesium carbonate (35.4 mg, 0.109 mmol), BrettPhos (2.25 mg, 4.18 µmol), and BrettPhos Pd G4 (3.85 mg, 4.18 µmol) in degassed 1,4-dioxane (1.5 ml) was heated at 110° C. for 16 h. The reaction mixture was concentrated in vacuum. TFA (226 µl) and DCM (188 µl) were added to the residue and heated at 45° C. for 30 min. TFA was removed in vacuum and the residue was purified by preparative HPLC chromatography using a gradient (5 to 75%) of acetonitrile in water with 0.05% trifluoroacetic acid to yield a TFA salt of the title compound (3.6 mg). [M+H]$^+$ calcd for $C_{26}H_{27}N_9$ 465.57, found 466.1.

Example 15: Synthesis of N2-(1,3-dihydrospiro[indene-2,3'-pyrrolidin]-5-yl)-N4-(2-(6-methylpyridin-2-yl)pyrimidin-4-yl)pyrimidine-2,4-diamine (277)

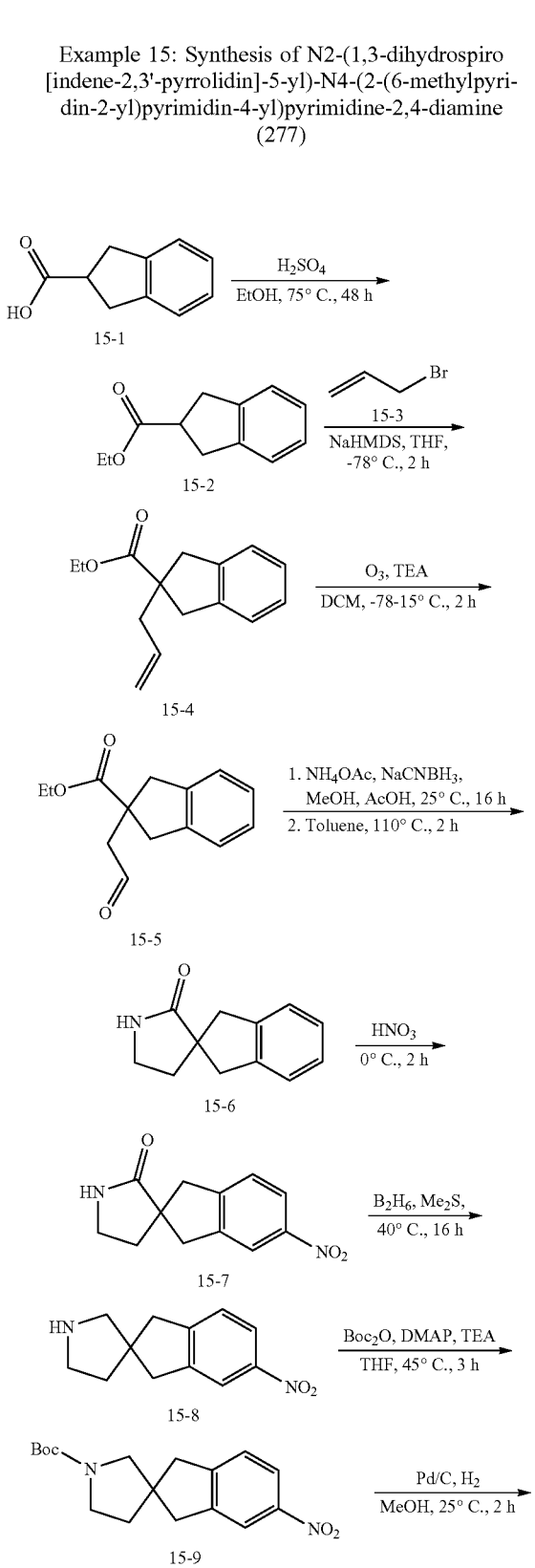

-continued

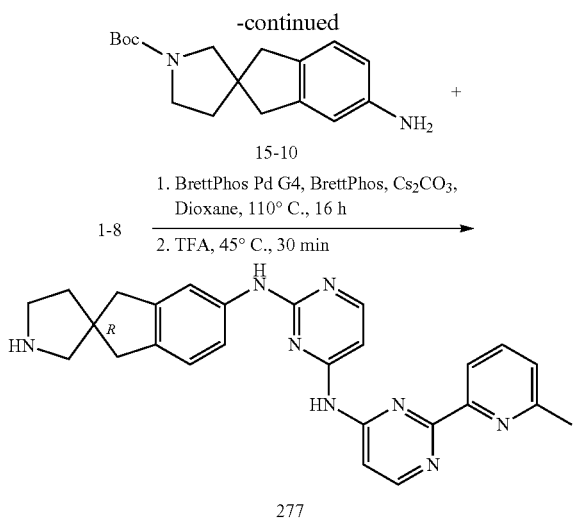

Step A: Preparation of ethyl 2,3-dihydro-1H-indene-2-carboxylate (15-2). To a mixture of 15-1 (10 g, 61.6 mmol) in ethanol (300 ml) was added $H_2SO_4$ (36 ml). The mixture was heated at 75° C. for 48 h. The reaction mixture was concentrated and the residue was partitioned between EtOAc (200 ml) and $H_2O$ (200 ml). The reaction mixture was basified by 5N NaOH aq. to pH=11, then the organic layer was separated. The aqueous layer was extracted with EtOAc (200 mL×2) and all organic layers were combined and dried over $Na_2SO_4$. Concentration in vacuum gave 15-2 (10.5 g) as colorless oil.

Step B: Preparation of ethyl 2-allyl-2,3-dihydro-1H-indene-2-carboxylate (15-4). To a solution of 15-2 (6.0 g, 31.5 mmol) in THF (120 ml) was added NaHMDS (38 mL, 37.8 mmol) dropwise at −78° C. The reaction mixture was stirred at −78° C. for 1 h under $N_2$, then 15-3 (4.6 g, 37.8 mmol) was added at −78° C. The reaction mixture was stirred at −78° C. for 2 h. The reaction mixture was diluted with sat. $NH_4Cl$ aq (120 mL), then extracted with EtOAC (150 ml×3). The combined organic layer was concentrated in vacuum and purified by silica-gel column chromatography using a gradient (0 to 2%) of EtOAc in PE to obtain 15-4 (6.5 g) as a colorless oil.

Step C: Preparation of ethyl 2-(2-oxoethyl)-2,3-dihydro-1H-indene-2-carboxylate (15-5). A solution of 15-4 (6.5 g, 28.2 mmol) in DCM (80 ml) and cooled to −78° C. $O_3$ was bubbled through the solution for 15 min, at which time a light blue color persisted. Then TEA (5.7 g, 56.4 mmol) was added dropwise and the mixture was stirred at 25° C. for 1.75 h. The reaction mixture was diluted with sat. $NaHCO_3$ aq (150 ml), then extracted with DCM (150 ml×3). The combined organic layer was dried with $Na_2SO_4$, filtered and concentrated in vacuum to obtain 15-5 (6.0 g) as a light yellow oil, used directly in the next step.

Step D: Preparation of 1,3-dihydrospiro[indene-2,3'-pyrrolidin]-2'-one (15-6). To a solution of 15-5 (1.0 g, 4.30 mmol) in MeOH (25 ml) and AcOH (25 ml) was added $NH_4OAc$ (16.6 g, 215.0 mmol), the mixture was stirred at 25° C. for 4 h. Then $NaCNBH_3$ (405 mg, 6.45 mmol) was added and the mixture was stirred at 25° C. for 12 h. The reaction mixture was diluted with sat. $NaHCO_3$ aq (250 ml) and extracted with DCM (150 ml×3). The combined organic layer was dried with $Na_2SO_4$ and concentrated in vacuum. The residue was dissolved in toluene (10 ml) and heated at 110° C. for 2 h. The reaction mixture was concentrated in vacuum and purified by silica-gel column chromatography using a gradient (10 to 100%) of EtOAc in PE to obtain 15-6 (160 mg) as a white solid.

Step E: Preparation of 5-nitro-1,3-dihydrospiro[indene-2,3'-pyrrolidin]-2'-one (15-7). A solution of 15-6 (900 mg, 4.80 mmol) in $HNO_3$ (20 ml, 70%) was stirred at 0° C. for 2 h. The reaction mixture was diluted with $H_2O$ (30 ml) and extracted with DCM (30 ml×3). The combined organic layer was concentrated in vacuum and purified by silica-gel column chromatography using a gradient (10 to 80%) of EtOAc in PE to obtain 15-7 (700 mg) as light yellow solid.

Step F: Preparation of 5-nitro-1,3-dihydrospiro[indene-2,3'-pyrrolidine] (15-8). To a solution of 15-7 (100 mg, 0.43 mmol) in THF (4 ml) was added $B_2H_6$-$Me_2S$ (0.8 ml, 8.60 mmol), then the mixture was heated at 45° C. for 16 h. The reaction mixture was quenched with MeOH (50 ml), then concentrated in vacuum and purified by preparative HPLC chromatography with acetonitrile in water with 0.05% HCl to obtain 15-8 (50 mg) as light yellow oil. $[M+H]^+$ calcd for $C_{12}H_{14}N_2O_2$ 218.26, found 219.1.

Step G: Preparation of tert-butyl 5-nitro-1,3-dihydrospiro[indene-2,3'-pyrrolidine]-1'-carboxylate (15-9). To a solution of 15-8 (217 mg, 0.99 mmol), DMAP (61 mg, 0.50 mmol), and TEA (1.0 g, 9.90 mmol) in THF (10 ml) was added $Boc_2O$ (648 mg, 2.97 mmol), then the reaction mixture was heated at 45° C. for 2 h. The reaction mixture was diluted with $H_2O$ (20 ml) and extracted with EtOAc (20 ml×3). The combined organic layer was concentrated in vacuum and purified by silica-gel column chromatography using a gradient (0 to 20%) of EtOAc in PE to obtain 15-9 (250 mg) as light yellow oil.

Step H: Preparation of tert-butyl 5-amino-1,3-dihydrospiro[indene-2,3'-pyrrolidine]-1'-carboxylate (15-10). To a solution of 15-9 (40 mg, 0.12 mmol) in MeOH (3 ml) was added Pd/C (10 mg, 10%), then the resulting mixture was stirred at 25° C. for 2 h under $H_2$ atmosphere (15 psi). The reaction mixture was filtered and concentrated in vacuum. The residue was purified by preparative HPLC chromatography (acetonitrile in water with 0.225% formic acid), then the aqueous phase was adjusted to pH=8 by added sat. $NaHCO_3$ aq at 0° C. and the product extracted in DCM (10 ml×3) at 0° C. The combined organic layer was washed with brine (30 ml×3) at 0° C., dried with $Na_2SO_4$ and concentrated in vacuum to obtain 15-9 (35 mg) as yellow solid. $[M+Na]^+$ calcd for $C_{17}H_{24}N_2O_2$ 311.38, found 311.1.

Step I: Preparation of N2-(1,3-dihydrospiro[indene-2,3'-pyrrolidin]-5-yl)-N4-(2-(6-methylpyridin-2-yl)pyrimidin-4-yl)pyrimidine-2,4-diamine (277). A vial of 1-8 (25 mg, 0.075 mmol), 15-10 (28 mg, 0.112 mmol), cesium carbonate (48.6 mg, 0.149 mmol), BrettPhos (8.01 mg, 0.015 mmol), and BrettPhos Pd G4 (13.73 mg, 0.015 mmol) in degassed 1,4-dioxane (1 ml) was heated to 110° C. for 16 h. The reaction mixture was concentrated in vacuum. TFA (1 ml) and DCM (1 ml) were added to the residue and heated at 45° C. for 30 min. TFA was removed in vacuum and the residue was purified by preparative HPLC chromatography using a gradient (5 to 65%) of acetonitrile in water with 0.05% trifluoroacetic acid to yield a TFA salt of the title compound (16.7 mg). $[M+H]^+$ calcd for $C_{23}H_{22}N_8$ 410.49, found 411.1.

Example 16: Synthesis of N4-(2-(6-methylpyridin-2-yl)pyrimidin-4-yl)-N2-(1-(2-morpholinoethyl)-1H-pyrazol-4-yl)pyrimidine-2,4-diamine (84)

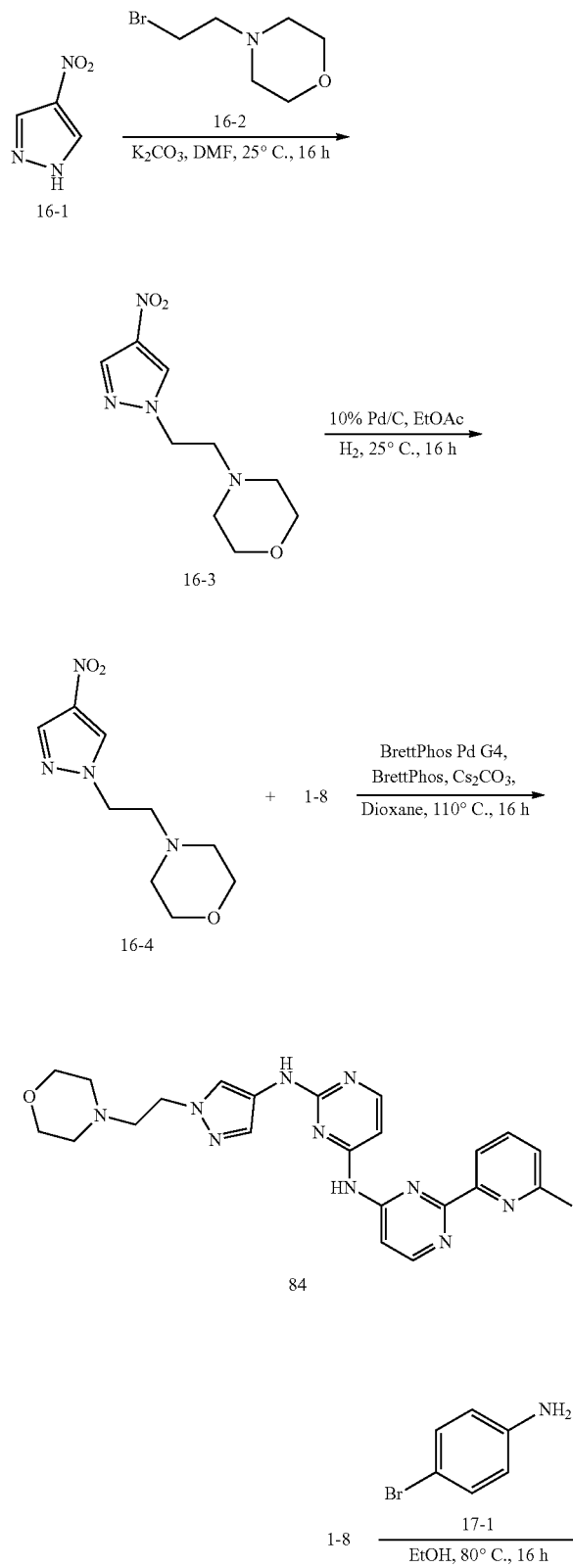

Step A: Preparation of 4-(2-(4-nitro-1H-pyrazol-1-yl)ethyl)morpholine (16-3). To a stirred solution of 16-1 (0.5 g, 4.42 mmol) in DMF (5.0 ml) was added $K_2CO_3$ (1.83 g, 13.26 mmol) and 16-2 (1.06 g, 5.52 mmol). The reaction mixture was stirred at 25° C. for 16 h. The reaction mixture was diluted with ice-cold water and extracted with EtOAc (50 ml×3). The combined organic layer was washed with ice cold water, brine and dried over anhydrous $Na_2SO_4$, filtered and concentrated under reduced pressure to afford crude residue 16-3 (550 mg) as a viscous liquid. The crude product was used directly in the next step without further purification.

Step B: Preparation of 1-(2-morpholinoethyl)-1H-pyrazol-4-amine (16-4). To a solution of 16-3 (500 mg, 2.2 mmol) in EtOAc (25 ml) was added 10% Pd/C (50 mg). The reaction mixture stirred at 25° C. for 16 h under $H_2$ balloon pressure. The reaction mixture was filtered through a pad of Celite and the filtrate was concentrated under reduced pressure to get crude residue 16-4 (275 mg) as a viscous liquid. The crude product was used directly in the next step without further purification.

Step C: Preparation of N4-(2-(6-methylpyridin-2-yl)pyrimidin-4-yl)-N2-(1-(2-morpholinoethyl)-1H-pyrazol-4-yl)pyrimidine-2,4-diamine (84). A vial of 1-8 (20 mg, 0.067 mmol), 16-4 (20 mg, 0.100 mmol), cesium carbonate (43.6 mg, 0.134 mmol), BrettPhos (7.19 mg, 0.013 mmol), and BrettPhos Pd G4 (12.33 mg, 0.013 mmol) in degassed 1,4-dioxane (1 ml) was heated at 110° C. for 16 h. The reaction mixture was concentrated in vacuum. TFA (1 ml) and DCM (1 ml) were added to the residue and stirred at 25° C. for 16 h. TFA was removed in vacuum and the residue was purified by preparative HPLC chromatography using a gradient (2 to 20%) of acetonitrile in water with 0.05% trifluoroacetic acid to yield a TFA salt of the title compound (10 mg). $[M+H]^+$ calcd for $C_{23}H_{26}N_{10}O$ 458.53, found 459.2.

Example 17: Synthesis of N4-(2-(6-methylpyridin-2-yl)pyrimidin-4-yl)-N2-(4-(1-(oxetan-3-yl)-1H-pyrazol-4-yl)phenyl)pyrimidine-2,4-diamine (538)

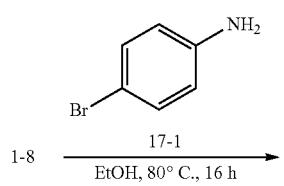

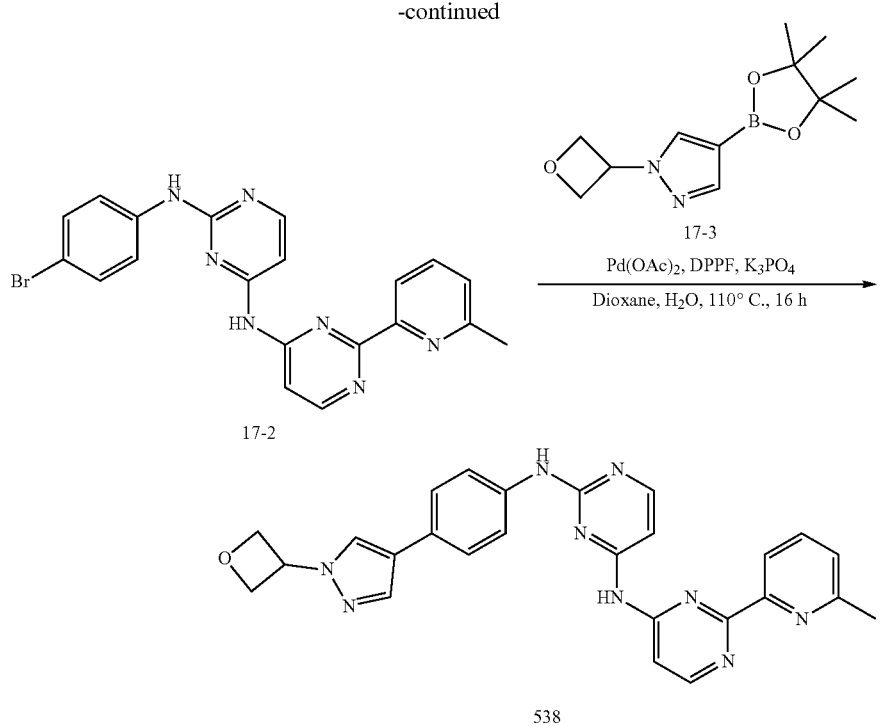

Step A: Preparation of N2-(4-bromophenyl)-N4-(2-(6-methylpyridin-2-yl)pyrimidin-4-yl)pyrimidine-2,4-diamine (17-2). A vial of 1-8 (485 mg, 1.624 mmol), and 17-1 (559 mg, 3.25 mmol) in ethanol (8 ml) was heated at 80° C. for 16 h. The precipitate from the reaction mixture was collected by vacuum filtration to give the crude residue 17-2 (620 mg), used directly in the next step without further purification. [M+H]+ calcd for $C_{20}H_{16}BrN_7$ 434.30, found 436.2.

Step B: Preparation of N4-(2-(6-methylpyridin-2-yl)pyrimidin-4-yl)-N2-(4-(1-(oxetan-3-yl)-1H-pyrazol-4-yl)phenyl)pyrimidine-2,4-diamine (538). A vial of 17-2 (25 mg, 0.058 mmol), 17-3 (21.6 mg, 0.086 mmol), potassium phosphate tribasic (36.7 mg, 0.173 mmol), palladium (II) acetate (2.58 mg, 0.012 mmol), and DPPF (5.46 mg, 0.012 mmol) in degassed 1,4-dioxane (461 µl) and H2O (115 µl) was heated at 110° C. for 16 h. The reaction mixture was concentrated in vacuum and the residue was purified by preparative HPLC chromatography using a gradient (5 to 65%) of acetonitrile in water with 0.05% trifluoroacetic acid to yield a TFA salt of the title compound (5.4 mg). [M+H]+ calcd for $C_{26}H_{23}N_9O$ 477.53, found 478.1.

Example 18: Synthesis of N2-(4-(1-(2-(methylamino)ethyl)-1H-pyrazol-4-yl)phenyl)-N4-(2-(6-methylpyridin-2-yl)pyrimidin-4-yl)pyrimidine-2,4-diamine (347)

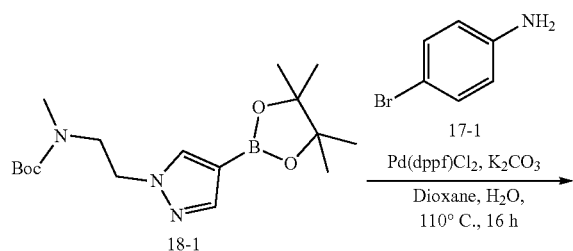

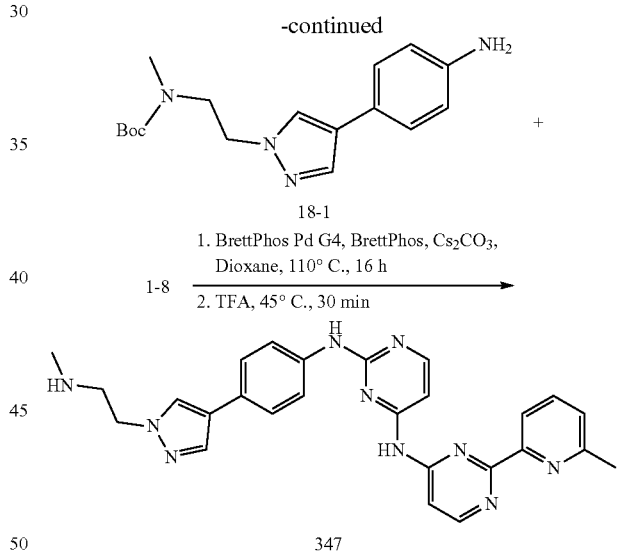

Step A: Preparation of tert-butyl (2-(4-(4-aminophenyl)-1H-pyrazol-1-yl)ethyl)(methyl)carbamate (18-2). A vial of 18-1 (96 mg, 0.274 mmol), 17-1 (39.3 mg, 0.228 mmol), potassium carbonate (95 mg, 0.685 mmol), and Pd(dppf)Cl2 (33.4 mg, 0.046 mmol) in degassed 1,4-dioxane (1218 µl) and H2O (304 µl) was heated at 110° C. for 16 h. The reaction mixture was concentrated in vacuum and the residue was purified by preparative HPLC chromatography using a gradient (10 to 50%) of acetonitrile in water with 0.05% trifluoroacetic acid to yield a TFA salt of 18-2 (32 mg). [M+H]+ calcd for $C_{17}H_{24}N_4O_2$ 316.41, found 317.2.

Step B: Preparation of N2-(4-(1-(2-(methylamino)ethyl)-1H-pyrazol-4-yl)phenyl)-N4-(2-(6-methylpyridin-2-yl)pyrimidin-4-yl)pyrimidine-2,4-diamine (347). A vial of 1-8 (25 mg, 0.084 mmol), 18-2 (34.4 mg, 0.109 mmol), cesium carbonate (54.5 mg, 0.167 mmol), BrettPhos (8.98 mg, 0.017 mmol), and BrettPhos Pd G4 (15.41 mg, 0.017 mmol) in degassed 1,4-dioxane (418 μl) was heated at 110° C. for 16 h. The reaction mixture was concentrated in vacuum. TFA (226 μl) and DCM (188 μl) were added to the residue and heated at 45° C. for 30 min. TFA was removed in vacuum and the residue was purified by preparative HPLC chromatography using a gradient (2 to 60%) of acetonitrile in water with 0.05% trifluoroacetic acid to yield a TFA salt of the title compound (26.9 mg). [M+H]$^+$ calcd for $C_{26}H_{26}N_{10}$ 478.56, found 479.2.

Example 19: Synthesis of N4-(2-(3-methyl-1H-indazol-4-yl)pyrimidin-4-yl)-N2-(4-morpholinophenyl)pyrimidine-2,4-diamine (19-6)

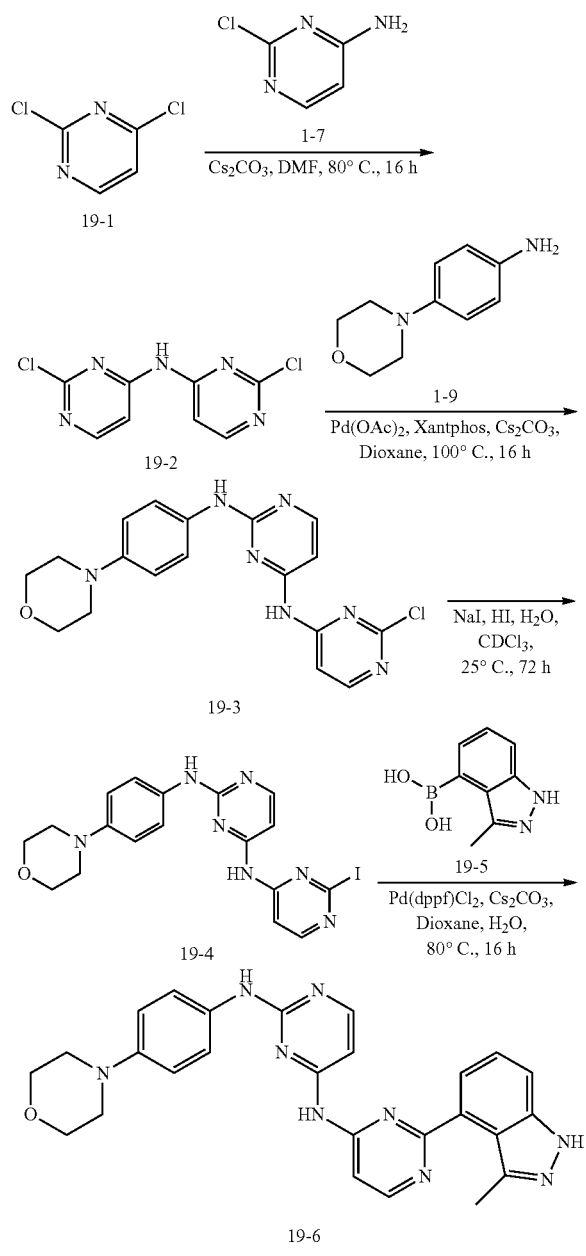

Step A: Preparation of bis(2-chloropyrimidin-4-yl)amine (19-2). A suspension of 19-1 (11.5 g, 77.2 mmol), 1-7 (10.0 g, 77.2 mmol) and $Cs_2CO_3$ (50.3 g, 154 mmol) in DMF (300 ml) was heated at 80° C. for 16 h. The reaction mixture was filtered and the filtrate was concentrated in vacuum and purified by preparative HPLC chromatography using a gradient (2 to 55%) of acetonitrile in water with 0.1% trifluoroacetic acid to yield 19-2 (4.5 g) as yellow solid. [M+H]$^+$ calcd for $C_8H_5Cl_2N_5$ 242.06, found 242.1.

Step B: Preparation of N4-(2-chloropyrimidin-4-yl)-N2-(4-morpholinophenyl)pyrimidine-2,4-diamine (19-3). To a suspension of 19-2 (2.0 g, 8.26 mmol) in 1,4-dioxane (80 ml) was added 1-9 (982 mg, 5.51 mmol), $Cs_2CO_3$ (3.6 g, 11.0 mmol), $Pd(OAc)_2$ (123 mg, 0.551 mmol) and Xantphos (319 mg, 0.551 mmol). The reaction mixture was degassed under vacuum and $N_2$ was purged for 3 times. The reaction mixture was heated at 100° C. for 16 h. The reaction mixture was concentrated in vacuum and purified by silica-gel column chromatography using a gradient (10 to 50%) of EtOAc in PE to obtain 19-3 (690 mg) as yellow solid. [M+H]$^+$ calcd for $C_{18}H_{18}ClN_7O$ 383.84, found 384.0.

Step C: Preparation of N4-(2-iodopyrimidin-4-yl)-N2-(4-morpholinophenyl)pyrimidine-2,4-diamine (19-4). To a solution of 19-3 (690 mg, 1.80 mmol) and NaI (1.6 g, 10.8 mmol) in $CHCl_3$ (10 ml) was added HI/$H_2O$ (20 ml, 45%) at 0° C. and was stirred at 25° C. for 72 h. The mixture was basified by NaOH solution (2 M) to pH=8 and extracted with EtOAc (30 ml×2). The organic layer was concentrated in vacuum and purified by preparative HPLC chromatography using a gradient (10 to 35%) of acetonitrile in water with 0.225% formic acid to yield 19-4 (720 mg) as white solid. [M+H]$^+$ calcd for $C_{18}H_{18}IN_7O$ 475.29, found 475.8.

Step D: Preparation of N4-(2-(3-methyl-1H-indazol-4-yl)pyrimidin-4-yl)-N2-(4-morpholinophenyl)pyrimidine-2,4-diamine (19-6). To a vial containing compound 19-4 (20 mg, 0.042 mmol) was added 19-5 (15 mg, 0.084 mmol) followed by sodium carbonate (22.30 mg, 0.210 mmol), and Pd(dppf)$Cl_2$ (6.16 mg, 0.0084 mmol). The resulting mixture was purged with $N_2$ before degassed water (1 ml) and 1,4-dioxane (1 ml) was added. The vial was capped and heated at 80° C. for 16 h. The reaction was then cooled and concentrated in vacuum. The resulting residue was purified by preparative HPLC chromatography using a gradient (5 to 65%) of acetonitrile in water with 0.05% trifluoroacetic acid to yield a TFA salt of the title compound (3.5 mg). [M+H]$^+$ calcd for $C_{26}H_{25}N_9O$ 479.55, found 480.1.

Example 20: Synthesis of N4-(2-(6-(difluoromethyl)-5-fluoropyridin-2-yl)pyrimidin-4-yl)-N2-(4-morpholinophenyl)pyrimidine-2,4-diamine (426)

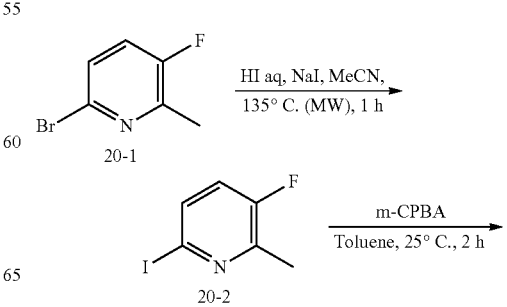

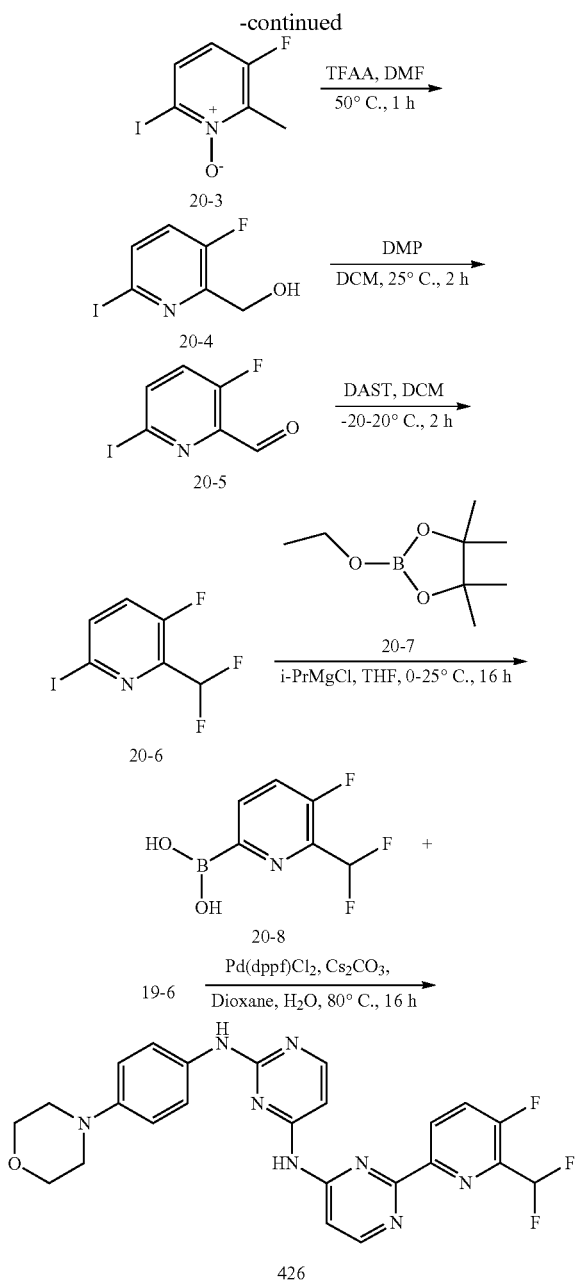

Step A: Preparation of 3-fluoro-6-iodo-2-methylpyridine (20-2). To a solution of 20-1 (2.0 g, 10.5 mmol) in MeCN (10 ml) was added NaI (4.8 g, 31.5 mmol) and HI aq. (2.5 ml, 47% in H₂O). The mixture was heated at 135° C. for 1 h under microwave. The reaction was poured into cold sat. NaHCO₃ (300 ml). The resulting mixture was extracted with EtOAc (150 ml×3). The organic layers were washed with sat. Na₂SO₃ (200 ml×3) and concentrated in vacuum to dryness to give crude residue 20-2 (2.0 g) as white solid, used directly in the next step. [M+H]⁺ calcd for C₆H₅FIN 237.02, found 237.9.

Step B: Preparation of 3-fluoro-6-iodo-2-methylpyridine 1-oxide (20-3). To a solution of 20-2 (10 g, 42.2 mmol) in toluene (200 ml) was added mCPBA (17.1 g, 84.4 mmol, 85% purity) in portions. The mixture was stirred at 25° C. for 2 h. The reaction mixture was poured into ice saturated NaHCO₃ aq. (500 ml). The resulting mixture was extracted with EtOAc (500 ml×5). The combined organic layer was washed with Na₂SO₃ aq. (1000 ml×3), concentrated to dryness and purified by column (PE/EA=20/1 to 1/1) to give 20-3 (4.67 g) as yellow solid. [M+H]⁺ calcd for C₆H₅FINO 253.01, found 253.9.

Step C: Preparation of (3-fluoro-6-iodopyridin-2-yl)methanol (20-4). 20-3 (10.5 g, 41.49 mmol) was added into TFAA (100 ml) in batches. The reaction mixture was stirred at 35° C. for 16 h. The reaction mixture was poured into ice NaHCO₃ aq. (500 ml). The resulting mixture was extracted with EtOAc (200 ml×3). The combined organic layer was concentrated to dryness to give a crude product. This crude product was dissolved in DCM (80 ml) and H₂O (80 ml). Then K₂CO₃ (22.9 g, 165.97 mmol) was added. The reaction mixture was heated at 40° C. for 16 h. The reaction mixture was poured into ice water (300 ml). The resulting mixture was extracted with EtOAc (200 ml×3). The combined organic layer was concentrated to dryness and purified by column (PE/EA=100/1 to 10/1) to obtain 20-4 (7.3 g) as light yellow solid. [M+H]⁺ calcd for C₆H₅FINO 253.01, found 253.9.

Step D: Preparation of 3-fluoro-6-iodopicolinaldehyde (20-5). To a solution of 20-4 (7.3 g, 28.9 mmol) in DCM (160 ml) was added DMP (24.5 g, 57.8 mmol). The mixture was stirred at 25° C. for 2 h. The reaction was poured into cold sat. NaHCO₃ (500 ml). The mixture was extracted with EtOAc (200 ml×5). The organic layer was concentrated in vacuum to dryness and purified by column (PE/EA=100/1 to 10/1) to obtain 20-5 (6.5 g) as light yellow solid.

Step E: Preparation of 2-(difluoromethyl)-3-fluoro-6-iodopyridine (20-6). To a solution of 20-5 (6.5 g, 25.9 mmol) in DCM (100 ml) was dropwise added DAST (7.5 g, 46.6 mmol) at −20° C. The reaction mixture was warmed slowly and stirred at 20° C. for another 2 h. The reaction mixture was neutralized with sat. NaHCO₃ aq. (500 ml), then the resulting mixture was extracted with EtOAc (150 ml×3). The combined organic layers were concentrated to dryness and purified by silica-gel column chromatography (PE/EA=100/1 to 10/1) to obtain 20-6 (6.5 g) as light pink solid. [M+H]⁺ calcd for C₆H₃F₃IN 273.00, found 273.9.

Step F: Preparation of (6-(difluoromethyl)-5-fluoropyridin-2-yl)boronic acid (20-8). To a solution of 20-6 (1.8 g, 6.59 mmol) and B(OPr-i)₃ (2.5 g, 13.4 mmol) in THF (70 ml) was dropwise added i-PrMgCl (16.5 mL, 32.9 mmol, 2.0 M/L) at 0° C. The reaction mixture was warmed and stirred at 25° C. for 16 h. The reaction mixture was quenched with H₂O (100 ml). The resulting reaction mixture was extracted with MTBE (50 ml×3). The aqueous phase was lyophilized to give a crude product. This crude product was triturated with EtOAc (100 ml×3) for 2 h at 25° C. The mother liquor was lyophilized again, and then added to H₂O (50 ml) and extracted with MTBE (50 ml×3) and PE (50 ml×3). The aqueous phase was lyophilized again to give crude residue 20-8 (720 mg) as white solid, used directly in the next step. [M+H]⁺ calcd for C₆H₅BF₃NO₂ 190.92, found 191.3.

Step G: Preparation of N4-(2-(6-(difluoromethyl)-5-fluoropyridin-2-yl)pyrimidin-4-yl)-N2-(4-morpholinophenyl)pyrimidine-2,4-diamine (426). To a vial containing 19-6 (20 mg, 0.042 mmol) was added 20-8 (16 mg, 0.084 mmol) followed by sodium carbonate (22.30 mg, 0.210 mmol) and Pd(dppf)Cl₂ (6.16 mg, 0.0084 mmol). The resulting mixture was purged with N₂ before degassed water (1 ml) and 1,4-dioxane (1 ml) was added. The vial was capped and heated at 80° C. for 16 h. The reaction was then cooled and concentrated in vacuum. The resulting residue was purified by preparative HPLC chromatography using a gradient (15 to 75%) of acetonitrile in water with 0.05% trifluoroacetic acid to yield a TFA salt of the title compound (4.7 mg). [M+H]+ calcd for $C_{24}H_{21}F_3N_8O$ 494.48, found 495.0.

Example 21: Synthesis of N4-(2-(5-chloro-2,4-difluorophenyl)pyrimidin-4-yl)-N2-(4-(piperazin-1-yl)phenyl)pyrimidine-2,4-diamine (556)

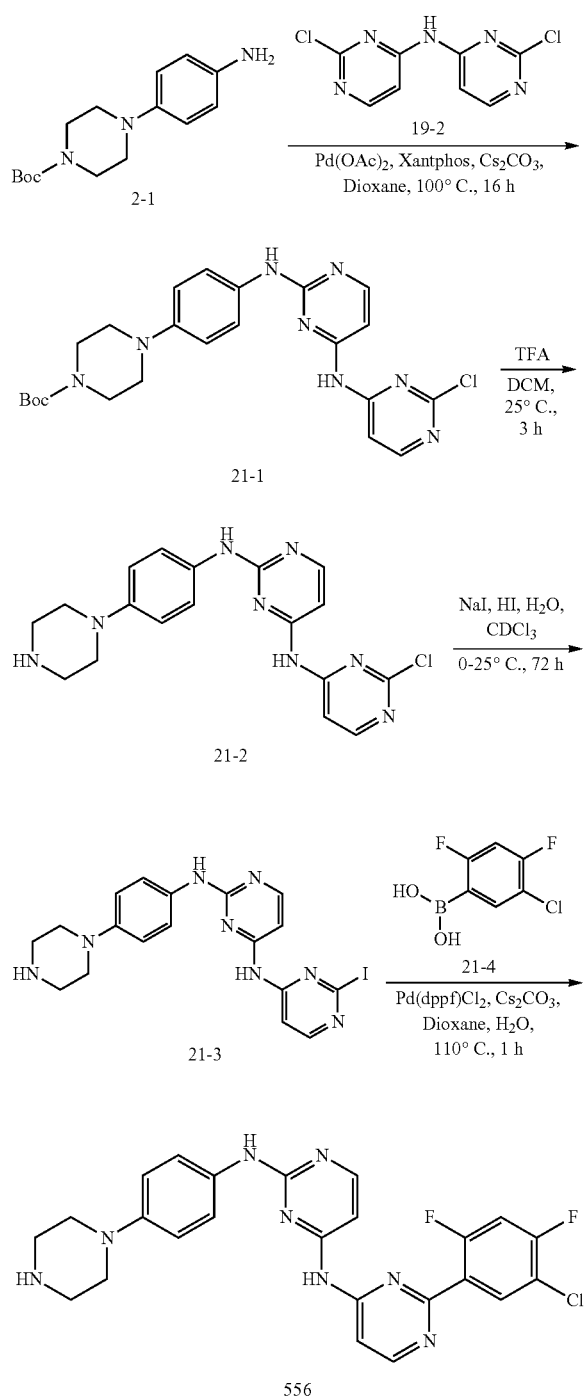

Step A: Preparation of tert-butyl 4-(4-((4-((2-chloropyrimidin-4-yl)amino)pyrimidin-2-yl)amino)phenyl)piperazine-1-carboxylate (21-1). To a suspension of 19-2 (2.6 g, 10.8 mmol) in 1,4-dioxane (72 ml) was added 2-1 (2.0 g, 7.21 mmol), $Cs_2CO_3$ (4.7 g, 14.2 mmol), $Pd(OAc)_2$ (162 mg, 0.721 mmol) and Xantphos (417 mg, 0.721 mmol). The reaction mixture was degassed under vacuum and $N_2$ was purged 3 times. The mixture was heated at 100° C. for 16 h. The reaction mixture was concentrated in vacuum and purified by silica gel column chromatography using a gradient (20 to 50%) of EtOAc in PE to obtain 21-1 (730 mg) as yellow solid. [M+H]+ calcd for $C_{23}H_{27}ClN_8O_2$ 482.97, found 483.4.

Step B: Preparation of N4-(2-chloropyrimidin-4-yl)-N2-(4-(piperazin-1-yl)phenyl)pyrimidine-2,4-diamine (21-2). To a solution of 21-1 (730 mg, 1.51 mmol) in DCM (8 ml) was added TFA (1.0 g, 15.1 mmol) and the resulting mixture was stirred at 25° C. for 3 h. The reaction mixture was concentrated in vacuum and the residue was basified by saturated $NaHCO_3$ solution to pH=8. The reaction mixture was filtered and the filtrate was dried in vacuum to obtain 21-2 (520 mg) as white solid, used directly in the next step. [M+H]+ calcd for $C_{18}H_{19}ClN_8$ 382.86, found 383.2.

Step C: Preparation of N4-(2-iodopyrimidin-4-yl)-N2-(4-(piperazin-1-yl)phenyl)pyrimidine-2,4-diamine (21-3). To a solution of 21-2 (520 mg, 1.36 mmol) and NaI (1.2 g, 8.15 mmol) in $CHCl_3$ (10 ml) was added $HI/H_2O$ (20 ml, 45%) at 0° C. and the resulting mixture was stirred at 25° C. for 7 d. The reaction mixture was basified by sat. $NaHCO_3$ solution to pH=8 at 0° C., washed with saturated $Na_2SO_3$ solution (20 ml) and extracted with EtOAc (30 ml×3). The organic layer was concentrated in vacuum and purified by preparative HPLC chromatography using a gradient (10 to 40%) of acetonitrile in water with 0.05% HCl to obtain 21-3 (120 mg) as yellow solid. [M+H]+ calcd for $C_{18}H_{19}IN_8$ 474.31, found 475.83.

Step D: Preparation of N4-(2-(5-chloro-2,4-difluorophenyl)pyrimidin-4-yl)-N2-(4-(piperazin-1-yl)phenyl)pyrimidine-2,4-diamine (556). To a vial containing compound 21-3 (10 mg, 0.021 mmol) was added 21-4 (8.08 mg, 0.042 mmol) followed by sodium carbonate (11.17 mg, 0.105 mmol) and $Pd(dppf)Cl_2$ (3.09 mg, 0.0042 mmol). The resulting mixture was purged with $N_2$ before degassed water (290 µl) and 1,4-dioxane (290 µl) was added. The vial was capped and heated at 110° C. for 1 h. The reaction was then cooled and concentrated in vacuum. The resulting residue was purified by preparative HPLC chromatography using a gradient (15 to 75%) of acetonitrile in water with 0.05% trifluoroacetic acid to yield a TFA salt of the title compound (5.7 mg). [M+H]+ calcd for $C_{24}H_{21}ClF_2N_8$ 494.94, found 495.1.

Example 22: Synthesis of 4-methyl-3-(4-((2-((4-(4-(4-methylpiperazin-1-yl)piperidin-1-yl)phenyl)amino)pyrimidin-4-yl)amino)pyrimidin-2-yl)phenol (255)
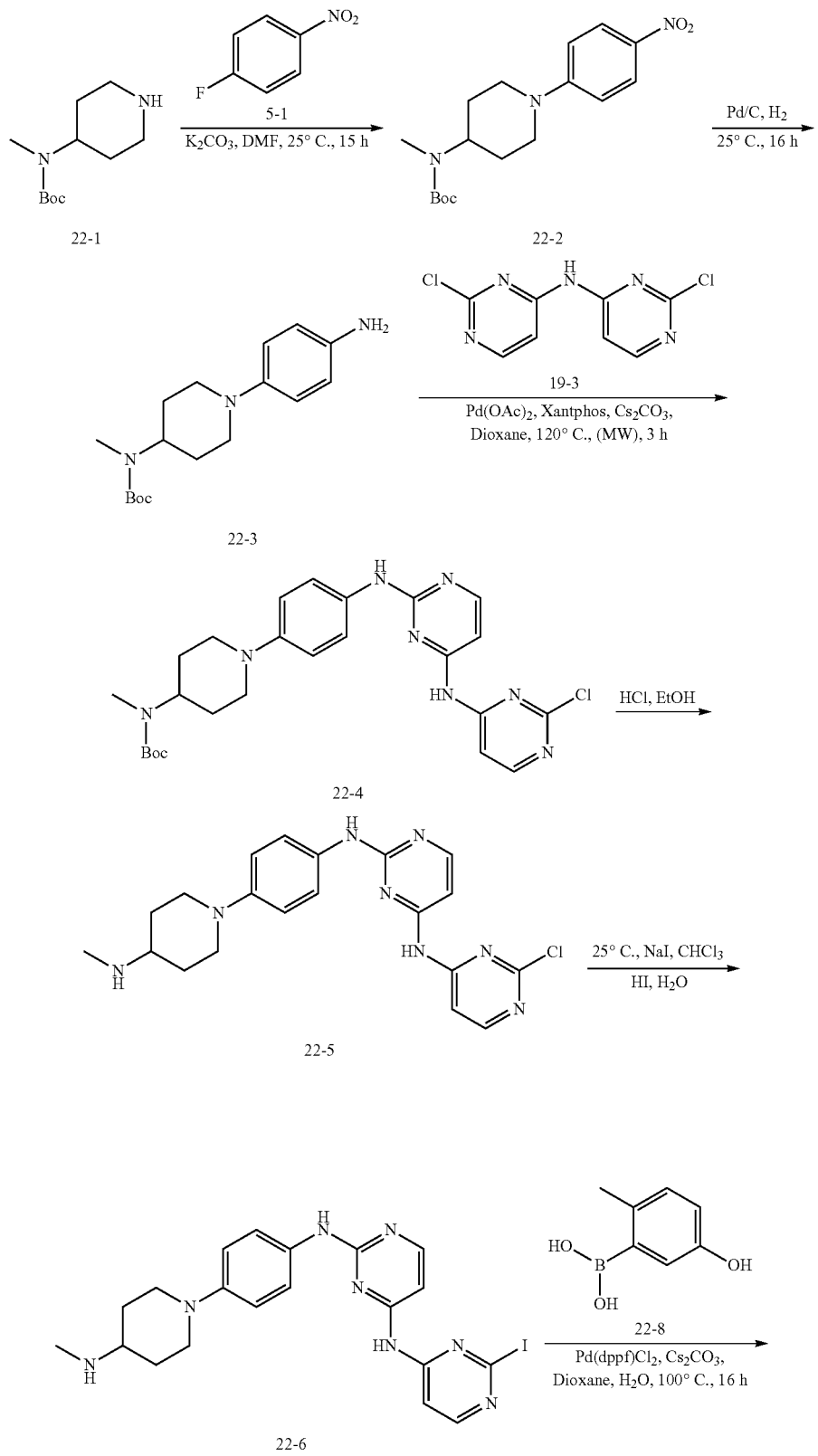

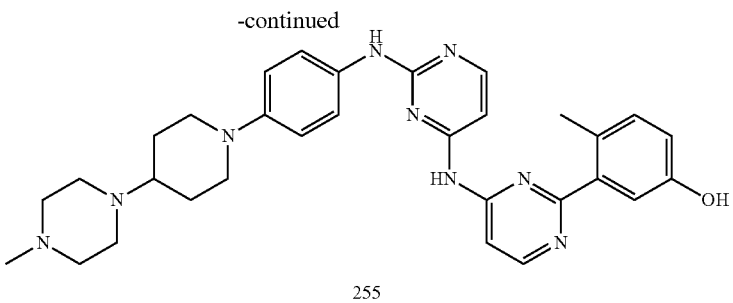

255

Step A: Preparation of tert-butyl methyl(1-(4-nitrophenyl)piperidin-4-yl)carbamate (22-2). To a solution of 5-1 (4.0 g, 18.7 mmol) in DMF (60 ml) was added 22-1 (2.6 g, 18.7 mmol) and $K_2CO_3$ (5.2 g, 37.3 mmol). The reaction mixture was stirred at 25° C. for 15 h. The reaction was filtrated and the cake was washed with EtOAc (80 ml×2). The filtrate was poured into 250 ml of $H_2O$. The mixture was extracted with EtOAc (150 ml×3). The organic layer was washed with sat. NaCl (100 ml×3), dried over with $Na_2SO_4$ and concentrated in vacuum to dryness to give crude product. The crude product was purified by column (PE:EA=50:1 to 3:1) to give 22-2 (5.8 g) as yellow solid.

Step B: Preparation of tert-butyl (1-(4-aminophenyl)piperidin-4-yl)(methyl)carbamate (22-3). To a solution of 22-2 (5.7 g, 16.99 mmol) in MeOH (80 ml) was added Pd/C (500 mg, 10%). The reaction mixture was stirred at 25° C. for 15 h under $H_2$ balloon. The reaction mixture was filtrated through a pad of Celite and the solvent was removed in vacuum to dryness to give crude residue 22-3 (4.5 g) as light pink solid, used directly in the next step.

Step C: Preparation of tert-butyl (1-(4-((4-((2-chloropyrimidin-4-yl)amino)pyrimidin-2-yl)amino)phenyl)piperidin-4-yl)(methyl)carbamate (22-4). A suspension of 19-3 (95 mg, 0.393 mmol), 22-3 (100 mg, 0.327 mmol), Pd(OAc)$_2$ (7 mg, 0.033 mmol), Xantphos (19 mg, 0.033 mmol) and $Cs_2CO_3$ (213 mg, 0.655 mmol) in 1,4-dioxane (9 ml) was heated at 120° C. under microwave for 3 h under $N_2$. The reaction mixture was filtrated and the filtrate was purified by preparative HPLC chromatography using a gradient (15 to 45%) of acetonitrile in water with 0.1% trifluoroacetic acid to give 22-4 (400 mg) as brown solid. [M+H]$^+$ calcd for $C_{25}H_{31}ClN_8O_2$ 511.03, found 511.4.

Step D: Preparation of N4-(2-chloropyrimidin-4-yl)-N2-(4-(4-(methylamino)piperidin-1-yl)phenyl)pyrimidine-2,4-diamine (22-5). A suspension of 22-4 (400 mg, 0.783 mmol) in HCl/EA (25 ml, 4M) was stirred at 0° C. for 1 h. The solvent was removed in vacuum to give crude residue 22-5 (500 mg) as pink solid, used directly in the next step. [M+H]$^+$ calcd for $C_{20}H_{23}ClN_8$ 410.91, found 410.3.

Step E: Preparation of N4-(2-iodopyrimidin-4-yl)-N2-(4-(4-(methylamino)piperidin-1-yl)phenyl)pyrimidine-2,4-diamine (22-6). To a suspension of 22-5 (400 mg, 0.973 mmol) in CHCl$_3$ (5 ml) was added HI/H$_2$O (30 ml, 45% in H$_2$O). The reaction mixture was stirred at 25° C. for 11 d. The reaction was poured into 100 ml of ice water at 0° C. 15 g of $Na_2SO_3$ was added to the solution. pH of the solution was adjusted to 8 with sat. NaHCO$_3$. The solution was extracted with EtOAc (50 ml×6). The organic layer was dried with $Na_2SO_4$ and concentrated in vacuum to dryness to give crude residue. The residue was purified by preparative HPLC chromatography using a gradient (7 to 37%) of acetonitrile in water with 0.05% HCl to give the HCl salt of 22-6 (180 mg) as yellow solid. [M+H]$^+$ calcd for $C_{20}H_{23}IN_8$ 502.36, found 503.2.

Step F: Preparation of 4-methyl-3-(4-((2-((4-(4-(4-methylpiperazin-1-yl)piperidin-1-yl)phenyl)amino)pyrimidin-4-yl)amino)pyrimidin-2-yl)phenol (255). To a vial containing compound 22-6 (15 mg, 0.026 mmol) was added 22-7 (12 mg, 0.079 mmol) followed by sodium carbonate (13.91 mg, 0.131 mmol), and Pd(dppf)Cl$_2$ (3.85 mg, 0.0052 mmol). The resulting mixture was purged with $N_2$ before degassed water (0.5 ml) and 1,4-dioxane (1 ml) was added. The vial was capped and heated at 100° C. for 16 h. The reaction was then cooled and concentrated in vacuum. The resulting residue was purified by preparative HPLC chromatography using a gradient (5 to 65%) of acetonitrile in water with 0.05% trifluoroacetic acid to yield a TFA salt of the title compound (14.5 mg). [M+H]$^+$ calcd for $C_{31}H_{37}N_9O$ 551.70, found 552.2.

Example 23: Synthesis of N4-(2-(6-methylpyridin-2-yl)pyrimidin-4-yl)-N2-(4-(piperazin-1-ylmethyl)thiazol-2-yl)pyrimidine-2,4-diamine (287)

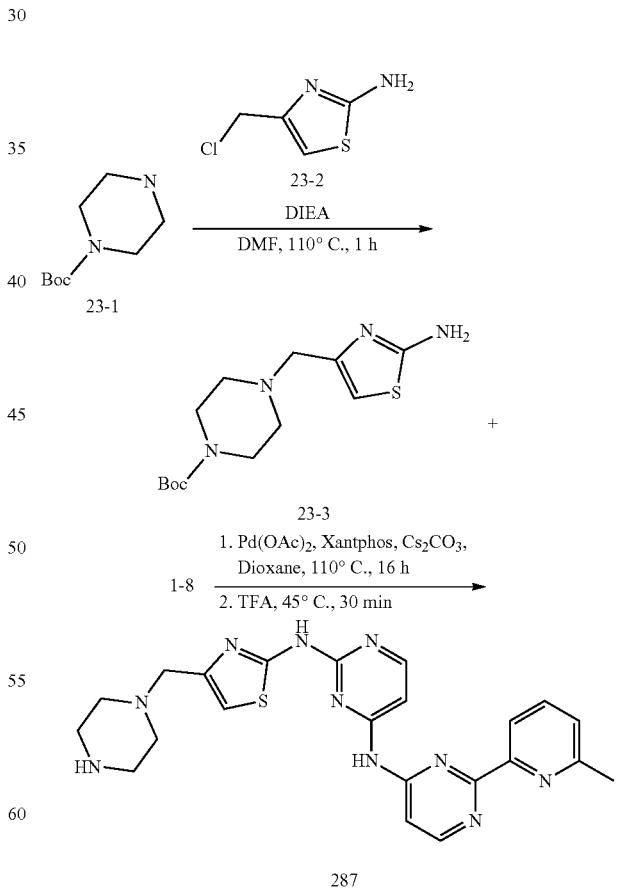

287

Step A: Preparation of tert-butyl 4-((2-aminothiazol-4-yl)methyl)piperazine-1-carboxylate (23-3). To a solution of 23-1 (150 mg, 0.807 mmol), and 23-2 (100 mg, 0.673 mmol)

in DMF (2.7 ml) was added DIEA (0.59 ml, 3.36 mmol). The reaction mixture was heated at 110° C. for 1 h. The reaction mixture was concentrated in vacuum and was purified by silica-gel column chromatography using a gradient (0 to 15%) of MeOH in DCM to obtain 23-3 (120 mg) as yellow oil. [M+H]+ calcd for $C_{13}H_{22}N_4O_2S$ 298.41, found 299.4.

Step B: Preparation of N4-(2-(6-methylpyridin-2-yl)pyrimidin-4-yl)-N2-(4-(piperazin-1-ylmethyl)thiazol-2-yl)pyrimidine-2,4-diamine (287). A vial of 1-8 (100 mg, 0.335 mmol), 23-3 (120 mg, 0.402 mmol), cesium carbonate (218 mg, 0.669 mmol), Xantphos (38.7 mg, 0.067 mmol), and Pd(OAc)$_2$ (15.03 mg, 0.067 mmol) in degassed 1,4-dioxane (3.3 ml) was heated at 110° C. for 16 h. The reaction mixture was concentrated in vacuum. TFA (903 μl) and DCM (754 μl) were added to the residue and stirred at 45° C. for 30 min. TFA was removed in vacuum and the residue was purified by preparative HPLC chromatography using a gradient (5 to 60%) of acetonitrile in water with 0.05% trifluoroacetic acid to yield a TFA salt of the title compound (124 mg). [M+H]+ calcd for $C_{22}H_{24}N_{10}S$ 460.56, found 461.2.

Example 24: Synthesis of N4-(2-(6-methylpyridin-2-yl)pyrimidin-4-yl)-N2-(5-(piperazin-1-ylmethyl)thiophen-3-yl)pyrimidine-2,4-diamine (94)

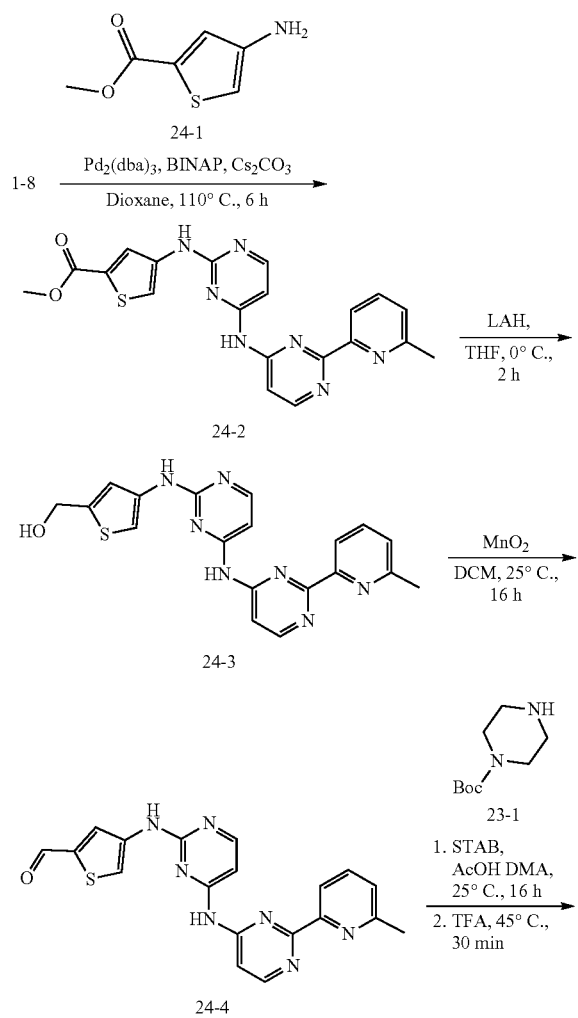

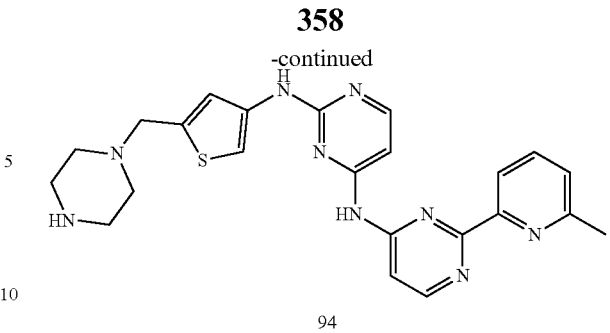

94

Step A: Preparation of methyl 4-((4-((2-(6-methylpyridin-2-yl)pyrimidin-4-yl)amino)pyrimidin-2-yl)amino)thiophene-2-carboxylate (24-2). To a solution of 1-8 (800 mg, 5.09 mmol) in 1,4-dioxane (10 ml) was added 24-1 (1.21 g, 4.07 mmol) under N$_2$ atmosphere. Then Cs$_2$CO$_3$ (3.30 g, 10.18 mmol) was added. The reaction mixture was purged with N$_2$ for 5 min, followed by addition of Pd$_2$(dba)$_3$ (233 mg, 0.25 mmol) and BINAP (317 mg, 0.05 mmol), then heated at 110° C. for 6 h in a sealed vial. The reaction mixture was diluted with EtOAc, filtered through a Celite bed, and concentrated to obtain the crude residue. The residue was purified by silica-gel column chromatography using a gradient (0 to 3%) of MeOH in DCM to obtain 24-2 (820 mg) as yellow solid. [M+H]+ calcd for $C_{20}H_{17}N_7O_2S$ 419.46, found 420.12.

Step B: Preparation of (4-((4-((2-(6-methylpyridin-2-yl)pyrimidin-4-yl)amino)pyrimidin-2-yl)amino)thiophen-2-yl)methanol (24-3). To a solution of 24-2 (800 mg, 1.90 mmol) in dry THF (10 ml) was added LAH (1.90 ml, 3.81 mmol) under N$_2$ atmosphere at 0° C. The reaction stirred at 25° C. for 2 h. The reaction mixture was cooled to −30° C. and quenched with saturated ammonium chloride solution, diluted with EtOAc and filtered through Celite bed, then concentrated to get crude residue. The residue was purified by silica-gel column chromatography using a gradient (0 to 8%) of MeOH in DCM to obtain 24-3 (300 mg) as off-white solid. [M+H]+ calcd for $C_{19}H_{17}N_7OS$ 391.45, found 392.15.

Step C: Preparation of 4-((4-((2-(6-methylpyridin-2-yl)pyrimidin-4-yl)amino)pyrimidin-2-yl)amino)thiophene-2-carbaldehyde (24-4). To a solution of 24-3 (250 mg, 0.63 mmol) in DCM (8 ml) was added MnO$_2$ (1.39 g, 15.98 mmol) at 25° C. The resulting suspension was stirred at 25° C. for 16 h. The reaction mixture was diluted with DCM, filtered through Celite bed, and concentrated to afford the crude residue which was purified by washing with diethyl ether and ACN to obtain 24-4 (180 mg) as yellow solid. [M+H]+ calcd for $C_{19}H_{15}N_7OS$ 389.44, found 390.27.

Step D: Preparation of N4-(2-(6-methylpyridin-2-yl)pyrimidin-4-yl)-N2-(5-(piperazin-1-ylmethyl)thiophen-3-yl)pyrimidine-2,4-diamine (94). To a stirred solution 24-4 (75 mg, 0.193 mmol) in DMA (800 μl) was added 23-1 (30 mg, 0.161 mmol) followed by the addition of STAB (102 mg, 0.483 mmol). The reaction mixture was stirred at 25° C. for 16 h. The reaction mixture was concentrated in vacuum. DCM (400 μl) and TFA (400 μl) were added to the reaction mixture and the resulting mixture heated at 45° C. for 30 min. TFA was removed in vacuum. The residue was purified by preparative HPLC chromatography using a gradient (2 to 15%) of acetonitrile in water with 0.05% trifluoroacetic acid to yield a TFA salt of the title compound (29.6 mg). [M+H]+ calcd for $C_{23}H_{25}N_9S$ 459.58, found 460.2.

Example 25: Synthesis of N-(4-((4-((2-(6-methylpyridin-2-yl)pyrimidin-4-yl)amino)pyrimidin-2-yl)amino)phenyl)-1-(piperidin-3-yl)methanesulfonamide (106)

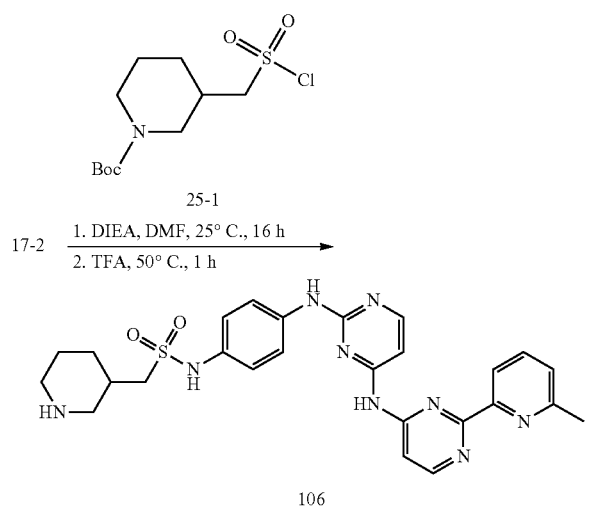

To a vial of 17-2 (20 mg, 0.054 mmol) and 25-1 (24 mg, 0.081 mmol) in DMF (1 ml) was added DIEA (0.028 ml, 0.162 mmol) and the resulting mixture was stirred at 25° C. for 16 h. TFA (1 ml) was added to the reaction mixture and heated at 50° C. for 1 h. The reaction mixture was concentrated in vacuum and the residue was purified by preparative HPLC chromatography using a gradient (2 to 60%) of acetonitrile in water with 0.05% trifluoroacetic acid to yield a TFA salt of the title compound (10.3 mg). [M+H]$^+$ calcd for $C_{26}H_{29}N_9O_2S$ 531.64, found 532.1.

Example 26: Synthesis of N-(4-((4-((2-(6-methylpyridin-2-yl)pyrimidin-4-yl)amino)pyrimidin-2-yl)amino)phenyl)piperazine-1-carboxamide (228)

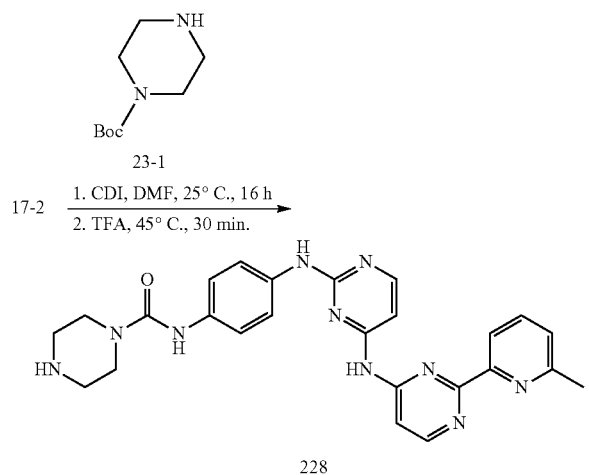

To a solution of 17-2 (25 mg, 0.067 mmol) in DCM (1 ml) was added CDI (12.04 mg, 0.074 mmol) and the resulting mixture stirred at 25° C. for 16 h. 23-1 (13.83 mg, 0.074 mmol) was added to the reaction mixture and stirred at 25° C. for 16 h. The reaction mixture was concentrated in vacuum. TFA (1 ml) and DCM (1 ml) were added to the residue and heated at 45° C. for 30 min. TFA was removed in vacuum and the residue was purified by preparative HPLC chromatography using a gradient (5 to 65%) of acetonitrile in water with 0.05% trifluoroacetic acid to yield a TFA salt of the title compound (11.8 mg). [M+H]$^+$ calcd for $C_{25}H_{26}N_{10}O$ 482.55, found 483.1.

Example 27: Synthesis of N-(4-((4-((2-(6-methylpyridin-2-yl)pyrimidin-4-yl)amino)pyrimidin-2-yl)amino)phenyl)piperidine-4-carboxamide (14)

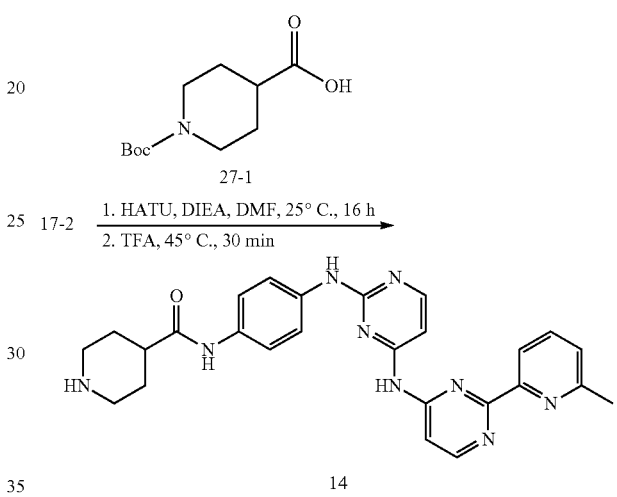

To a solution of 17-2 (12 mg, 0.032 mmol) and 27-1 (14.86 mg, 0.065 mmol) in DMF (1 ml) was added HATU (18.48 mg, 0.049 mmol) and DIEA (0.017 ml, 0.097 mmol) and the resulting mixture stirred at 25° C. for 16 h. The reaction mixture was concentrated in vacuum. TFA (1 ml) and DCM (1 ml) were added to the residue and heated at 45° C. for 30 min. TFA was removed in vacuum and the residue was purified by preparative HPLC chromatography using a gradient (5 to 65%) of acetonitrile in water with 0.05% trifluoroacetic acid to yield a TFA salt of the title compound (19.7 mg). [M+H]$^+$ calcd for $C_{26}H_{27}N_9O$ 481.56, found 482.1.

Example 28: Synthesis of 3-(hydroxymethyl)-N-(4-((4-((2-(6-methylpyridin-2-yl)pyrimidin-4-yl)amino)pyrimidin-2-yl)amino)phenyl)azetidine-3-carboxamide (209)

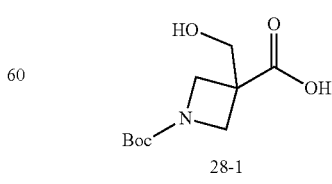

17-2  1. HATU, DIEA, DMF, 25° C., 1 h
      2. TFA, 45° C., 30 min

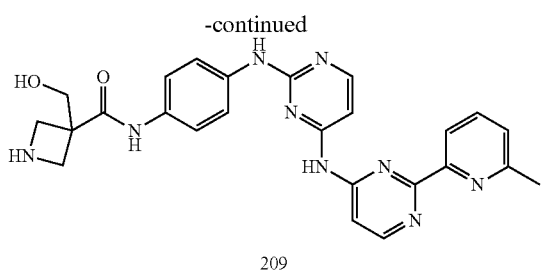

209

To a solution of 17-2 (20 mg, 0.054 mmol) and 28-1 (18.73 mg, 0.081 mmol) in DMF (1 ml) was added HATU (30.8 mg, 0.081 mmol) and DIEA (0.028 ml, 0.162 mmol) and the resulting mixture was stirred at 25° C. for 1 h. The reaction mixture was concentrated in vacuum. TFA (229 µl) and DCM (191 µl) were added to the residue and heated at 45° C. for 30 min. TFA was removed in vacuum and the residue was purified by preparative HPLC chromatography using a gradient (2 to 60%) of acetonitrile in water with 0.05% trifluoroacetic acid to yield a TFA salt of the title compound (35.1 mg). [M+H]$^+$ calcd for $C_{25}H_{25}N_9O_2$ 483.54, found 484.0.

Example 29: Synthesis of N-(3-((4-((2-(6-methylpyridin-2-yl)pyrimidin-4-yl)amino)pyrimidin-2-yl)amino)phenyl)piperidine-3-carboxamide (443)

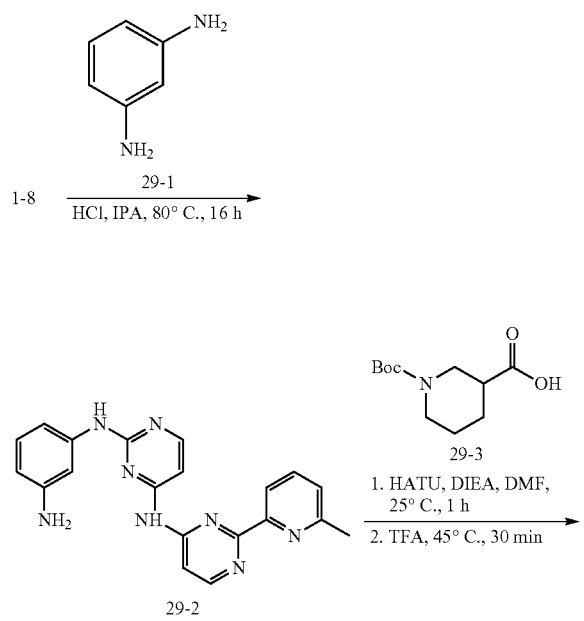

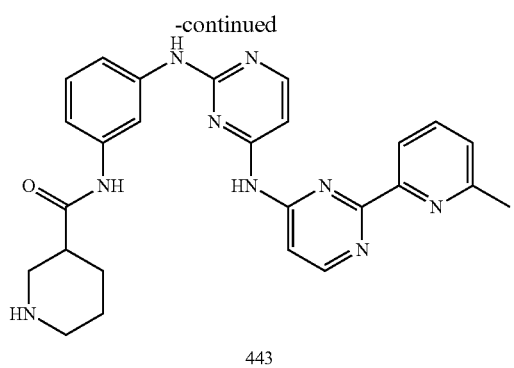

443

Step A: Preparation of N2-(3-aminophenyl)-N4-(2-(6-methylpyridin-2-yl)pyrimidin-4-yl)pyrimidine-2,4-diamine (29-2). To a mixture of 1-8 (400 mg, 1.34 mmol) and 29-1 (144 mg, 1.34 mmol) in IPA (10 ml) was added HCl (0.5 ml). The reaction mixture was heated at 80° C. for 16 h. The reaction mixture was filtered. The filtrate was concentrated in vacuum and purified by silica-gel column chromatography using a gradient (0 to 5%) of MeOH in DCM to give 29-2 (280 mg) as yellow solid. [M+H]$^+$ calcd for $C_{20}H_{18}N_8$ 370.42, found 371.2.

Step B: Preparation of N-(3-((4-((2-(6-methylpyridin-2-yl)pyrimidin-4-yl)amino)pyrimidin-2-yl)amino)phenyl)piperidine-3-carboxamide (443). To a solution of 29-2 (20 mg, 0.054 mmol) and 29-3 (18.73 mg, 0.081 mmol) in DMF (1 ml) was added HATU (30.8 mg, 0.081 mmol) and DIEA (0.028 ml, 0.162 mmol) and the resulting mixture was stirred at 25° C. for 1 h. The reaction mixture was concentrated in vacuum. TFA (229 µl) and DCM (191 µl) were added to the residue and heated at 45° C. for 30 min. TFA was removed in vacuum and the residue was purified by preparative HPLC chromatography using a gradient (2 to 60%) of acetonitrile in water with 0.05% trifluoroacetic acid to yield a TFA salt of the title compound (35.1 mg). [M+H]$^+$ calcd for $C_{25}H_{25}N_9O_2$ 483.54, found 484.0.

Example 30: Synthesis of N-(4-((4-((2-(6-methylpyridin-2-yl)pyrimidin-4-yl)amino)pyrimidin-2-yl)amino)thiophen-2-yl)piperidine-4-carboxamide 452)

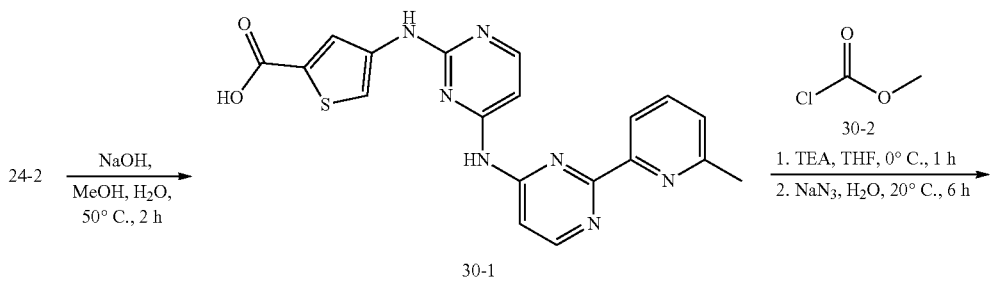

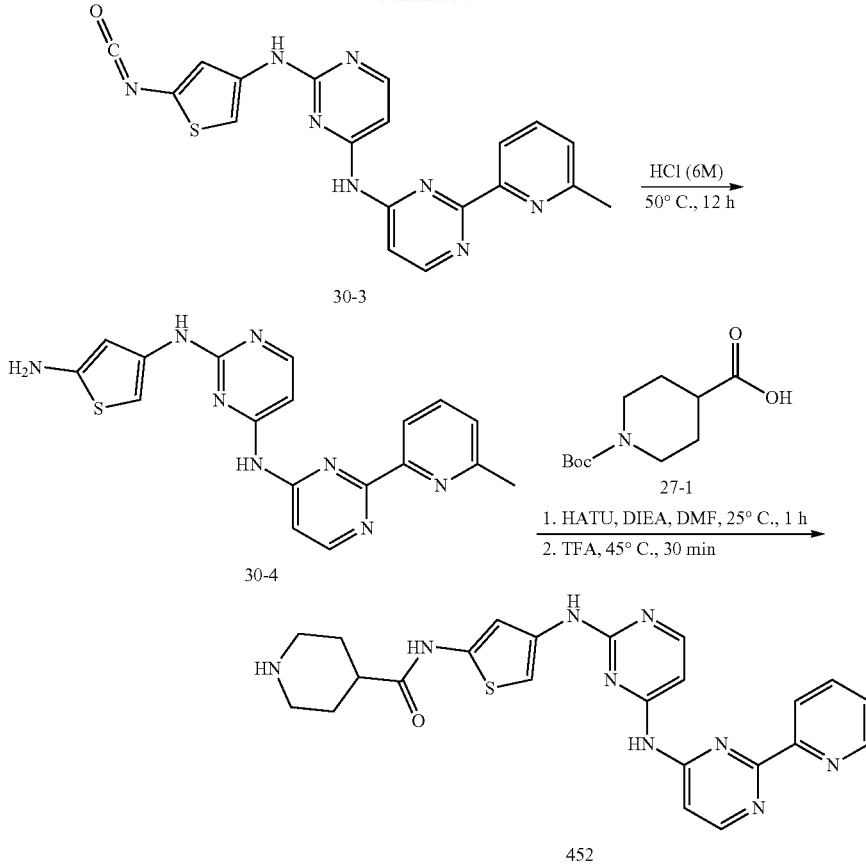

Step A: Preparation of 4-((4-((2-(6-methylpyridin-2-yl)pyrimidin-4-yl)amino)pyrimidin-2-yl)amino)thiophene-2-carboxylic acid (30-1). A mixture of 24-2 (1.3 g, 3.10 mmol) and NaOH (1.2 g, 31.0 mmol) in MeOH (30 ml) and $H_2O$ (15 ml) was heated at 50° C. for 2 h. The reaction mixture was acidified with AcOH to pH=7 and filtered. The cake was dried in vacuum to afford 30-1 (1.2 g) as a yellow solid. $[M+H]^+$ calcd for $C_{19}H_{15}N_7O_2S$ 405.44, found 406.0.

Step B: Preparation of N2-(5-isocyanatothiophen-3-yl)-N4-(2-(6-methylpyridin-2-yl)pyrimidin-4-yl)pyrimidine-2,4-diamine (30-3). To a solution of 30-1 (1.0 g, 2.46 mmol) and TEA (1.5 g, 14.8 mmol) in THF (20 ml) was added 30-2 (2.1 g, 22.3 mmol) at 0° C. The reaction mixture was stirred at 0° C. for 6 h. Then $NaN_3$ (1.0 g, 15.4 mmol) in $H_2O$ (5.0 ml) was added at 0° C. The reaction mixture was stirred at 20° C. for 12 h. The reaction mixture was concentrated in vacuum. The residue was washed with $H_2O$ (50 ml×2) and the cake was dried in vacuum to afford 30-3 (900 mg) as a white solid. $[M+H]^+$ calcd for $C_{19}H_{14}N_8OS$ 402.44, found 403.0.

Step C: Preparation of N2-(5-aminothiophen-3-yl)-N4-(2-(6-methylpyridin-2-yl)pyrimidin-4-yl)pyrimidine-2,4-diamine (30-4). A solution of 30-3 (800 mg, 1.19 mmol) in HCl (10 ml, 6.0 M) was stirred at 50° C. for 12 h. The reaction mixture was concentrated in vacuum. The residue was purified by preparative HPLC chromatography using a gradient (0 to 32%) of acetonitrile in water with 0.05% HCl to obtain 30-4 (120 mg) as a white solid. $[M+H]^+$ calcd for $C_{18}H_{16}N_8S$ 376.44, found 377.1.

Step D: Preparation of N-(4-((4-((2-(6-methylpyridin-2-yl)pyrimidin-4-yl)amino)pyrimidin-2-yl)amino)thiophen-2-yl)piperidine-4-carboxamide (452). A solution of 30-4 (20 mg, 0.053 mmol), 27-1 (18.27 mg, 0.080 mmol), HATU (30.3 mg, 0.080 mmol), and DIEA (28.0 μl, 0.159 mmol) in DMF (1 ml) was stirred at 25° C. for 1 h. The reaction mixture was concentrated in vacuum. DCM (200 μl) and TFA (225 μl) were added to the reaction mixture and the mixture was heated at 45° C. for 30 min. TFA was removed in vacuum and the crude mixture purified by preparative HPLC chromatography using a gradient (2 to 60%) of acetonitrile in water with 0.05% trifluoroacetic acid to yield a TFA salt of the title compound (26.9 mg). $[M+H]^+$ calcd for $C_{24}H_{25}N_9OS$ 487.59, found 488.0.

Example 31: Synthesis of (R)-sec-butyl 2-(5-((4-((2-(6-methylpyridin-2-yl)pyrimidin-4-yl)amino)pyrimidin-2-yl)amino)-2-(piperazin-1-yl)phenyl)acetate (13)

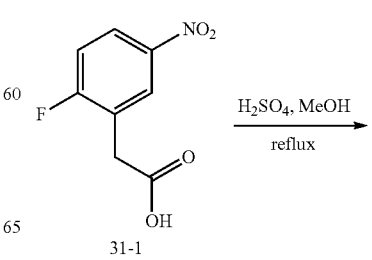

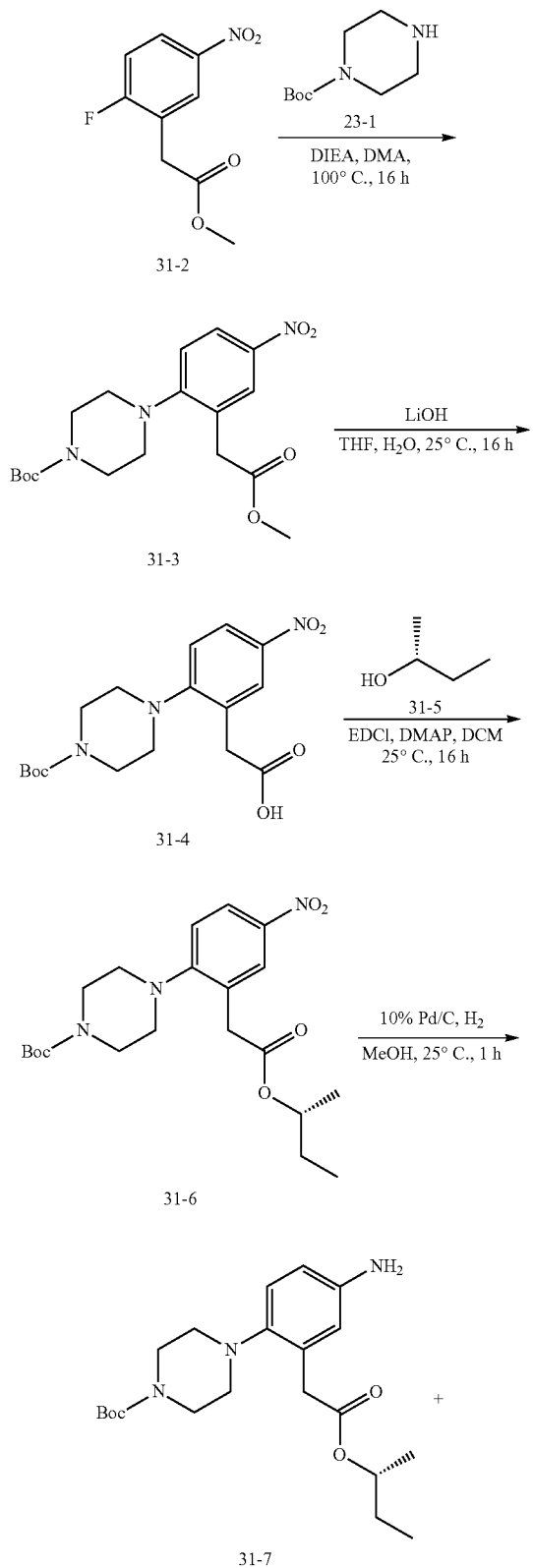

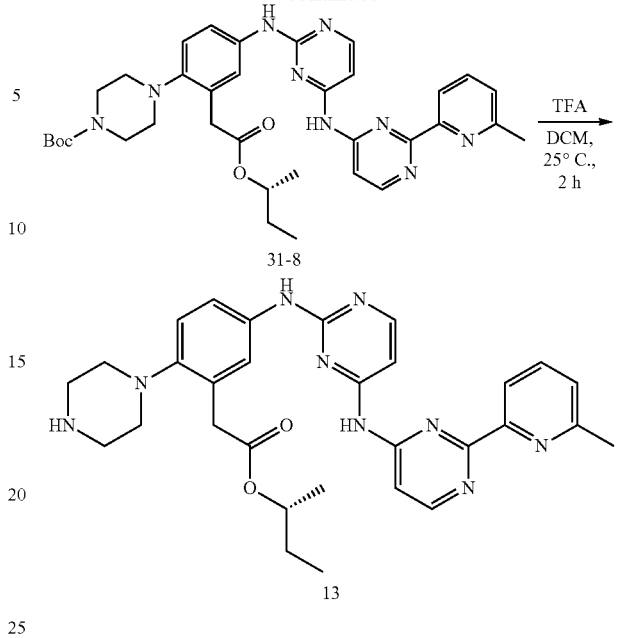

Step A: Preparation of methyl 2-(2-fluoro-5-nitrophenyl) acetate (31-2). To a stirred solution of 31-1 (10 g, 50.25 mmol) in MeOH (70 ml) was added $H_2SO_4$ (5.3 ml, 100 mmol) at 0° C. under $N_2$ atmosphere. The reaction mixture was refluxed for 16 h. Solvent was removed under reduced pressure and was carefully quenched using bicarbonate solution and extracted with EtOAc. The organic layer was dried over anhydrous sodium sulfate and concentrated under reduced pressure to obtain the crude product 31-2 (10 g). $[M+Na]^+$ calcd for $C_9H_8FNO_4$ 236.15, found 236.31.

Step B: Preparation of tert-butyl 4-(2-(2-methoxy-2-oxo-ethyl)-4-nitrophenyl)piperazine-1-carboxylate (31-3). To a stirred solution of 31-2 (5.0 g, 23.47 mmol) in DMA (70 ml) was added DIPEA (12.61 ml, 70.41 mmol) followed by 23-1 (4.3 g, 23.47 mmol). The reaction mixture was heated at 100° C. for 16 h. The reaction mixture was then diluted with water and extracted with EtOAc (100 ml×3). The combined organic layer was again washed with ice cold water followed by brine and dried over anhydrous $Na_2SO_4$, filtered and concentrated under reduced pressure. Crude residue obtained was purified by silica-gel column chromatography using a gradient (20 to 25%) of acetone in hexanes to obtain 31-3 (4.05 g) as a white solid. $[M+H]^+$ calcd for $C_{18}H_{25}N_3O_6$ 379.41, found 380.34.

Step C: Preparation of 2-(2-(4-(tert-butoxycarbonyl)piperazin-1-yl)-5-nitrophenyl)acetic acid (31-4). To a stirred solution of 31-3 (1.0 g, 2.63 mmol) in THF (5 ml) and $H_2O$ (5 ml) was added $LiOH.H_2O$ (540 mg, 13.19 mmol). The reaction mixture was stirred at 25° C. for 16 h, then diluted with water and extracted with EtOAc at pH ~3. The organic layer was washed with brine, dried over sodium sulphate and concentrated under reduced pressure to give the crude residue. The residue was purified by precipitating and triturating with ACN, diethyl ether and hexane to obtain 31-4 (600 mg) as a yellow solid. $[M+H]^+$ calcd for $C_{17}H_{23}N_3O_6$ 365.39, found 366.16.

Step D: Preparation of tert-butyl (R)-4-(2-(2-(sec-butoxy)-2-oxoethyl)-4-nitrophenyl)piperazine-1-carboxylate (31-6). To a stirred solution of 31-4 (550 mg, 1.50 mmol) in DCM (20 ml) was added 31-5 (0.37 ml, 3.01 mmol) and DMAP (18 mg, 0.15 mmol) followed by addition of EDC- HCl (573 mg, 3.01 mmol) at 0° C. The reaction mixture was allowed to stir at 25° C. for 16 h, then diluted with water and extracted three times using EtOAc. The combined organic layers were washed with water and brine, dried over anhydrous sodium sulfate and concentrated under vacuum to afford crude compound which was purified by silica-gel column chromatography using a gradient (10 to 15%) of EtOAc in Hexanes to obtain 31-6 (400 mg). [M+H]+ calcd for $C_{21}H_{31}N_3O_6$ 421.49, found 422.10.

Step E: Preparation of tert-butyl (R)-4-(4-amino-2-(2-(sec-butoxy)-2-oxoethyl)phenyl)piperazine-1-carboxylate (31-7). To a stirred solution of 31-6 (400 mg, 0.95 mmol) in IPA (10 ml) and THF (4 ml) was added 10% Pd/C (400 mg) and subjected to hydrogenation under $H_2$ balloon pressure. The reaction mixture was allowed to stir at 25° C. for 1 h, then filtered through Celite bed and washed with MeOH. Filtrate was concentrated under vacuum to get crude residue 31-7 (350 mg), used in next step without any purification. [M+H]+ calcd for $C_{21}H_{33}N_3O_4$ 391.51, found 392.13.

Step F: Preparation of tert-butyl (R)-4-(2-(2-(sec-butoxy)-2-oxoethyl)-4-((4-((2-(6-methylpyridin-2-yl)pyrimidin-4-yl)amino)pyrimidin-2-yl)amino)phenyl)piperazine-1-carboxylate (31-8). To a solution of 31-7 (344 mg, 0.88 mmol) in 1,4-dioxane (10 ml) was added 1-8 (175 mg, 0.587 mmol) and $Cs_2CO_3$ (381 mg, 1.17 mmol) under $N_2$ atmosphere. The reaction mixture was degassed with $N_2$ for 10 min, followed by addition of Brettphos (63 mg, 0.117 mmol) and Brettphos Pd G4 (54 mg, 0.058 mmol), then heated at 110° C. for 16 h. The reaction mixture was diluted with EtOAc and filtered through Celite bed. Filtrate was diluted with cold water and extracted with ethyl acetate (25 mL×2). The organic layer was dried over dry $Na_2SO_4$, filtered and concentrated to get crude residue. The residue was purified by silica-gel column chromatography using a gradient (0 to 3%) of MeOH in DCM to obtain 31-8 (200 mg). [M+H]+ calcd for $C_{35}H_{43}N_9O_4$ 653.79, found 654.17.

Step G: Preparation of (R)-sec-butyl 2-(5-((4-((2-(6-methylpyridin-2-yl)pyrimidin-4-yl)amino)pyrimidin-2-yl)amino)-2-(piperazin-1-yl)phenyl)acetate (13). To a stirred solution of 31-8 (200 mg, 0.306 mmol) in DCM (5 ml) was added TFA (1 ml) at 0° C. The reaction mixture was stirred at 25° C., then concentrated under reduced pressure and further triturated with diethyl ether to get the title compound (205 mg) as an off white solid. [M+H]+ calcd for $C_{30}H_{35}N_9O_2$ 553.67, found 554.32.

Example 32: Synthesis of (R)-1-methylpyrrolidin-3-yl 1-(4-((4-((2-(6-methylpyridin-2-yl)pyrimidin-4-yl)amino)pyrimidin-2-yl)amino)benzyl)piperidine-4-carboxylate (414)

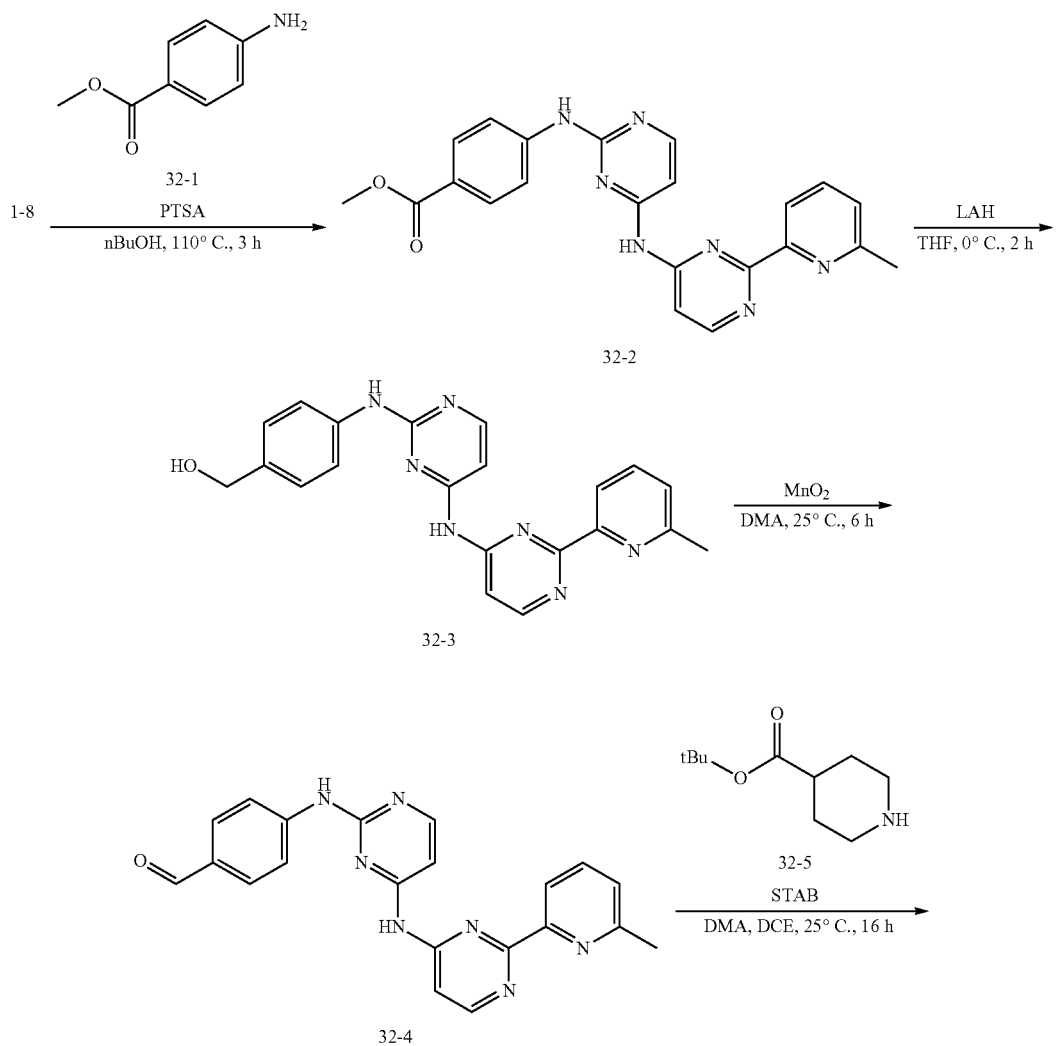

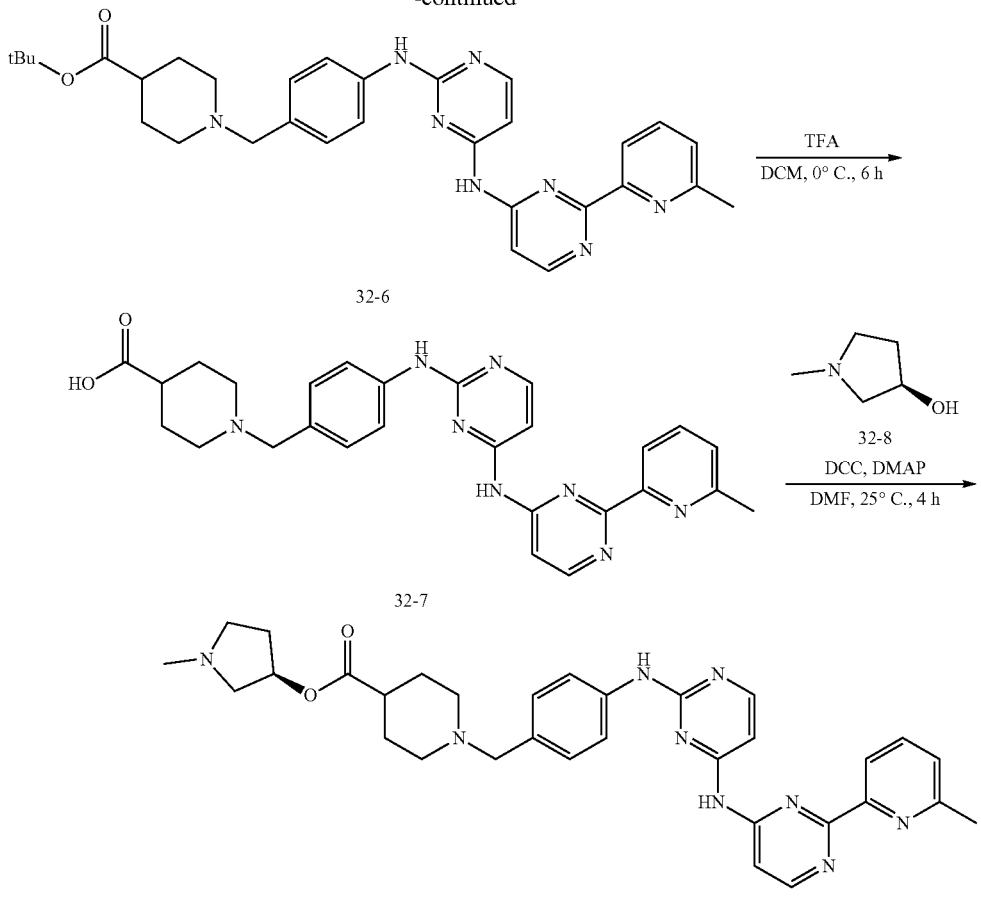

Step A: Preparation of methyl 4-((4-((2-(6-methylpyridin-2-yl)pyrimidin-4-yl)amino)pyrimidin-2-yl)amino)benzoate (32-2). To a stirred solution of 1-8 (3.5 g, 11.74 mmol) and 32-1 (2.3 g, 15.27 mmol) in n-butanol (35 ml) was added PTSA (1.11 g, 5.87 mmol) and the resulting mixture heated at 110° C. for 3 h. The reaction mixture was concentrated to dryness and triturated using diethyl ether to get the 32-2 (4.1 g) as PTSA salt. [M+H]+ calcd for $C_{22}H_{19}N_7O_2$ 413.44, found 414.15.

Step B: Preparation of (4-((4-((2-(6-methylpyridin-2-yl)pyrimidin-4-yl)amino)pyrimidin-2-yl)amino)phenyl)methanol (32-3). To a stirred solution 32-2 (4.1 g, 9.92 mmol) in THF (50 ml) was added LAH (15.0 ml, 29.71 mmol) dropwise at 0° C. The reaction mixture was allowed to stir at 0° C. for 2 h, then quenched with water:THF (6:18 ml) under cooling followed by the addition of 15% NaOH (15 ml). It was then filtered through Celite bed and the organic layer separated and concentrated to get crude residue. The residue was purified by silica-gel column chromatography to obtain 32-3 (3.0 g). [M+H]+ calcd for $C_{21}H_{19}N_7O$ 385.43, found 386.14.

Step C: Preparation of 4-((4-((2-(6-methylpyridin-2-yl)pyrimidin-4-yl)amino)pyrimidin-2-yl)amino)benzaldehyde (32-4). To a stirred solution 32-3 (3.0 g, 7.8 mmol) in DMA (30 ml) was added $MnO_2$ (20.4 g, 234 mmol) at 25° C. The reaction mixture was allowed to stir at 25° C. for 6 h, then filtered and the filtrate concentrated to get crude residue. The residue obtained was triturated with ACN to obtain 32-4 (2.2 g), used in next step without further purification. [M+H]+ calcd for $C_{21}H_{17}N_7O$ 383.42, found 384.16.

Step D: Preparation of tert-butyl 1-(4-((4-((2-(6-methylpyridin-2-yl)pyrimidin-4-yl)amino)pyrimidin-2-yl)amino)benzyl)piperidine-4-carboxylate (32-6). To a stirred solution of 32-4 (2.1 g, 5.48 mmol) in DMA:DCE (10:20 ml) was added 32-5 (1.52 g, 8.22 mmol) followed by the addition of STAB (3.48 g, 16.44 mmol). The reaction mixture was stirred at 25° C. for 16 h. The reaction mixture was diluted with water and extracted with 10% MeOH:DCM to obtained the crude residue. The residue was purified by silica-gel column chromatography using a gradient (0 to 5%) of MeOH in DCM to obtain 32-6 (1.4 g). [M+H]+ calcd for $C_{31}H_{36}N_8O_2$ 552.68, found 553.33.

Step E: Preparation of 1-(4-((4-((2-(6-methylpyridin-2-yl)pyrimidin-4-yl)amino)pyrimidin-2-yl)amino)benzyl)piperidine-4-carboxylic acid (32-7). To a stirred solution 32-6 (1.4 g, 2.53 mmol) in DCM (20 ml) was added TFA (14 ml) dropwise at 0° C. The reaction mixture was stirred at 0° C. for 6 h. The reaction mixture was concentrated and triturated with diethyl ether and ACN to obtain 32-7 (1.2 g). [M+H]+ calcd for $C_{27}H_{28}N_8O_2$ 496.58, found 497.48.

Step F: Preparation of (R)-1-methylpyrrolidin-3-yl 1-(4-((4-((2-(6-methylpyridin-2-yl)pyrimidin-4-yl)amino)pyrimidin-2-yl)amino)benzyl)piperidine-4-carboxylate (414). To the solution of, 32-7 (300 mg, 0.604 mmol) in DMF (5.0 ml) was added 32-8 (170 mg, 0.906 mmol), DCC (373 mg, 1.812 mmol) followed by addition of DMAP (37 mg, 0.302 mmol) and stirred at 25° C. for 4 h. The reaction mixture was poured onto ice water and extracted using 10% MeOH:DCM. Combined organic layers were washed with brine, dried over sodium sulfate and concentrated to get the crude residue. The residue was purified by preparative HPLC chromatography using a gradient (5 to 250%) of acetonitrile in water with 0.1% trifluoroacetic acid to yield a TFA salt of the title compound (180 mg). [M+H]+ calcd for $C_{32}H_{37}N_9O_2$ 579.71, found 580.30.
Example 33: Synthesis of azetidin-3-ylmethyl (R)-1-(4-((4-((2-(6-methylpyridin-2-yl)pyrimidin-4-yl)amino)pyrimidin-2-yl)amino)benzyl)piperidine-3-carboxylate (400)
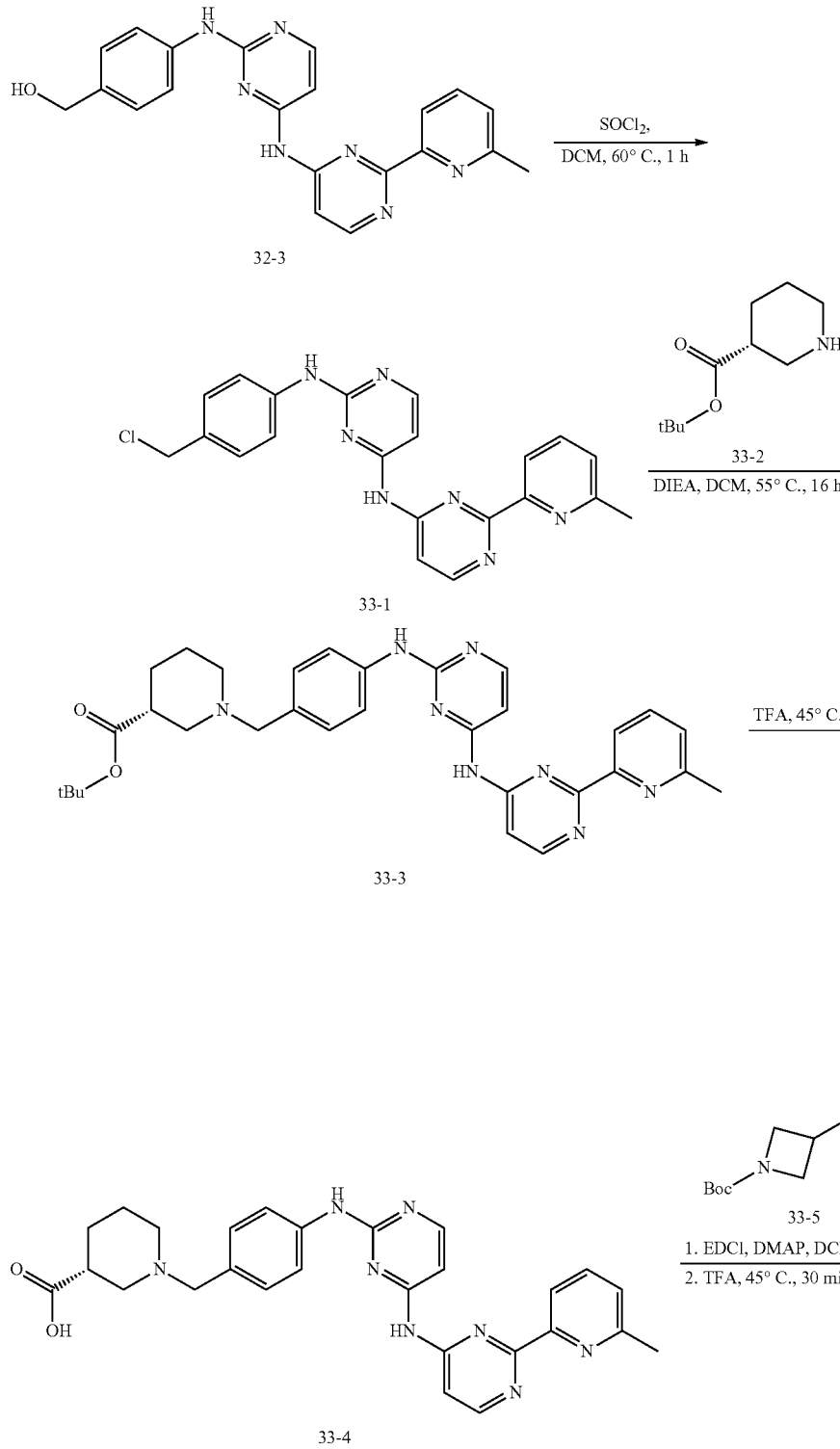

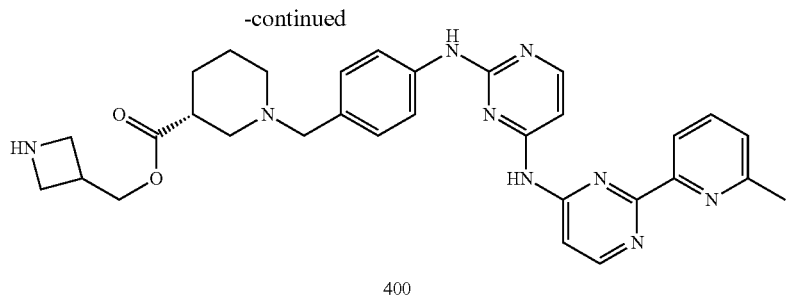

400

Step A: Preparation of N2-(4-(chloromethyl)phenyl)-N4-(2-(6-methylpyridin-2-yl)pyrimidin-4-yl)pyrimidine-2,4-diamine (33-1). To a solution of 32-2 (425 mg, 1.103 mmol) in DCM (31.5 ml) was added SOCl$_2$ (177 μl, 2.426 mmol) and the resulting mixture heated at 60° C. for 1 h. The reaction mixture was concentrated in vacuum to obtain 33-1 (445 mg) as a yellow solid, used directly in the next step.

Step B: Preparation of tert-butyl (R)-1-(4-((4-((2-(6-methylpyridin-2-yl)pyrimidin-4-yl)amino)pyrimidin-2-yl)amino)benzyl)piperidine-3-carboxylate (33-3). To a solution of 33-1 (445 mg, 1.1 mmol) in DCM (18 ml) was added 33-2 (488 mg, 2.2 mmol) and DIEA (0.961 ml, 5.0 mmol) and the resulting mixture heated at 55° C. for 16 h. The reaction mixture was concentrated in vacuum to give a crude residue. The residue was purified by silica-gel column chromatography using a gradient (0 to 15%) of MeOH in DCM to produce 33-3 (608 mg). [M+H]$^+$ calcd for C$_{31}$H$_{36}$N$_8$O$_2$ 552.68, found 553.1.

Step C: Preparation of (R)-1-(4-((4-((2-(6-methylpyridin-2-yl)pyrimidin-4-yl)amino)pyrimidin-2-yl)amino)benzyl)piperidine-3-carboxylic acid (33-4). To a solution of 33-3 (608 mg, 1.1 mmol) in DCM (3.5 ml) was added TFA (4.2 ml) at 0° C. and the reaction mixture was stirred at 25° C. for 16 h. TFA was removed in vacuum. The residue was purified by preparative HPLC chromatography using a gradient (5 to 30%) of acetonitrile in water with 0.05% trifluoroacetic acid to yield a TFA salt of 33-4 (440 mg). [M+H]$^+$ calcd for C$_{27}$H$_{28}$N$_8$O$_2$ 496.58, found 497.1.

Step D: Preparation of azetidin-3-ylmethyl (R)-1-(4-((4-((2-(6-methylpyridin-2-yl)pyrimidin-4-yl)amino)pyrimidin-2-yl)amino)benzyl)piperidine-3-carboxylate (400). A solution of 33-4 (75 mg, 0.104 mmol), 33-5 (38.8 mg, 0.207 mmol), EDCI (39.7 mg, 0.207 mmol), and DMAP (1.27 mg, 10.4 μmol) in DCM (0.5 ml) was stirred at 25° C. for 16 h. TFA (279 μl) was added to the reaction mixture and was heated at 45° C. for 30 min. The reaction mixture was concentrated in vacuum and was purified by preparative HPLC chromatography using a gradient (2 to 60%) of acetonitrile in water with 0.05% trifluoroacetic acid to yield a TFA salt of the title compound (62.1 mg). [M+H]$^+$ calcd for C$_{31}$H$_{35}$N$_9$O$_2$ 565.68, found 566.1.

Example 34: Synthesis of azetidin-3-ylmethyl 1-(4-((4-((2-(6-methylpyridin-2-yl)pyrimidin-4-yl)amino)pyrimidin-2-yl)amino)benzyl)azetidine-3-carboxylate (88)

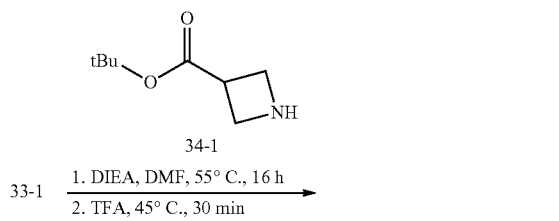

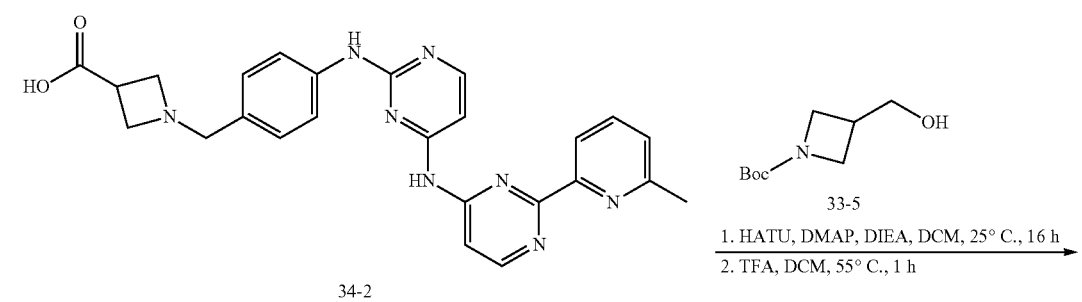

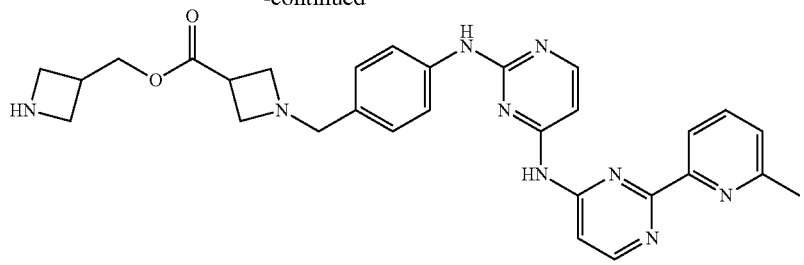

88

Step A: Preparation of 1-(4-((4-((2-(6-methylpyridin-2-yl)pyrimidin-4-yl)amino)pyrimidin-2-yl)amino)benzyl)azetidine-3-carboxylic acid (34-2). To a solution of 33-1 (262 mg, 0.65 mmol) in DCM (10 ml) was added 34-1 (204 mg, 1.30 mmol) and DIEA (0.567 ml, 3.25 mmol) and the resulting mixture heated at 55° C. for 16 h. The reaction mixture was concentrated in vacuum to give a crude residue. To the residue was directly added DCM (2 ml) and TFA (2 ml) and was heated at 55° C. for 1 h. The reaction mixture was concentrated in vacuum and was purified by preparative HPLC chromatography using a gradient (5 to 30%) of acetonitrile in water with 0.05% trifluoroacetic acid to yield a TFA salt of 34-2 (118 mg). [M+H]$^+$ calcd for $C_{25}H_{24}N_8O_2$ 468.52, found 469.0.

Step B: Preparation of azetidin-3-ylmethyl 1-(4-((4-((2-(6-methylpyridin-2-yl)pyrimidin-4-yl)amino)pyrimidin-2-yl)amino)benzyl)azetidine-3-carboxylate (88). A solution of 34-2 (23 mg, 0.033 mmol), 33-5 (9.27 mg, 0.050 mmol), HATU (18.83 mg, 0.050 mmol), DMAP (0.40 mg, 3.3 μmol), and DIEA (23.0 μl, 0.132 mmol) in DCM (0.5 ml) was stirred at 25° C. for 16 h. TFA (127 μl) was added to the reaction mixture and was heated at 45° C. for 30 min. The reaction mixture was concentrated in vacuum and was purified by preparative HPLC chromatography using a gradient (2 to 40%) of acetonitrile in water with 0.05% trifluoroacetic acid to yield a TFA salt of the title compound (24.0 mg). [M+H]$^+$ calcd for $C_{29}H_{31}N_9O_2$ 537.63, found 538.2.

Example 35: Synthesis of (S)-1-methylpyrrolidin-3-yl (R)-1-((2-((4-((2-(6-methylpyridin-2-yl)pyrimidin-4-yl)amino)pyrimidin-2-yl)amino)thiazol-4-yl)methyl)piperidine-3-carboxylate (508)

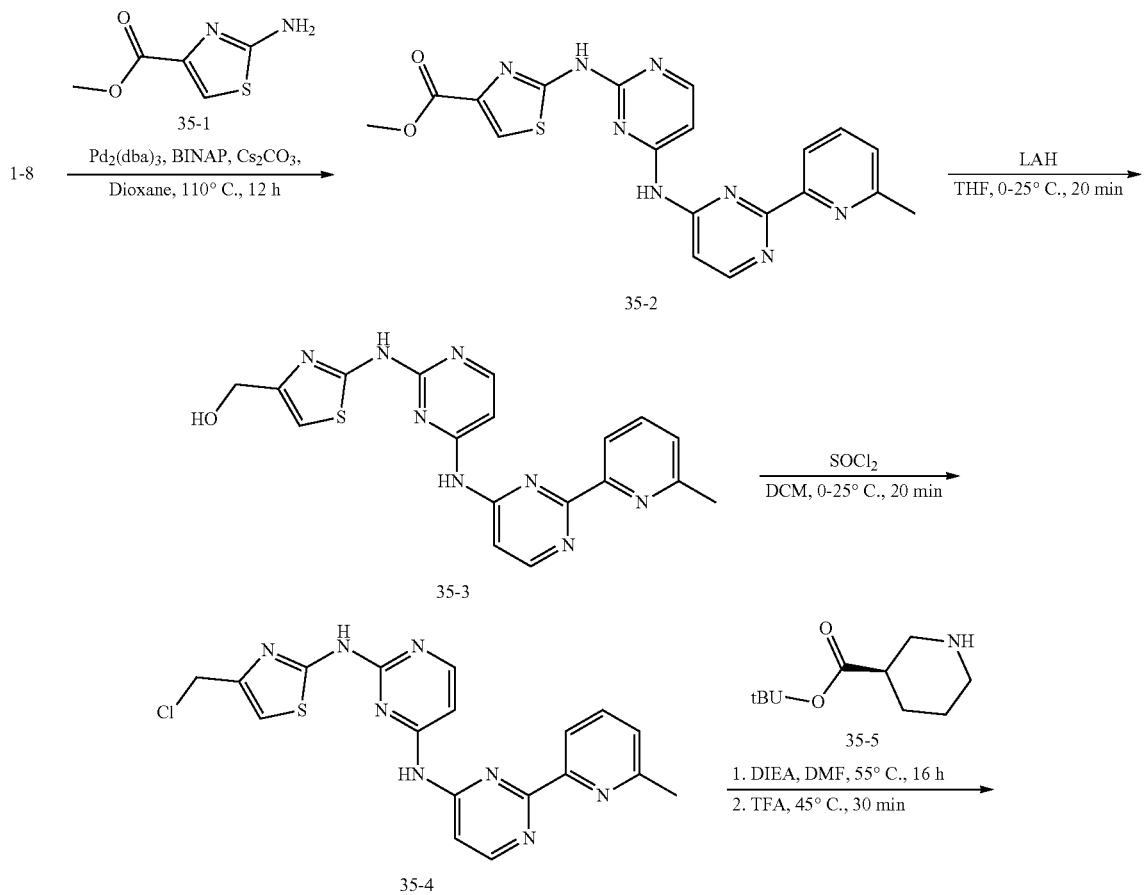

-continued

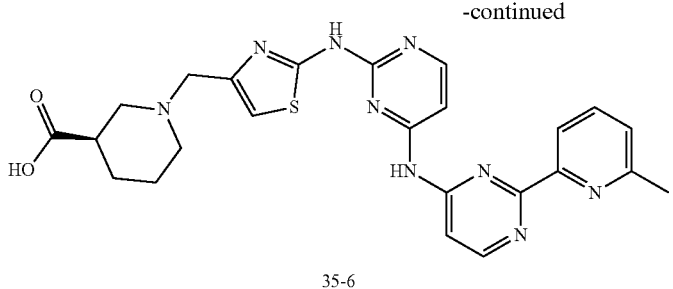

35-6

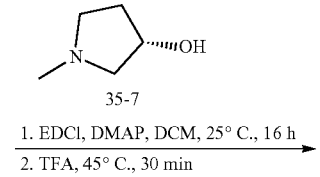

35-7

1. EDCl, DMAP, DCM, 25° C., 16 h
2. TFA, 45° C., 30 min

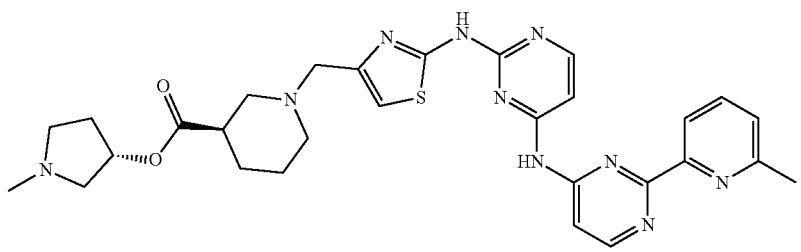

508

Step A: Preparation of methyl 2-((4-((2-(6-methylpyridin-2-yl)pyrimidin-4-yl)amino)pyrimidin-2-yl)amino)thiazole-4-carboxylate (35-2). To a suspension of 1-8 (3.6 g, 12.2 mmol) in 1,4-dioxane (100 ml) was added 35-1 (2.5 g, 15.8 mmol), $Cs_2CO_3$ (8.0 g, 24.4 mmol), $Pd_2(dba)_3$ (1.1 g, 1.22 mmol) and BINAP (760 mg, 1.22 mmol). The reaction mixture was degassed under vacuum and $N_2$ was purged for 3 times. The reaction mixture was heated at 110° C. for 12 h. The reaction mixture was concentrated in vacuum to give the residue. The residue was purified by preparative HPLC chromatography using a gradient (12 to 42%) of acetonitrile in water with 0.1% trifluoroacetic acid to yield a TFA salt of 35-2 (1.7 g). [M+H]$^+$ calcd for $C_{19}H_{16}N_8O_2S$ 420.45, found 421.0.

Step B: Preparation of (2-((4-((2-(6-methylpyridin-2-yl)pyrimidin-4-yl)amino)pyrimidin-2-yl)amino)thiazol-4-yl)methanol (35-3). To a solution of 35-2 (50 mg×16, 0.119 mmol×16) in THF (1 mL×16) was added LAH (9 mg×16, 0.238 mmol×16) at 0° C. The mixture was stirred at 25° C. for 20 min. The reaction mixture was diluted with Rochelle salt solution (100 ml) and extracted with DCM (200 ml×3), The organic layer was dried over $Na_2SO_4$, filtered, and concentrated in vacuum. The residue was purified by preparative HPLC chromatography using a gradient (10 to 35%) of acetonitrile in water with 0.225% formic acid to obtain 35-3 (86 mg) as yellow solid. [M+H]$^+$ calcd for $C_{18}H_{16}N_8OS$ 392.44, found 393.1.

Step C: Preparation of N2-(4-(chloromethyl)thiazol-2-yl)-N4-(2-(6-methylpyridin-2-yl)pyrimidin-4-yl)pyrimidine-2,4-diamine (35-4). To a solution of 35-3 (101 mg, 0.257 mmol) in DCM (6 ml) was added $SOCl_2$ (92 mg, 0.771 mmol) dropwise at 0° C. The reaction mixture was stirred at 25° C. for 2 h. The reaction mixture was concentrated in vacuum. The residue was purified by trituration to give 35-4 (50 mg) as yellow solid. [M+H]$^+$ calcd for $C_{18}H_{15}ClN_8OS$ 410.88, found 411.0.

Step D: Preparation of (R)-1-((2-((4-((2-(6-methylpyridin-2-yl)pyrimidin-4-yl)amino)pyrimidin-2-yl)amino)thiazol-4-yl)methyl)piperidine-3-carboxylic acid (35-6). To a solution of 35-4 (200 mg, 0.487 mmol), 35-5 (162 mg, 0.730 mmol), and DIEA (425 µl, 2.434 mmol) in DCM (7.8 ml) was heated at 55° C. for 2 h. TFA (938 µl) was added to the reaction mixture and was heated at 45° C. for 30 min. The reaction mixture was concentrated in vacuum. The residue was purified by preparative HPLC chromatography using a gradient (5 to 75%) of acetonitrile in water with 0.05% trifluoroacetic acid to yield a TFA salt of 35-6 (253 mg). [M+H]$^+$ calcd for $C_{24}H_{25}N_9O_2S$ 503.59, found 504.0.

Step E: Preparation of (S)-1-methylpyrrolidin-3-yl (R)-1-((2-((4-((2-(6-methylpyridin-2-yl)pyrimidin-4-yl)amino)pyrimidin-2-yl)amino)thiazol-4-yl)methyl)piperidine-3-carboxylate (508). A solution of 35-6 (25 mg, 0.034 mmol), 35-7 (5.18 mg, 0.051 mmol), EDCI (9.83 mg, 0.051 mmol), and DMAP (0.84 mg, 6.83 µmol) in DCM (0.5 ml) was stirred at 25° C. for 16 h. TFA (132 µl) was added to the reaction mixture and was heated at 45° C. for 30 min. The reaction mixture was concentrated in vacuum and was purified by preparative HPLC chromatography using a gradient (2 to 50%) of acetonitrile in water with 0.05% trifluoroacetic acid to yield a TFA salt of the title compound (18.2 mg). [M+H]$^+$ calcd for $C_{29}H_{34}N_{10}O_2S$ 586.72, found 587.1.

Example 36: Synthesis of (R)-1-methylpyrrolidin-3-yl 2-(1-(4-((4-((2-(6-methylpyridin-2-yl)pyrimidin-4-yl)amino)pyrimidin-2-yl)amino)phenyl)piperazin-2-yl)acetate (103)
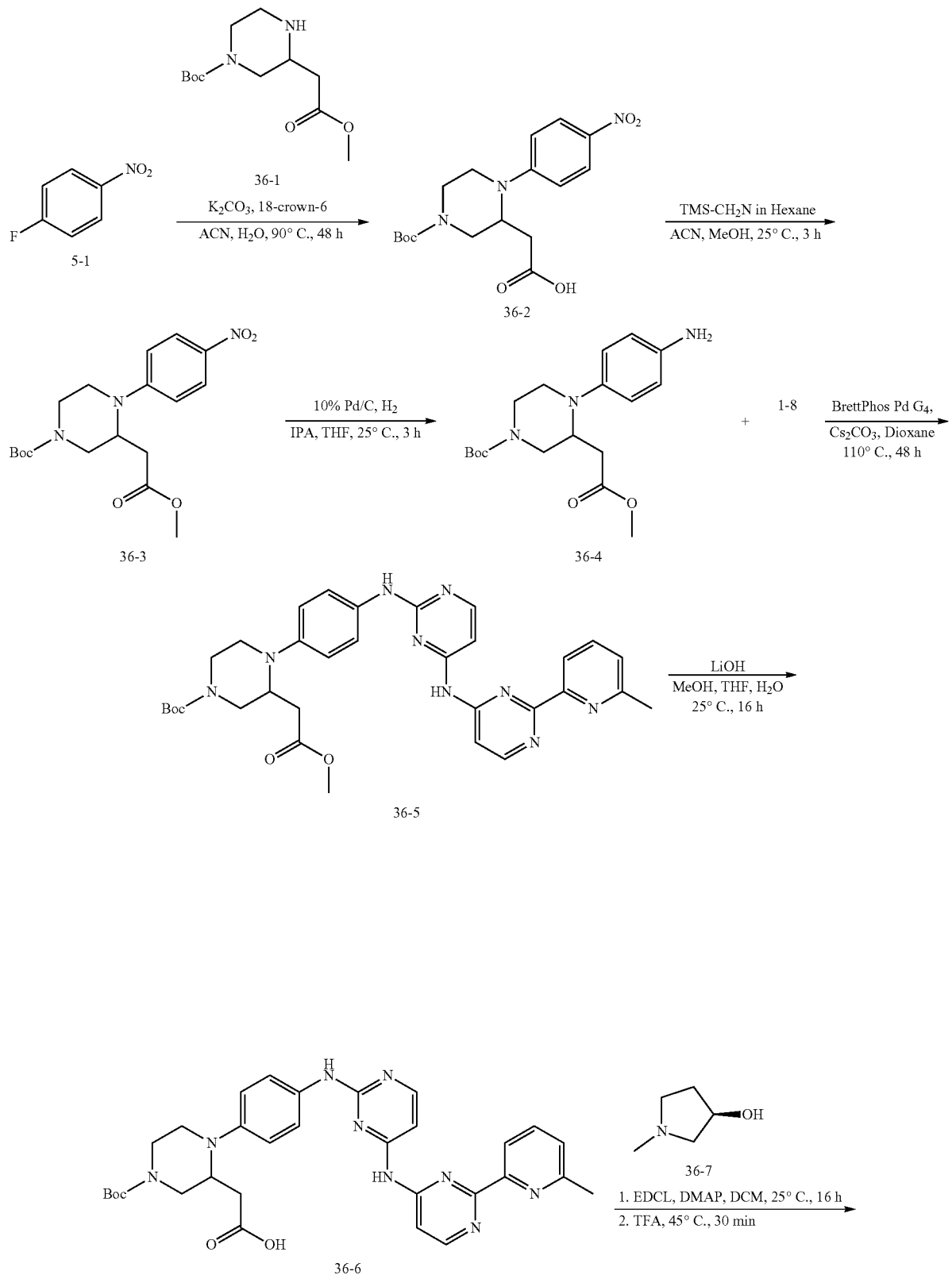

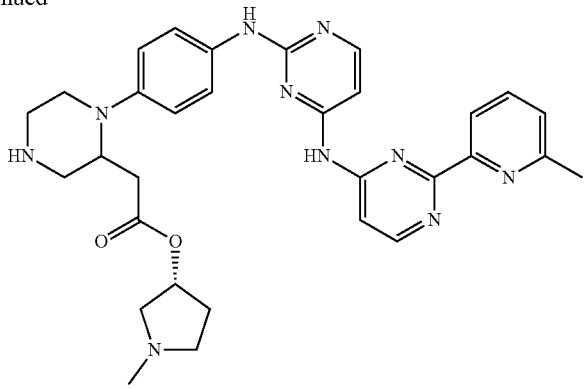

103

Step A: Preparation of 2-(4-(tert-butoxycarbonyl)-1-(4-nitrophenyl)piperazin-2-yl)acetic acid (36-2). To a solution of 5-1 (1.0 g, 7.09 mmol) and 36-1 (2.195 g, 8.51 mmol) in ACN (12 ml) and water (3 ml) was added potassium carbonate (4.9 g, 35.46 mmol), followed by 18-crown-6 (93 mg, 0.354 mmol). The reaction mixture was heated at 90° C. for 48 h. The reaction mixture was concentrated and the crude mixture diluted with water (10 ml). The aqueous layer was washed with EtOAc and the pH of aqueous layer was adjusted to ~4 using saturated citric acid solution and extracted with DCM (5 ml×2). The organic layer was concentrated to get the crude residue of 36-2 (750 mg) as a yellow solid. [M+H]$^+$ calcd for $C_{17}H_{23}N_3O_6$ 365.39, found 366.22.

Step B: Preparation of tert-butyl 3-(2-methoxy-2-oxoethyl)-4-(4-nitrophenyl)piperazine-1-carboxylate (36-3). To a solution of 36-2 (700 mg, 1.91 mmol) in ACN (7 ml) and MeOH (3 ml) was added TMS-CHN$_2$ in hexane (2M) (5.8 mL 11.5 mmol) and the reaction mixture was stirred at 25° C. for 3 h. To the reaction mixture was added excess methanol and stirred at 25° C. for 15 min, then residual solvent was distilled off to obtain the crude residue. The residue was purified by silica-gel column chromatography using a gradient (0 to 15%) of EtOAc in Hexane to give 36-3 (700 mg) as yellow solid. [M+H]$^+$ calcd for $C_{18}H_{25}N_3O_6$ 379.41, found 380.03.

Step C: Preparation of tert-butyl 4-(4-aminophenyl)-3-(2-methoxy-2-oxoethyl)piperazine-1-carboxylate (36-4). To a solution of 36-3 (1.3 g, 3.43 mmol) in THF:IPA (20 ml, 1:1) was added 10% Pd/C (1.3 g), then the resulting suspension was stirred at 25° C. under H$_2$ atmosphere for 3 h. The reaction mixture was filtered through Celite bed and the residue was washed with EtOAc. The organic layer was then evaporated under reduced pressure to get the crude product 36-4 (1.3 g), which was used directly for the next step. [M+H]$^+$ calcd for $C_{18}H_{27}N_3O_4$ 349.43, found 350.10.

Step D: Preparation of tert-butyl 3-(2-methoxy-2-oxoethyl)-4-(4-((4-((2-(6-methylpyridin-2-yl)pyrimidin-4-yl)amino)pyrimidin-2-yl)amino)phenyl)piperazine-1-carboxylate (36-5). To a stirred solution of 1-8 (1.2 g, 4.02 mmol) and 36-4 (1.6 g, 4.83 mmol) in 1,4-dioxane (15 ml) was added Cs$_2$CO$_3$ (2.62 g, 8.05 mmol) and the reaction mixture was purged with N$_2$ for 30 min. To the reaction mixture was added Brettphos Pd G4 (0.370 g, 0.40 mmol), then purging was repeated with N2 for 5 min. The reaction mixture was heated at 110° C. for 3 h. The reaction mixture was filtered through a Celite bed, washed with 5% MeOH:DCM, and concentrated to afford a crude residue. The residue was purified by silica-gel column chromatography using a gradient (0 to 100%) of EtOAc in PE to give 36-5 (1.18 g) as a white solid.

Step E: Preparation of 2-(4-(tert-butoxycarbonyl)-1-(4-((4-((2-(6-methylpyridin-2-yl)pyrimidin-4-yl)amino)pyrimidin-2-yl)amino)phenyl)piperazin-2-yl)acetic acid (36-6). To a stirred solution of 36-5 (1.4 g, 2.29 mmol) in MeOH (10 ml), THF (5 ml) and water (2.5 ml) was added LiOH.H$_2$O (0.48 g, 11.45 mmol) and the reaction mixture was stirred at 25° C. for 16 h. The reaction mixture pH was adjusted to ~3-4 by using aq. citric acid solution. Desired acid was extracted from the aqueous layer using 10% MeOH:DCM. The organic layer was dried over Na$_2$SO$_4$, filtered and concentrated to get crude residue. The residue was purified by silica-gel column chromatography using a gradient (5 to 10%) of MeOH in DCM to give 36-6 (1.12 g) as an off-white solid. [M+H]$^+$ calcd for $C_{31}H_{35}N_9O_4$ 597.68, found 598.32.

Step F: Preparation of (R)-1-methylpyrrolidin-3-yl 2-(1-(4-((4-((2-(6-methylpyridin-2-yl)pyrimidin-4-yl)amino)pyrimidin-2-yl)amino)phenyl)piperazin-2-yl)acetate (103). A solution of 36-6 (30 mg, 0.050 mmol), 36-7 (7.62 mg, 0.075 mmol), EDCI (14.43 mg, 0.075 mmol), and DMAP (1.20 mg, 10.0 µmol) in DCM (0.5 ml) was stirred at 25° C. for 16 h. TFA (193 µl) was added to the reaction mixture and was heated at 45° C. for 30 min. The reaction mixture was concentrated in vacuum and was purified by preparative HPLC chromatography using a gradient (2 to 50%) of acetonitrile in water with 0.05% trifluoroacetic acid to yield a TFA salt of the title compound (11.4 mg). [M+H]$^+$ calcd for $C_{31}H_{36}N_{10}O_2$ 580.70, found 581.1.

Example 37: Synthesis of azetidin-3-ylmethyl 4-((4-((2-(6-methylpyridin-2-yl)pyrimidin-4-yl)amino)pyrimidin-2-yl)amino)thiophene-2-carboxylate (96)

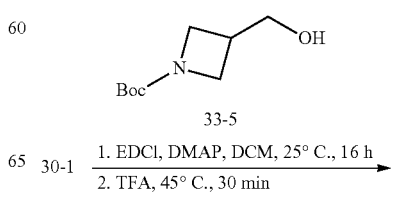

33-5

30-1  $\xrightarrow{\text{1. EDCl, DMAP, DCM, 25° C., 16 h}}_{\text{2. TFA, 45° C., 30 min}}$

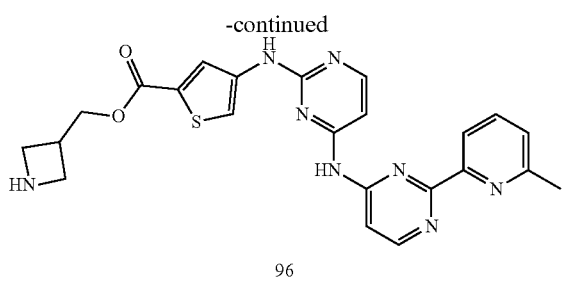

96

A solution of 30-1 (50 mg, 0.123 mmol), 33-5 (34.6 mg, 0.185 mmol), EDCI (35.5 mg, 0.185 mmol), and DMAP (3.01 mg, 0.025 mmol) in DCM (0.5 ml) was stirred at 25° C. for 16 h. TFA (475 µl) was added to the reaction mixture and was heated at 45° C. for 30 min. The reaction mixture was concentrated in vacuum and was purified by preparative HPLC chromatography using a gradient (2 to 30%) of acetonitrile in water with 0.05% trifluoroacetic acid to yield a TFA salt of the title compound (22.8 mg). [M+H]$^+$ calcd for $C_{23}H_{22}N_8O_2S$ 474.54, found 475.1.

Example 38: Synthesis of azetidin-3-ylmethyl 5-((4-((2-(6-methylpyridin-2-yl)pyrimidin-4-yl)amino)pyrimidin-2-yl)amino)thiophene-3-carboxylate (142)

Step A: Preparation of methyl 5-((4-((2-(6-methylpyridin-2-yl)pyrimidin-4-yl)amino)pyrimidin-2-yl)amino)thiophene-3-carboxylate (38-2). A solution of 1-8 (1.6 g, 5.36 mmol), 38-1 (842 mg, 5.36 mmol) and conc. HCl (0.6 ml) in IPA (16 ml) was heated at 80° C. for 12 h. The reaction mixture was then allowed to cool to 25° C., diluted with IPA and filtered to obtain the HCl salt of 38-2 (900 mg) as an off-white solid. [M+H]$^+$ calcd for $C_{20}H_{17}N_7O_2S$ 419.46, found 420.17.

Step B: Preparation of 5-((4-((2-(6-methylpyridin-2-yl)pyrimidin-4-yl)amino)pyrimidin-2-yl)amino)thiophene-3-carboxylic acid (38-3). To a stirred solution of 38-2 (900 mg, 2.14 mmol) in MeOH (6 ml), THF (4 ml) and water (2 ml) was added KOH (240 mg, 4.29 mmol) and the resulting mixture stirred and heated at 65° C. for 3 h. The reaction mixture was concentrated and diluted with water and acidified with 3 N HCl to (pH 4-5) until light brown solid fell out, which was filtered and washed with acetonitrile and diethyl ether to get the desired compound 38-3 (215 mg) as a light brown solid. [M+H]$^+$ calcd for $C_{19}H_{15}N_7O_2S$ 405.44, found 406.03.

Step C: Preparation of azetidin-3-ylmethyl 5-((4-((2-(6-methylpyridin-2-yl)pyrimidin-4-yl)amino)pyrimidin-2-yl)amino)thiophene-3-carboxylate (142). A solution of 38-3 (25 mg, 0.062 mmol), 33-5 (17.32 mg, 0.092 mmol), EDCI (17.73 mg, 0.092 mmol), and DMAP (1.50 mg, 0.012 mmol) in DCM (0.5 ml) was stirred at 25° C. for 16 h. TFA (238 µl) was added to the reaction mixture and was heated at 45° C.

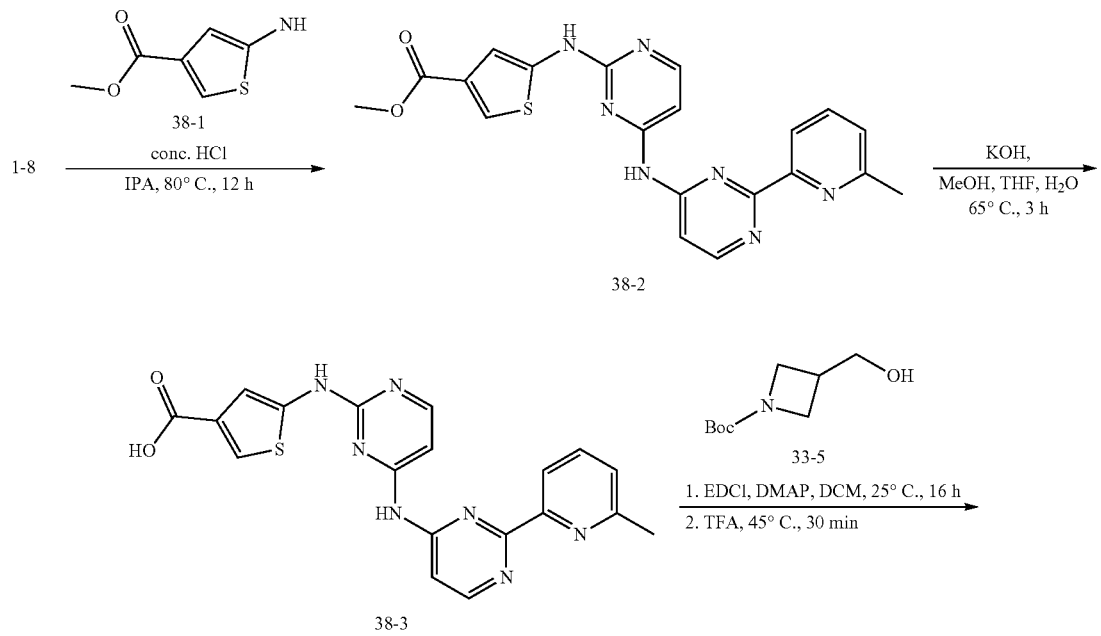

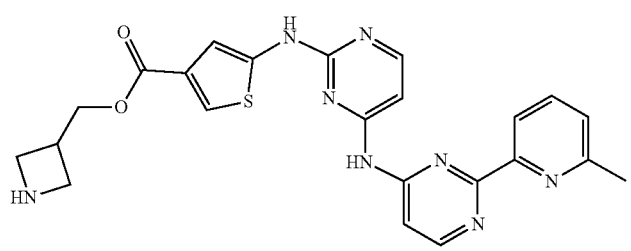

142 for 30 min. The reaction mixture was concentrated in vacuum and was purified by preparative HPLC chromatography using a gradient (5 to 50%) of acetonitrile in water with 0.05% trifluoroacetic acid to yield a TFA salt of the title compound (17.3 mg). [M+H]+ calcd for $C_{23}H_{22}N_8O_2S$ 474.54, found 475.1.

Example 39: Synthesis of piperidin-4-yl 2-((4-((2-(6-methylpyridin-2-yl)pyrimidin-4-yl)amino)pyrimidin-2-yl)amino)thiazole-4-carboxylate (148)

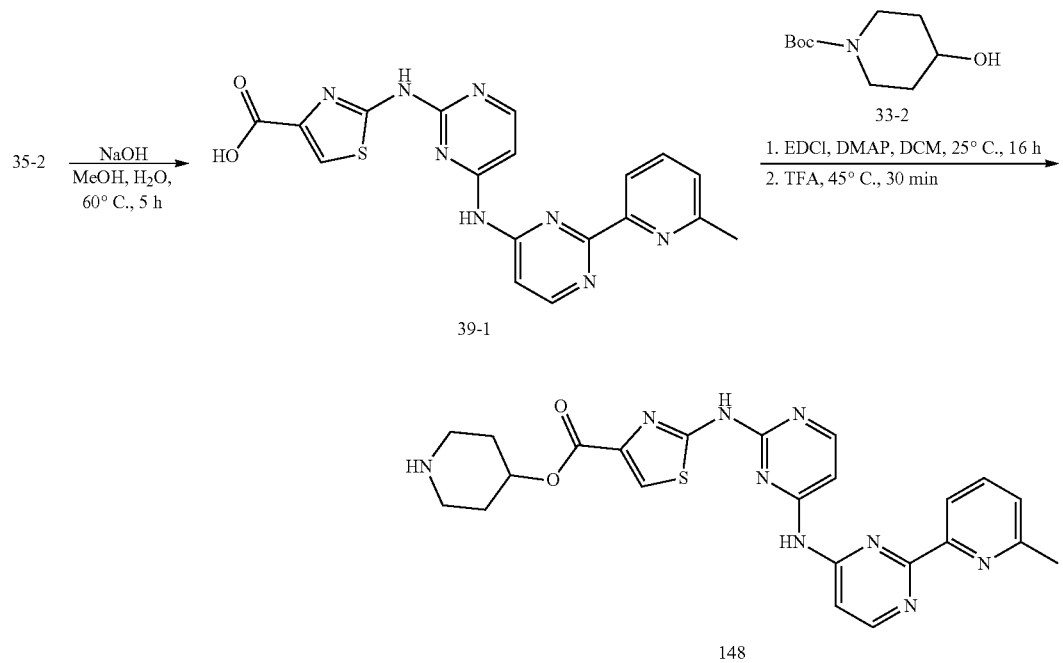 [SMILES: "NaOH" ; Cc1cccc(-c2nccc(Nc3ccnc(Nc4nc(C(=O)O)cs4)n3)n2)n1 ; CC(C)(C)OC(=O)N1CCC(O)CC1 ; Cc1cccc(-c2nccc(Nc3ccnc(Nc4nc(C(=O)OC5CCNCC5)cs4)n3)n2)n1]

Step A: Preparation of 2-((4-((2-(6-methylpyridin-2-yl)pyrimidin-4-yl)amino)pyrimidin-2-yl)amino)thiazole-4-carboxylic acid (39-1). A suspension of 35-2 (1.0 g, 2.38 mmol) and NaOH (1.9 g, 47.6 mmol) in MeOH (30 ml) and H2O (30 ml) was heated at 60° C. for 5 h. The reaction mixture was concentrated in vacuum to remove MeOH and acidified by 2M HCl to pH=6~7. The reaction mixture was filtered. The cake was washed with H2O (50 ml) and lyophilized to obtain 39-1 (600 mg) as yellow solid. [M+H]+ calcd for $C_{18}H_{14}N_8O_2S$ 406.42, found 407.0.

Step B: Preparation of piperidin-4-yl 2-((4-((2-(6-methylpyridin-2-yl)pyrimidin-4-yl)amino)pyrimidin-2-yl)amino)thiazole-4-carboxylate (148). A solution of 39-1 (25 mg, 0.062 mmol), 39-2 (18.57 mg, 0.092 mmol), EDCI (17.69 mg, 0.092 mmol), and DMAP (1.50 mg, 0.012 mmol) in DCM (0.5 ml) was stirred at 25° C. for 16 h. TFA (351 μl) was added and the reaction mixture was heated at 45° C. for 30 min. The reaction mixture was concentrated in vacuum and was purified by preparative HPLC chromatography using a gradient (5 to 65%) of acetonitrile in water with 0.05% trifluoroacetic acid to yield a TFA salt of the title compound (9.2 mg). [M+H]+ calcd for $C_{23}H_{23}N_9O_2S$ 489.56, found 490.0.

Example 40: Synthesis of azetidin-3-ylmethyl 2-((4-((2-(6-methylpyridin-2-yl)pyrimidin-4-yl)amino)pyrimidin-2-yl)amino)thiazole-5-carboxylate (338)

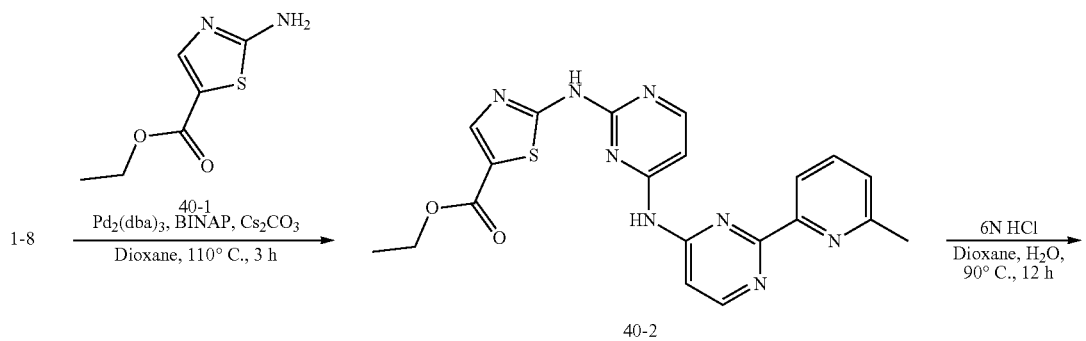

-continued

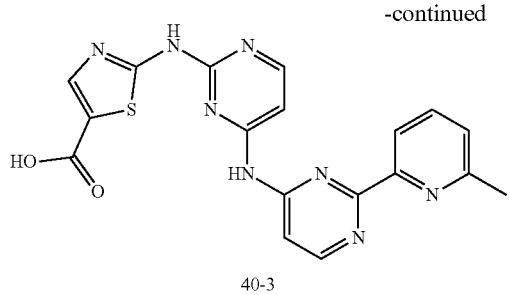

40-3

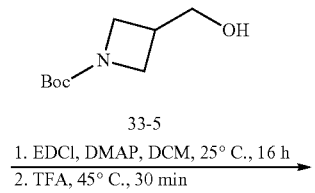

33-5

1. EDCl, DMAP, DCM, 25° C., 16 h
2. TFA, 45° C., 30 min

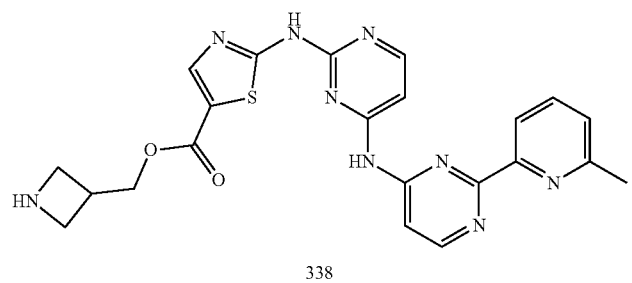

338

Step A: Preparation of ethyl 2-((4-((2-(6-methylpyridin-2-yl)pyrimidin-4-yl)amino)pyrimidin-2-yl)amino)thiazole-5-carboxylate (40-2). To a stirred solution of 1-8 (600 mg, 2.013 mmol) and 40-1 (519 mg, 3.019 mmol) in 1,4-dioxane (12 ml) was added cesium carbonate (1.3 g, 4.026 mmol) and purged for 15 min. Pd2(dba)3 (184 mg, 0.201 mmol) and BINAP (250 mg, 0.402 mmol) were then added. The reaction mixture was then heated at 110° C. for 3 h. The reaction mixture was diluted with 10% MeOH in DCM, filtered through Celite bed and concentrated to get crude residue. The residue was purified by silica-gel column chromatography using a gradient (0 to 5%) of MeOH in DCM to give 40-2 (430 mg). [M+H]$^+$ calcd for $C_{20}H_{18}N_8O_2S$ 434.48, found 435.10.

Step B: Preparation of 2-((4-((2-(6-methylpyridin-2-yl)pyrimidin-4-yl)amino)pyrimidin-2-yl)amino)thiazole-5-carboxylic acid (40-3). To the solution of 40-2 (300 mg, 0.69 mmol) in 1,4-dioxane:water (9.0:0.5 ml) was added 6N HCl (1.5 ml). The reaction mixture was heated at 90° C. for 12 h. The reaction mixture was concentrated completely to dryness. The resulting residue was triturated using MeOH, DCM, diethyl ether and ACN to get desired compound which was purified further through preparative HPLC chromatography to obtain 40-3 (70 mg). [M+H]$^+$ calcd for $C_{18}H_{14}N_8O_2S$ 406.42, found 407.18.

Step C: Preparation of azetidin-3-ylmethyl 2-((4-((2-(6-methylpyridin-2-yl)pyrimidin-4-yl)amino)pyrimidin-2-yl)amino)thiazole-5-carboxylate (338). A solution of 40-3 (15 mg, 0.037 mmol), 33-5 (10.37 mg, 0.055 mmol), EDCI (10.61 mg, 0.055 mmol), and DMAP (0.90 mg, 7.38 μmol) in DCM (0.5 ml) was stirred at 25° C. for 16 h. TFA (142 μl) was added to the reaction mixture and was heated at 45° C. for 30 min. The reaction mixture was concentrated in vacuum and was purified by preparative HPLC chromatography using a gradient (5 to 50%) of acetonitrile in water with 0.05% trifluoroacetic acid to yield a TFA salt of the title compound (5.7 mg). [M+H]$^+$ calcd for $C_{25}H_{24}N_8O_2S$ 475.53, found 476.0.

Example 41: Synthesis of azetidin-3-ylmethyl 3-((4-((2-(6-methylpyridin-2-yl)pyrimidin-4-yl)amino)pyrimidin-2-yl)amino)benzoate (178)

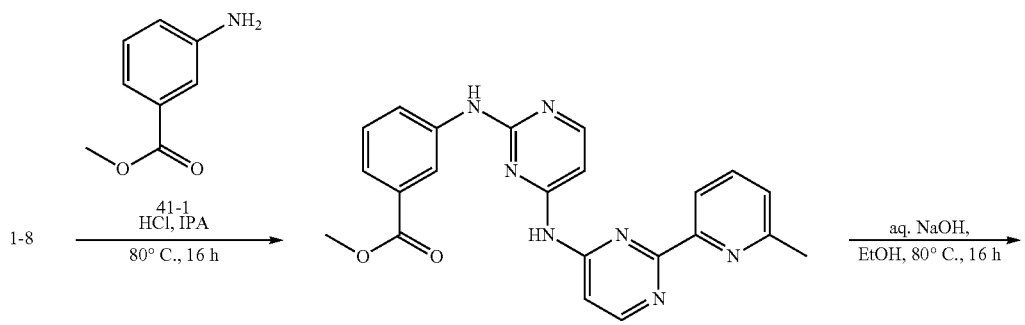

41-2

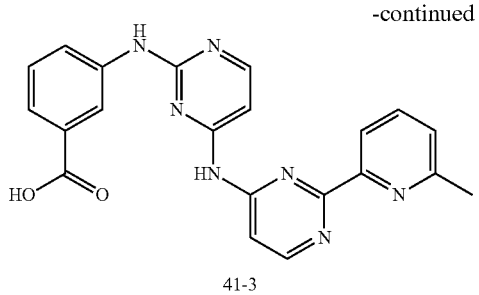

41-3

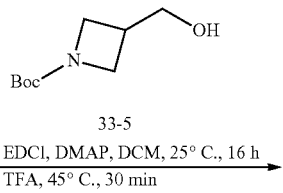

33-5
1. EDCl, DMAP, DCM, 25° C., 16 h
2. TFA, 45° C., 30 min

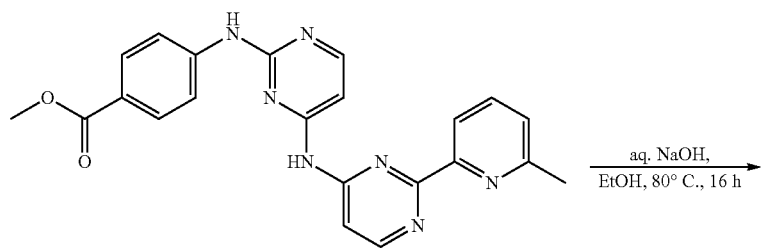

178

Step A: Preparation of methyl 3-((4-((2-(6-methylpyridin-2-yl)pyrimidin-4-yl)amino)pyrimidin-2-yl)amino)benzoate (41-2). To a mixture of 1-8 (600 mg, 2.01 mmol) and 41-1 (304 mg, 2.01 mmol) in IPA (10 ml) was added HCl (0.5 mL). The reaction mixture was heated at 80° C. for 16 h. The reaction mixture was quenched with H$_2$O (30 ml) and filtered. The filter cake was evaporated to dryness to give 41-2 (820 mg) as white solid. [M+H]$^+$ calcd for C$_{22}$H$_{19}$N$_7$O$_2$ 413.44, found 414.2.

Step B: Preparation of 3-((4-((2-(6-methylpyridin-2-yl)pyrimidin-4-yl)amino)pyrimidin-2-yl)amino)benzoic acid (41-3). A mixture of 41-2 (780 mg, 1.87 mmol) in EtOH (10 ml) and aq. NaOH (10 ml) was heated at 80° C. for 16 h. The reaction mixture was concentrated in vacuum to remove EtOH. To the residue was added HCl to adjust the pH to 5, then the mixture was filtered. The filter cake was washed with H$_2$O (30 ml) and the residue was evaporated to dryness to give 41-3 (530 mg) as yellow solid. [M+H]$^+$ calcd for C$_{21}$H$_{17}$N$_7$O$_2$ 399.41, found 399.9.

Step C: Preparation of azetidin-3-ylmethyl 3-((4-((2-(6-methylpyridin-2-yl)pyrimidin-4-yl)amino)pyrimidin-2-yl)amino)benzoate (178). A solution of 41-3 (25 mg, 0.063 mmol), 33-5 (17.58 mg, 0.094 mmol), EDCI (18.00 mg, 0.094 mmol), and DMAP (1.53 mg, 0.013 mmol) in DCM (0.5 ml) was stirred at 25° C. for 16 h. TFA (240 µl) was added to the reaction mixture and was heated at 45° C. for 30 min. The reaction mixture was concentrated in vacuum and was purified by preparative HPLC chromatography using a gradient (5 to 50%) of acetonitrile in water with 0.05% trifluoroacetic acid to yield a TFA salt of the title compound (29.5 mg). [M+H]$^+$ calcd for C$_{25}$H$_{24}$N$_8$O$_2$ 468.52, found 469.1.

Example 42: Synthesis of azetidin-3-ylmethyl 4-((4-((2-(6-methylpyridin-2-yl)pyrimidin-4-yl)amino)pyrimidin-2-yl)amino)benzoate (33)

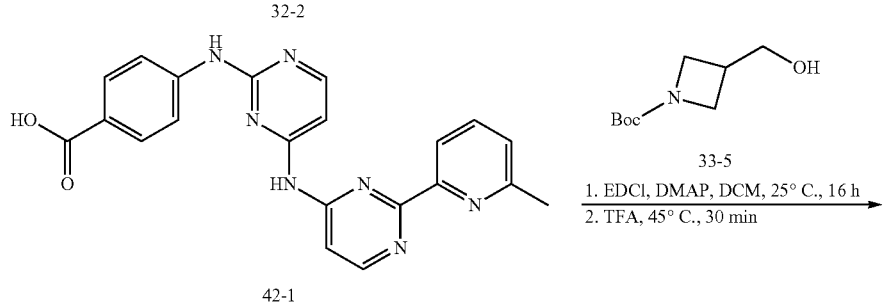

32-2 aq. NaOH,
EtOH, 80° C., 16 h 42-1

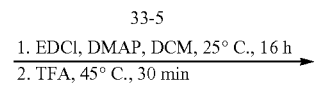

33-5
1. EDCl, DMAP, DCM, 25° C., 16 h
2. TFA, 45° C., 30 min

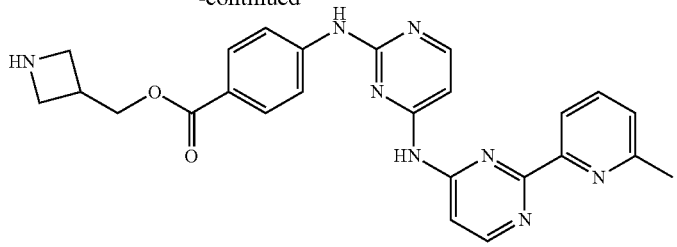

33

Step A: Preparation of 4-((4-((2-(6-methylpyridin-2-yl)pyrimidin-4-yl)amino)pyrimidin-2-yl)amino)benzoic acid (42-1). A mixture of 32-2 (780 mg, 1.87 mmol) in EtOH (10 ml) and aq. NaOH (10 ml) was stirred at 80° C. for 16 h. The reaction mixture was concentrated in vacuum to remove EtOH. To the residue was added HCl to adjust the pH to 5, then the mixture was filtered. The filter cake was washed with H$_2$O (30 ml) and the residue evaporated to dryness to give 42-1 (530 mg) as yellow solid. [M+H]$^+$ calcd for C$_{21}$H$_{17}$N$_7$O$_2$ 399.41, found 399.9.

Step B: Preparation of azetidin-3-ylmethyl 4-((4-((2-(6-methylpyridin-2-yl)pyrimidin-4-yl)amino)pyrimidin-2-yl)amino)benzoate (33). A solution of 42-1 (25 mg, 0.063 mmol), 33-5 (17.58 mg, 0.094 mmol), EDCI (18.00 mg, 0.094 mmol), and DMAP (1.53 mg, 0.013 mmol) in DCM (0.5 ml) was stirred at 25° C. for 16 h. TFA (240 µl) was added to the reaction mixture and was heated at 45° C. for 30 min. The reaction mixture was concentrated in vacuum and was purified by preparative HPLC chromatography using a gradient (5 to 65%) of acetonitrile in water with 0.05% trifluoroacetic acid to yield a TFA salt of the title compound (21.1 mg). [M+H]$^+$ calcd for C$_{25}$H$_{24}$N$_8$O$_2$ 468.52, found 469.1.

Example 43: Synthesis of azetidin-3-ylmethyl 5-((4-((2-(6-methylpyridin-2-yl)pyrimidin-4-yl)amino)pyrimidin-2-yl)amino)picolinate (545)

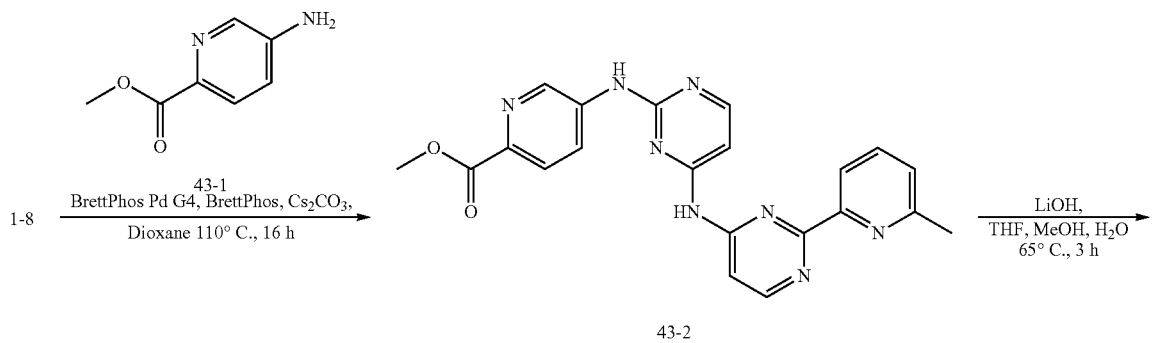

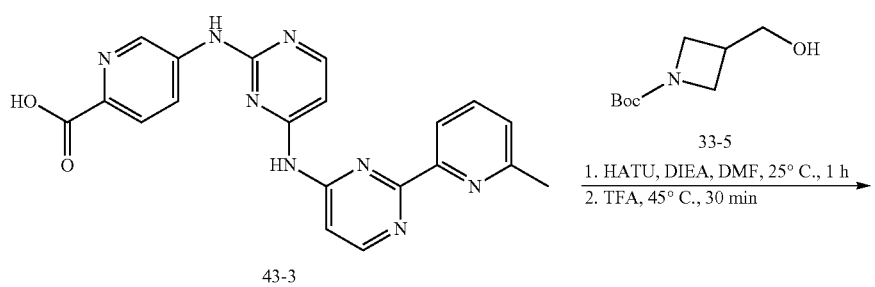

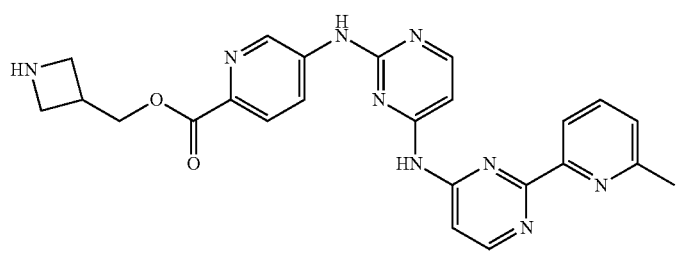

545

Step A: Preparation of methyl 5-((4-((2-(6-methylpyridin-2-yl)pyrimidin-4-yl)amino)pyrimidin-2-yl)amino)picolinate (43-2). A vial of 1-8 (250 mg, 0.837 mmol), 44-1 (127 mg, 0.837 mmol), cesium carbonate (545 mg, 1.674 mmol), BrettPhos (44.9 mg, 0.084 mmol), and BrettPhos Pd G4 (77 mg, 0.084 mmol) in degassed 1,4-dioxane (4.2 ml) was heated to 110° C. for 16 h. The reaction mixture was concentrated in vacuum and purified by silica-gel column chromatography using a gradient (0 to 15%) of MeOH in DCM to obtain 43-2 (164 mg) as an orange oil. [M+H]+ calcd for $C_{21}H_{18}N_8O_2$ 414.43, found 415.

Step B: Preparation of 5-((4-((2-(6-methylpyridin-2-yl)pyrimidin-4-yl)amino)pyrimidin-2-yl)amino)picolinic acid (43-3). A solution of 43-2 (164 mg, 0.396 mmol), and LiOH (24.73 mg, 1.033 mmol) in a 3:2:1 mixture of THF (1291 µl), MeOH (861 µl), and H₂O (430 µl) was heated to 65° C. for 3 h. The reaction mixture was concentrated in vacuum and purified by preparative HPLC chromatography using a gradient (5 to 30%) of acetonitrile in water with 0.05% trifluoroacetic acid to yield a TFA salt of 43-3 (129 mg). [M+H]+ calcd for $C_{20}H_{16}N_8O_2$ 400.40, found 401.1.

Step C: Preparation of azetidin-3-ylmethyl 5-((4-((2-(6-methylpyridin-2-yl)pyrimidin-4-yl)amino)pyrimidin-2-yl)amino)picolinate (545). A solution of 43-3 (20 mg, 0.039 mmol), 33-5 (10.92 mg, 0.058 mmol), HATU (22.17 mg, 0.058 mmol), and DIEA (27.2 µl, 0.156 mmol) in DCM (0.5 ml) was heated to 50° C. for 1 h. TFA (120 µl) was added to the reaction mixture and stirred at 25° C. for 30 min. The reaction mixture was concentrated in vacuum and was purified by preparative HPLC chromatography using a gradient (2 to 60%) of acetonitrile in water with 0.05% trifluoroacetic acid to yield a TFA salt of the title compound (22.8 mg). [M+H]+ calcd for $C_{24}H_{23}N_9O_2$ 469.51, found 470.1.

Example 44: Synthesis of (R)-pyrrolidin-3-yl 5-((4-((2-(6-methylpyridin-2-yl)pyrimidin-4-yl)amino)pyrimidin-2-yl)amino)nicotinate (549)

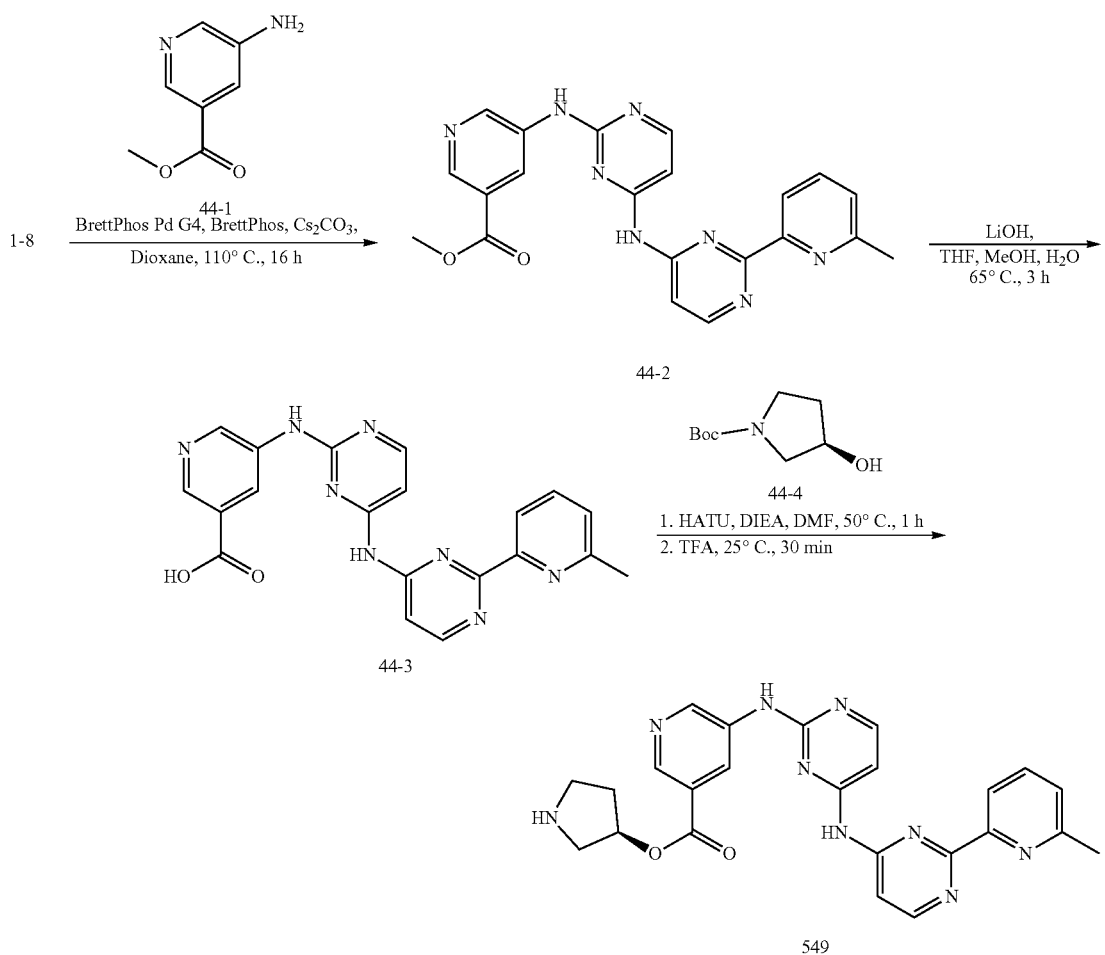

Step A: Preparation of methyl 5-((4-((2-(6-methylpyridin-2-yl)pyrimidin-4-yl)amino)pyrimidin-2-yl)amino)nicotinate (44-2). A vial of 1-8 (250 mg, 0.837 mmol), 44-1 (127 mg, 0.837 mmol), cesium carbonate (545 mg, 1.674 mmol), BrettPhos (44.9 mg, 0.084 mmol), and BrettPhos Pd G4 (77 mg, 0.084 mmol) in degassed 1,4-dioxane (4.2 ml) was heated to 110° C. for 16 h. The reaction mixture was concentrated in vacuum and purified by silica-gel column chromatography using a gradient (0 to 15%) of MeOH in DCM to obtain 44-2 (214 mg) as an orange oil. [M+H]+ calcd for $C_{21}H_{18}N_8O_2$ 414.43, found 415.

Step B: Preparation of 5-((4-((2-(6-methylpyridin-2-yl)pyrimidin-4-yl)amino)pyrimidin-2-yl)amino)nicotinic acid (44-3). A solution of 44-2 (214 mg, 0.516 mmol) and LiOH (24.73 mg, 1.033 mmol) in a 3:2:1 mixture of THF (1291 µl), MeOH (861 µl), and H$_2$O (430 µl) was heated to 65° C. for 3 h. The reaction mixture was concentrated in vacuum and purified by preparative HPLC chromatography using a gradient (5 to 30%) of acetonitrile in water with 0.05% trifluoroacetic acid to yield a TFA salt of 44-3 (77 mg). [M+H]$^+$ calcd for C$_{20}$H$_{16}$N$_8$O$_2$ 400.40, found 401.1.

Step C: Preparation of (R)-pyrrolidin-3-yl 5-((4-((2-(6-methylpyridin-2-yl)pyrimidin-4-yl)amino)pyrimidin-2-yl) amino)nicotinate (549). A solution of 44-3 (20 mg, 0.039 mmol), 44-4 (10.92 mg, 0.058 mmol), HATU (22.17 mg, 0.058 mmol), and DIEA (27.2 µl, 0.156 mmol) in DCM (0.5 ml) was heated to 50° C. for 1 h. TFA (120 µl) was added to the reaction mixture and stirred at 25° C. for 30 min. The reaction mixture was concentrated in vacuum and was purified by preparative HPLC chromatography using a gradient (2 to 60%) of acetonitrile in water with 0.05% trifluoroacetic acid to yield a TFA salt of the title compound (12.8 mg). [M+H]$^+$ calcd for C$_{24}$H$_{23}$N$_9$O$_2$ 469.51, found 470.1.

Example 45: Biochemical ALK5 (TGF-βR1) Assay to Measure pKi

Apparent pK$_i$ values for compounds of the present disclosure were determined using a recombinant human ALK5 (TGF-βR1) protein (Product No. PR9075A or equivalent, Life Technologies) and a commercially-available kinase assay (LANCE® (lanthanide chelate excite) Ultra ULight™ kinase assay, Product Nos. TRF0130-M and TRF02108-M, Perkin Elmer) as described below.

The assays were performed in a 384-well plate (24 columns×16 wells/rows). An Echo®550 Liquid Handler (Labcyte) was used to prepare various intermediate concentrations of compounds of the present disclosure in 100% DMSO. From the intermediate concentrations, a range of concentrations (from 10 µM to 25 pM corresponding to volumes up to 105 nL) were prepared and ejected into a final assay plate to be used to create individual dose response curves for each of the subject compounds. To a separate column within the assay plate, 105 nL of DMSO in each well was used to establish a maximum assay signal. Additionally, 105 nL of 100 µM SD-208, a selective TGF-βR1 inhibitor (Catalog #S7624, Selleck Chemicals), was used in another column of wells to establish a minimal assay signal.

With a multidrop dispenser, 8 µL of enzyme mixture (1.25× final) was added to each well. The enzyme mixture consisted of 250 pM ALK5 enzyme and 62.5 nM peptide substrate (LANCE® (lanthanide chelate excite) Ultra ULight™-DNA Topoisomerase 2-alpha (Thr1342)) prepared in assay buffer (50 mM HEPES, 10 mM MgCl$_2$, 1 mM EGTA, 0.01% Tween-20, pH 7.5 at room temperature) with 2 mM DTT added prior to use. The plate was then sealed with an adhesive seal and allowed to equilibrate for 60 minutes at room temperature.

Next, 2 µL of 125 µM ATP (5× final, 125 µM ATP prepared in assay buffer with 2 mM DTT) was added to the incubated mixtures, covered with a MicroClime® Environmental Lid (Product No. LLS-0310, Labcyte) and immediately transferred to 37° C. The reactions were allowed to proceed at 37° C. for 60 minutes before terminating with the addition of 10 µL of detection antibody (LANCE® (lanthanide chelate excite) Ultra Europium-anti-phospho-DNA Topoisomerase 2-alpha (Thr1342)) in detection mixture (12 mM EDTA, 4 nM detection antibody prepared in detection buffer (50 mM Tris-HCl, 150 mM NaCl, 0.5% BSA (Fraction V), pH 7.0)) at room temperature. The plate was then read on a Perkin Elmer EnVision Plate Reader using europium specific reader settings with excitation and emission wavelengths set to 320 or 340 nm and 665 nm, respectively. These data were used to calculate percent enzyme inhibition values based on DMSO and SD-208 background controls.

For dose-response analyses, percent inhibition versus compound concentrations were plotted, and pIC$_{50}$ values were determined from a 4-parameter robust fit model with GraphPad Prism V5 Software (GraphPad Software, Inc., La Jolla, Calif.). This model obtains pIC$_{50}$ values by fitting the sigmoidal dose-response (variable slope) equation to the data. Results were expressed as pIC$_{50}$ (negative logarithm of IC$_{50}$) and subsequently converted to pK$_i$ (negative logarithm of dissociate constant, K$_i$) using the Cheng-Prusoff equation. The higher the value of pK$_i$ (lower value of K$_i$), the greater the inhibition of ALK5 activity. Certain compounds disclosed herein exhibited pK$_i$ values of greater than 8 or greater than 9 when tested in the biochemical ALK5 assay.

Table 3 shows biological activities of selected compounds in a biochemical ALK5 assay. Compound numbers correspond to the numbers and structures provided in Tables 1 and 2 and Examples 1-44.

TABLE 3

| | | 7.5 to 8.4 (+) | 8.5 to 9.4 (++) | 9.5 to 10.4 (+++) | ≥10.5 (++++) |
|---|---|---|---|---|---|
| ALK5 pK$_i$ | | 19, 30, 35, 87, 119, 165, 166, 226, 234, 306, 309, 325, 333, 338, 348, 399, 410, 426, 468, 502, 526, 529, 535, 564, 574, 575, 578, 579, 581, 585, 592, 601, 604, 608, 622, 624, 630, 632, 633, 634, 636, 640, 1000, 1003, 1004, 1008, 1020, 1043 | 2, 3, 5, 16, 18, 20, 26, 36, 43, 47, 54, 56, 62, 66, 72, 82, 86, 90, 91, 103, 107, 114, 117, 121, 126, 146, 148, 155, 162, 169, 170, 171, 176, 178, 179, 191, 201, 230, 236, 250, 255, 256, 257, 267, 281, 284, 285, 287, 291, 292, 296, 303, 304, 308, 310, 316, 321, 323, 329, 339, 349, 350, 354, 355, 363, 369, 371, 379, 386, 388, 391, | 1, 4, 6, 7, 8, 9, 10, 11, 12, 13, 14, 15, 17, 21, 22, 23, 25, 27, 28, 31, 32, 33, 34, 37, 38, 39, 40, 41, 44, 45, 48, 49, 50, 51, 52, 53, 55, 57, 58, 59, 60, 61, 63, 64, 65, 67, 68, 69, 70, 71, 73, 74, 75, 76, 77, 78, 79, 80, 81, 83, 84, 85, 88, 92, 93, 95, 96, 97, 98, 100, 101, 102, 104, 105, 106, 108, 109, 110, 111, 112, 113, 115, 116, 118, 120, 122, 124, 125, 127, 128, 129, 130, 131, 132, 133, 134, 135, 136, 137, 138, 139, 140, 141, 142, 143, 145, 147, 149, 150, 151, 152, 154, 156, 157, 158, 159, 160, 161, 163, 164, 167, 168, 172, 173, 174, 177, 180, 181, 182, 183, 184, 185, 186, 187, 190, 192, 193, 194, 195, 196, 197, 198, 199, 200, 202, 203, 204, 205, 206, 207, 209, 210, 211, 212, 213, 214, 215, 216, 217, 218, 219, 220, 221, 222, 224, 225, 227, 228, 229, 231, 232, 233, 235, 237, 238, 239, 240, 241, 242, 243, 244, 245, 246, 247, 248, 249, 251, 253, 254, 258, 259, 260, 262, 263, 264, 265, | 24, 29, 42, 46, 89, 94, 99, 123, 144, 153, 175, 188, 189, 208, 223, 252, 261, 319, 327, 331, 336, 343, 364, 373, 378, 385, 404, 405, 474, 503, 539 |

TABLE 3-continued

| 7.5 to 8.4 (+) | 8.5 to 9.4 (++) | 9.5 to 10.4 (+++) | ≥10.5 (++++) |
|---|---|---|---|
| | 396, 401, 402, 406, 408, 413, 423, 425, 437, 439, 442, 446, 455, 459, 461, 467, 469, 471, 481, 485, 492, 498, 500, 505, 508, 511, 512, 513, 514, 517, 525, 527, 532, 548, 549, 550, 551, 553, 570, 580, 586, 589, 593, 595, 606, 609, 611, 613, 615, 616, 618, 623, 641, 1001, 1006, 1007, 1009, 1017, 1019, 1021, 1022, 1023, 1044, 1045 | 266, 268, 269, 270, 271, 272, 273, 274, 275, 276, 277, 278, 279, 280, 282, 283, 286, 288, 289, 290, 293, 294, 295, 297, 298, 299, 300, 301, 302, 305, 307, 311, 312, 313, 314, 315, 317, 318, 320, 322, 324, 326, 328, 330, 332, 334, 335, 337, 340, 341, 342, 344, 345, 346, 347, 351, 352, 353, 356, 357, 358, 359, 360, 361, 362, 365, 366, 367, 368, 370, 372, 374, 375, 376, 377, 380, 381, 382, 383, 384, 387, 389, 390, 392, 393, 394, 395, 397, 398, 400, 403, 407, 409, 411, 412, 414, 415, 416, 417, 418, 419, 420, 421, 422, 424, 427, 428, 429, 430, 431, 432, 433, 434, 435, 436, 438, 440, 441, 443, 444, 445, 447, 448, 449, 450, 451, 452, 453, 454, 456, 457, 458, 460, 462, 463, 464, 465, 466, 470, 472, 473, 475, 476, 477, 478, 479, 480, 482, 483, 484, 486, 487, 488, 489, 490, 491, 493, 494, 495, 496, 497, 499, 501, 504, 506, 507, 509, 510, 515, 516, 518, 519, 520, 521, 522, 523, 524, 528, 530, 531, 533, 534, 536, 537, 538, 540, 541, 542, 543, 544, 545, 546, 547, 552, 554, 556, 557, 558, 560, 561, 562, 563, 565, 566, 567, 568, 569, 571, 572, 573, 576, 577, 582, 583, 584, 587, 588, 590, 591, 594, 596, 597, 598, 599, 600, 602, 603, 605, 607, 610, 612, 614, 617, 619, 620, 621, 625, 626, 627, 628, 629, 631, 635, 637, 638, 639, 642, 1002, 1005, 1010, 1011, 1012, 1013, 1014, 1015, 1016, 1018, 1024, 1025, 1026, 1027, 1028, 1029, 1030, 1031, 1032, 1033, 1034, 1035, 1036, 1037, 1038, 1039, 1040, 1041, 1042 | |

Example 46: Cellular ALK5 Potency Assay to Measure pIC$_{50}$, Inhibition of TGF-β Stimulated pSMAD3 Formation in BEAS-2B Cells The potency of compounds of the present disclosure for inhibition of TGF-β-stimulated SMAD3 phosphorylation was measured in BEAS-2B cells, a human lung epithelial cell line. TGF-β signals through activin receptor-like kinase 5 (ALK5) immediately prior to SMAD3 phosphorylation. As the AlphaLISA SureFire Ultra kit (Perkin Elmer) quantitatively measures pSMAD3 levels in lysate, the assay demonstrates the ALK5 cellular potency of a test compound.

BEAS-2B cells were grown using 50% DMEM (Life Technologies) and 50% F-12 (Life Technologies) media, supplemented with 10% Fetal Bovine Serum (ATCC), 25 mM HEPES (Life Technologies), and 1× Pen-Strep (Life Technologies). Cells were cultured in a humidified incubator set at 37° C., 5% CO$_2$, and trypsonized using 0.25% Trypsin with 0.5% polyvinylpyrrolidone (PVP).

For the assay, BEAS-2B cells were seeded at 7,500 cells/well (25 μL/well) in a 384-well plate and cultured overnight. Before dosing, growth media was aspirated and the wells were rinsed with HBSS Buffer (HBSS with Calcium and Magnesium, Life Technologies) supplemented with 25 mM HEPES (Life Technologies) and 1% Bovine Serum Albumin (Roche). Compounds were serially diluted in DMSO, then further diluted with supplemented HBSS Buffer (50 μL/well) to create a compound plate 3× of the final assay concentration, at 0.3% DMSO. The diluted compounds were then added to the cells (8 μL/well) and incubated at 37° C., 5% CO$_2$ for 1 hour. After the compound incubation, TGF-β (R&D Systems) reconstituted in supplemented HBSS Buffer was added to the cells (12 μL/well, final concentration 10 ng/mL) and incubated for a further 30 minutes, after which the cells were immediately lysed with AlphaLISA lysis buffer (PerkinElmer). AlphaLISA Acceptor and Detector beads (PerkinElmer) were added 2 hours apart, then incubated overnight to be read the next day. The potency of the compound was determined through analysis of dose-dependent quantified changes in pSMAD3 signal from baseline (non-compound treated TGF-β stimulated cells). Data are expressed as pIC$_{50}$ (negative decadic logarithm IC$_{50}$) values. Certain compounds disclosed herein exhibited pIC$_{50}$ values of greater than 6 or greater than 7 when tested in BEAS-2B3 cells.

Table 4 shows biological activities of selected compounds in a cellular ALK5 potency assay. Compound numbers correspond to the numbers and structures provided in Tables 1 and 2 and Examples 1-44.

TABLE 4

| | 5 to 5.8 (+) | 5.9 to 6.7 (++) | 6.8 to 7.6 (+++) | ≥7.7 (++++) |
|---|---|---|---|---|
| BEAS2B pIC$_{50}$ | 26, 82, 386, 423, 540, 603, 610, 629, 636, | 11, 30, 31, 37, 48, 53, 57, 68, 86, 87, 91, 93, | 1, 2, 3, 4, 6, 7, 8, 9, 12, 13, 15, 16, 17, 18, 19, 21, 22, 23, 24, 25, 27, 32, 33, 34, 35, 36, 38, 39, 40, 41, 42, 44, 46, 47, 49, | 5, 10, 14, 20, 28, 29, 43, 45, 58, 76, 78, 89, |

TABLE 4-continued

| 5 to 5.8 (+) | 5.9 to 6.7 (++) | 6.8 to 7.6 (+++) | ≥7.7 (++++) |
|---|---|---|---|
| 1012, 1014, 1044 | 95, 103, 107, 114, 117, 155, 157, 159, 162, 181, 200, 206, 215, 224, 237, 245, 251, 256, 269, 283, 286, 296, 297, 308, 309, 326, 338, 339, 340, 348, 349, 358, 363, 373, 379, 390, 394, 402, 406, 413, 416, 422, 428, 429, 439, 450, 454, 455, 468, 471, 473, 478, 483, 484, 488, 497, 498, 499, 517, 530, 532, 551, 557, 562, 563, 564, 569, 574, 575, 578, 580, 585, 594, 596, 601, 604, 605, 608, 611, 615, 624, 630, 633, 1001, 1002, 1003, 1006, 1007, 1008, 1009, 1010, 1013, 1017, 1019, 1020, 1022, 1023, 1043 | 50, 51, 52, 54, 55, 56, 59, 60, 61, 62, 63, 64, 65, 66, 67, 69, 70, 71, 72, 73, 74, 75, 77, 79, 80, 81, 83, 84, 85, 88, 90, 96, 97, 98, 99, 100, 101, 102, 104, 105, 106, 108, 109, 110, 111, 112, 113, 115, 116, 118, 119, 120, 121, 122, 123, 124, 125, 127, 129, 130, 131, 132, 133, 134, 136, 137, 138, 140, 141, 142, 143, 144, 145, 146, 147, 148, 149, 150, 151, 152, 153, 154, 156, 158, 160, 163, 164, 165, 166, 167, 168, 169, 170, 171, 172, 173, 174, 175, 176, 177, 178, 179, 180, 182, 183, 184, 185, 186, 187, 188, 189, 190, 191, 192, 194, 195, 196, 197, 198, 199, 201, 202, 204, 205, 207, 211, 212, 213, 214, 216, 217, 218, 219, 220, 221, 222, 223, 225, 226, 228, 229, 230, 231, 232, 233, 234, 236, 238, 239, 240, 241, 242, 243, 244, 246, 247, 248, 249, 250, 252, 253, 255, 257, 258, 259, 260, 262, 263, 264, 267, 270, 271, 272, 273, 274, 275, 276, 277, 278, 279, 280, 281, 282, 285, 287, 289, 290, 291, 292, 293, 295, 298, 299, 300, 301, 302, 303, 304, 305, 306, 307, 310, 311, 312, 313, 314, 316, 317, 318, 320, 321, 322, 323, 324, 325, 327, 329, 330, 332, 333, 334, 335, 336, 337, 341, 342, 343, 344, 345, 346, 347, 350, 352, 353, 354, 355, 356, 357, 359, 360, 361, 362, 366, 367, 368, 369, 370, 371, 372, 374, 375, 376, 377, 378, 380, 381, 382, 383, 384, 385, 389, 391, 392, 393, 395, 396, 397, 398, 399, 400, 401, 403, 404, 405, 407, 408, 409, 410, 411, 412, 414, 415, 417, 418, 419, 420, 424, 425, 426, 427, 430, 431, 432, 433, 434, 435, 436, 437, 438, 440, 441, 442, 444, 445, 446, 447, 448, 449, 451, 453, 456, 457, 458, 459, 460, 461, 462, 463, 464, 466, 467, 469, 470, 472, 474, 476, 479, 480, 481, 482, 485, 486, 487, 489, 490, 491, 492, 493, 494, 495, 496, 500, 501, 502, 503, 504, 505, 506, 507, 508, 509, 510, 511, 512, 513, 515, 516, 518, 519, 520, 521, 522, 524, 525, 526, 527, 528, 529, 531, 533, 534, 536, 537, 538, 539, 541, 542, 543, 544, 545, 546, 547, 548, 549, 550, 552, 553, 554, 556, 558, 560, 561, 565, 566, 567, 568, 570, 572, 573, 576, 577, 579, 581, 582, 583, 584, 586, 587, 588, 589, 590, 591, 592, 593, 595, 597, 598, 599, 600, 602, 606, 607, 609, 612, 613, 614, 616, 617, 618, 619, 620, 621, 622, 623, 625, 626, 627, 628, 631, 632, 634, 635, 637, 638, 639, 641, 642, 1000, 1004, 1005, 1011, 1015, 1016, 1018, 1021, 1024, 1025, 1026, 1027, 1028, 1029, 1030, 1031, 1032, 1033, 1034, 1035, 1036, 1037, 1038, 1039, 1040, 1041, 1042, 1045 | 92, 94, 126, 128, 135, 139, 161, 193, 203, 208, 209, 210, 227, 235, 254, 261, 265, 268, 284, 288, 294, 315, 328, 331, 351, 364, 365, 387, 388, 421, 443, 452, 465, 475, 477, 514, 523, 535, 571 |

Example 47: Cytotoxicity Measured by Premature Chromosome Condensation [15] (pCC$_{15}$)

The impact of a compound of the present disclosure on cellular adenosine triphosphate (ATP) levels was measured in Beas2B cells, a human lung epithelial cell line. Levels of ATP are correlated with the viability of cells and are often measured to determine the potential cytotoxicity of compounds. CellTiter-Glo, which lyses the cells and produces a luminescent signal proportional to the amount of ATP present, was used to determine the effect of test compound on cell viability.

Beas2B cells were grown in 5000 DMEM (Life Technologies) and 50% F-12 (Life Technologies) media, supplemented with 10% Fetal Bovine Serum (ATCC), 25 mM HEPES (Life Technologies), and 1× Pen-Strep (Life Technologies). Cells were cultured in a humidified incubator set at 37° C., 5% CO$_2$, and trypsinized using 0.25% Trypsin with 0.5% polyvinylpyrrolidone (PVP).

For the assay, Beas2B cells were seeded at 500 cells/well (25 μL/well) in a 384-well plate and cultured overnight. Compounds were serially diluted in DMSO, then further diluted with growth media (40 μL/well) to create a compound plate 6× of the final assay concentration, at 0.6% DMSO. The diluted compounds were then added to the cells (5 μL/well) and incubated at 37° C., 500 $CO_2$ for 48 hours. After the compound incubation, CellTiter-Glo (Promega) was added directly to the cells (30 μL/mL). The assay plate was sealed and shaken at 700 rpm for 15 minutes in a darkened environment, then centrifuged for 2 minutes at 1500 rpm to settle the lysate at the bottom of the well. The effect of the compound on cell viability was determined through analysis of dose-dependent quantified changes in ATP from baseline (non-compound treated cells) and wells treated with 60 μM AT9283, a well-characterized cytotoxic compound. Data are expressed as $pCC_{15}$ (negative decadic logarithm $CC_{15}$) values. Certain compounds disclosed herein exhibited $pCC_{15}$ values of less than 6 or less than 5.5 when tested in Beas2B cells.

Table 5 shows cytotoxicities of selected compounds in a premature chromosome condensation assay. Compound numbers correspond to the numbers and structures provided in Tables 1 and 2 and Examples 1-44.

TABLE 5

| | ≤5(+++) | 5.1 to 5.7 (++) | 5.8 to 6.4 (+) |
|---|---|---|---|
| Cytotoxicity $pCC_{15}$ | 5, 6, 10, 12, 14, 17, 19, 22, 26, 29, 30, 31, 33, 36, 37, 40, 42, 43, 44, 47, 48, 50, 52, 53, 54, 56, 57, 58, 59, 60, 62, 63, 67, 69, 71, 73, 76, 78, 82, 83, 84, 86, 87, 88, 89, 92, 93, 95, 97, 98, 100, 101, 103, 105, 106, 107, 108, 114, 118, 119, 121, 122, 124, 125, 126, 128, 130, 134, 135, 136, 138, 139, 140, 141, 142, 146, 148, 149, 150, 152, 154, 155, 157, 159, 161, 162, 163, 164, 167, 168, 169, 170, 171, 172, 173, 174, 176, 178, 180, 181, 182, 184, 185, 186, 195, 200, 201, 203, 206, 208, 209, 210, 211, 212, 214, 215, 220, 222, 224, 225, 226, 227, 228, 229, 230, 232, 235, 236, 237, 238, 244, 245, 248, 250, 254, 256, 258, 261, 264, 265, 267, 268, 269, 271, 272, 273, 275, 276, 281, 282, 283, 284, 287, 288, 290, 292, 294, 295, 296, 297, 298, 299, 303, 306, 307, 308, 309, 310, 311, 313, 316, 318, 320, 323, 325, 327, 328, 329, 330, 336, 337, 338, 339, 340, 341, 348, 349, 353, 354, 357, 358, 363, 364, 365, 368, 369, 371, 373, 378, 380, 383, 385, 386, 387, 388, 390, 391, 392, 400, 401, 402, 404, 406, 407, 410, 411, 413, 416, 419, 420, 421, 422, 423, 425, 426, 427, 428, 430, 431, 433, 435, 437, 439, 440, 441, 443, 444, 448, 452, 454, 455, 456, 458, 460, 465, 467, 468, 472, 473, 475, 477, 483, 484, 485, 486, 488, 490, 491, 495, 497, 498, 502, 505, 507, 508, 510, 511, 512, 513, 517, 518, 520, 527, 530, 532, 535, 536, 537, 538, 541, 545, 546, 547, 548, 549, 550, 551, 552, 555, 557, 558, 560, 561, 562, 564, 565, 567, 569, 570, 573, 574, 575, 576, 577, 578, 579, 580, 581, 582, 584, 585, 587, 589, 592, 593, 594, 595, 596, 597, 601, 602, 603, 605, 606, 608, 610, 611, 612, 613, 614, 615, 616, 617, 618, 620, 622, 624, 625, 628, 629, 630, 632, 633, 634, 636, 641, 642, 1000, 1001, 1002, 1007, 1008, 1010, 1011, 1012, 1017, 1018, 1019, 1020, 1021, 1022, 1023, 1024, 1025, 1029, 1034, 1035, 1036, 1043, 1044, 1045 | 1, 2, 3, 4, 7, 8, 9, 11, 15, 18, 20, 21, 23, 24, 25, 27, 28, 32, 34, 38, 39, 41, 45, 49, 51, 55, 61, 64, 65, 66, 68, 70, 72, 74, 75, 77, 79, 80, 81, 85, 91, 94, 96, 102, 104, 110, 111, 112, 113, 115, 116, 117, 120, 127, 129, 131, 132, 133, 144, 145, 147, 158, 165, 166, 175, 177, 183, 187, 188, 189, 190, 191, 192, 193, 194, 196, 198, 199, 202, 204, 205, 207, 213, 216, 217, 218, 219, 221, 233, 234, 239, 240, 241, 242, 243, 247, 249, 251, 257, 259, 260, 262, 263, 266, 270, 274, 277, 278, 279, 280, 285, 286, 289, 291, 293, 300, 301, 302, 304, 305, 312, 315, 317, 319, 321, 322, 324, 331, 332, 333, 334, 335, 342, 344, 345, 346, 347, 350, 352, 355, 356, 359, 360, 361, 362, 366, 367, 370, 372, 374, 375, 376, 377, 381, 382, 384, 389, 394, 395, 396, 397, 399, 403, 405, 408, 409, 414, 417, 424, 429, 432, 434, 438, 442, 449, 451, 453, 457, 459, 461, 462, 463, 464, 469, 471, 474, 476, 478, 479, 480, 481, 482, 487, 489, 492, 494, 499, 500, 501, 503, 504, 506, 509, 514, 516, 519, 521, 522, 523, 524, 525, 526, 528, 529, 531, 533, 534, 539, 540, 542, 543, 544, 553, 554, 563, 566, 568, 571, 572, 583, 586, 588, 590, 591, 598, 599, 600, 604, 607, 609, 619, 621, 623, 626, 627, 631, 635, 637, 638, 639, 640, 1003, 1004, 1005, 1006, 1009, 1013, 1014, 1015, 1016, 1026, 1027, 1028, 1030, 1031, 1032, 1033, 1037, 1038, 1040, 1041, 1042 | 13, 16, 35, 46, 90, 99, 109, 123, 137, 143, 151, 153, 156, 160, 179, 197, 223, 231, 246, 252, 253, 255, 314, 326, 343, 351, 379, 393, 398, 412, 415, 418, 436, 445, 446, 447, 450, 466, 470, 493, 496, 515, 556, 1039 |

Example 48: In Vitro Human Liver Microsome Intrinsic Clearance (HLM $Cl_{int}$)

Liver microsomes were used for in vitro determination of hepatic clearance of compounds of the present disclosure. A microsomal incubation cofactor solution was prepared with 100 mM potassium phosphate buffered to pH 7.4 (BD Biosciences, Woburn, Mass.) supplemented with 2 mM NADPH (Sigma-Aldrich, St. Louis, Mo.). 10 mM DMSO stocks of test compound were diluted and spiked into the cofactor solution to yield a 0.2 μM concentration (0.02% v/v DMSO). Aliquots of frozen human liver microsomes (Bioreclamation IVT, Baltimore Md.) were thawed and diluted into 100 mM potassium phosphate buffer to yield microsomal protein concentrations of 0.2 mg/mL. Cofactor/drug and microsomal solutions were pre-warmed separately for 4 minutes in a water bath held at 37° C. Incubations (n=1) were started by the combination of equal volumes of cofactor/drug solution with microsomal solution. The final concentration of test compound was 0.1 µM with a final protein concentration of 0.1 mg/mL and final NADPH concentration of 1 mM. Samples were collected at times 0, 3, 8, 15, 30, and 45 minutes to monitor the disappearance of test compound. At each time point, 50 µL of incubation sample was removed and spiked into 25 µL of water plus 3% formic acid plus Internal Standard for reaction termination. Samples were then injected onto an AB Sciex API 4000 triple quadrupole mass spectrometer for quantitation by LC-MS/MS. Mobile Phase A consisted of HPLC grade water with 0.2% formic acid and Mobile Phase B consisted of HPLC grade acetonitrile with 0.2% formic acid with all samples run through a Thermo HyPURITY C18 50×2.1 mm column (Waltham, Mass.). HLM Clint data was reported in units of µL/min/mg. See Riley, R. I., et al., *Drug Metab. Dispos.*, 2005, September, 33(9), pp. 1304-1311. Certain compounds disclosed herein exhibited HLM $Cl_{int}$ of greater than 50 µL/min/mg or greater than 100 µL/min/mg.

Example 49: Lung PK/PD

In-Life Portion

C57bl/6n mice were acclimated for at least 3 days before use. On the day of the experiment, animals were grouped into sample sizes of 5 (n=10 for the TGF-β stimulated group). Compounds of the present disclosure (formulated in 3% glycerol in PBS; pH=4) were pre-treated via oral aspiration (OA; animals are forced to aspirate solution into the lungs by covering their nose). All oral aspirations were performed using a 50 µL dosing volume and accompanied by the appropriate vehicle control groups. Following compound OA treatment, the animals were returned to their home cages and monitored. Compound pre-treatment occurred 4 hours prior to harvest for screening and dose-response studies; duration studies had variable compound pre-treatment times. One hour prior to harvest, animals were challenged via oral aspiration a second time with PBS vehicle or recombinant human TGF-β1 protein (0.01 µg per animal dissolved in 1 part 4 mM HCl and 2 parts 3% glycerol in PBS). Five minutes prior to harvest, animals were deeply anesthetized under isoflurane and euthanized via cervical dislocation. Bronchoalveolar lavage fluid (BALF), plasma and left lung lobes were collected during harvest.

Sample Collection and Processing

Blood plasma was collected via open cardiac puncture. After whole blood collection, the samples were placed in EDTA-coated tubes to prevent coagulation. Blood samples were spun at 15300×g's for 4 minutes at 4° C. to separate the plasma. Plasma was immediately isolated, frozen and submitted for bioanalytical (BA) analysis.

In order to collect BALF, the lungs were flushed via the trachea with 0.7 mL of PBS 3 times. The BALF, which consists almost entirely of tissue-derived macrophages, was immediately centrifuged at 700×g's for 15 minutes. After centrifugation, the supernatant was removed, the BALF was re-suspended in 1× cell lysis buffer, and immediately frozen. Prior to BA submission, the BALF was dethawed and sonicated for 30 minutes on cold water to lyse open the cells Left lung lobes were harvested immediately after BALF collection. Lung samples were homogenized in 500 µL of 1× cell lysis buffer. After homogenization, the samples were split: half of the sample was immediately placed on a rotisserie for 10 minutes while the other half was immediately frozen for BA analysis. The samples placed on the rotisserie were then centrifuged at 10,000×g's for 10 minutes in order to separate the protein in the supernatant from pelleted debris. Following collection of the supernatant, a total protein quantification assay (Bradford) was performed to normalize the concentrations of all samples. Using the Hamilton star liquid handling system, each sample was diluted in 1× cell lysis buffer to 2 mg/mL of protein. Samples were stored at −80° C. or immediately processed using the Meso-scale Discovery system.

Phospho-SMAD3 (pSMAD3) and Total-SMAD3 (tSMAD3) Quantification Using Meso-Scale Discovery Meso-scale Discovery (MSD) is an electrochemical protein quantification assay that requires specialized microplates with carbon electrodes attached to the bottom. These carbon electrodes allow for greater attachment of biological reagent to microplates, thus allowing for a more sensitive read-out when compared to a traditional ELISA. Similar to a standard sandwich ELISA, MSD requires use of a coating antibody that binds the target protein(s) within the sample. After sample incubation, a primary antibody is used to bind the epitope of interest. Following addition of the primary antibody, a secondary-antibody with a SULFO-TAG detection is used to allow for quantification of the epitope of interest. Lastly, the microplate is read via an electric pulse that causes the SULFO-TAG to emit light, which serves as the final read-out of the assay.

The coating antibody (SMAD3, clone=5G-11) was incubated overnight in the specialized MSD microplates at 4° C. The next day, the microplates were blocked in 3% BSA (bovine serum albumin) for 70 minutes to prevent non-specific protein binding to the bottom of the microplate. After a wash step, 50 µg of lung samples were loaded into the MSD-plate and incubated for 2 hours at room temperature. The plates were washed again to remove unbound sample; either phospho-SMAD3 (pSMAD3; clone=EP568Y) or total-SMAD3 (tSMAD3) primary antibody were incubated for 1 hour. Following a wash step, the anti-rabbit SULFO-tag detection antibody was incubated for 50 minutes. After a final wash step, MSD-read buffer was added to each sample. pSMAD3 and tSMAD3 quantification was performed using an MSD-specific plate reader (Sector S 600).

Data Analysis

Samples were immediately analyzed using an outlier analysis (Grubbs test, α=0.05). After outlier removal, the raw pSMAD3 were divided by the tSMAD3 luminescent readings. In screening and dose-response studies, the pSMAD3/tSMAD3 ratio was normalized to the TGF-β induction group (set to 100%) in order to minimize the variability between stimulation. First, the 3% glycerol/PBS group was compared with the 3% glycerol/TGF-β with a student's t-test (cut-off: p=0.05) to ensure a pSMAD3 window was present. A one-way ANOVA (fisher's uncorrected LSD) was used to compare all drug treated groups with the 3% glycerol/TGF-β group to determine if statistically significant differences are observed. Percent pSMAD3 inhibition was calculated using the vehicle pSMAD3 as a baseline value and displayed as the final readout. Dose-response curves were fitted with a 4-parameter non-linear regression algorithm; the minimum response was set to 0% pSMAD3 inhibition and the maximum response set to 100% pSMAD3 inhibition. Compound potencies were obtained from the regression and reported as ID50s.

PK Study

Plasma, lung and macrophage drug concentrations were quantified. Total macrophage concentration was normalized to the total macrophage cell volume over the total drug recovered in the BALF. The alveolar macrophage volume used in the calculation was based on a publication by Krombach et al. (*Environmental Health Perspectives*, September 1997, Vol. 105, Supplement 5, pp. 1261-1263) which estimated the rat alveolar macrophage volume to be approximately 1200 µm³ or $1.2e^{-9}$ mL. The assumption was made that the mouse alveolar macrophage volume is similar to that of the rat. Normalized total macrophage concentration recovered=(total drug recovered from BALF)/(total cell counts*$1.2e^{-9}$ mL).

Certain compounds disclosed herein exhibited (lung $AUC_{0-t}$):(plasma $AUC_{0-t}$) ratios of greater than 10, such as greater than 50, greater than 75 or greater than 100. A compound intended for local delivery to the lung with minimal systemic exposure preferably exhibits a (lung $AUC_{0-t}$):(plasma $AUC_{0-t}$) ratio of greater than 50. Certain compounds provided in Table 3 having $pK_i$ values of greater than 9.5 exhibited a (lung $AUC_{0-t}$):(plasma $AUC_{0-t}$) ratio of greater than 75.

Example 50: Cardiac PK/PD

In-Life Portion

C57bl/6n mice were acclimated for at least 3 days before use. On the day of the experiment, animals were grouped into sample sizes of 5-10. Test compounds were pre-treated via oral aspiration (OA; animals are forced to aspirate solution into the lungs by covering their nose). All oral aspirations were performed using a 50 µL dosing volume and accompanied by a vehicle control group (3% glycerol in PBS, pH=4). Following compound OA treatment, the animals were returned to their home cages and monitored. Compound pre-treatment occurred either 2 or 4 hours prior to harvest. One hour prior to harvest, animals were challenged via tail-vein intravenous injection with PBS vehicle or recombinant human TGF-β1 protein (1 µg per animal dissolved in 1 part 4 mM HCl and 2 parts 3% glycerol in PBS). Five minutes prior to harvest, animals were deeply anesthetized under isoflurane and euthanized via cervical dislocation. Plasma, left lung lobes and whole hearts were collected during harvest.

Sample Collection and Processing

Blood plasma was harvested as described above in the Lung PK/PD experiment. Whole hearts were processed in the same manners as left lung lobes in the Lung PK/PD experiment. Left lung lobes were homogenized in 500 µL of water and submitted for BA Analysis.

Phospho-SMAD3 (pSMAD3) and Total-SMAD3 (tS-MAD3) Quantification Using Meso-Scale Discovery Heart samples were processed using MSD in the same manner as the left lung lobes above. Data analysis was performed in the same manners as the lung PK/PD experiment. Plasma, lung and heart drug concentrations were quantified.

There was minimal target engagement systemically following treatment with one or more compound disclosed herein, as measured by SMAD3 phosphorylation inhibition. In some examples, a compound disclosed herein exhibited less than 10% target engagement systemically as measured by SMAD3 phosphorylation inhibition.

Example 51: Efficacy Study in Syngeneic Cancer Model

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 45), are expected to suppress tumor growth in syngeneic cancer models when administered alone or in combination with an immunotherapeutic agent. Six- to 8-week old BALB/c mice are used for in vivo efficacy studies in accordance with IACUC guidelines. Commercially available 4T1 cells (0.5-2.0×10⁴ cells/mouse) are implanted subcutaneously into the right flanks of BALB/c mice. When the tumor reaches a palpable size of approximately 8-10 mm in diameter, the primary tumors are surgically removed, and the mice are randomly assigned to vehicle control or compound treatment groups. Alternatively, CT26 cells (0.5-2.0×10⁴ cells/mouse) are injected intravenously into BALB/c mice to generate the cancer model. Two days following the surgery, or 7 days following injection of CT26 cells, the mice are treated with either (1) vehicle control, (2) a compound of the present disclosure at an appropriate amount and frequency (formulated in 3% glycerol in PBS; pH=4) via oral aspiration or intranasally, (3) an immunotherapeutic agent (e.g., pembrolizumab or durvalumab) at an appropriate amount and frequency, or (4) a compound of the present disclosure and an immunotherapeutic agent, each at an appropriate amount and frequency.

Body weight is measured twice weekly. Following 2- to 4-weeks of treatment, the lung and liver of each animal is harvested, and the number of metastatic cells in each tissue sample determined using a clonogenic metastasis assay. Cells may be further subjected to one or more of FACS analysis, T-cell function assay, and RNA extraction. It is expected that the animal group treated with one or more of the ALK5 inhibitors disclosed herein exhibits reduction in lung tumor burden. Activation of an immune response by the ALK5 inhibitor may stimulate both local and systemic antitumor T-cell activation, thus a reduction in liver tumor burden may also be observed. When administered in combination with an immunotherapeutic agent, a compound of the present disclosure, such as a compound provided in Table 1, is expected to produce an increased reduction in lung tumor burden relative to the reduction in tumor burden observed in animals treated with either single agent alone. The compounds described herein are expected to interact synergistically with an immunotherapeutic agent to suppress tumor growth and increase survival.

Example 52: Prophylactic Study in Murine DSS-Induced Intestinal Fibrosis Model

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 45), are expected to slow, halt or reverse the progression of intestinal fibrosis in a murine colitis model. Six to 8-week old male C57BL/6J mice are tagged and weighed. The drinking water of the animals is treated with 2.5% dextran sulfate sodium (DSS) for 7 days to induce acute colitis, followed by 2 days of normal drinking water. Three, 3-week cycles of 2.5% DSS treatment (1 week of 2.5% DSS in water; 2 weeks of normal water) are then completed to induce intestinal fibrosis.

Starting on day one of DSS administration, mice are treated with either vehicle control or a compound of the present disclosure at an appropriate amount and frequency via oral gavage (e.g., once daily). The animals are sacrificed 9 weeks after the first DSS administration, then distal, mid and proximal sections of the colon harvested for histologic analysis, RNA extraction and cytokine measurement. A compound of the present disclosure, such as a compound provided in Table 1, is expected to decrease ALK5 activity in the colon and to slow or prevent intestinal fibrosis as evidenced by one or more of (1) reduction in the ratio of colon weight to colon length; (2) reduction in deposition of extracellular matrix as observed by histology; (3) reduction in expression of collagen 1 (Col1a1) and connective tissue growth factor (Ctgf) in colon tissue; and (4) reduction in production of TGF-β1 and IL6 in the colon, relative to vehicle-treated controls.

Example 53: Efficacy Study in Murine DSS-Induced Intestinal Fibrosis Model

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 45), are expected to slow, halt or reverse the progression of intestinal fibrosis in a murine colitis model. Six to 8-week old male C57BL/6J mice are tagged and weighed. The drinking water of the animals is treated with 2.5% dextran sulfate sodium (DSS) for 7 days to induce acute colitis, followed by 2 days of normal drinking water. Three, 3-week cycles of 2.5% DSS treatment (1 week of 2.5% DSS in water; 2 weeks of normal water) are then completed to induce intestinal fibrosis.

Following the second of the 3 cycles of DSS administration, mice are treated with either vehicle control or a compound of the present disclosure at an appropriate amount and frequency via oral gavage (e.g., once daily). Animals are sacrificed at either 6, 9 or 12 weeks after the first DSS cycle, then distal, mid and proximal sections of the colon harvested for histologic analysis, RNA extraction and cytokine measurement. A compound of the present disclosure, such as a compound provided in Table 1, is expected to decrease ALK5 activity in the colon and to slow, halt or reverse intestinal fibrosis as evidenced by one or more of (1) reduction in the ratio of colon weight to colon length; (2) reduction in deposition of extracellular matrix as observed by histology; (3) reduction in expression of collagen 1 (Col1a1) and connective tissue growth factor (Ctgf) in colon tissue; and (4) reduction in production of TGF-β1 and IL6 in the colon, relative to vehicle-treated controls.

Example 54: Efficacy Study in Adoptive T-Cell Transfer Model of Colitis

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 45), are expected to slow, halt or reverse the progression of intestinal fibrosis in an adoptive T-cell transfer model of colitis. Six- to 8-week old female CB17 SCID mice are tagged and weighed, then administered CD4+ CD25− CD62L+ naïve T cells isolated from the spleens of Balb/C mice (IP; 1×10^6 cells) to induce colitis.

Once diarrhea and a 10% or greater decrease in body weight are observed (typically around week 2), mice are treated with either vehicle control or a compound of the present disclosure at an appropriate amount and frequency via oral gavage (e.g., once daily). Animals are sacrificed 45 days after induction of colitis, then distal, mid and proximal sections of the colon harvested for histologic analysis, RNA extraction and cytokine measurement. A compound of the present disclosure, such as a compound provided in Table 1, is expected to decrease ALK5 activity in the colon and to slow, halt or reverse intestinal fibrosis as evidenced by one or more of (1) reduction in the ratio of colon weight to colon length; (2) reduction in deposition of extracellular matrix as observed by histology; (3) reduction in expression of collagen 1 (Col1a1) and connective tissue growth factor (Ctgf) in colon tissue; and (4) reduction in production of TGF-β1 and IL6 in the colon, relative to vehicle-treated controls.

Example 55: Efficacy Study in Monocrotaline Model of Severe Pulmonary Hypertension One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 45), are expected to slow, halt or reverse the progression of pulmonary hypertension in a monocrotaline (MCT) model of severe pulmonary hypertension. Male Sprague-Dawley rats are tagged, weighed, and randomly divided into control and MCT-treated groups. The rats in the MCT-treated group are administered a single dose of MCT (60 mg/kg, s.c.), then treated with either (1) vehicle control; (2) sildenafil (30 mg/kg, p.o., b.i.d.); or (3) a compound of the present disclosure at an appropriate amount and frequency (formulated in 3% glycerol in PBS; pH=4) via oral aspiration.

Following 2-weeks of treatment, the animals are anesthetized with ketamine/xylazine for terminal monitoring of pulmonary and systemic arterial pressures along with heart rate. The lungs of each animal are then harvested for histologic analysis. A compound of the present disclosure, such as a compound provided in Table 1, is expected to decrease ALK5 activity in the lung and slow, halt or reverse the progression of pulmonary hypertension as evidenced by one or more of (1) reduction in systolic pulmonary arterial pressure; (2) reduction in right ventricular (RV) systolic pressure; (3) reduction in RV diastolic pressure; (4) increase in cardiac output; (5) reduction in RV hypertrophy; (6) reduction in pSmad2 or pSmad3 staining within vascular and/or alveolar cells; (7) reduction in medial thickness; (8) reduction in vascular smooth muscle cell proliferation; (9) reduction in vascular smooth muscle hypertrophy; and (10) reduction in expression of matrix metalloproteinase (MMP)-2 and/or MMP-9.

What is claimed is:
1. A compound of Formula (I-A):

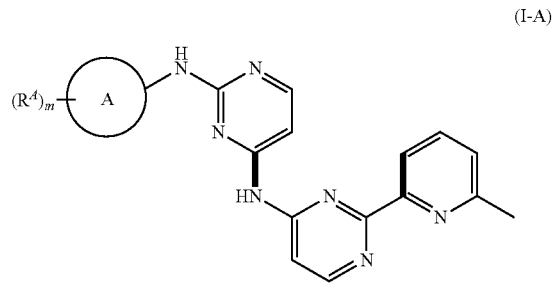

(I-A)

or a pharmaceutically acceptable salt thereof, wherein:
A is selected from phenyl and 5- to 6-membered heteroaryl;

$R^A$ is independently selected at each occurrence from:
halogen, —OR$^1$, —N(R$^1$)$_2$, —S(=O)$_2$R$^1$, —S(=O)$_2$N(R$^1$)$_2$, —S(=O)$_2$NR$^2$R$^3$, —NR$^1$S(=O)$_2$R$^1$, —NR$^1$S(=O)$_2$N(R$^1$)$_2$, —C(O)R$^1$, —C(O)OR$^1$, —NR$^1$C(O)R$^1$, —NR$^1$C(O)N(R$^1$)$_2$, —C(O)N(R$^1$)$_2$, —C(O)NR$^2$R$^3$;

C$_{1-6}$ alkyl and —N(R$^1$)—C$_{1-10}$ alkyl, each of which is independently optionally substituted at each occurrence with one or more substituents selected from —OR$^1$, —N(R$^1$)$_2$, —C(O)OR$^1$, C$_{3-8}$ carbocycle, and 3- to 10-membered heterocycle; and C$_{3-8}$ carbocycle and 3- to 10-membered heterocycle, wherein each C$_{3-8}$ carbocycle and 3- to 10-membered heterocycle in R$^A$ is independently optionally substituted with one or more substituents selected from —OR$^1$, —CH$_2$N(R$^1$)$_2$N(R$^1$)$_2$, —C(O)R$^1$, —CH$_2$C(O)OR$^1$, —C(O)OR$^1$, —C(O)N(R$^1$)$_2$, R$^1$, and C$_{1-6}$ alkyl;

R$^1$ is independently selected at each occurrence from hydrogen; and C$_{1-6}$ alkyl, 1- to 6-membered heteroalkyl, C$_{0-3}$ alkyl-(C$_{3-8}$ carbocycle), and C$_{0-3}$ alkyl-(3- to 10-membered heterocycle), each of which is optionally substituted by one or more substituents selected from —NH$_2$, —NHCH$_3$, —N(CH$_3$)$_2$, —CH$_2$CH$_2$N(CH$_3$)$_2$, —C(O)CH$_3$, —C(O)OH, —C(O)NH$_2$, =O, —OH, —CH$_2$OH, —CH$_2$CH$_2$OH, —OCH$_3$, —OCH$_2$CH$_3$, —CH$_3$, —CH$_2$CH$_3$, —CH(CH$_3$)$_2$, —C(CH$_3$)$_3$, C$_{3-8}$ carbocycle, and 3- to 6-membered heterocycle;

R$^2$ and R$^3$ are taken together with the nitrogen atom to which they are attached to form a heterocycle, optionally substituted with one or more R$^1$; and m is 0,1,or 2.

2. The compound or salt of claim 1, wherein A is selected from phenyl, pyridinyl, thiazolyl, and thiophenyl.

3. The compound or salt of claim 1, wherein A is phenyl.

4. The compound or salt of claim 1, wherein R$^A$ is independently selected at each occurrence from:
halogen, —OR$^1$, —N(R$^1$)$_2$, —S(=O)$_2$R$^1$, —S(=O)$_2$N(R$^1$)$_2$, —NR$^1$S(=O)$_2$R$^1$, —NR$^1$S(=O)$_2$N(R$^1$)$_2$, —C(O)R$^1$, —C(O)OR$^1$, —NR$^1$C(O)R$^1$, —NR$^1$C(O)N(R$^1$)$_2$, —C(O)N(R$^1$)$_2$;

C$_{1-6}$ alkyl and —N(R$^1$)-C$_{1-10}$ alkyl, each of which is independently optionally substituted at each occurrence with one or more substituents selected from —OR$^1$, —N(R$^1$)$_2$, and 3- to 10-membered heterocycle; and 3- to 10-membered heterocycle,
wherein each 3- to 10-membered heterocycle in R$^A$ is independently optionally substituted with one or more substituents selected from —OR$^1$, —N(R$^1$)$_2$, —C(O)R$^1$, —CH$_2$C(O)OR$^1$, —C(O)OR$^1$, —C(O)N(R$^1$)$_2$, and R$^1$.

5. The compound or salt of claim 1, wherein R$^A$ is —NR$^1$C(O)R$^1$.

6. The compound or salt of claim 1, wherein R$^A$ is —C(O)OR$^1$.

7. The compound or salt of claim 1, wherein R$^A$ is C$_{1-6}$ alkyl substituted with 4- to 8-membered heterocycle, wherein the 4- to 8-membered heterocycle is substituted with —C(O)OR$^1$.

8. The compound or salt of claim 1, wherein m is 1.

9. The compound or salt of claim 1, wherein the compound is a compound of Formula (I-D):

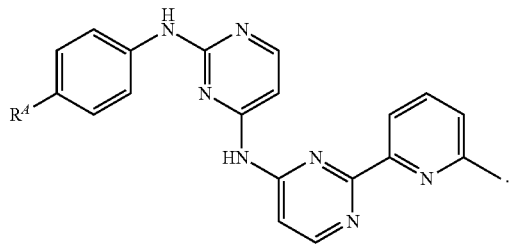

(I-D)

10. The compound or salt claim 1, wherein the compound is provided in at least 90% enantiomeric excess.

11. A pharmaceutical composition comprising the compound or salt of claim 1 and a pharmaceutically acceptable carrier.

12. The pharmaceutical composition of claim 11, wherein the pharmaceutical composition is formulated for inhalation.

13. A method of treating an ALK5-mediated disease or condition in a subject, comprising administering to the subject a therapeutically effective amount of the compound or salt of claim 1.

14. The method of claim 13, wherein the disease or condition is fibrosis.

15. The method of claim 14, wherein the fibrosis is selected from cardiac fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis.

16. The method of claim 15, where the pulmonary fibrosis is selected from idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis and chemotherapy-induced lung fibrosis.

17. The method of claim 14, wherein the fibrosis is idiopathic pulmonary fibrosis (IPF).

18. The method of claim 14, wherein the fibrosis is intestinal fibrosis.

19. The method of claim 13, wherein the disease or condition is selected from breast cancer, colon cancer, prostate cancer, lung cancer, hepatocellular carcinoma, glioblastoma, melanoma, and pancreatic cancer.

20. The method of claim 19, wherein the lung cancer is non-small cell lung cancer.

21. The method of claim 13, comprising administering a second therapeutic agent.

22. The method of claim 21, wherein the second therapeutic agent is an immunotherapeutic agent.

23. The method of claim 13, wherein the compound or salt is administered by inhalation.

* * * * *